(12) United States Patent
Takahashi et al.

(10) Patent No.: US 12,029,119 B2
(45) Date of Patent: *Jul. 2, 2024

(54) ORGANIC ELECTROLUMINESCENCE ELEMENT AND ELECTRONIC DEVICE

(71) Applicant: IDEMITSU KOSAN CO., LTD., Chiyoda-ku (JP)

(72) Inventors: Ryota Takahashi, Chiba (JP); Satomi Tasaki, Chiba (JP); Yuichiro Kawamura, Chiba (JP); Hidetsugu Ikeda, Sodegaura (JP); Yuki Nakano, Kisarazu (JP); Masakazu Funahashi, Chiba (JP); Tomoki Kato, Ichihara (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 577 days.

This patent is subject to a terminal disclaimer.

(21) Appl. No.: 16/485,132

(22) PCT Filed: Feb. 13, 2018

(86) PCT No.: PCT/JP2018/004785
§ 371 (c)(1),
(2) Date: Aug. 9, 2019

(87) PCT Pub. No.: WO2018/151065
PCT Pub. Date: Aug. 23, 2018

(65) Prior Publication Data
US 2020/0052225 A1 Feb. 13, 2020

Related U.S. Application Data

(63) Continuation of application No. 15/476,682, filed on Mar. 31, 2017, now Pat. No. 9,954,187.

(30) Foreign Application Priority Data

Feb. 14, 2017 (JP) ................................ 2017-025393
Oct. 6, 2017 (JP) ................................ 2017-196433
Dec. 6, 2017 (JP) ................................ 2017-234726

(51) Int. Cl.
*H01L 51/00* (2006.01)
*C07D 487/06* (2006.01)
(Continued)

(52) U.S. Cl.
CPC ....... *H10K 85/6572* (2023.02); *C07D 487/06* (2013.01); *C07D 487/16* (2013.01);
(Continued)

(58) Field of Classification Search
CPC ............ H01L 51/0072; H01L 51/0052; H01L 51/0058; H01L 51/0061; H01L 51/0073; H01L 51/5012; H01L 51/501; C07D 487/06; C07D 487/16; C09K 11/06; C09K 2211/1007; C09K 2211/1011; C09K 2211/1014; C09K 2211/1029; C09K 2211/1033; C09K 2211/1037;
(Continued)

(56) References Cited

U.S. PATENT DOCUMENTS 5,281,489 A 1/1994 Mori et al.
9,954,187 B2 * 4/2018 Takahashi .......... H10K 85/6572
(Continued)

FOREIGN PATENT DOCUMENTS

CN 1453886 A 11/2003
CN 104119347 A 10/2014
(Continued)

OTHER PUBLICATIONS

Office Action issued Jul. 18, 2017 in Japanese Patent Application No. 2017-072816, 3 pages.
Office Action issued Dec. 18, 2018 in European Patent Application No. 17777472.6, 4 pages.
Office Action issued Jun. 17, 2019 in European Patent Application No. 17777472.6, 3 pages.
Office Action mailed Oct. 21, 2021 in co-pending U.S. Appl. No. 16/201,484, 12 pages.
Japanese Office Action issued Feb. 2, 2021 in Japanese Patent Application No. 2018-568509 (with unedited computer generated English translation), 7 pages.
Office Action mailed May 8, 2020 in co-pending U.S. Appl. No. 16/201,484.
(Continued)

*Primary Examiner* — Alexander C Kollias
(74) *Attorney, Agent, or Firm* — Oblon, McClelland, Maier & Neustadt, L.L.P.

(57) ABSTRACT

Organic EL devices having excellent performance and electronic devices comprising the organic EL devices are provided. The organic EL device comprises a cathode, an anode, and an organic layer disposed between the cathode and the anode, wherein the organic layer comprises one or more layers that comprise a fluorescent emitting layer and the fluorescent emitting layer comprises a first compound represented by formula (P) and a second compound that is not the same as the first compound. The electronic device comprises the organic EL device.

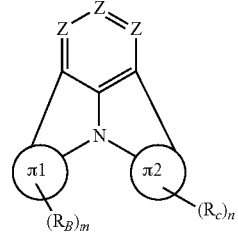

wherein, π1, π2, Z, $R_B$, $R_C$, m, and n are as defined in the description.

17 Claims, 2 Drawing Sheets

(51) Int. Cl.
  *C07D 487/16* (2006.01)
  *C09K 11/06* (2006.01)
  *H10K 85/60* (2023.01)
  *H10K 50/11* (2023.01)
  *H10K 101/10* (2023.01)

(52) U.S. Cl.
  CPC ............ *C09K 11/06* (2013.01); *H10K 85/615* (2023.02); *H10K 85/626* (2023.02); *H10K 85/636* (2023.02); *H10K 85/6574* (2023.02); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1037* (2013.01); *C09K 2211/1044* (2013.01); *C09K 2211/1088* (2013.01); *C09K 2211/1092* (2013.01); *H10K 50/11* (2023.02); *H10K 2101/10* (2023.02)

(58) Field of Classification Search
  CPC .... C09K 2211/1044; C09K 2211/1088; C09K 2211/1092; H10K 85/6572; H10K 85/626; H10K 85/636; H10K 85/6574
  See application file for complete search history.

(56) References Cited

U.S. PATENT DOCUMENTS

| | | | |
|---|---|---|---|
| 10,230,058 B2* | 3/2019 | Takahashi | C07D 487/06 |
| 10,658,594 B2 | 5/2020 | Takahashi et al. | |
| 10,672,989 B2 | 6/2020 | Takahashi et al. | |
| 10,680,181 B2 | 6/2020 | Takahashi et al. | |
| 11,489,123 B2* | 11/2022 | Takahashi | H10K 85/615 |
| 2004/0076853 A1 | 4/2004 | Jarikov et al. | |
| 2006/0154107 A1* | 7/2006 | Kubota | C07F 7/0807 |
| | | | 428/690 |
| 2007/0155991 A1* | 7/2007 | Funahashi | C09K 11/06 |
| | | | 564/426 |
| 2009/0001882 A1* | 1/2009 | Park | H10K 50/125 |
| | | | 313/504 |
| 2009/0140637 A1* | 6/2009 | Hosokawa | C07D 235/18 |
| | | | 313/504 |
| 2013/0026422 A1 | 1/2013 | Parham et al. | |
| 2013/0320310 A1* | 12/2013 | Yamamoto | H01L 51/0072 |
| | | | 257/40 |
| 2014/0167028 A1 | 6/2014 | Sekiguchi et al. | |
| 2014/0319507 A1* | 10/2014 | Yamamoto | C07D 495/16 |
| | | | 257/40 |
| 2014/0330017 A1* | 11/2014 | Kadoma | H01L 51/0059 |
| | | | 544/343 |
| 2015/0179949 A1 | 6/2015 | Miyata | |
| 2015/0179956 A1 | 6/2015 | Miyata et al. | |
| 2016/0111659 A1 | 4/2016 | Yang et al. | |
| 2016/0111660 A1* | 4/2016 | Yang | H10K 85/6572 |
| | | | 257/40 |
| 2016/0149142 A1 | 5/2016 | Kim et al. | |
| 2016/0181542 A1* | 6/2016 | Kawamura | C09K 11/06 |
| | | | 257/40 |
| 2016/0293853 A1* | 10/2016 | Zeng | H10K 85/6576 |
| 2017/0213984 A1* | 7/2017 | Kim | H01L 51/0054 |
| 2017/0324045 A1 | 11/2017 | Takahashi et al. | |
| 2018/0094000 A1 | 4/2018 | Hatakeyama et al. | |
| 2018/0114924 A1* | 4/2018 | Lee | H10K 85/654 |
| 2018/0198072 A1 | 7/2018 | Lee et al. | |
| 2020/0052212 A1* | 2/2020 | Tasaki | H01L 51/0054 |
| 2021/0005825 A1* | 1/2021 | Tasaki | C07D 487/22 |
| 2021/0005826 A1* | 1/2021 | Tasaki | C07D 487/22 |

FOREIGN PATENT DOCUMENTS

| | | | | |
|---|---|---|---|---|
| CN | 105524071 A | 4/2016 | | |
| CN | 108026106 A | 5/2018 | | |
| EP | 1 359 790 A2 | 11/2003 | | |
| EP | 3 009 494 A1 | 4/2016 | | |
| EP | 3 269 720 A1 | 1/2018 | | |
| JP | 2012-191031 A | 10/2012 | | |
| JP | 2013-183011 A | 9/2013 | | |
| JP | 2014-73965 A | 4/2014 | | |
| JP | 2014-231510 A | 12/2014 | | |
| JP | WO 2015033559 | * | 3/2017 | ............ C07C 13/66 |
| KR | 10-2014-0034710 A | 3/2014 | | |
| KR | 10-2014-0102947 | 8/2014 | | |
| KR | 10-2015-0114791 A | 10/2015 | | |
| KR | 10-2015-0135125 | 12/2015 | | |
| WO | WO 2011/128017 A1 | 10/2011 | | |
| WO | WO 2013/077344 A1 | 5/2013 | | |
| WO | WO 2016/006925 A1 | 1/2016 | | |
| WO | WO 2016/152418 A1 | 9/2016 | | |
| WO | WO 2016/195441 A1 | 12/2016 | | |
| WO | WO 2017/014460 A1 | 1/2017 | | |
| WO | WO 2017/175690 A1 | 10/2017 | | |

OTHER PUBLICATIONS

Office Action mailed Oct. 6, 2020 in co-pending U.S. Appl. No. 16/201,484.

Combined Chinese Office Action and Search Report issued Aug. 23, 2021 in Chinese Patent Application No. 201880011725.7 (with English translation of Categories of Cited Documents), citing documents AO-AR and AT therein, 10 pages.

Combined Chinese Office Action and Search Report issued Nov. 23, 2020 in Chinese Patent Application No. 201780001022.1 (with English translation of Categories of Cited Documents), citing documents AA, AB, AO and AP therein, 9 pages.

Extended European Search Report issued Dec. 3, 2020 in European Patent Application No. 18754903.5, citing documents AQ and AR therein, 6 pages.

International Search Report issued May 15, 2018 in PCT/2018/004785 filed Feb. 13, 2018.

Mi, B. X., et al., "Reduction of molecular aggregation and its application to the high-performance blue perylene-doped organic electroluminescent device," Applied Physics Letters, vol. 75, No. 26, Dec. 27, 1999, 4 pages.

Office Action mailed Apr. 13, 2021, in corresponding U.S. Appl. No. 16/201,484, filed Nov. 27, 2018, (References AA, AB, AC, AX, AY, and AZ are cited therein).

Yirang Im, et al., "Deep blue thermally activated delayed fluorescent emitters using CN-modified indolocarbazole as an acceptor and carbazole-derived donors", Journal of Materials Chemistry C, vol. 6, pp. 5012-5017, 2018.

Vilas Venunath Patil et al., "Dibenzo[c,g]indolo[3,2,1-jk]carbazole as a new chromophore for blue organic light-emitting diodes", *Journal of Materials Chemistry C*, vol. 7, pp. 14301-14305. 2019.

Paul Kautny et al., "Indolo[3,2,1-jk]carbazole based planarized CBP derivatives as host materials for PhOLEDs with low efficiency roll-off", *Organic Electronics*, vol. 34, pp. 237-245, 2016.

Office Action in Korean Patent Application No. 10-2019-7023511, dated Aug. 15, 2022, with English Translation.

* cited by examiner

ORGANIC ELECTROLUMINESCENCE ELEMENT AND ELECTRONIC DEVICE

TECHNICAL FIELD

The present invention relates to organic electroluminescence devices and electronic devices.

BACKGROUND ART

An organic electroluminescence device (hereinafter "electroluminescence" may be simply referred to as "EL") generally comprises an anode, a cathode, and one or more organic thin film layers sandwiched between the anode and the cathode. When a voltage is applied between the electrodes, electrons from the cathode and holes from the anode are injected into a light emitting region. The injected electrons recombine with the injected holes in the light emitting region to form excited state. When the excited state returns to the ground state, the energy is released as light.

Many researches have been made on the applications of organic EL device to display, etc. because of its possibility of wide selection of emission colors by using various emitting materials in a light emitting layer. Particularly, the research on the emitting materials which emit three primary red, green, and blue colors has been made actively, and the intensive research has been made to improve their properties.

The material for organic EL devices has been proposed, for example, in Patent Literatures 1 to 6.

Non-Patent Literature 1 relates to a dopant used in an organic EL device and discloses a substituted perylene having five rings as a blue dopant material.

CITATION LIST

Patent Literature

Patent Literature 1: JP 2014-73965A
Patent Literature 2: WO 2016/006925
Patent Literature 3: CN 104119347B
Patent Literature 4: WO 2011/128017
Patent Literature 5: KR 10-2015-0135125A
Patent Literature 6: WO 2013/077344

Non-Patent Literature

Non-Patent Literature

Non-Patent Literature 1: Mi et al., Applied Physics Letters Volume 75, Number 26

SUMMARY OF INVENTION

Technical Problem

Non-Patent Literature 1 teaches that the use of perylene as a dopant involves a problem of a large shift of chromaticity coordinates attributable to the packing of perylene molecules and reports that the detrimental effect of packing is removed by introducing a t-Bu group as a sterically hindered group.

A highly planar skeleton having a long π-conjugated system with alternating single and carbon-carbon double bonds, for example as in perylene, is rigid and the skeletal vibration of such a skeleton is weak. Therefore, since a high PLQY and a narrow half-width may be easily achieved, a highly planar skeleton has high potential abilities as a light emitting material.

However, there is a problem of easy packing because of its planarity that is characteristic of the π-conjugated system. One of the methods for solving the problem of packing is the introduction of a sterically hindered group into the main skeleton. However, since this method limits the position of introducing the substituent and the structure of the substituent to be introduced, the freedom of molecular design is largely narrowed. Therefore, it has been demanded to develop a skeleton that combines a rigid π-conjugated system and a low packing ability without introducing a substituent.

Thus, an object of the invention is to provide organic EL devices showing excellent performance and electronic devices comprising such organic EL devices.

Solution to Problem

As a result of extensive research for solving the above problems, the inventors have found that the problems are solved by an organic EL device having a fluorescent emitting layer that comprises a first compound represented by formula (P) mentioned below and a second compound described below which is not the same as the first compound.

The present invention includes the following aspects (1) to (4).

(1) In an aspect of the invention, provided is an organic electroluminescence device comprising a cathode, an anode, and an organic layer disposed between the cathode and the anode, wherein the organic layer comprises one or more layers that comprise a fluorescent emitting layer and the fluorescent emitting layer comprises a first compound represented by formula (P) and a second compound that is not the same as the first compound:

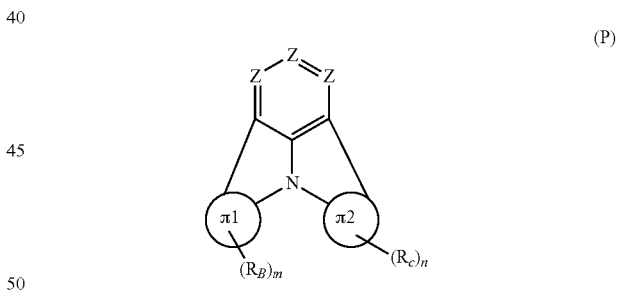

(P)

wherein:
Z is $CR_A$ or N;
π1 is a substituted or unsubstituted aromatic hydrocarbon ring having 6 to 50 ring carbon atoms or a substituted or unsubstituted aromatic heterocyclic ring having 5 to 50 ring atoms;
π2 is a substituted or unsubstituted aromatic hydrocarbon ring having 6 to 50 ring carbon atoms or a substituted or unsubstituted aromatic heterocyclic ring having 5 to 50 ring atoms;
$R_A$, $R_B$, and $R_C$ are each independently a hydrogen atom or a substituent, when $R_A$, $R_B$, or $R_C$ is the substituent, the substituent is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, or a substituted or unsubstituted heteroaryl group having 5 to 50 ring atoms;

$R_{101}$ to $R_{105}$ are each independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

each of n and m is an integer of 1 or more and 4 or less;

adjacent $R_A$'s are bonded to each other to form a ring structure or not bonded to each other thereby failing to form a ring;

adjacent $R_B$'s are bonded to each other to form a ring structure or not bonded to each other thereby failing to form a ring; and adjacent $R_C$'s are bonded to each other to form a ring structure or not bonded to each other thereby failing to form a ring.

(2) In another aspect of the invention, provided is the organic electroluminescence device of (1), wherein the first compound represented by formula (P) comprises a compound represented by formula (Q):

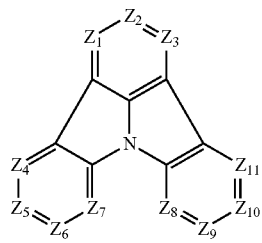

(Q)

wherein:

$Z_1$ is $CR_1$ or N; $Z_2$ is $CR_2$ or N; $Z_3$ is $CR_3$ or N; $Z_4$ is $CR_4$ or N; $Z_5$ is $CR_5$ or N; $Z_6$ is $CR_6$ or N; $Z_7$ is $CR_7$ or N; $Z_8$ is $CR_8$ or N; $Z_9$ is $CR_9$ or N; $Z_{10}$ is $CR_{10}$ or N; and $Z_{11}$ is $CR_{11}$ or N;

$R_1$ to $R_{11}$ are each independently a hydrogen atom or a substituent, when any of $R_1$ to $R_{11}$ is the substituent, the substituent is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, or a substituted or unsubstituted heteroaryl group having 5 to 50 ring atoms;

$R_{101}$ to $R_{105}$ are each independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

adjacent two selected from $R_1$ to $R_3$ are bonded to each other to form a ring structure or not bonded to each other thereby failing to form a ring;

adjacent two selected from $R_4$ to $R_7$ are bonded to each other to form a ring structure or not bonded to each other thereby failing to form a ring; and adjacent two selected from $R_8$ to $R_{11}$ are bonded to each other to form a ring structure or not bonded to each other thereby failing to form a ring.

(3) In another aspect of the invention, provided is the organic electroluminescence device of (1) or (2), wherein the first compound represented by formula (P) comprises a compound represented by formula (1):

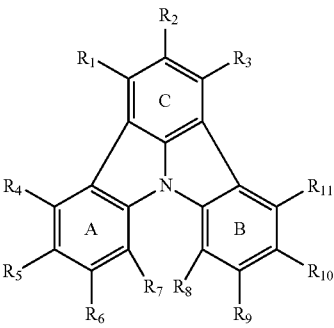

(1)

wherein:

in each pair selected from $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$, $R_n$ and $R_{n+1}$, wherein n is an integer selected from 1, 2, 4 to 6, and 8 to 10, are bonded to each other to form, together with two ring carbon atoms to which $R_n$ and $R_{n+1}$ are bonded, a ring structure having 3 or more atoms selected from the group consisting of carbon, oxygen, sulfur, nitrogen and combinations thereof, or $R_n$ and $R_{n+1}$ are not bonded to each other thereby failing to form a ring structure;

when a ring atom of the ring structure has a hydrogen atom or a substituent, the substituent is independently selected from a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, and a substituted or unsubstituted heteroaryl group having 5 to 50 ring atoms;

the substituents are optionally bonded to each other to form a further ring structure;

the number of ring atoms of the ring structure having 3 or more atoms does not include the atom in the substituent; and each of $R_1$ to $R_{11}$ not forming the ring structure having 3 or more atoms is a hydrogen atom or a substituent, wherein the substituent is the same as described above.

(4) In another aspect of the invention, provided is an electronic device comprising the organic electroluminescence device of (1).

Advantageous Effects of Invention

The organic EL device of the invention comprising the first compound and the second compound that is not the same as the first compound as the materials for organic EL device has an excellent performance. The organic EL device of the invention is useful as an electronic device.

DESCRIPTION OF EMBODIMENTS

Figure 1:
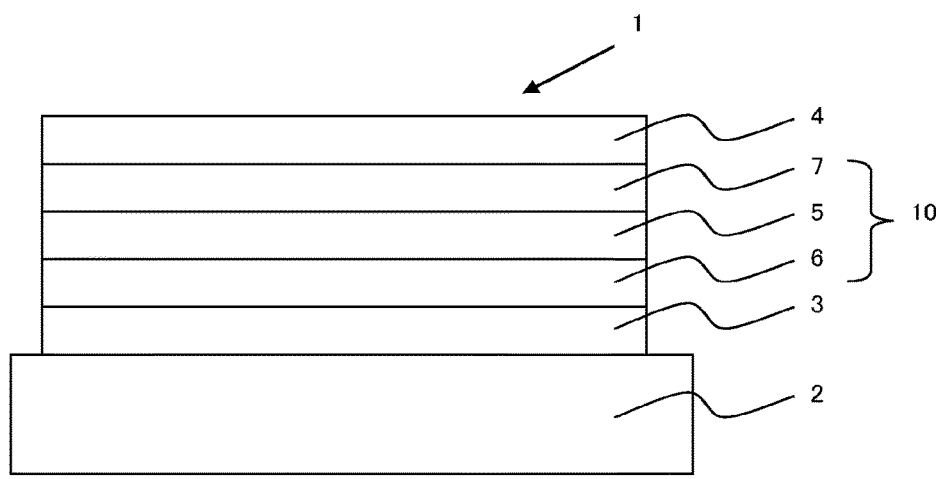
FIG. 1 is a schematic illustration showing an example of the structure of one embodiment of the organic electroluminescence device of the invention.

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The number of "ring carbon atoms" referred to herein means the number of the carbon atoms included in the atoms which are members forming the ring itself of a compound in which a series of atoms is bonded to form the ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring The definition of "hydrogen atom" used herein includes isotopes different in the neutron numbers, i.e., light hydrogen (protium), heavy hydrogen (deuterium), and tritium.

The terms of "heteroaryl group", "heteroarylene group", and "heterocyclic group" used herein means a group having at least one ring heteroatom, which is preferably at least one selected from a nitrogen atom, an oxygen atom, a sulfur atom, a silicon atom, and a selenium atom.

The term of "a substituted or unsubstituted carbazolyl group" referred to herein includes the following carbazolyl groups:

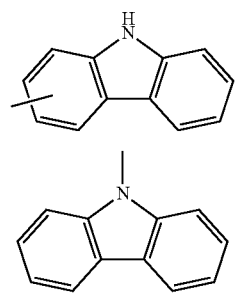

and a substituted carbazolyl group, wherein each of the above groups has an optional substituent.

The substituents of the substituted carbazolyl group may be bonded to each other to form a fused ring structure, the substituted carbazolyl group may include a heteroatom, such as a nitrogen atom, an oxygen atom, a silicon atom, and selenium atom, and the bonding site of the carbazolyl group may be any of 1- to 9-positions. Examples of such substituted carbazolyl groups are shown below.

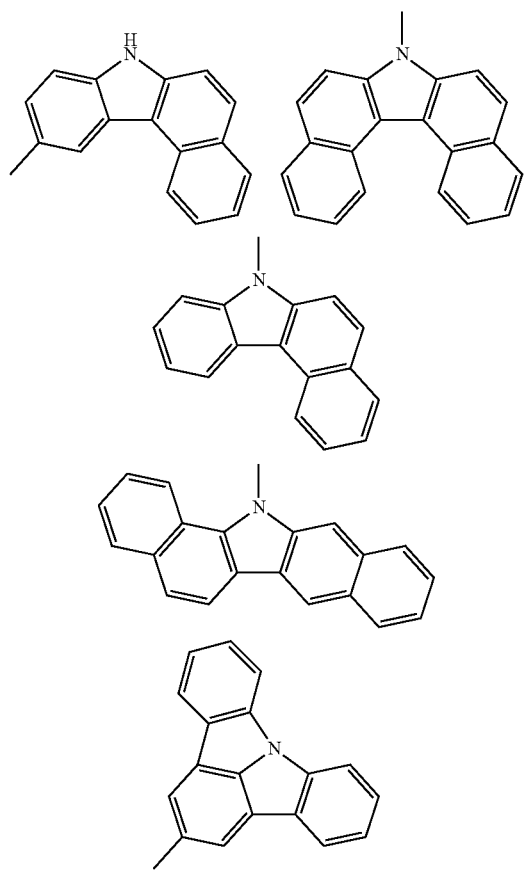

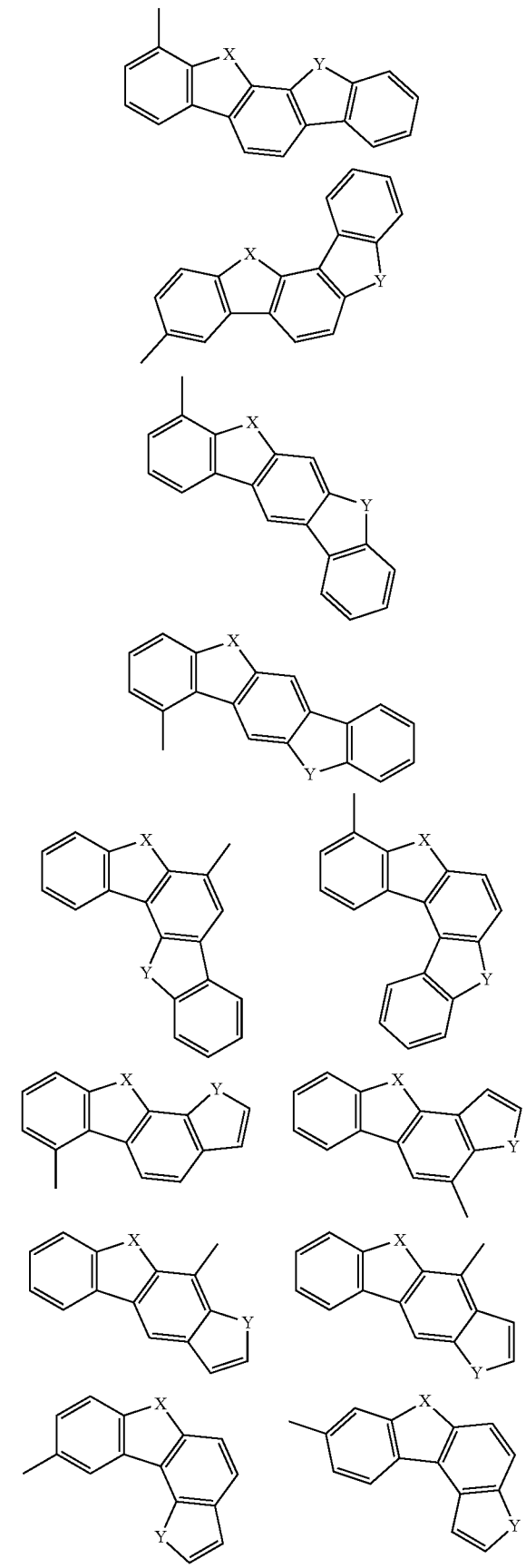

The terms of "a substituted or unsubstituted dibenzofuranyl group" and "a substituted or unsubstituted dibenzothiophenyl group" referred to herein include the following dibenzofuranyl group and the following dibenzothiophenyl group:

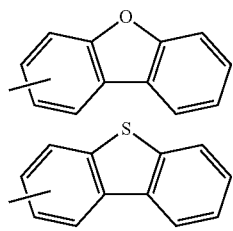

and a substituted dibenzofuranyl group and a substituted dibenzothiophenyl group, wherein each of the above groups has an optional substituent.

The substituents of the substituted dibenzofuranyl group and the substituted dibenzothiophenyl group may be bonded to each other to form a fused ring structure, the substituted dibenzofuranyl group and the substituted dibenzothiophenyl group may include a heteroatom, such as a nitrogen atom, an oxygen atom, a silicon atom, and selenium atom, and the bonding cite of the dibenzofuranyl group and the dibenzothiophenyl group may be any of 1- to 8-positions. Examples of such substituted dibenzofuranyl groups and substituted dibenzothiophenyl groups are shown below:

-continued

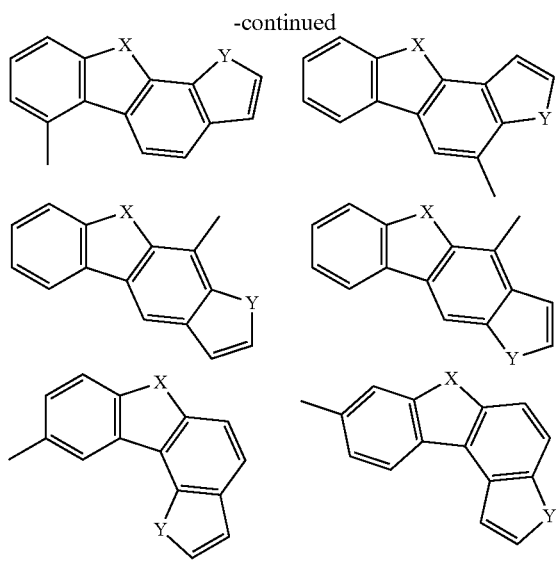

wherein X represents an oxygen atom or a sulfur atom and Y represents an oxygen atom, a sulfur atom, NH, NR$^a$ wherein R$^a$ represents an alkyl group or an aryl group, CH$_2$, or CR$^b_2$ wherein R$^b$ represents an alkyl group or an aryl group.

The substituent referred to by "a substituent" or "a substituted or unsubstituted" used herein is preferably, unless otherwise noted, at least one selected from the group consisting of an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; an aralkyl group having 7 to 51, preferably 7 to 30, more preferably 7 to 20 carbon atoms which includes an aryl group having 6 to 50, preferably 6 to 25, more preferably 6 to 18 ring carbon atoms; an amino group; a mono- or di-substituted amino group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a haloalkyl group having 1 to 50, preferably 1 to 18, more preferably 1 to 8 carbon atoms; a halogen atom selected from a fluorine atom, a chlorine atom, a bromine atom and an iodine atom; a cyano group; a nitro group; a substituted sulfonyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a di-substituted phosphoryl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth)acryloyl group; an epoxy group; and an oxetanyl group, although not particularly limited thereto.

These substituents may be further substituted with the substituent mentioned above. The substituents may be bonded to each other to form a ring.

The term "unsubstituted" referred to by "a substituted or unsubstituted" means that a hydrogen atom is not substituted by the substituent mentioned above.

Of the above substituents, preferred are an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; a mono- or di-substituted amino group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a halogen atom; and a cyano group.

Examples of the alkyl group having 1 to 50 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups). Preferred are a methyl group, an ethyl group, a n-propyl group, an isopropyl group, a n-butyl group, an isobutyl group, a s-butyl group, a t-butyl group, and a pentyl group (inclusive of isomeric groups), with a methyl group, an ethyl group, a n-propyl group, an isopropyl group, a n-butyl group, an isobutyl group, a s-butyl group, and a t-butyl group being more preferred, and a methyl group, an ethyl group, an isopropyl group, and a t-butyl group being particularly preferred.

Examples of the cycloalkyl group having 3 to 50 ring carbon atoms include a cyclopropyl group, a cyclobutyl group, a cyclopentyl group, a cyclohexyl group, a cycloheptyl group, a cyclooctyl group, and an adamantyl group, with a cyclopentyl group and a cyclohexyl group being preferred.

Examples of the aryl group having 6 to 50 ring carbon atoms include a phenyl group, a biphenylyl group, a terphenylyl group, a naphthyl group, an acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, a s-indacenyl group, an as-indacenyl group, a fluoranthenyl group, a benzo[k]fluoranthenyl group, a triphenylenyl group, a benzo[b]triphenylenyl group, and a perylenyl group, with a phenyl group, a biphenylyl group, a terphenylyl group, a naphthyl group, an anthryl group, a pyrenyl group, and a fluoranthenyl group being preferred, and a phenyl group, a biphenylyl group, and a terphenylyl group being more preferred, and a phenyl group being still more preferred.

In the aralkyl group having 7 to 51 carbon atoms which includes an aryl group having 6 to 50, the aryl portion is selected from the examples of the above aryl group having 6 to 50 ring carbon atoms and the alkyl portion is selected from the examples of the above alkyl group having 1 to 50 carbon atoms. Preferred examples thereof include those having an aryl portion selected from the preferred examples of the above aryl group having 6 to 50 ring carbon atoms and an alkyl portion selected from the preferred examples of the above alkyl group having 1 to 50 carbon atoms. The same applies to more preferred examples and still more preferred examples thereof.

In the mono- or di-substituted amino group, wherein the substituent is selected from an alkyl group having 1 to 50 and an aryl group having 6 to 50, the aryl substituent is selected from the examples of the above aryl group having 6 to 50 ring carbon atoms and the alkyl substituent is selected from the examples of the above alkyl group having 1 to 50 carbon atoms. Preferred examples thereof include those having an aryl substituent selected from the preferred examples of the above aryl group having 6 to 50 ring carbon atoms and an alkyl substituent selected from the preferred examples of the above alkyl group having 1 to 50 carbon atoms. The same applies to more preferred examples, still more preferred examples, and particularly preferred examples thereof.

In the alkoxy group having an alkyl group having 1 to 50 carbon atoms, the alkyl portion is selected from the examples of the above alkyl group having 1 to 50 carbon atoms. Preferred examples thereof include those having an alkyl portion selected from the preferred examples of the above alkyl group having 1 to 50 carbon atoms. The same applies to more preferred examples, still more preferred examples, and particularly preferred examples thereof.

In the aryloxy group having an aryl group having 6 to 50 ring carbon atoms, the aryl portion is selected from the examples of the above aryl group having 6 to 50 ring carbon atoms. Preferred examples thereof include those having an aryl portion selected from the preferred examples of the above aryl group having 6 to 50 ring carbon atoms. The same applies to more preferred examples and still more preferred examples thereof.

Examples of the mono-, di- or tri-substituted silyl group, wherein the substituent is selected from an alkyl group having 1 to 50 and an aryl group having 6 to 50, includes a monoalkylsilyl group, a dialkylsilyl group, a trialkylsilyl group, a monoarylsilyl group, a diarylsilyl group, a triarylsilyl group, a monoalkyldiarylsilyl group, and a dialkylmonoarylsilyl group, wherein the alkyl substituent is selected from the examples of the above alkyl group having 1 to 50 carbon atoms and the aryl substituent is selected from the examples of the above aryl group having 6 to 50 ring carbon atoms. Preferred examples thereof include a monoalkylsilyl group, a dialkylsilyl group, a trialkylsilyl group, a monoarylsilyl group, a diarylsilyl group, a triarylsilyl group, a monoalkyldiarylsilyl group, and a dialkylmonoarylsilyl group, wherein the alkyl substituent is selected from the preferred examples of the above alkyl group having 1 to 50 carbon atoms and the aryl substituent is selected from the preferred examples of the above aryl group having 6 to 50 ring carbon atoms. The same applies to more preferred examples, still more preferred examples, and particularly preferred examples thereof.

Examples of the heteroaryl group having 5 to 50 ring atoms include a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a 9-phenylcarbazolyl group, a phenanthridinyl group, an acridinyl group, a phenanthrolinyl group, a phenazinyl group, a phenothiazinyl group, a phenoxazinyl group, and a xanthenyl group. Preferred are a pyridyl group, an imidazopyridyl group, a pyridazinyl group, a pyrimidinyl group, a pyrazinyl group, a triazinyl group, a benzimidazolyl group, a dibenzofuranyl group, a dibenzothiophenyl group, a carbazolyl group, a 9-phenylcarbazolyl group, a phenanthrolinyl group, and a quinazolinyl group.

The halogen atom includes a fluorine atom, a chlorine atom, a bromine atom, and an iodine atom.

Examples of the haloalkyl group having 1 to 50 carbon atoms include the above alkyl group having 1 to 50 carbon atoms wherein a hydrogen atom is substituted by the above halogen atom. Preferred examples thereof include the above preferred alkyl group having 1 to 50 carbon atoms wherein a hydrogen atom is substituted by the above halogen atom. The same applies to more preferred examples, still more preferred examples, and particularly preferred examples thereof.

In each of the substituted sulfonyl group, wherein the substituent is selected from an alkyl group having 1 to 50 and an aryl group having 6 to 50; the di-substituted phosphoryl group, wherein the substituent is selected from an alkyl group having 1 to 50 and an aryl group having 6 to 50; the alkylsulfonyloxy group; the arylsulfonyloxy group; the alkylcarbonyloxy group; the arylcarbonyloxy group; and the alkyl-substituted or aryl-substituted carbonyl group; the aryl substituent is selected from the examples of the above aryl group having 6 to 50 ring carbon atoms and the alkyl substituent is selected from the examples of the above alkyl group having 1 to 50 carbon atoms. In each of the preferred examples thereof, the aryl substituent is selected from the preferred examples of the above aryl group having 6 to 50 ring carbon atoms and the alkyl substituent is selected from the preferred examples of the above alkyl group having 1 to 50 carbon atoms. The same applies to more preferred examples, still more preferred examples, and particularly preferred examples thereof.

A preferred embodiment, for example, for the compounds, the groups, and the numerical ranges described herein may be combined with any of other preferred embodiments, for example, for the compounds, the groups, and the numerical ranges. A combination of preferred embodiments (inclusive of more preferred embodiments, still more preferred embodiments, and particularly preferred embodiments) is a more preferred embodiment.

Organic EL Device

First Compound

The organic electroluminescence device in an aspect of the invention comprises a cathode, an anode, and an organic layer disposed between the cathode and the anode, wherein the organic layer comprises one or more layers that comprise a fluorescent emitting layer and the fluorescent emitting layer comprises a first compound represented by formula (P) and a second compound described below, which is not the same as the first compound:

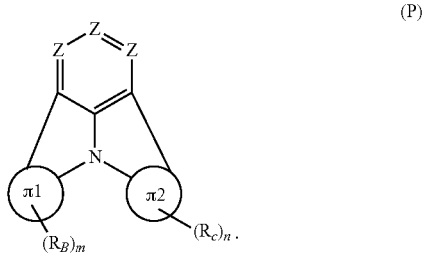
(P)

In formula (P):

$Z$ is $CR_A$ or $N$.

$\pi 1$ is a substituted or unsubstituted aromatic hydrocarbon ring having 6 to 50 ring carbon atoms or a substituted or unsubstituted aromatic heterocyclic ring having 5 to 50 ring atoms.

$\pi 2$ is a substituted or unsubstituted aromatic hydrocarbon ring having 6 to 50 ring carbon atoms or a substituted or unsubstituted aromatic heterocyclic ring having 5 to 50 ring atoms.

$R_A$, $R_B$, and $R_C$ are each independently a hydrogen atom or a substituent, when $R_A$, $R_B$, or $R_C$ is a substituent, the substituent is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having to 20 carbon atoms, a substituted or unsubstituted arylthio group having 6 to 50 ring carbon atoms, a group represented by $—Si(R_{101})(R_{102})(R_{103})$, a group represented by $—N(R_{104})(R_{105})$, a substituted or unsubstituted aryl group having 6 to 50 ring carbon atoms, or a substituted or unsubstituted heteroaryl group having 5 to 50 ring atoms.

$R_{101}$ to $R_{105}$ are each independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms.

$R_A$, $R_B$, and $R_C$ mentioned above are the same as $R_1$ to $R_{11}$ described below, and examples, preferred numbers of carbon atoms, preferred numbers of atoms, and preferred groups are also the same.

Each of n and m is an integer of 1 or more and 4 or less.

Adjacent $R_A$'s are bonded to each other to form a ring structure or not bonded to each other thereby failing to form a ring.

Adjacent $R_B$'s are bonded to each other to form a ring structure or not bonded to each other thereby failing to form a ring.

Adjacent $R_C$'s are bonded to each other to form a ring structure or not bonded to each other thereby failing to form a ring.

Each of $\pi 1$ is $\pi 2$ is an aromatic hydrocarbon ring having 6 to 50, preferably 6 to 24, and more preferably 6 to 18 ring carbon atoms or an aromatic heterocyclic ring having 5 to 50, preferably 5 to 24, more preferably 5 to 13 ring atoms.

Each $R_B$ is bonded to any one of the ring carbon atoms of the aromatic hydrocarbon ring $\pi 1$ or any one of the ring atoms of the aromatic heterocyclic ring $\pi 1$.

Each $R_C$ is bonded to any one of the ring carbon atoms of the aromatic hydrocarbon ring $\pi 2$ or any one of the ring atoms of the aromatic heterocyclic ring for $\pi 2$.

Examples of the aromatic hydrocarbon ring having 6 to 50 ring carbon atoms include a benzene ring, a naphthalene ring, an anthracene ring, a benzanthracene ring, a phenanthrene ring, a benzophenanthrene ring, a fluorene ring, a benzofluorene ring, a dibenzofluorene ring, a picene ring, a tetracene ring, a pentacene ring, a pyrene ring, a chrysene ring, a benzochrysene ring, a s-indacene ring, an as-indacene ring, a fluoranthene ring, a benzofluoranthene ring, a triphenylene ring, a benzotriphenylene ring, a perylene ring, a coronene ring, and a dibenzanthracene ring.

Examples of the aromatic heterocyclic ring having 5 to 50 ring atoms include a pyrrole ring, a pyrazole ring, an isoindole ring, a benzofuran ring, a benzothiophene ring, an isobenzofuran ring, a dibenzothiophene ring, an isoquinoline ring, a cinnoline ring, a quinoxaline ring, a phenanthridine ring, a phenanthroline ring, a pyridine ring, a pyrazine ring, a pyrimidine ring, a pyridazine ring, a triazine ring, an imidazopyridine ring, an indole ring, an indazole ring, a benzimidazole ring, a quinoline ring, an acridine ring, a pyrrolidine ring, a dioxane ring, a piperidine ring, a morpholine ring, a piperazine ring, a carbazole ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, a dibenzofuran ring, a benzo[c]dibenzofuran ring, a purine ring, and an acridine ring.

Preferably, the first compound of the invention represented by formula (P) includes the compound represented by formula (P-1):

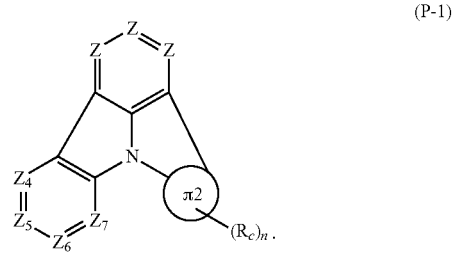
(P-1)

In formula (P-1):

$Z_4$ is $CR_4$ or $N$, $Z_5$ is $CR_5$ or $N$, $Z_6$ is $CR_6$ or $N$, and $Z_7$ is $CR_7$ or $N$.

$R_4$ to $R_7$ are each independently a hydrogen atom or a substituent. When any of $R_4$ to $R_7$ is the substituent, the substituent is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, or a substituted or unsubstituted heteroaryl group having 5 to 50 ring atoms.

$R_{101}$ to $R_{105}$ are each independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms.

Examples, preferred numbers of carbon atoms, preferred numbers of atoms, and preferred groups for $R_4$ to $R_7$ are described below.

Adjacent two selected from $R_4$ to $R_7$ are bonded to each other to form a ring structure or not bonded to each other thereby failing to form a ring.

Z, π2, $R_C$, and n are the same as those of formula (P).

Preferably, the first compound of the invention represented by formula (P) includes the compound represented by formula (P-2):

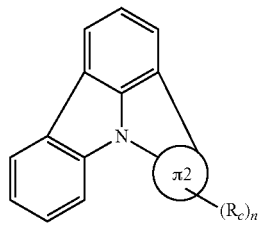

(P-2)

wherein π2, $R_C$, and n are the same as those of formula (P).

Preferably, the first compound of the invention represented by formula (P) includes the compound represented by formula (Q):

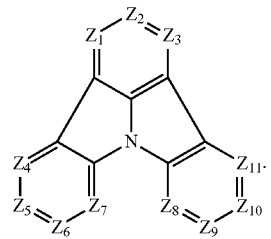

(Q)

In formula (Q):

$Z_1$ is $CR_1$ or N; $Z_2$ is $CR_2$ or N; $Z_3$ is $CR_3$ or N; $Z_4$ is $CR_4$ or N; $Z_5$ is $CR_5$ or N;

$Z_6$ is $CR_6$ or N; $Z_7$ is $CR_7$ or N; $Z_8$ is $CR_8$ or N; $Z_9$ is $CR_9$ or N; $Z_{10}$ is $CR_{10}$ or N; and $Z_{11}$ is $CR_{11}$ or N.

$R_1$ to $R_{11}$ are each independently a hydrogen atom or a substituent. When any of $R_1$ to $R_{11}$ is the substituent, the substituent is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, or a substituted or unsubstituted heteroaryl group having 5 to 50 ring atoms.

$R_{101}$ to $R_{105}$ are each independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms.

Examples, preferred numbers of carbon atoms, preferred numbers of atoms, and preferred groups for $R_1$ to $R_{11}$ are described below.

Adjacent two selected from $R_1$ to $R_3$ are bonded to each other to form a ring structure or not bonded to each other thereby failing to form a ring.

Adjacent two selected from $R_4$ to $R_7$ are bonded to each other to form a ring structure or not bonded to each other thereby failing to form a ring.

Adjacent two selected from $R_8$ to $R_{11}$ are bonded to each other to form a ring structure or not bonded to each other thereby failing to form a ring.

More preferably, the first compound of the invention represented by formula (P) includes the compound represented by formula (1):

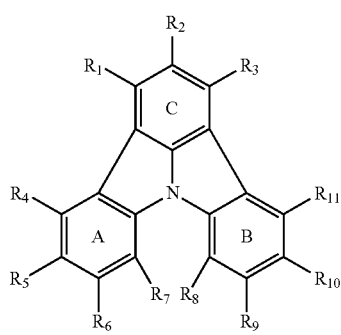

(1)

wherein:

in each pair selected from $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$, $R_n$ and $R_{n+1}$, wherein n is an integer selected from 1, 2, 4 to 6, and 8 to 10, are bonded to each other to form, together with two ring carbon atoms to which $R_n$ and $R_{n+1}$ are bonded, a ring structure having 3 or more atoms selected from the group consisting of carbon, oxygen, sulfur, nitrogen and combinations thereof, or $R_n$ and $R_{n+1}$ are not bonded to each other thereby failing to form a ring structure;

when a ring atom of the ring structure has a hydrogen atom or a substituent, the substituent is independently selected from a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, and a substituted or unsubstituted heteroaryl group having 5 to 50 ring atoms;

the substituents are optionally bonded to each other to form a further ring structure;

the number of ring atoms of the ring structure having 3 or more atoms does not include the atom in the substituent; and each of $R_1$ to $R_{11}$ not forming the ring structure having 3 or more atoms is a hydrogen atom or a substituent, wherein the substituent is the same as described above.

The ring structure having 3 or more atoms composed of a carbon atom, an oxygen atom, a sulfur atom, and a nitrogen atom, which is formed by $R_n$ and $R_{n+1}$ (wherein n is an integer selected from 1, 2, 4 to 6, and 8 to 10) bonded to each other together with two ring carbon atoms to which $R_n$ and $R_{n+1}$ are bonded is described below in more detail.

Each of $R_1$ to $R_{11}$ is a hydrogen atom or a substituent, or each of $R_1$ to $R_{11}$ may be one atom selected from a carbon atom, an oxygen atom, a sulfur atom, and a nitrogen atom, or a group of atoms wherein atoms selected from a carbon atom, an oxygen atom, a sulfur atom, and a nitrogen atom are bonded to each other.

When any of $R_1$ to $R_{11}$ is one atom selected from a carbon atom, an oxygen atom, a sulfur atom, and a nitrogen atom, or a group of atoms wherein atoms selected from a carbon atom, an oxygen atom, a sulfur atom, and a nitrogen atom are bonded to each other, in a pair selected from $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$, $R_n$ and $R_{n+1}$, wherein n is an integer selected from 1, 2, 4 to 6, and 8 to 10, are bonded to each other to form a ring structure together with two ring carbon atoms to which $R_n$ and $R_{n+1}$ are bonded, wherein the ring structure has 3 or more atoms selected from the group consisting of carbon, oxygen, sulfur, nitrogen and combinations thereof.

When $R_n$ and $R_{n+1}$, wherein n is an integer selected from 1, 2, 4 to 6, and 8 to 10, are bonded to each other, an atom in $R_n$ and an atom in $R_{n+1}$ are bonded to each other. If $R_n$ includes only one atom, "an atom in $R_n$" means said one atom. If $R_n$ is a group of atoms which are bonded to each other, "an atom in $R_n$" means a terminal atom or another atom. The same applies to "an atom in $R_{n+1}$."

The bond between $R_n$ and $R_{n+1}$ may be either a single bond, a double bond, or a bond with a bond order between 1 and 2. The same applies to the bond between atoms when each of $R_n$ and $R_{n+1}$ is a group of atoms which are bonded to each other.

In an embodiment of the invention, the first compound of formula (1) has preferably two ring structures, i.e., in two pairs selected from $R_1$ and $R_2$, $R_2$ and $R_3$, $R_4$ and $R_5$, $R_5$ and $R_6$, $R_6$ and $R_7$, $R_8$ and $R_9$, $R_9$ and $R_{10}$, and $R_{10}$ and $R_{11}$, $R_n$ and $R_{n+1}$, wherein n is an integer selected from 1, 2, 4 to 6, and 8 to 10, are bonded to each other to form a ring structure together with two ring carbon atoms to which $R_n$ and $R_{n+1}$ are bonded, wherein the ring structure has 3 or more atoms selected from the group consisting of carbon, oxygen, sulfur, nitrogen and combinations thereof. For example, in two or more pairs selected from $R_4$ and $R_5$, $R_5$ and $R_6$, $R_6$ and $R_7$, $R_8$ and $R_9$, $R_9$ and $R_{10}$, and $R_{10}$ and $R_{11}$, $R_n$ and $R_{n+1}$, wherein n is an integer selected from 4 to 6 and 8 to 10, are bonded to each other to form a ring structure together with two ring carbon atoms to which $R_n$ and $R_{n+1}$ are bonded, wherein the ring structure has 3 or more atoms composed of a carbon atom, an oxygen atom, a sulfur atom, and a nitrogen atom. In an embodiment of the invention, two pairs selected from $R_4$ and $R_5$, $R_5$ and $R_6$, $R_6$ and $R_7$, $R_8$ and $R_9$, $R_9$ and $R_{10}$, and $R_{10}$ and $R_{11}$ form the ring structures.

In an embodiment of the invention, the compound of formula (1) has preferably three ring structures. Particularly preferably, each of the benzene rings in the main skeleton of formula (1), i.e., each of the ring A, the ring B, and the ring C has one ring structure.

In an embodiment of the invention, the compound of formula (1) has preferably four or more ring structures.

In an embodiment of the invention, $R_1$ to $R_3$ of formula (1) is a hydrogen atom or a substituent, when any of $R_1$ to $R_3$ is the substituent, the substituent is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, or a substituted or unsubstituted heteroaryl group having 5 to 50 ring atoms.

In an embodiment of the invention, each two pairs selected from a pair of $R_1$ and $R_2$ and a pair of $R_2$ and $R_3$; a pair of $R_4$ and $R_5$ and a pair of $R_5$ and $R_6$; a pair of $R_5$ and $R_6$ and a pair of $R_6$ and $R_7$; a pair of $R_8$ and $R_9$ and a pair of $R_9$ and $R_{10}$; and a pair of $R_9$ and $R_{10}$ and a pair of $R_{10}$ and $R_{11}$ preferably do not form the ring structure at the same time.

In an embodiment of the invention, when two or more pairs form the ring structures, the two or more pairs are preferably selected such that two or three selected from the ring A, ring B, and ring C have the ring structures each having 3 or more atoms composed of a carbon atom, an oxygen atom, a sulfur atom, and a nitrogen atom. Two or more ring structures on two or more selected from the ring A, ring B, and ring C may be the same or different.

In formula (1), the halogen atom represented by $R_1$ to $R_{11}$ includes a fluorine atom, a chlorine atom, a bromine atom, and an iodine atom.

Examples of the alkyl group having 1 to 20, preferably 1 to 10, and more preferably 1 to 6 carbon atoms represented by $R_1$ to $R_{11}$ include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups). Preferred are a methyl group, an ethyl group, a n-propyl group, an isopropyl group, a n-butyl group, an isobutyl group, a s-butyl group, a t-butyl group, and a pentyl group (inclusive of isomeric groups), more preferred are a methyl group, an ethyl group, a n-propyl group, an isopropyl group, a n-butyl group, an isobutyl group, a s-butyl group, and a t-butyl group, and still more preferred are a methyl group, an ethyl group, an isopropyl group, and a t-butyl group.

Examples of the alkenyl group having 1 to 20, preferably 1 to 10, and more preferably 1 to 6 carbon atoms represented by $R_1$ to $R_{11}$ include a vinyl group, a 2-propenyl group, a 2-butenyl group, a 3-butenyl group, a 4-pentenyl group, a 2-methyl-2-propenyl group, a 2-methyl-2-butenyl group, and a 3-methyl-2-butenyl group.

Examples of the alkynyl group having 1 to 20, preferably 1 to 10, and more preferably 1 to 6 carbon atoms represented by $R_1$ to $R_{11}$ include a 2-propynyl group, a 2-butynyl group, a 3-butynyl group, a 4-pentynyl group, a 5-hexynyl group, a 1-methyl-2-propynyl group, a 1-methyl-2-butynyl group, and a 1,1-dimethyl-2-propynyl group.

Examples of the cycloalkyl group having 3 to 20, preferably 3 to 6, and more preferably 5 or 6 ring carbon atoms represented by $R_1$ to $R_{11}$ include a cyclopropyl group, a cyclobutyl group, a cyclopentyl group, a cyclohexyl group, a cycloheptyl group, a cyclooctyl group, and an adamantyl group, with a cyclopentyl group and a cyclohexyl group being preferred.

In the alkoxy group having 1 to 20, preferably 1 to 10, and more preferably 1 to 6 carbon atoms represented by $R_1$ to $R_{11}$, the alkyl portion is selected from the above alkyl group having 1 to 20 carbon atoms. Preferred examples thereof include those having an alkyl portion selected from the preferred examples of the above alkyl group having 1 to 50 carbon atoms. The same applies to more preferred examples and still more preferred examples thereof.

Examples of the fluoroalkyl group having 1 to 20, preferably 1 to 10, and more preferably 1 to 6 carbon atoms represented by $R_1$ to $R_{11}$ include the above alkyl group wherein a hydrogen atom is substituted by a fluorine atom. Preferred examples thereof include the above preferred alkyl group wherein a hydrogen atom is substituted by a fluorine atom. The same applies to more preferred examples and still more preferred examples thereof.

Examples of the fluoroalkoxy group having 1 to 20, preferably 1 to 10, and more preferably 1 to 6 carbon atoms represented by $R_1$ to $R_{11}$ include the above alkoxy group wherein a hydrogen atom is substituted by a fluorine atom. Preferred examples thereof include the above preferred alkoxy group wherein a hydrogen atom is substituted by a fluorine atom. The same applies to more preferred examples and still more preferred examples thereof.

In the aryloxy group having 6 to 50, preferably 6 to 30, more preferably 6 to 24, and still more preferably 6 to 18 ring carbon atoms represented by $R_1$ to $R_{11}$, the aryl portion is selected from the aryl group having 6 to 50 ring carbon atoms for $R_1$ to $R_{11}$ which is described below. Preferred examples thereof include those having an aryl portion selected from the preferred examples of the aryl group having 6 to 50 ring carbon atoms which is described below. The same applies to more preferred examples and still more preferred examples thereof.

In the alkylthio group having 1 to 20, preferably 1 to 10, and more preferably 1 to 6 carbon atoms represented by $R_1$ to $R_{11}$, the alkyl portion is selected from the above alkyl group having 1 to 20 carbon atoms. Preferred examples thereof include those having an alkyl portion selected from the preferred examples of the above alkyl group. The same applies to more preferred examples and still more preferred examples thereof.

In the arylthio group having 6 to 50, preferably 6 to 30, more preferably 6 to 24, and still more preferably 6 to 18 ring carbon atoms represented by $R_1$ to $R_{11}$, the aryl portion is selected from the aryl group having 6 to 50 ring carbon atoms for $R_1$ to $R_{11}$ which is described below. Preferred examples thereof include those having an aryl portion selected from the preferred examples of the aryl group having 6 to 50 ring carbon atoms which is described below. The same applies to more preferred examples and still more preferred examples thereof.

Examples of the group represented by —Si($R_{101}$)($R_{102}$)($R_{103}$) represented by $R_1$ to $R_{11}$ include a monoalkylsilyl group, a dialkylsilyl group, a trialkylsilyl group, a monoarylsilyl group, a diarylsilyl group, a triarylsilyl group, a monoalkyldiarylsilyl group, and a dialkylmonoarylsilyl group.

The alkyl portion of the above substituted silyl groups has preferably 1 to 20, more preferably 1 to 10, and still more preferably 1 to 6 carbon atoms. The aryl portion has preferably 6 to 50, more preferably 6 to 30, still more preferably 6 to 24, and particularly preferably 6 to 18 ring carbon atoms.

Preferred are a trialkylsilyl group and a triarylsilyl group and more preferred are a trimethylsilyl group, a triethylsilyl group, a triisopropylsilyl group, a t-butyldimethylsilyl group, a triphenylsilyl group, and a tritolylsilyl group.

Examples of the group represented by —N($R_{104}$)($R_{105}$) for $R_1$ to $R_{11}$ include a monoalkylamino group, a dialkylamino group, a monoarylamino group, a diarylamino group, a monoheteroarylamino group, a diheteroarylamino group, a monoalkylmonoarylamino group, a monoalkylmonoheteroarylamino group, and a monoarylmonoheteroarylamino group. The aryl portion of these substituted amino groups may have an alkyl substituent having 1 to 20, preferably 1 to 10, and more preferably 1 to 6 carbon atoms.

The alkyl portion of these substituted amino groups has preferably 1 to 20, more preferably 1 to 10, and still more preferably 1 to 6 carbon atoms. The aryl portion has preferably 6 to 50, more preferably 6 to 30, still more preferably 6 to 24, and particularly preferably 6 to 18 ring carbon atoms. The heteroaryl portion has preferably 5 to 50, more preferably 5 to 30, still more preferably 5 to 18, and particularly preferably 5 to 13 ring atoms.

Preferred are a dialkylamino group, a diarylamino group, a diheteroarylamino group, and a monoarylmonoheteroarylamino group and more preferred are a dimethylamino group, a diethylamino group, a diisopropylamino group, a diphenylamino group, a bis(alkyl-substituted phenyl)amino group, and a bis(aryl-substituted phenyl)amino group.

The alkyl portion is selected from the above alkyl group having 1 to 20 carbon atoms. The preferred alkyl portion is selected from the preferred examples of the above alkyl group having 1 to 20 carbon atoms. The same applies to more preferred examples and still more preferred examples thereof.

The aryl portion is selected from the examples of the aryl group having 6 to 50 ring carbon atoms which is described below. Preferred examples of the aryl portion are selected from the preferred examples of the aryl group having 6 to 50 ring carbon atoms which is described below. The same applies to more preferred examples and still more preferred examples thereof.

The heteroaryl portion is selected from the examples of the heteroaryl group having 5 to 50 ring atoms which is described below. Preferred examples of the heteroaryl portion are selected from the preferred examples of the heteroaryl group having 5 to 50 ring atoms which is described below. The same applies to more preferred examples and still more preferred examples thereof.

Two or more groups represented by —Si($R_{101}$)($R_{102}$)($R_{103}$) in formula (1), if any, may be the same or different. Two or more groups represented by —N($R_{104}$)($R_{105}$) in formula (1), if any, may be the same or different.

The aryl group having 6 to 50, preferably 6 to 30, more preferably 6 to 24, and still more preferably 6 to 18 ring carbon atoms for $R_1$ to $R_{11}$ may be a fused ring group or a non-fused ring group. Examples of the aryl group include a phenyl group, a biphenylyl group, a terphenylyl group, a naphthyl group, an acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, a s-indanyl group, an as-indanyl group, a fluoranthenyl group, a benzo[k]fluoranthenyl group, a triphenylenyl group, a benzo[b]triphenylenyl group, and a perylenyl group. Preferred are a phenyl group, a biphenylyl group, a terphenylyl group, a naphthyl group, an anthryl group, a pyrenyl group, and a fluoranthenyl group, more preferred are a phenyl group, a biphenylyl group, and a terphenylyl group, and still more preferred is a phenyl group.

The heteroaryl group having 5 to 50, preferably 5 to 30, more preferably 5 to 18, and particularly preferably 5 to 13 ring atoms for $R_1$ to $R_{11}$ comprises at least one, preferably 1 to 5, more preferably 1 to 4, and still more preferably 1 to 3 heteroatoms, which is selected from, for example, a nitrogen atom, a sulfur atom and an oxygen atom and preferably a nitrogen atom and an oxygen atom.

Examples of the heteroaryl group include a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a 9-phenylcarbazolyl group, a phenanthridinyl group, an acridinyl group, a phenanthrolinyl group, a phenazinyl group, a phenothiazinyl group, a phenoxazinyl group, and a xanthenyl group. Preferred are a pyridyl group, an imidazopyridyl group, a pyridazinyl group, a pyrimidinyl group, a pyrazinyl group, a triazinyl group, a benzimidazolyl group, a dibenzofuranyl group, a dibenzothiophenyl group, a carbazolyl group, a 9-phenylcarbazolyl group, a phenanthrolinyl group, and a quinazolinyl group.

Examples of the substituent of the ring structure having 3 or more atoms in formula (1) which is composed of a carbon atom, an oxygen atom, a sulfur atom, and a nitrogen atom together with two ring carbon atoms to which $R_n$ and $R_{n+1}$ are bonded, i.e., examples of the halogen atom, the cyano group, the substituted or unsubstituted alkyl group having 1 to 20 carbon atoms, the substituted or unsubstituted alkenyl group having 1 to 20 carbon atoms, the substituted or unsubstituted alkynyl group having 1 to 20 carbon atoms, the substituted or unsubstituted cycloalkyl group having 3 to 20 ring carbon atoms, the amino group, the substituted or unsubstituted alkoxy group having 1 to 20 carbon atoms, the substituted or unsubstituted fluoroalkyl group having 1 to 20 carbon atoms, the substituted or unsubstituted fluoroalkoxy group having 1 to 20 carbon atoms, the substituted or unsubstituted aryloxy group having 6 to 50 ring carbon atoms, the substituted or unsubstituted alkylthio group having 1 to 20 carbon atoms, the substituted or unsubstituted arylthio group having 6 to 50 ring carbon atoms, the group represented by —Si($R_{10}$)($R_{102}$)($R_{103}$), the group represented by —N($R_{104}$)($R_{105}$), the substituted or unsubstituted aryl group having 6 to 50 ring carbon atoms, and the substituted or unsubstituted heteroaryl group having 5 to 50 ring atoms are the same as the examples of the corresponding groups which are described above with respect to $R_1$ to $R_{11}$. The same applies to the preferred number of carbon atoms, the preferred number of atoms, and the preferred examples of the groups. The substituent is preferably a substituted or unsubstituted alkyl group having 1 to 20 carbon atoms or a substituted or unsubstituted aryl group having 6 to 50 ring carbon atoms.

The ring structure having 3 or more atoms in formula (1) selected from the group consisting of carbon, an oxygen, a sulfur, nitrogen and combinations thereof together with two ring carbon atoms to which $R_n$ and $R_{n+1}$ are bonded has preferably 3 to 7 atoms and particularly preferably 5 or 6 atoms, although not particularly limited thereto.

The ring structure having 3 or more atoms in formula (1) selected from the group consisting of carbon, oxygen, a sulfur, nitrogen and combinations thereof together with two ring carbon atoms to which $R_n$ and $R_{n+1}$ are bonded is preferably a ring selected from formulae (2) to (8), and also preferably a ring selected from formulae (9) to (11).

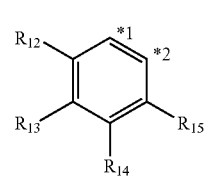

(2)

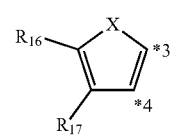

(3)

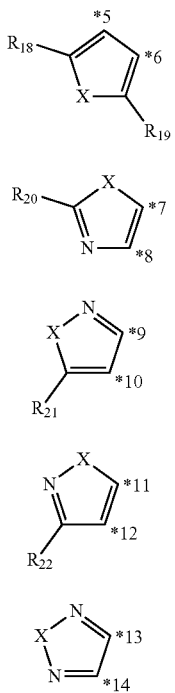

(4)

(5)

(6)

(7)

(8)

In formulae (2) to (8):

each pair selected from *1 and *2, *3 and *4, *5 and *6, *7 and *8, *9 and *10, *11 and *12, and *13 and *14 represents two ring carbon atoms to which $R_n$ and $R_n+_1$ are bonded;

$R_n$ may be bonded to either of two ring carbon atoms represented by *1 and *2, *3 and *4, *5 and *6, *7 and *8, *9 and *10, *11 and *12, or *13 and *14;

X is selected from $C(R_{23})(R_{24})$, $NR_{25}$, O, and S;

$R_{12}$ to $R_{25}$ are the same as $R_1$ to $R_{11}$ described above; and adjacent groups selected from $R_{12}$ to $R_{17}$ and $R_{23}$ to $R_{24}$ may be bonded to each other to form a ring structure.

Examples and preferred examples of $R_{12}$ to $R_{25}$ are the same as those described above with respect to $R_1$ to $R_{11}$ of formula (1).

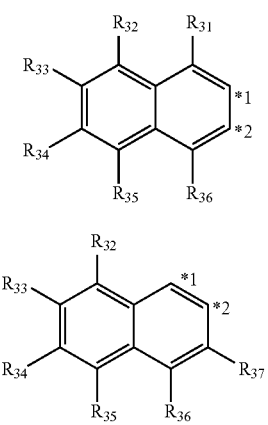

(9)

(10)

(11)

In formulae (9) to (11):

each pair selected from *1 and *2, and *3 and *4 represents two ring carbon atoms to which $R_n$ and $R_{n+1}$ are bonded;

$R_n$ may be bonded to either of two ring carbon atoms represented by *1 and *2, or *3 and *4;

$R_{31}$ to $R_{37}$ and $R_{41}$ to $R_{44}$ are the same as $R_{12}$ to $R_{25}$ described above;

X is the same as X described above; and adjacent groups selected from $R_{31}$ to $R_{37}$ and $R_{41}$ to $R_{44}$ may be bonded to each other to form a ring structure.

Examples and preferred examples of $R_{23}$ to $R_{25}$ in X, $R_{31}$ to $R_{37}$, and $R_{41}$ to $R_{44}$ are the same as those described above with respect to $R_1$ to $R_{11}$ of formula (1).

In formula (1), at least one selected from $R_2$, $R_4$, $R_5$, $R_{10}$, and $R_{11}$, preferably at least one selected from $R_2$, $R_5$, and $R_{10}$, and still more preferably $R_2$ preferably does not form the ring structure and is preferably a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group, having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$) wherein $R_{101}$ to $R_{103}$ are as defined above, a group represented by —N($R_{104}$)($R_{105}$) wherein $R_{104}$ and $R_{105}$ are as defined above, a substituted or unsubstituted aryl group having 6 to 50 ring carbon atoms, or a substituted or unsubstituted heteroaryl group having 5 to 50 ring atoms.

Examples, preferred numbers of carbon atoms, and preferred numbers of atoms of the above groups are the same as those described above with respect to $R_1$ to $R_{11}$.

Preferably, each of (i) the substituent of the ring structure having 3 or more atoms in formula (1) selected from the group consisting of carbon, an oxygen, sulfur, nitrogen and combinations thereof together with two ring carbon atoms to which $R_n$ and $R_{n+1}$ are bonded;

(ii) $R_1$ to $R_{11}$ in formula (1) not forming the ring structure; or (iii) $R_{12}$ to $R_{22}$, $R_{31}$ to $R_{37}$, and $R_{41}$ to $R_{44}$ in formulae (2) to (11) are each independently a hydrogen atom, a substituted or unsubstituted alkyl group having 1 to 20 carbon atoms, a group represented by —N($R_{104}$)($R_{105}$), a substituted or unsubstituted aryl group having 6 to 50 ring carbon atoms, a substituted or unsubstituted heteroaryl group having 5 to 50 ring atoms, or any of the following groups:

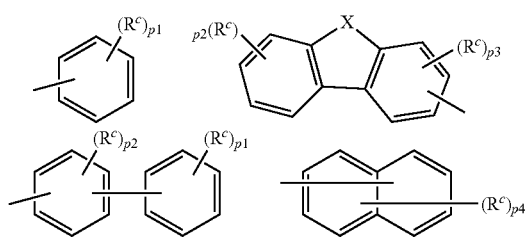

wherein:

each $R^c$ is independently the same as $R_1$ to $R_{11}$ described above;

X is as defined above; and p1 is an integer of 0 to 5, p2 is an integer of 0 to 4, p3 is an integer of 0 to 3, and p4 is an integer of 0 to 7.

Examples and preferred examples of $R_{23}$ to $R_{25}$ in X and $R^c$ are the same as those described above with respect to $R_1$ to $R_{11}$.

The compound of formula (1) is represented preferably by any of formulae (1-1) to (1-6), more preferably by any of formulae (1-1) to (1-3) and (1-5), and still more preferably by formula (1-1) or (1-5).

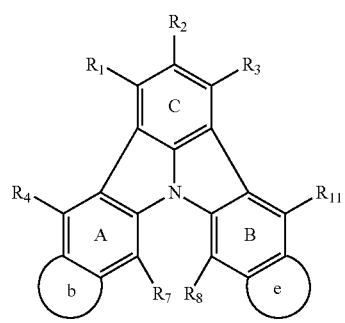

(1-1)

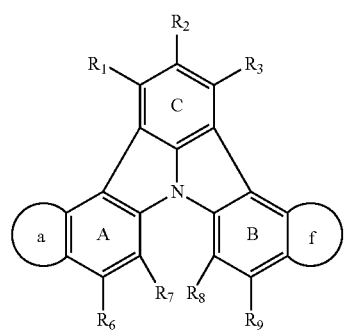

(1-2)

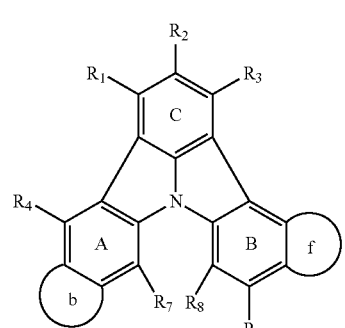

(1-3)

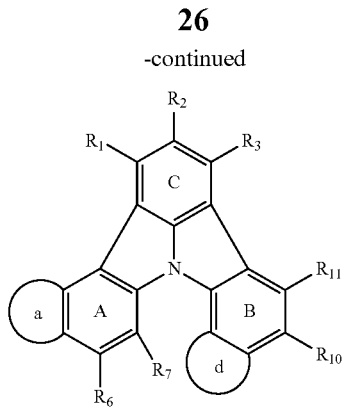

(1-4)

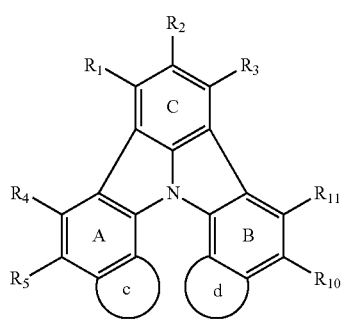

(1-5)

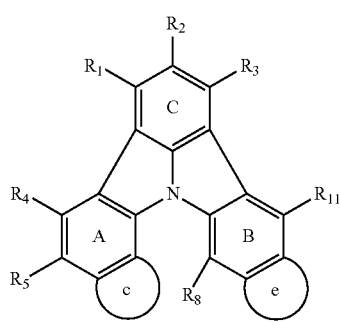

(1-6)

In formulae (1-1) to (1-6):

$R_1$ to $R_n$ are as defined above and examples, preferred number of carbon atoms, preferred number of atoms, and preferred examples thereof are as described above;

each of the rings a to f is independently the ring structure having 3 or more atoms composed of a carbon atom, an oxygen atom, a sulfur atom, and a nitrogen atom;

the ring structure may have a substituent and the substituents may be bonded to each other to form a ring structure;

the substituent is the same as defined with respect to the substituent represented by $R_1$ to $R_{11}$; and the number of atoms of the ring structure having 3 or more atoms does not include the atom in the substituent.

In formulae (1-1) to (1-6), the ring structure having 3 or more atoms selected from the group consisting of carbon, an oxygen, a sulfur, nitrogen and combinations thereof which is represented by any of the rings a to f preferably has 3 to 7 atoms and particularly preferably has 5 or 6 atoms, although not particularly limited thereto. Each of the rings a to f is preferably a ring represented by any of formulae (2) to (8), or preferably a ring represented by any of formulae (9) to (11).

In formulae (1-1) to (1-6), examples, preferred number of carbon atoms, preferred number of atoms, and preferred examples of the substituent are the same as those of the corresponding groups described above with respect to $R_1$ to $R_{11}$.

The compound of formula (1) is preferably represented by any of formulae (2-1) to (2-6), more preferably represented by formula (2-2) or (2-5).

(2-1)
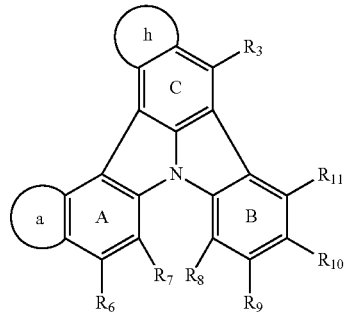

(2-2)
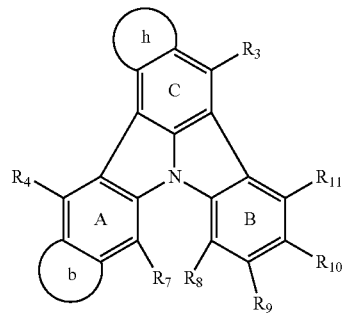

(2-3)
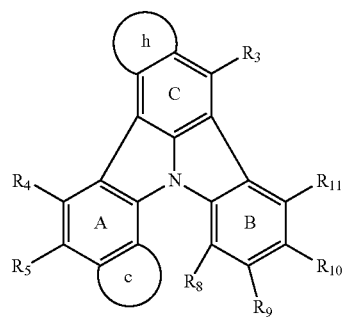

(2-4)
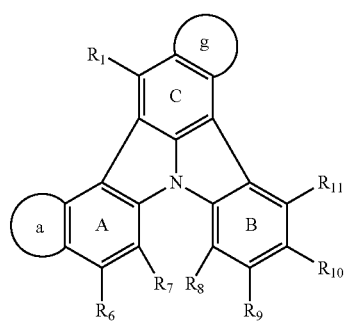

(2-5)
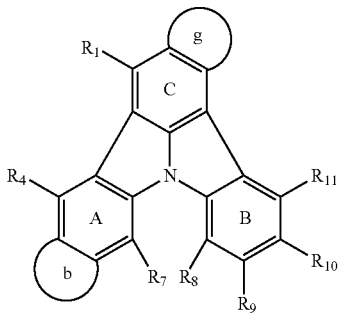

(2-6)
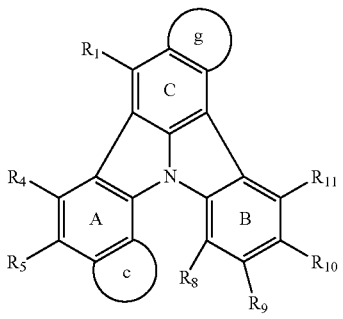

In formulae (2-1) to (2-6);

$R_1$ and $R_3$ to $R_{11}$ are as defined above and examples, preferred number of carbon atoms, preferred number of atoms, and preferred examples thereof are as described above;

each of the rings a to c and g to h is independently the ring structure having 3 or more atoms composed of a carbon atom, an oxygen atom, a sulfur atom, and a nitrogen atom;

the ring structure may have a substituent and the substituents may be bonded to each other to form a ring structure;

the substituent is the same as defined with respect to the substituent represented by $R_1$ to $R_{11}$; and the number of atoms of the ring structure having 3 or more atoms does not include the atom in the substituent.

In formulae (2-1) to (2-6), the ring structure having 3 or more atoms selected from the group consisting of carbon, oxygen, a sulfur, nitrogen and combinations thereof which is represented by any of the rings a to c and g to h preferably has 3 to 7 atoms and particularly preferably has 5 or 6 atoms, although not particularly limited thereto. Each of the rings a to c and g to h is preferably a ring represented by any of formulae (2) to (8), and also preferably a ring represented by any of formulae (9) to (11).

In formulae (2-1) to (2-6), examples, preferred number of carbon atoms, preferred number of atoms, and preferred examples of the optional substituent are the same as those of the corresponding groups described above with respect to $R_1$ to $R_{11}$.

The compound of formula (1) is preferably represented by any of formulae (3-1) to (3-9) and more preferably represented by formula (3-1).

(3-1)
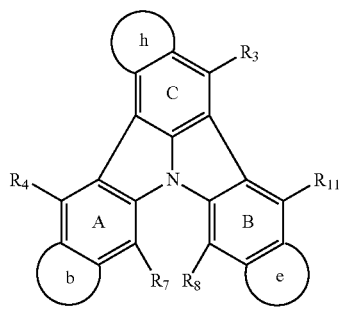

(3-2)
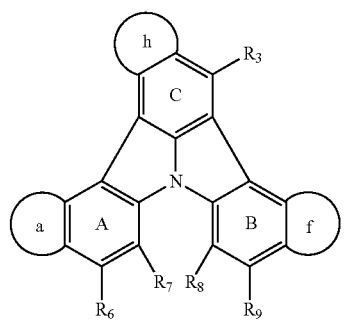

(3-3)
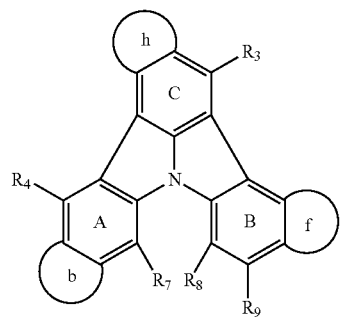

(3-4)
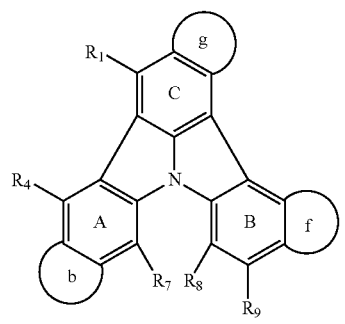

(3-5)
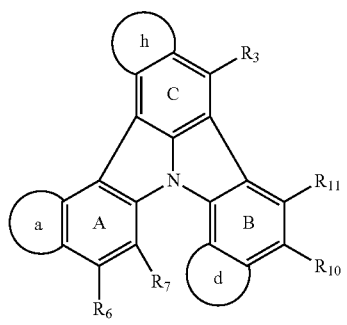

(3-6)
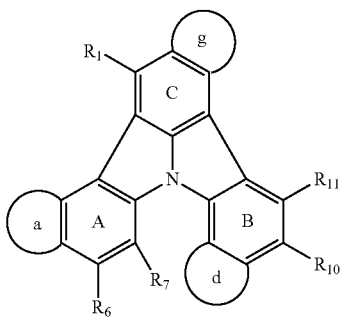

(3-7)
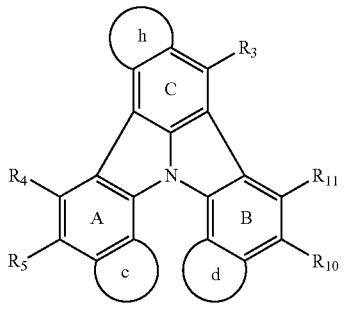

(3-8)
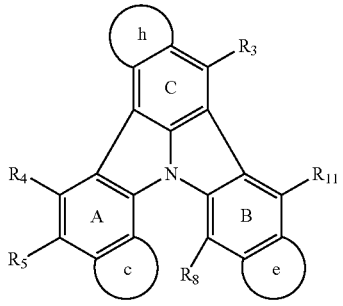

(3-9)
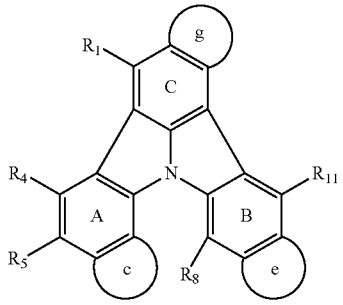

In formulae (3-1) to (3-9):

$R_1$ and $R_3$ to $R_{11}$ are as defined above and examples, preferred number of carbon atoms, preferred number of atoms, and preferred examples thereof are as described above;

each of the rings a to h is independently the ring structure having 3 or more atoms selected from the group consisting of carbon, oxygen, a sulfur, nitrogen and combinations thereof;

the ring structure may have a substituent and the substituents may be bonded to each other to form a ring structure;

the substituent is the same as defined above with respect to the substituent represented by $R_1$ to $R_{11}$; and the number of atoms of the ring structure having 3 or more atoms does not include the atom in the substituent.

In formulae (3-1) to (3-9), the ring structure having 3 or more atoms selected from the group consisting of carbon, oxygen, sulfur, nitrogen and combinations thereof which is represented by any of the rings a to h preferably has 3 to 7 atoms and particularly preferably has 5 or 6 atoms, although not particularly limited thereto. Each of the rings a to h is preferably a ring represented by any of formulae (2) to (8), or preferably a ring represented by any of formulae (9) to (11).

In formulae (3-1) to (3-9), the ring structure having 3 or more atoms composed of a carbon atom, an oxygen atom, a sulfur atom, and a nitrogen atom which is represented by any of the rings a to h is preferably a ring structure having 3 or more atoms composed of a carbon atom, an oxygen atom, and a sulfur atom. The heteroatom of the heteroaryl group as the substituent of the ring g or h is preferably a sulfur and/or an oxygen atom.

In formulae (3-1) to (3-9), examples, preferred number of carbon atoms, preferred number of atoms, and preferred examples of the substituent are the same as those of the corresponding groups described above with respect to $R_1$ to $R_{11}$.

Preferably, in formulae (1-1) to (1-6), (2-1) to (2-6), and (3-1) to (3-9), the substituent for the rings a to h and $R_1$ to $R_{11}$ not forming the rings a to h are each independently a hydrogen atom, a substituted or unsubstituted alkyl group having 1 to 20 carbon atoms, a group represented by —N($R_{104}$)($R_{105}$), a substituted or unsubstituted aryl group having 6 to 50 ring carbon atoms, a substituted or unsubstituted heteroaryl group having 5 to 50 ring atoms, or any one of the following groups:

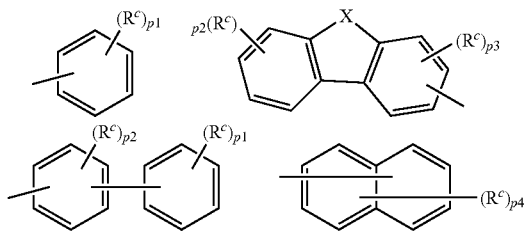

wherein:
each $R^c$ is independently the same as $R_1$ to $R_{11}$ described above;
X is as defined above; and
p1 is an integer of 0 to 5, p2 is an integer of 0 to 4, p3 is an integer of 0 to 3, and p4 is an integer of 0 to 7.

Examples and preferred examples of $R_{23}$ to $R_{25}$ in X and $R^c$ are the same as those described above with respect to $R_1$ to $R_{11}$.

The substituent of the rings g and h is preferably a substituted or unsubstituted alkyl group having 1 to 20 carbon atoms, a substituted or unsubstituted aryl group having 6 to 50 ring carbon atoms, or any of the following groups:

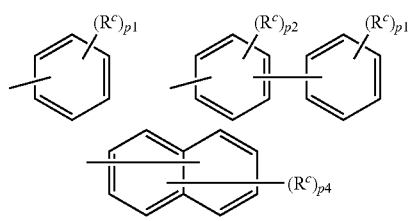

wherein:
$R^c$ is independently the same as $R_1$ to $R_{11}$ described above; and
p1 is an integer of 0 to 5, p2 is an integer of 0 to 4, and p4 is an integer of 0 to 7.

The compound of formula (1) is preferably represented by any of formulae (4-1) to (4-4):

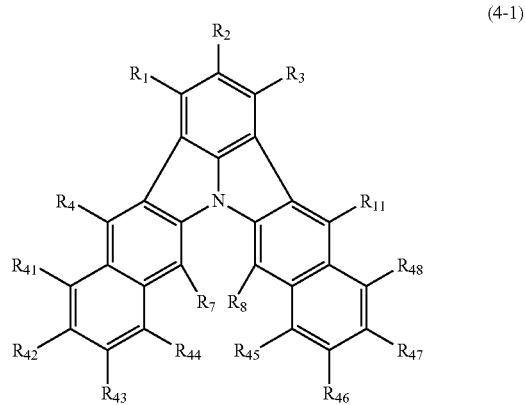

(4-1)

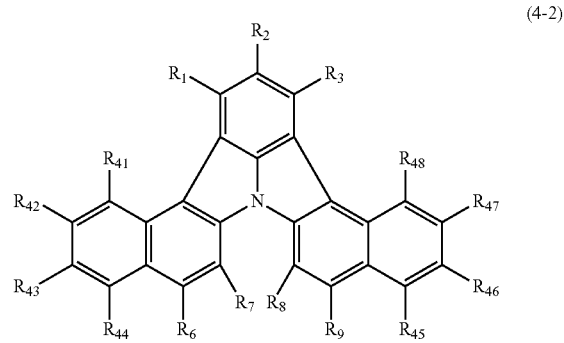

(4-2)

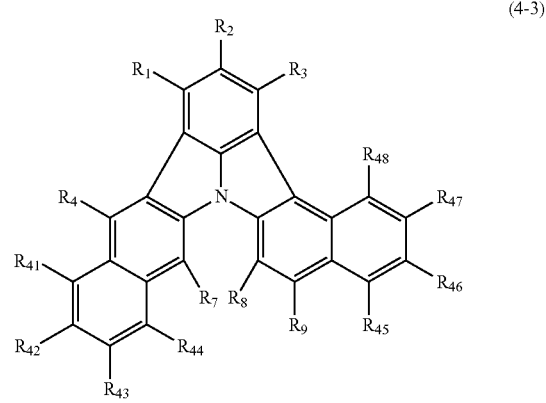

(4-3)

-continued

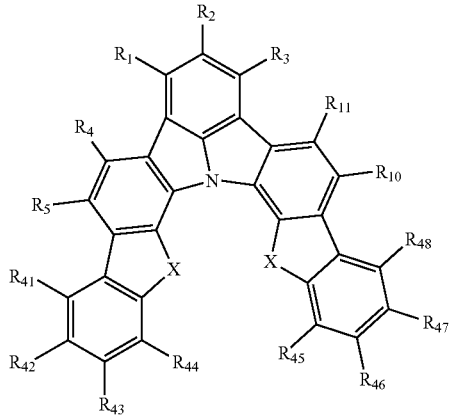

(4-4)

wherein:
X is selected from C(R$_{23}$)(R$_{24}$), NR$_{25}$, O, and S; and
R$_1$ to R$_5$, R$_7$ to R$_{11}$, R$_{41}$ to R$_{48}$, and R$_{23}$ to R$_{25}$ are the same as R$_1$ to R$_{11}$ described above.

Examples and preferred examples of R$_1$ to R$_5$, R$_7$ to R$_{11}$, R$_{41}$ to R$_{48}$, and R$_{23}$ to R$_{25}$ are the same as those described above with respect to R$_1$ to R$_{11}$.

The compound of formula (1) is preferably represented by formula (5-1):

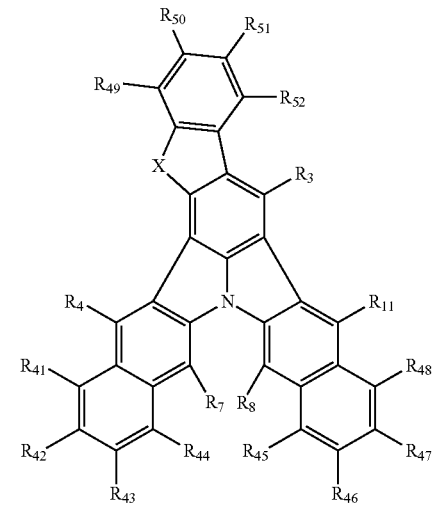

(5-1)

wherein:
X is selected from C(R$_{23}$)(R$_{24}$), NR$_{25}$, O, and S; and
R$_3$, R$_4$, R$_7$, R$_8$, R$_{11}$, R$_{41}$ to R$_{52}$, and R$_{23}$ to R$_{25}$ are the same as R$_1$ to R$_{11}$ described above.

Examples and preferred examples of R$_3$, R$_4$, R$_7$, R$_8$, R$_{11}$, R$_{41}$ to R$_{52}$, and R$_{23}$ to R$_{25}$ are the same as those described above with respect to R$_1$ to R$_{11}$. R$_{25}$ is preferably a substituted or unsubstituted aryl group having 6 to 50 ring carbon atoms.

Examples of the first compound usable in the invention are described below, although not particularly limited thereto.

In the following examples, Ph is a phenyl group and D is a heavy hydrogen atom.

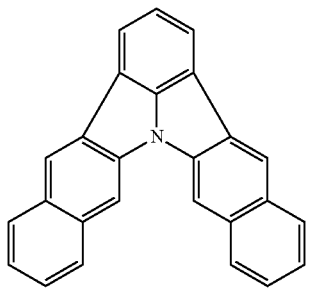

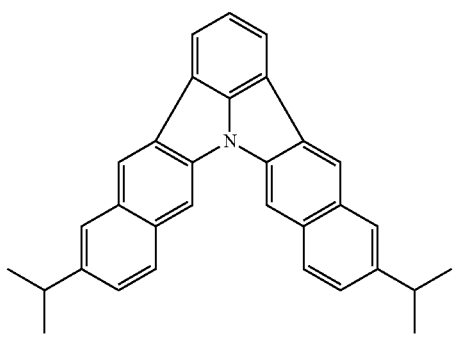

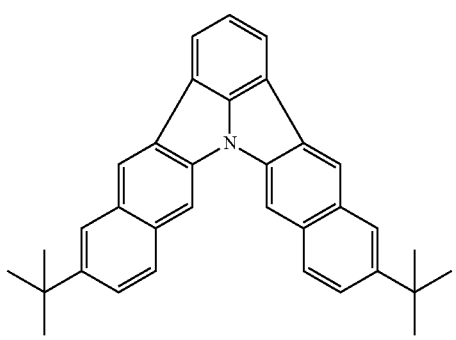

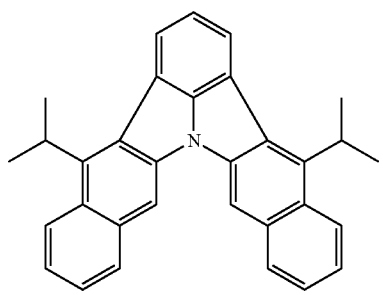

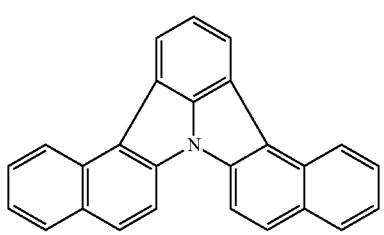

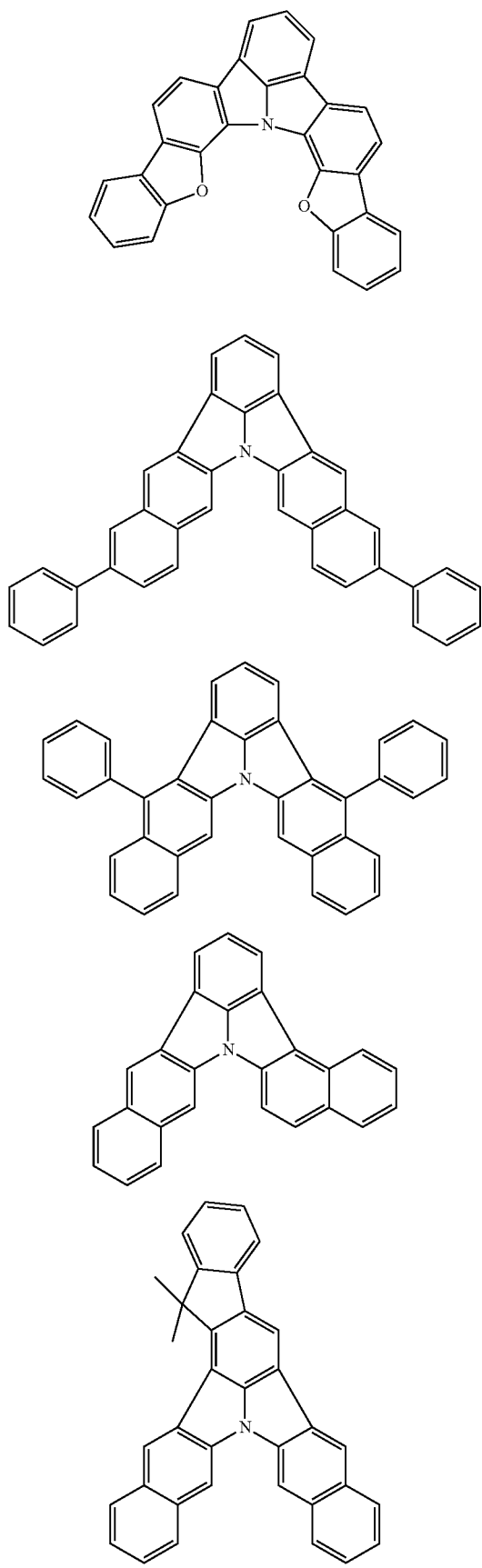
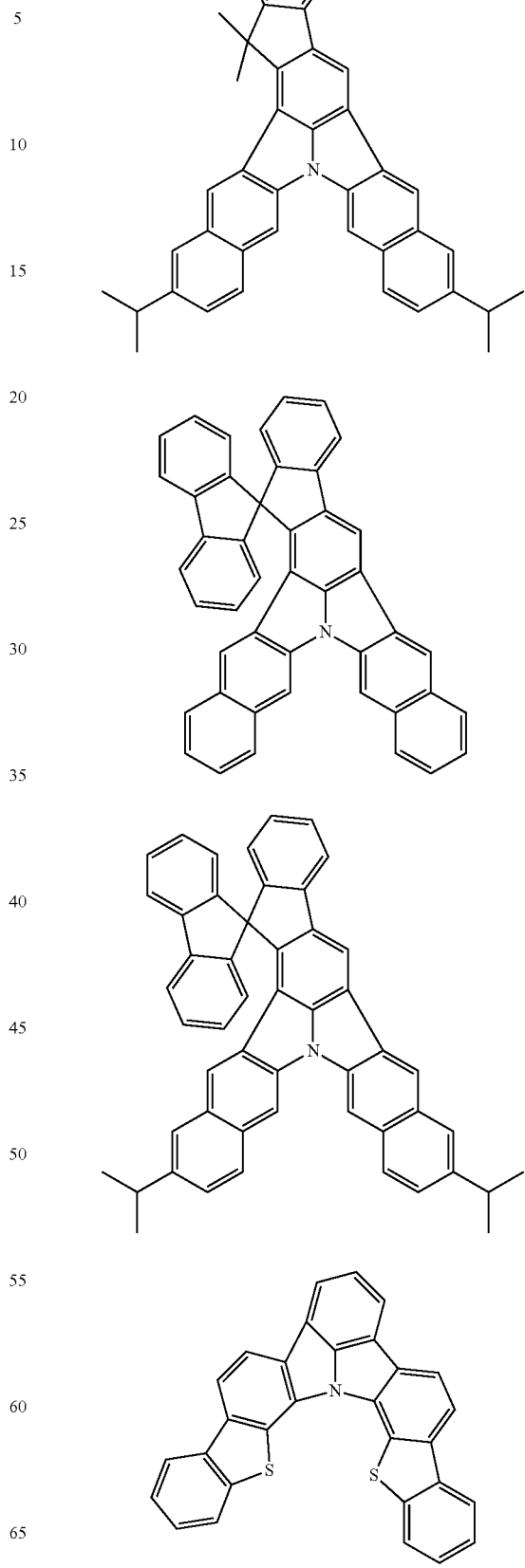

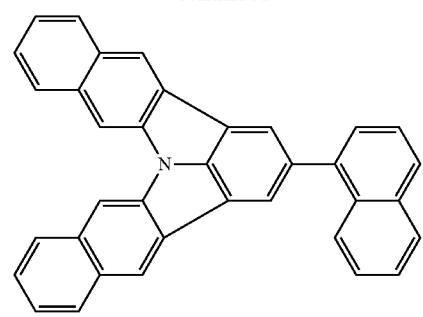
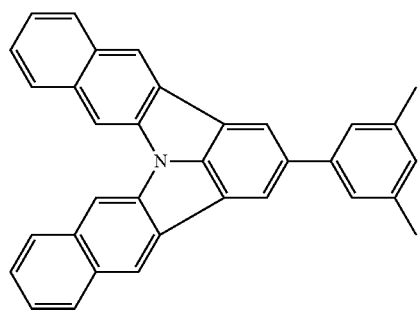
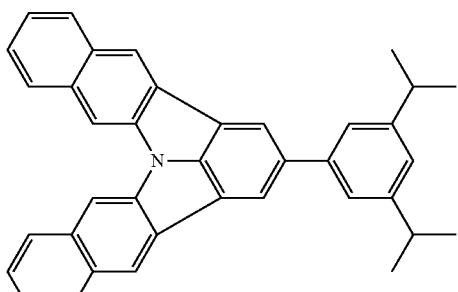
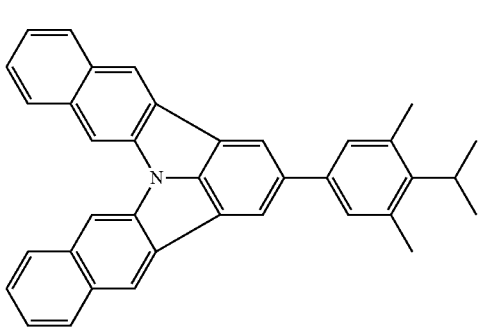
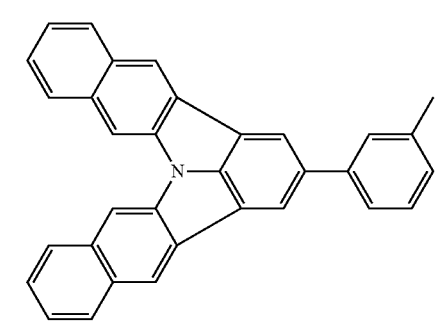
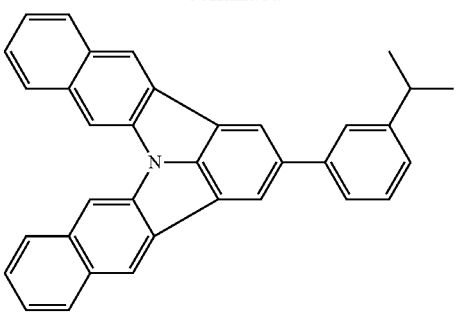
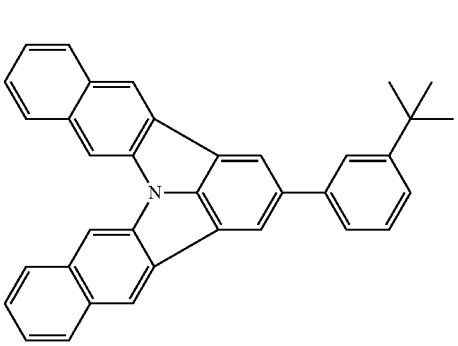
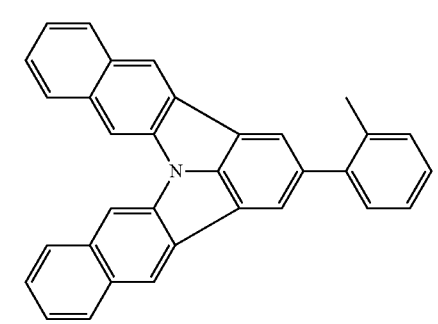
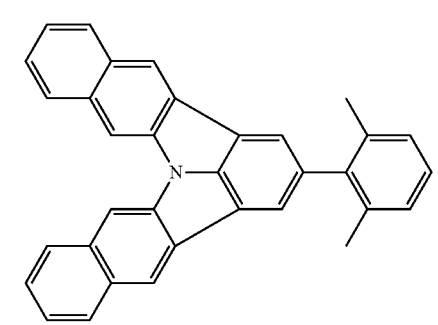
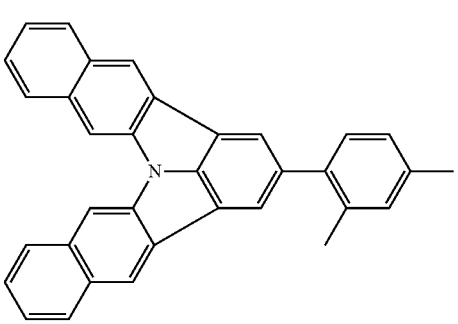

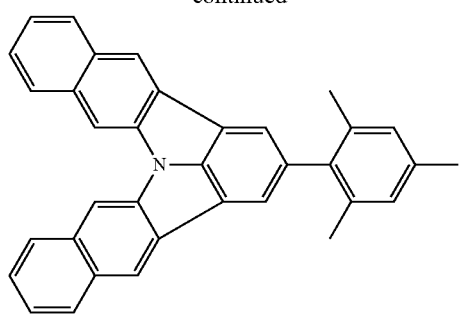
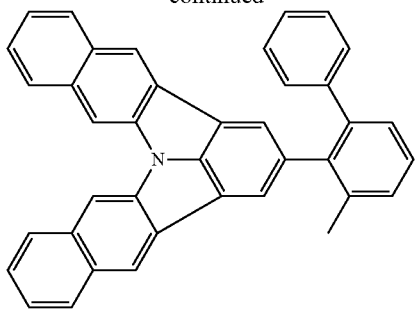
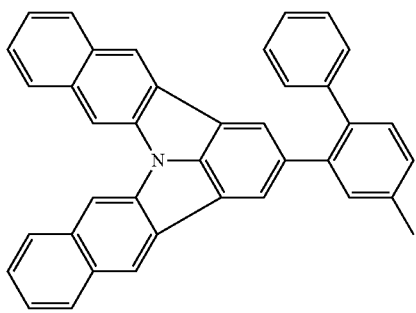
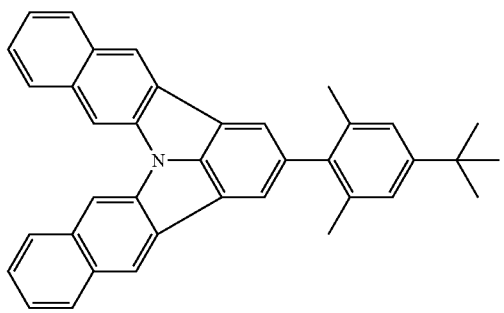
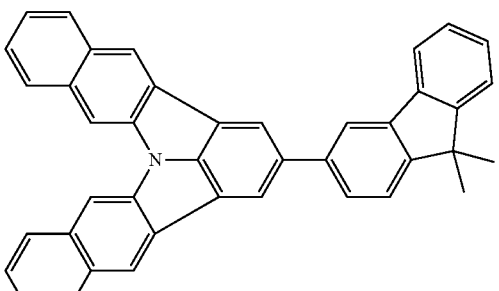
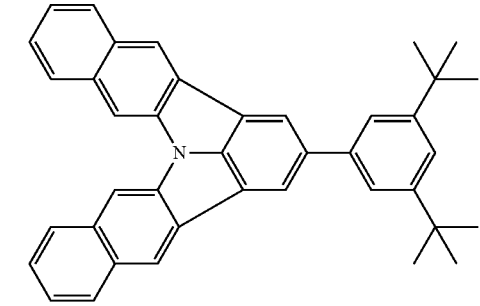
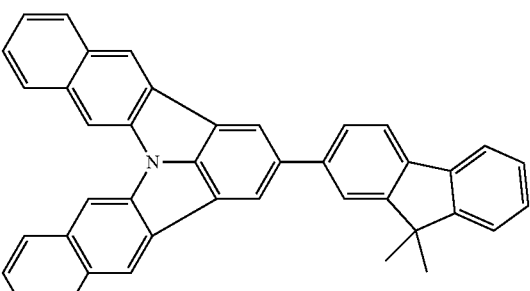
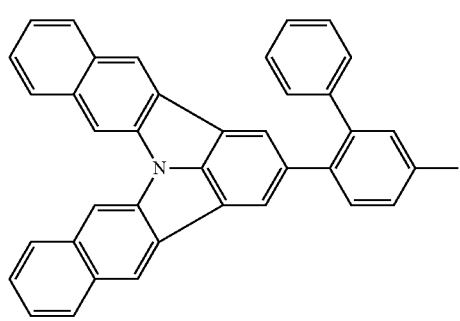
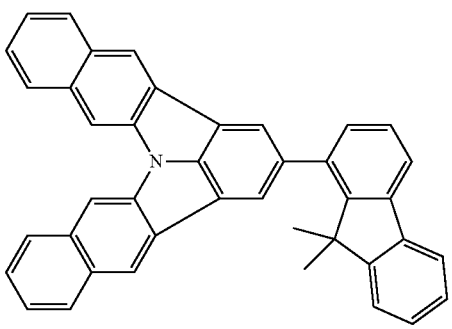

41
-continued
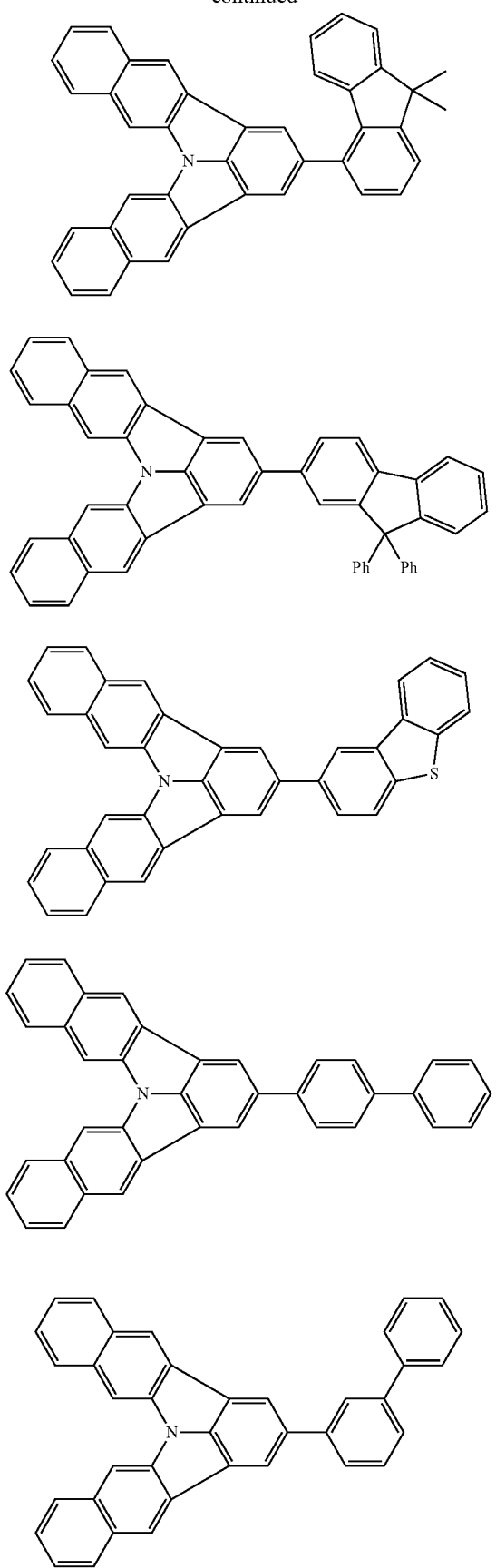
42
-continued
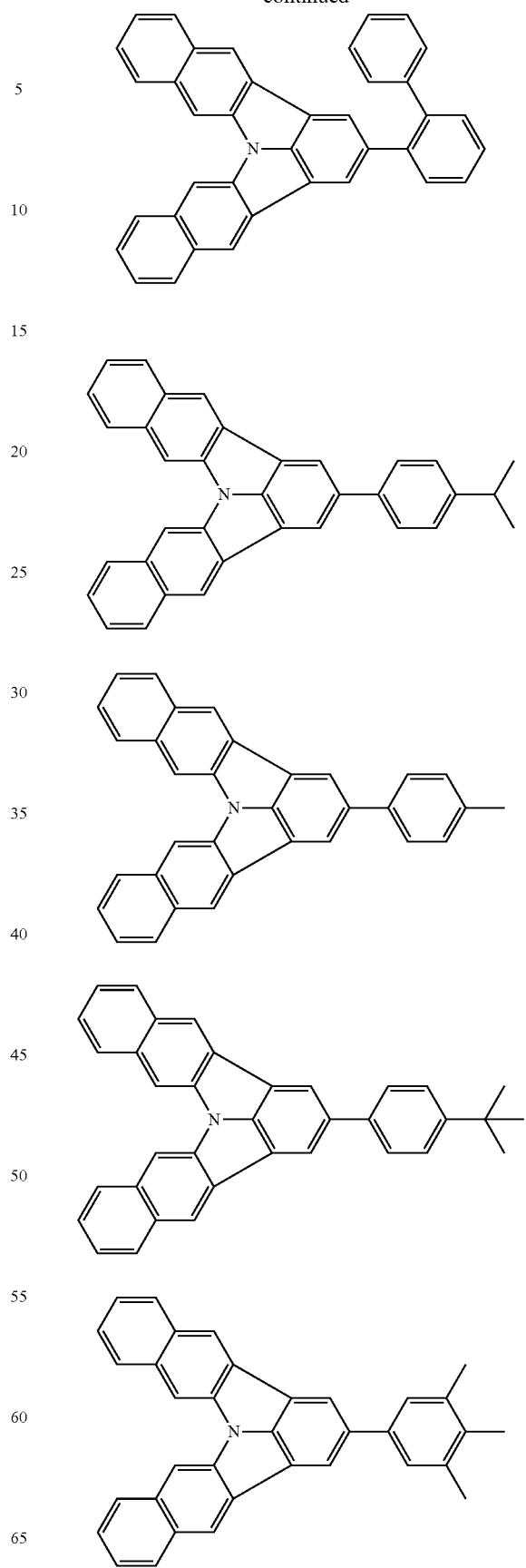

43
-continued
44
-continued
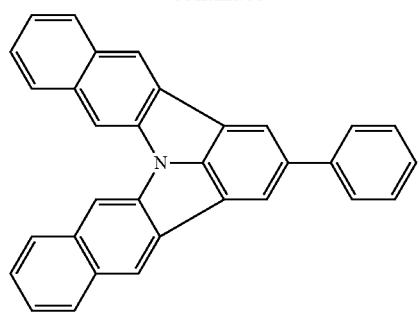
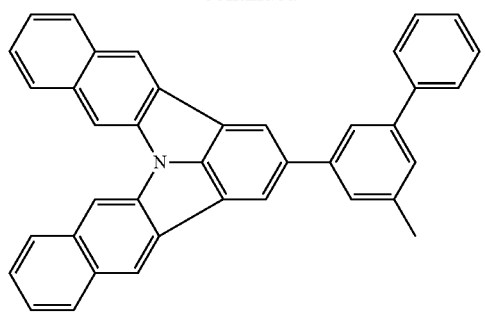
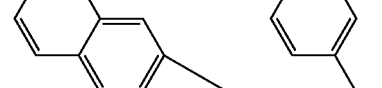

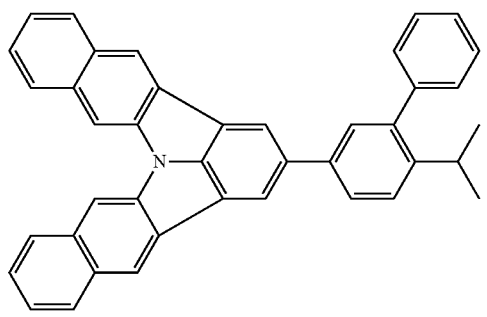
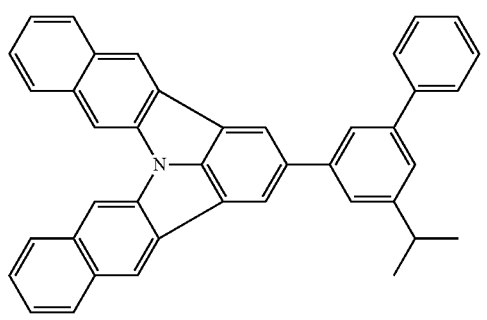
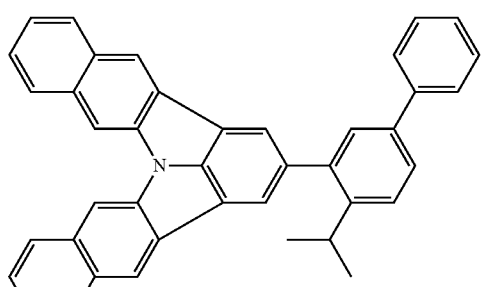
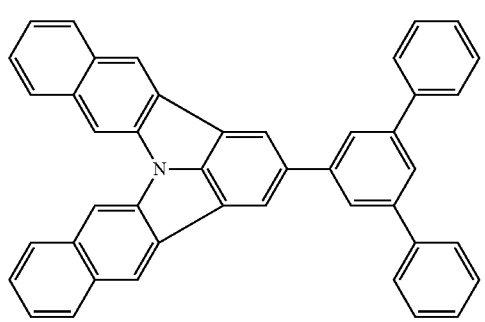
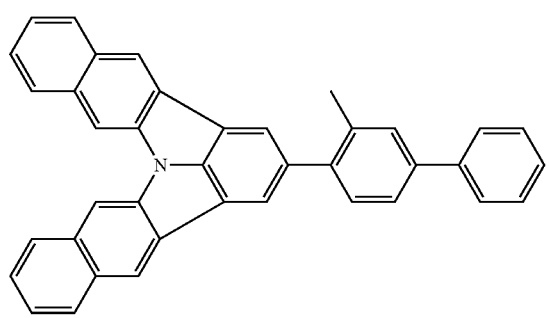
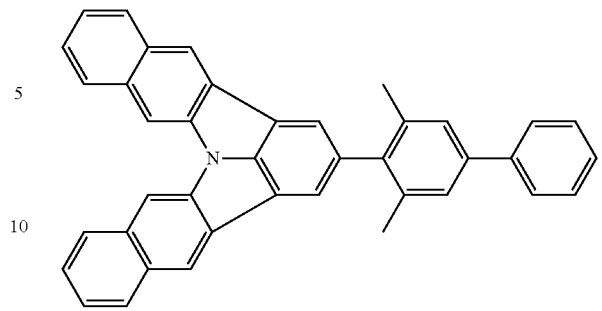
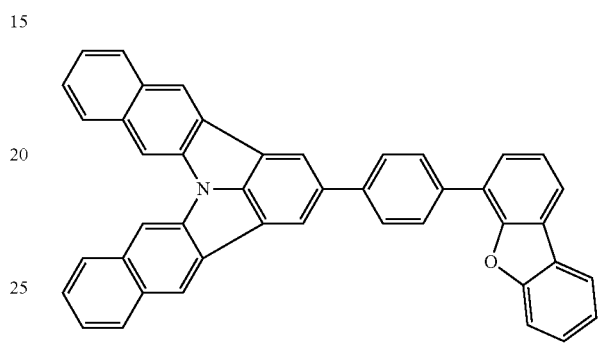
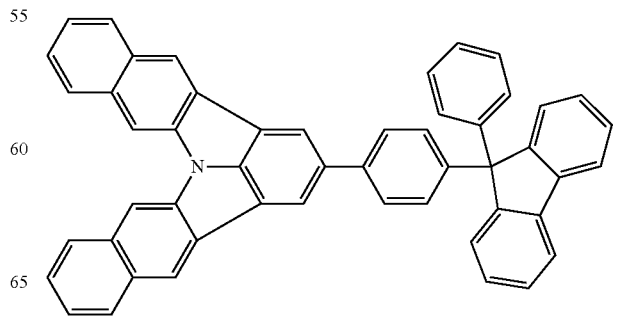

47
-continued
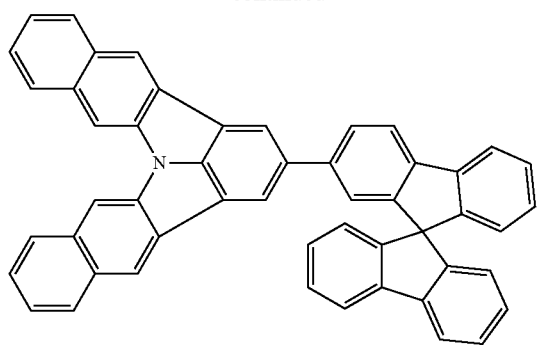
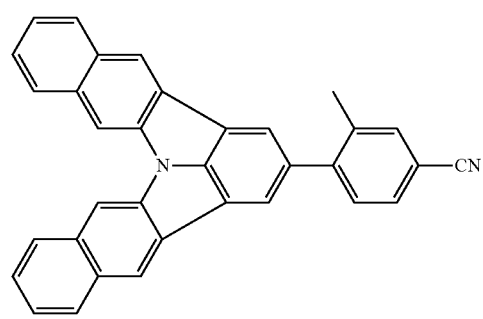
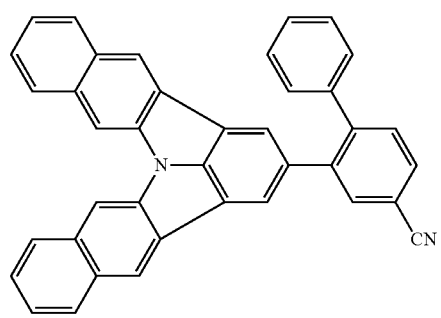
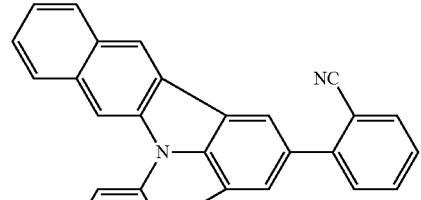
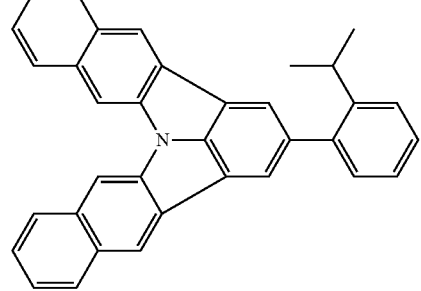
48
-continued
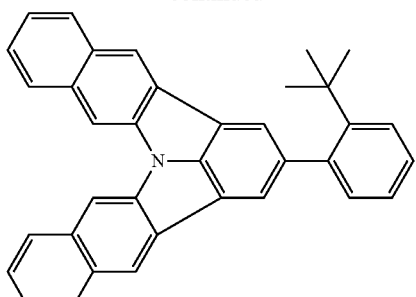
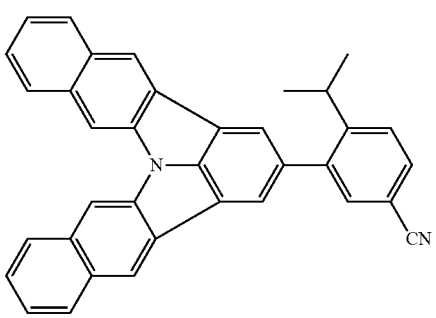
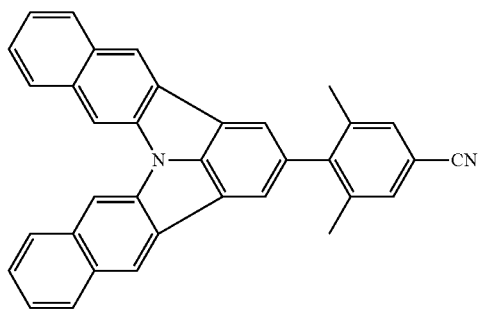
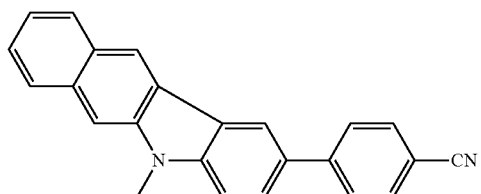
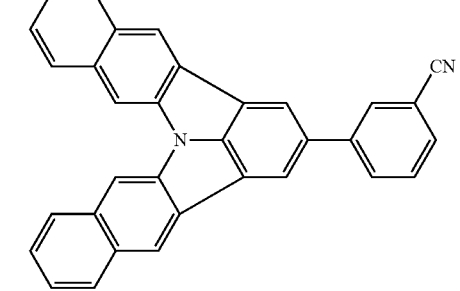

49
-continued
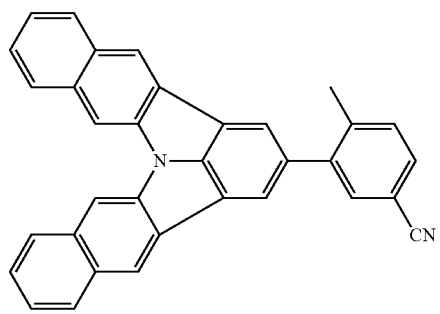
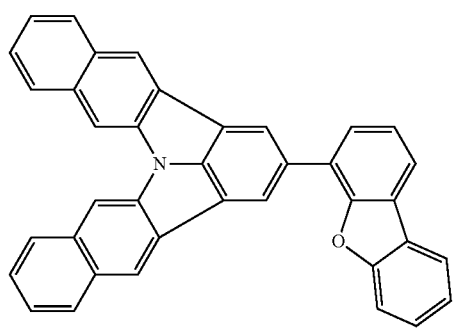
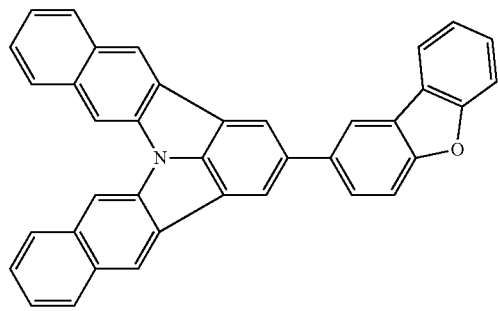
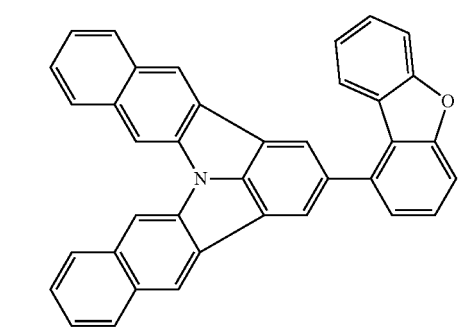
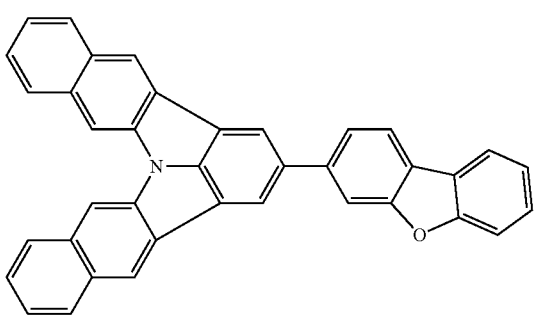
50
-continued
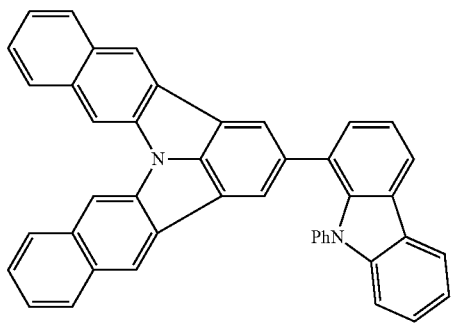
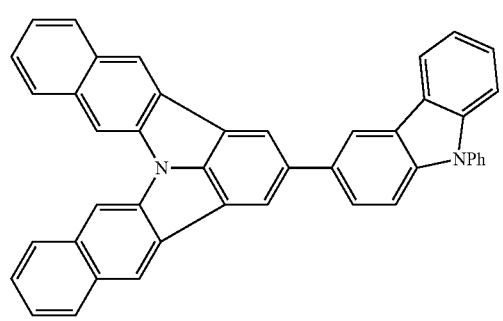
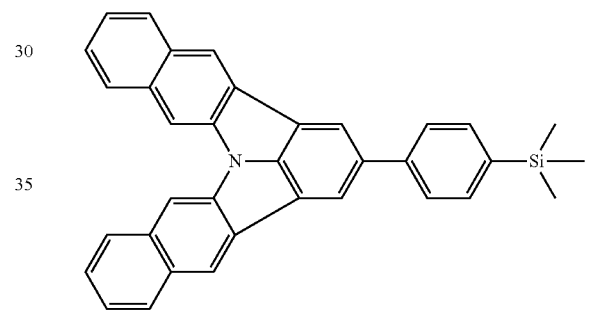
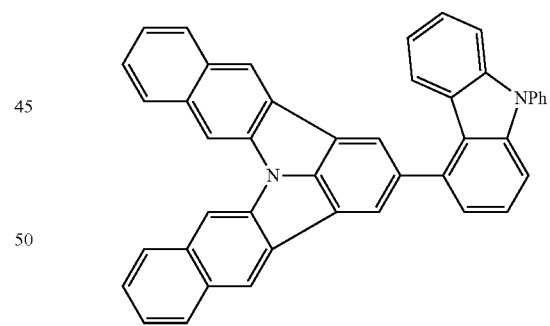
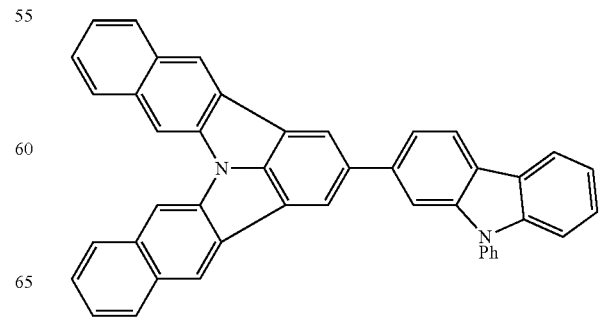

| 51 -continued | 52 -continued |
|---|---|
| 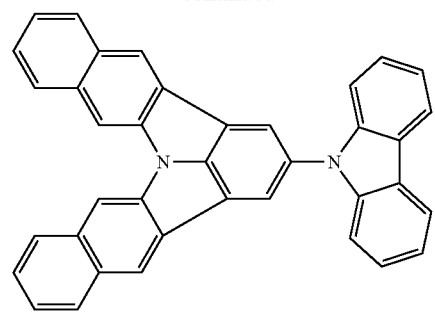 | 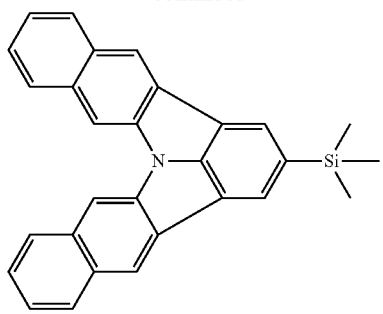 |
| 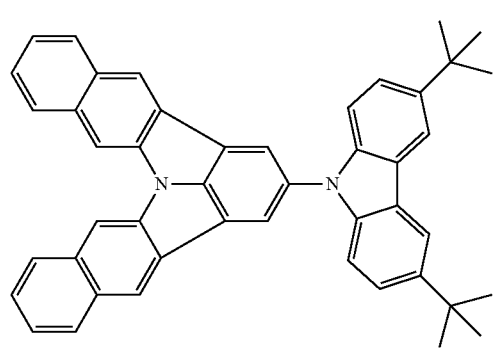 | 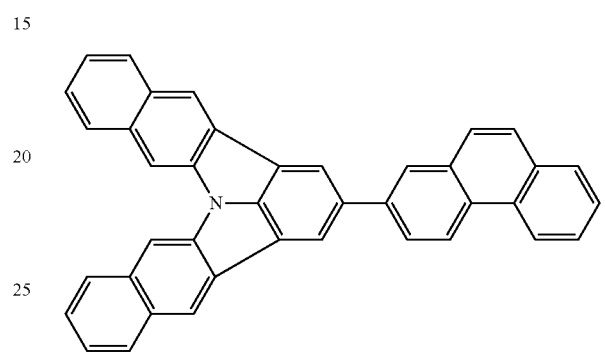 |
| 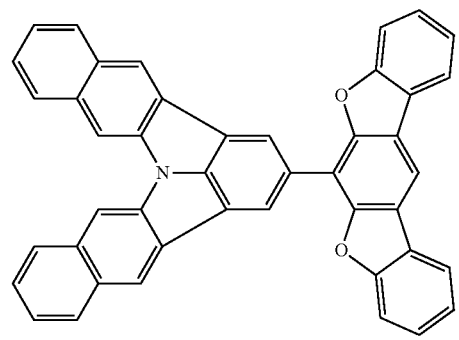 | 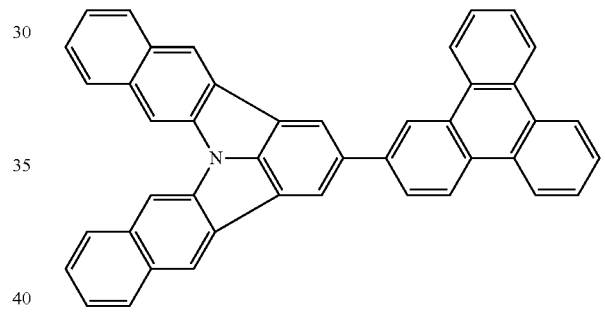 |
| 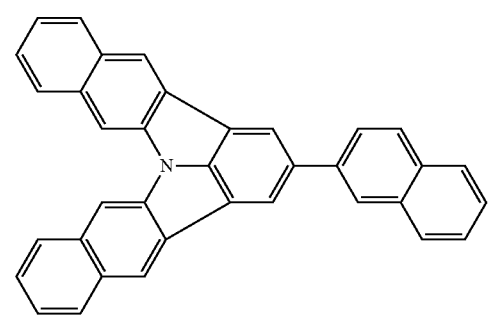 | 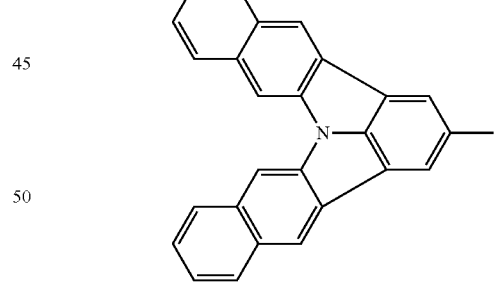 |
| 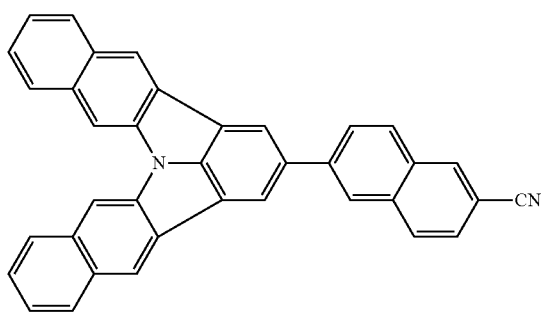 | 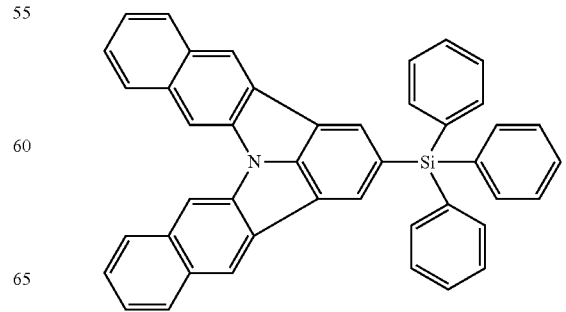 |

53
-continued
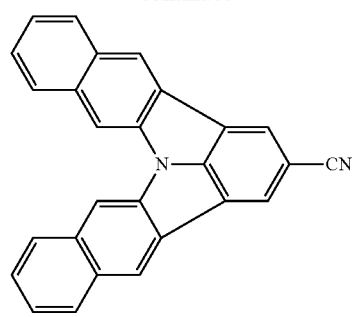
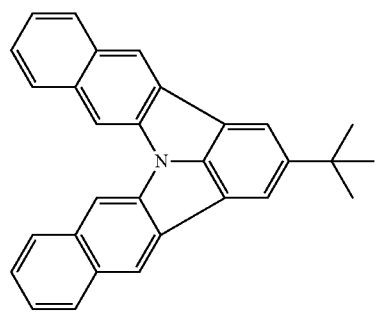
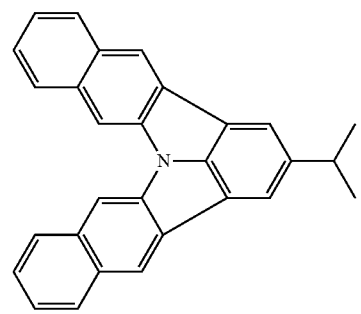
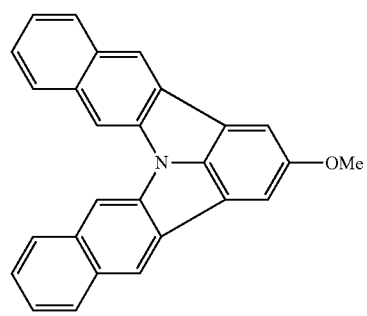
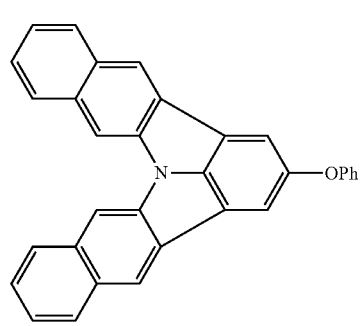
54
-continued
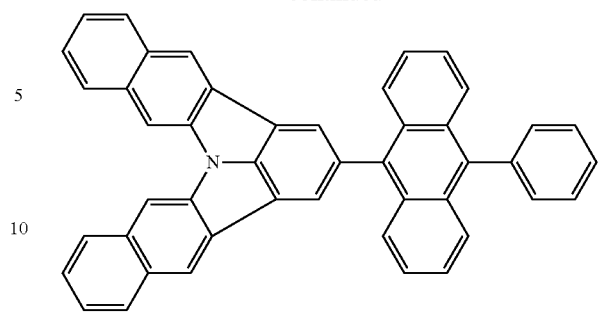
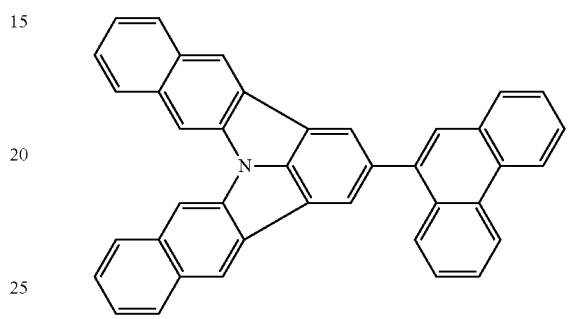
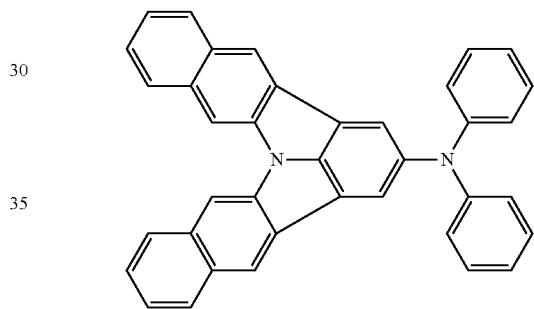
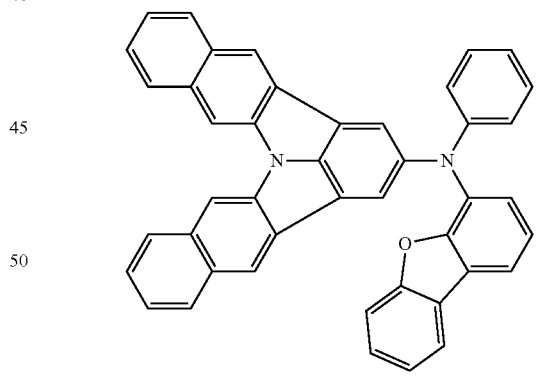
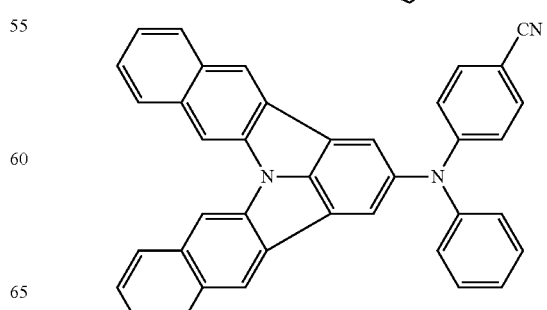

55
-continued
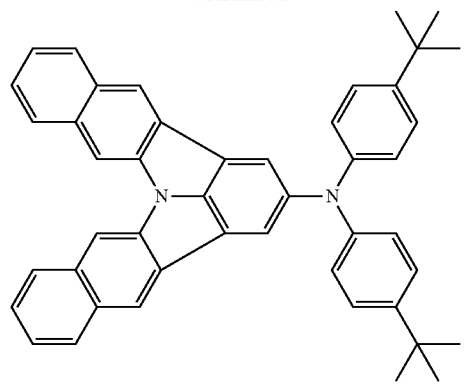
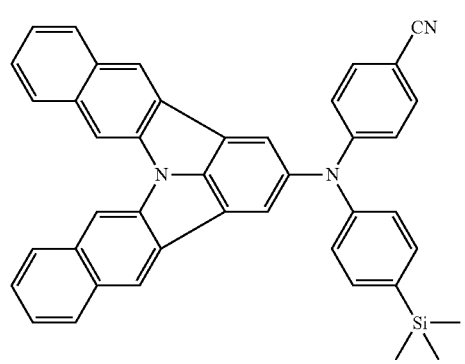
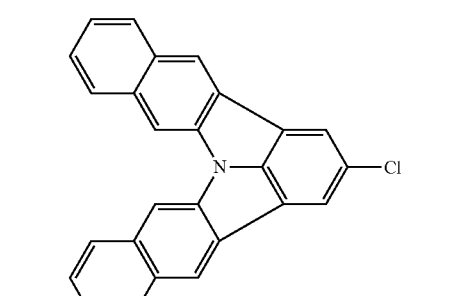
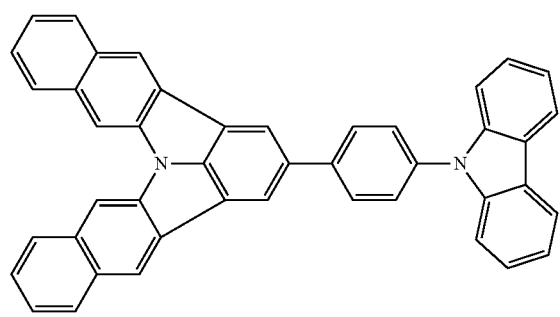
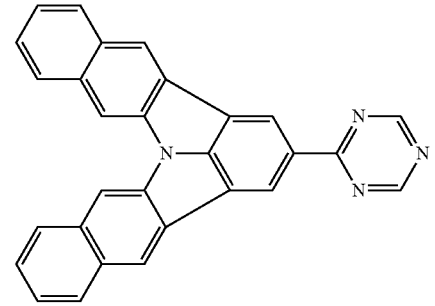
56
-continued
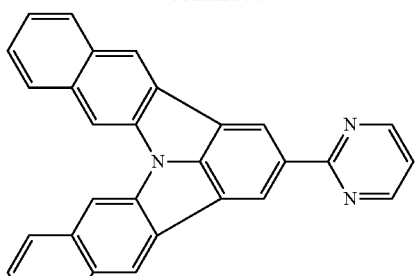
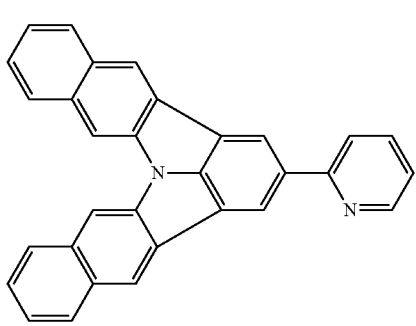
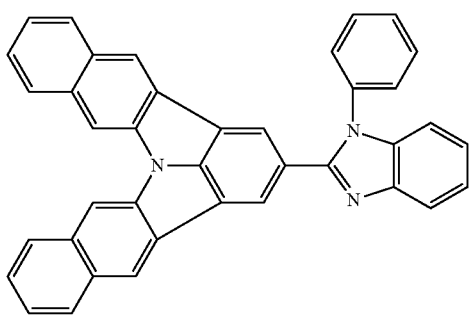
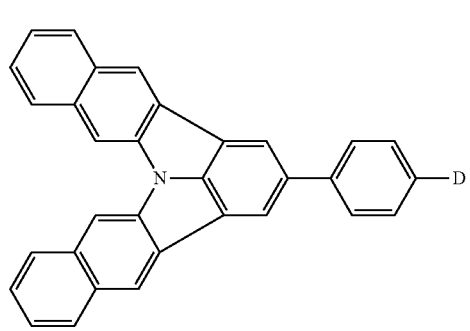
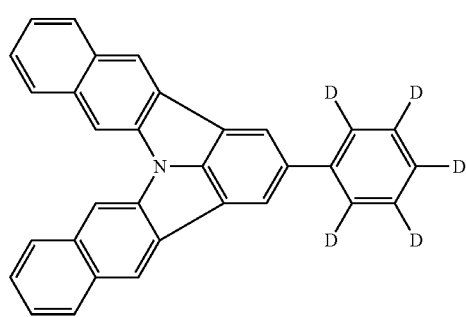

57
-continued
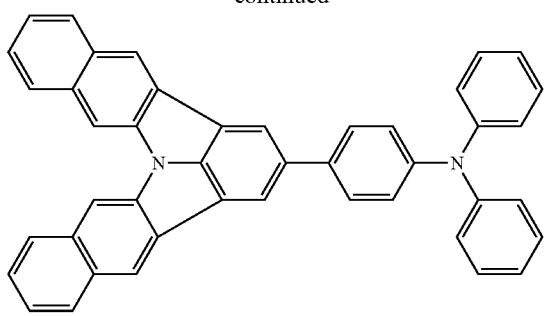
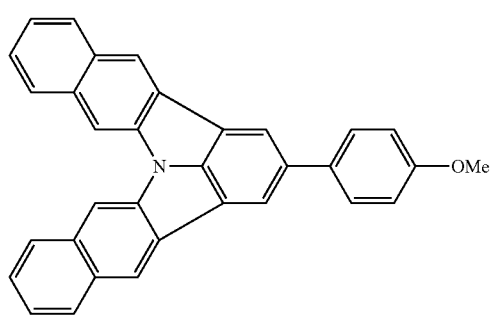
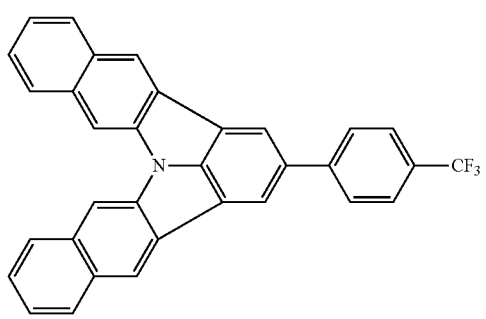
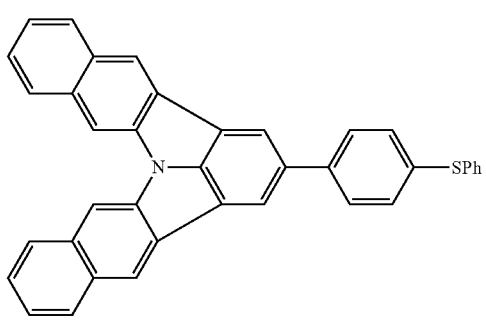
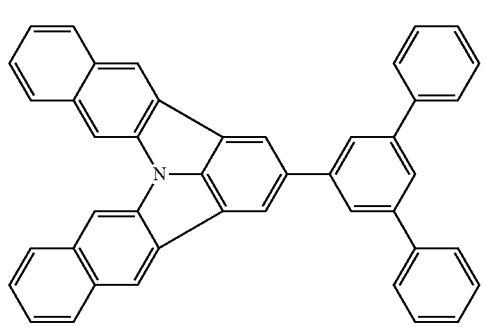
58
-continued
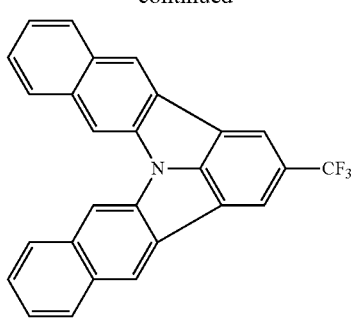
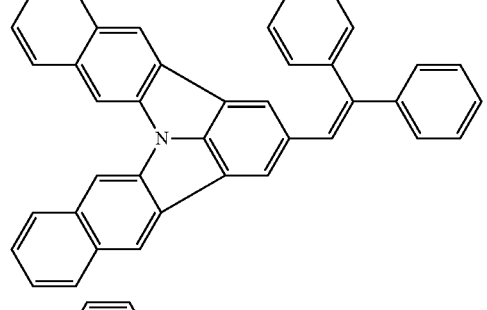
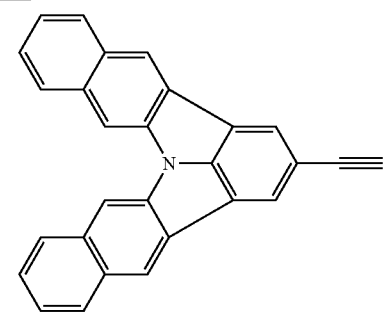
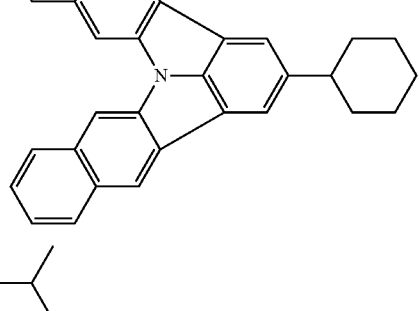
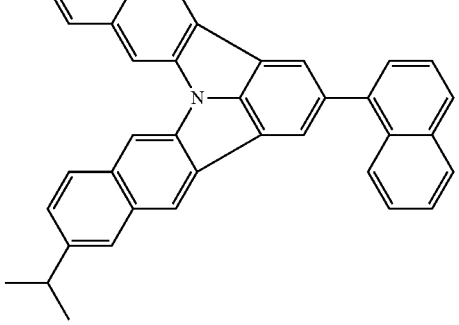

59
-continued
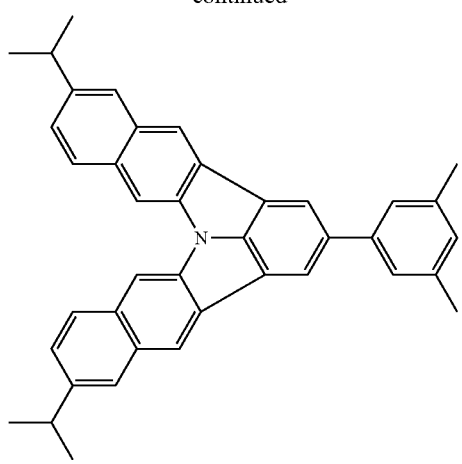
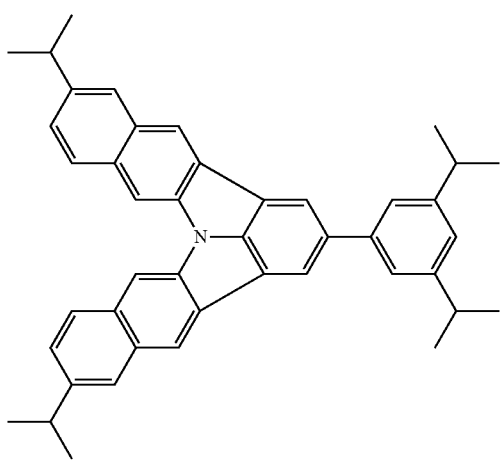
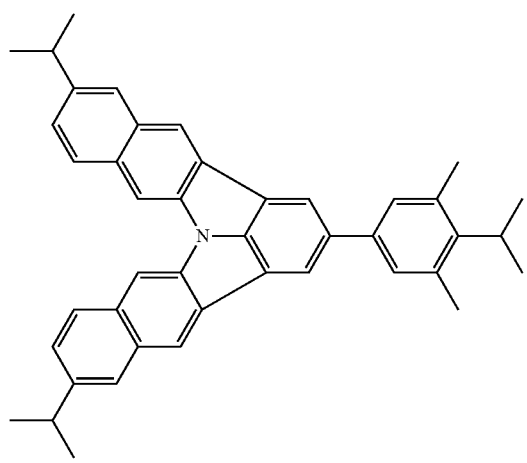
60
-continued
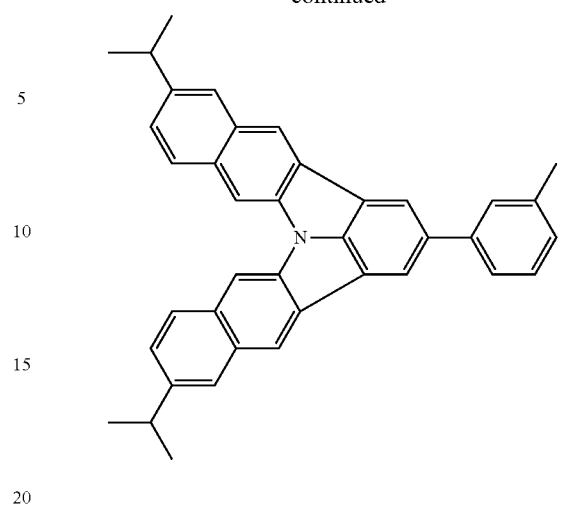
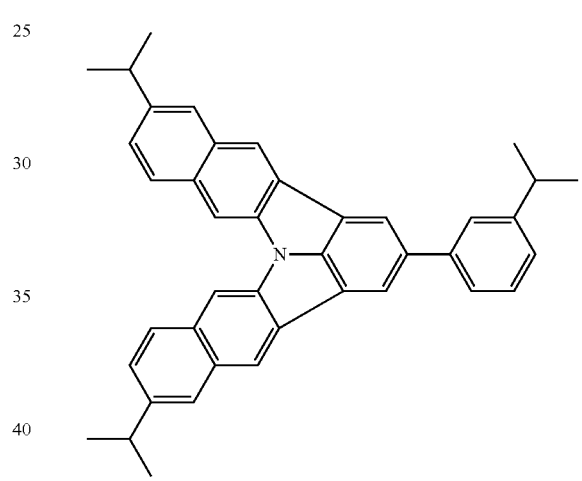
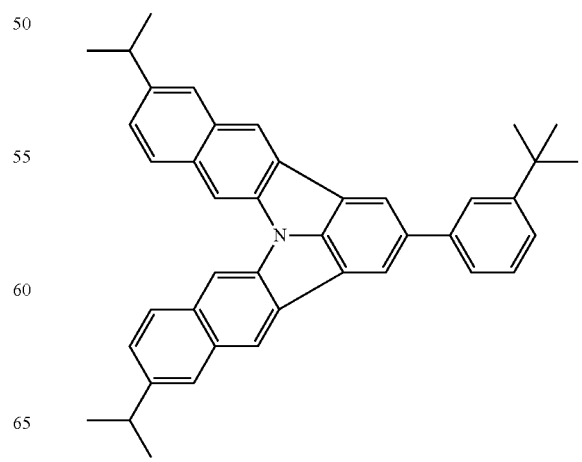

61
-continued
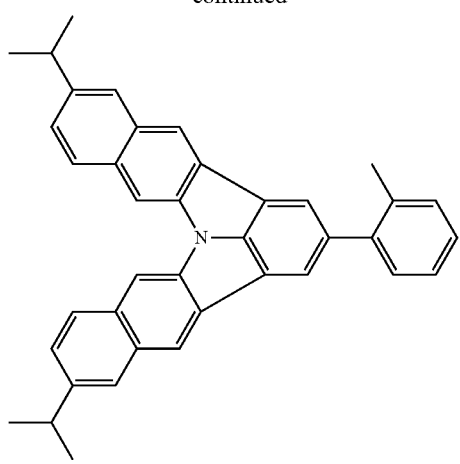
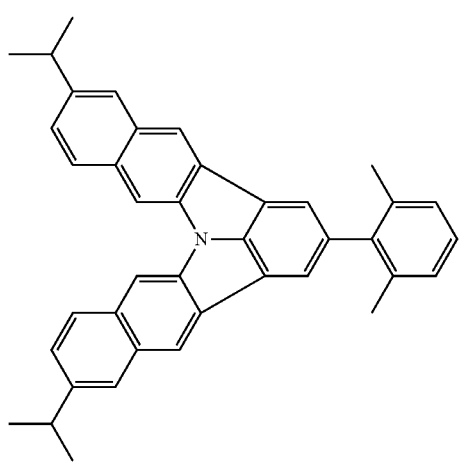
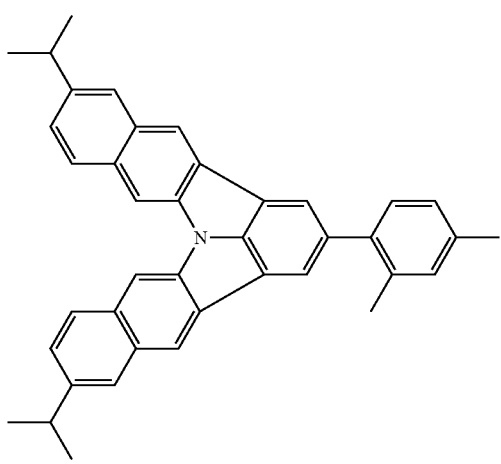
62
-continued
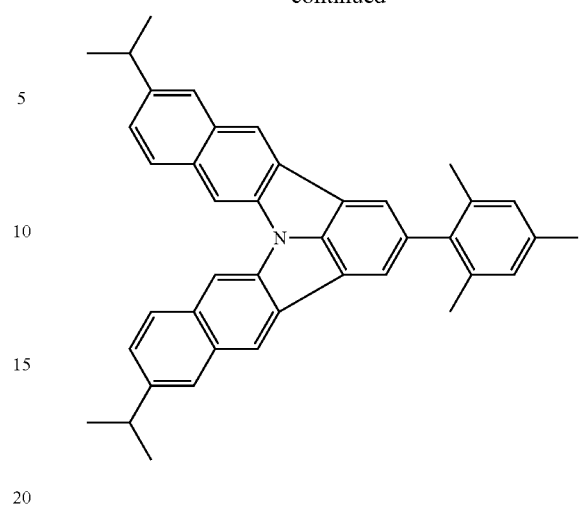
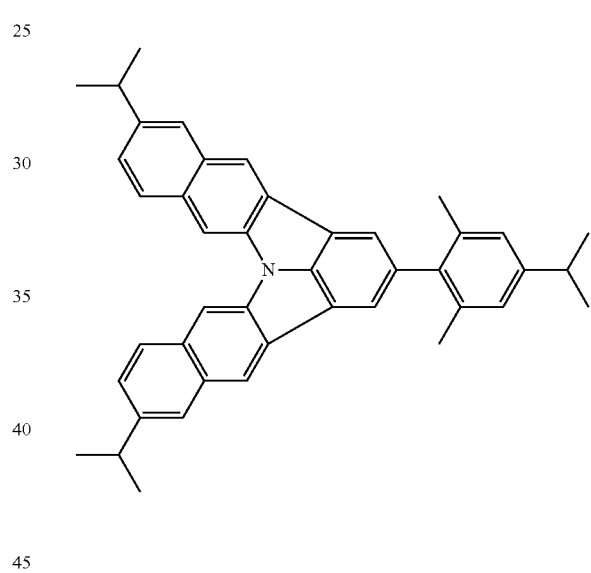
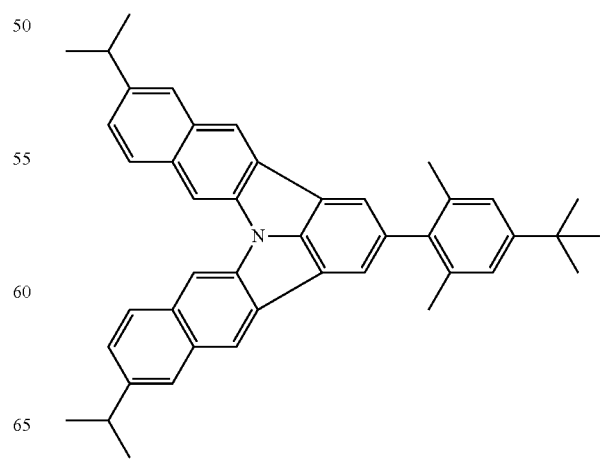

63
-continued
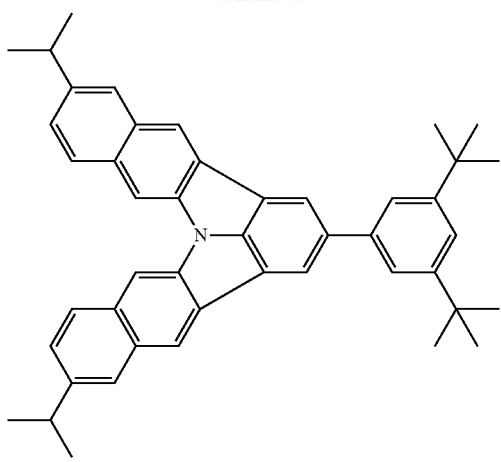
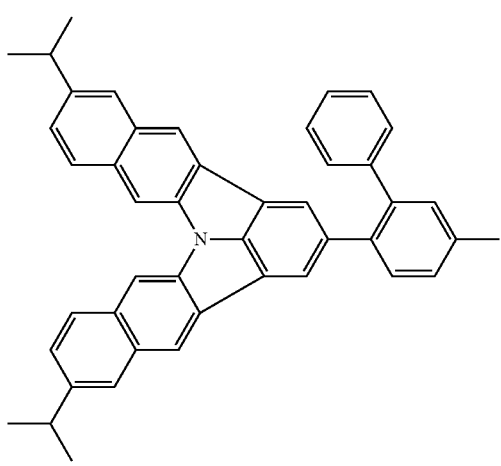
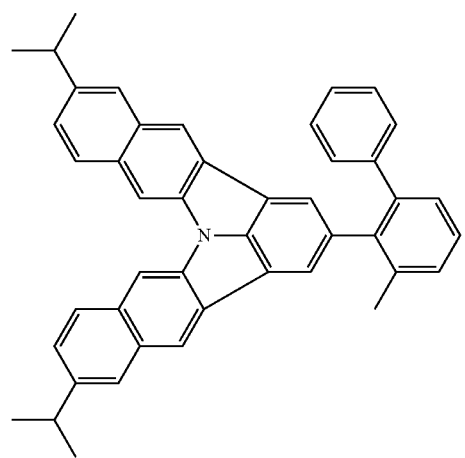
64
-continued
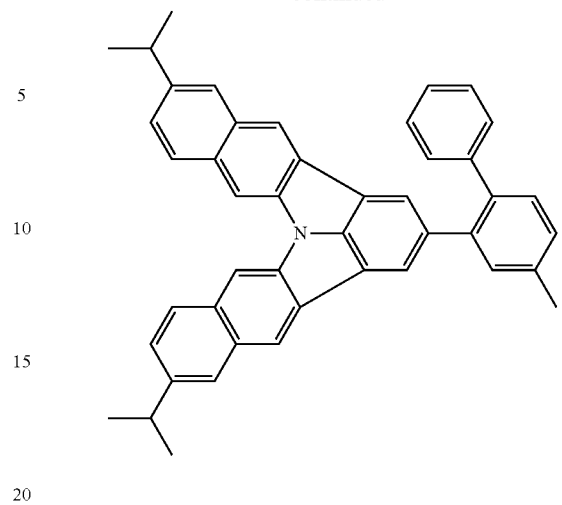
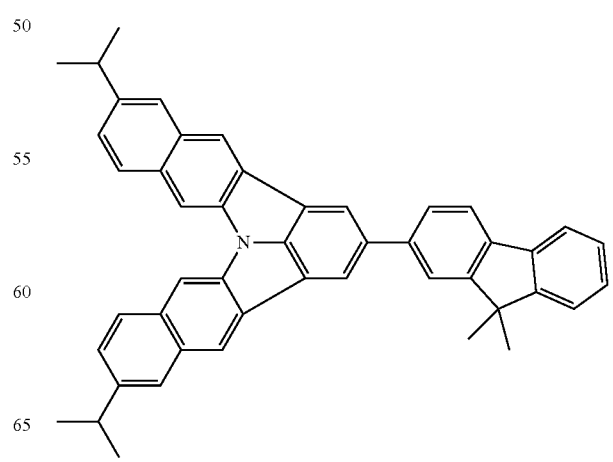

65
-continued
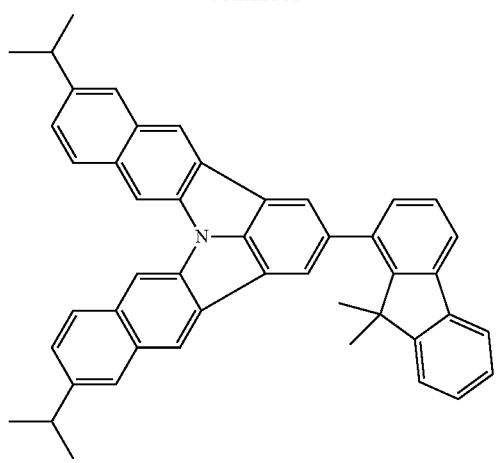
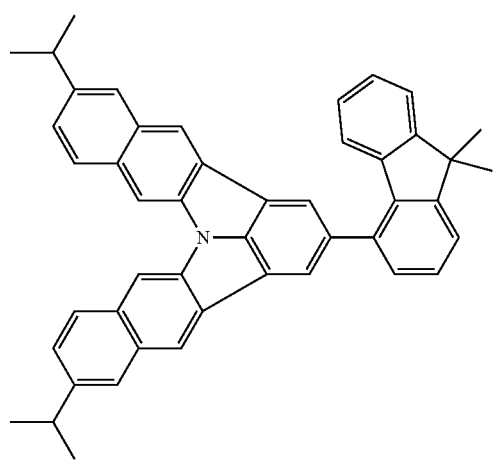
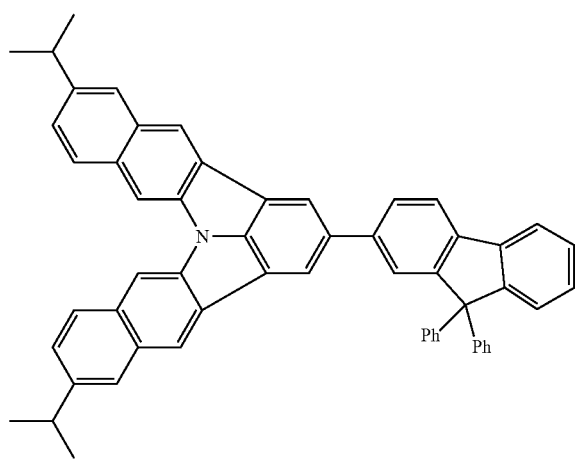
66
-continued
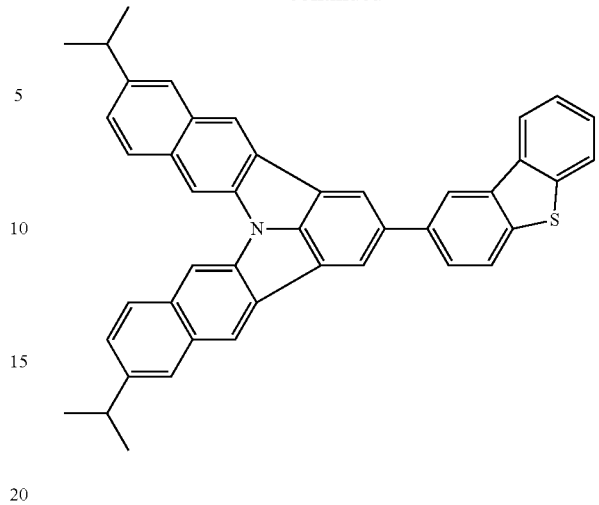
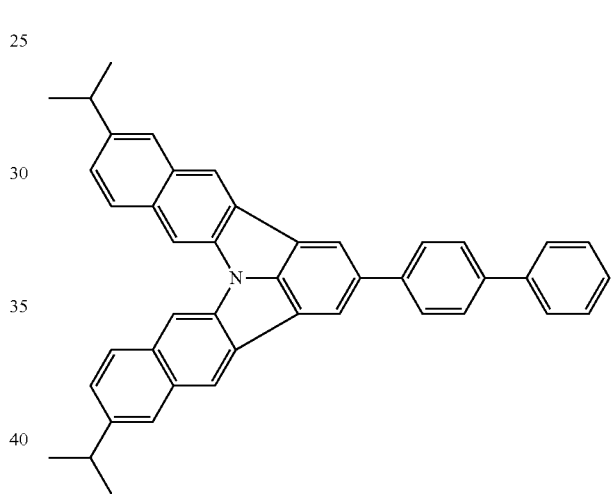
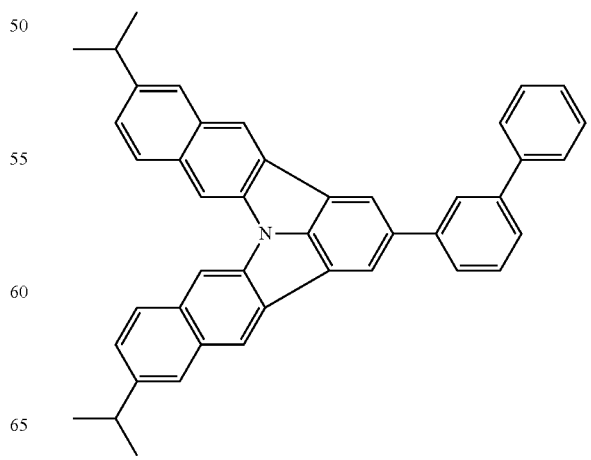

67
-continued
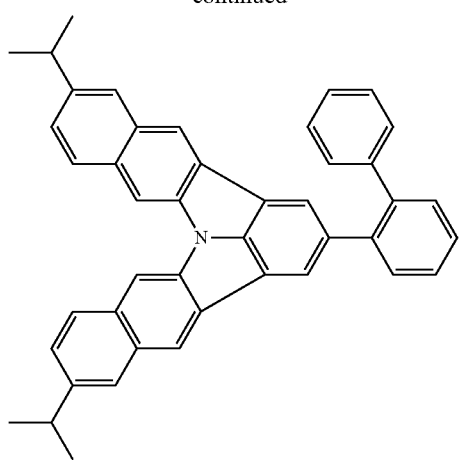
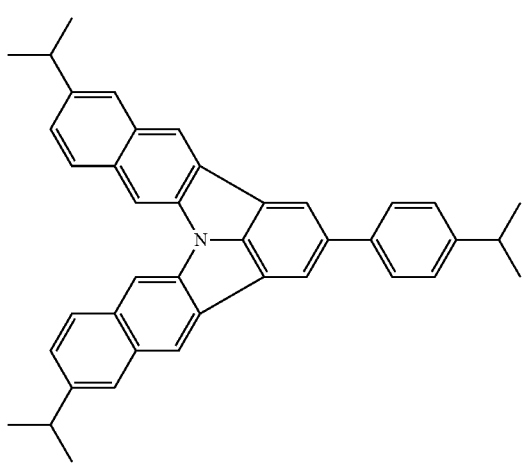
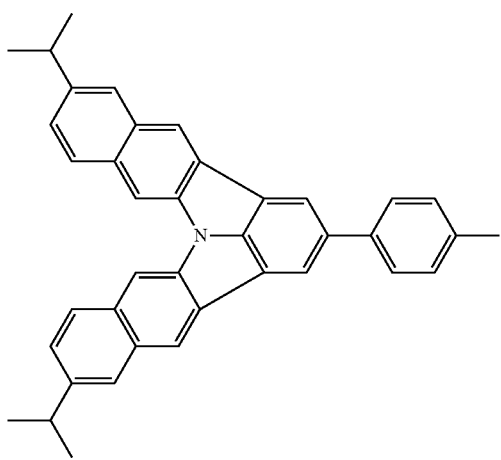
68
-continued
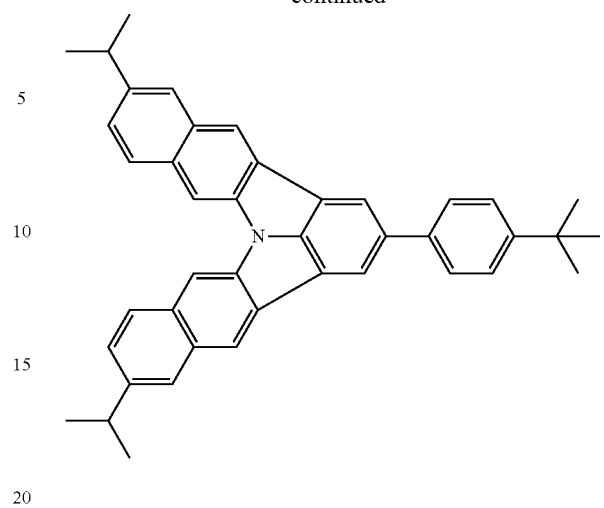
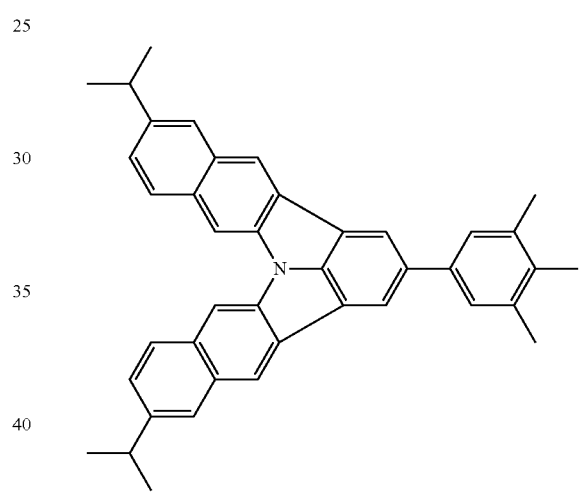
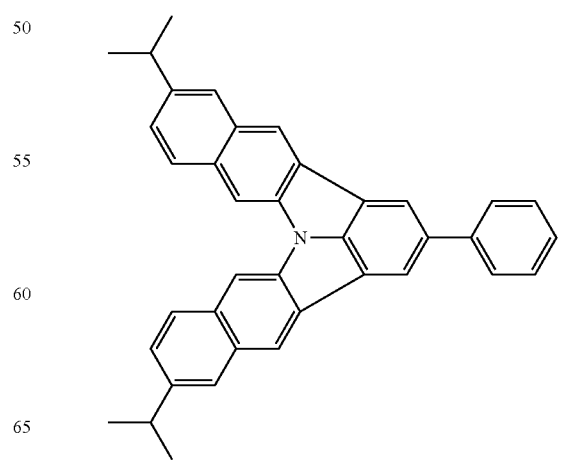

69
-continued
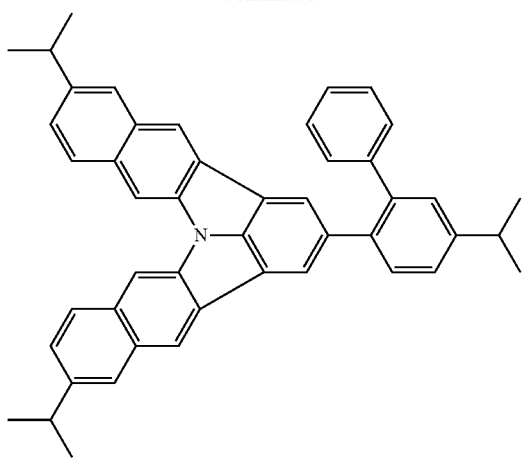
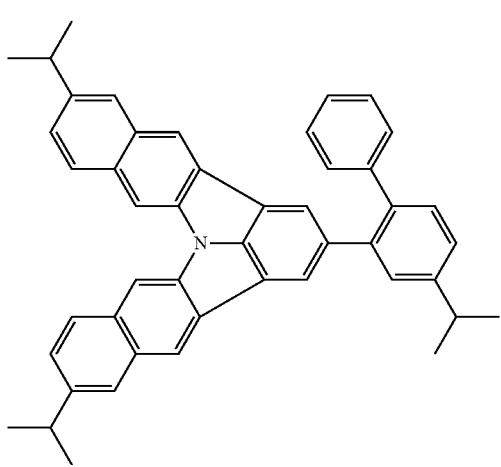
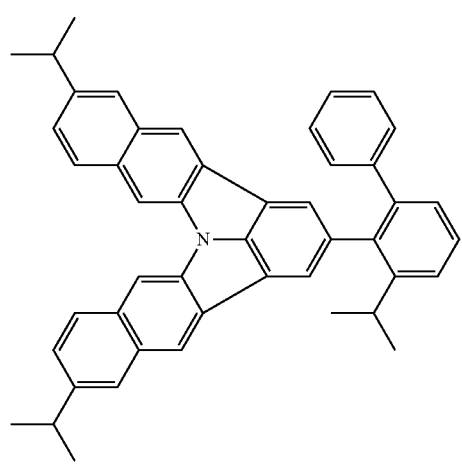
70
-continued
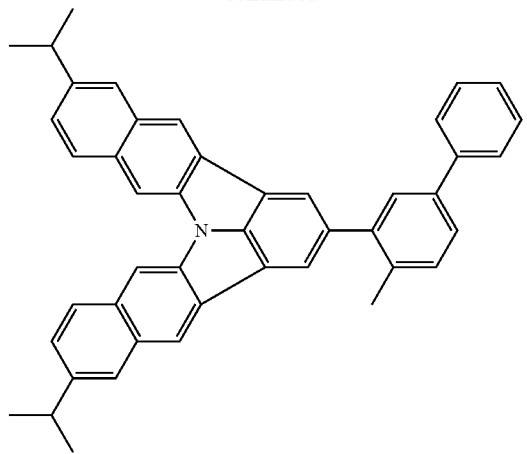
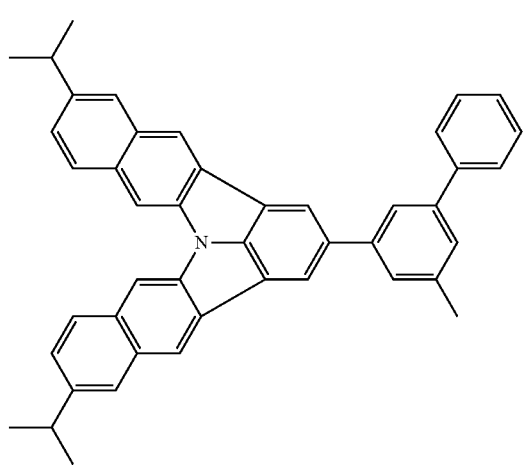
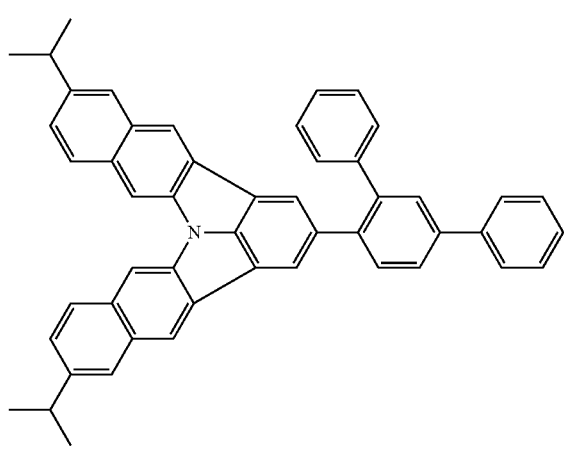

71
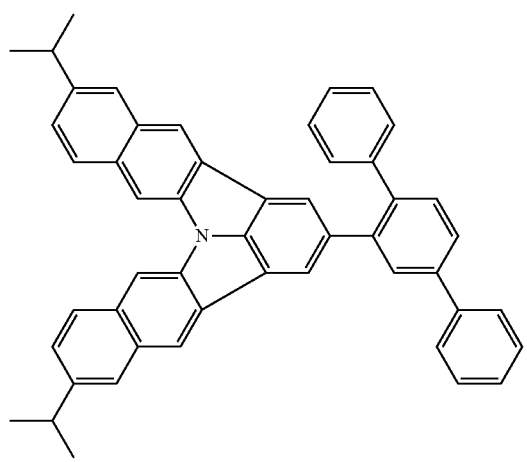
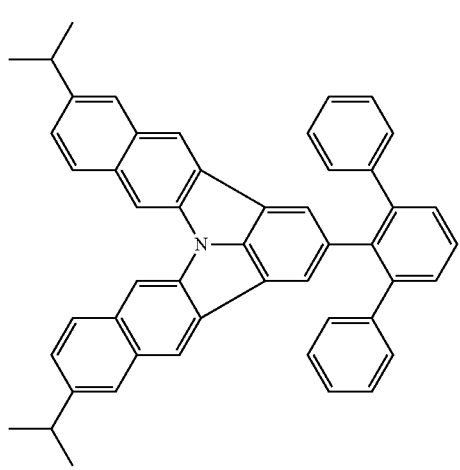
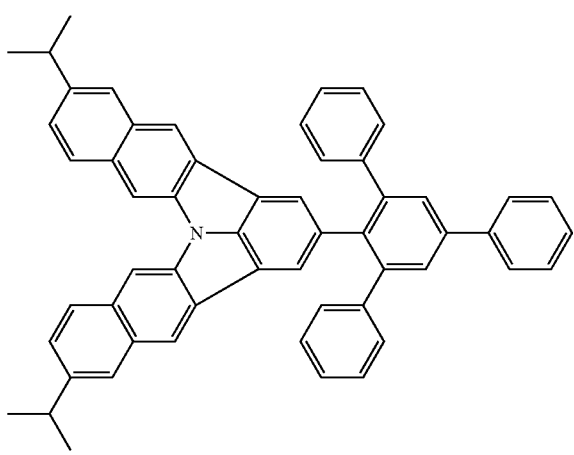
72
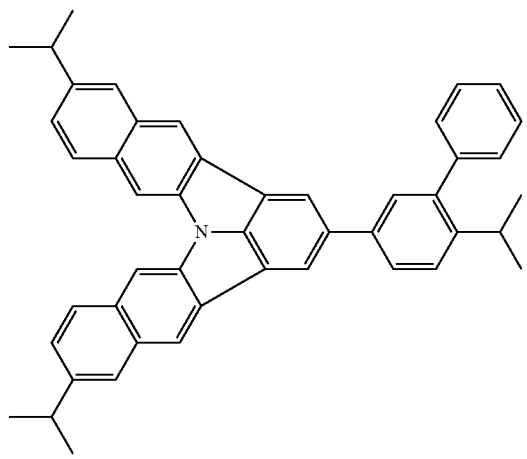
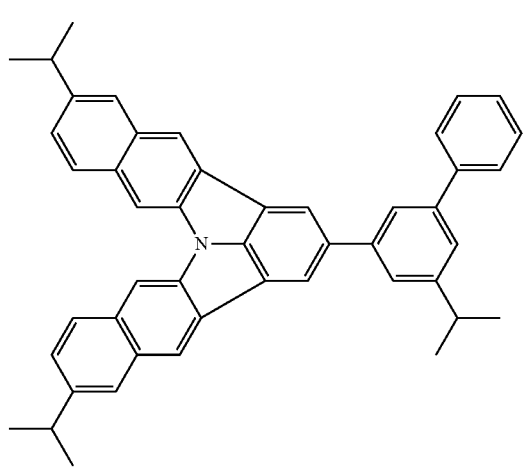

73
-continued
74
-continued
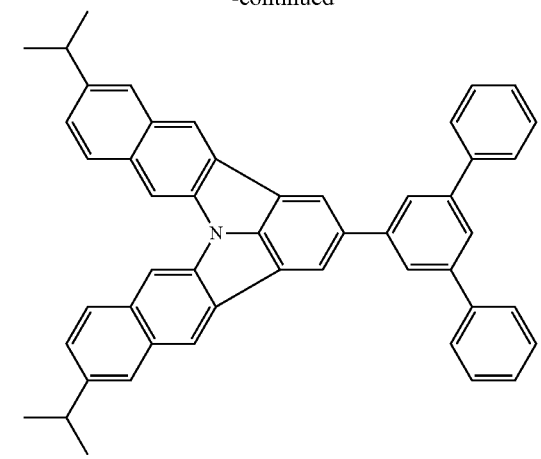
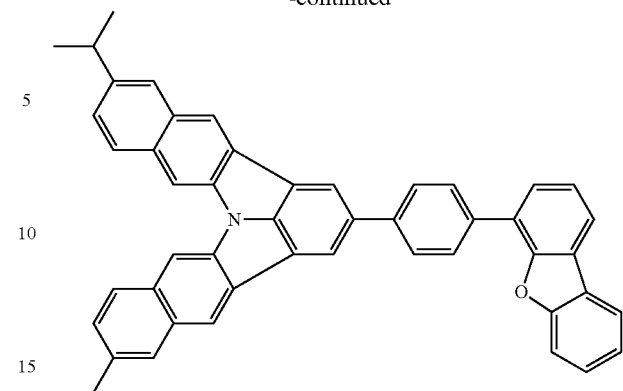
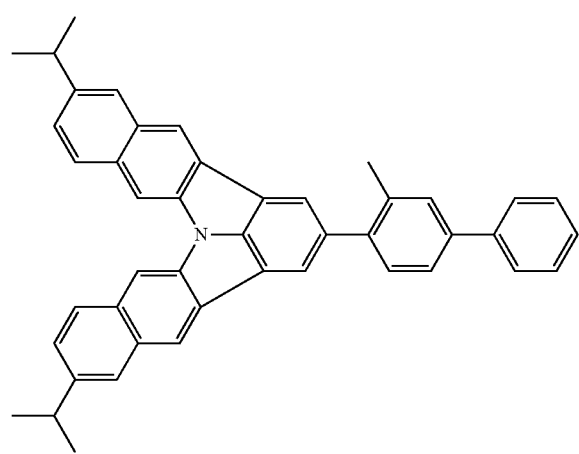
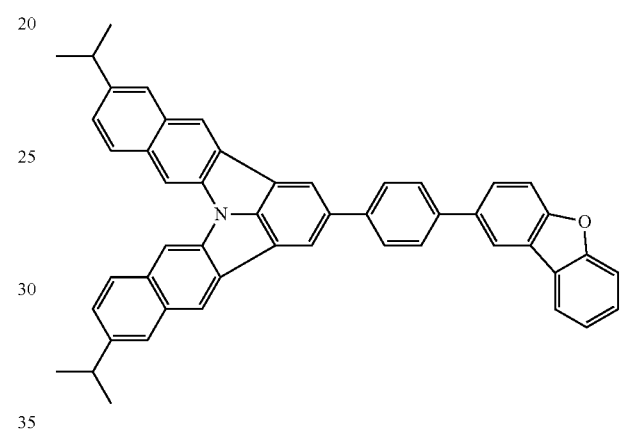
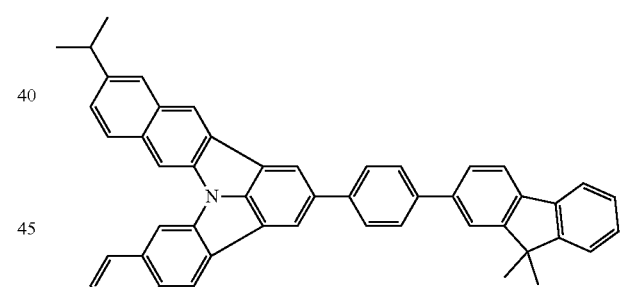
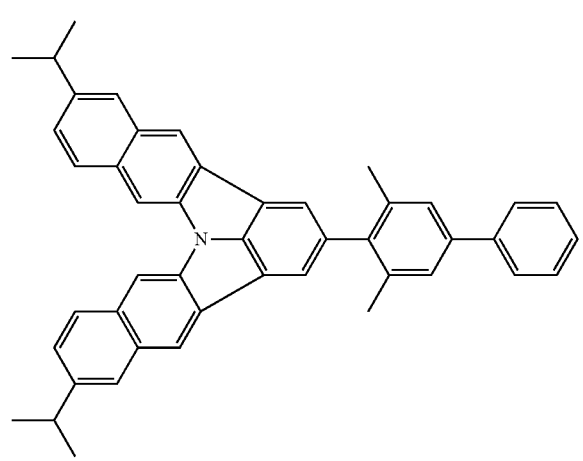
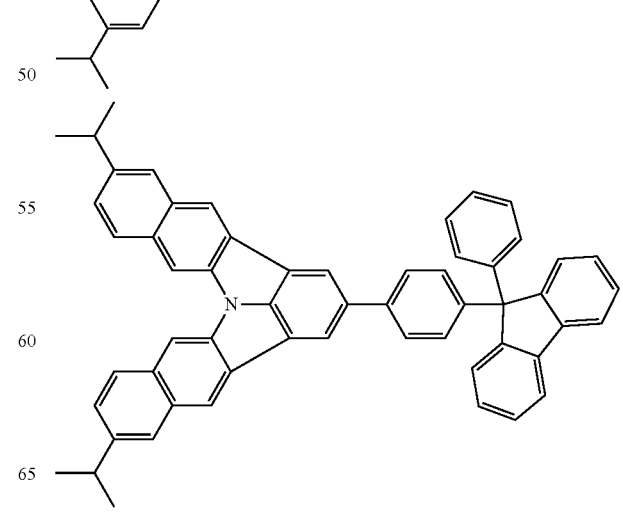

75
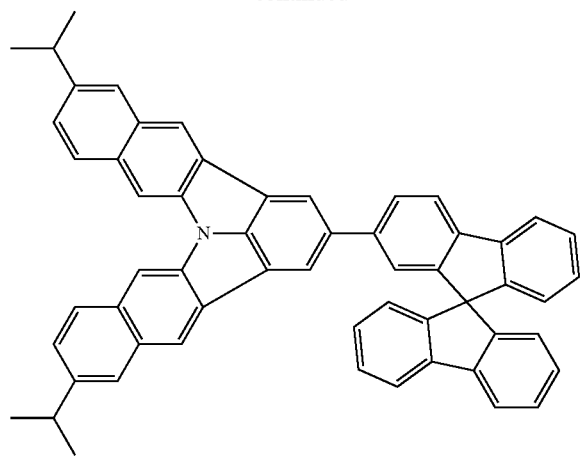
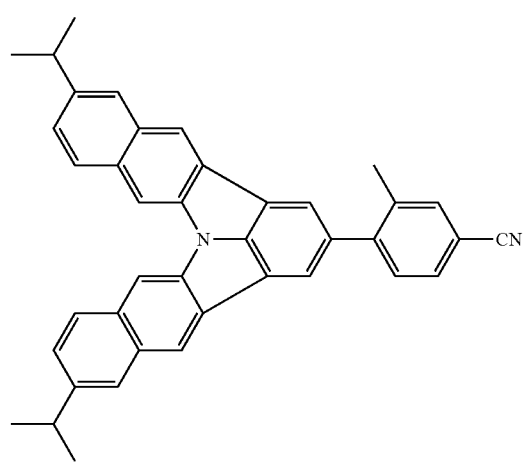
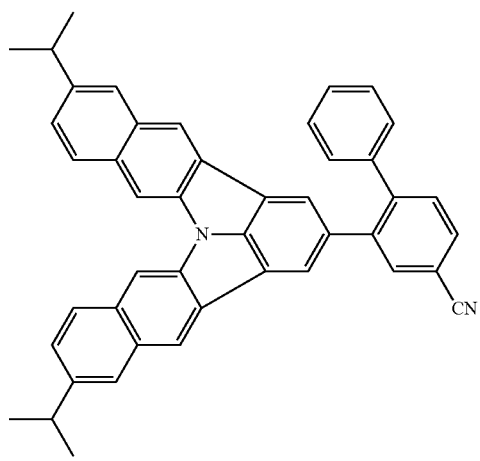
76
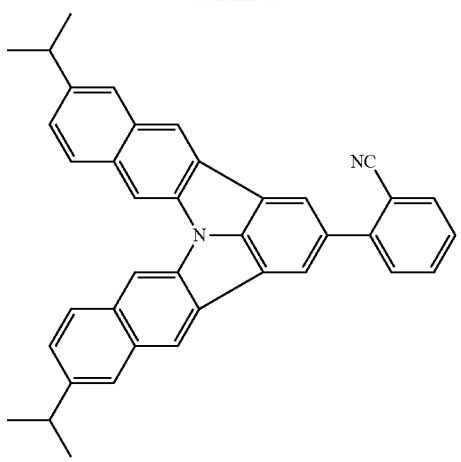
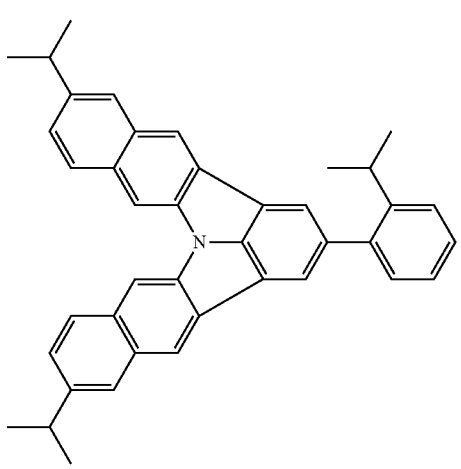
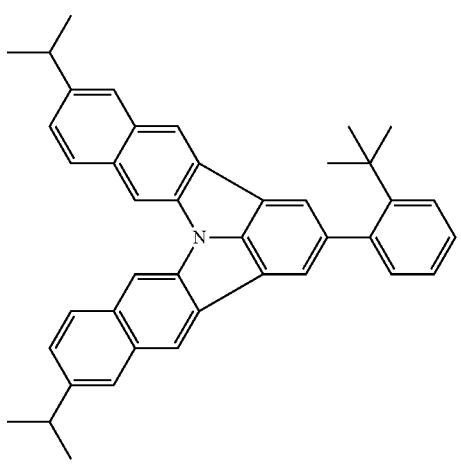

77
-continued
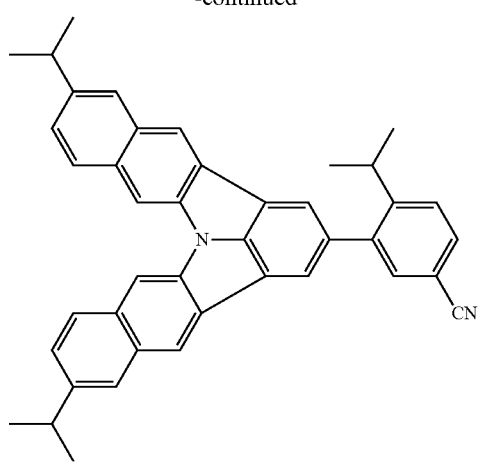
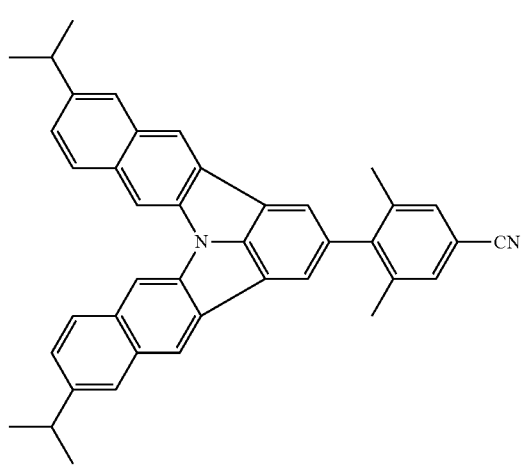
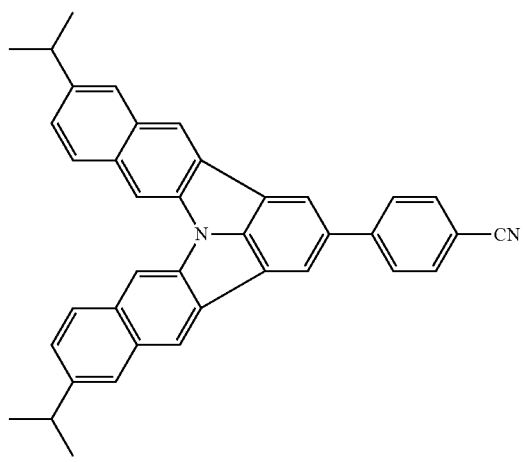
78
-continued
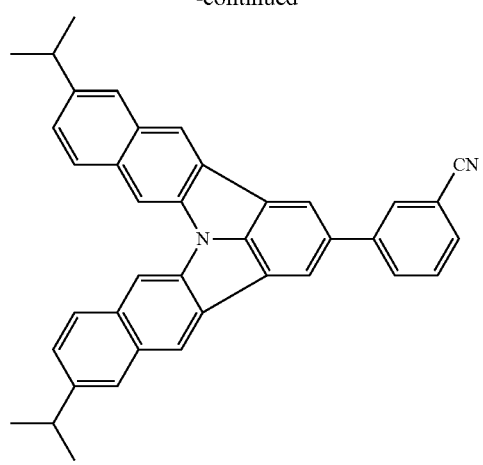
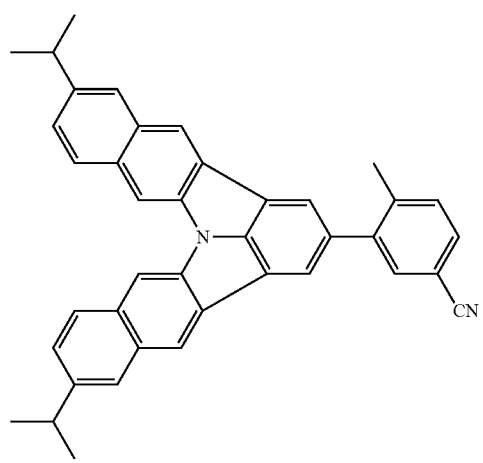
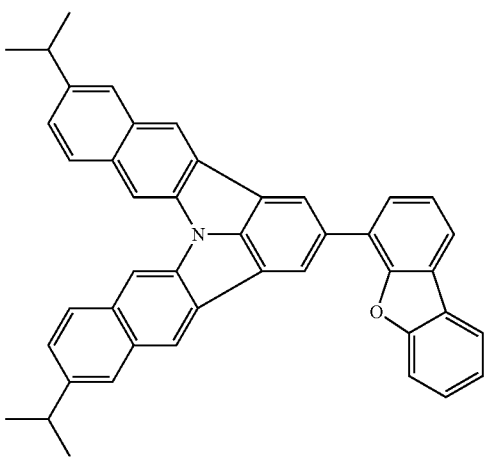

79
-continued
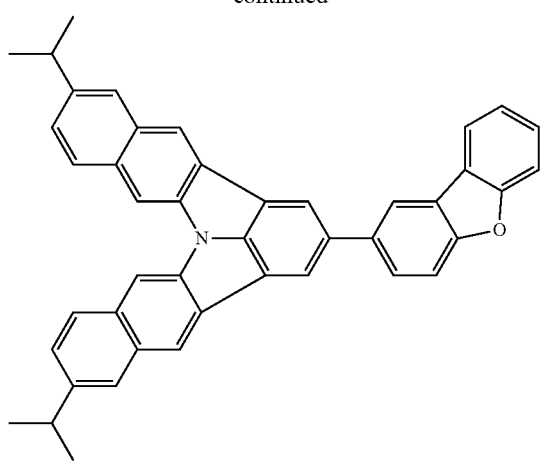
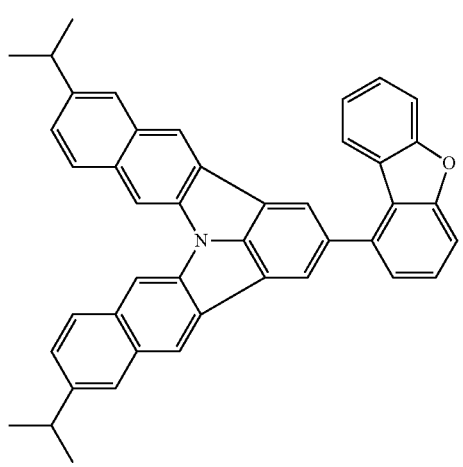
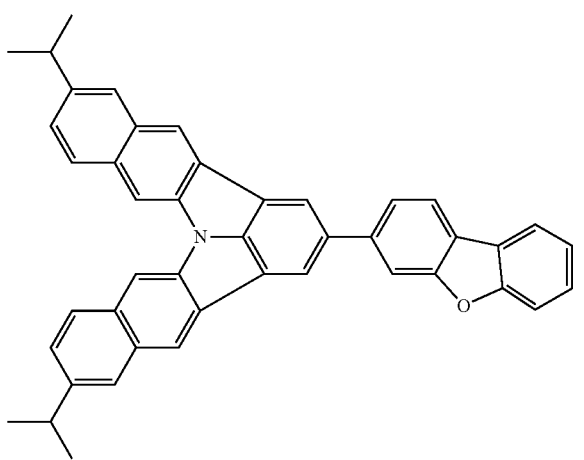
80
-continued
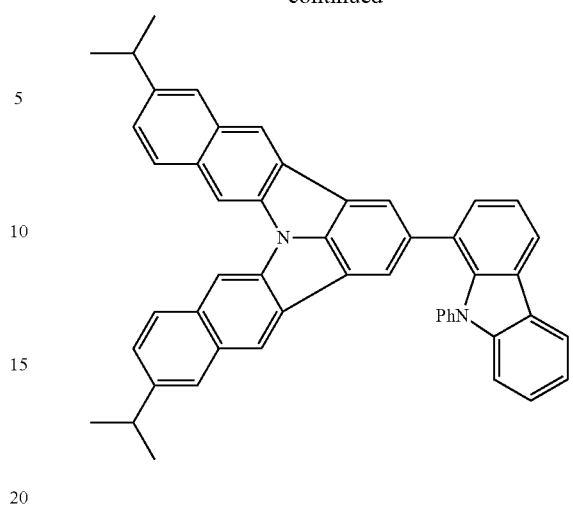
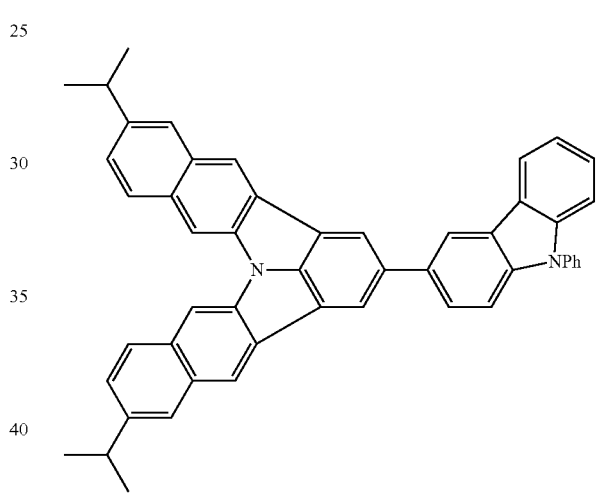
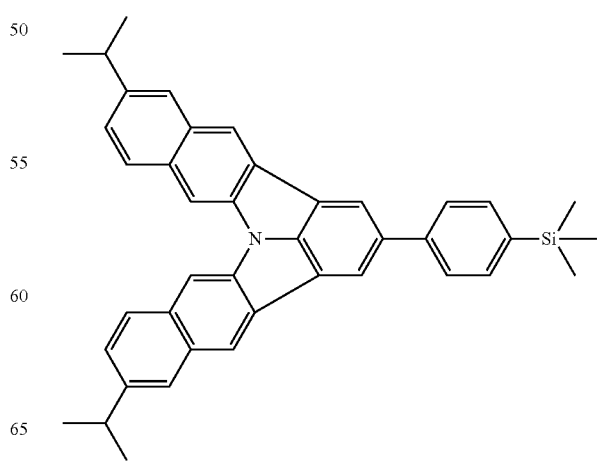

81
-continued
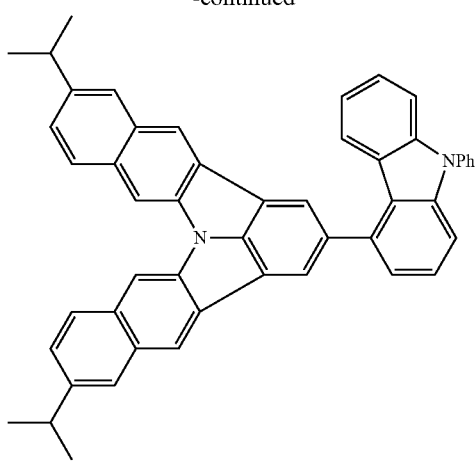
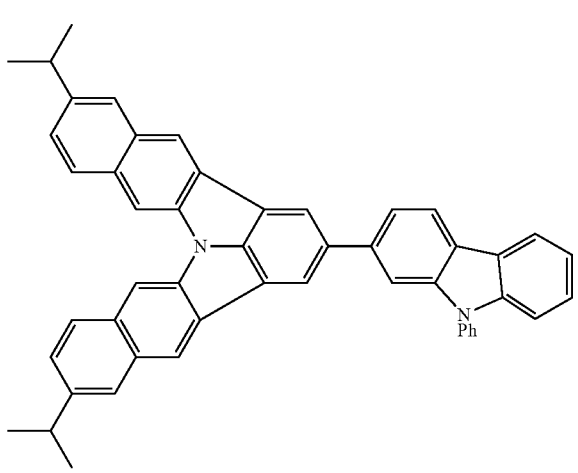
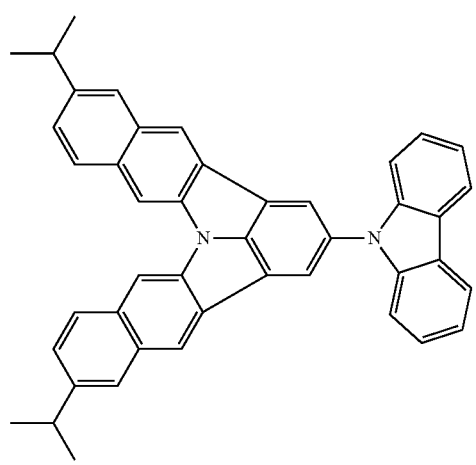
82
-continued
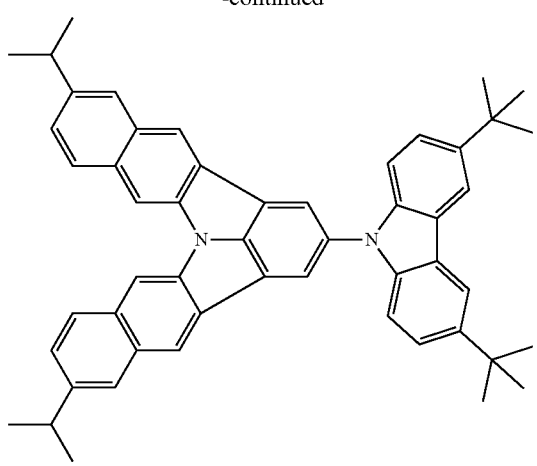
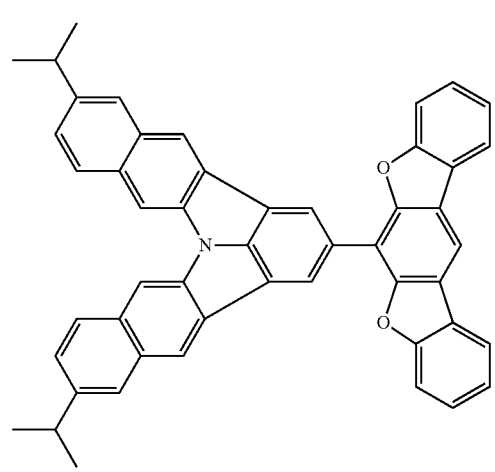
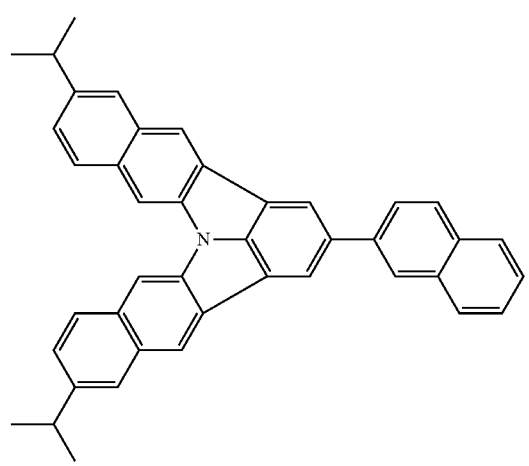

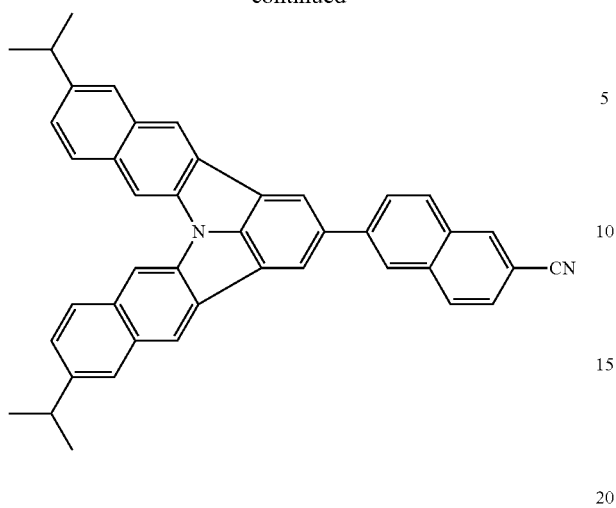
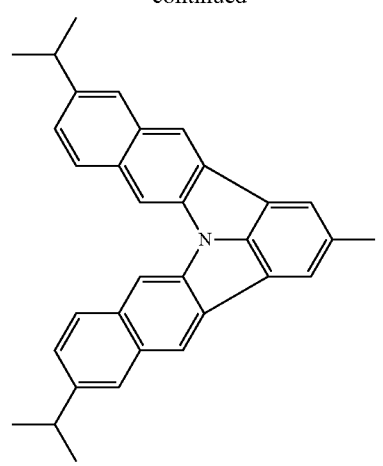
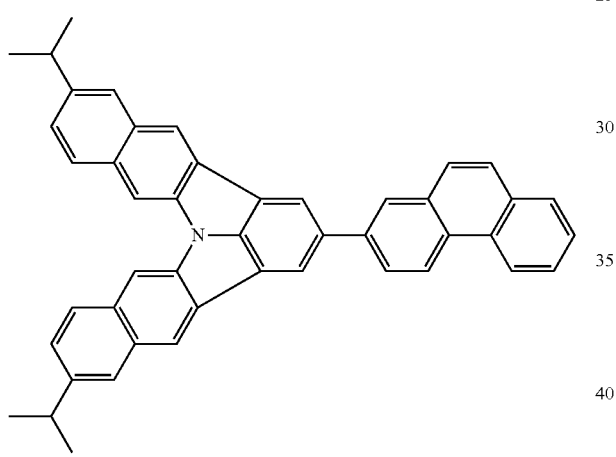
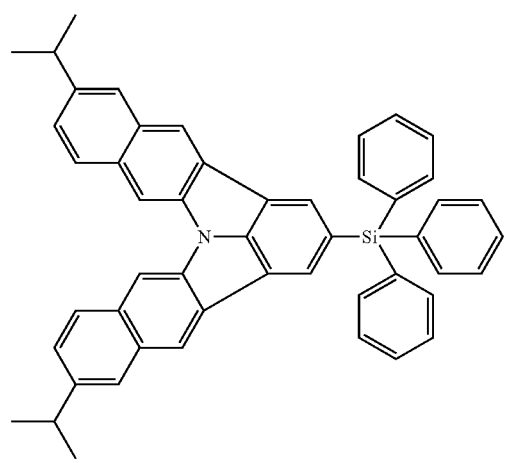
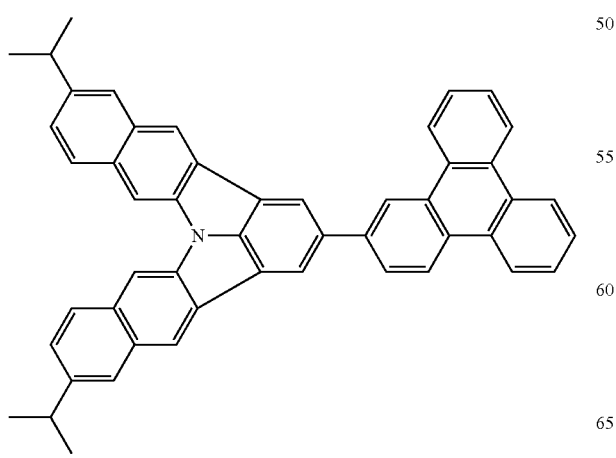
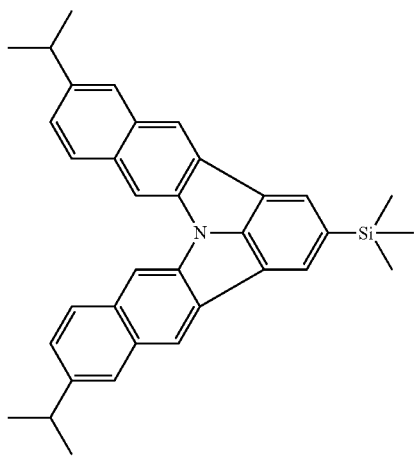

85
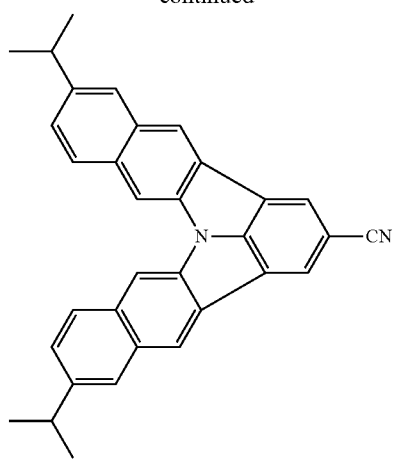
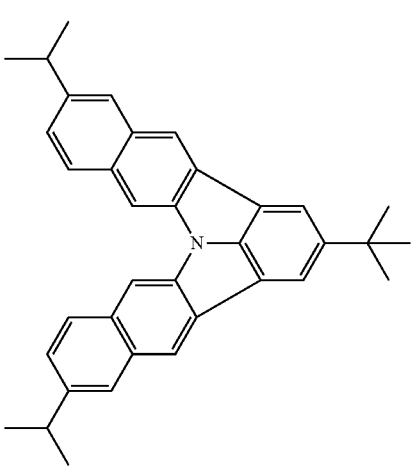
86
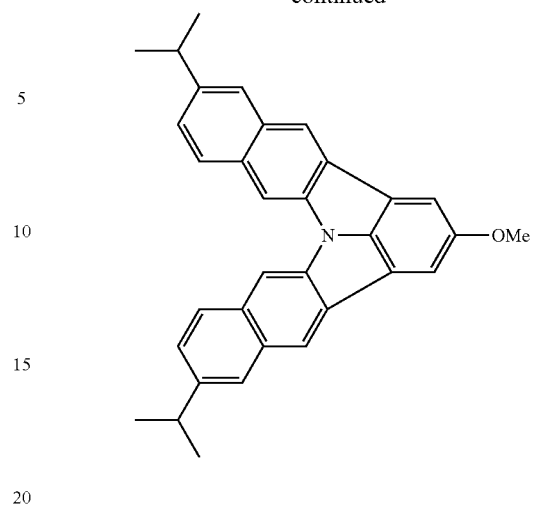
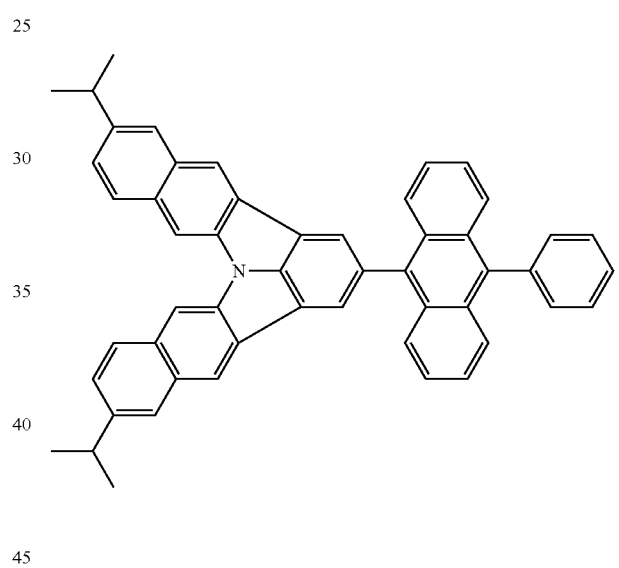
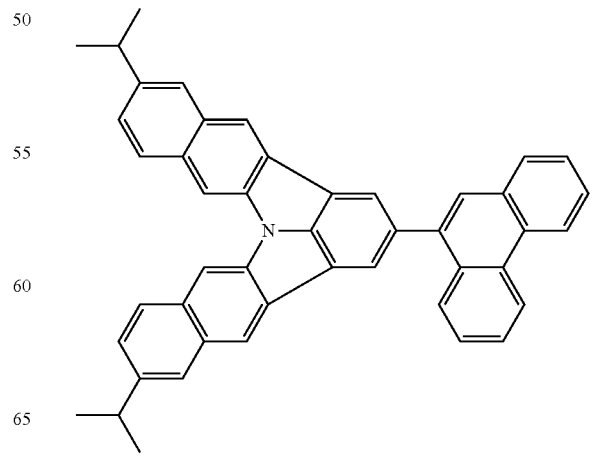

87
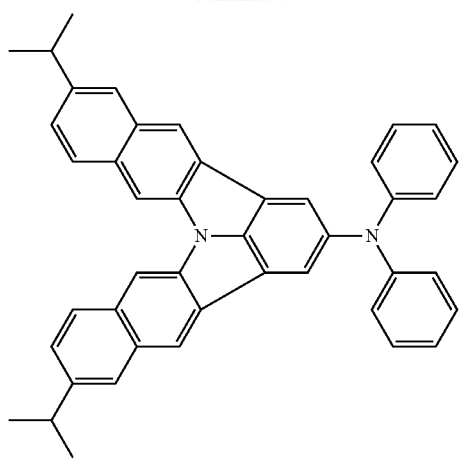
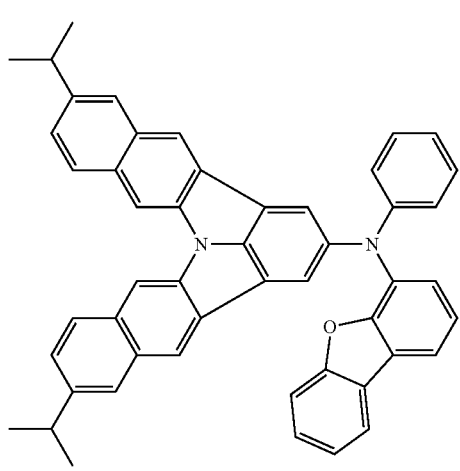
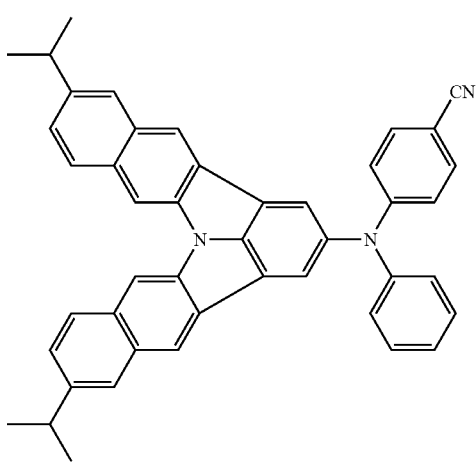
88
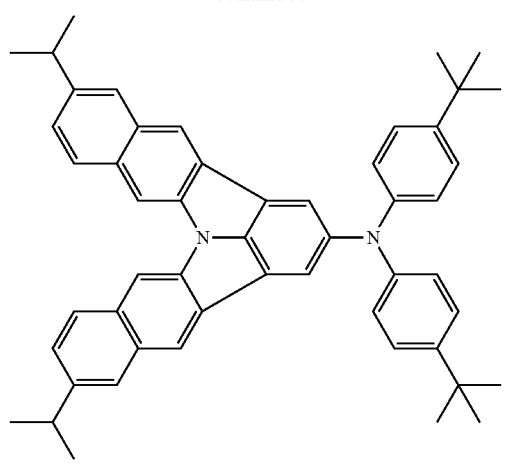
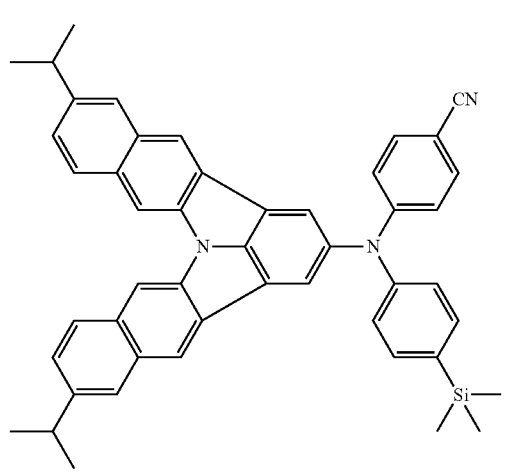
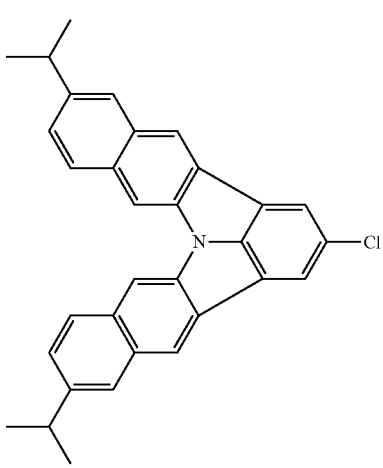

89
-continued
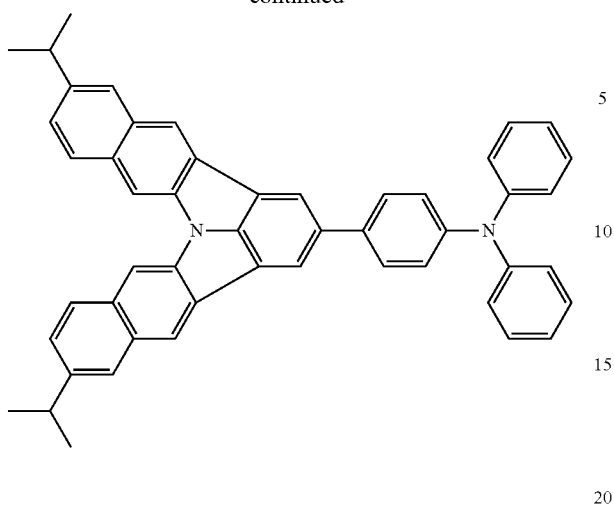
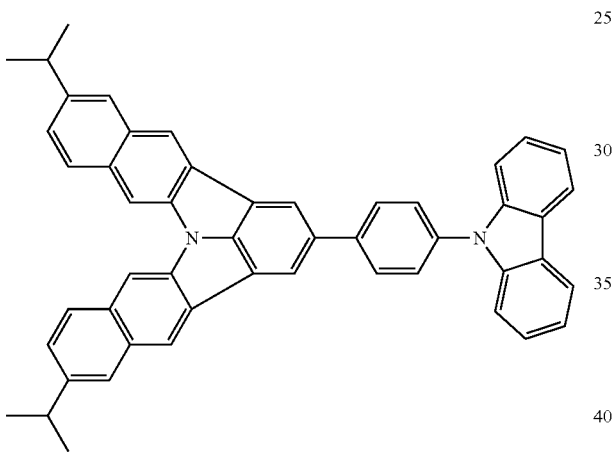
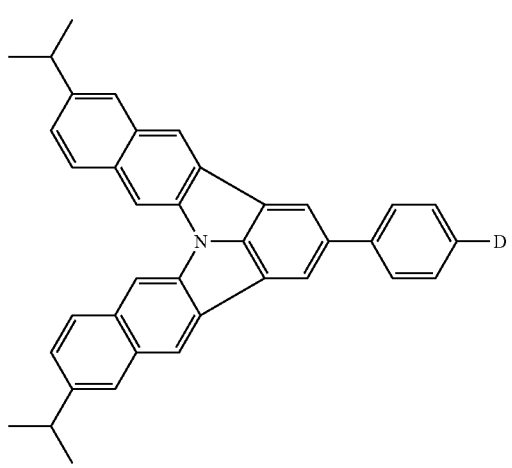
90
-continued
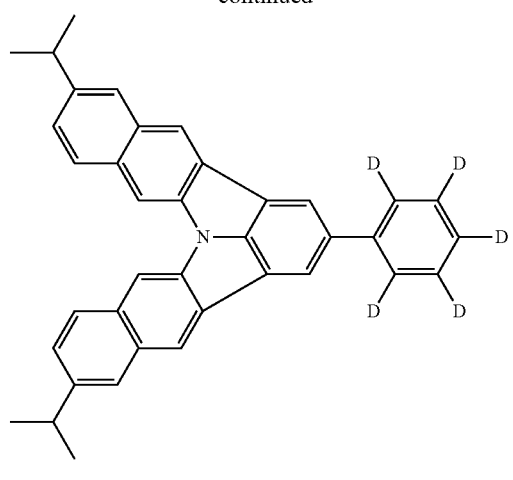
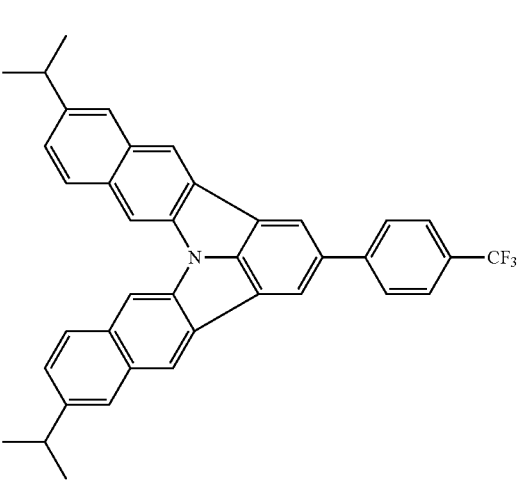
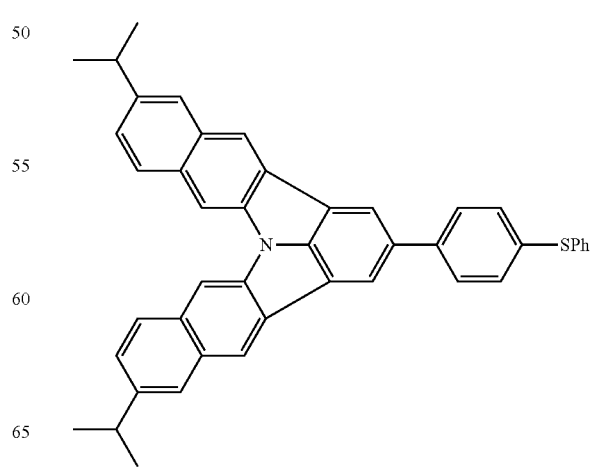

91
-continued
92
-continued
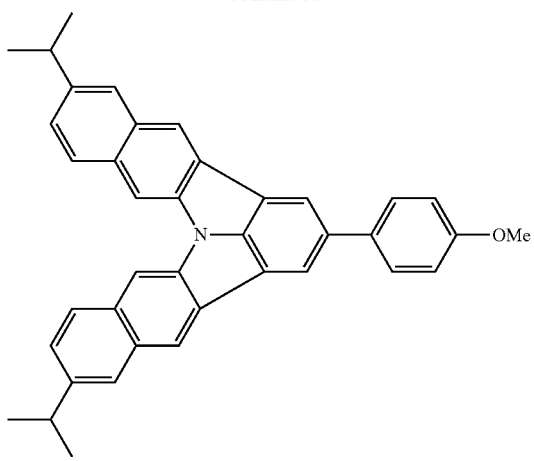
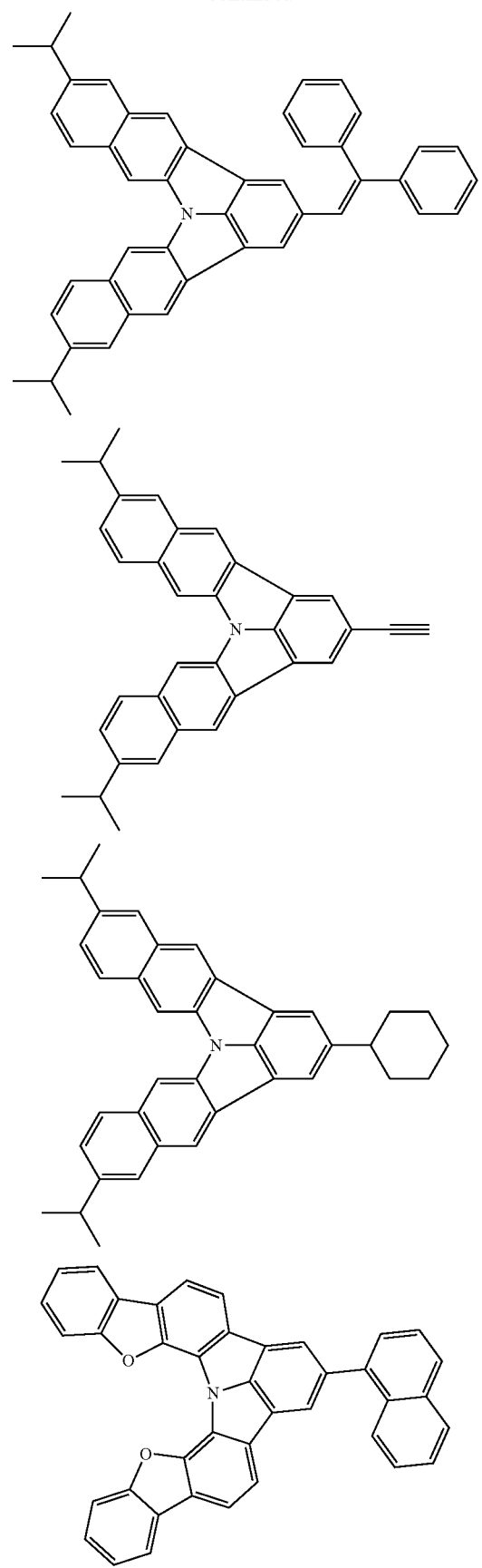

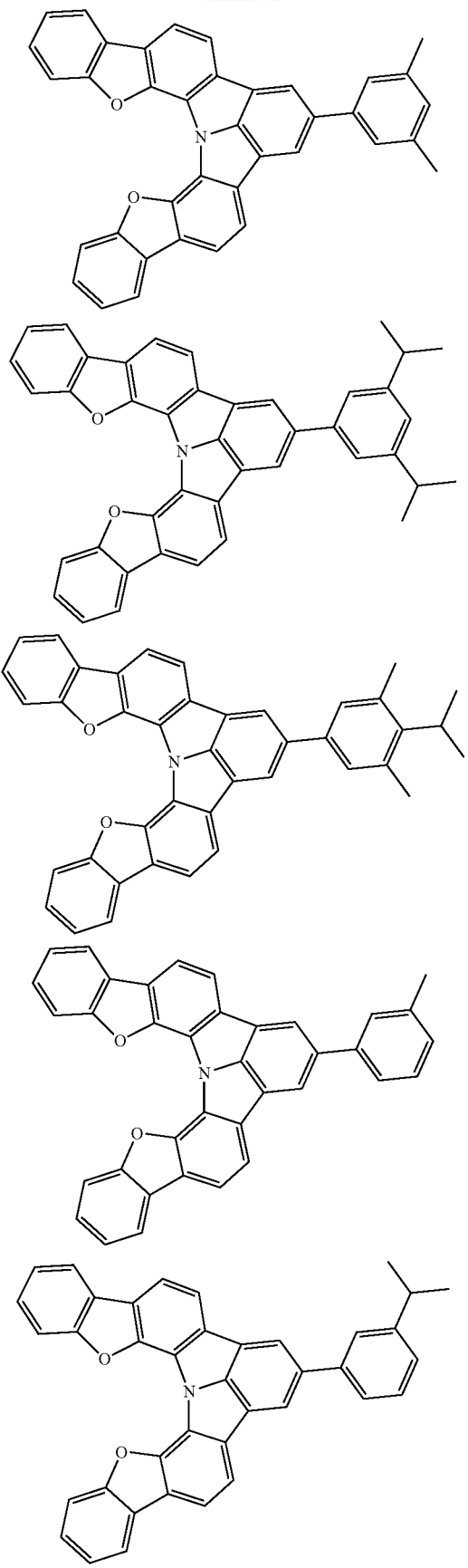
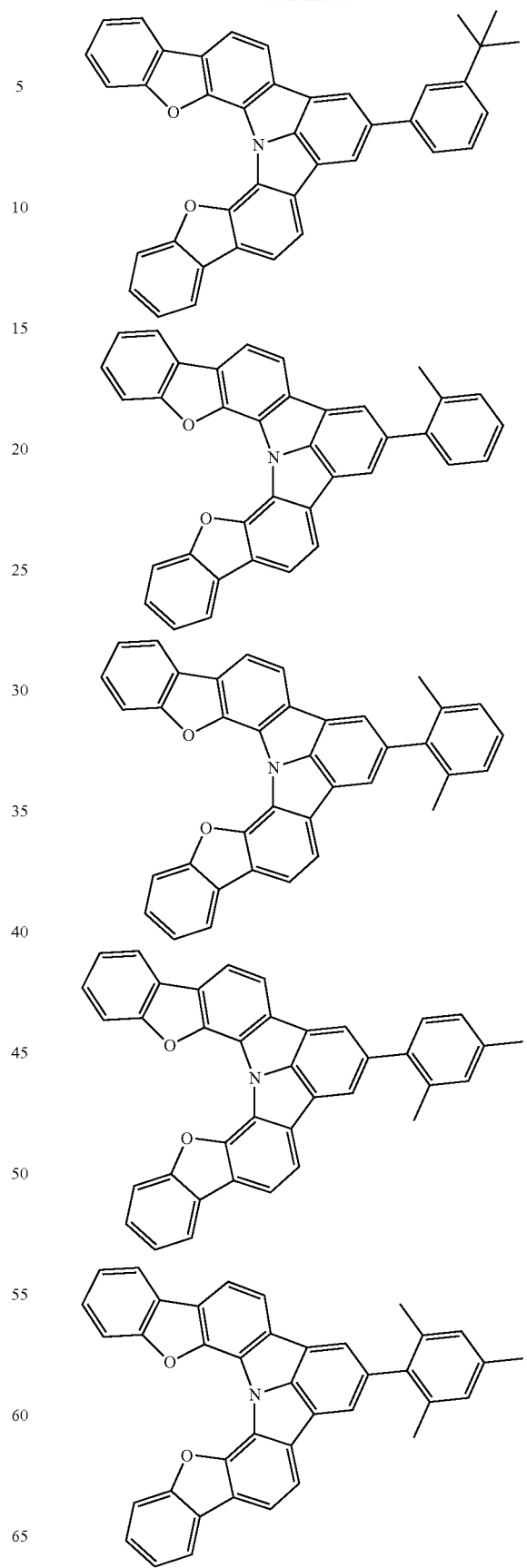

95
-continued
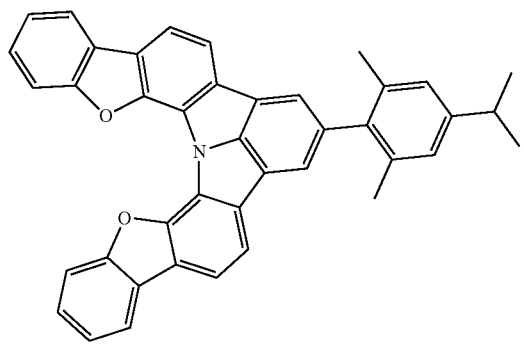
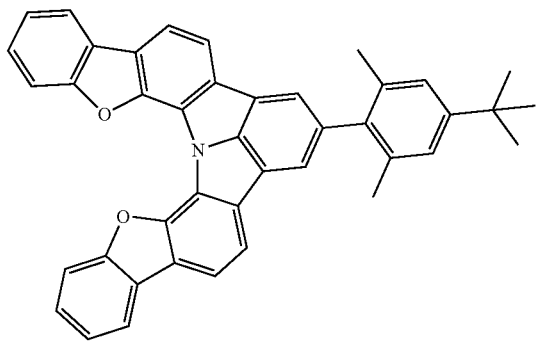
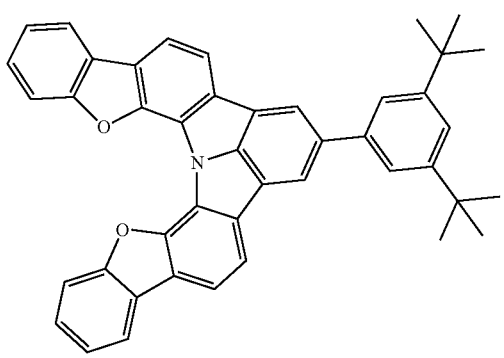
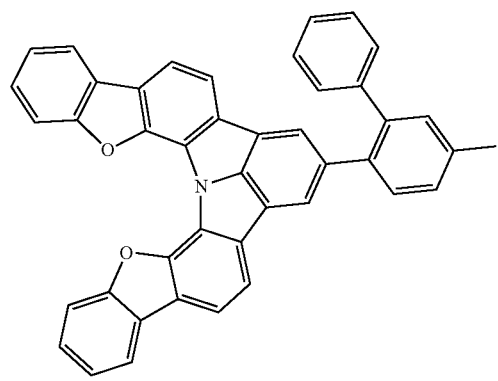
96
-continued
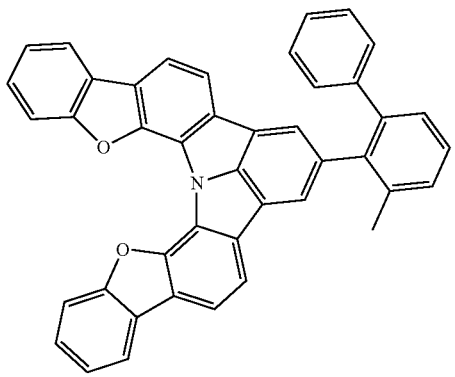
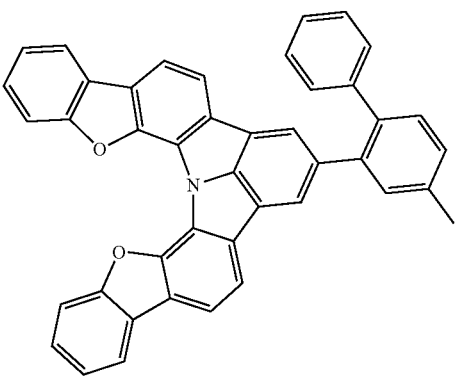
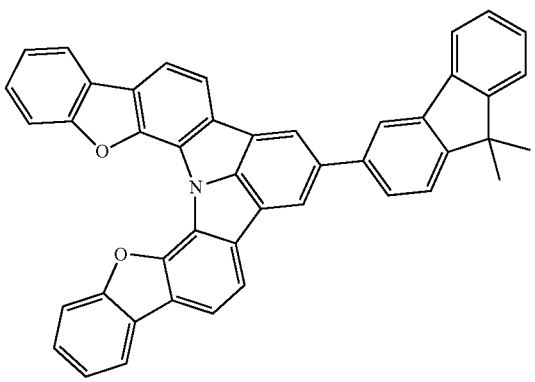
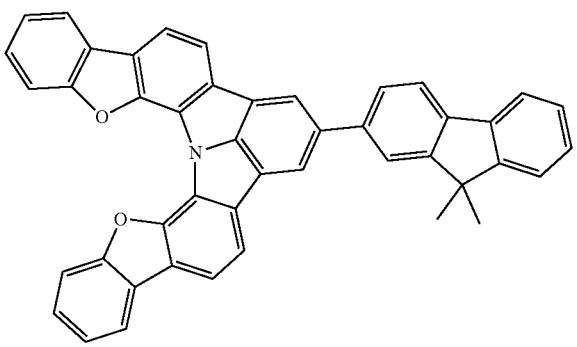

97
-continued
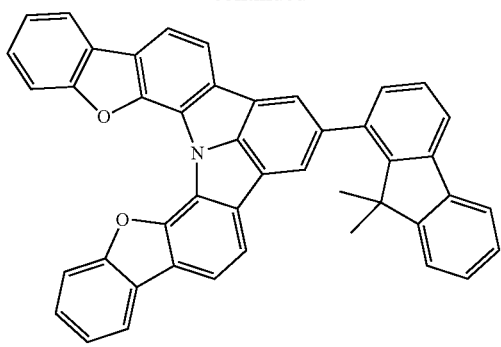
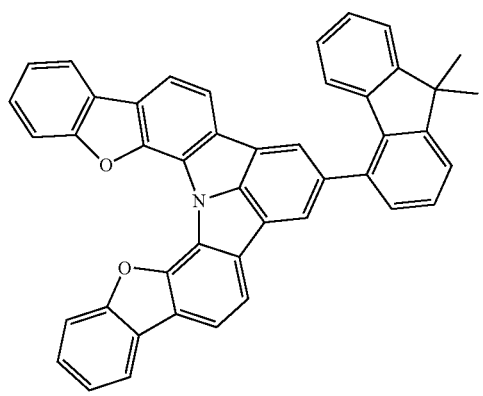
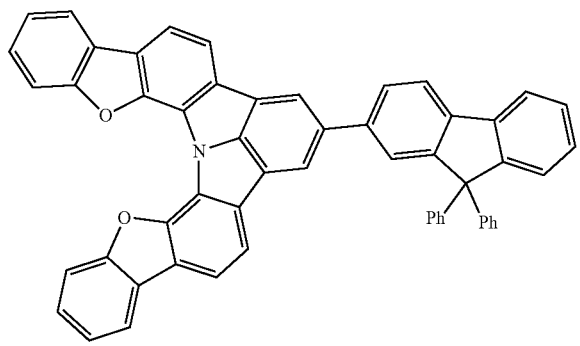
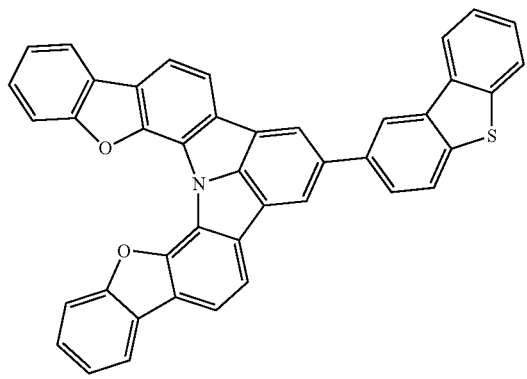
98
-continued
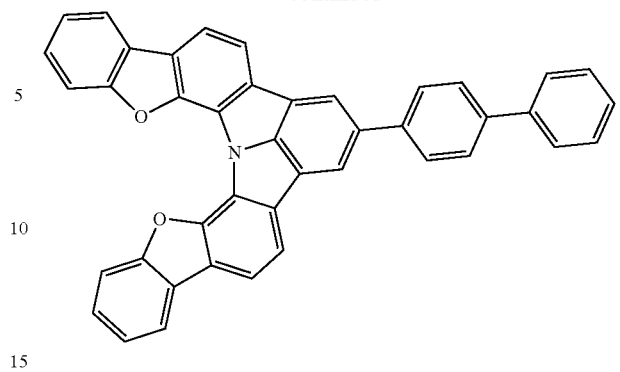
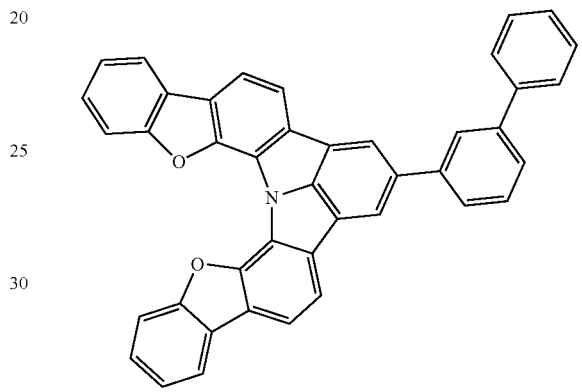
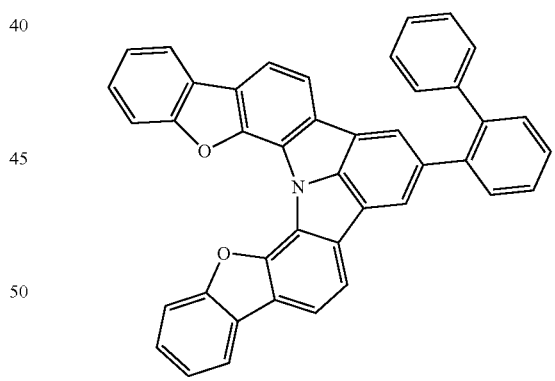
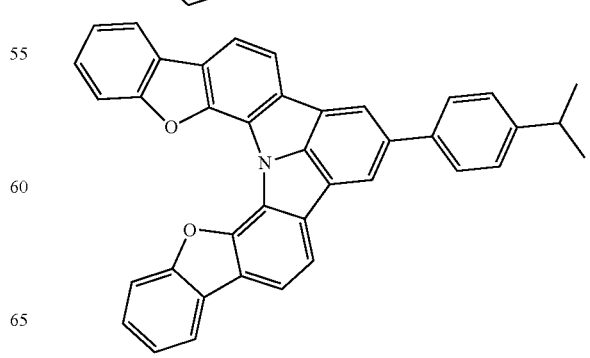

99
-continued
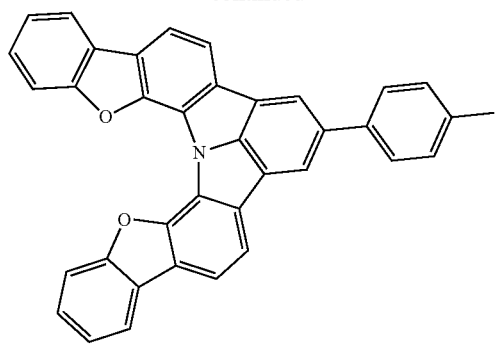
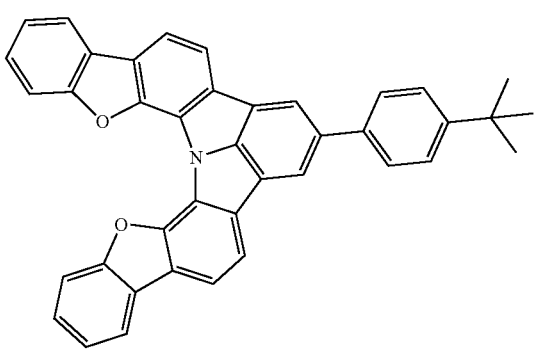
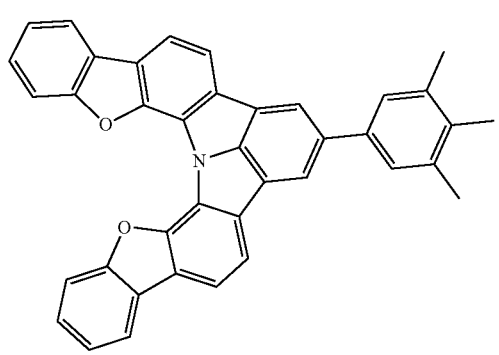
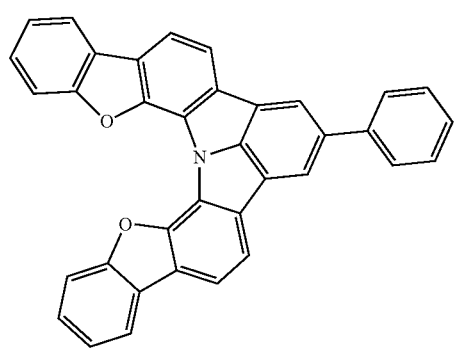
100
-continued
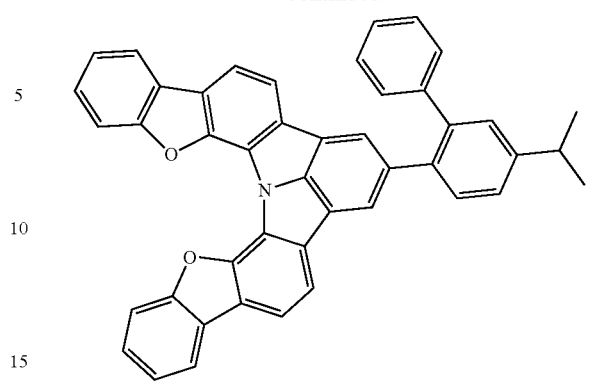
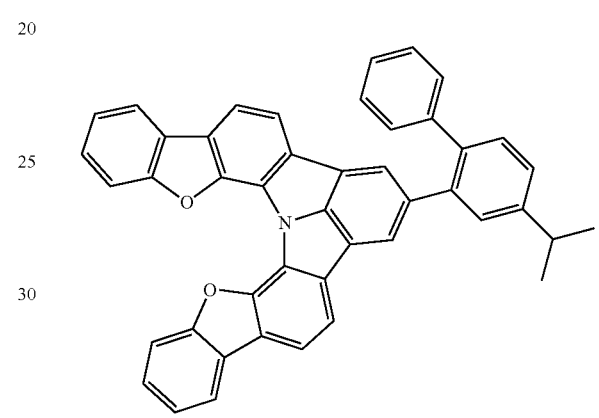
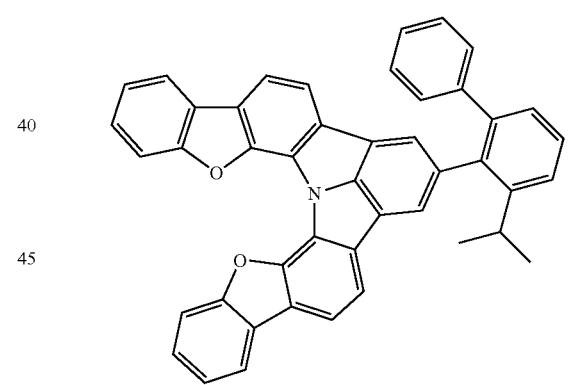
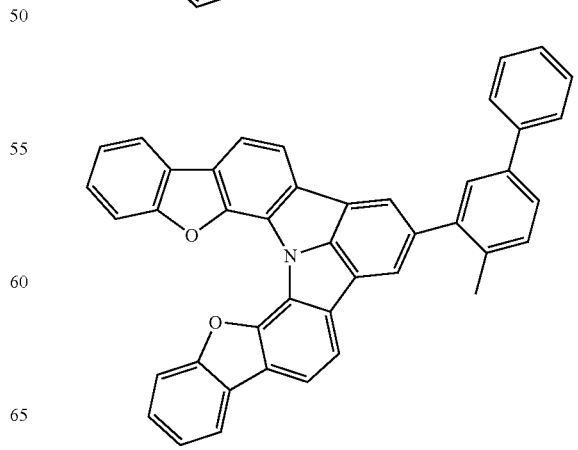

101
-continued
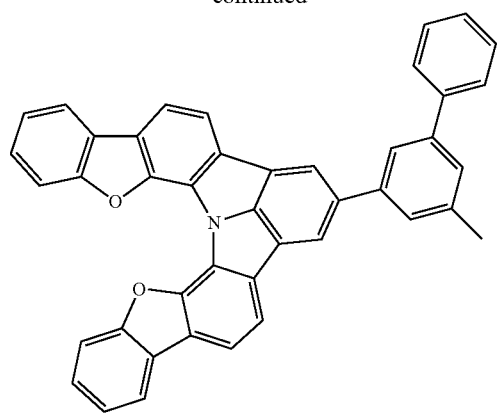
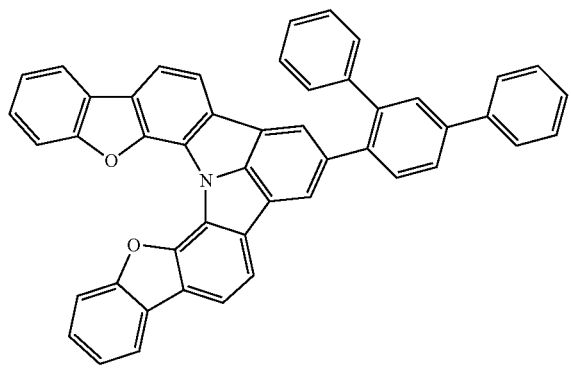
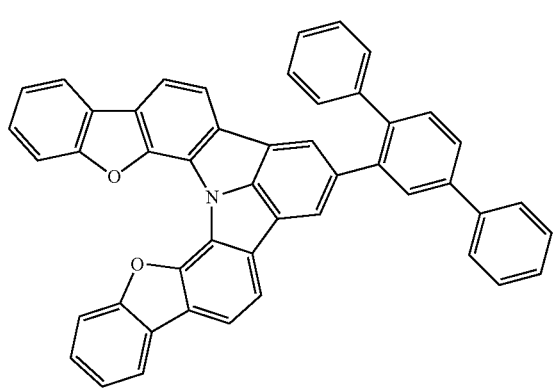
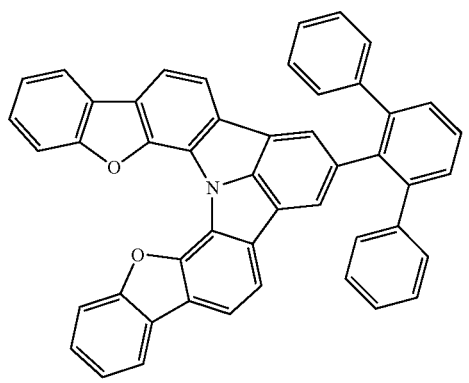
102
-continued
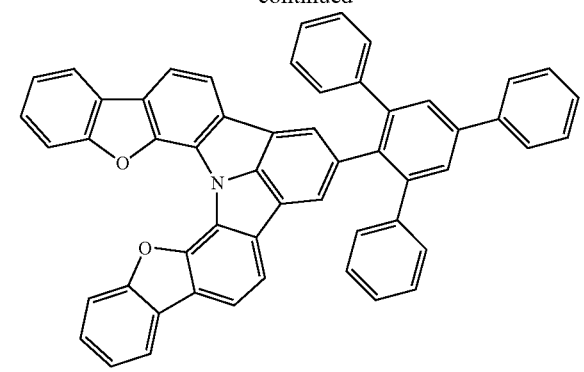
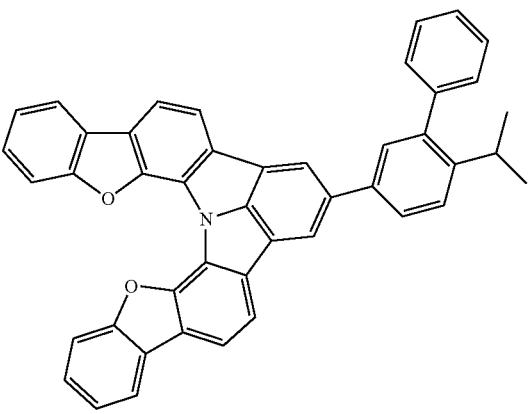
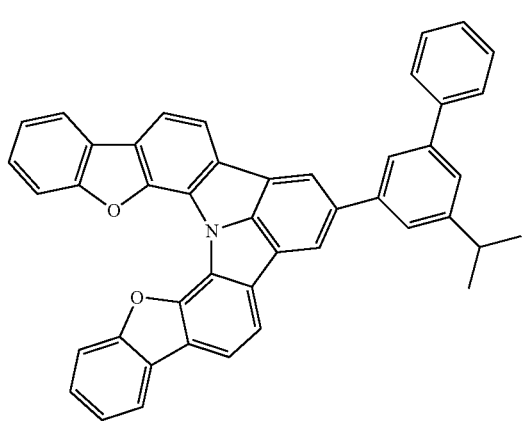
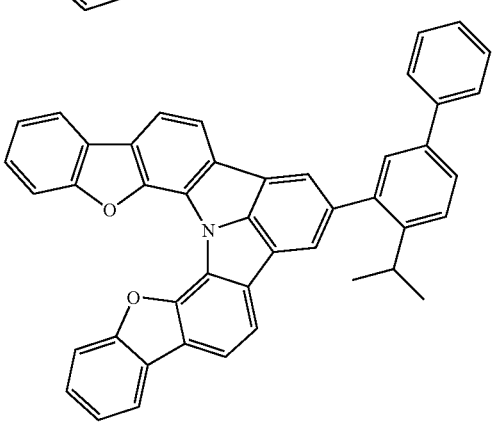

103
-continued
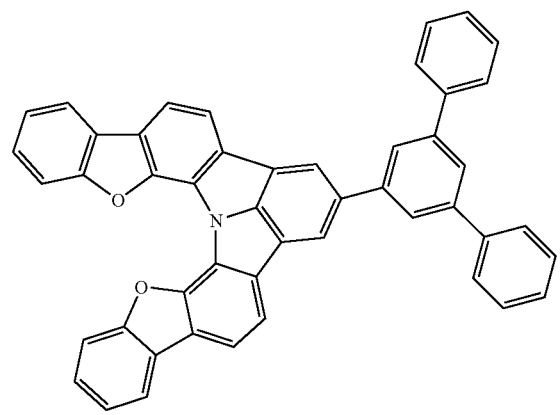
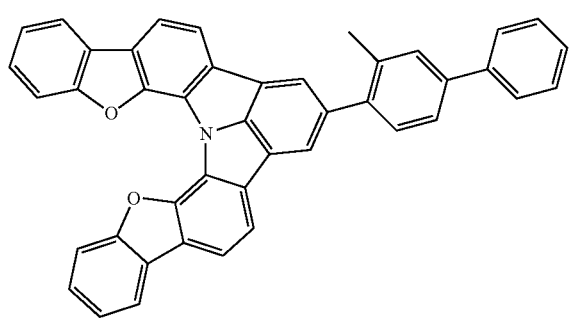
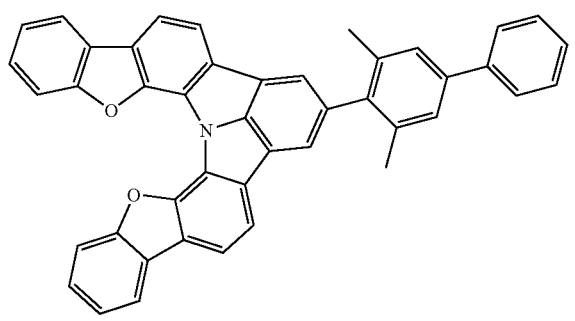
104
-continued
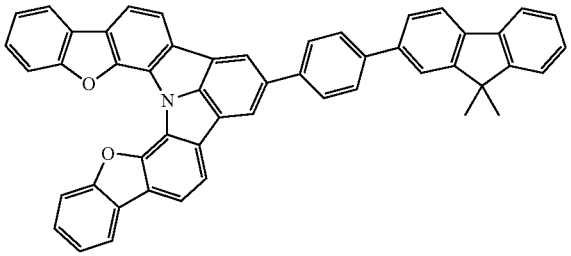
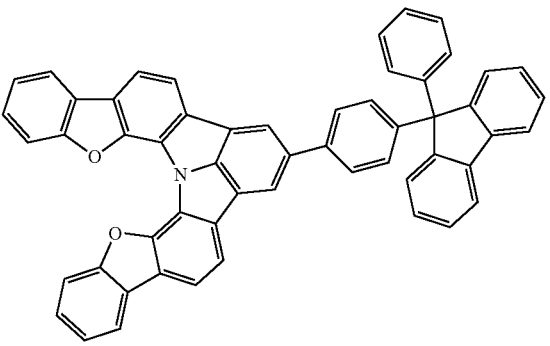
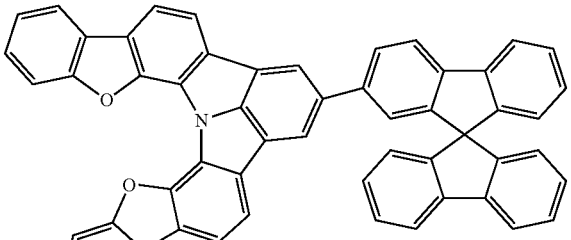
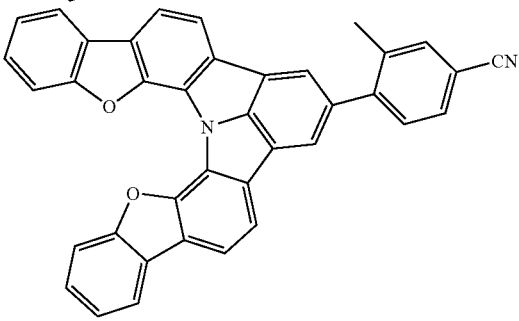
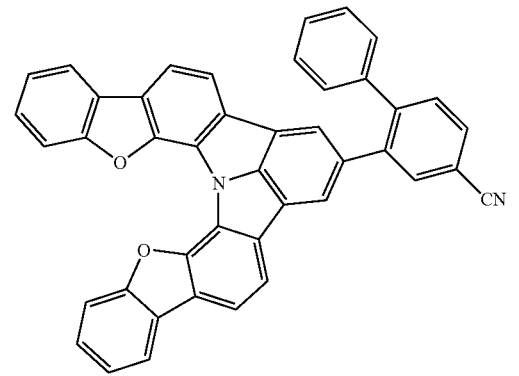

105
-continued
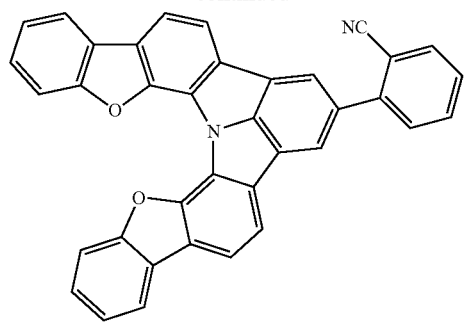
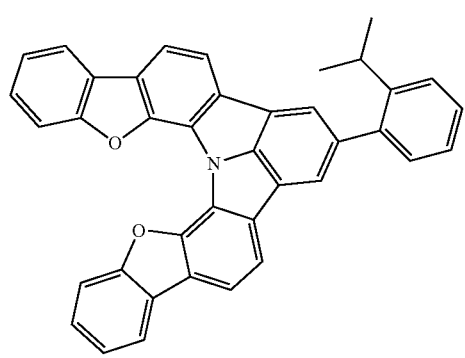
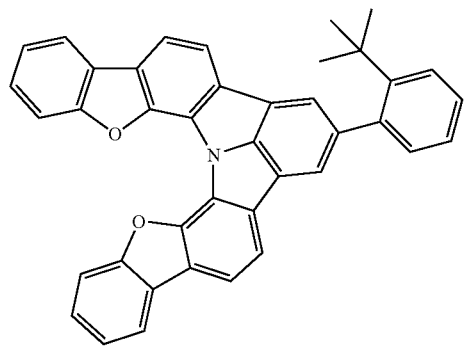
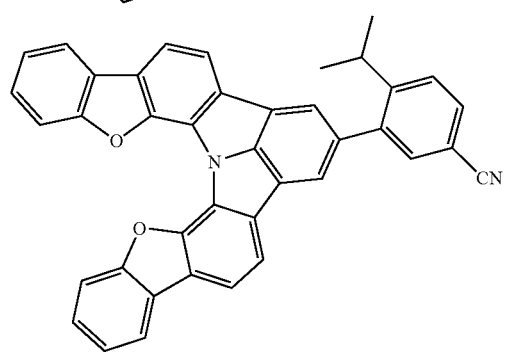
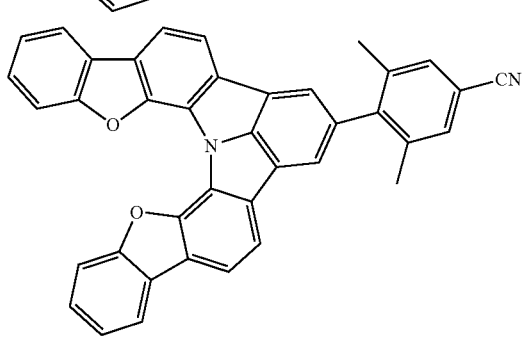
106
-continued
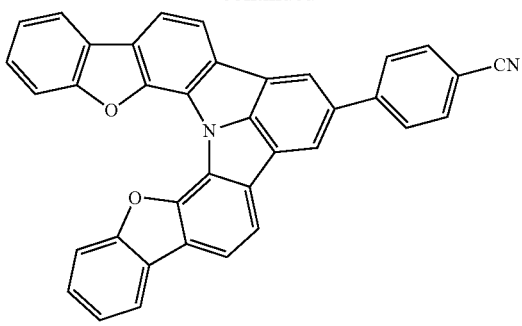
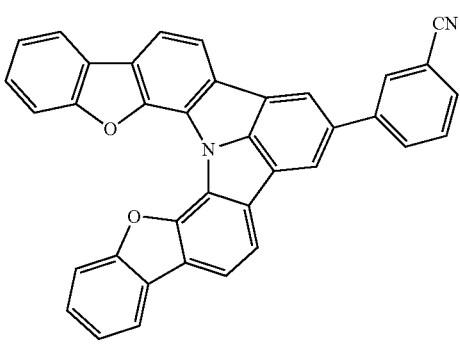
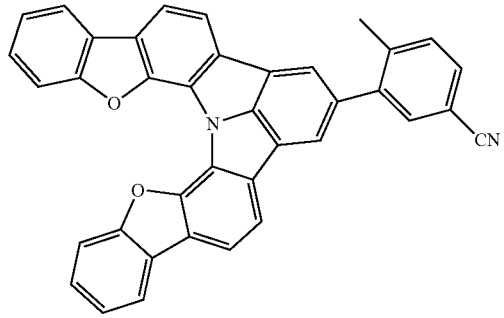
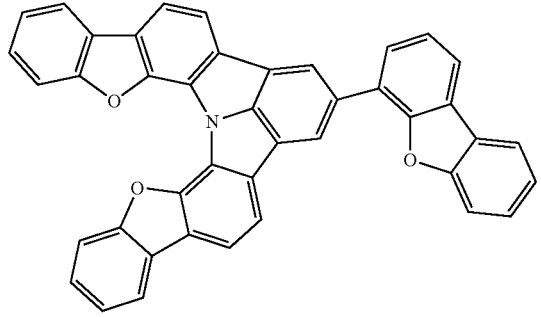
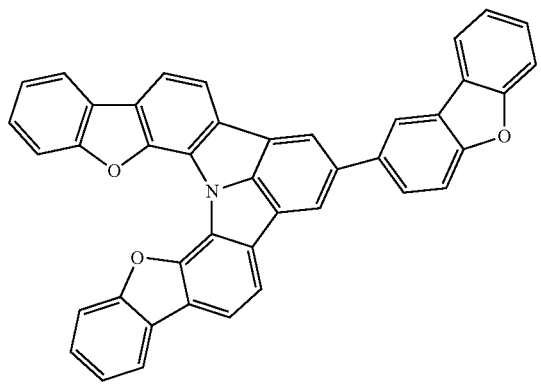

107
-continued
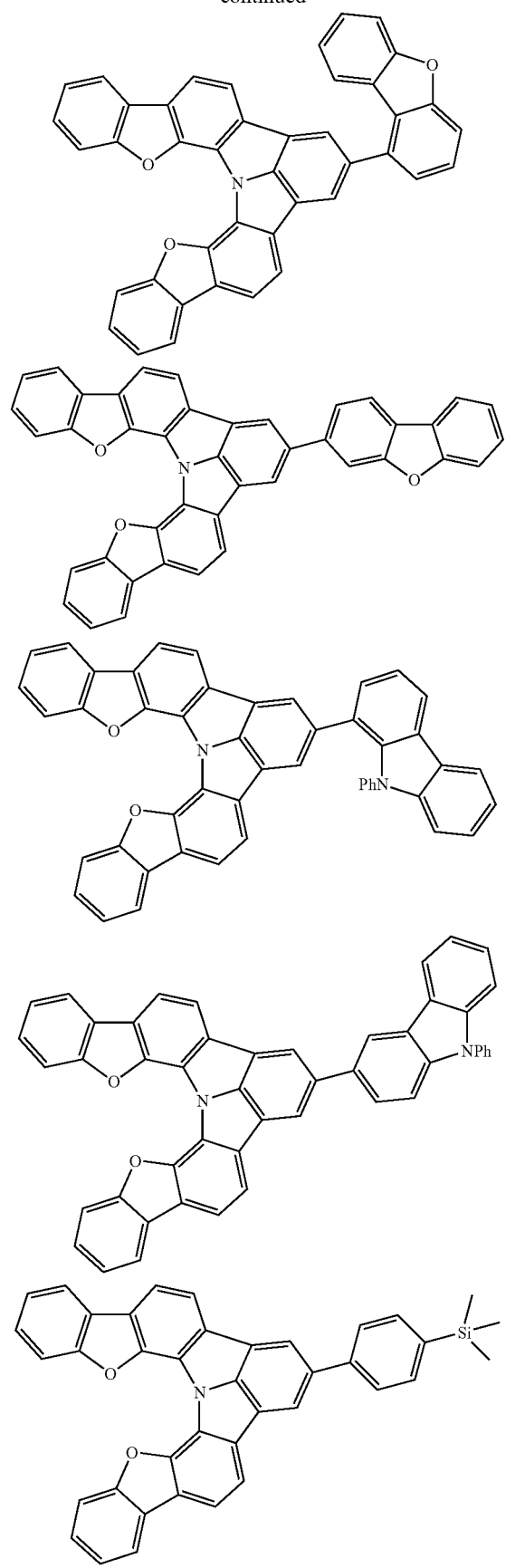
108
-continued
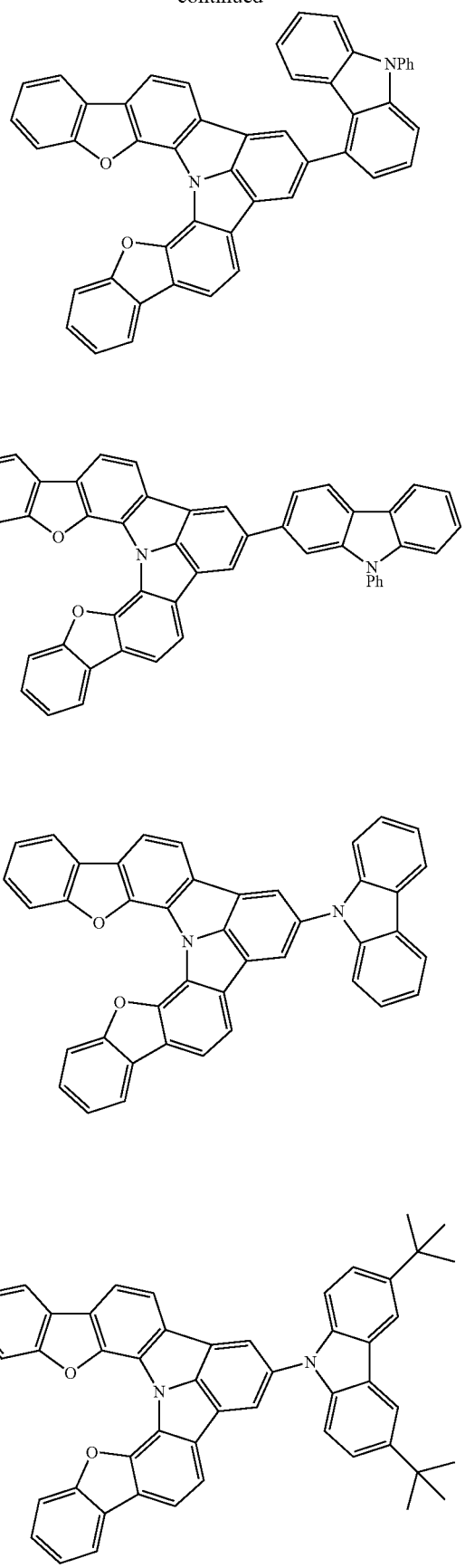

109
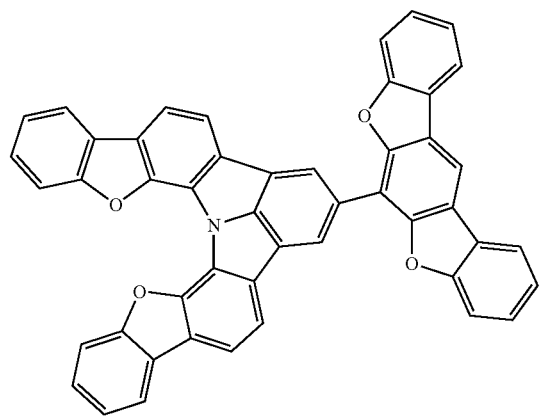
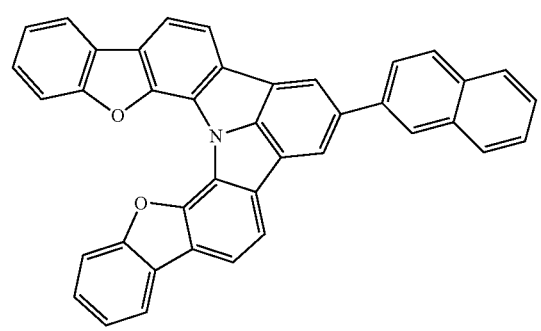
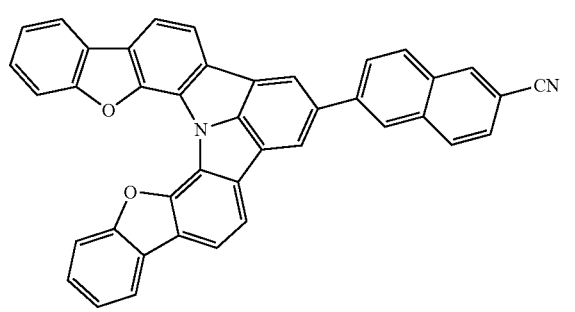
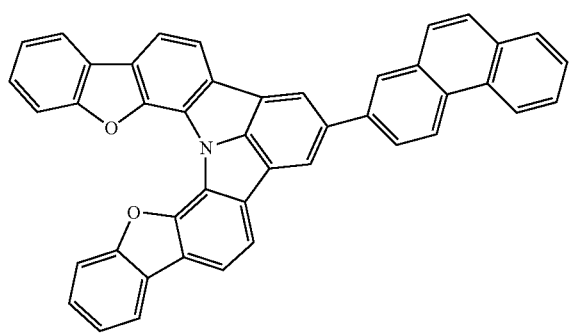
110
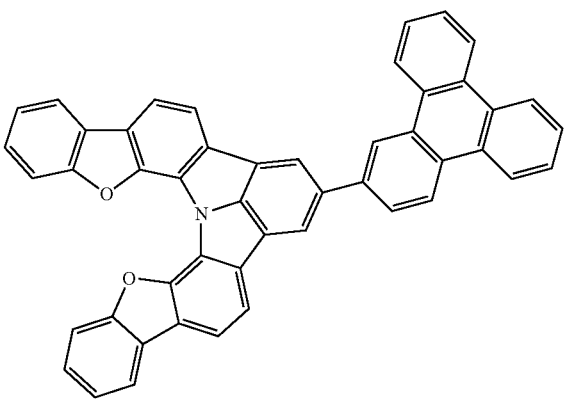
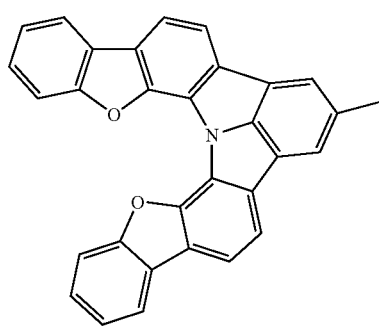
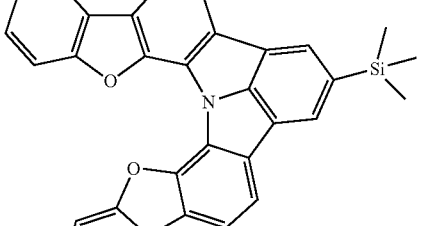
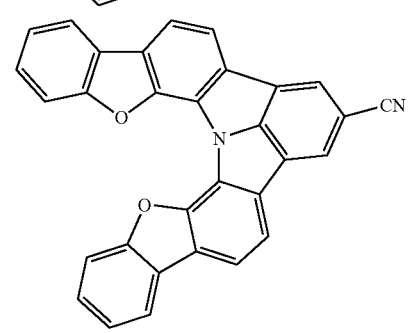
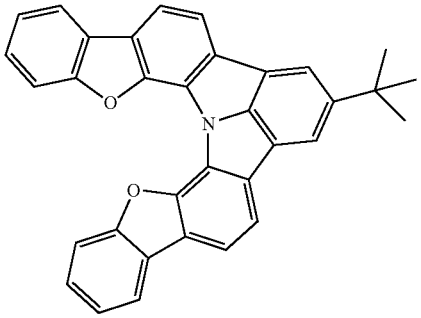

111
-continued
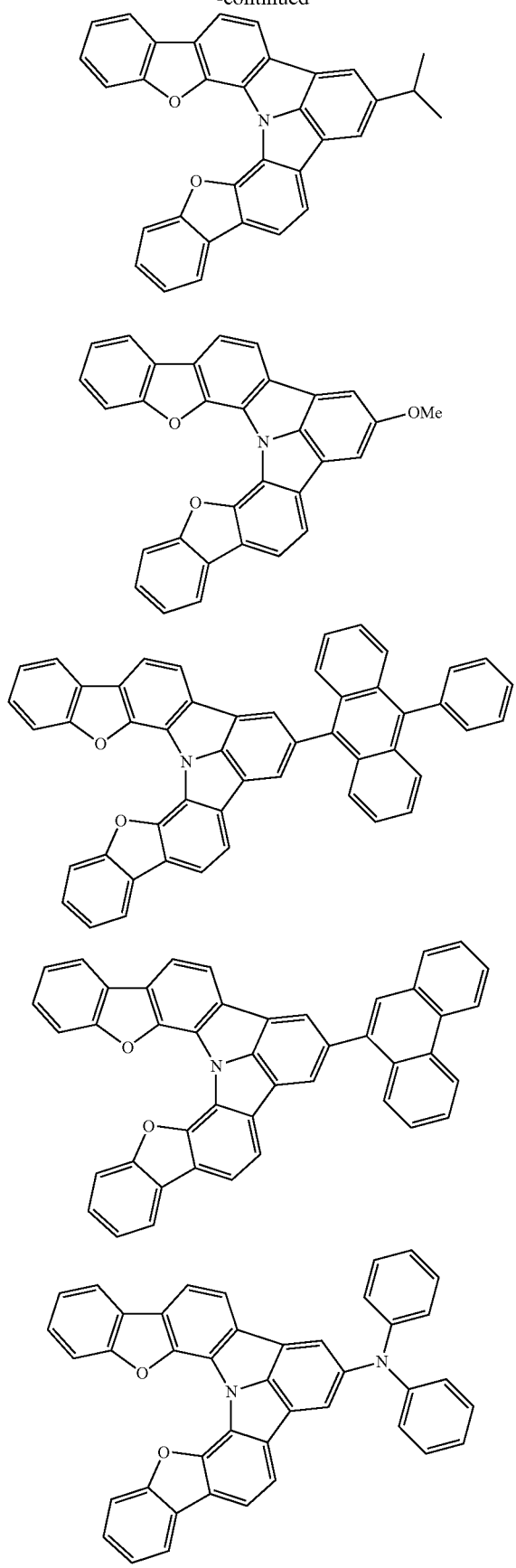
112
-continued
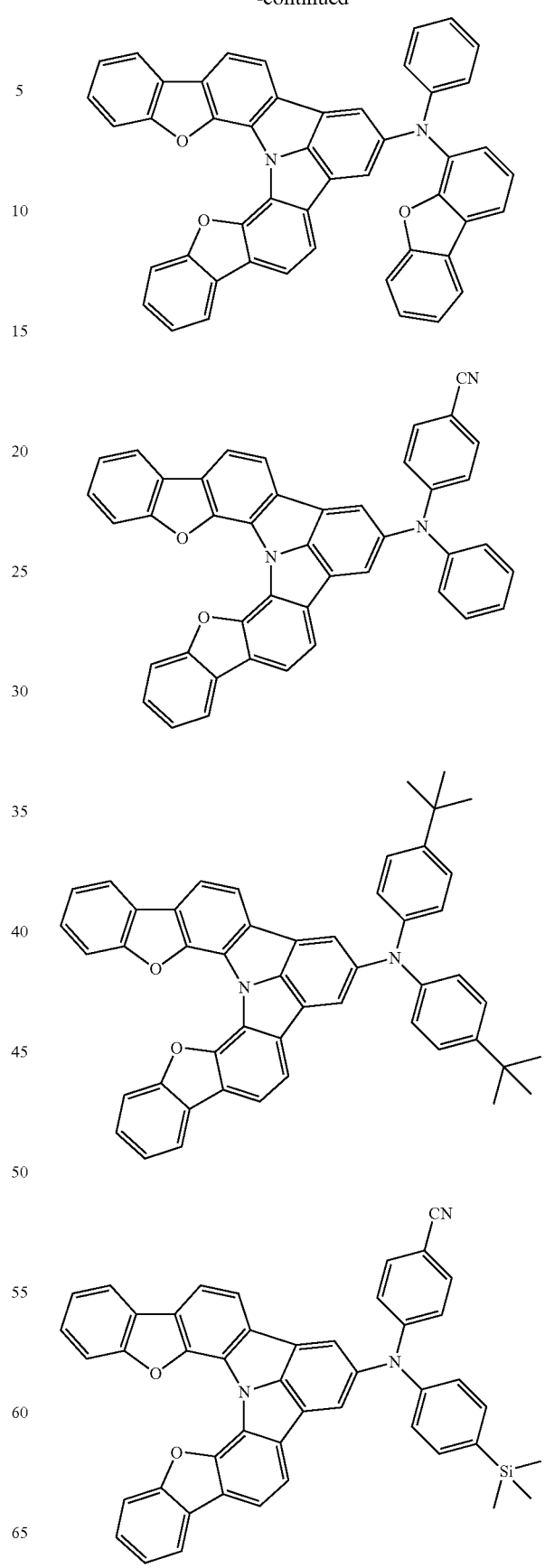

113
-continued
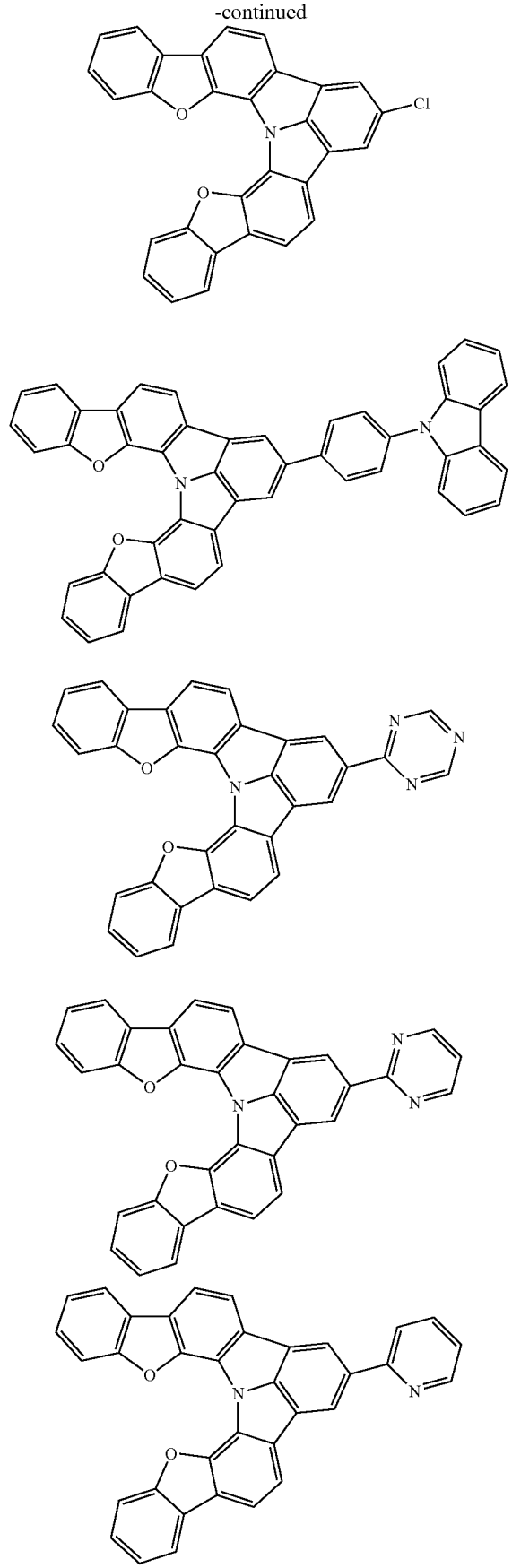
114
-continued
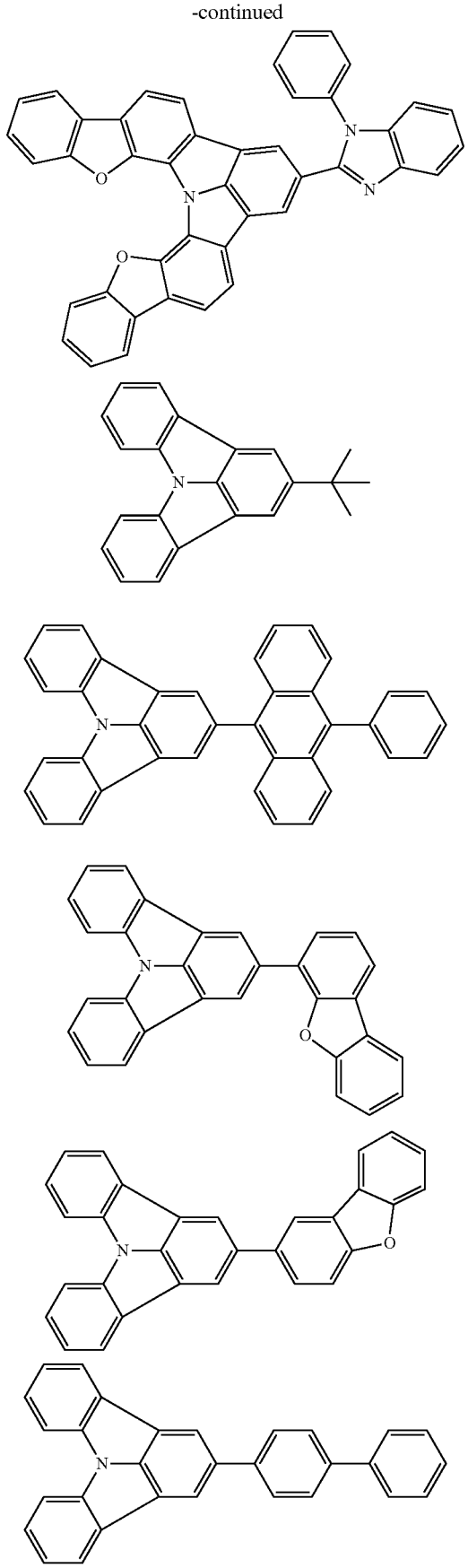

115
-continued
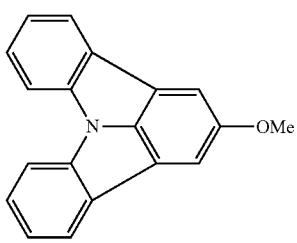
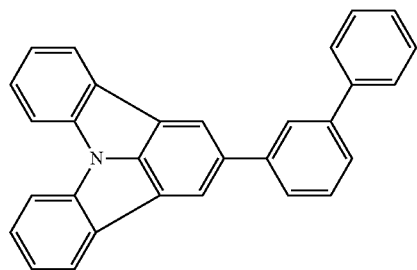
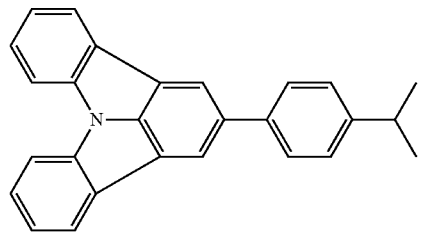
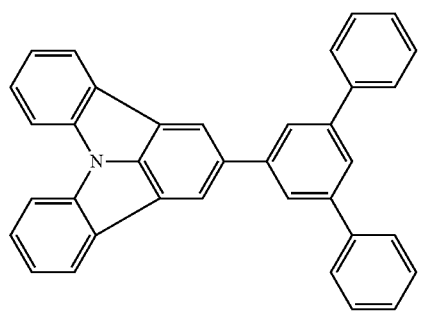
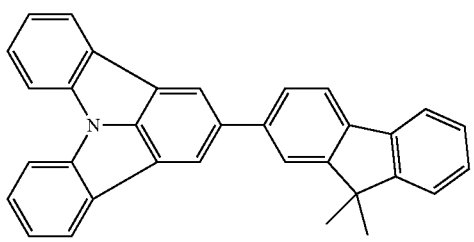
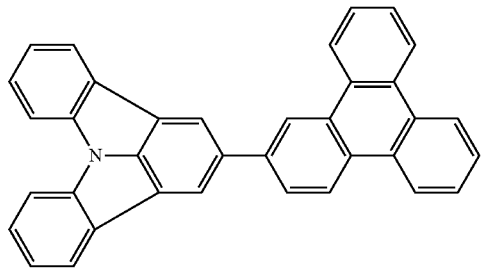
116
-continued
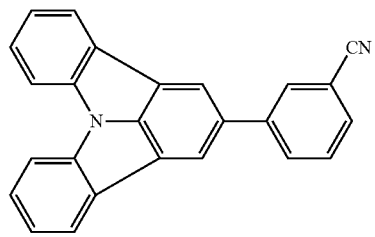
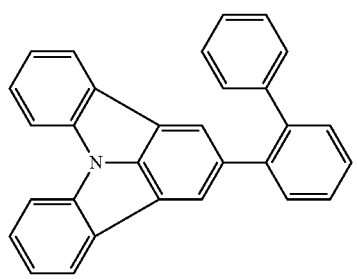
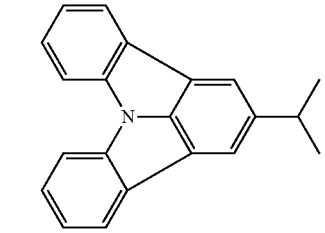
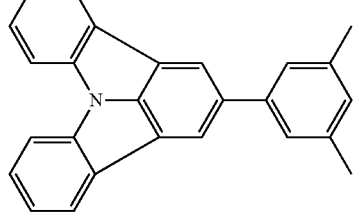
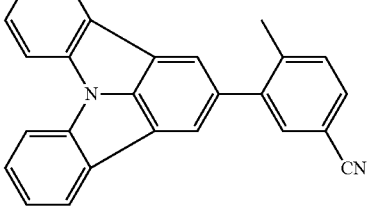
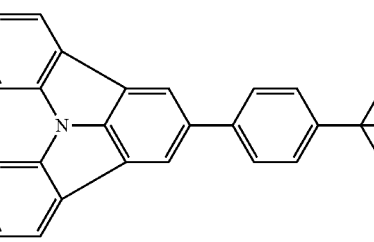
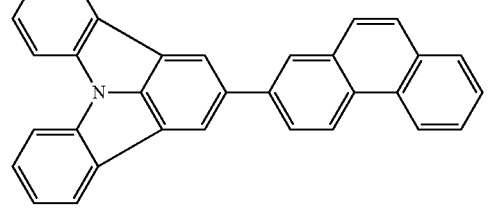

117
-continued
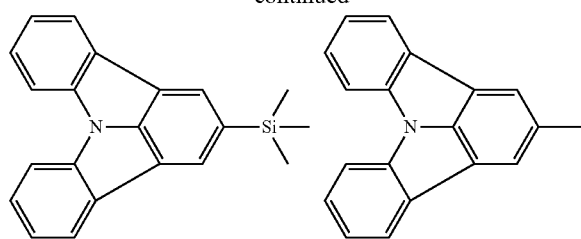
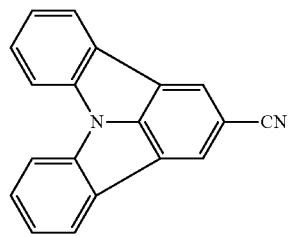
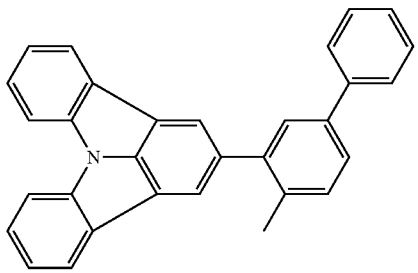
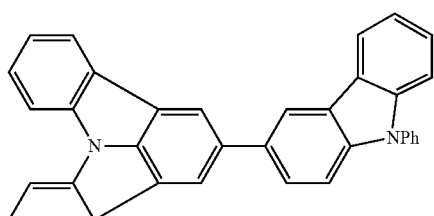
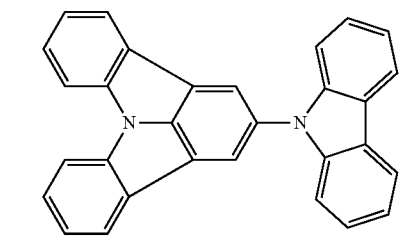
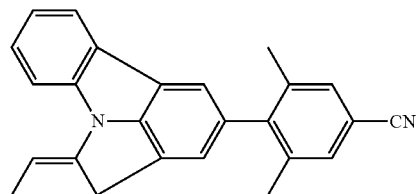
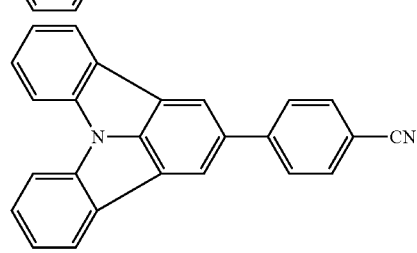
118
-continued
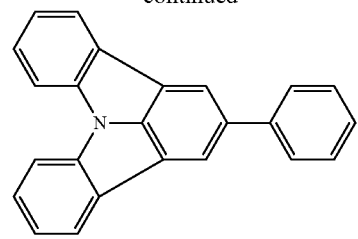
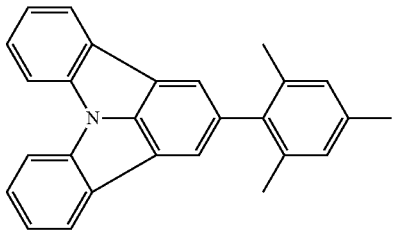
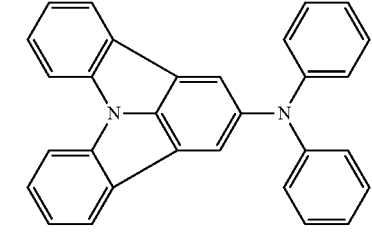
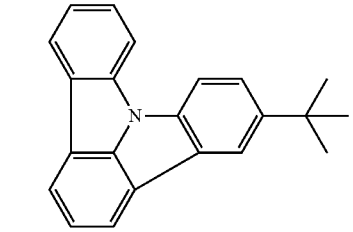
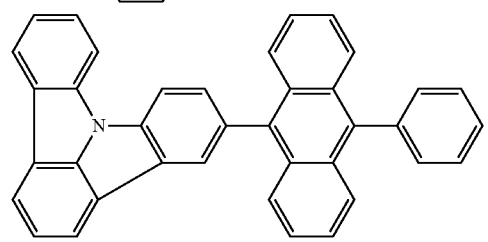
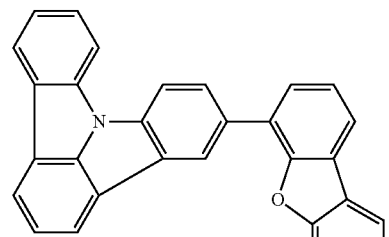
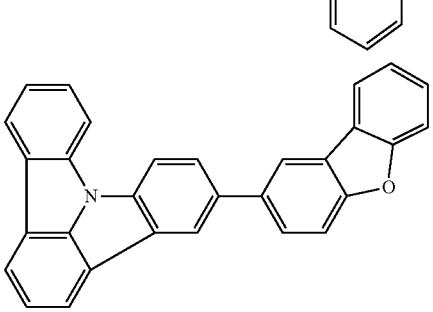

119
-continued
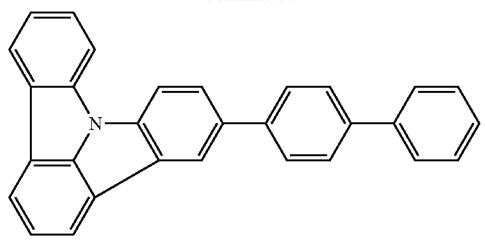
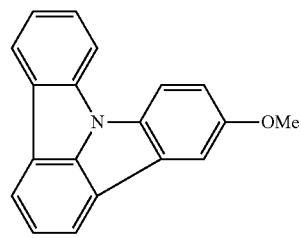
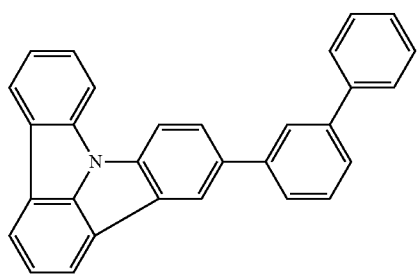
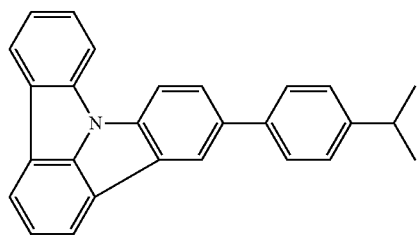
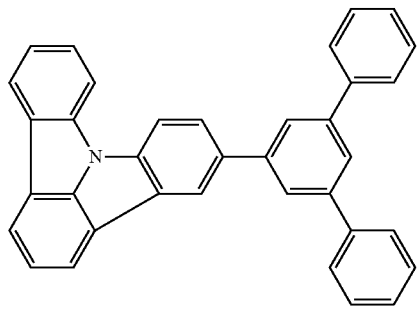
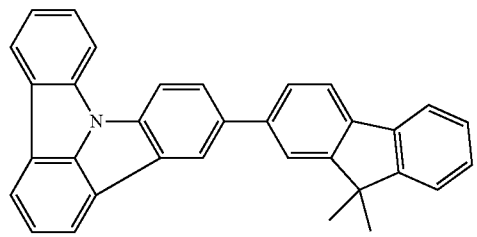
120
-continued
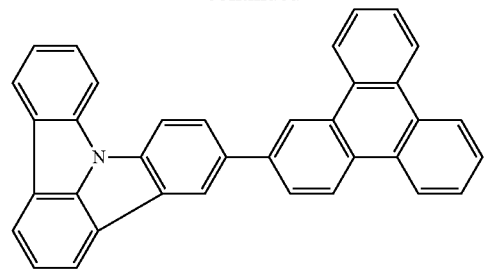
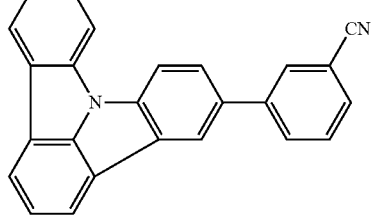
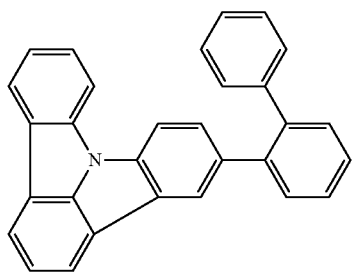
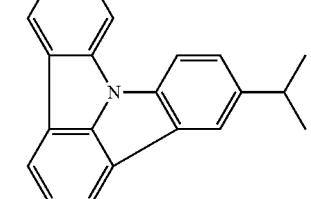
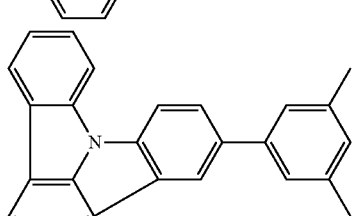
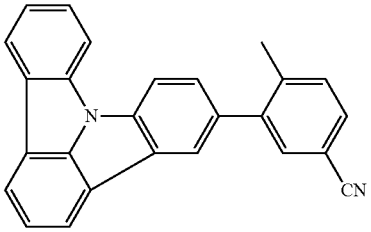
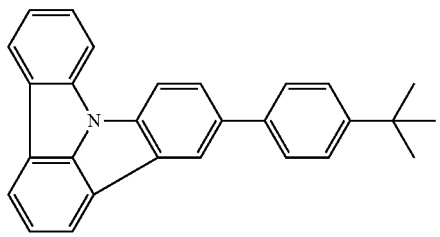

121
-continued
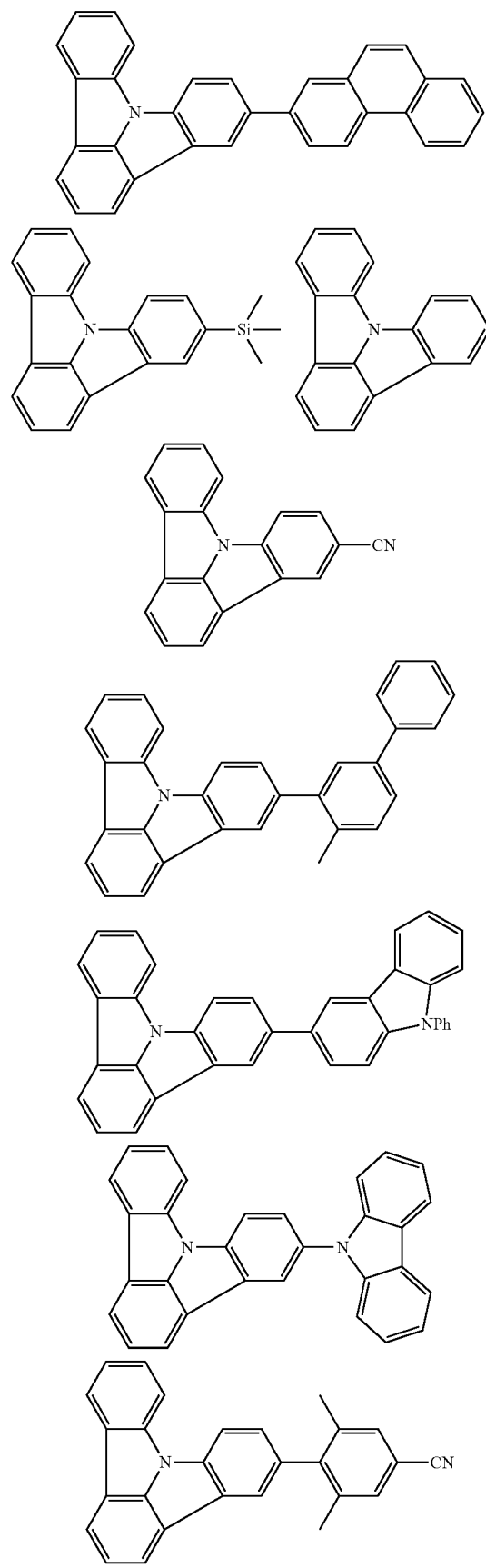
122
-continued
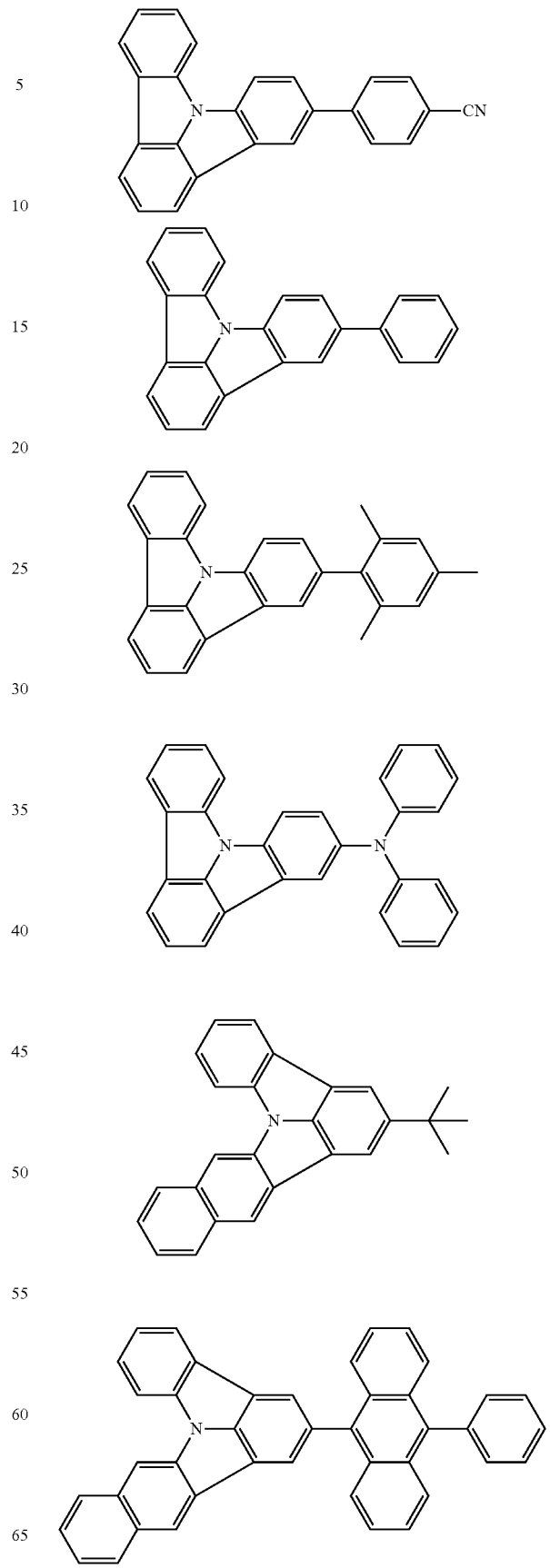

123
-continued
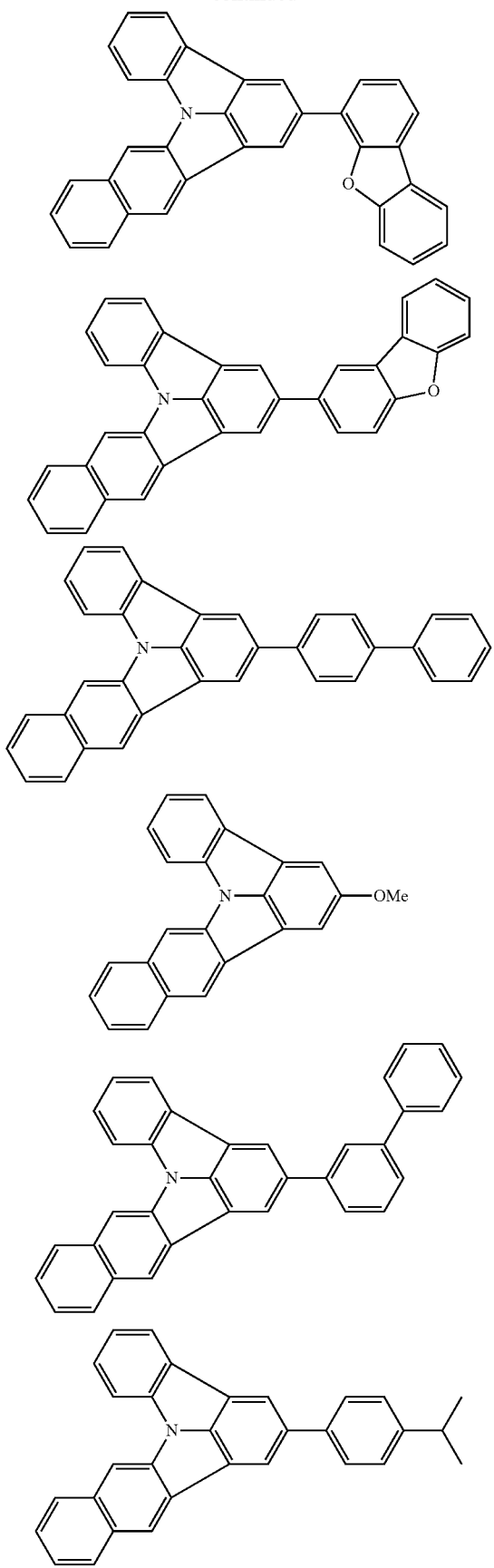
124
-continued
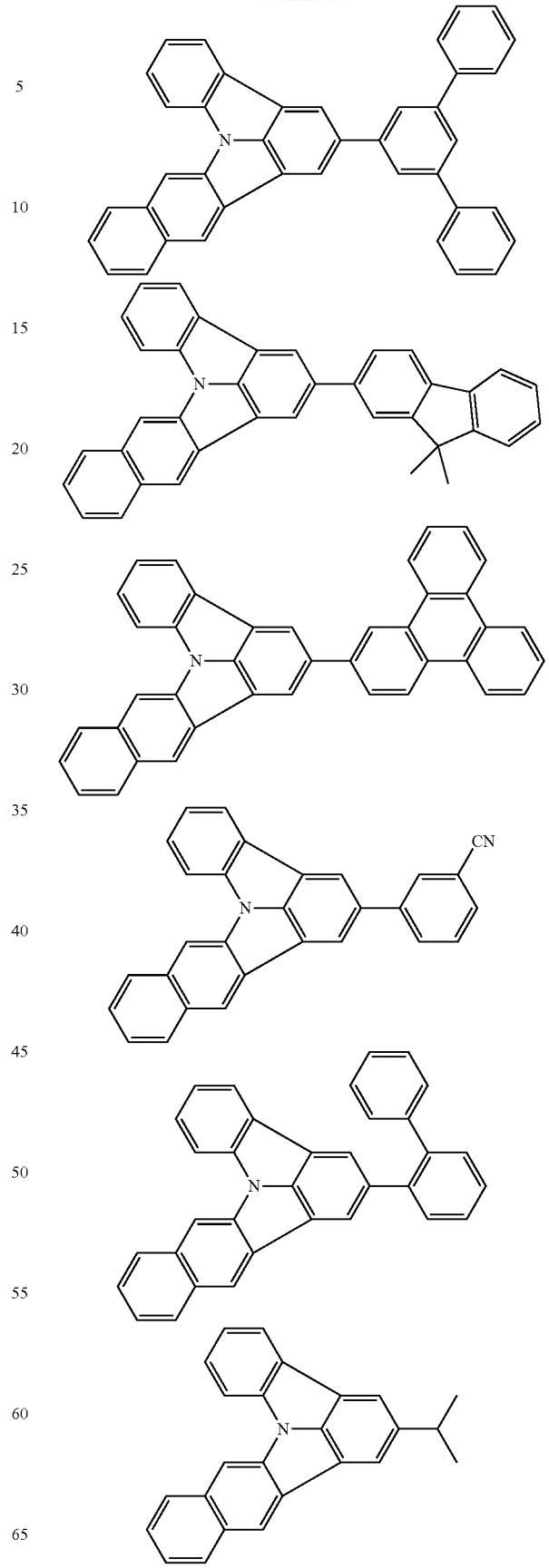

125
-continued
126
-continued
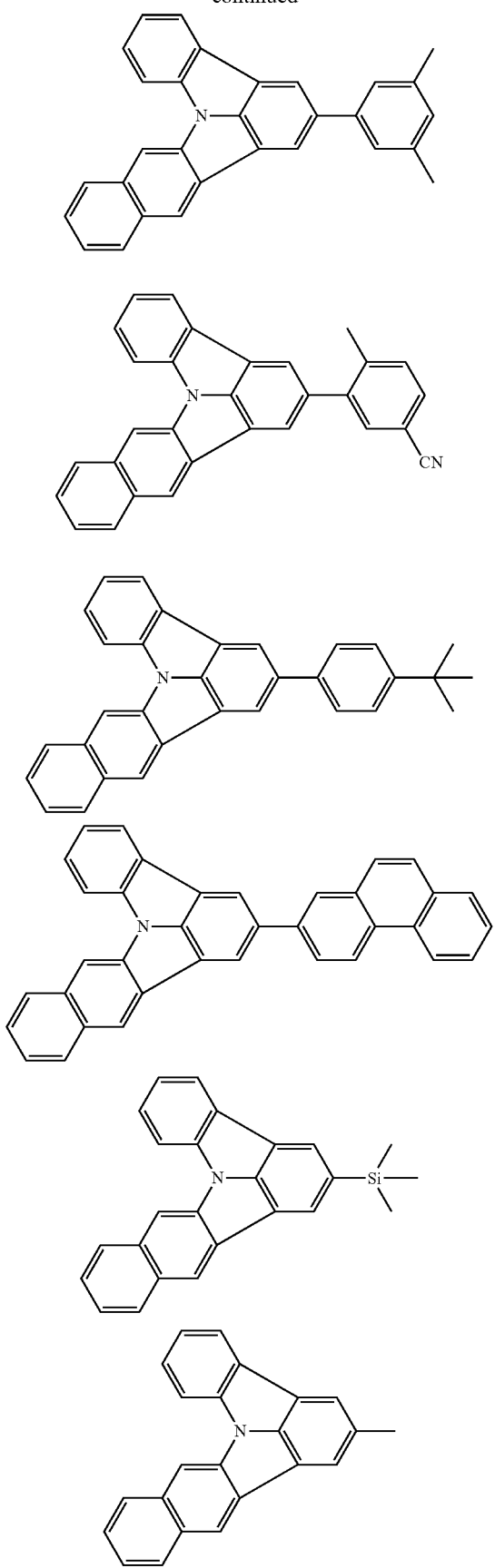
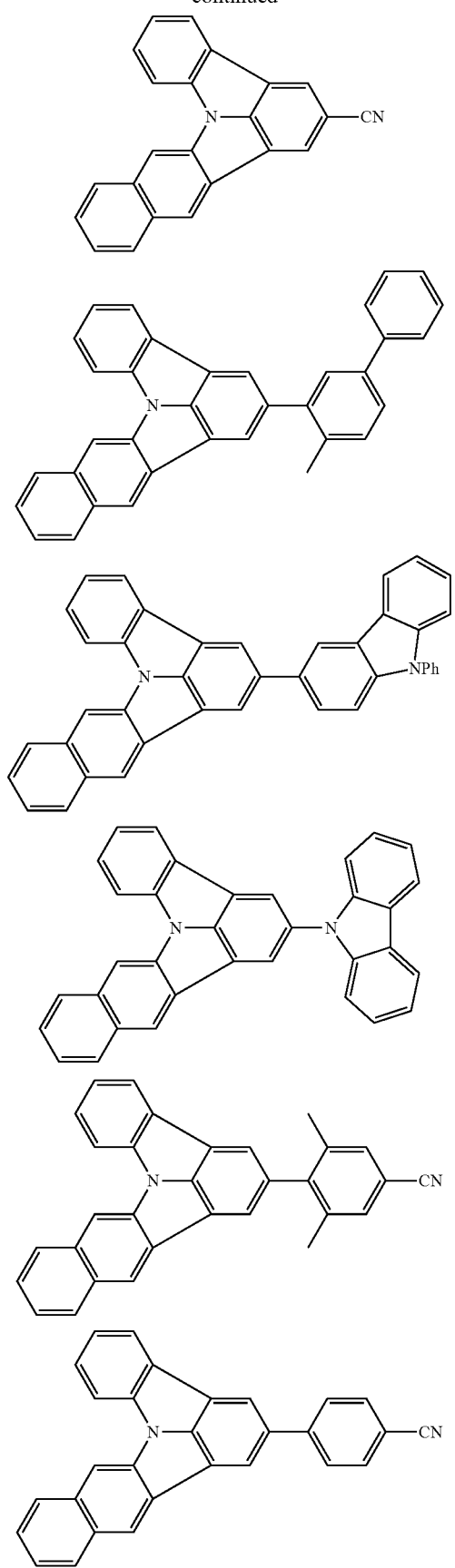

127
-continued
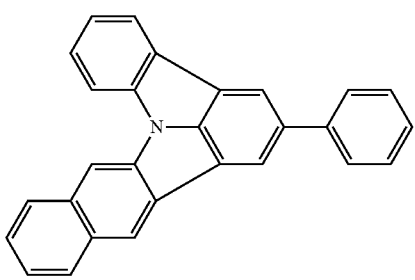
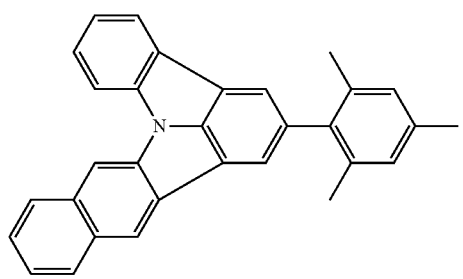
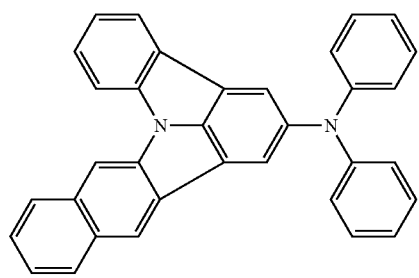
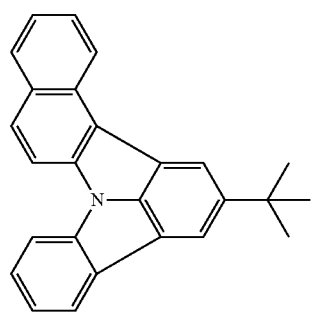
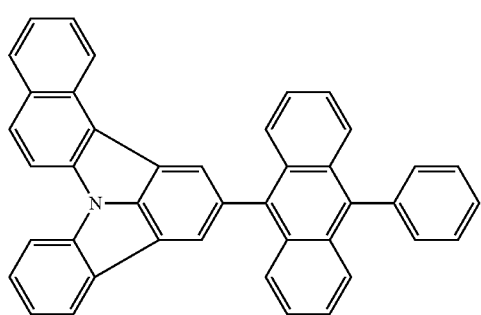
128
-continued
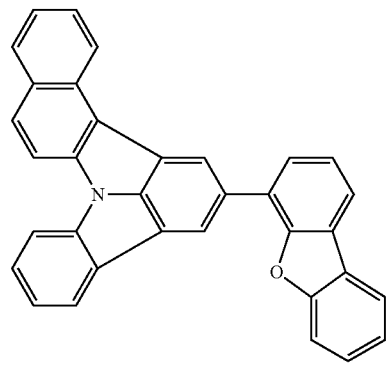
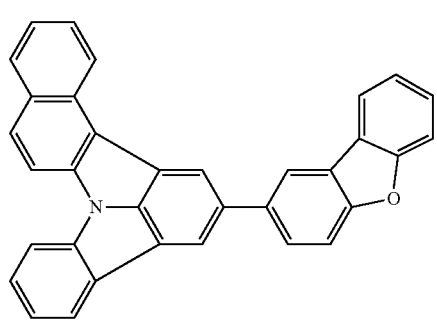
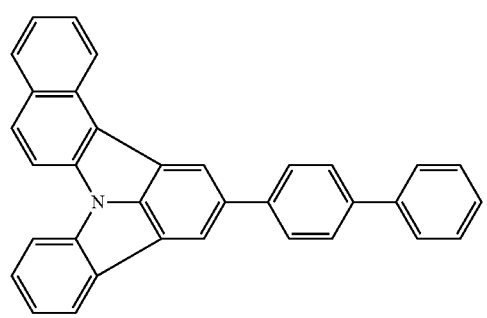
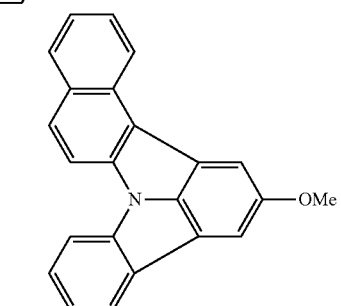
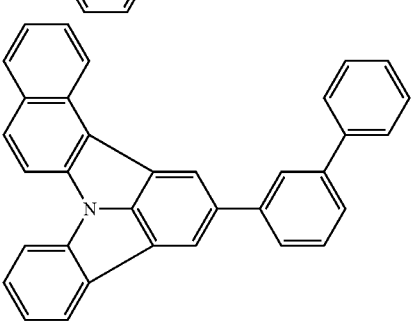

129
-continued
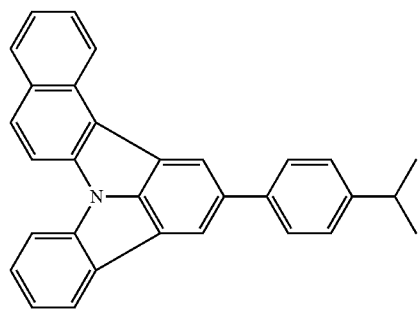
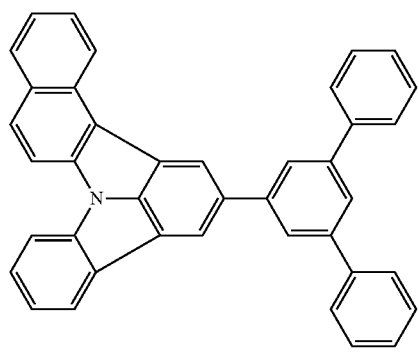
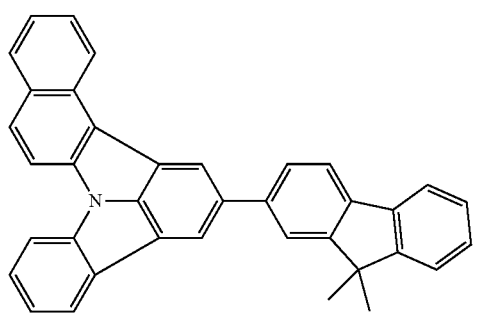
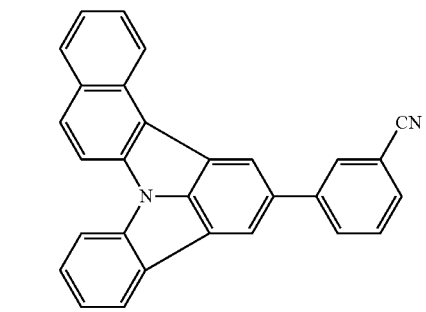
130
-continued
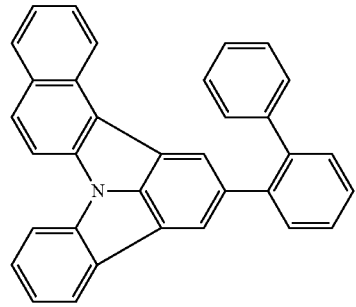
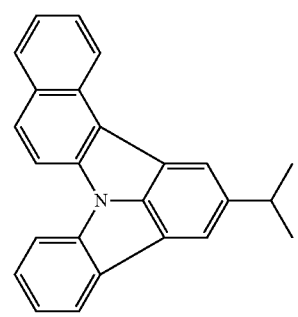
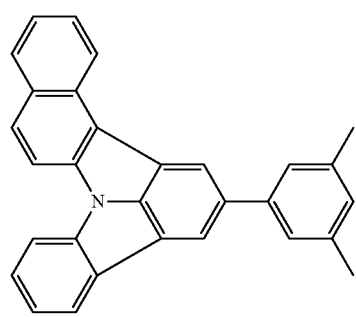
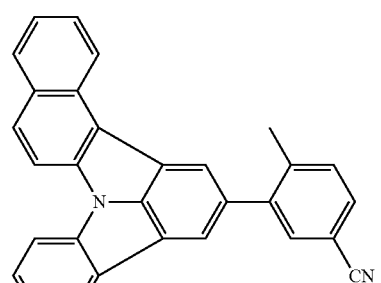
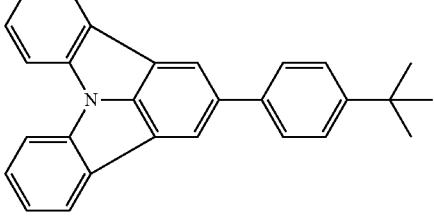

131
-continued
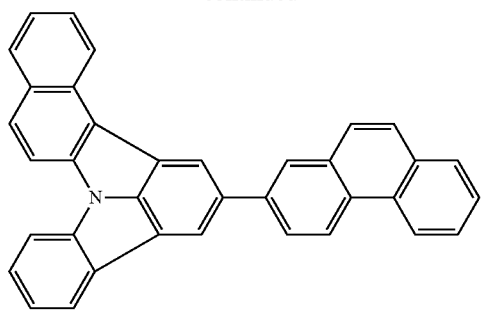
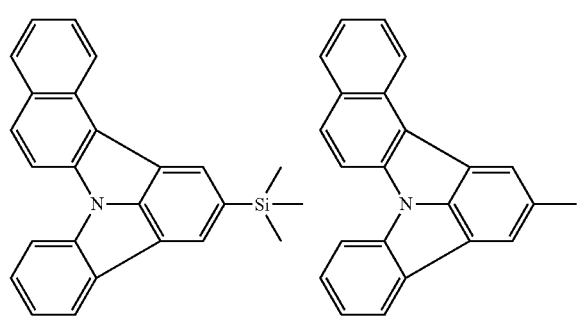
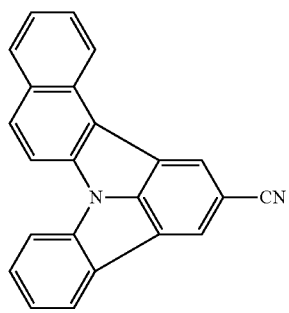
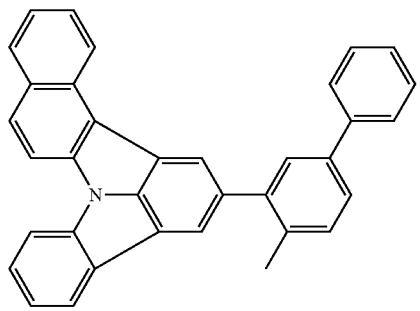
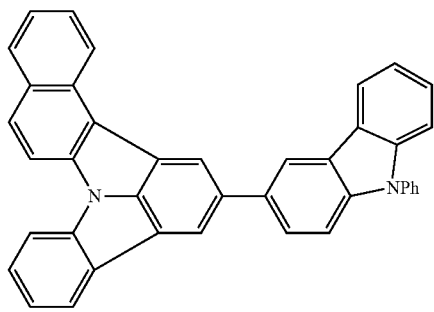
132
-continued
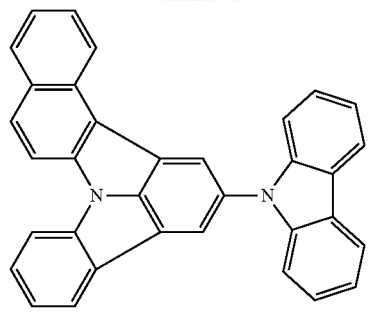
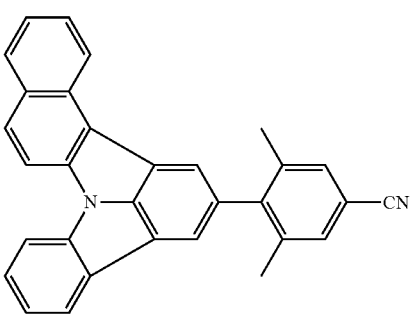
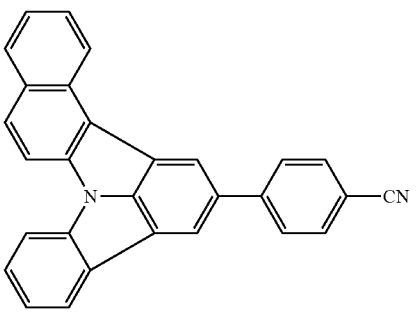
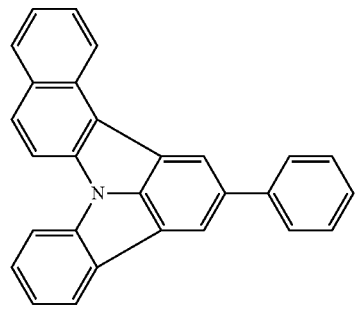
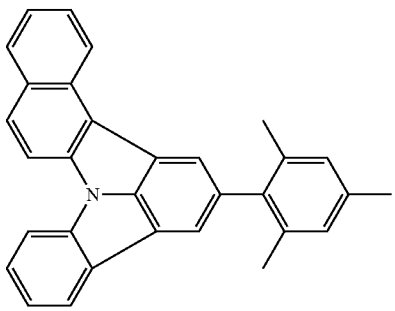

133
-continued
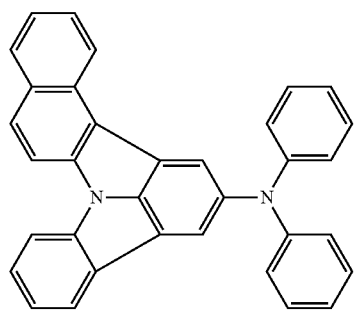
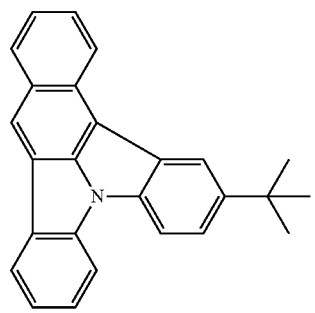
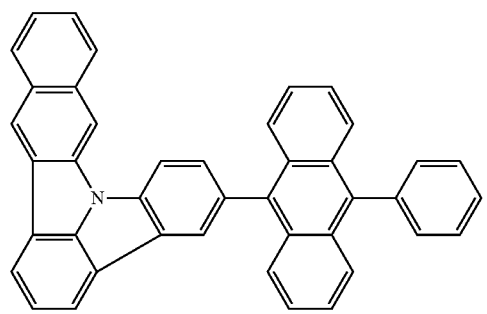
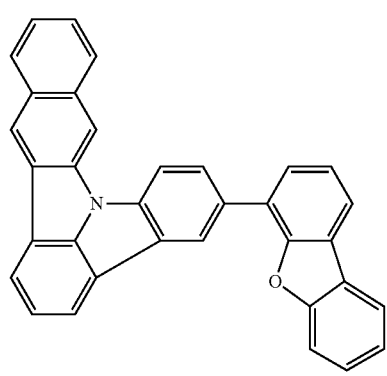
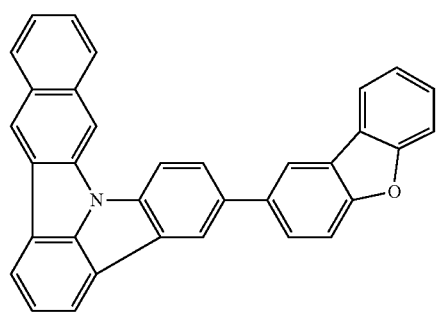
134
-continued
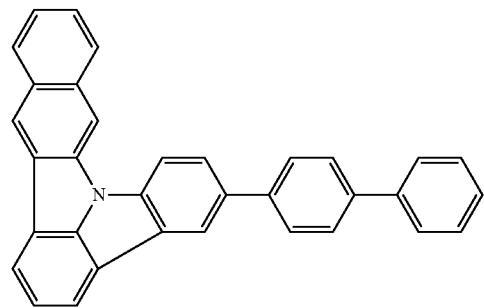
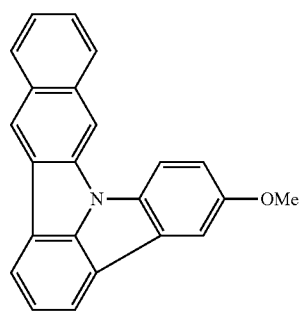
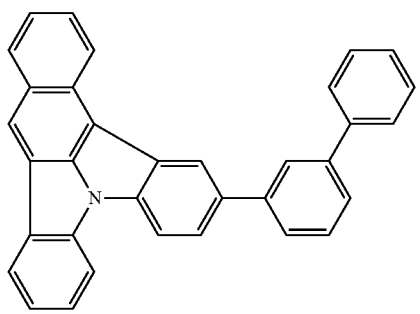
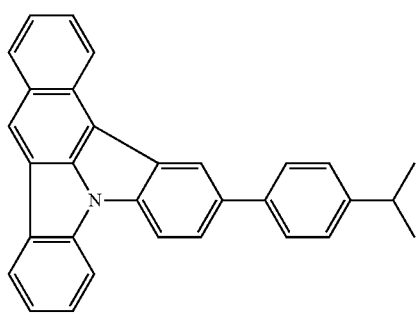
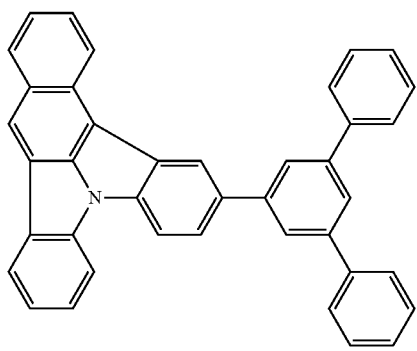

135
-continued
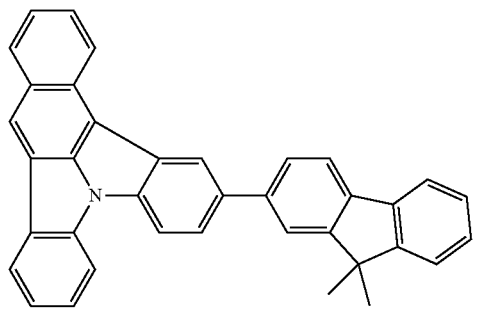
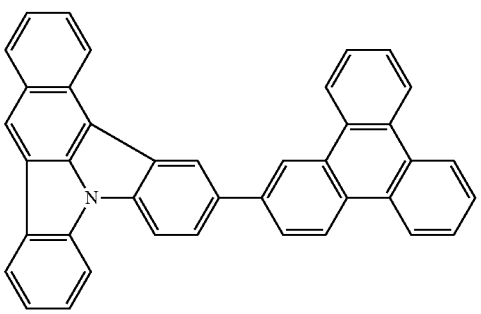
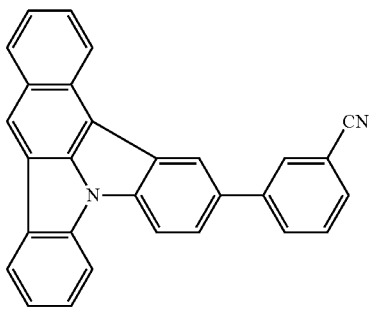
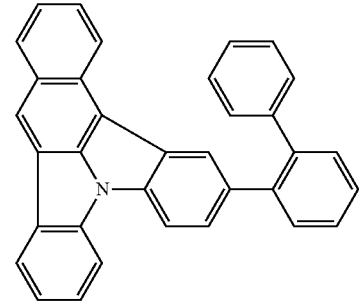
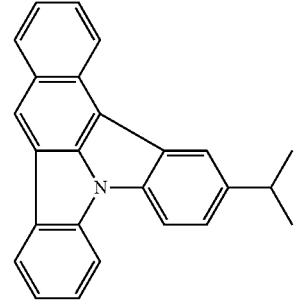
136
-continued
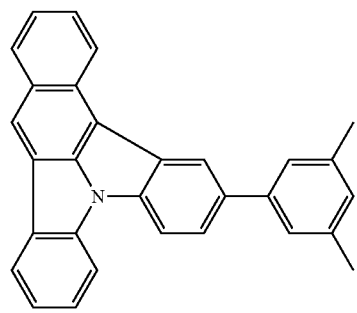
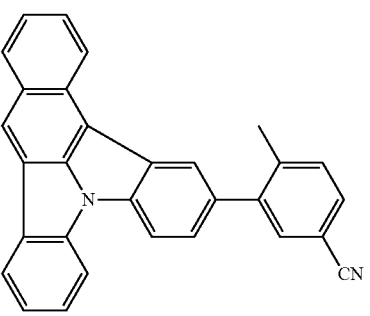
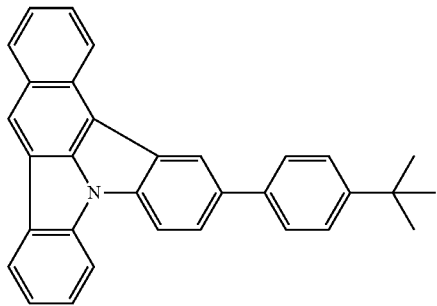
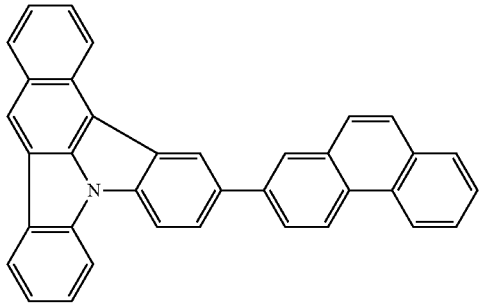
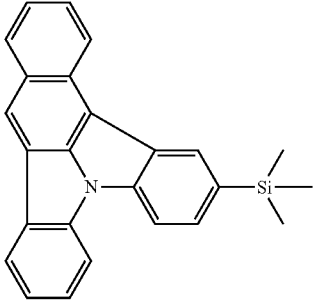

137
-continued
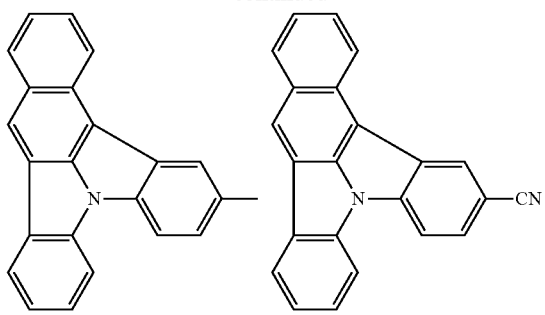
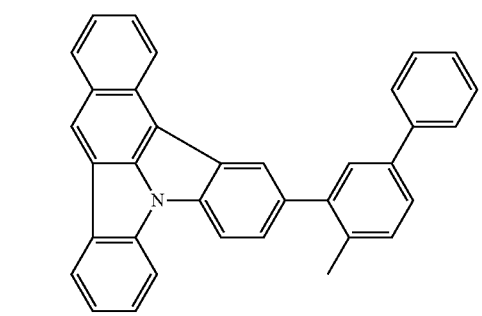
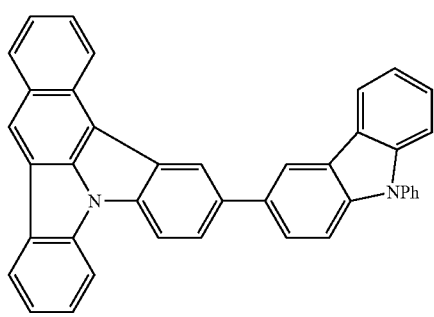
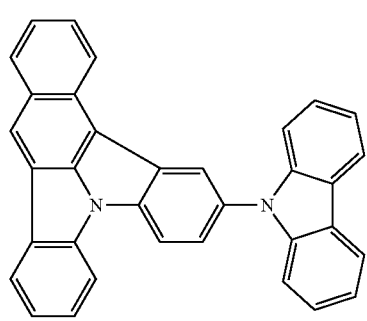
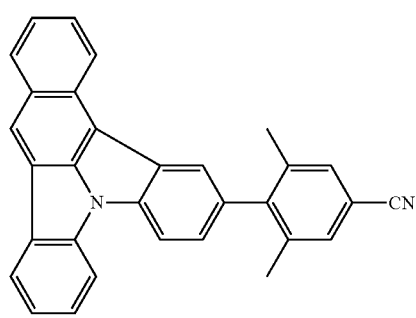
138
-continued
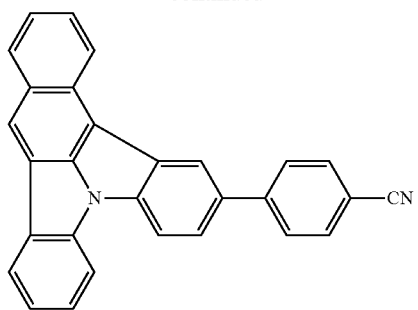
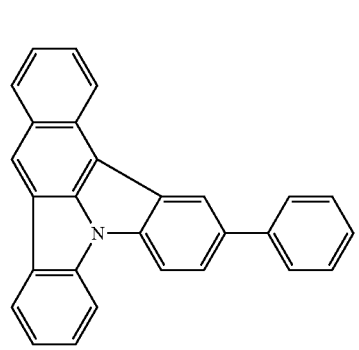
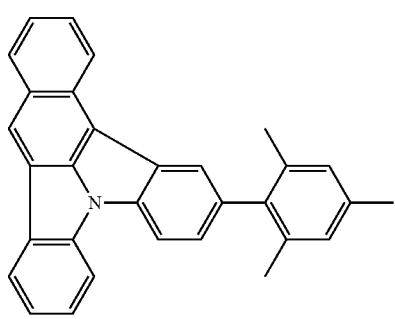
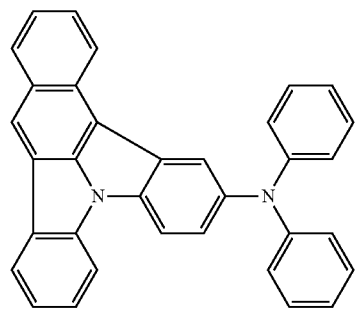
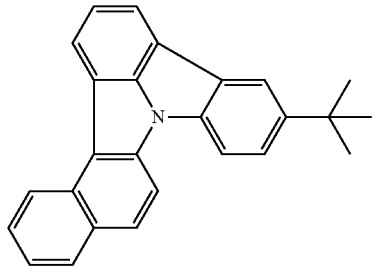

139
-continued
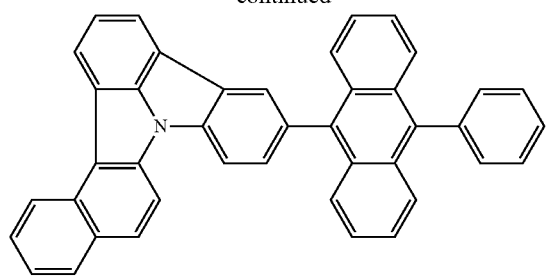
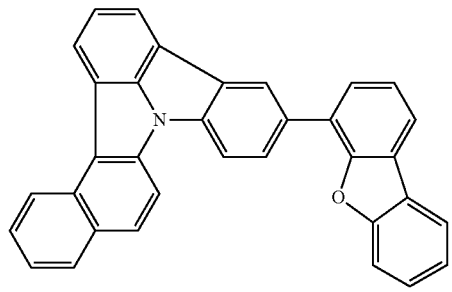
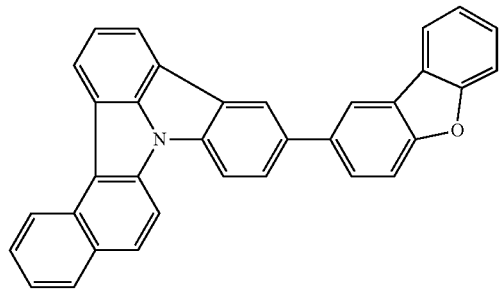
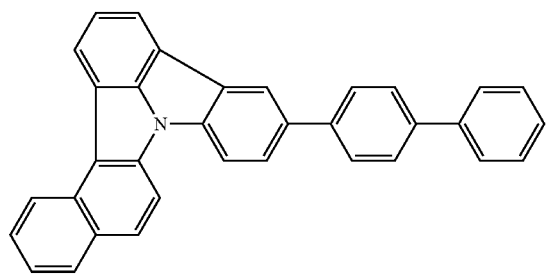
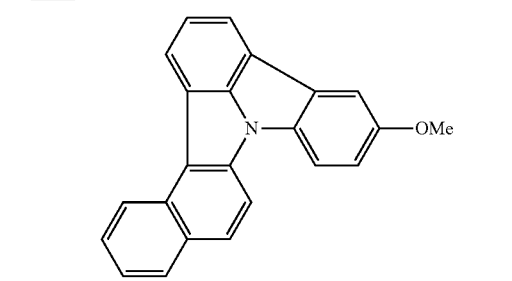
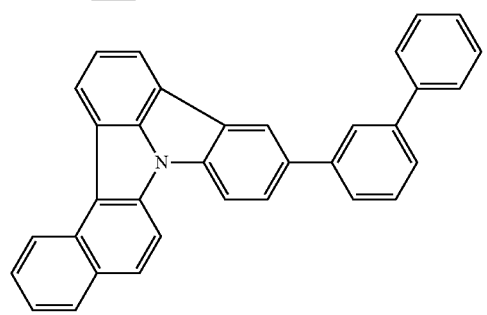
140
-continued
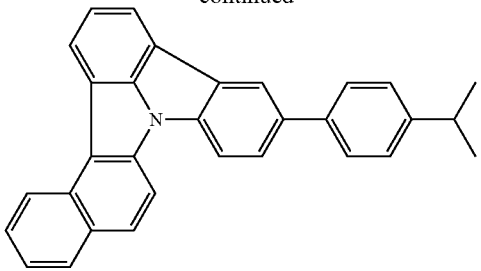
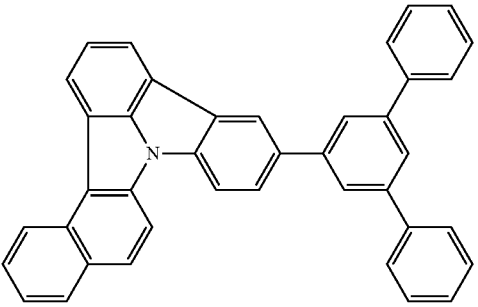
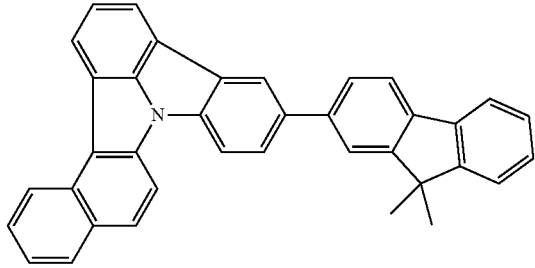
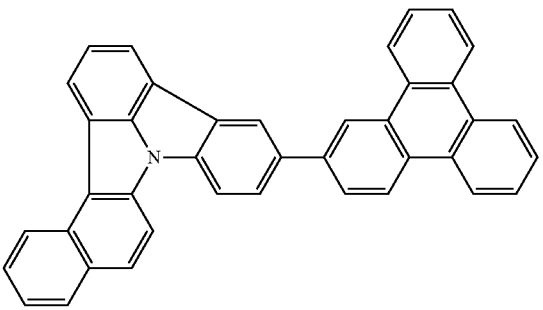
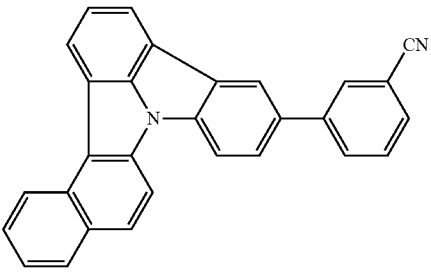
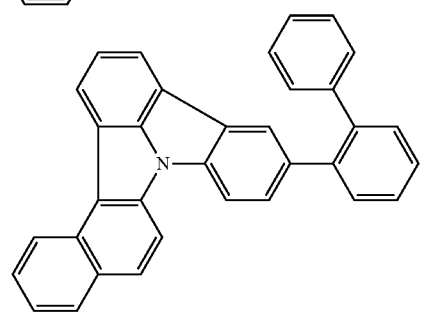

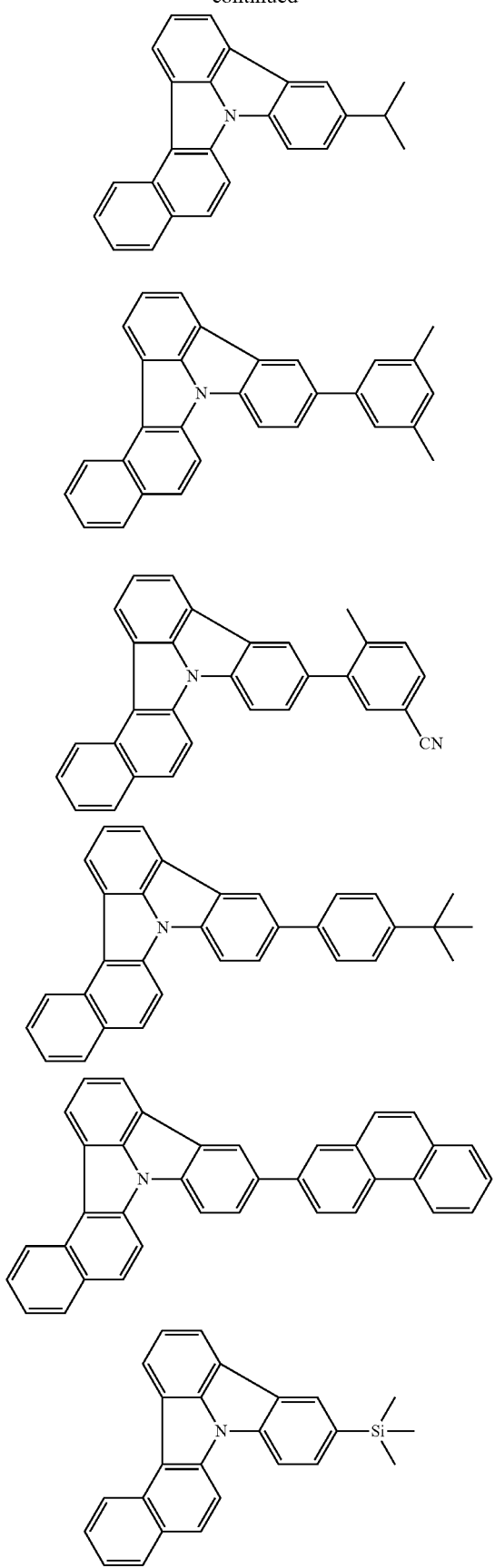

143
-continued
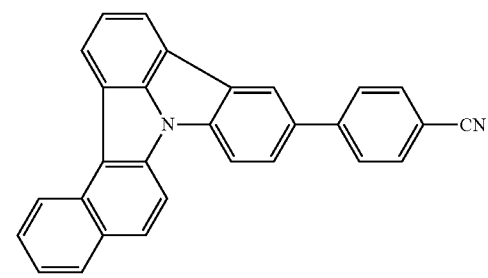
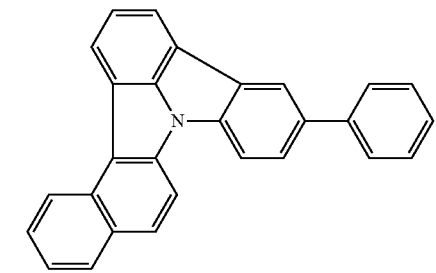
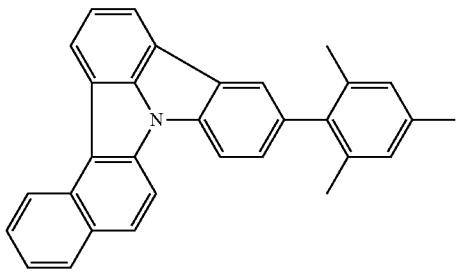
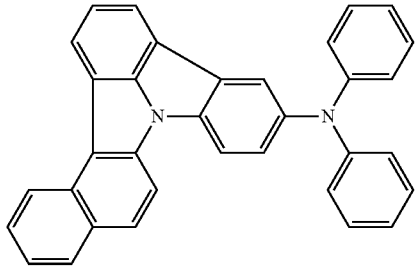
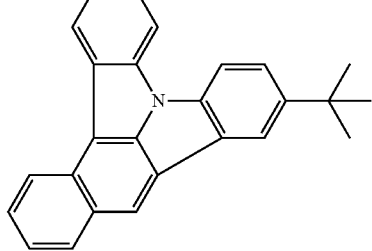
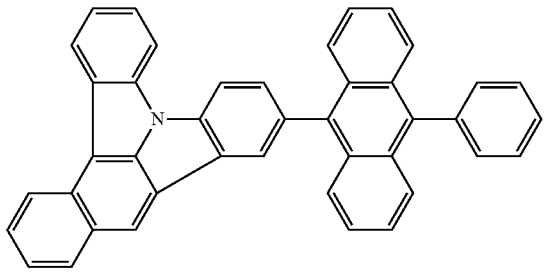
144
-continued
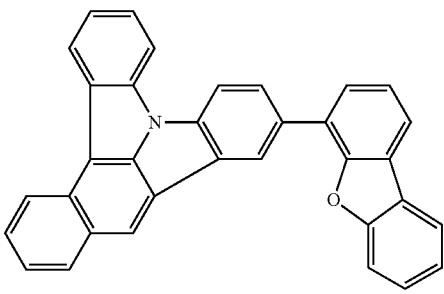
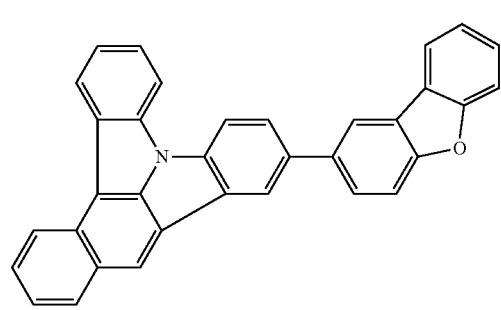
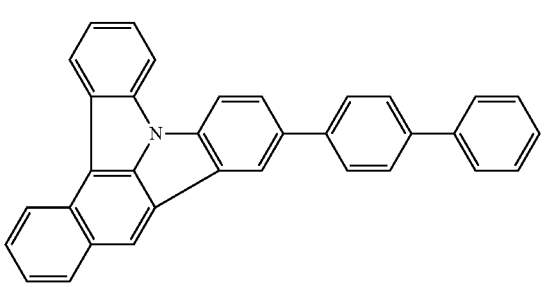
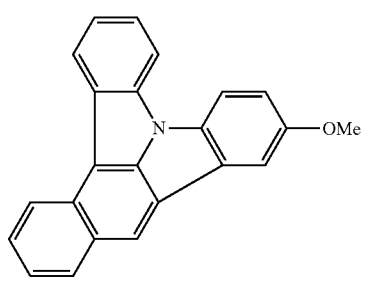
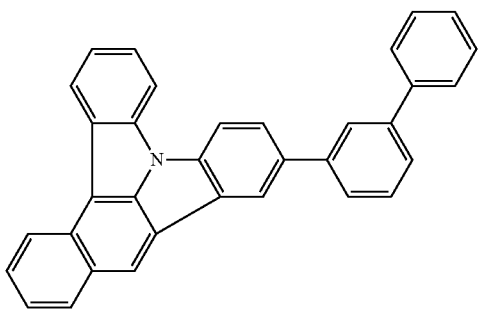

145
-continued
146
-continued
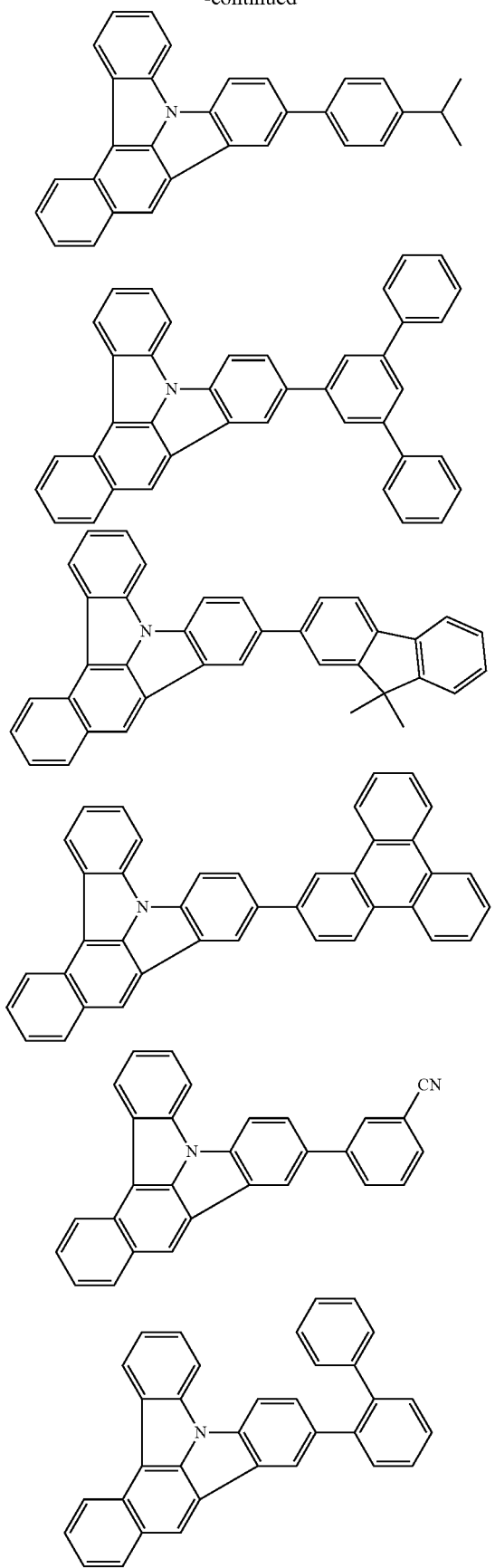
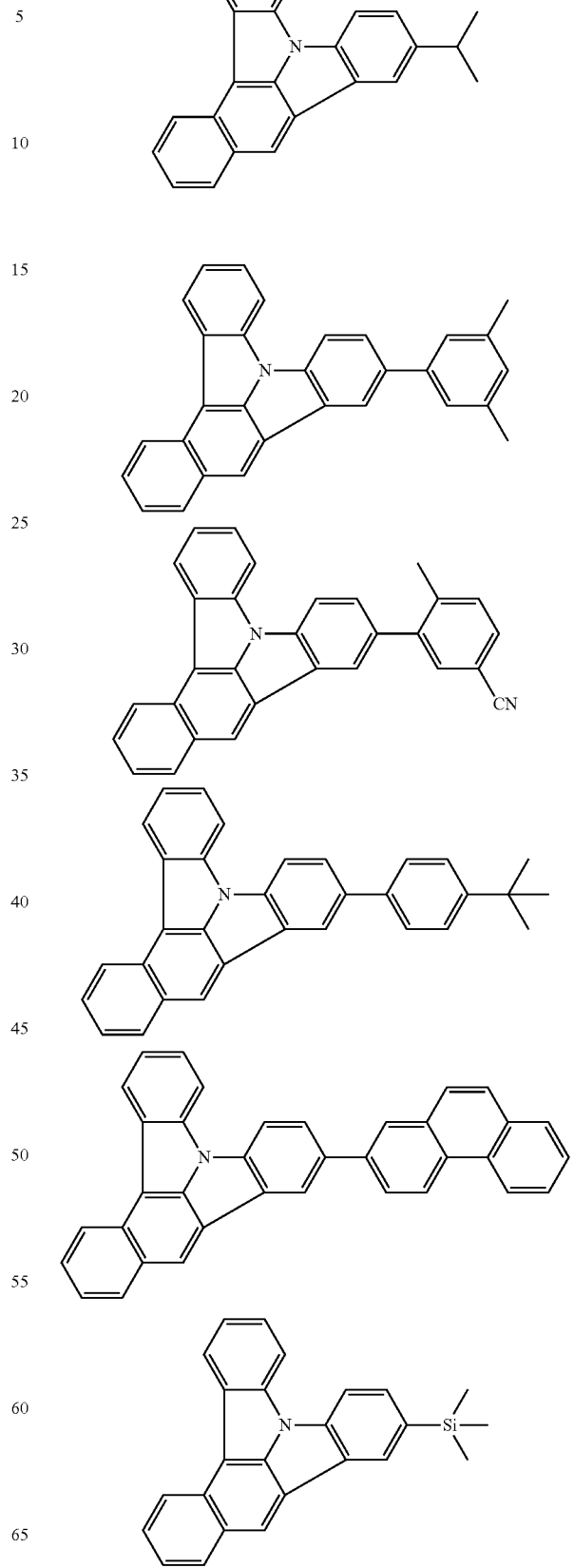

147
-continued
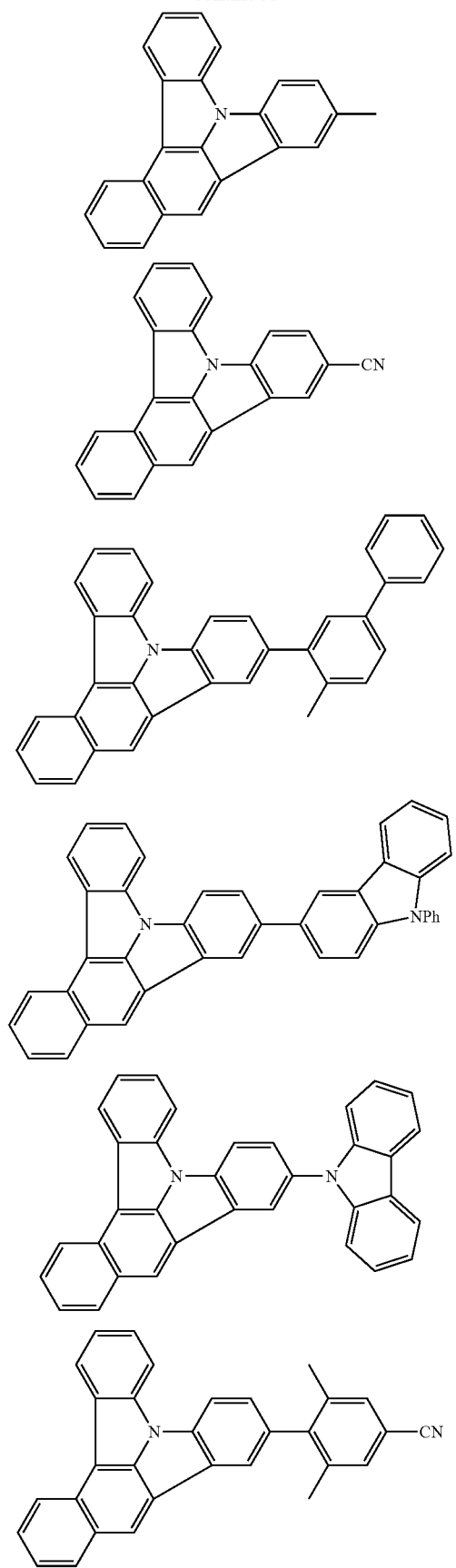
148
-continued
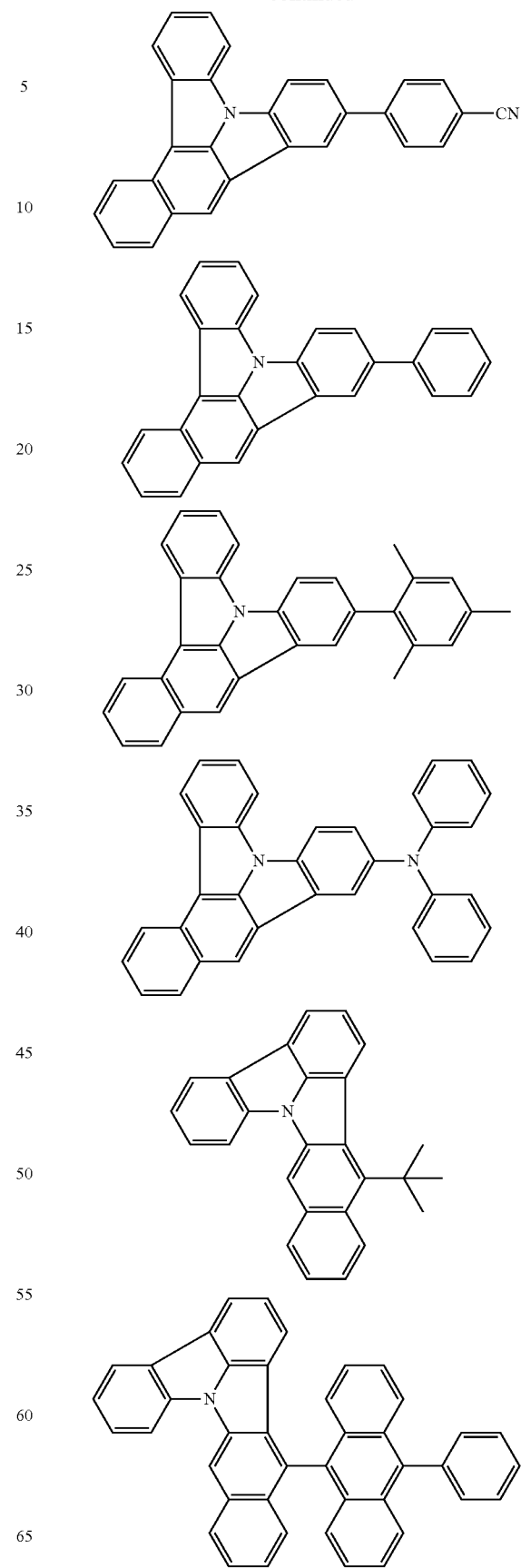

149
-continued
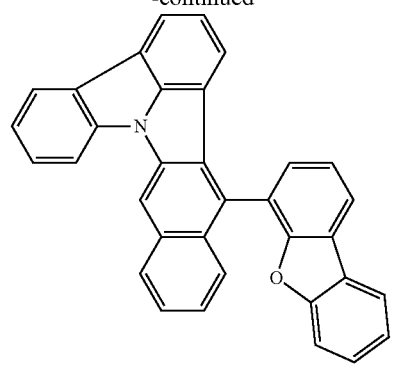
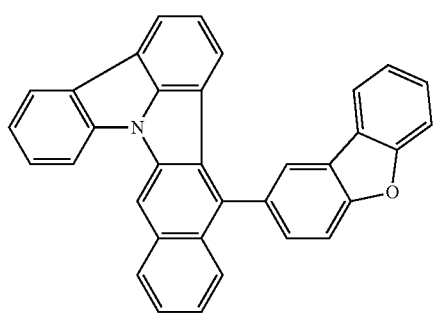
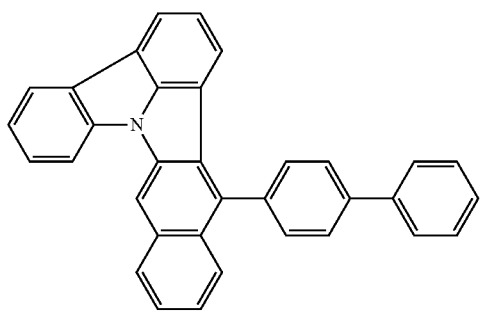
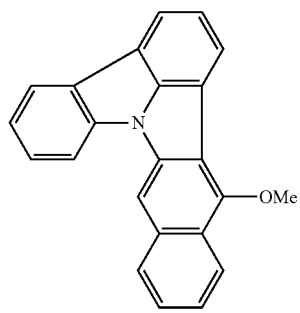
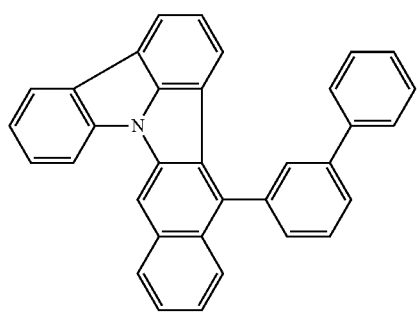
150
-continued
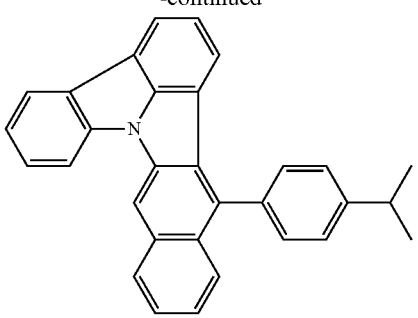
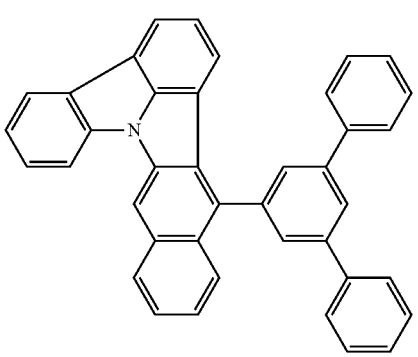
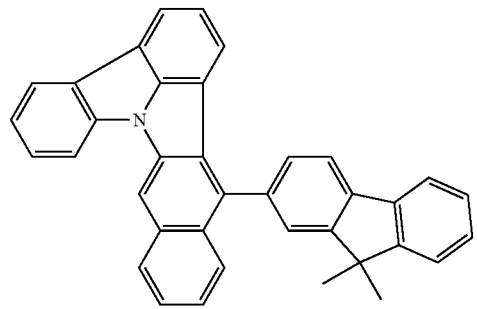
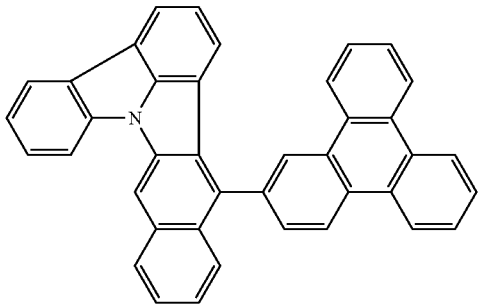
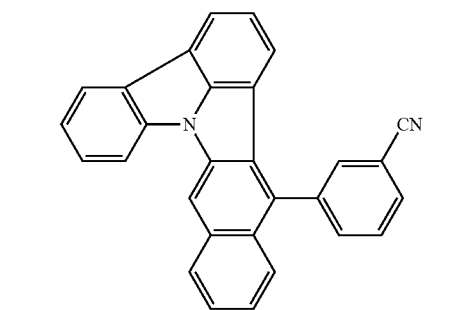

151
-continued
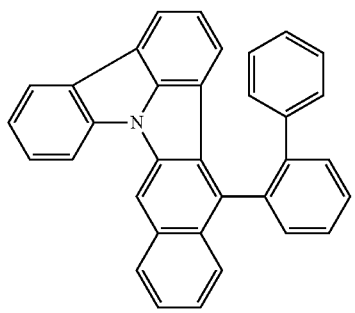
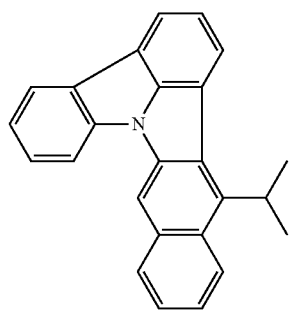
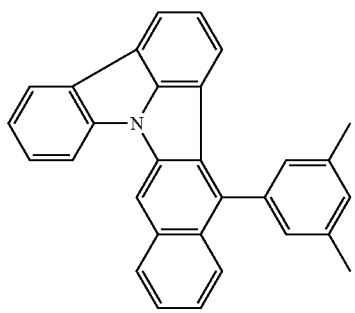
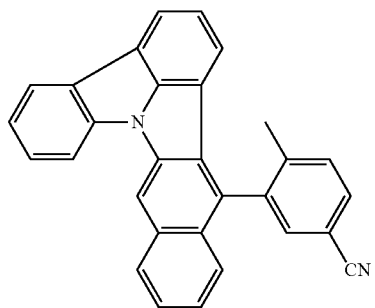
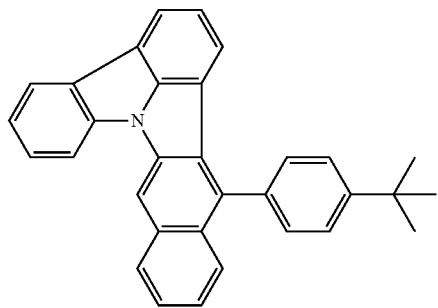
152
-continued
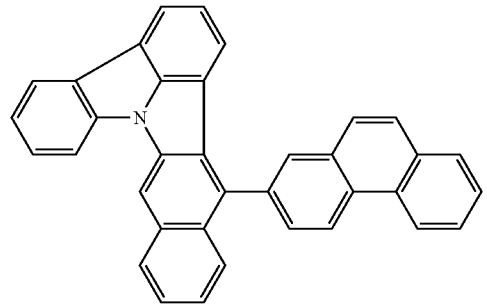
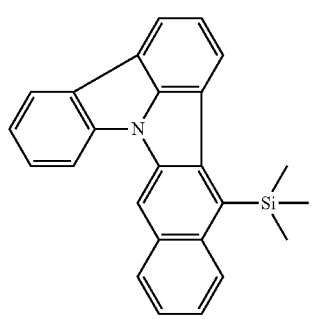
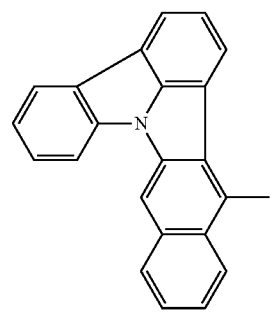
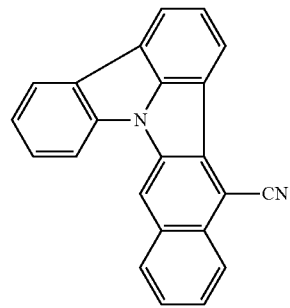
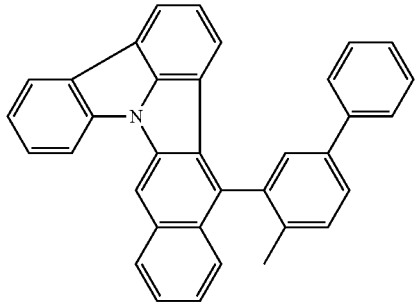

153
-continued
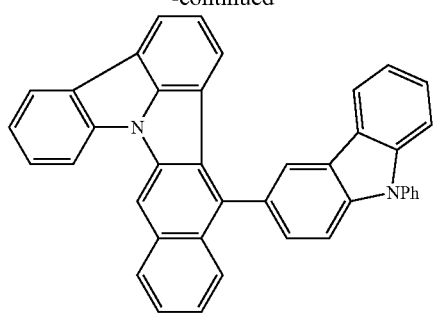
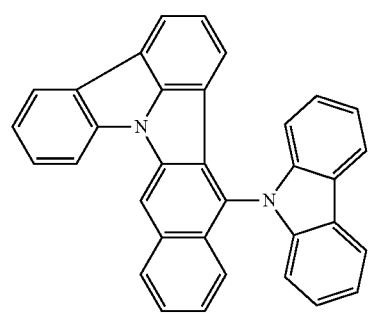
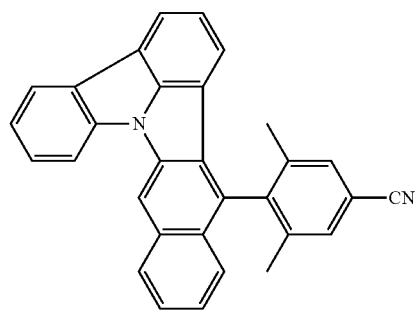
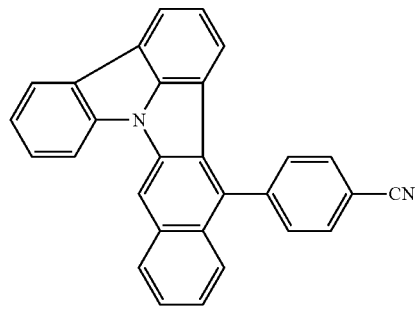
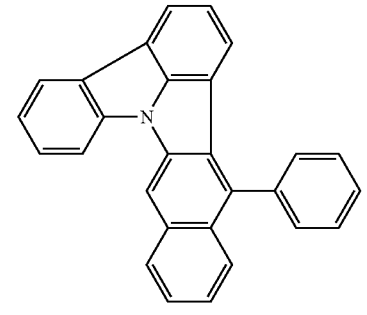
154
-continued
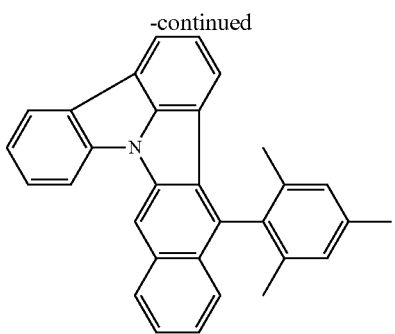
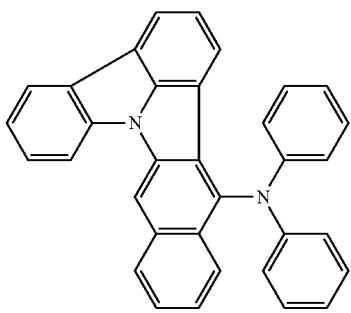
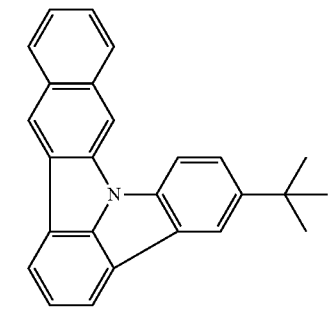
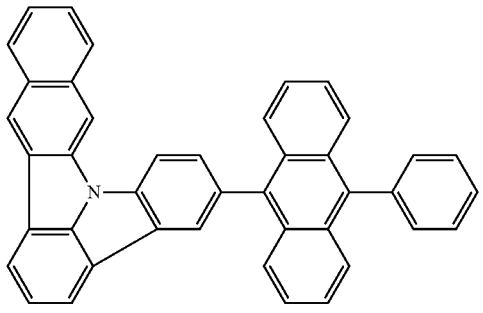
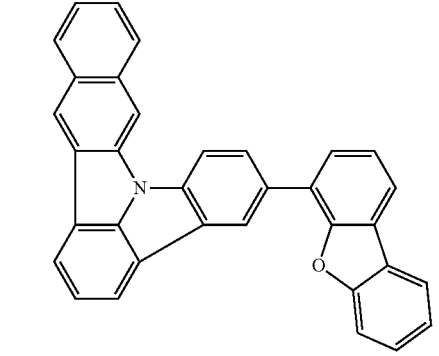

155
-continued
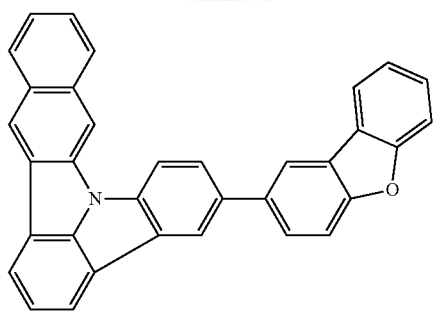
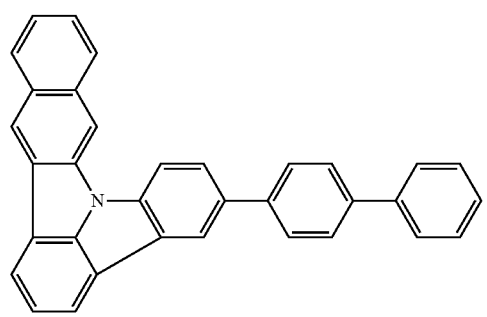
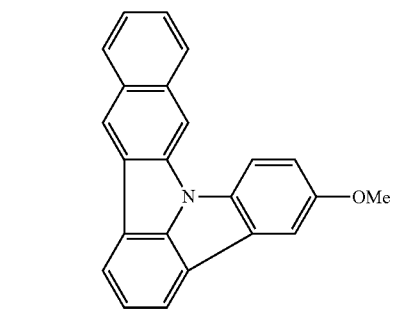
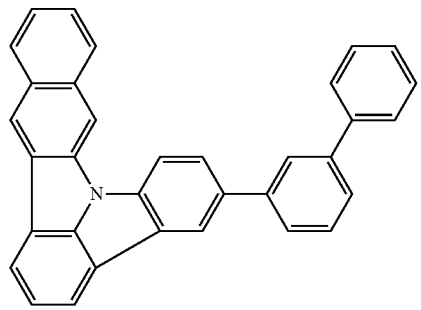
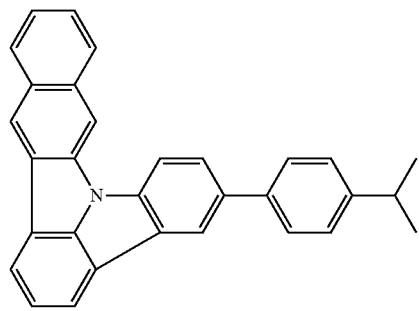
156
-continued
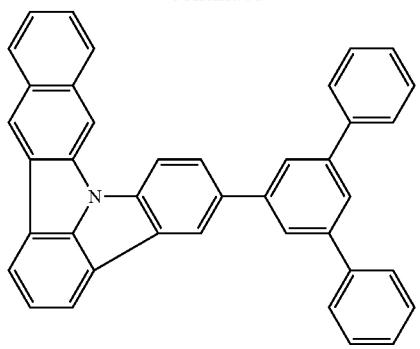
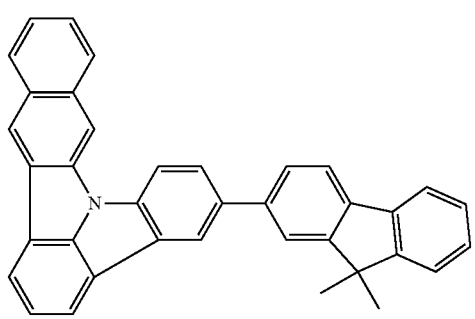
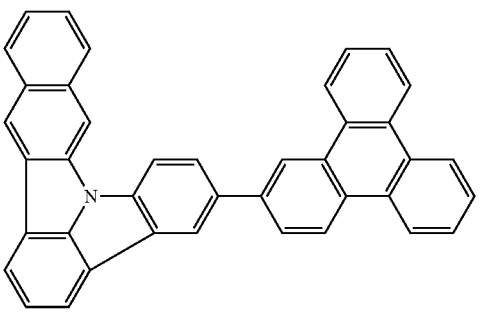
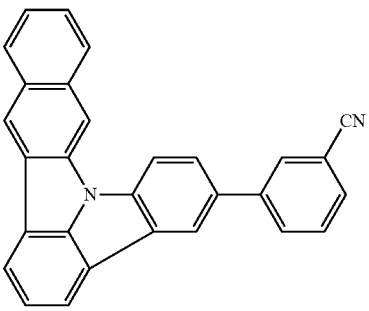
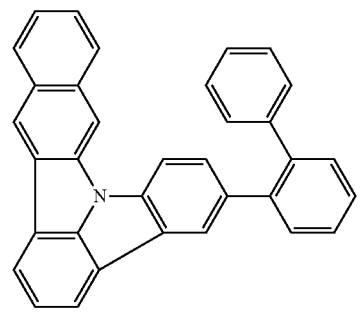

157
-continued
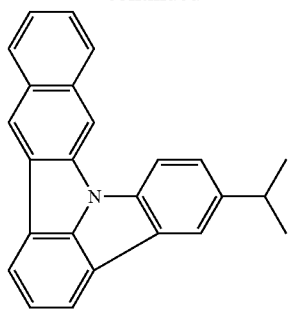
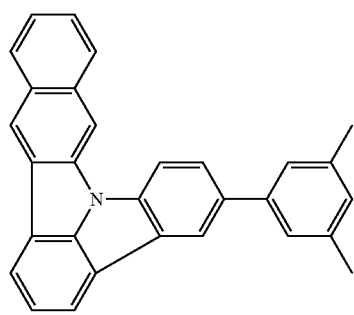
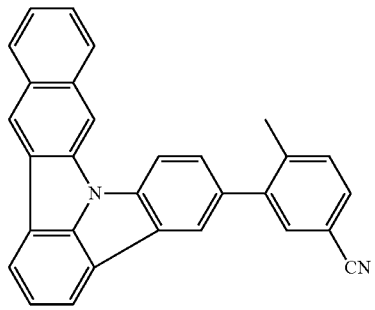
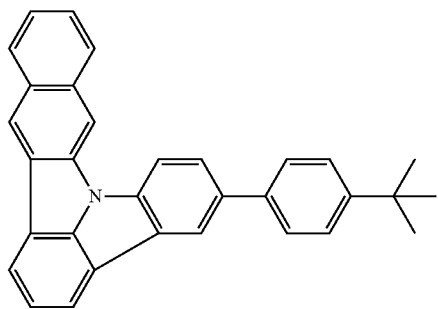
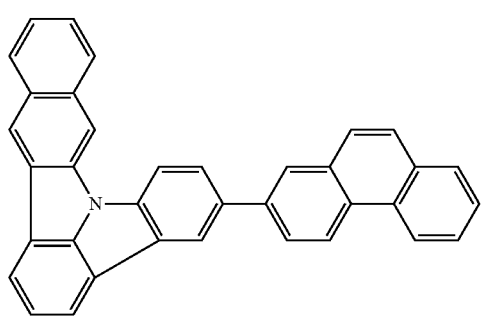
158
-continued
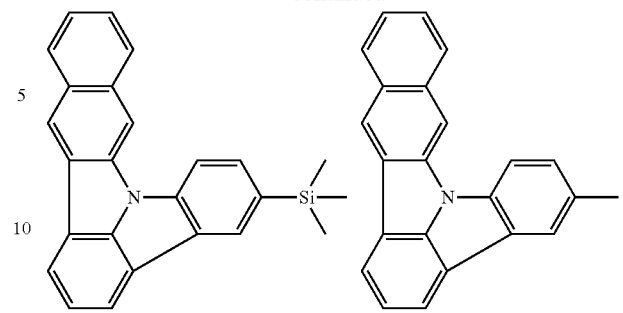
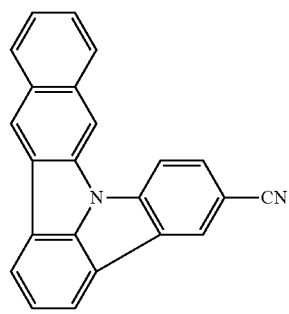
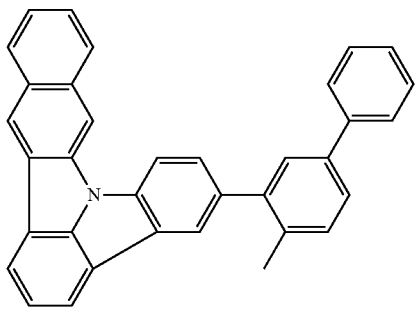
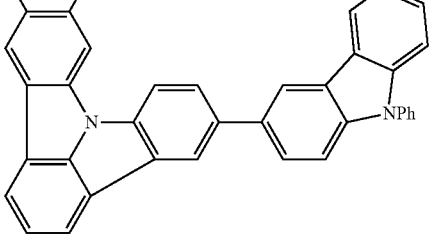
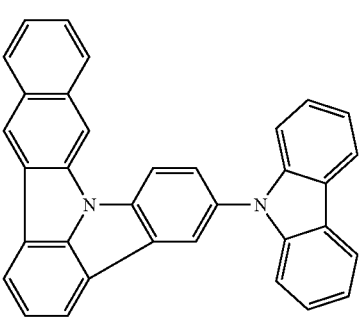

159
-continued
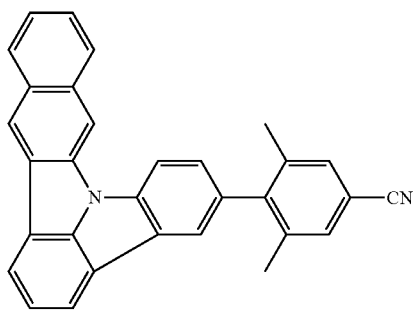
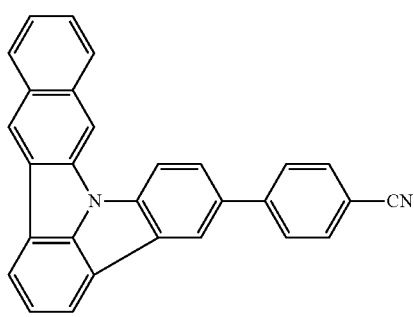
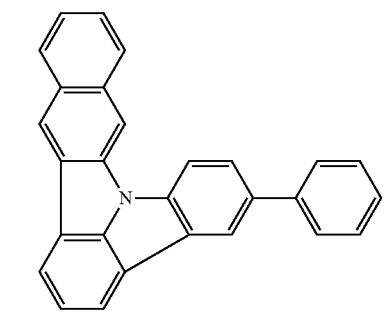
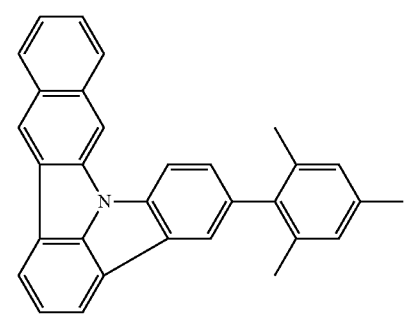
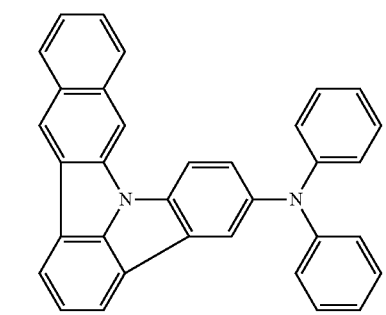
160
-continued
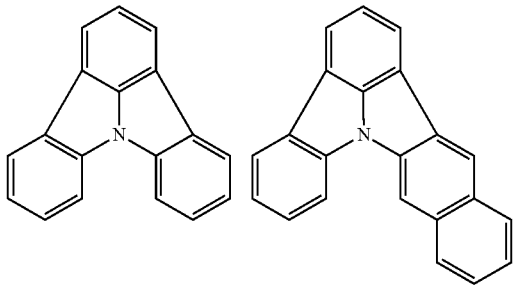
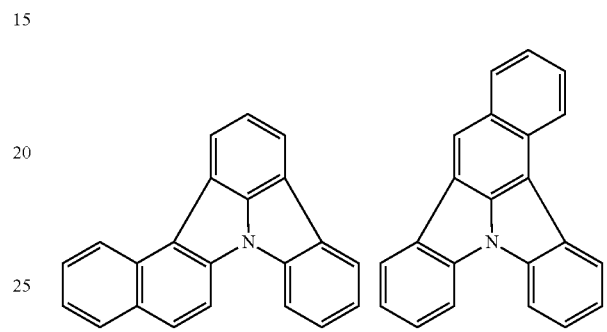
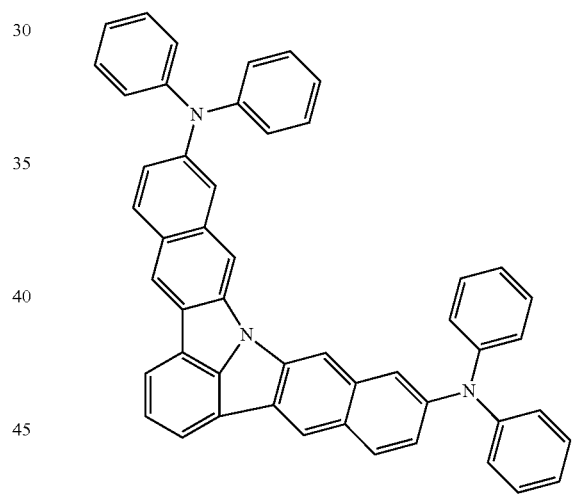
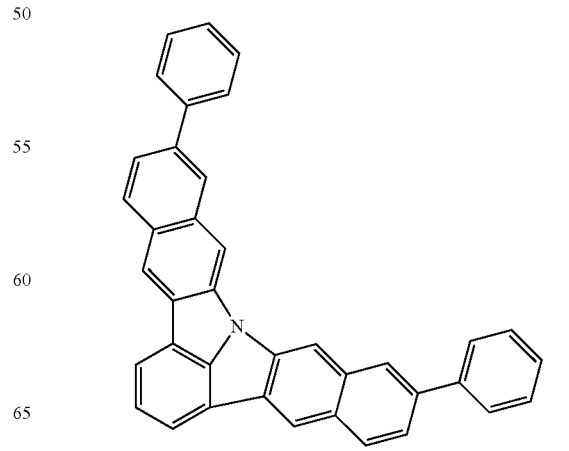

161
-continued
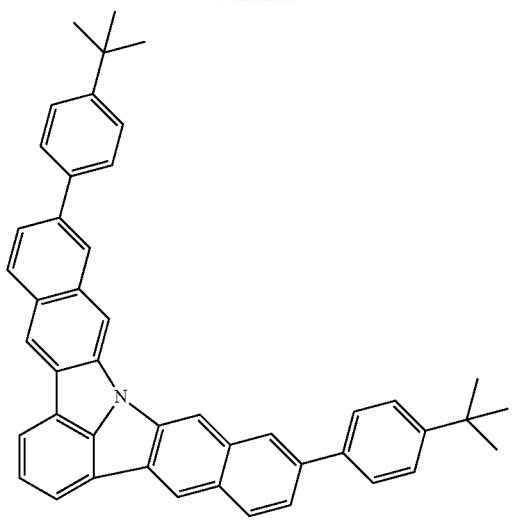
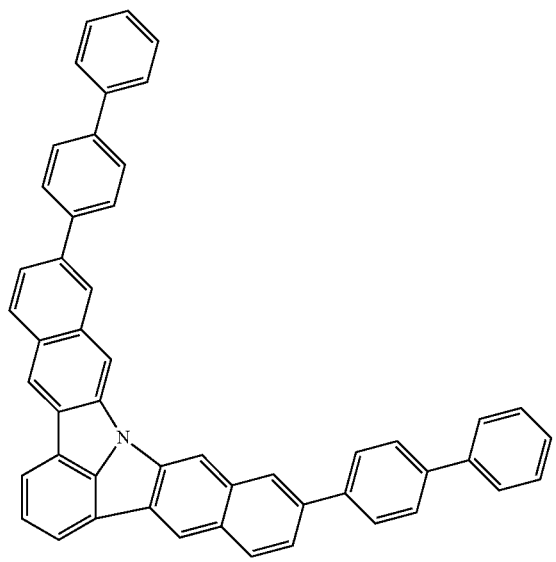
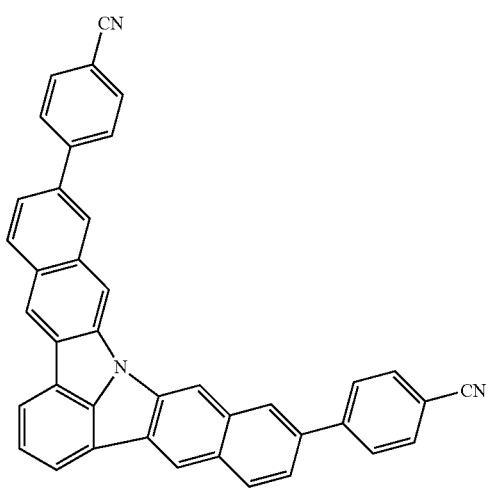
162
-continued
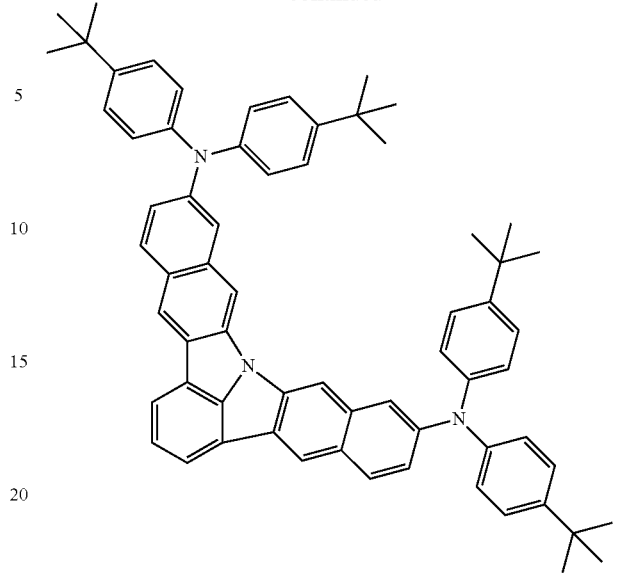
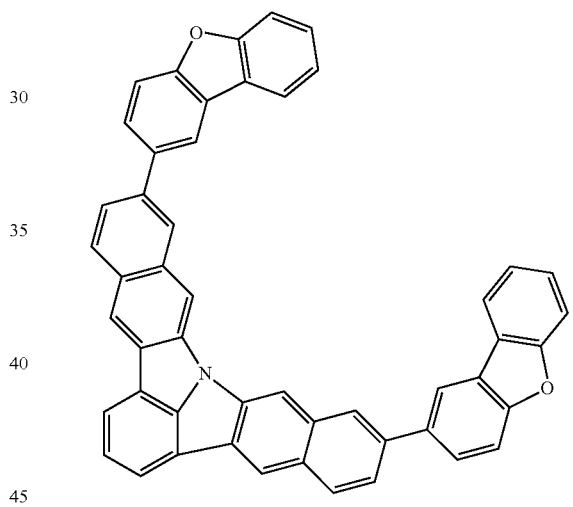
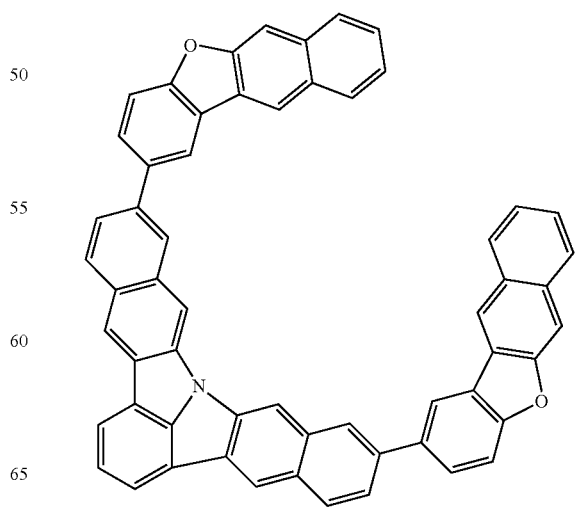

163
-continued
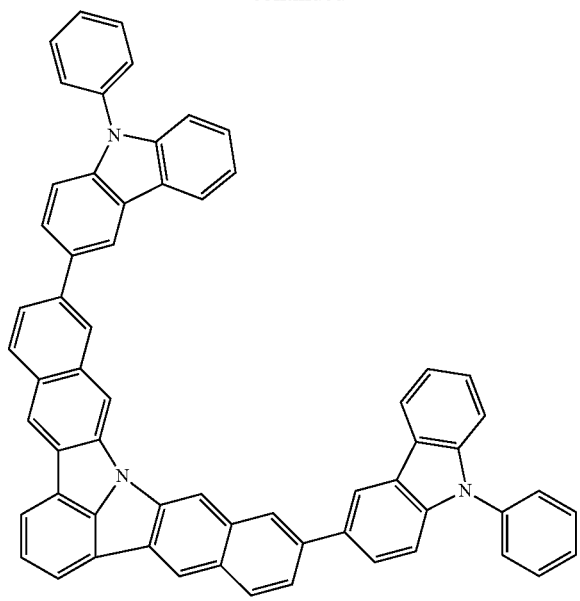
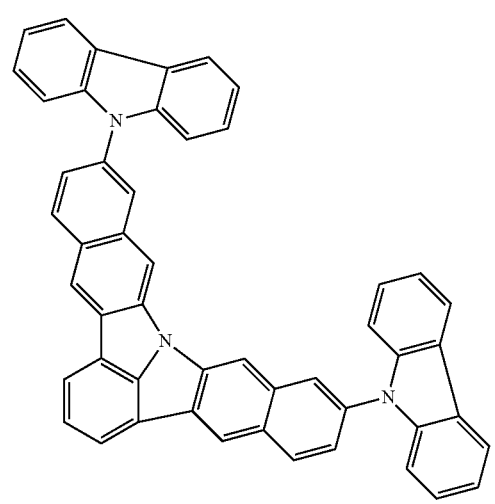
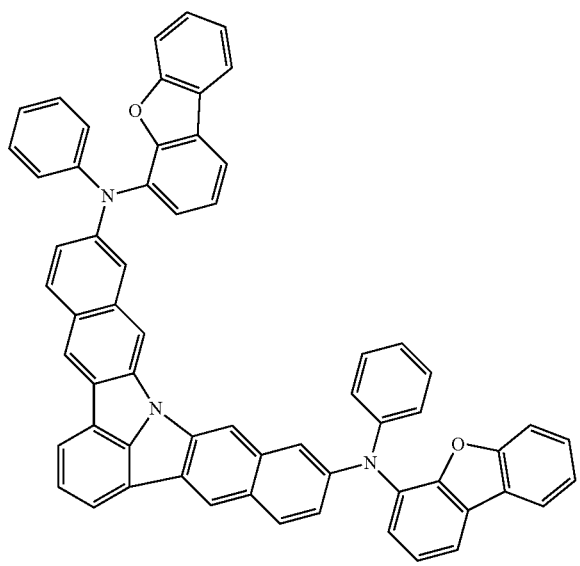
164
-continued
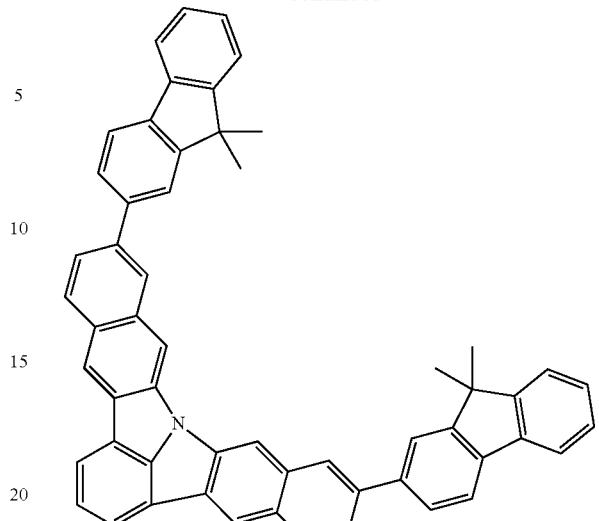
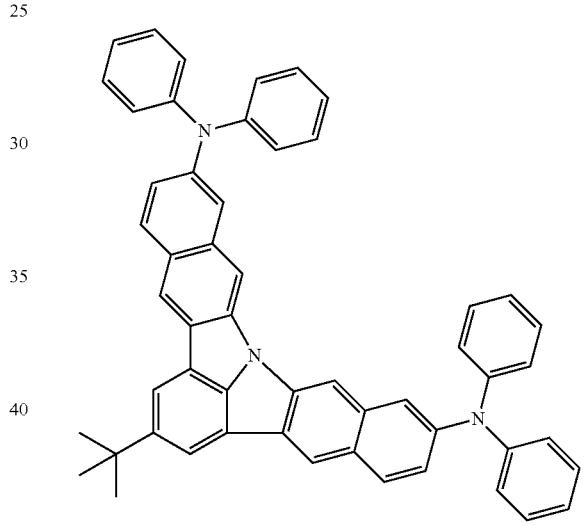
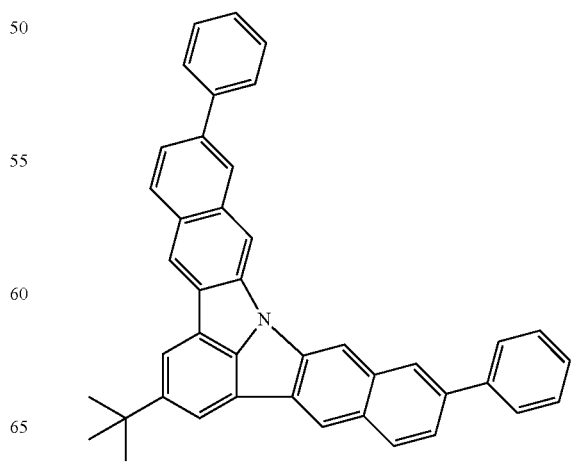

165 -continued
166 -continued
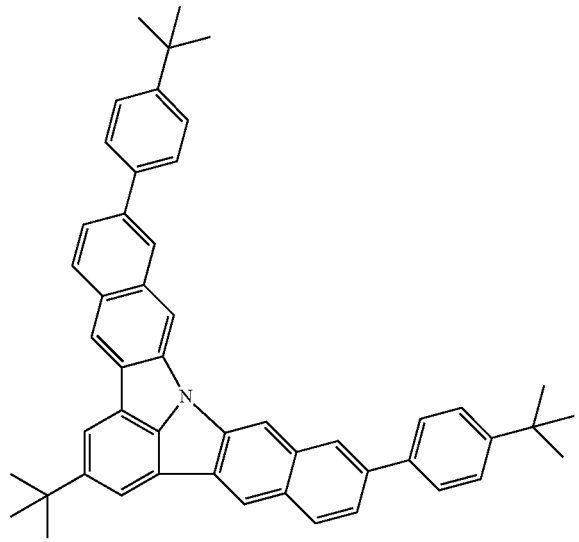
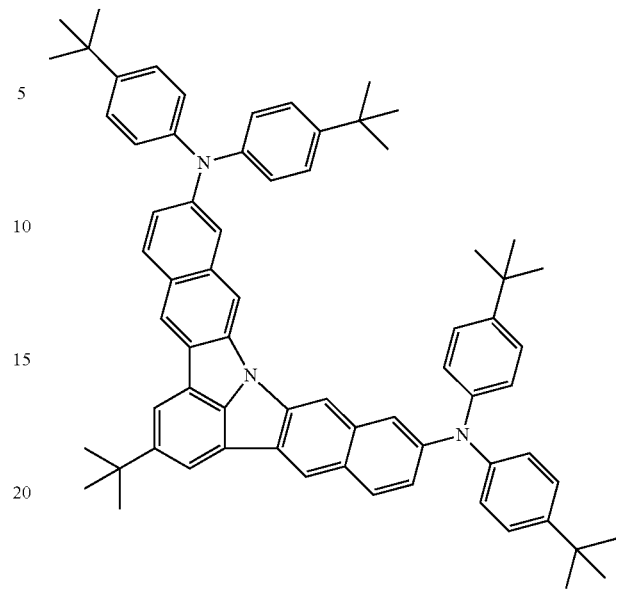
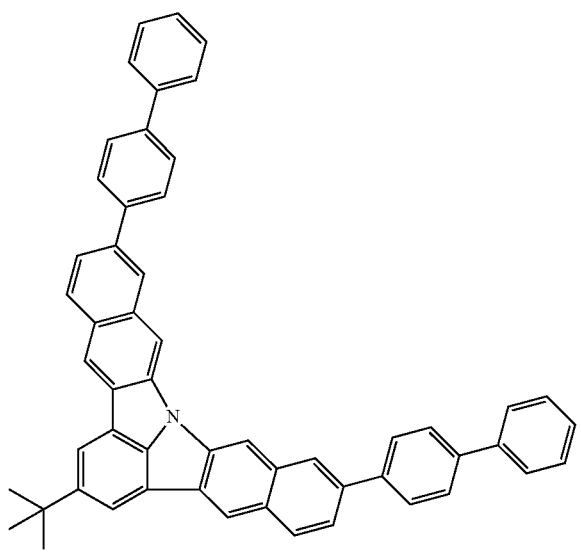
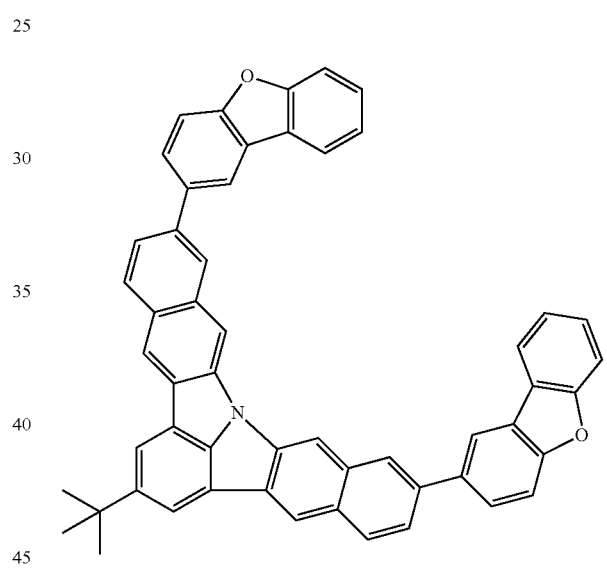
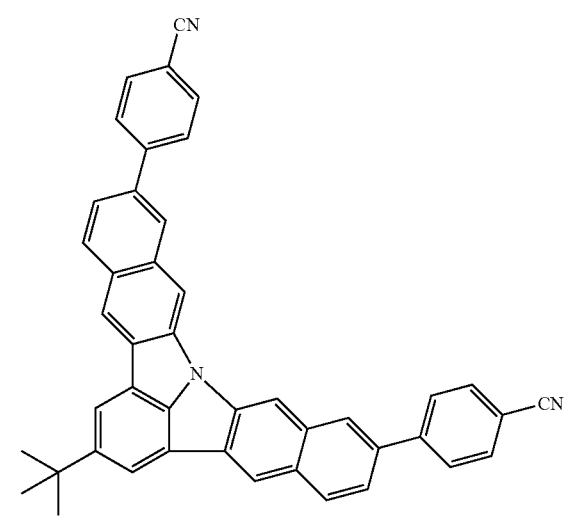
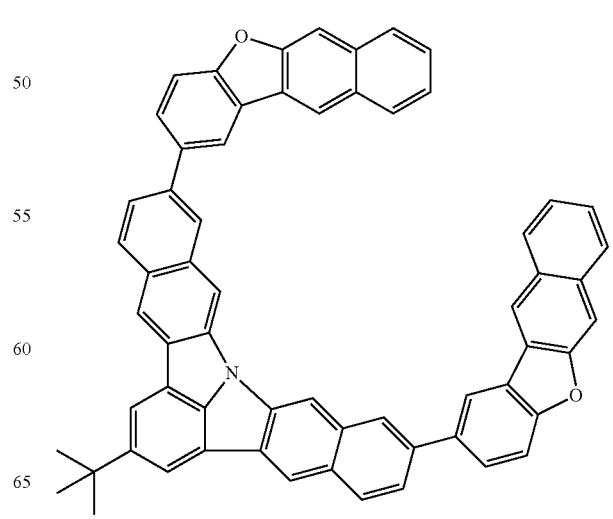

167
-continued
168
-continued
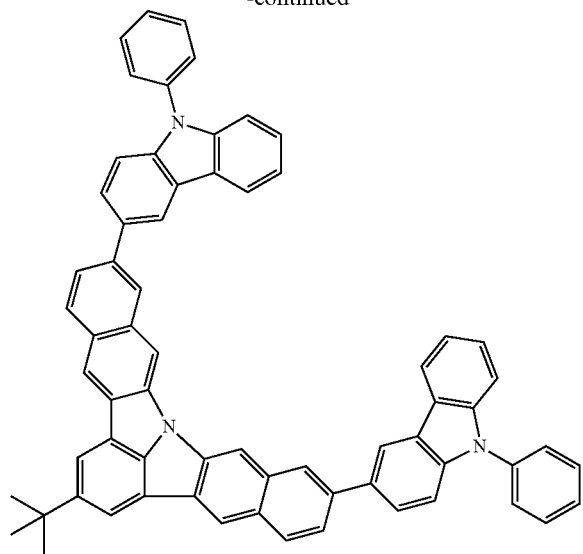
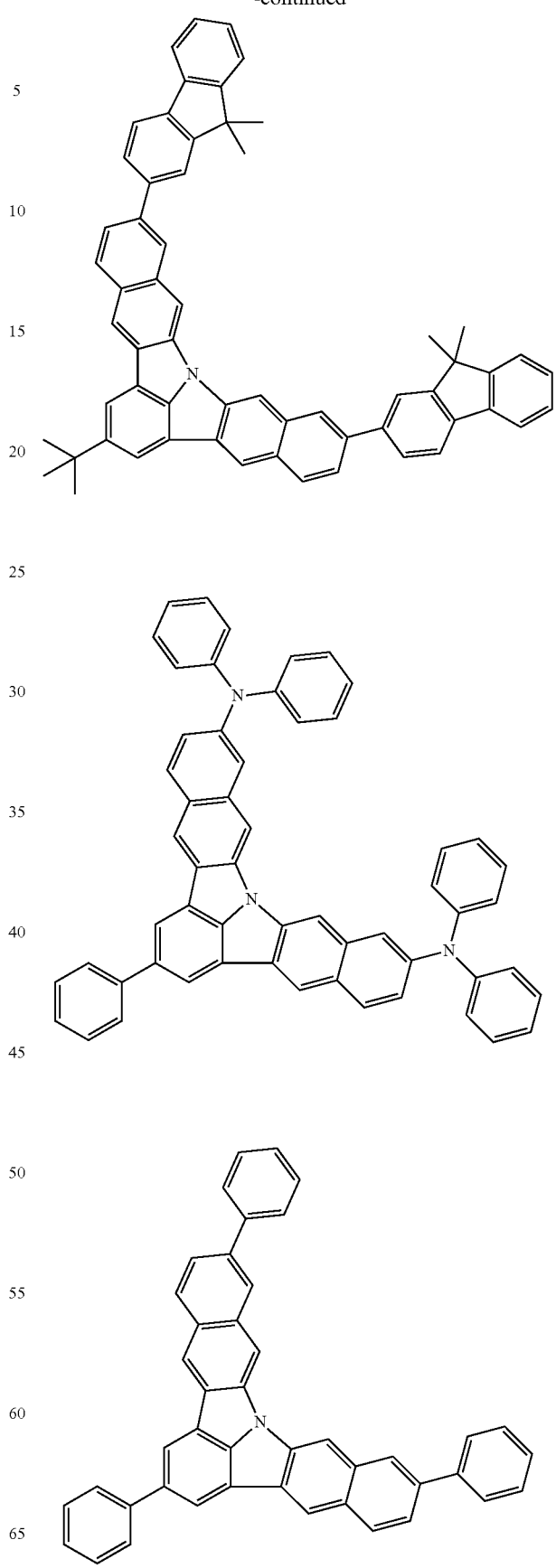

169
-continued
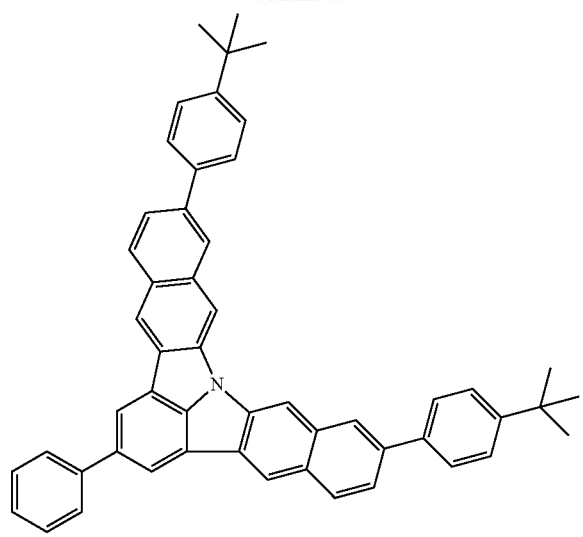
170
-continued
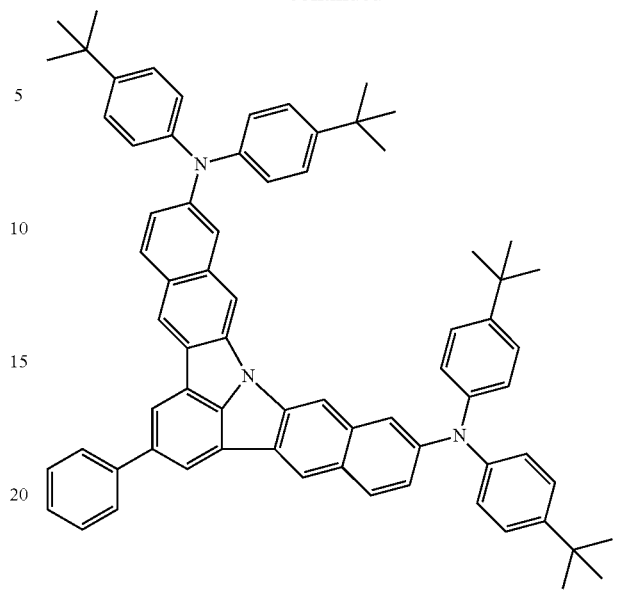
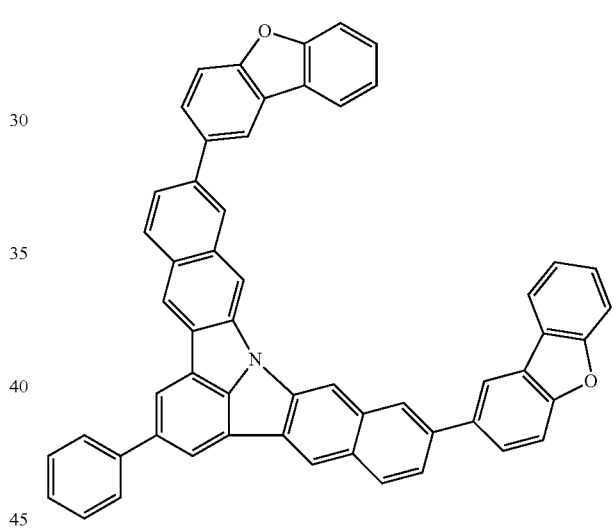
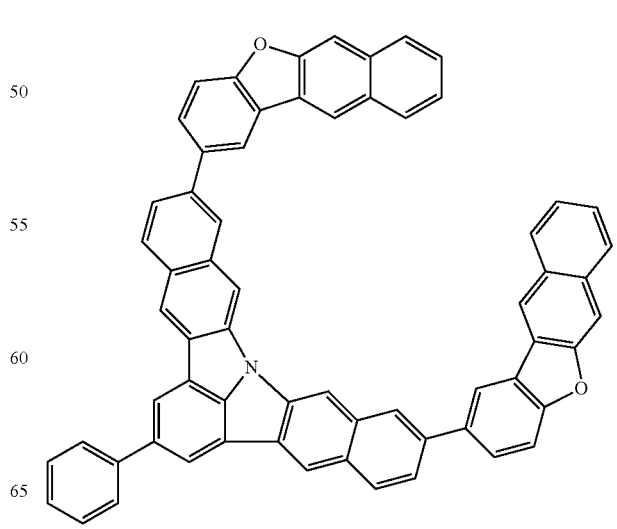

171
-continued
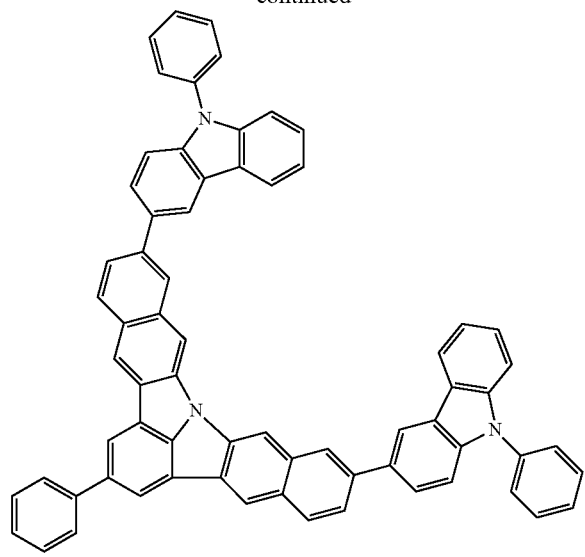
172
-continued
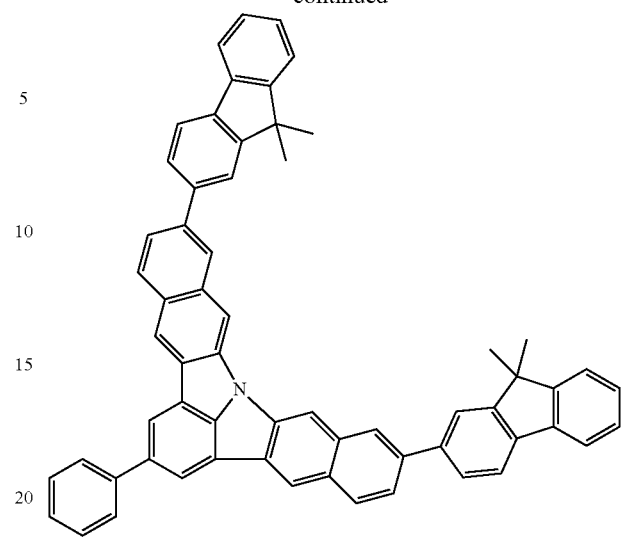
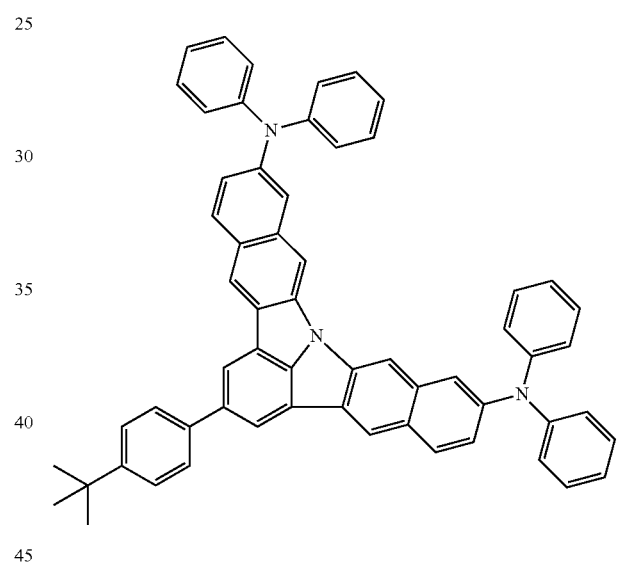
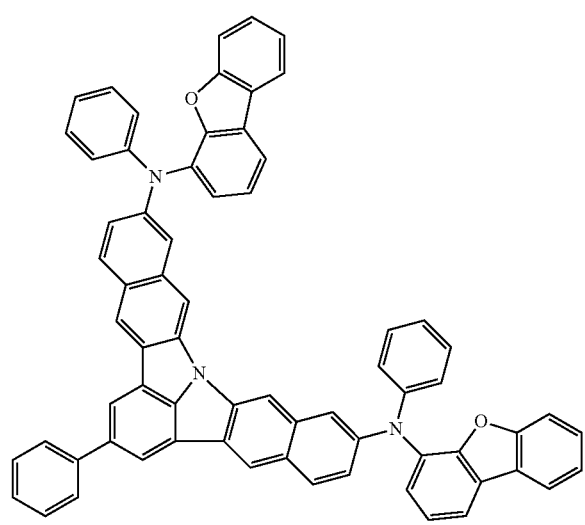
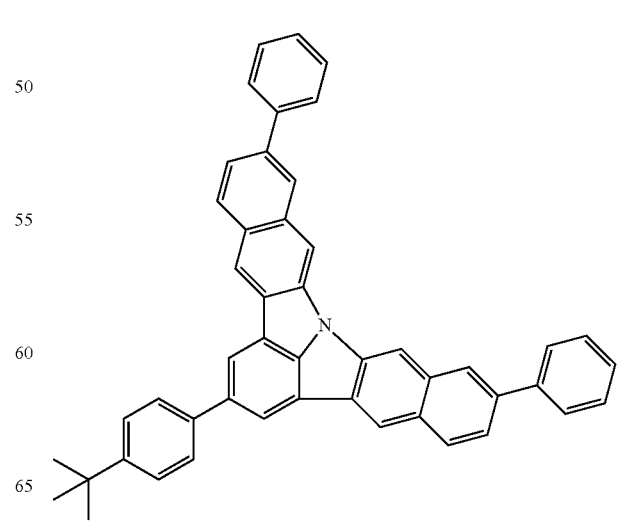

173
-continued
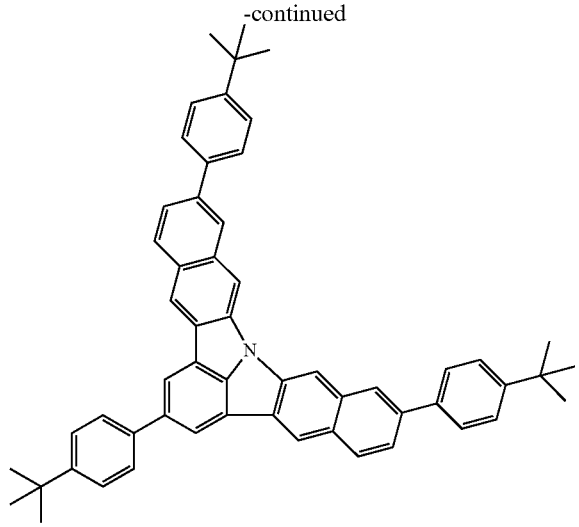
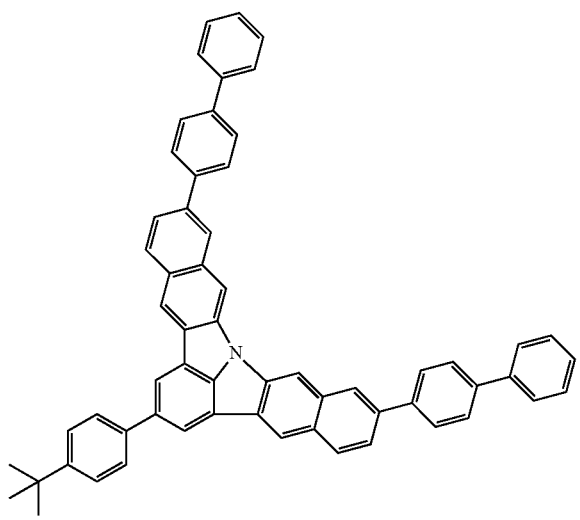
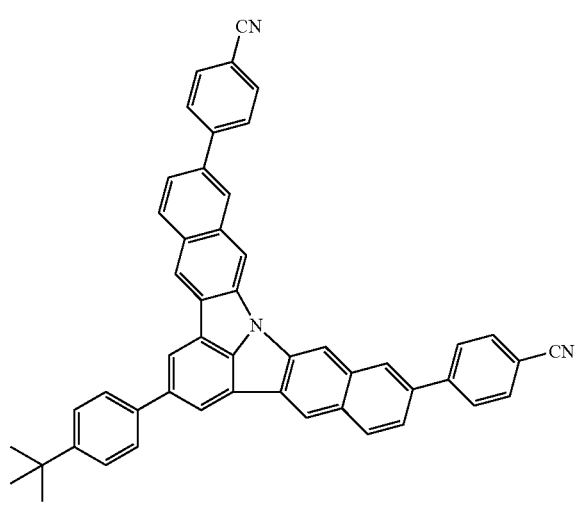
174
-continued
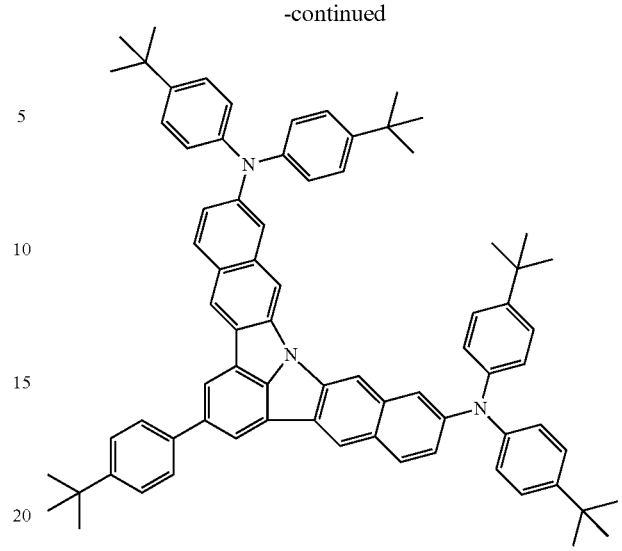
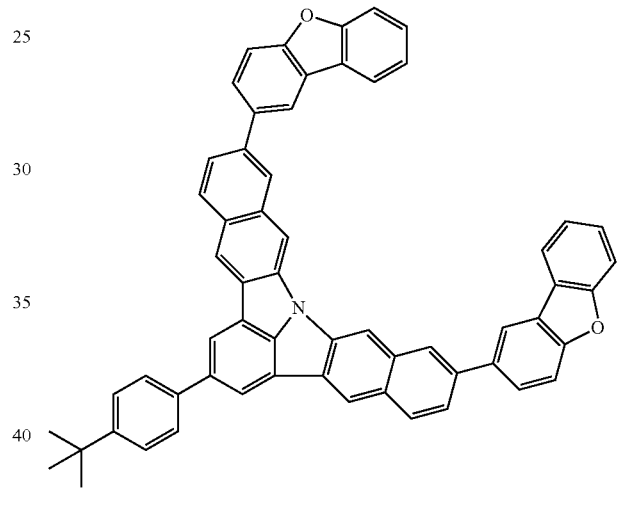
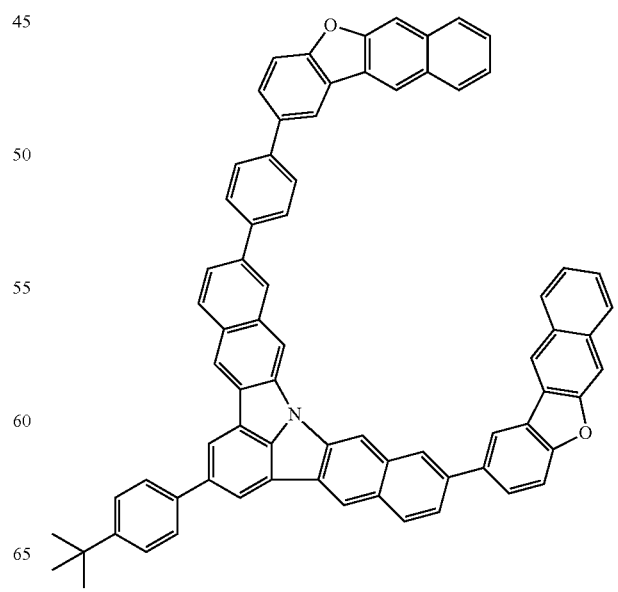

175
-continued
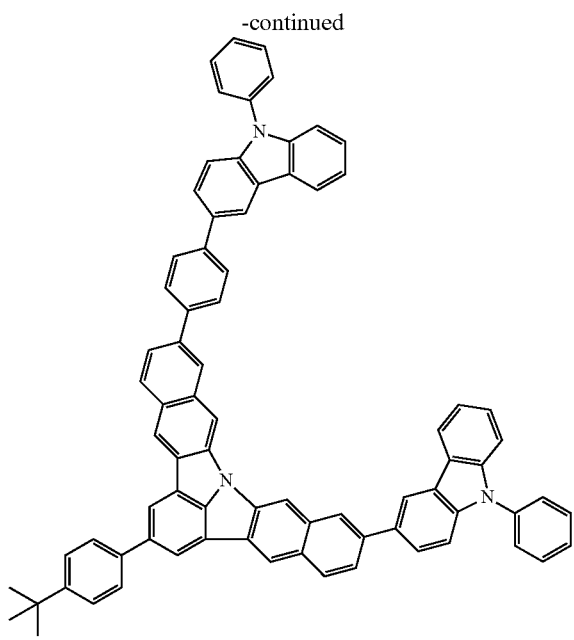
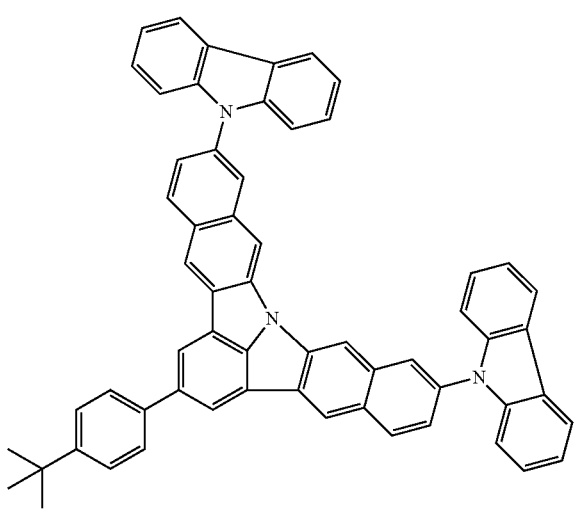
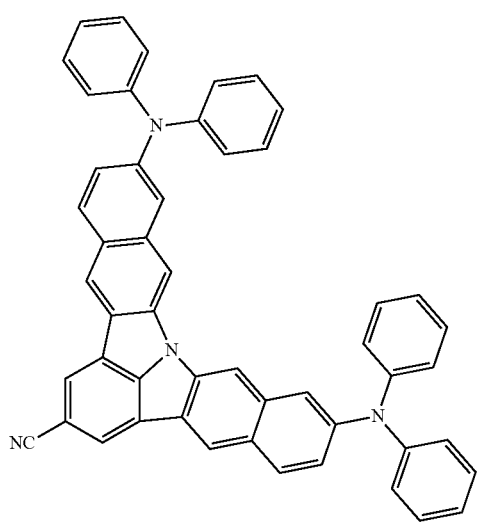
176
-continued
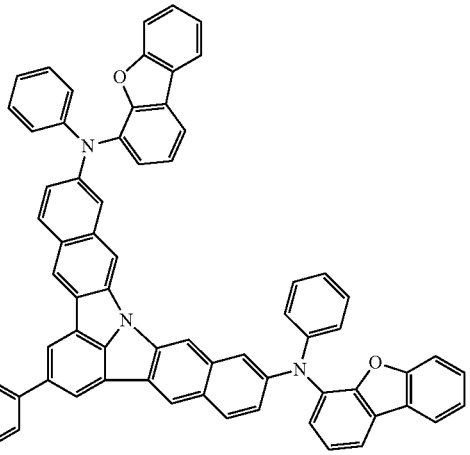
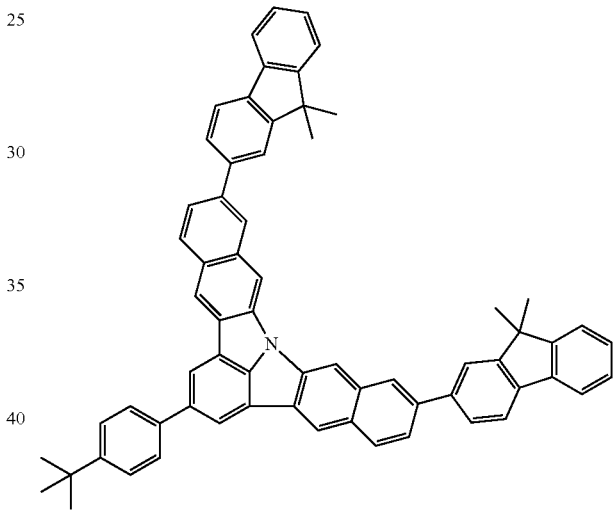
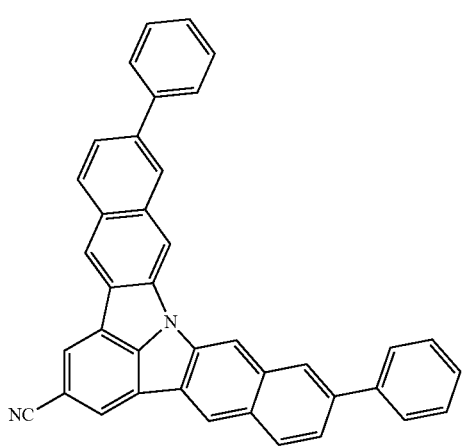

-continued
177
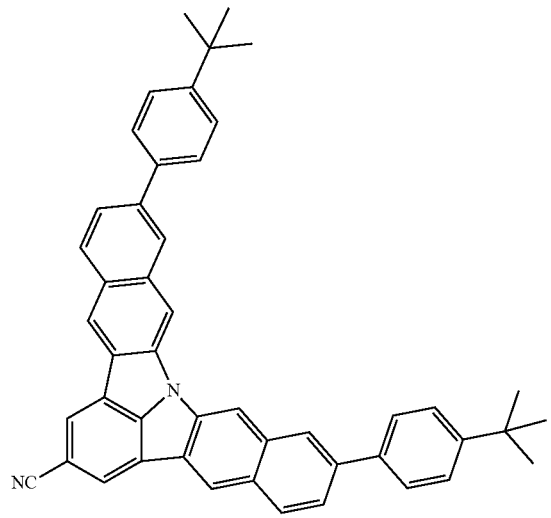
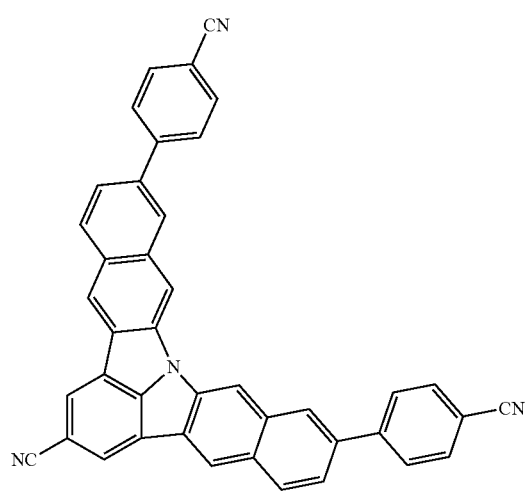
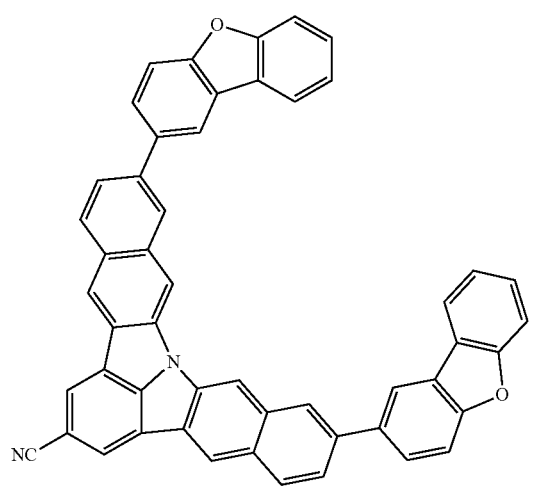
178
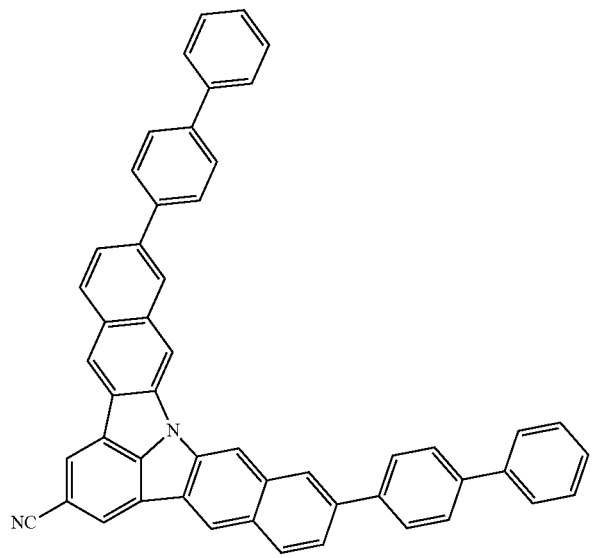
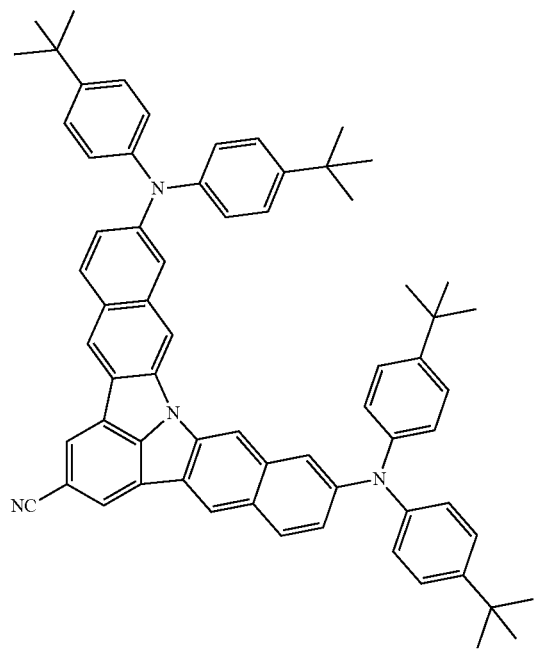
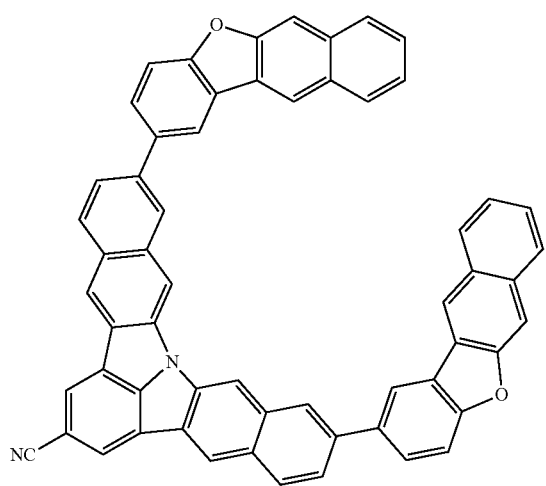

| 179 | 180 |
|---|---|
| 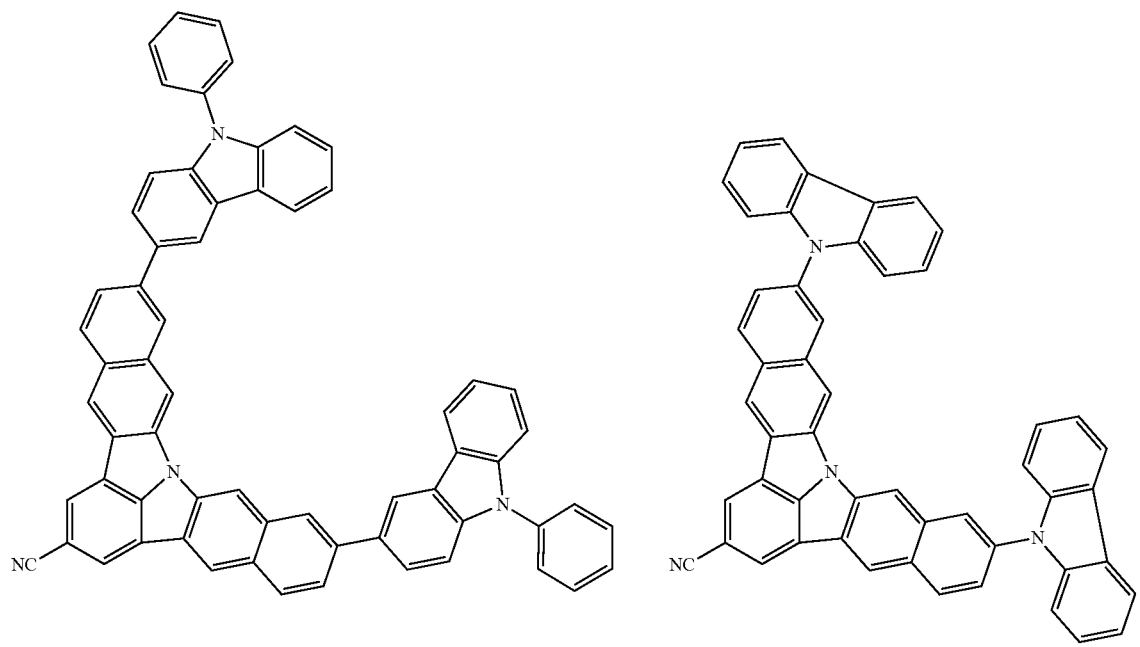 | |

-continued
181
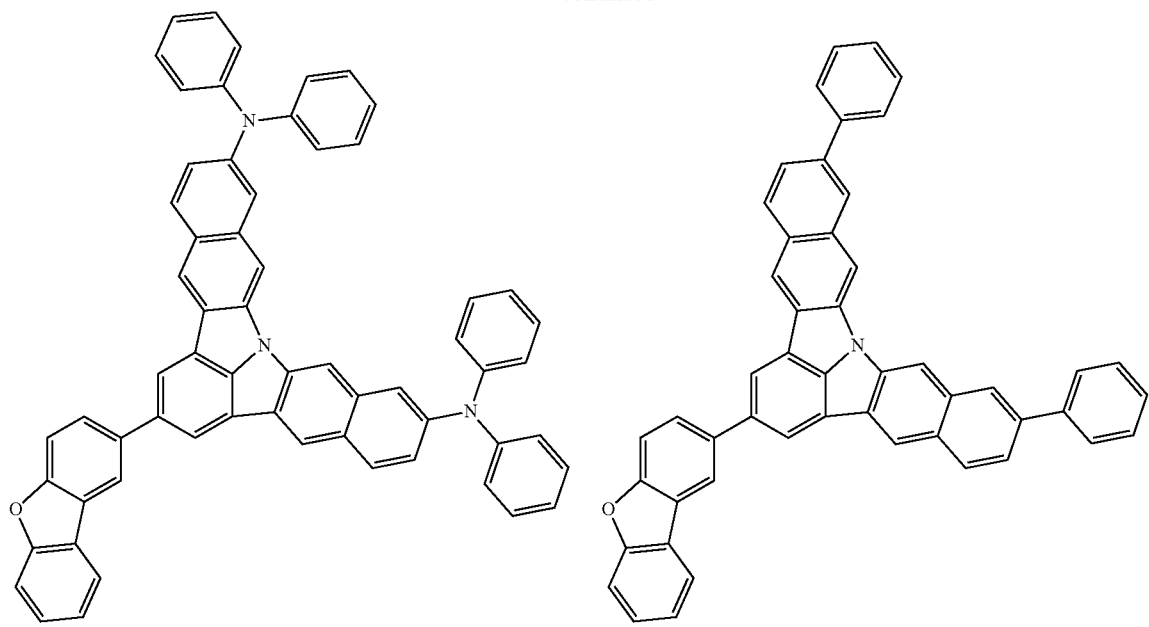
182
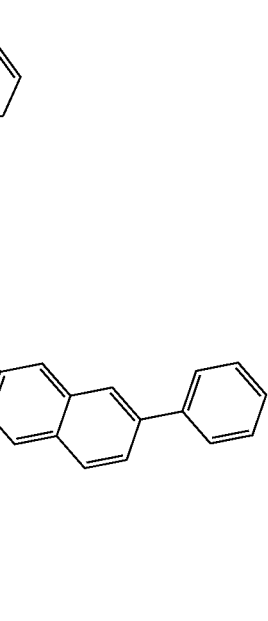
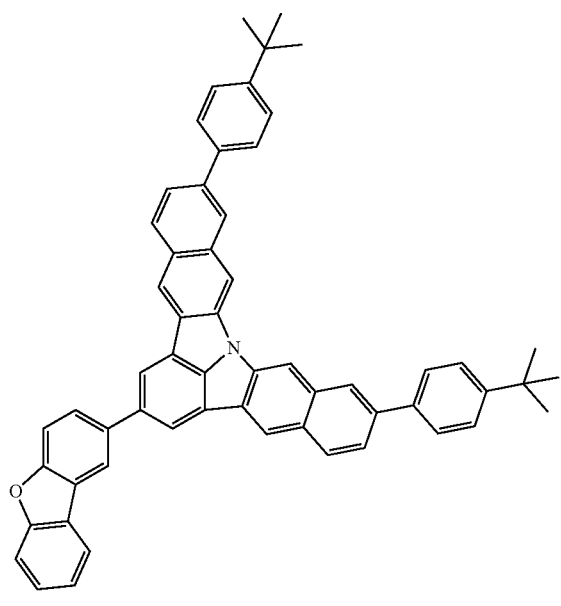
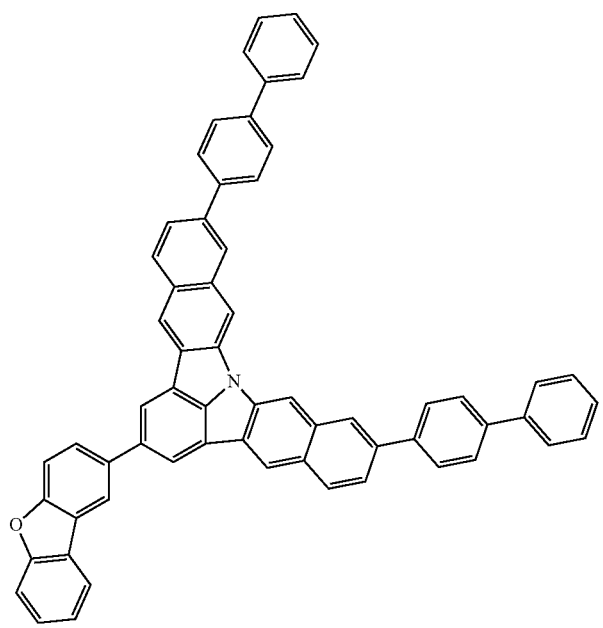

183
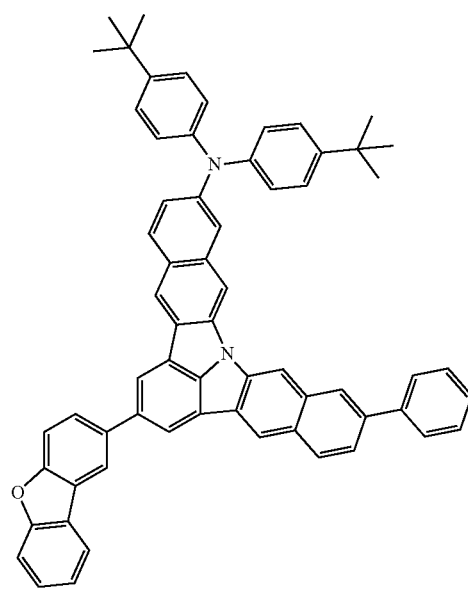
184
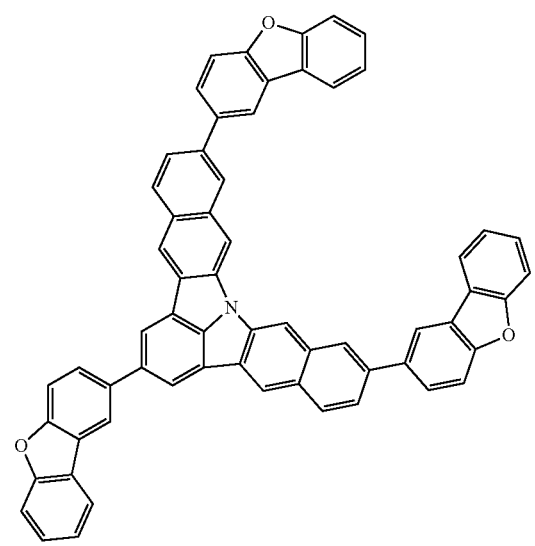
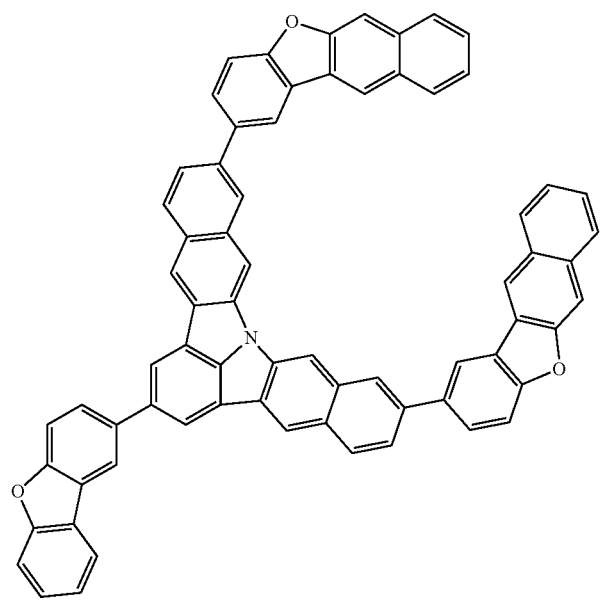
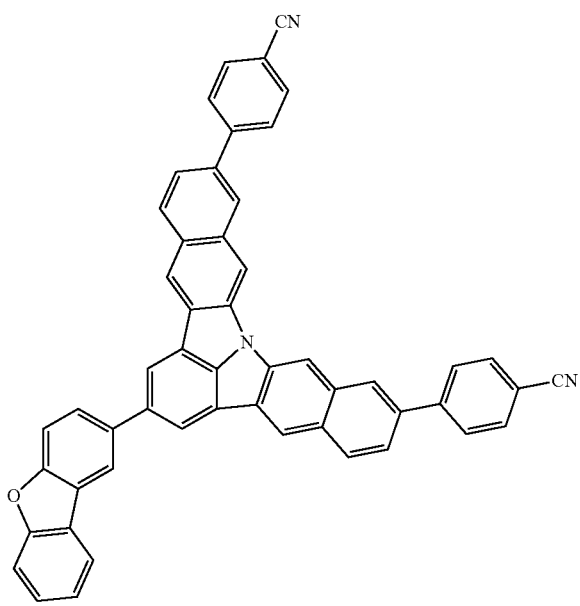

185 186
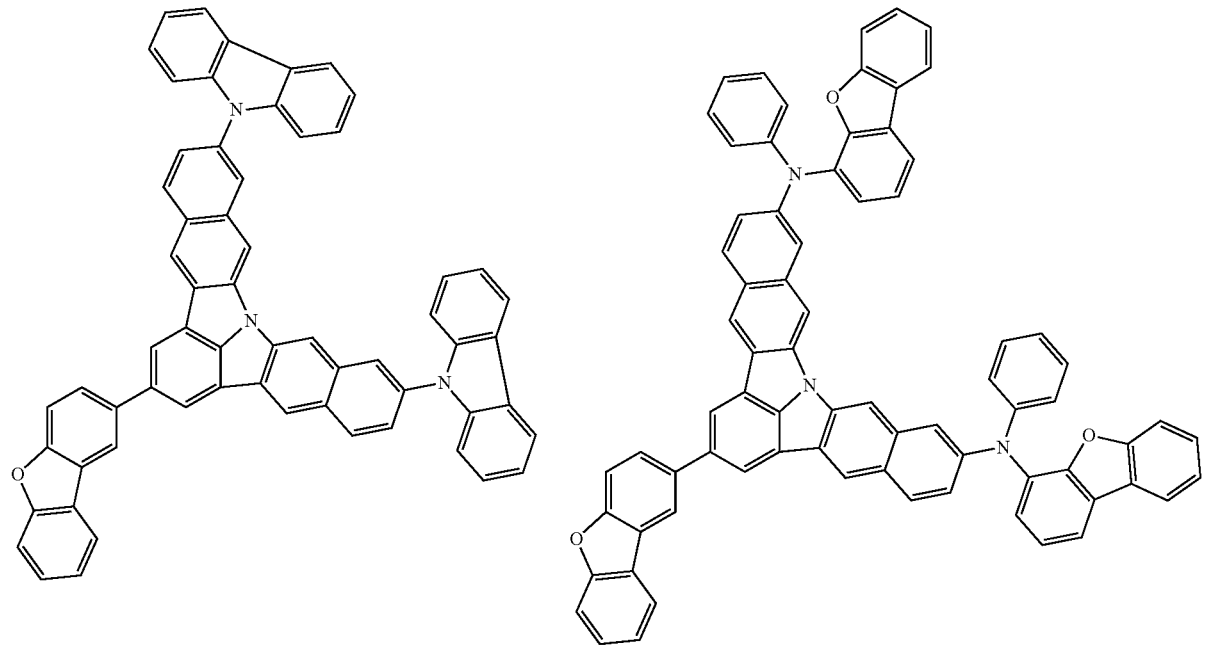
-continued
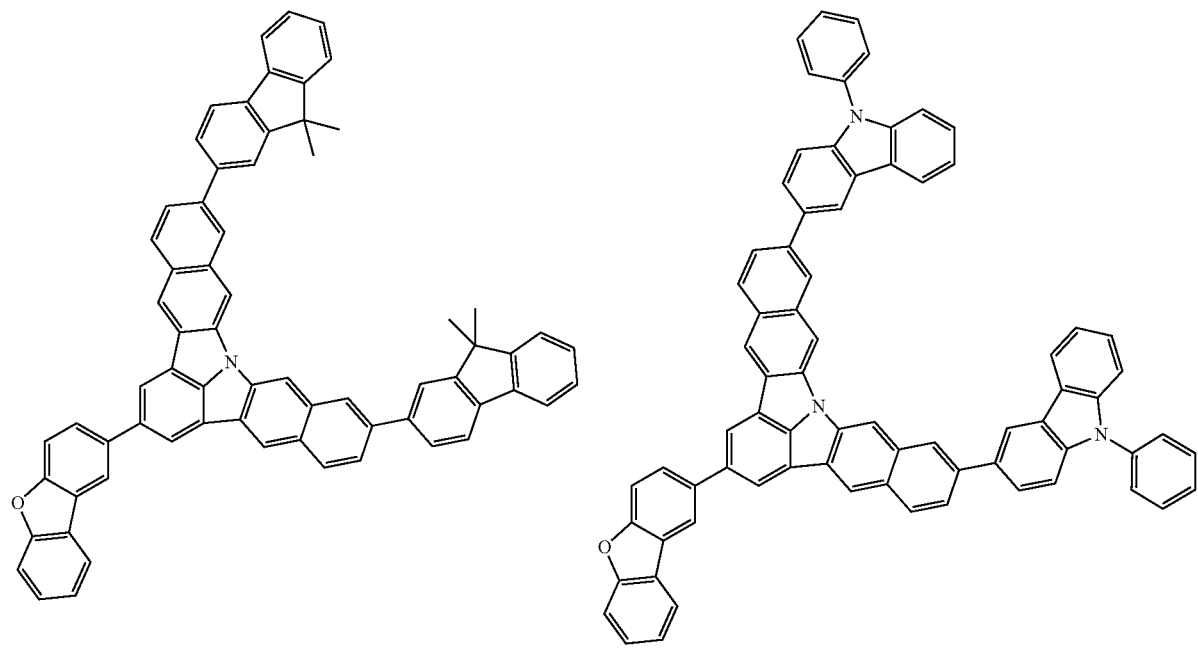

-continued
187
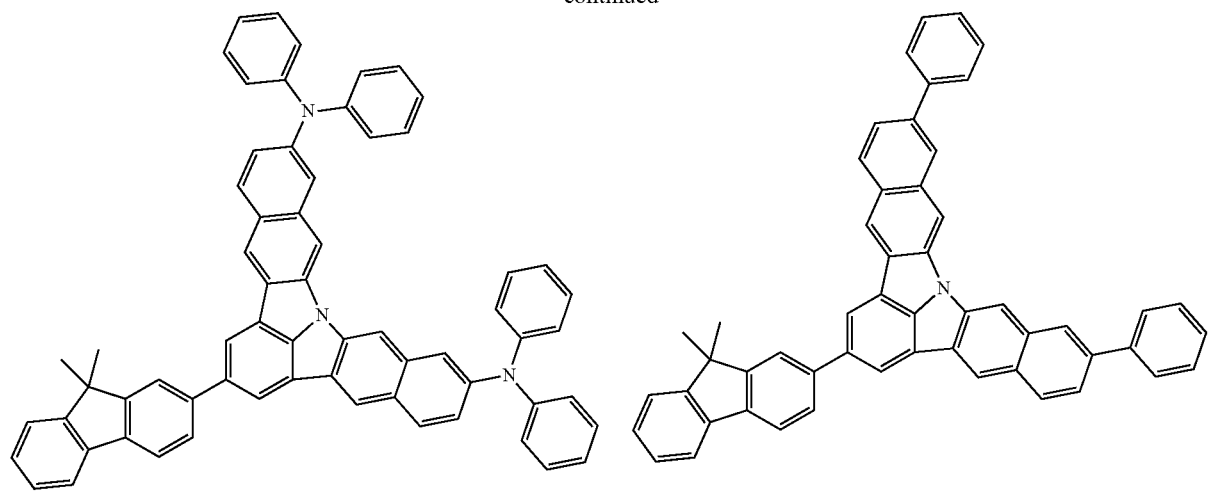
188
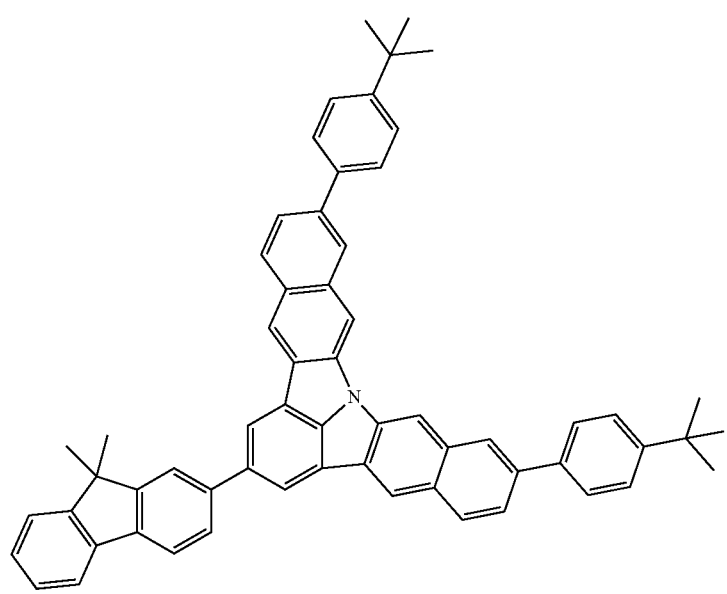
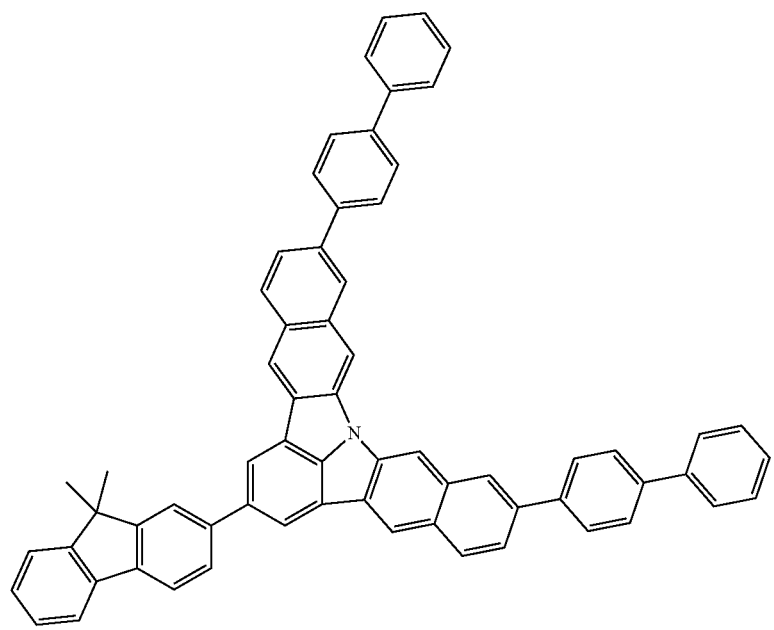

-continued
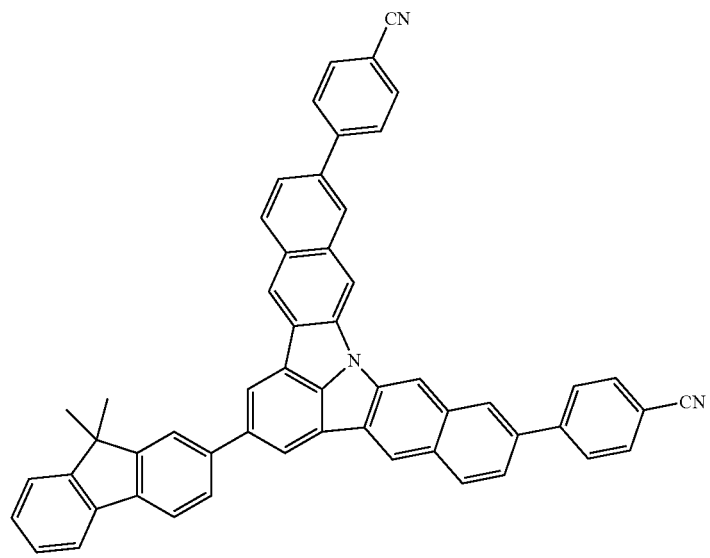
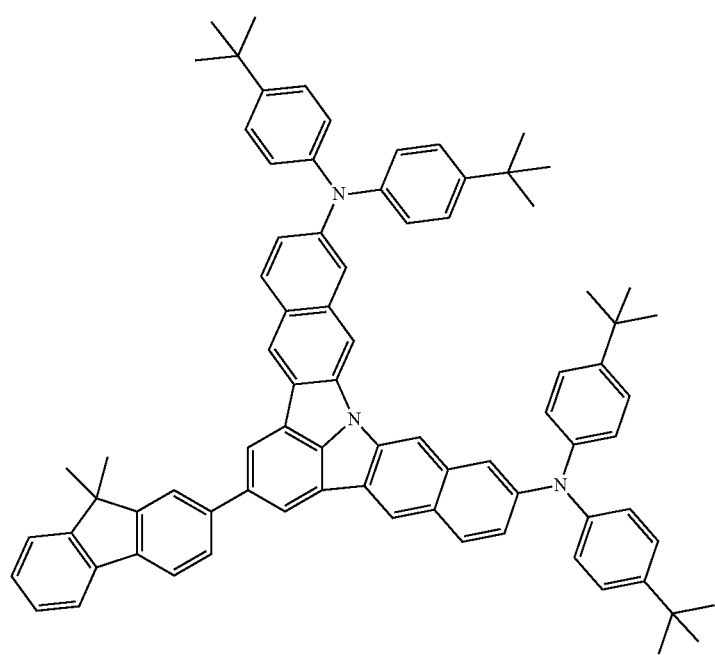

-continued
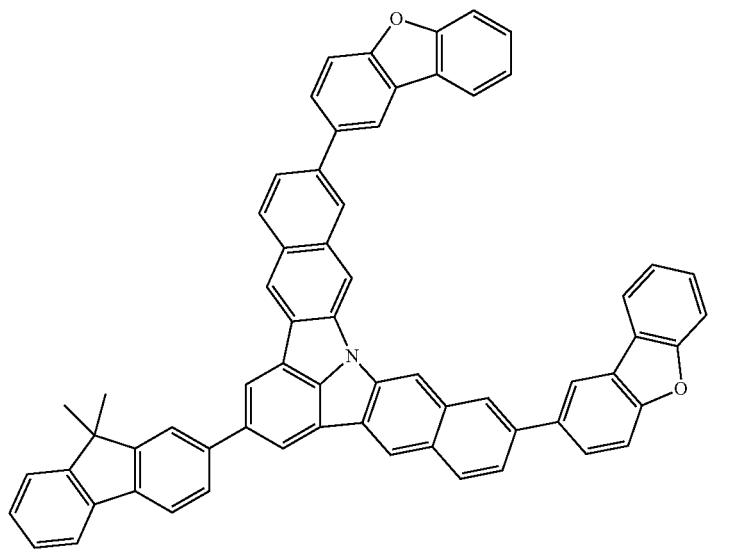
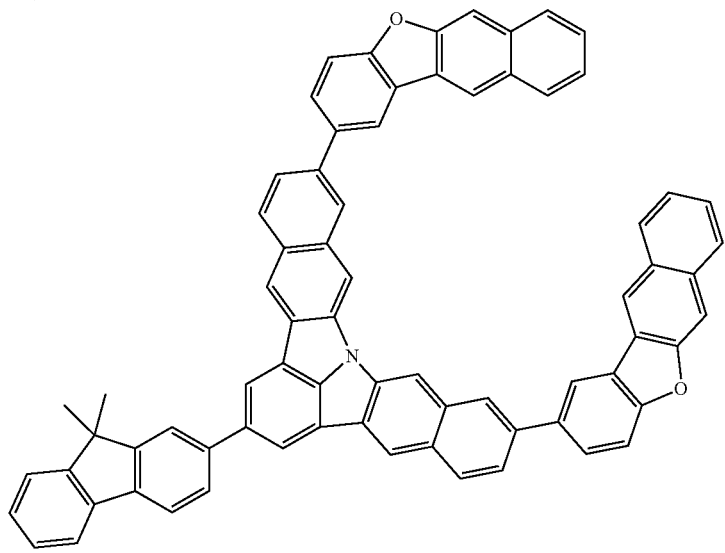
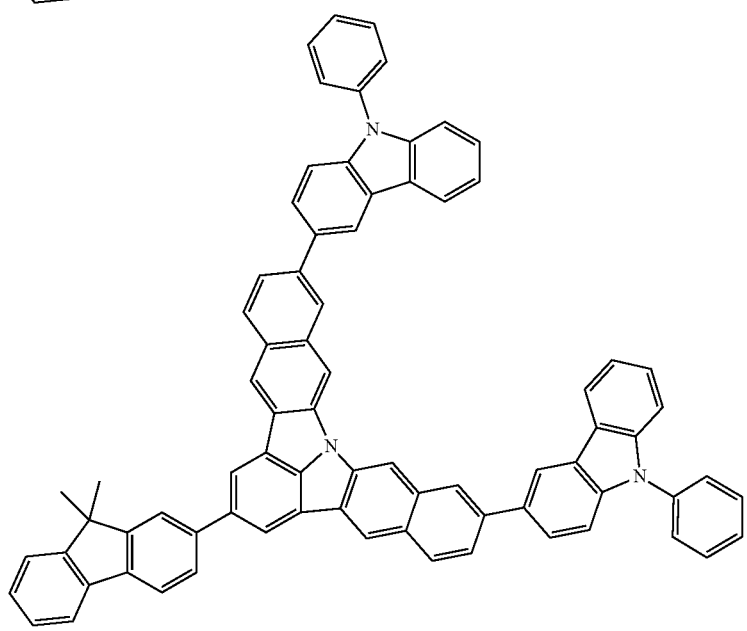

-continued
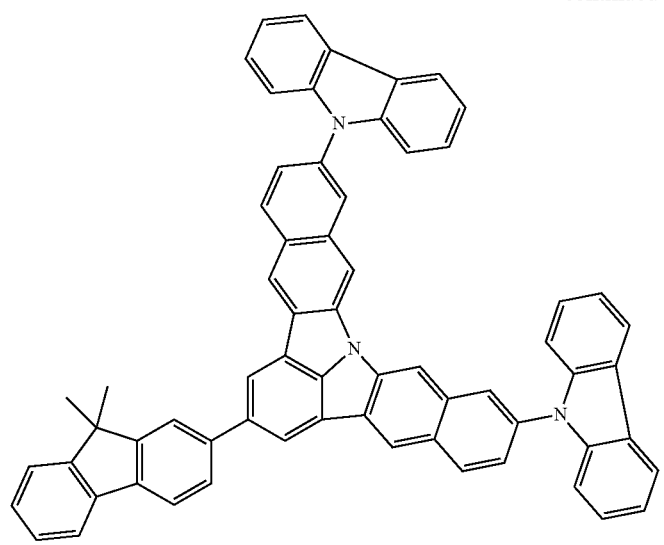
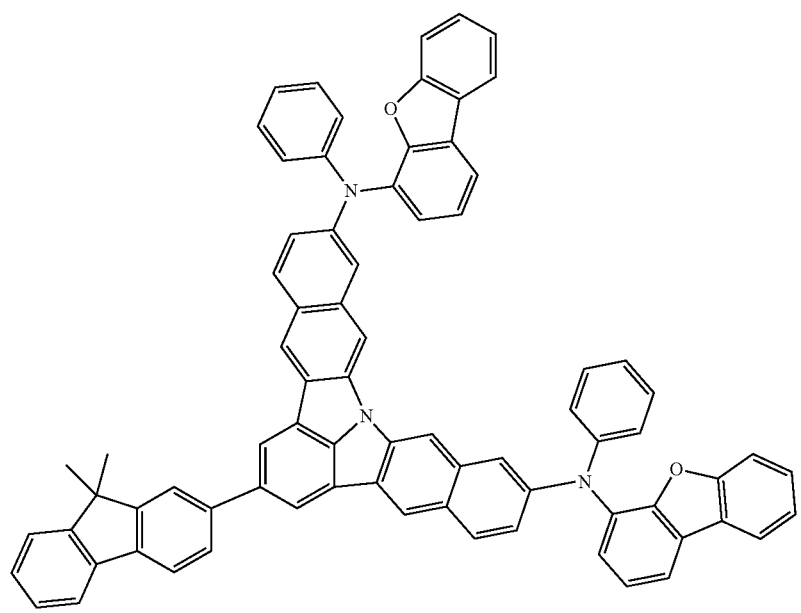

-continued
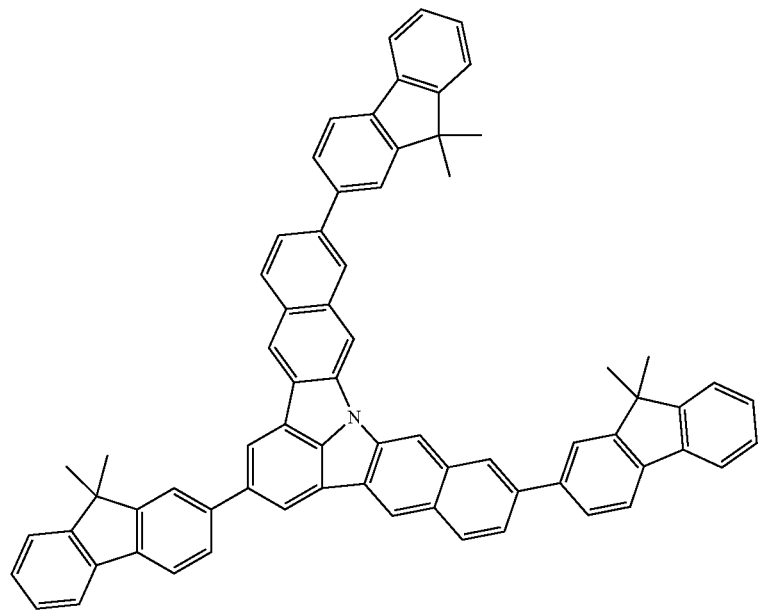
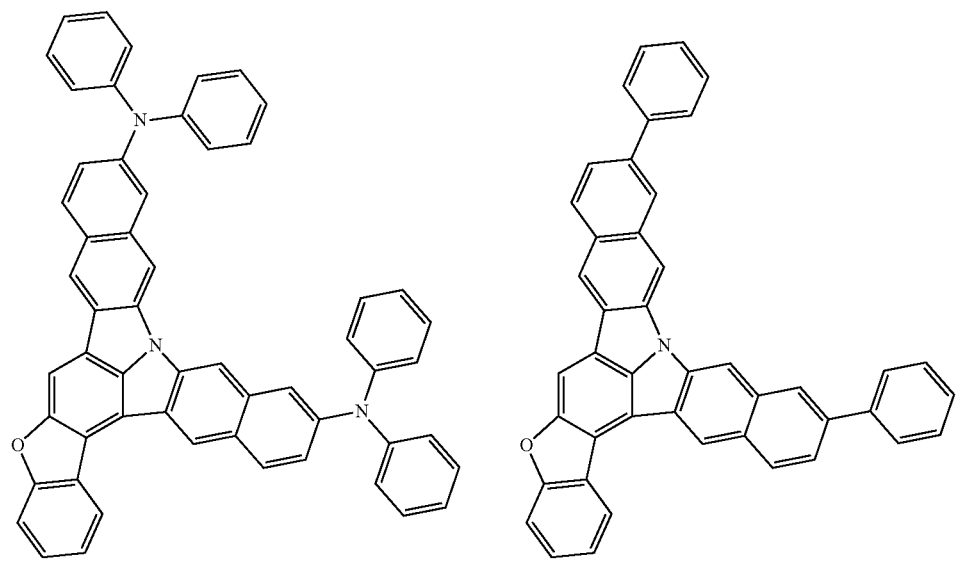

197
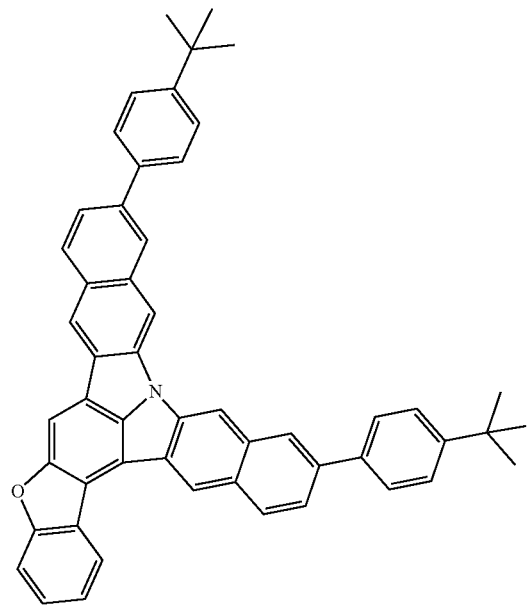
198
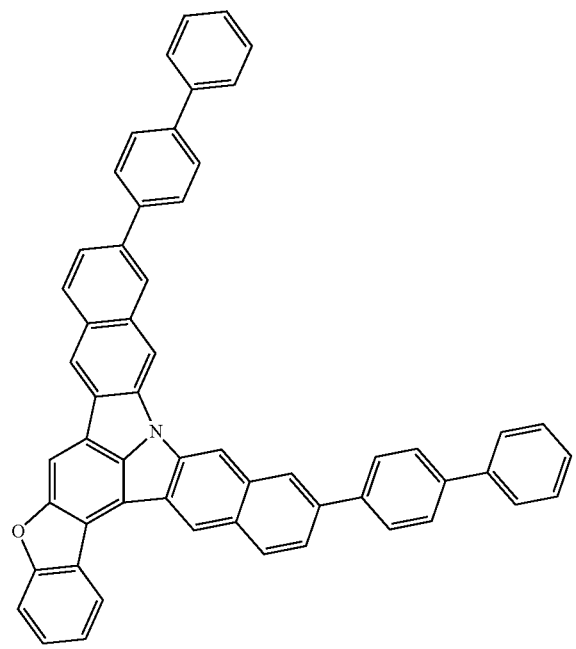
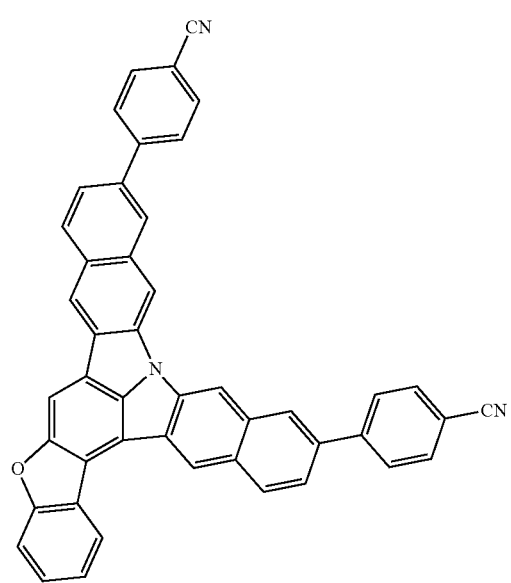
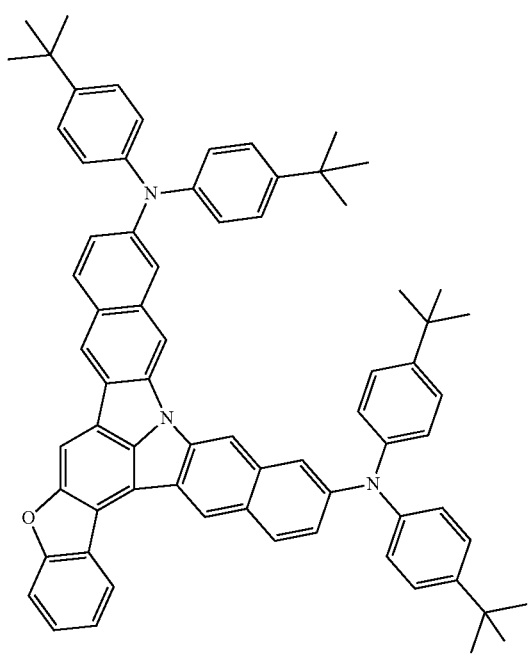

-continued
199
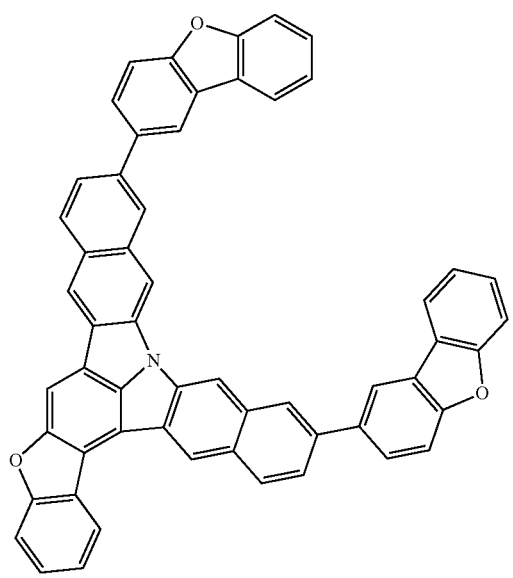
200
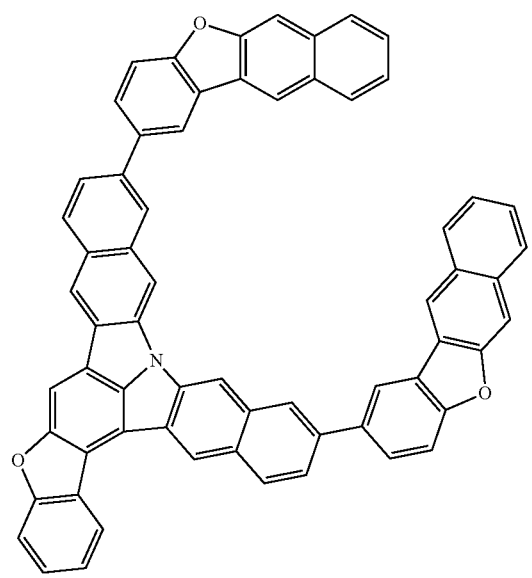
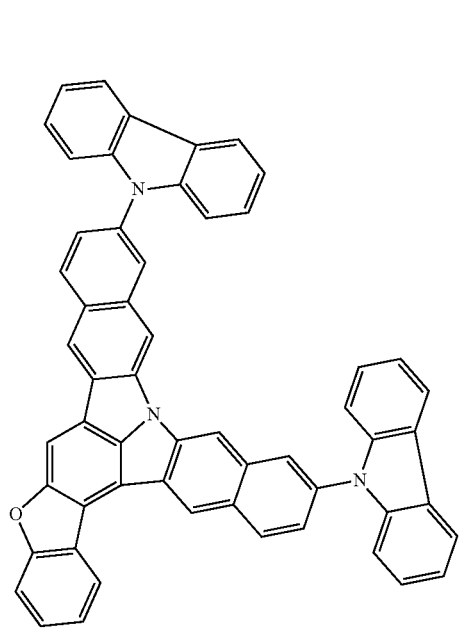
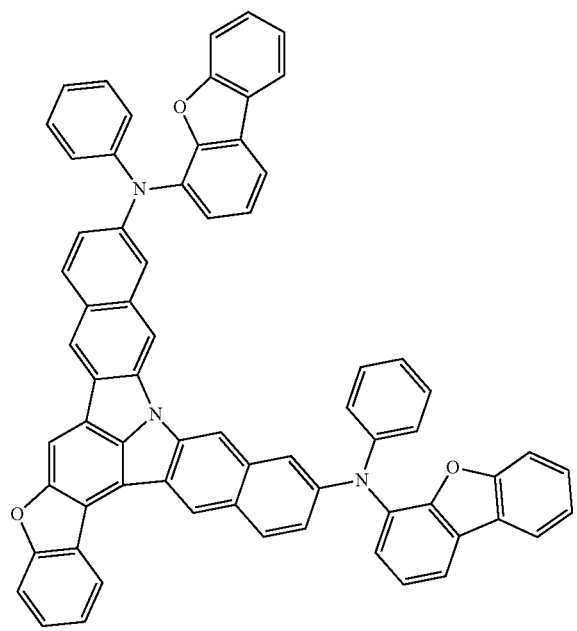

-continued
201
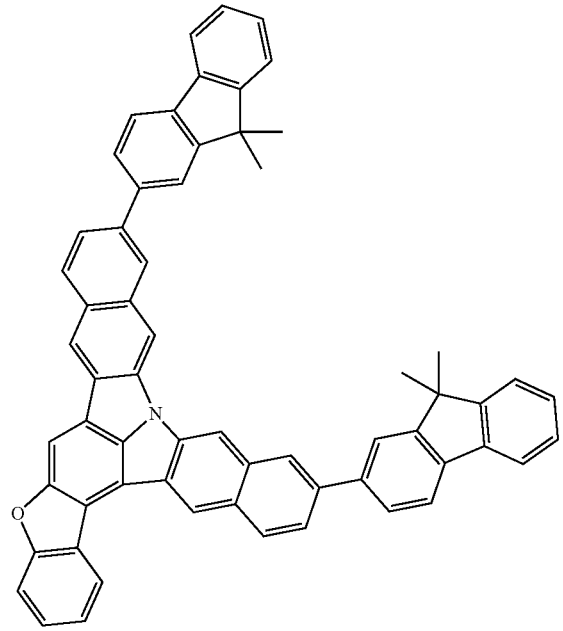
202
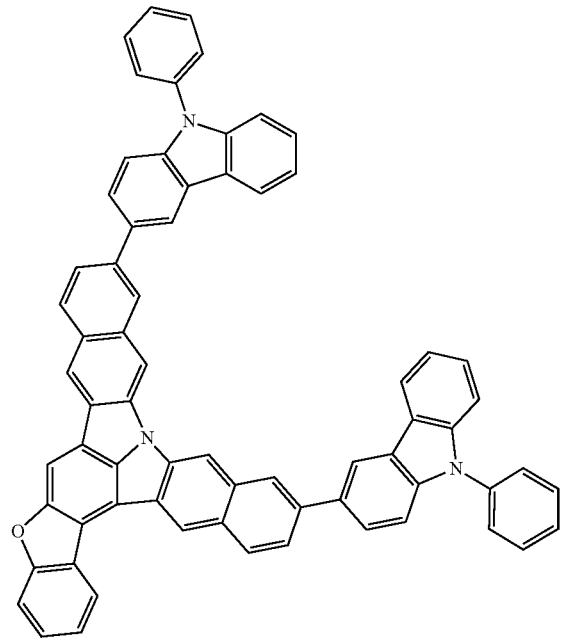
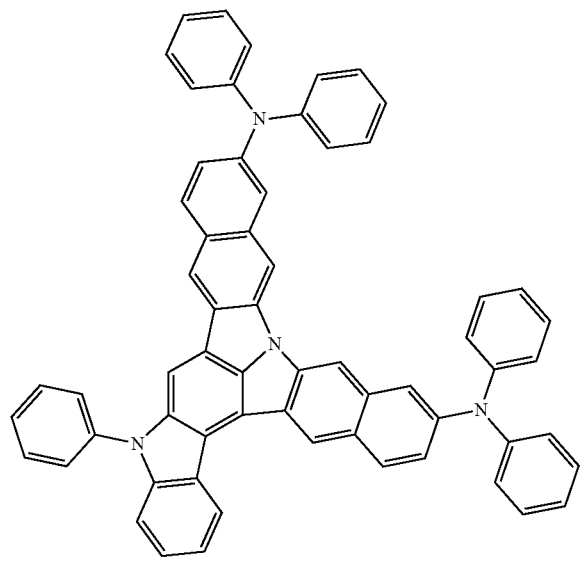
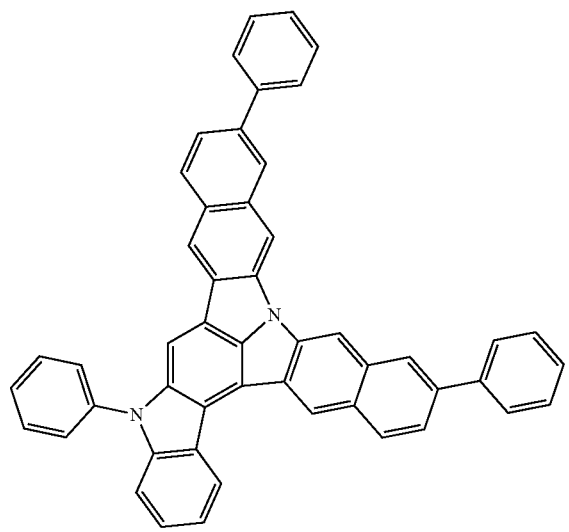

203 204
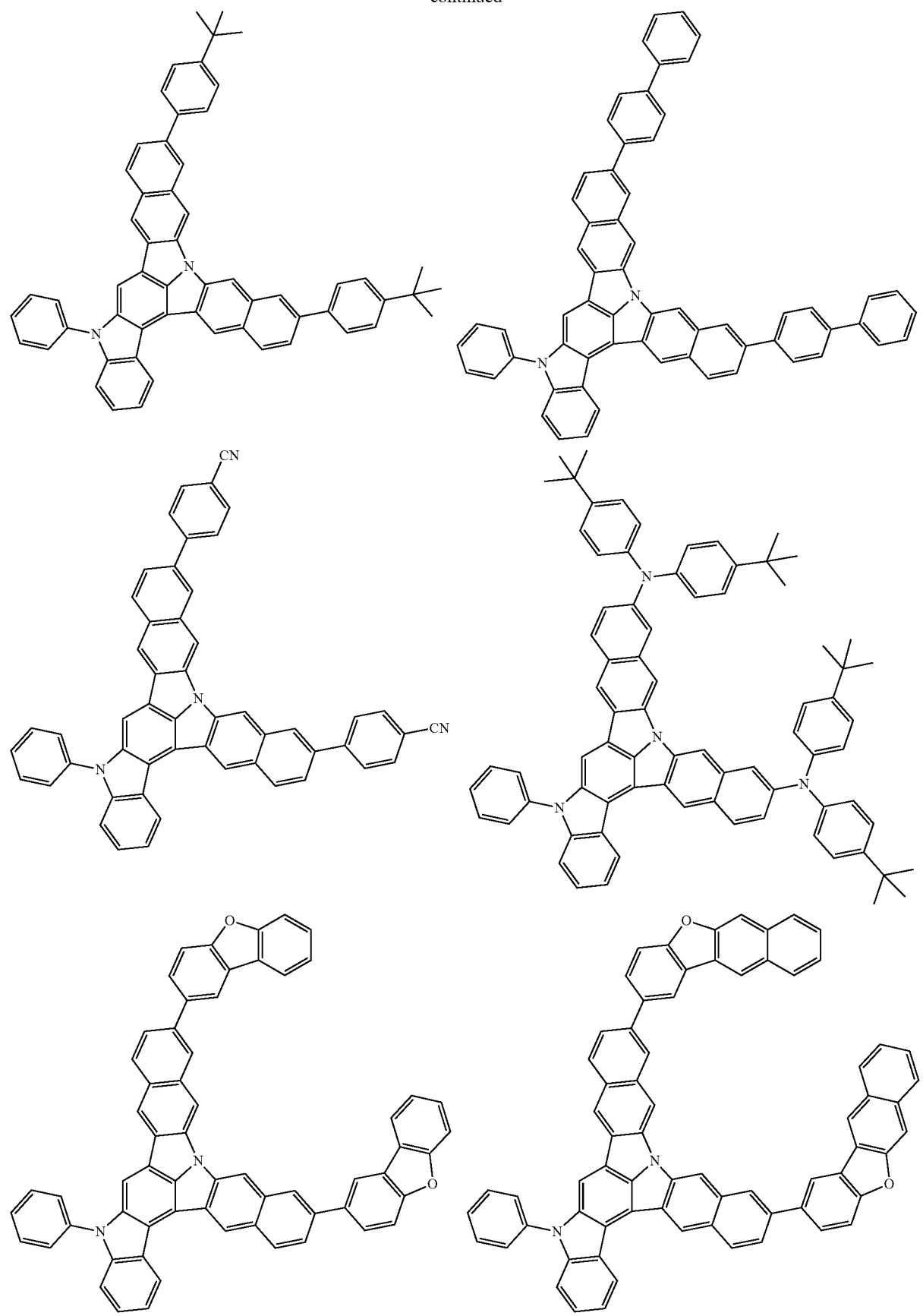
-continued 205 206
-continued
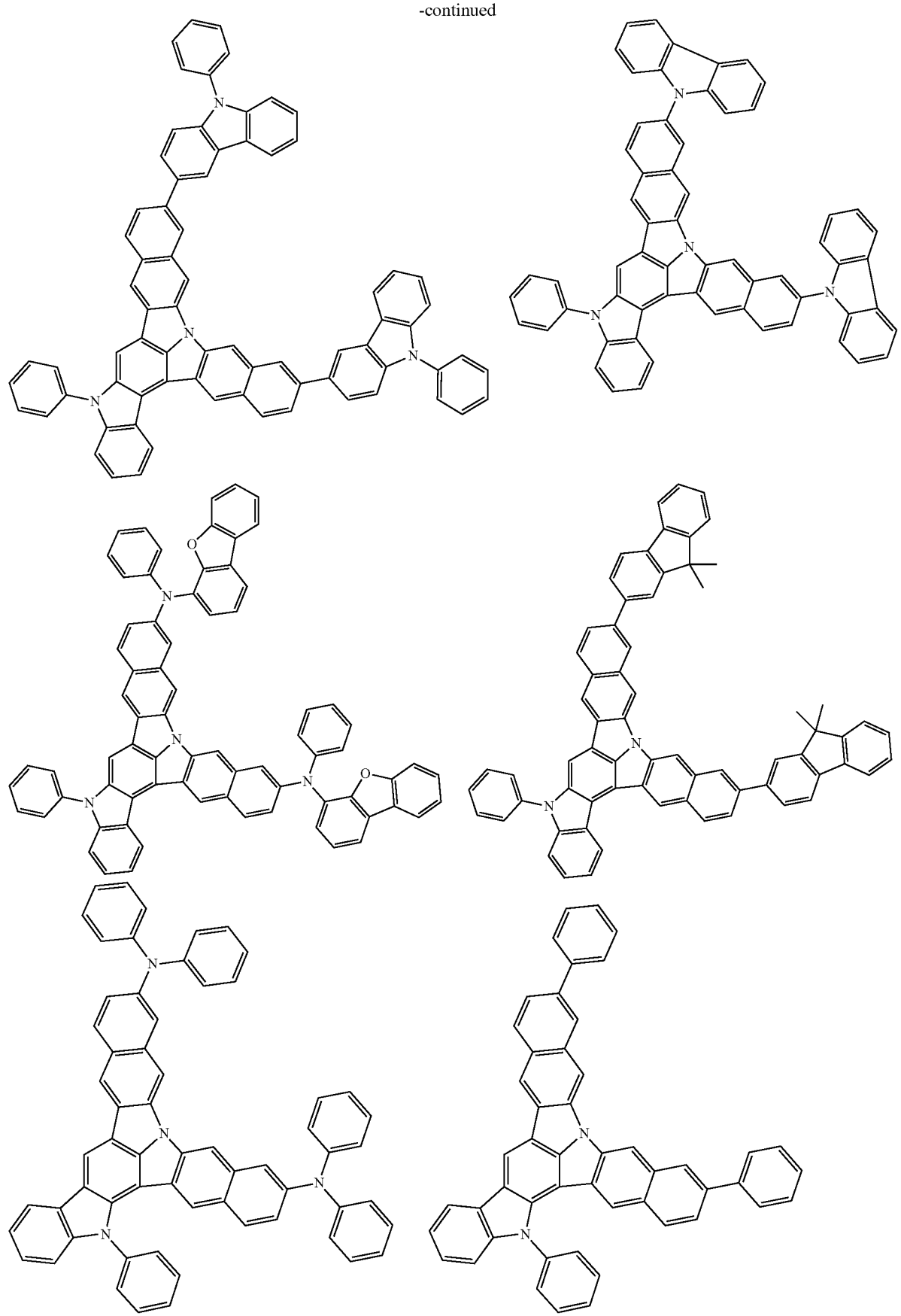

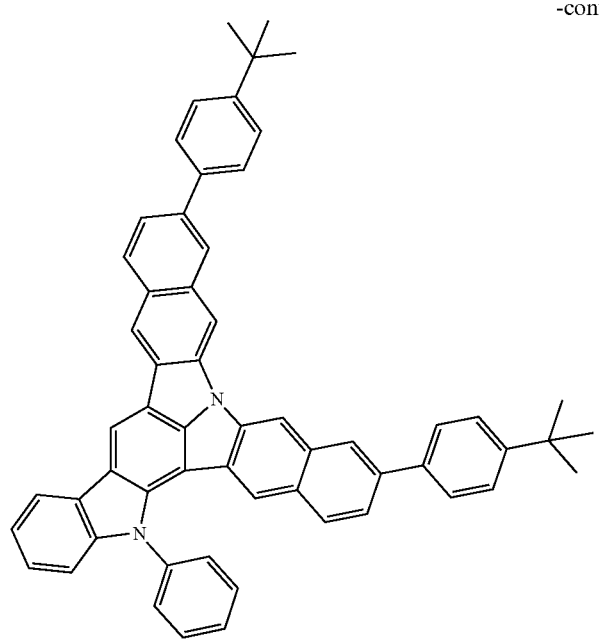
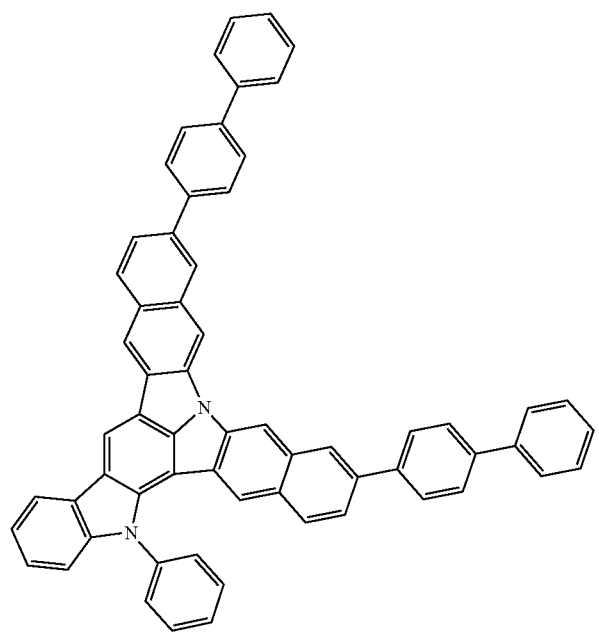

209 210
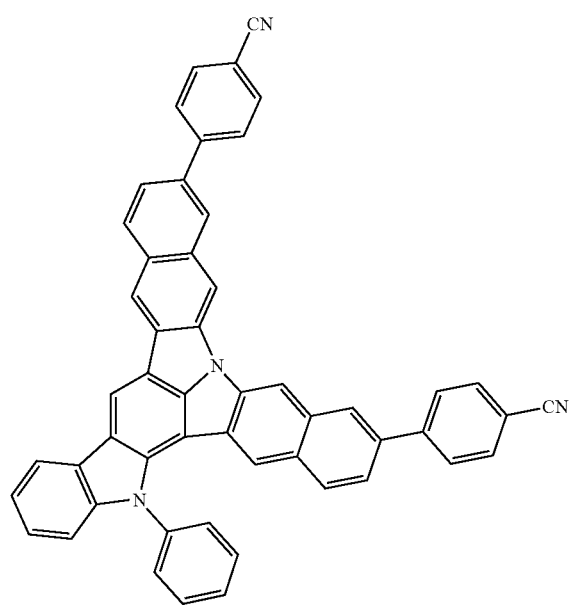 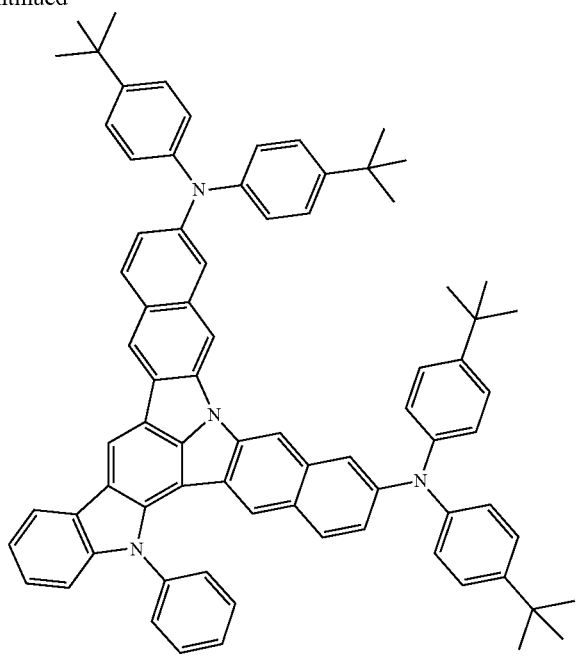
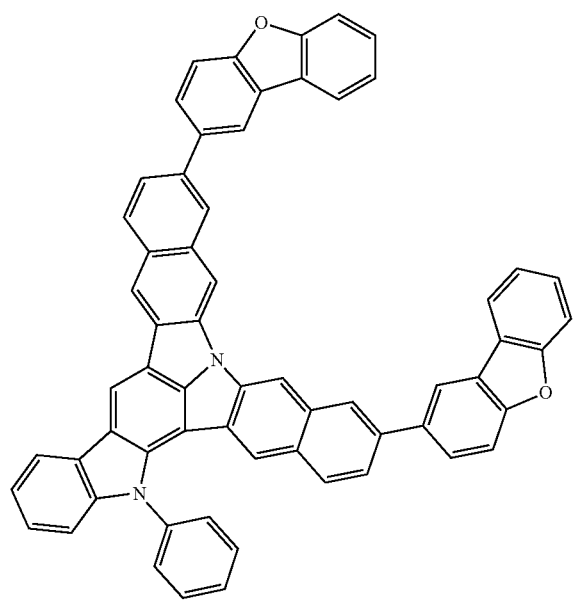 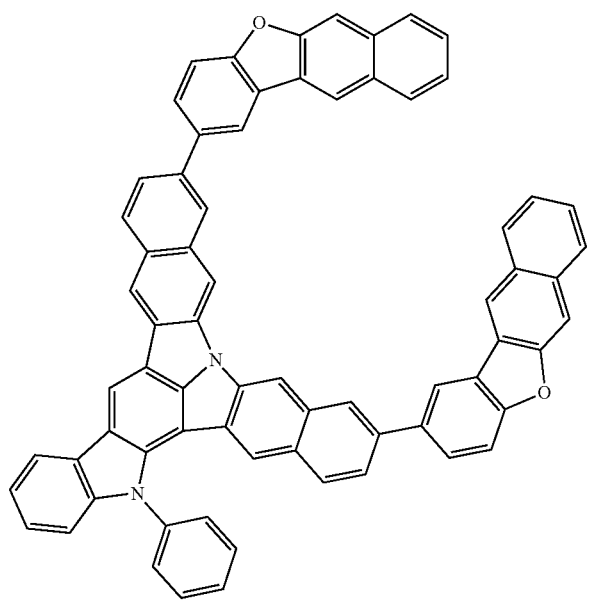

211
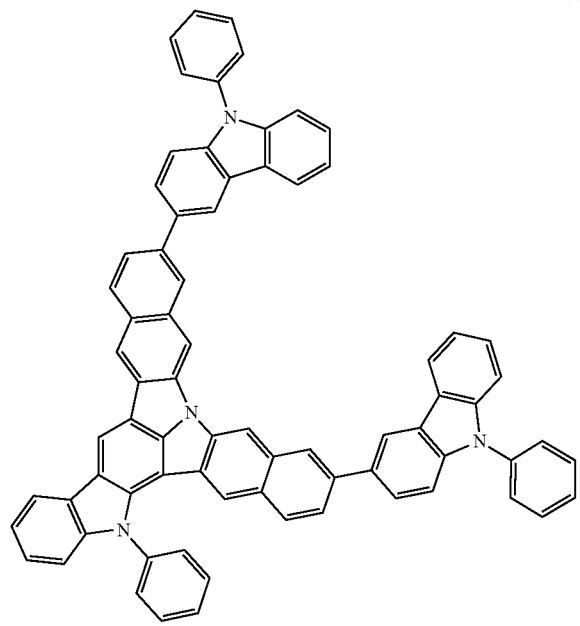
212
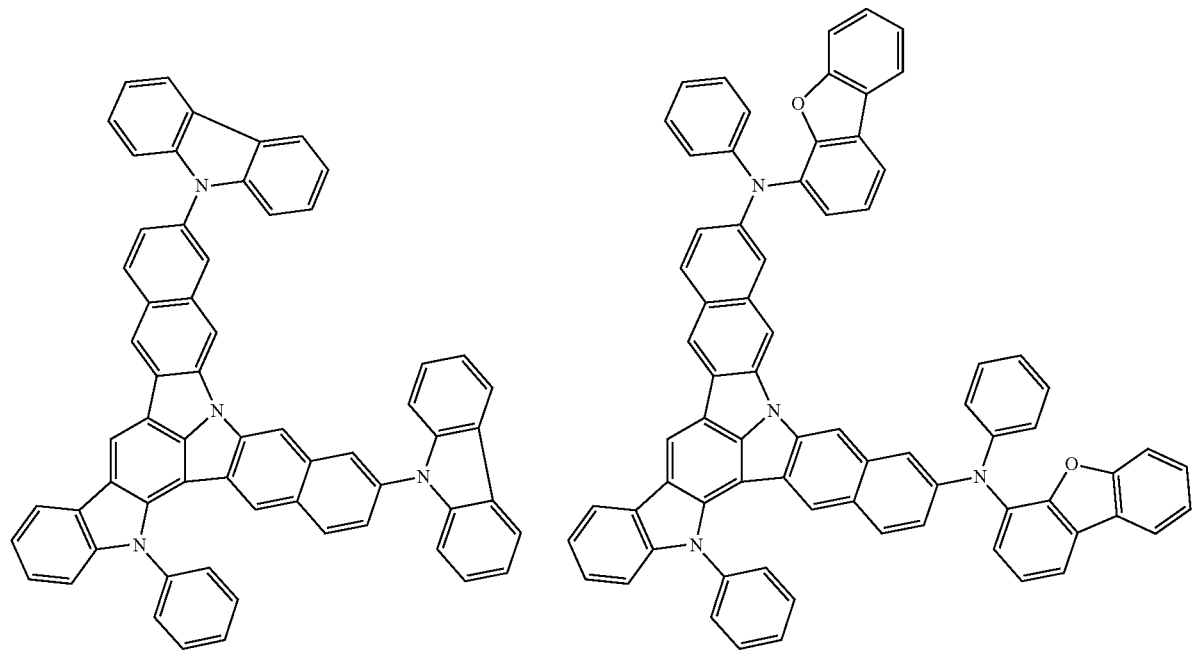

213
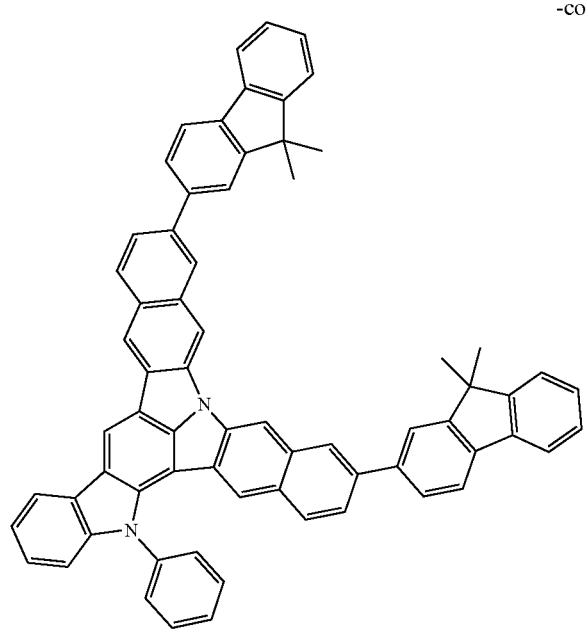
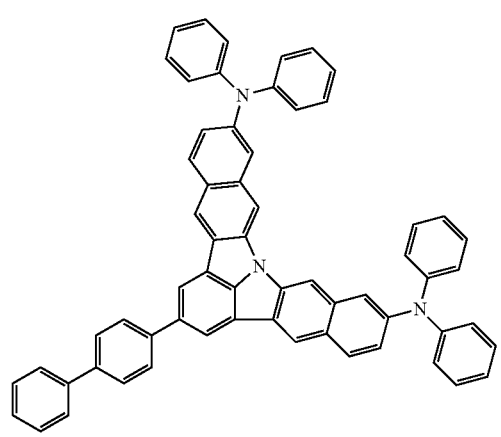
214
-continued
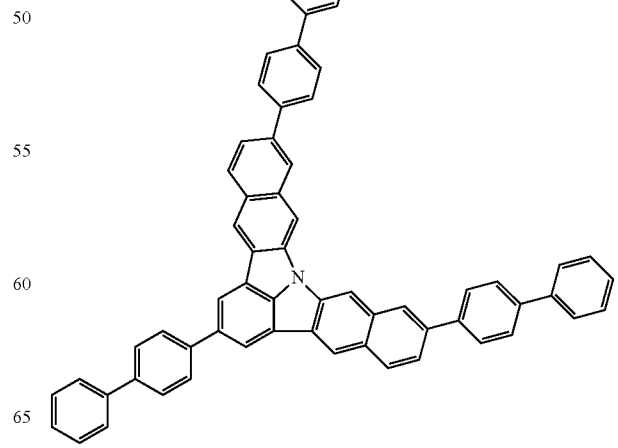

215
-continued
216
-continued
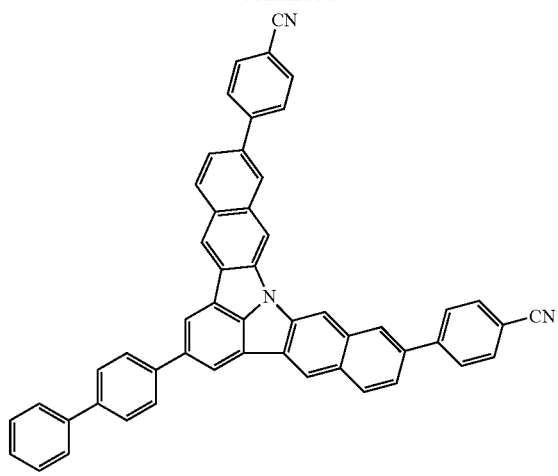
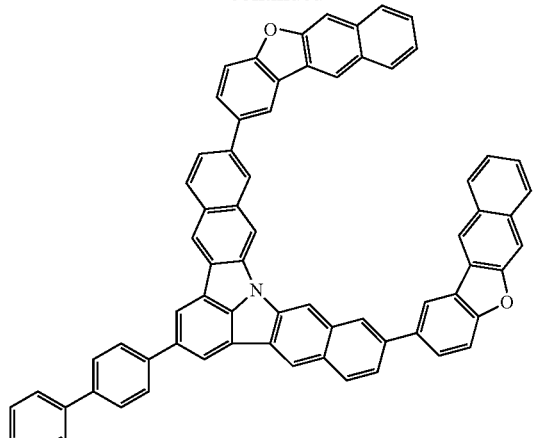
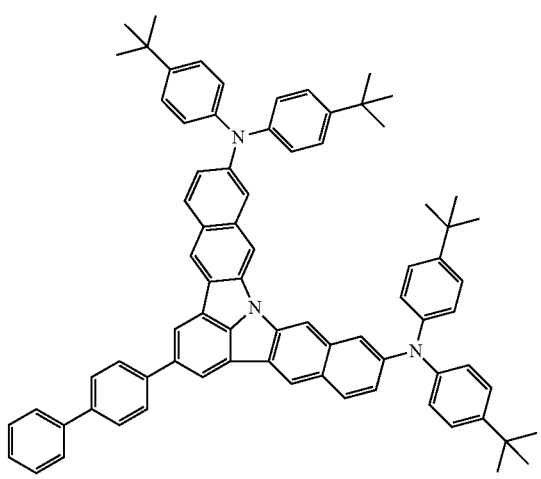
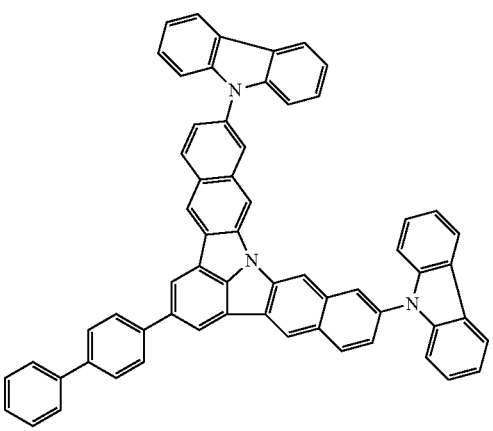
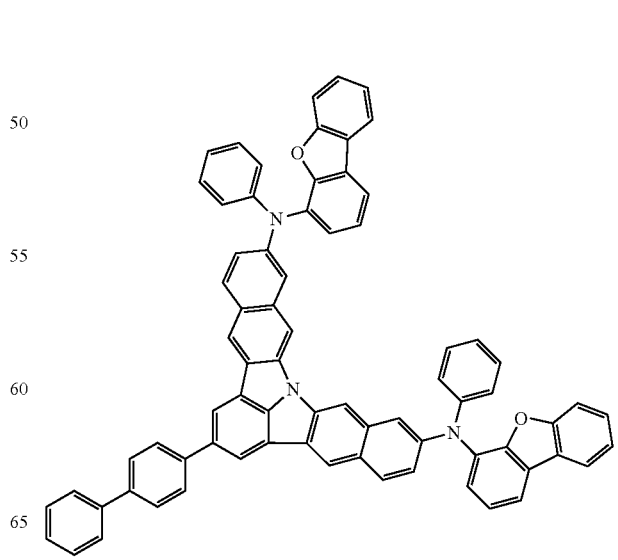

217
-continued
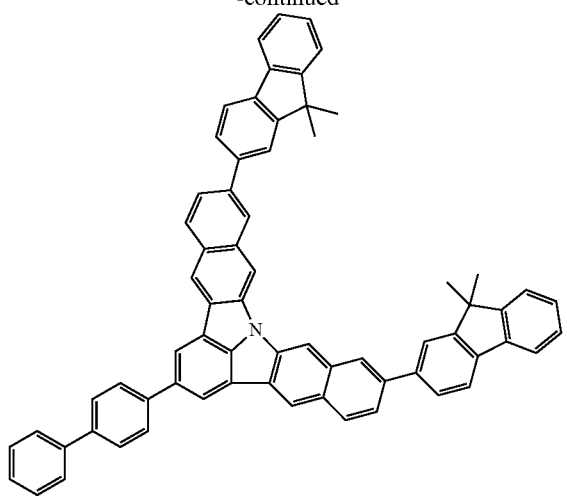
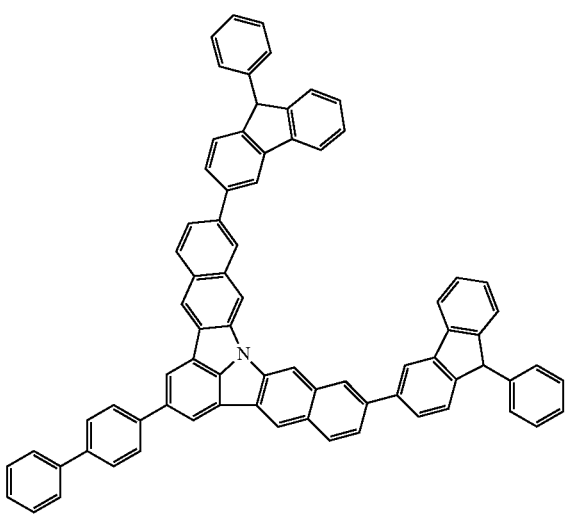
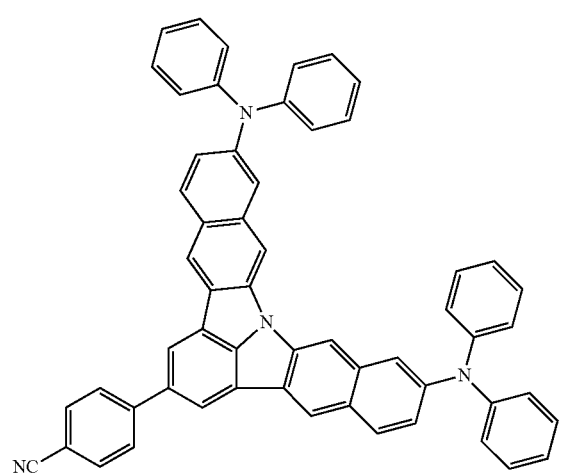
218
-continued
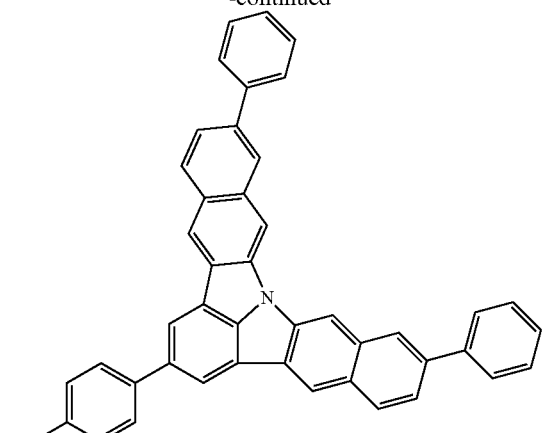
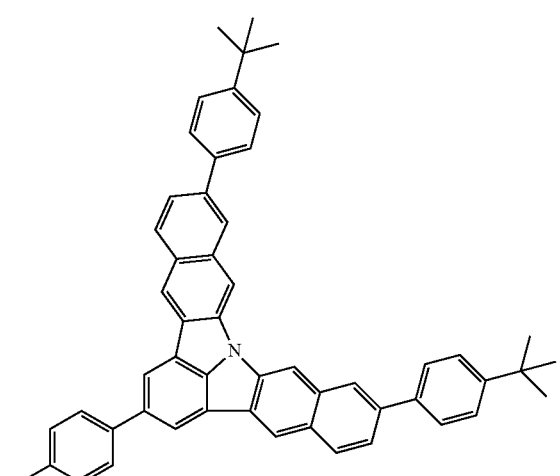
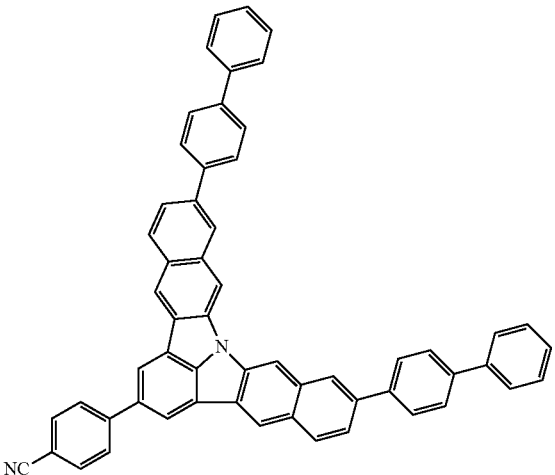

219 -continued
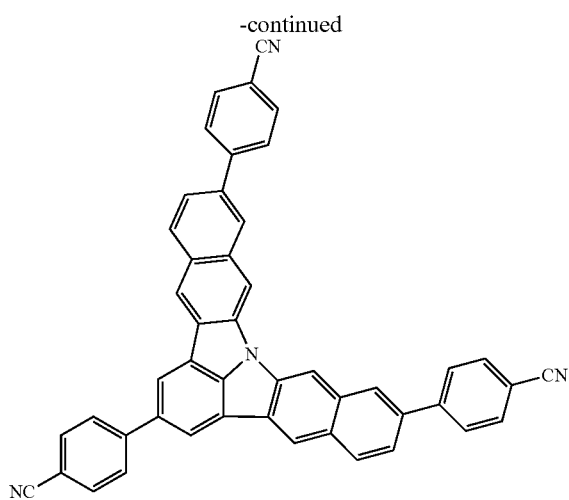
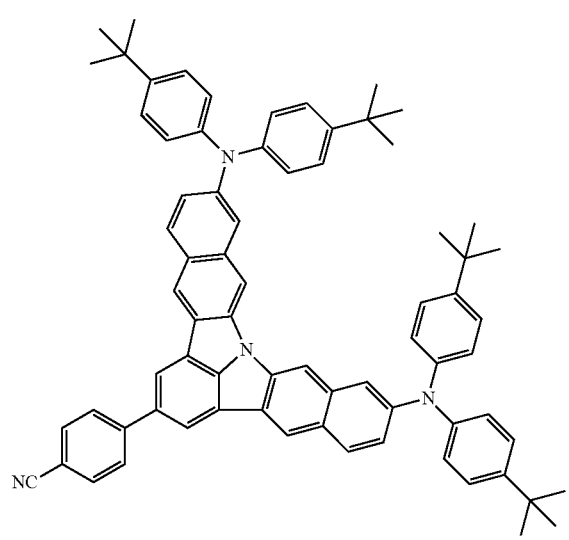
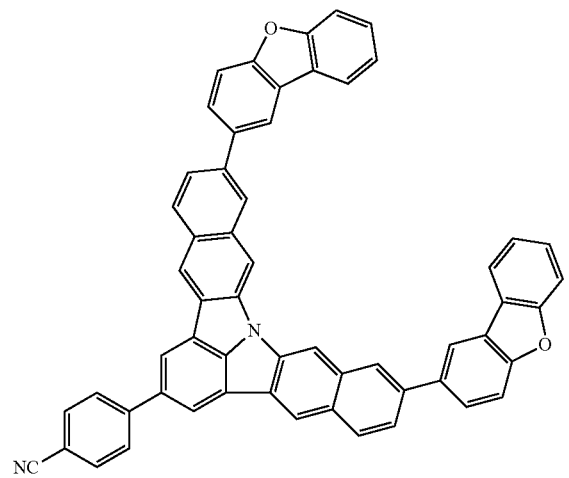
220 -continued
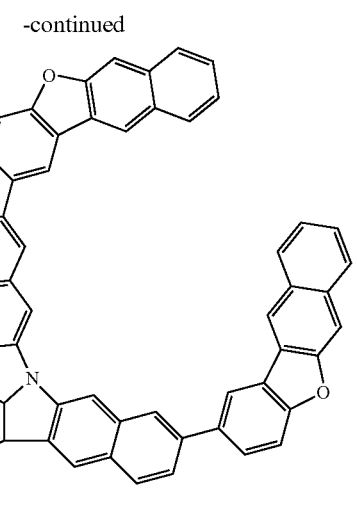
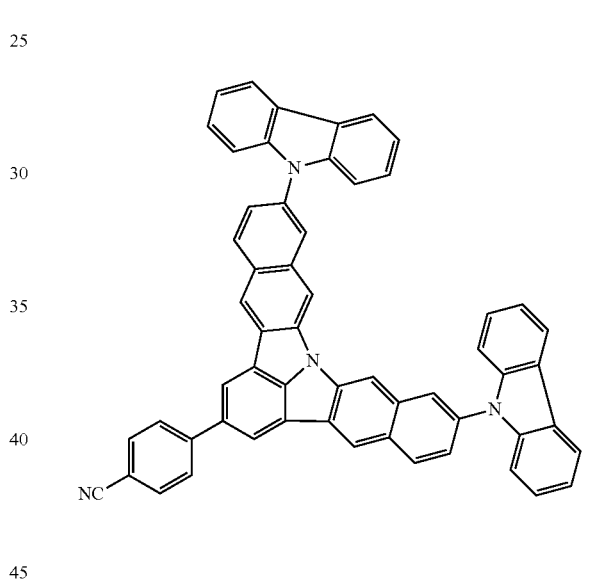
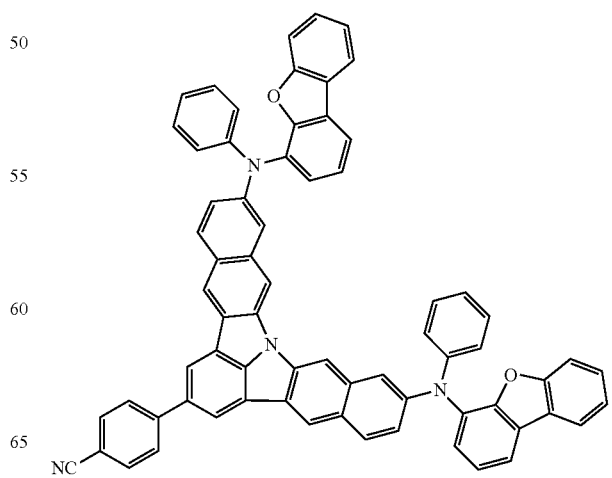

-continued
221
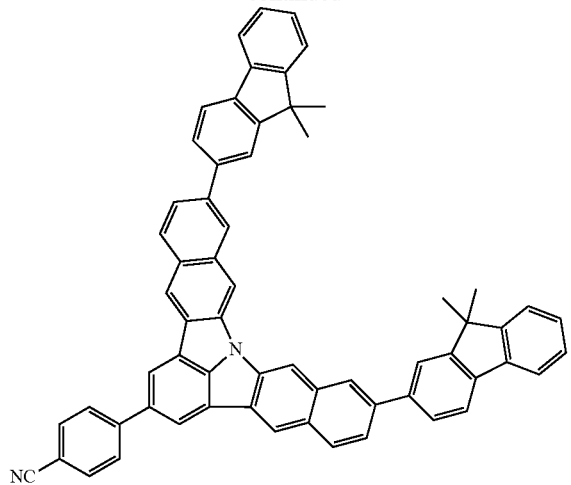
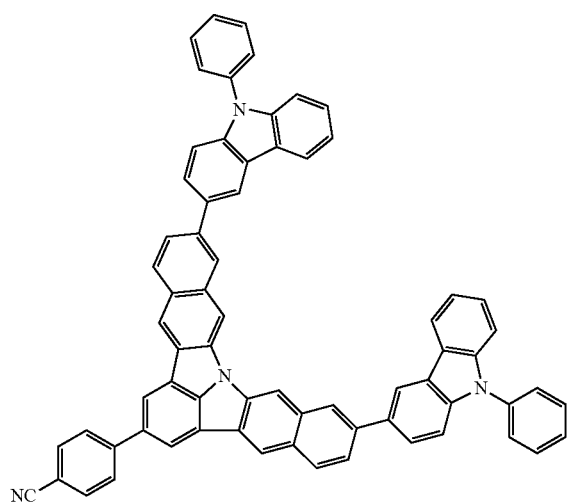
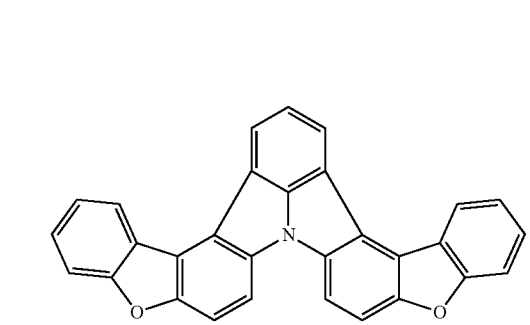
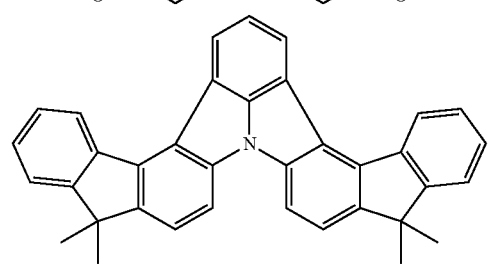
222
-continued
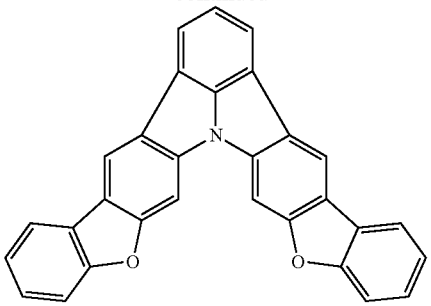
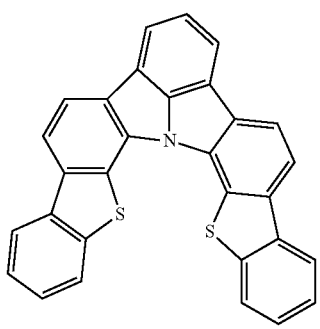
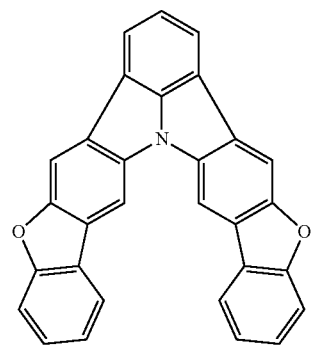
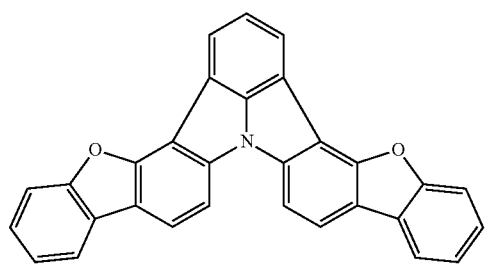
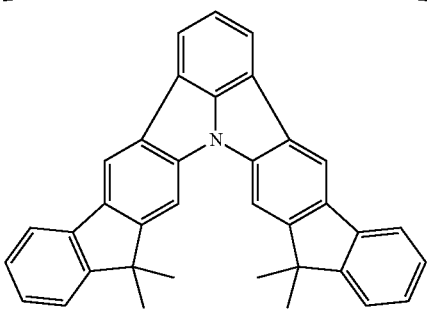

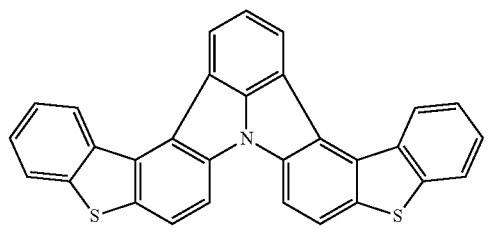
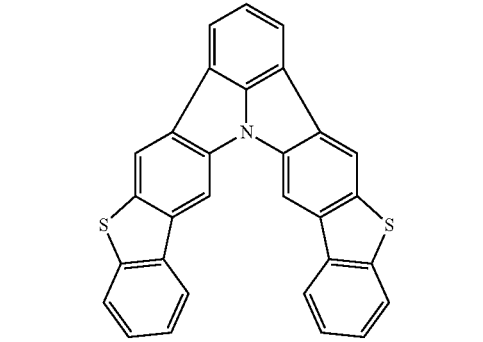
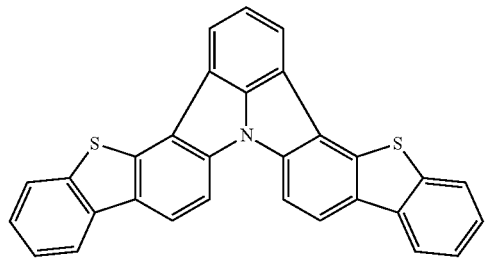
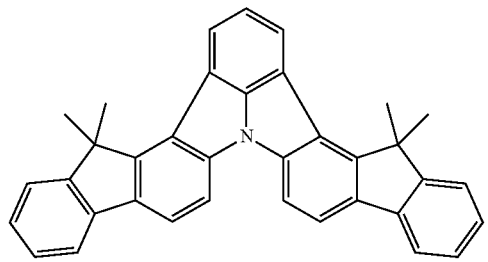
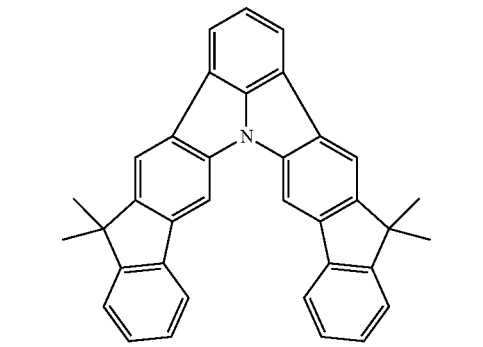
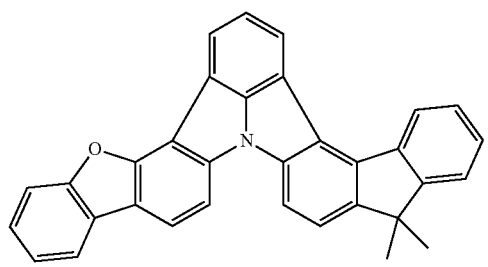
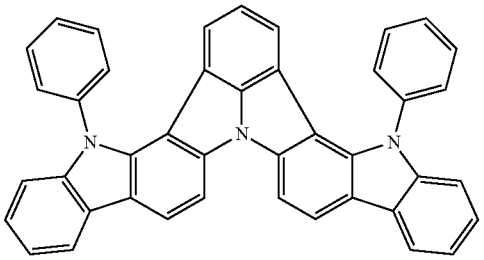
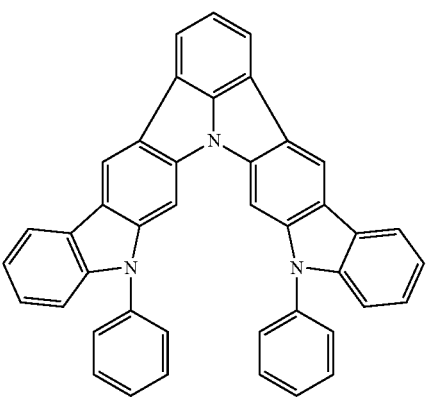
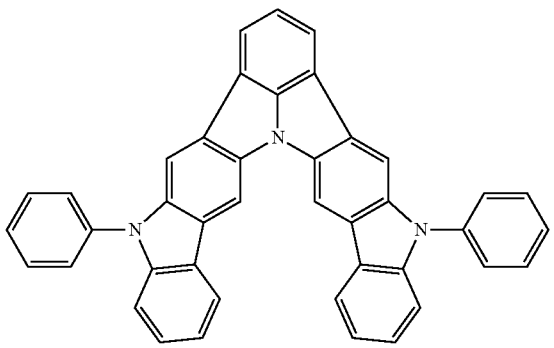
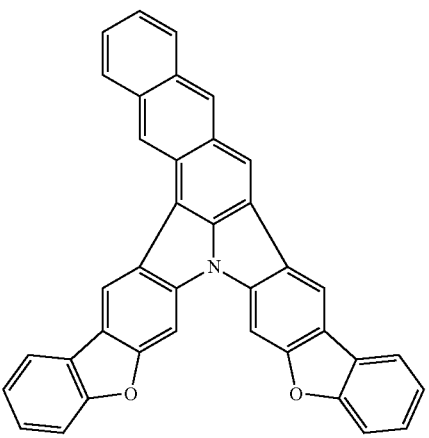

-continued
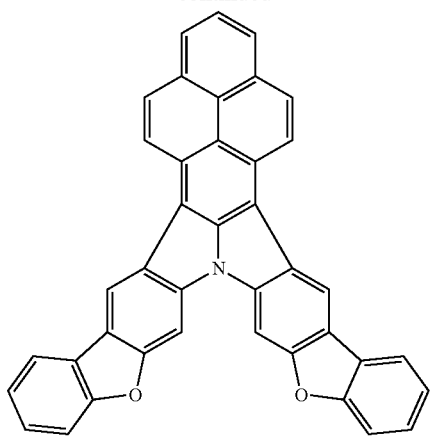
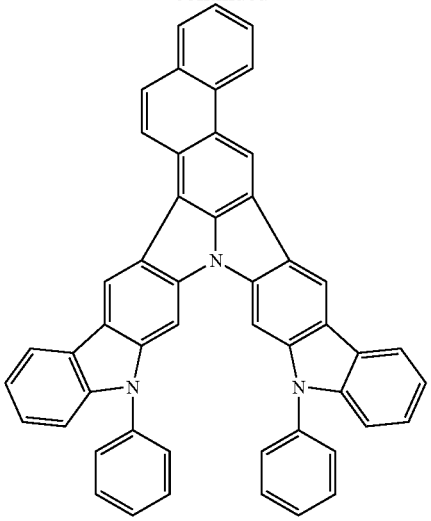
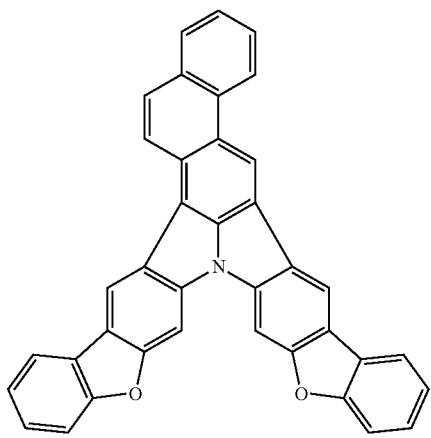
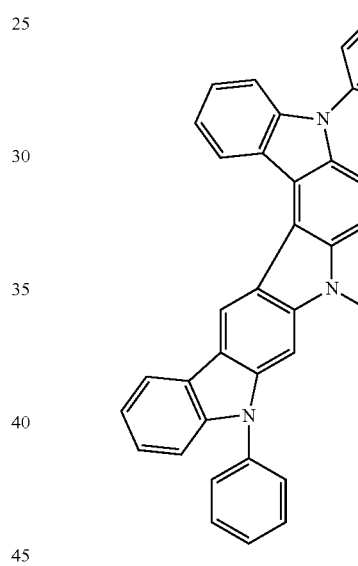
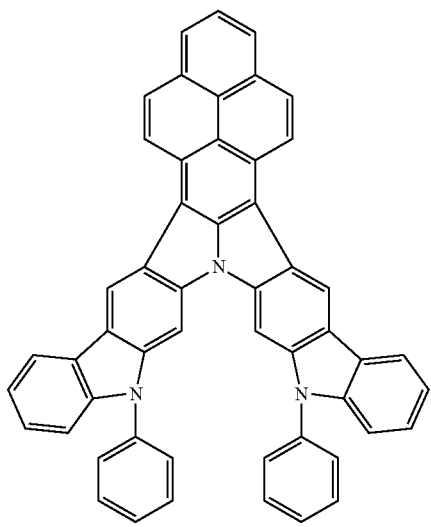
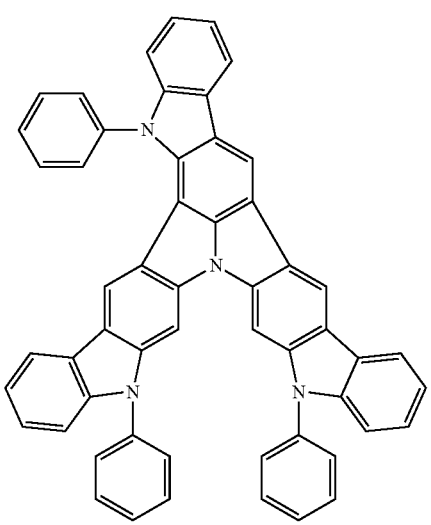

227
-continued
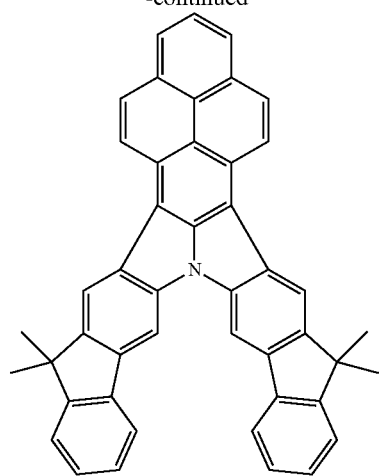
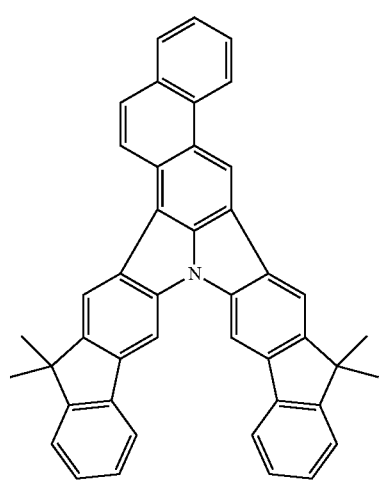
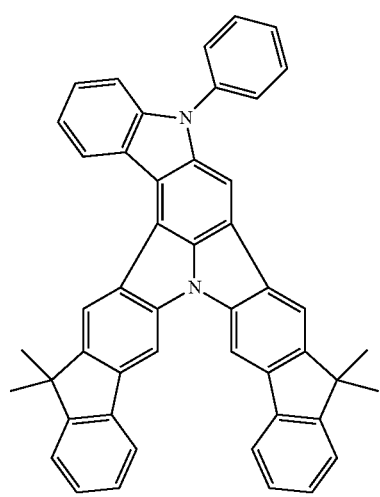
228
-continued
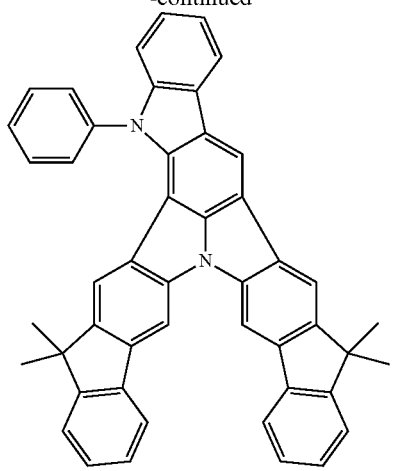
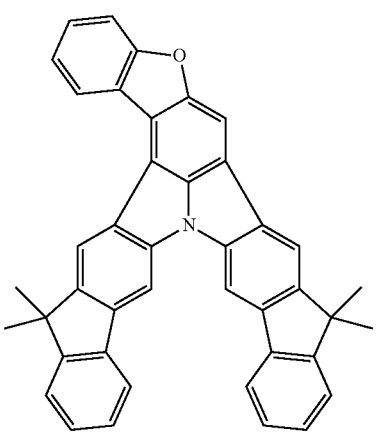
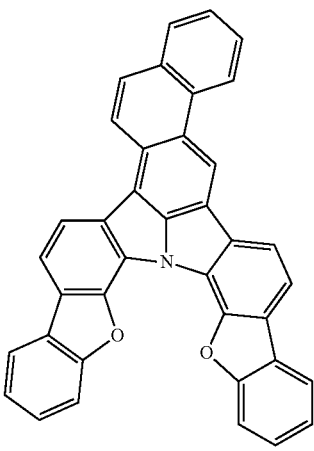

| 229 -continued | 230 -continued |
|---|---|
| 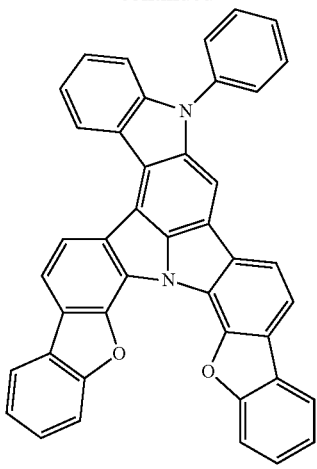 | 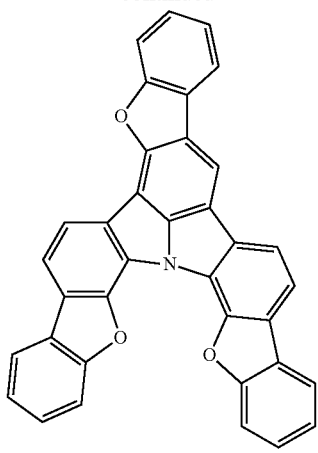 |
| 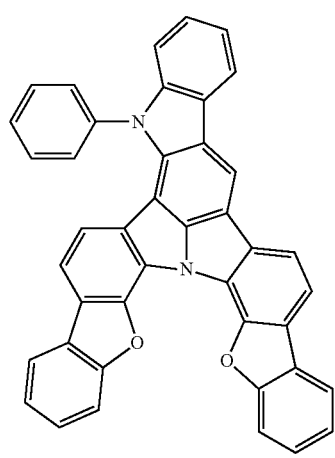 | 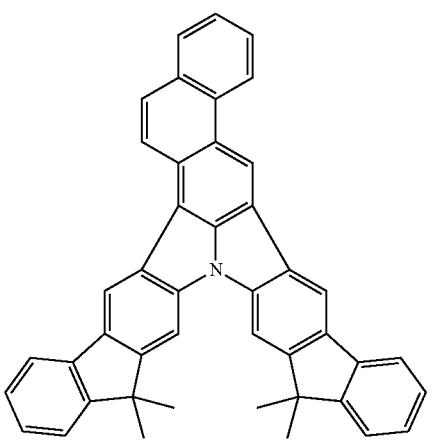 |
| 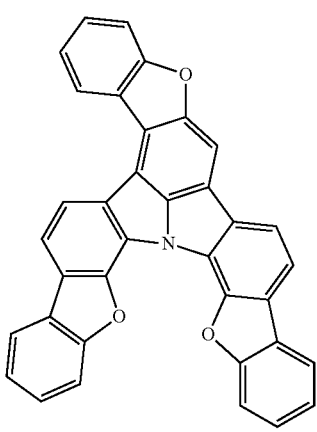 | 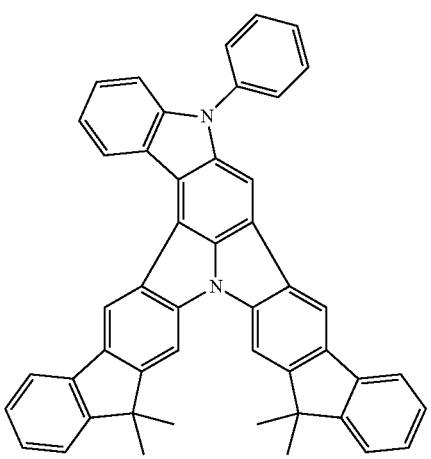 |

231
-continued
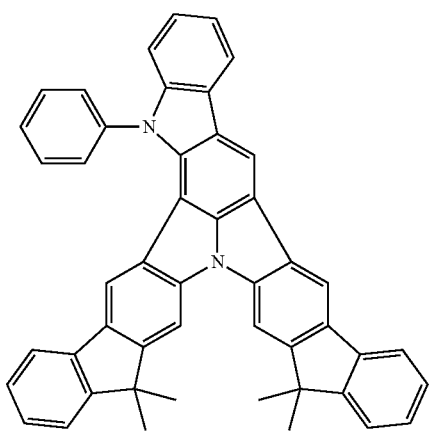
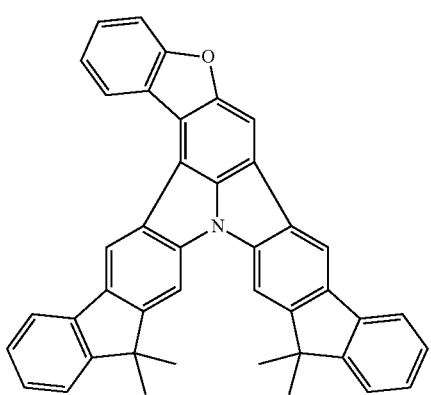
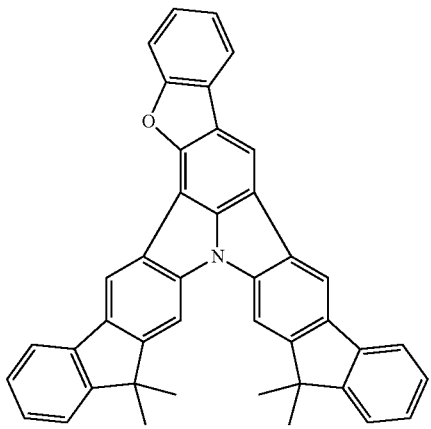
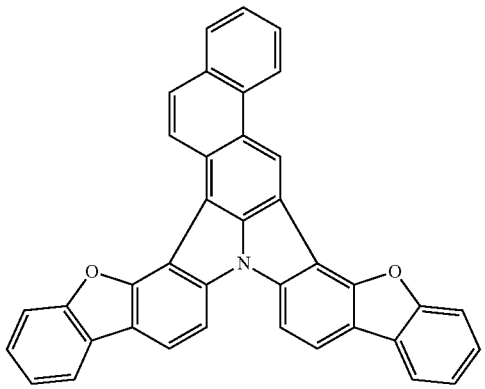
232
-continued
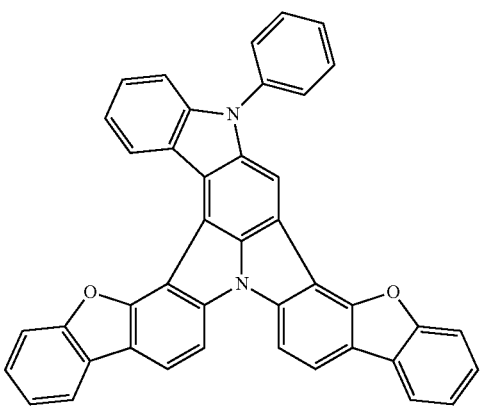
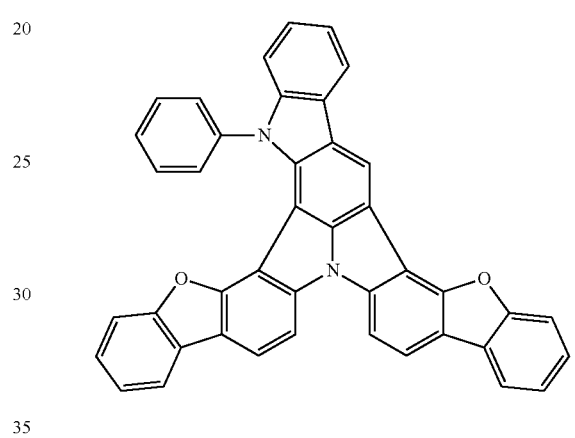
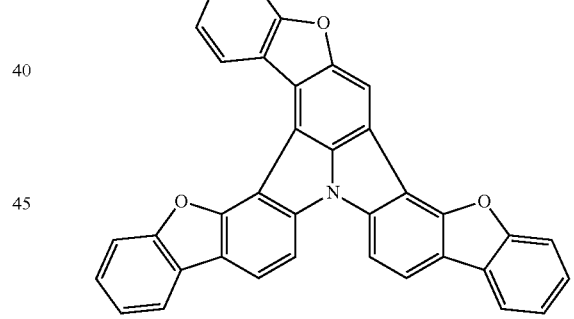
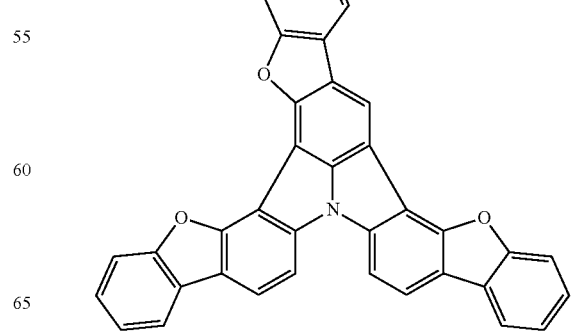

233
-continued
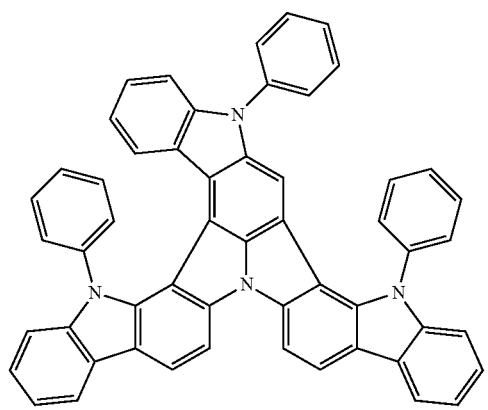
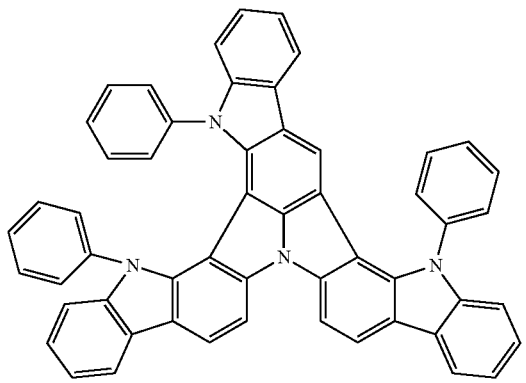
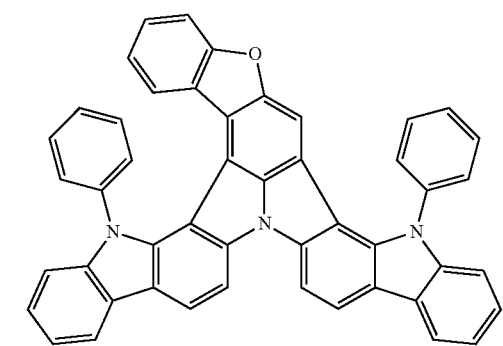
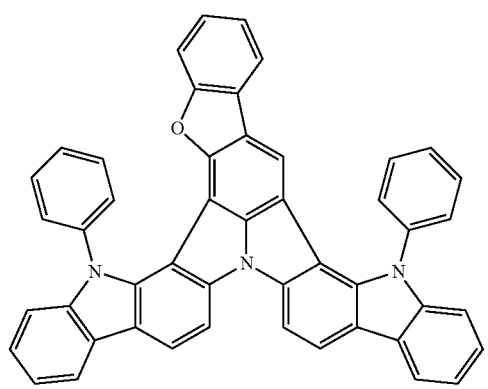
234
-continued
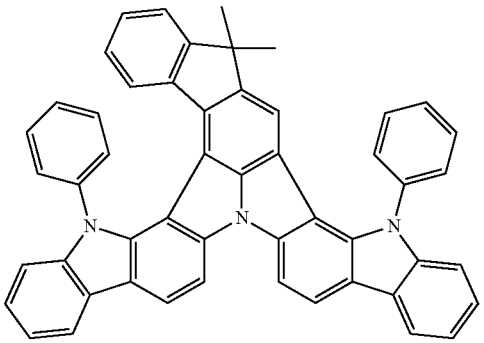
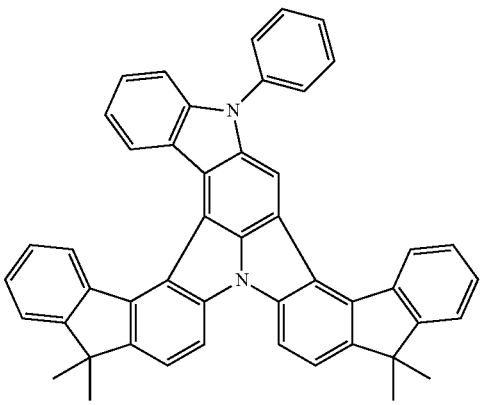
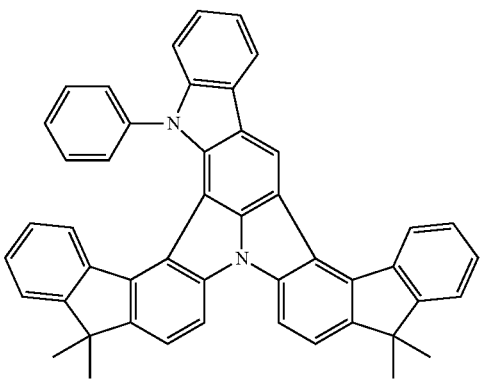
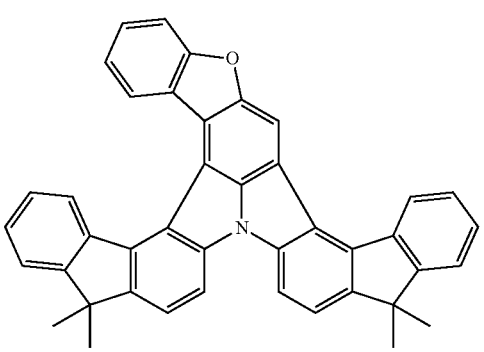

235
-continued
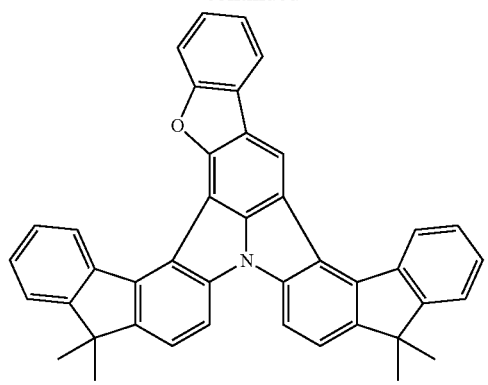
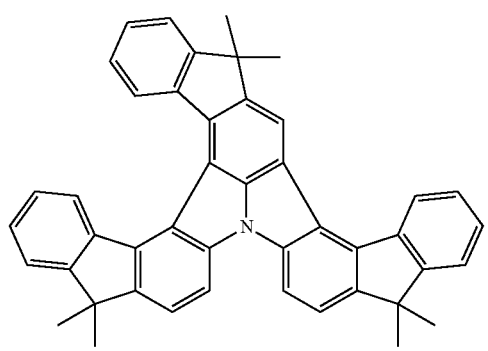
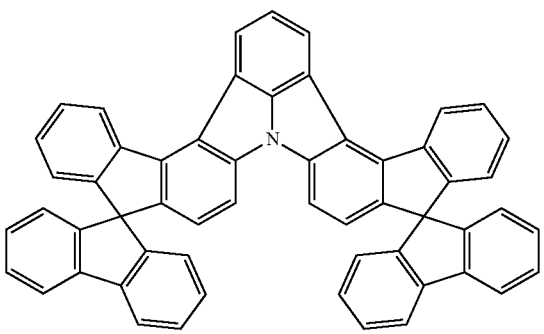
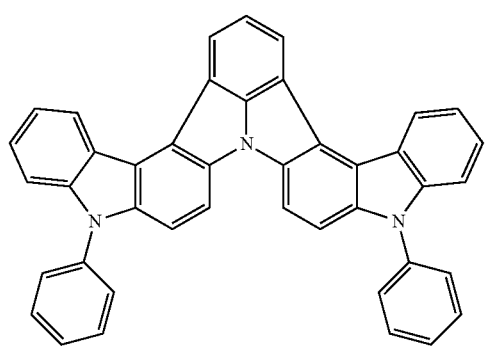
236
-continued
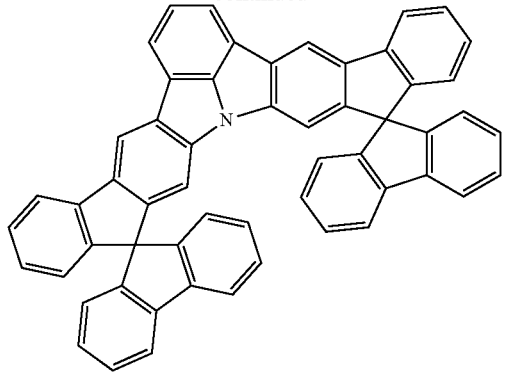
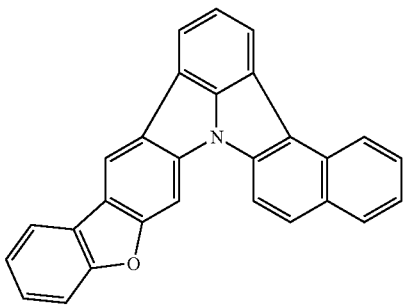
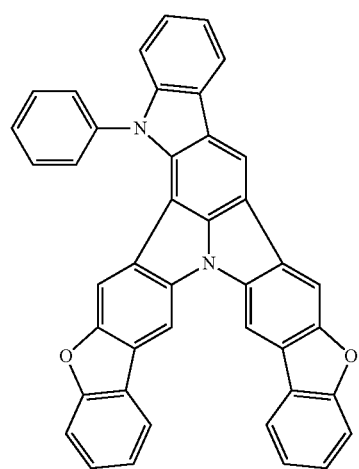
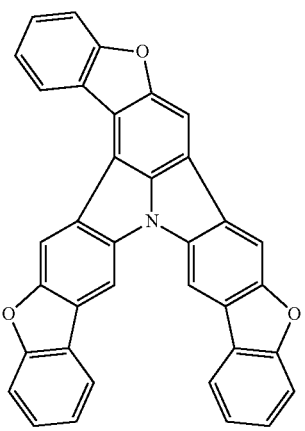

237
-continued
238
-continued
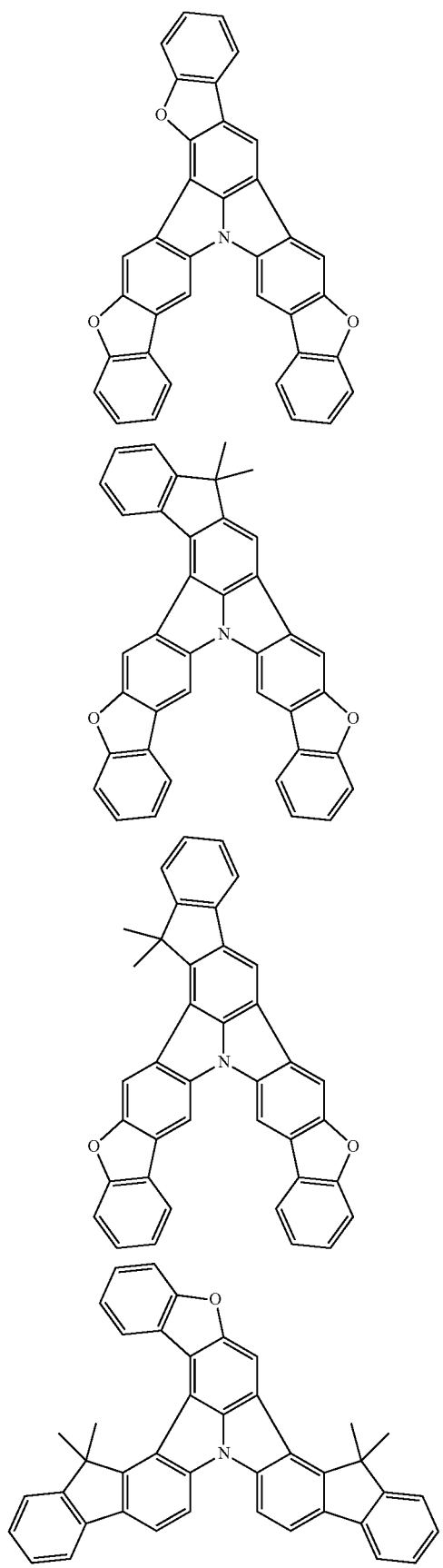
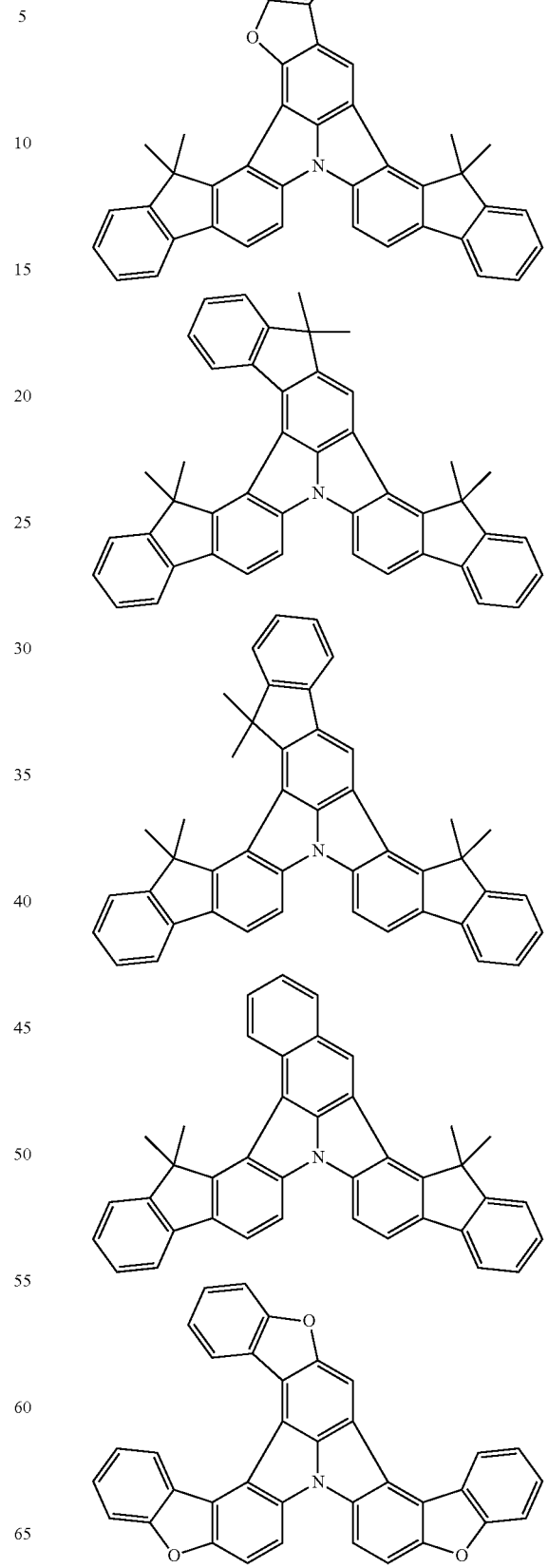

239
-continued
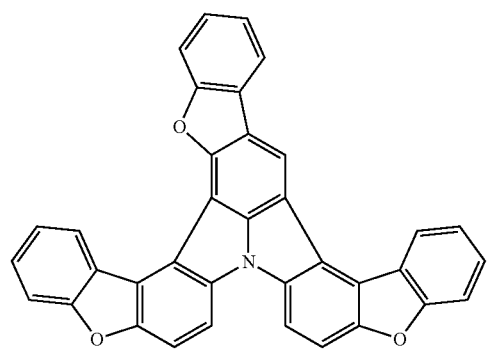
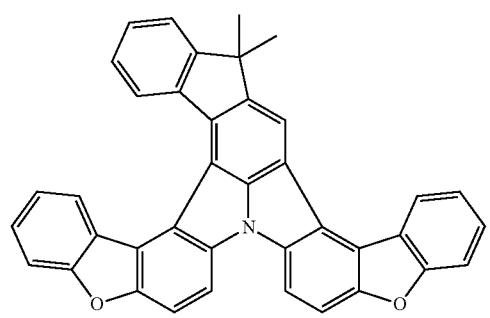
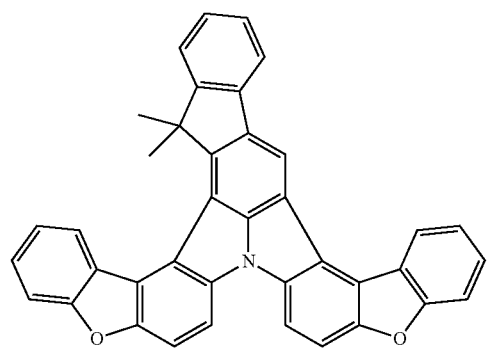
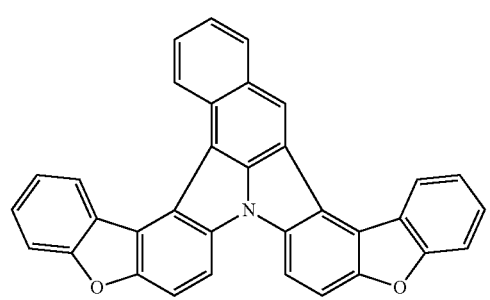
240
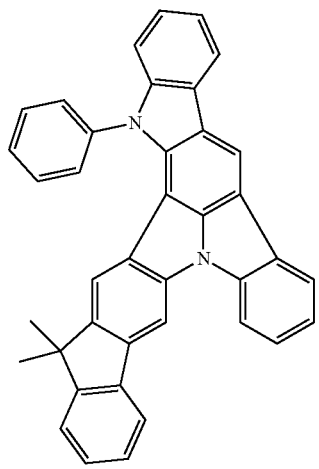
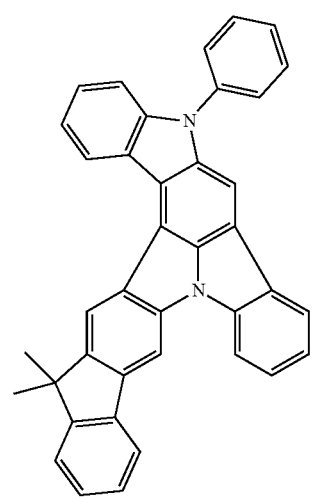
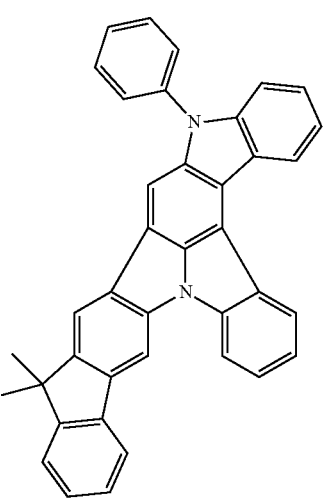

241
-continued
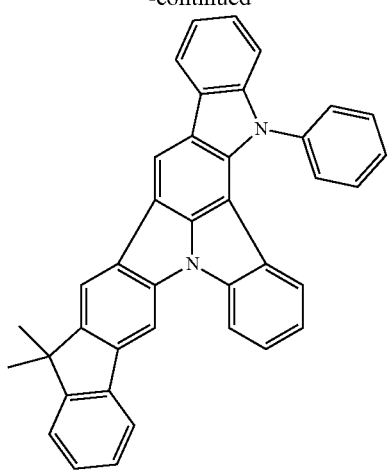
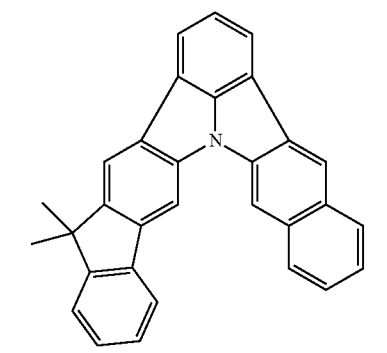
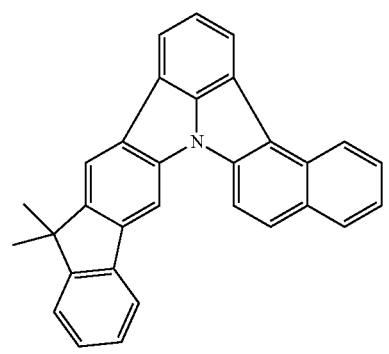
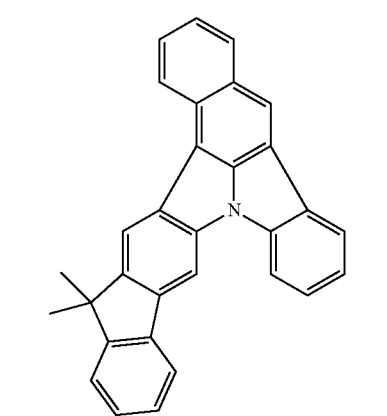
242
-continued
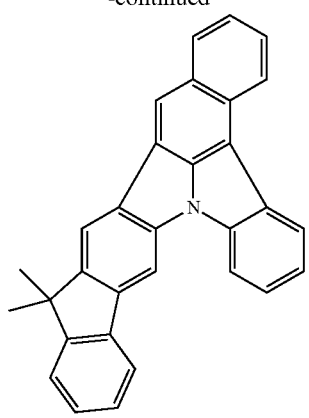
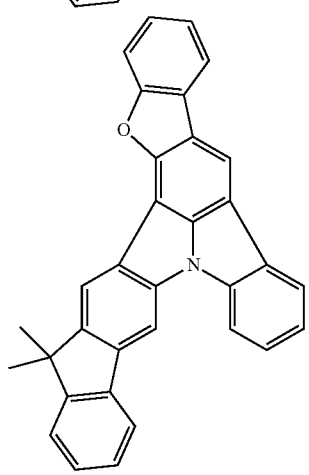
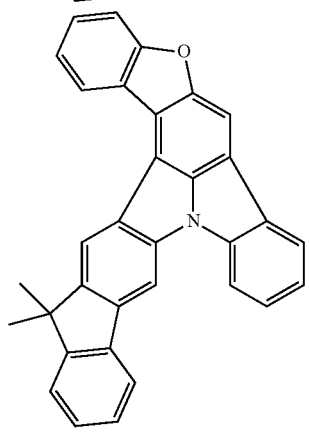
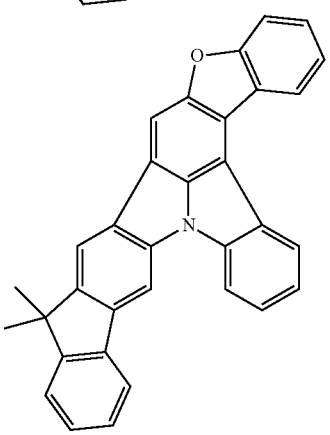

243
-continued
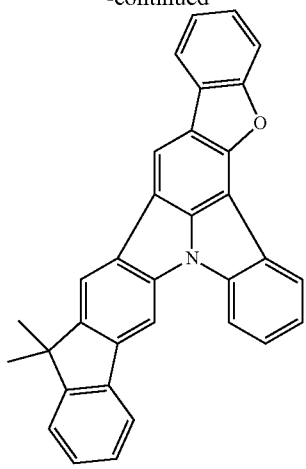
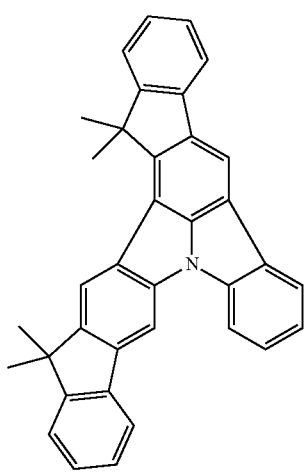
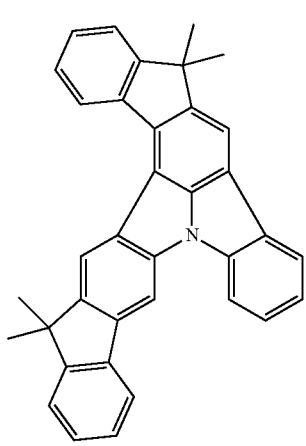
244
-continued
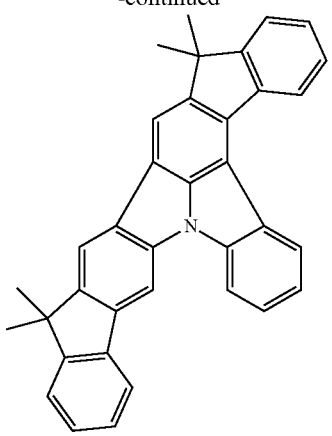
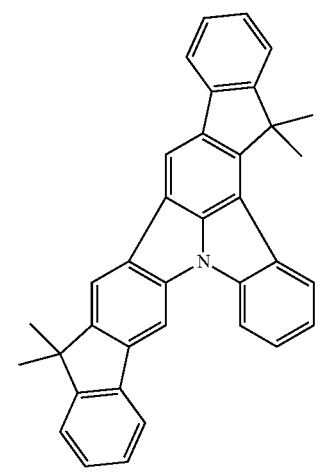
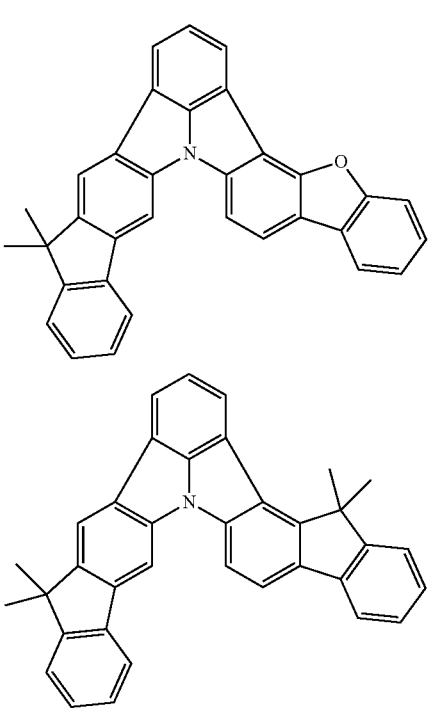

245
-continued
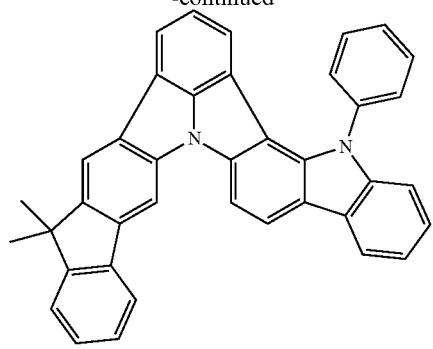
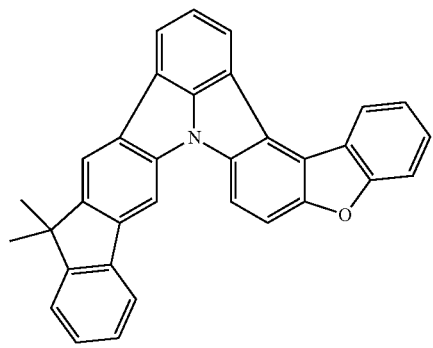
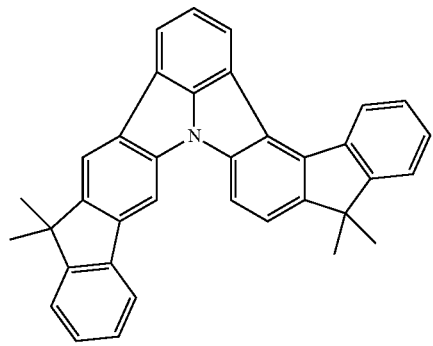
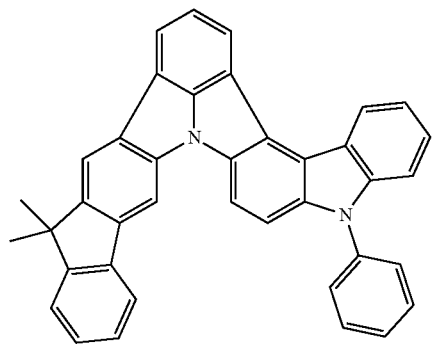
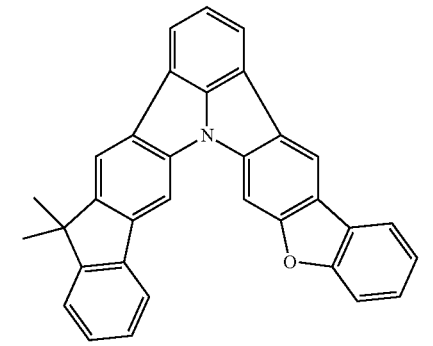
246
-continued
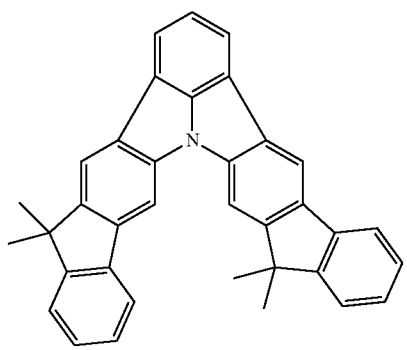
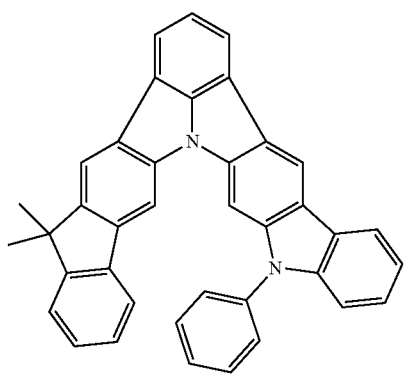
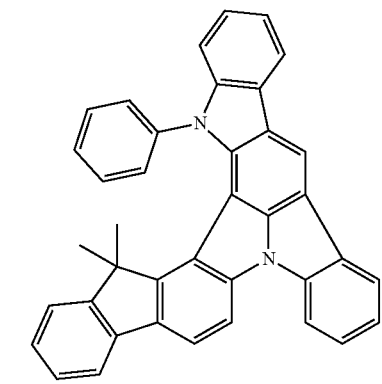
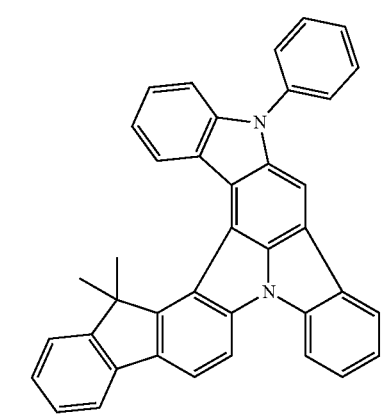

247
-continued
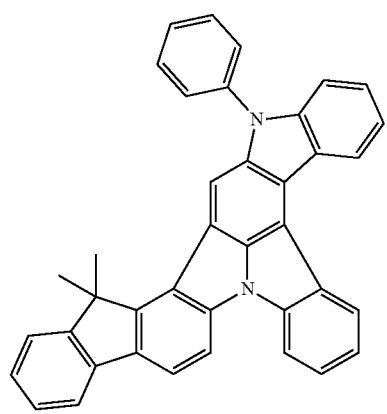
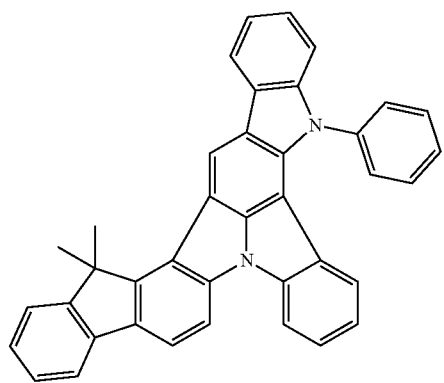
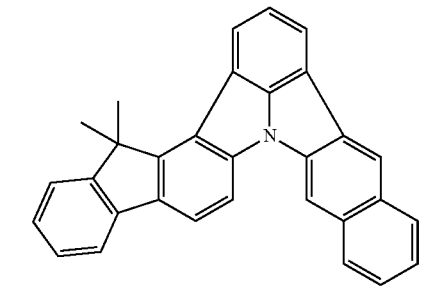
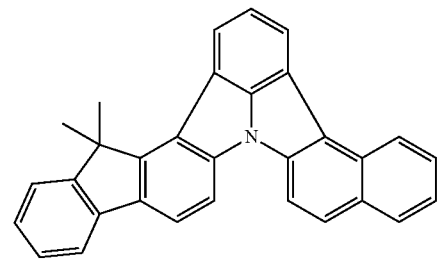
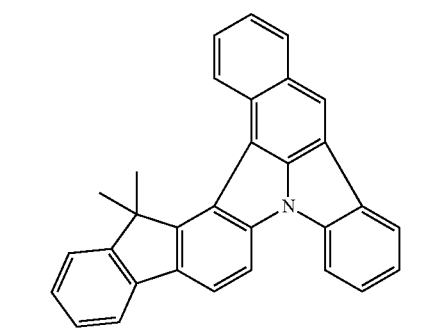
248
-continued
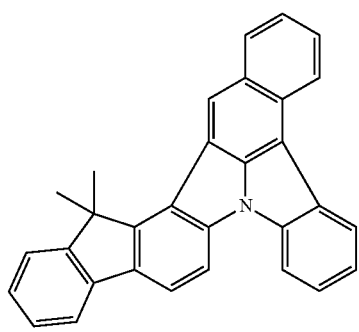
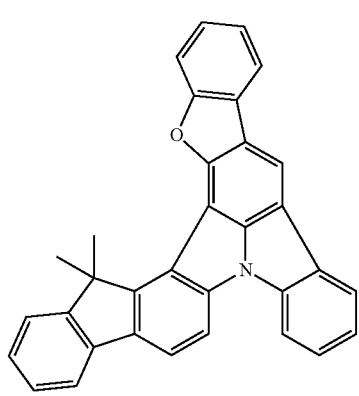
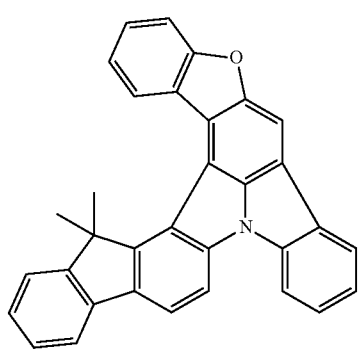
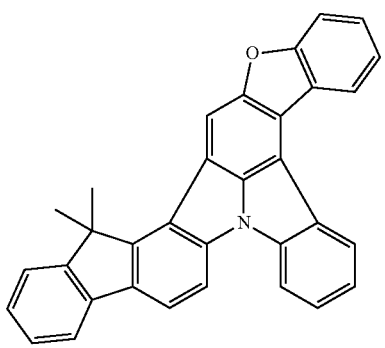

249
-continued
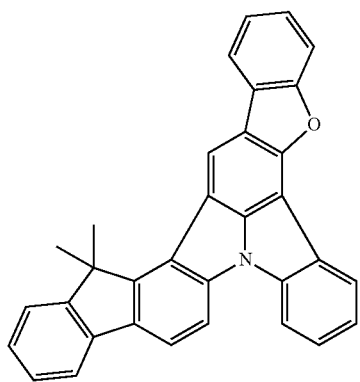
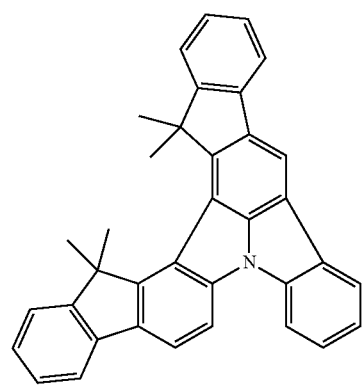
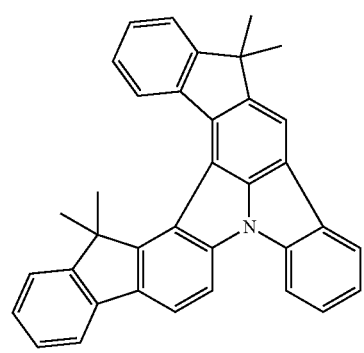
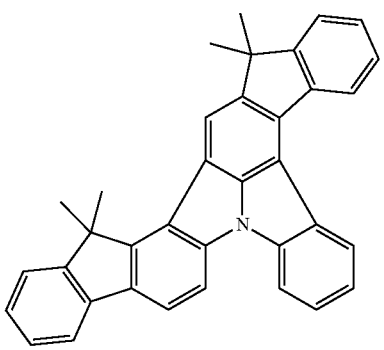
250
-continued
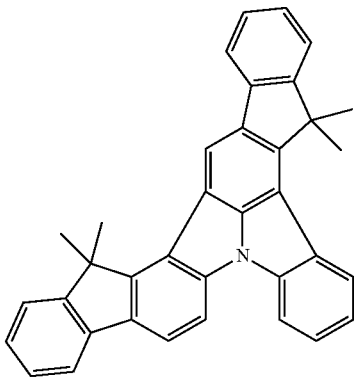
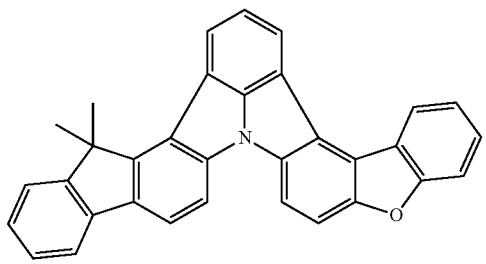
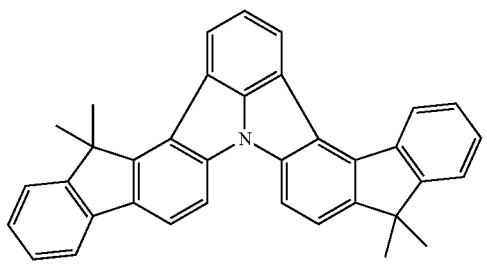
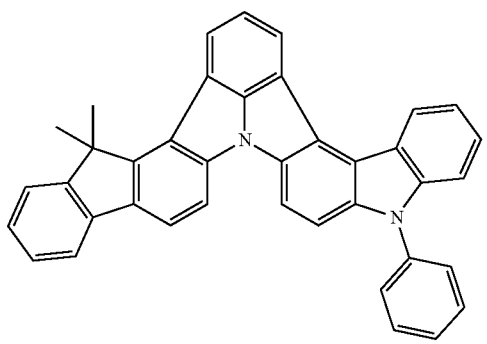
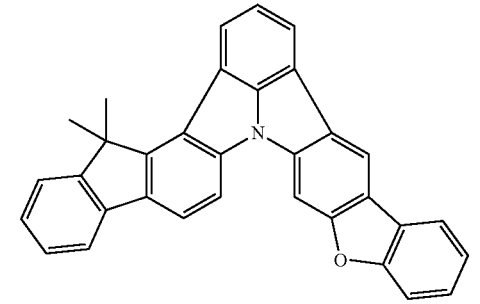

251
-continued
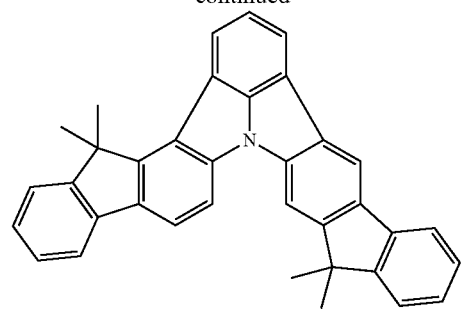
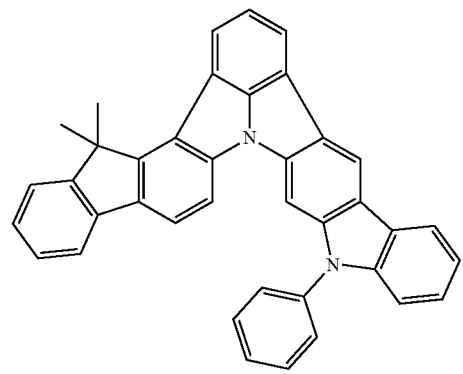
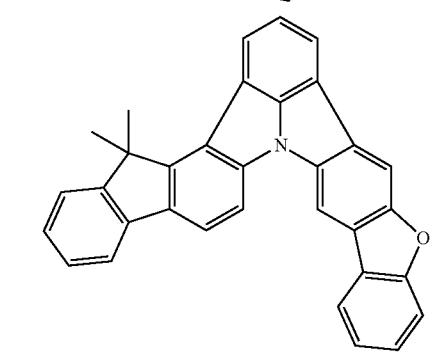
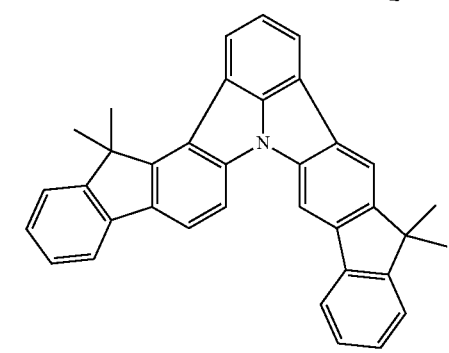
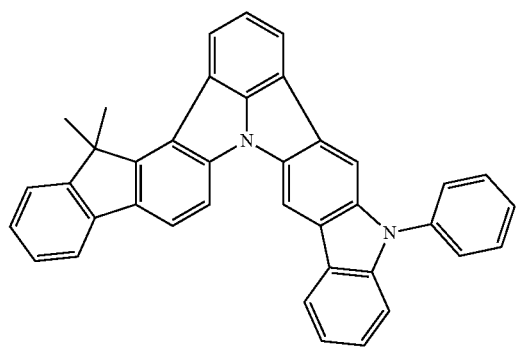
252
-continued
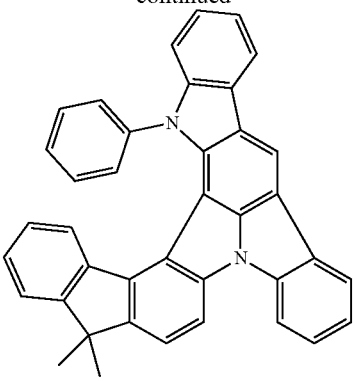
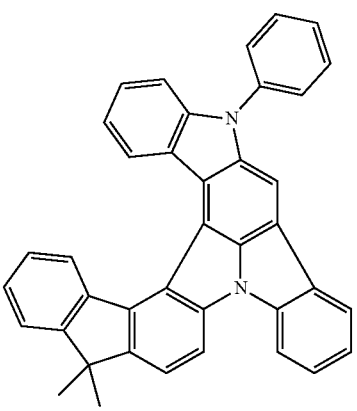
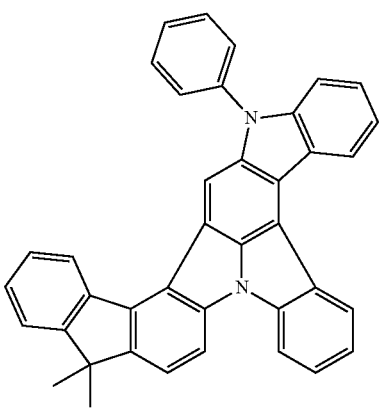
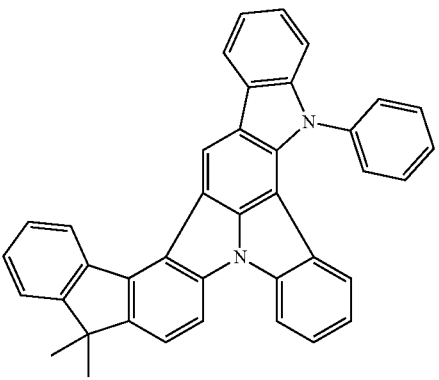

253
-continued
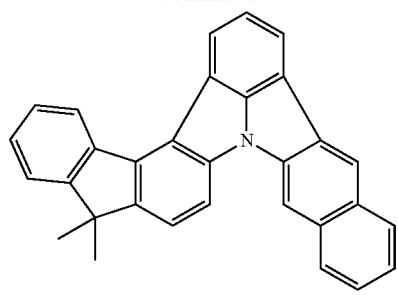
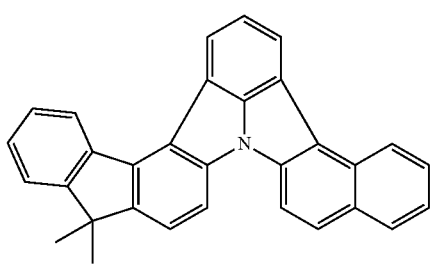
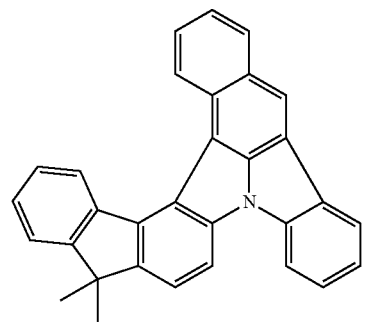
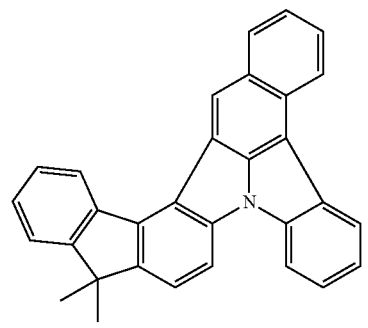
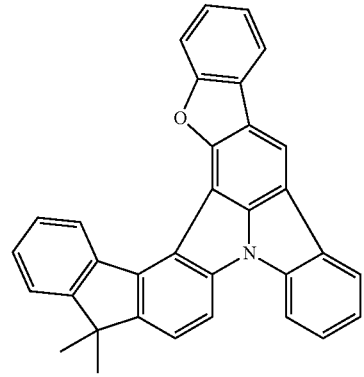
254
-continued
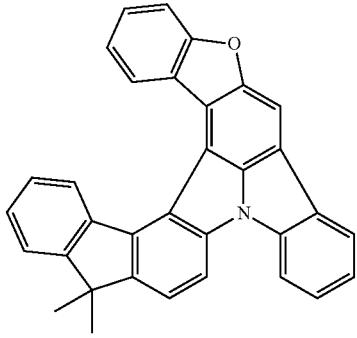
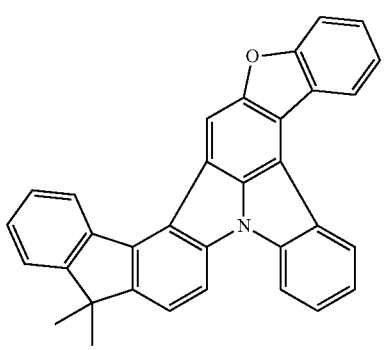
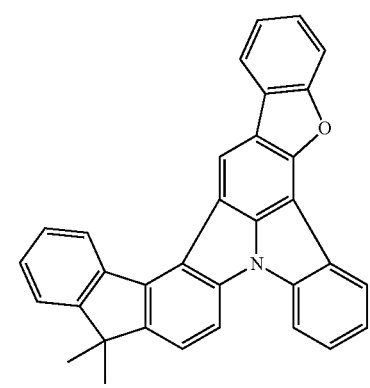
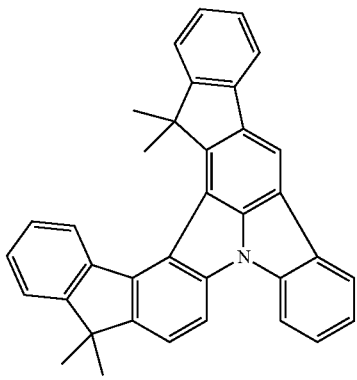

255
-continued
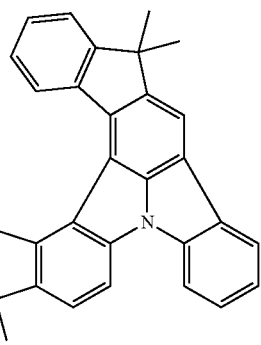
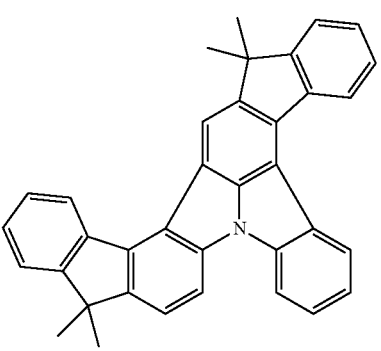
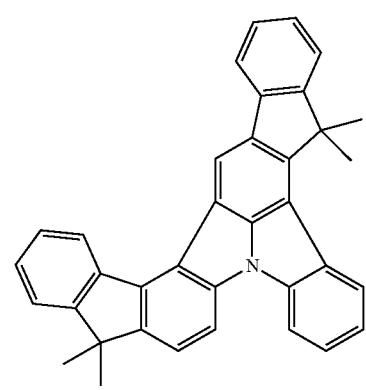
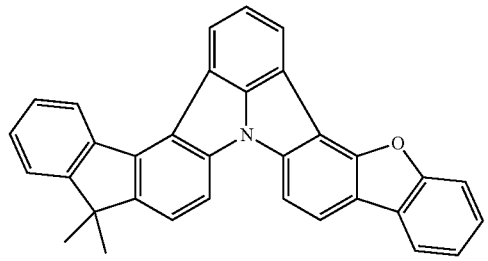
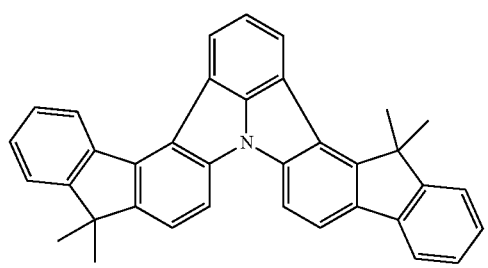
256
-continued
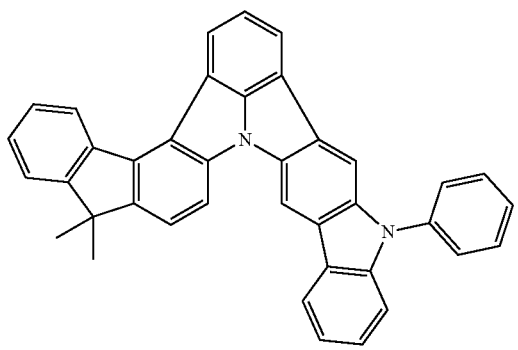
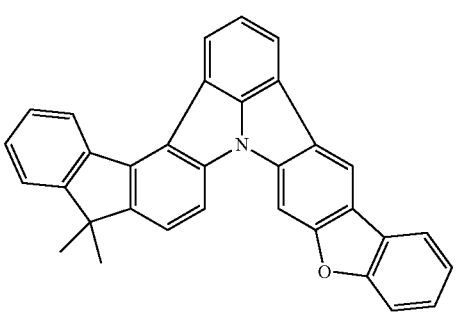
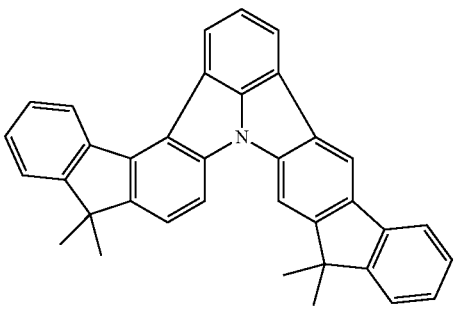
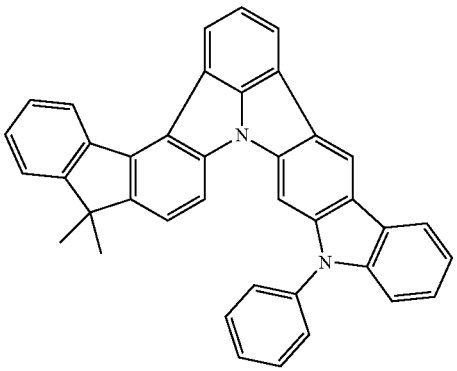
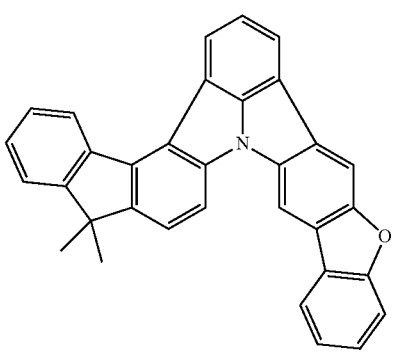

257
-continued
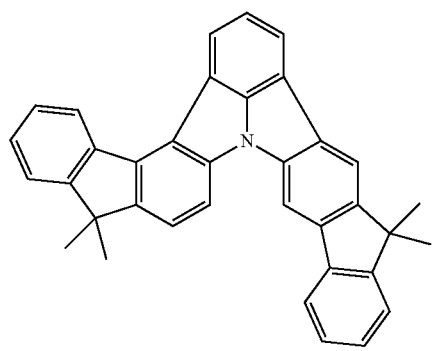
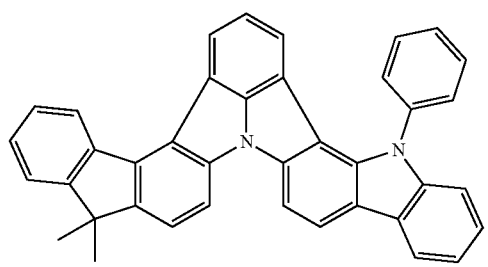
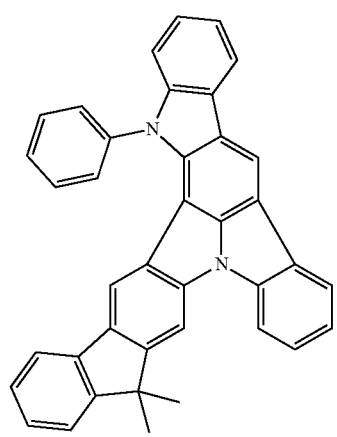
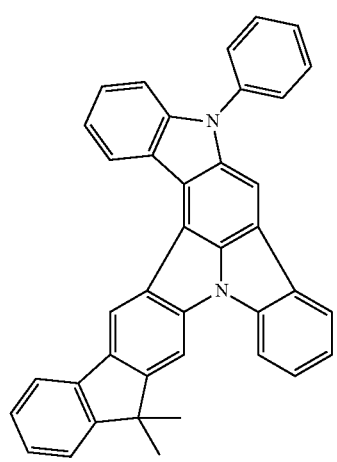
258
-continued
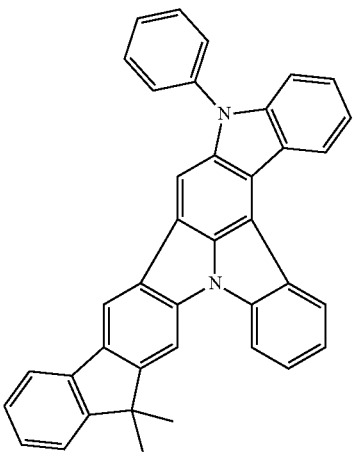
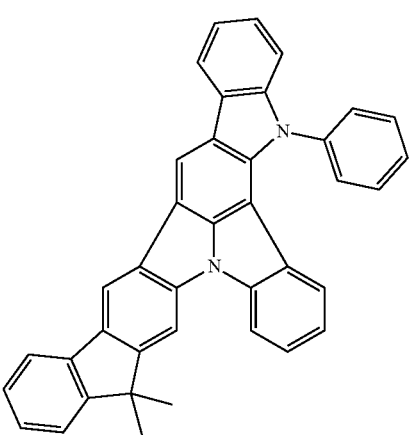
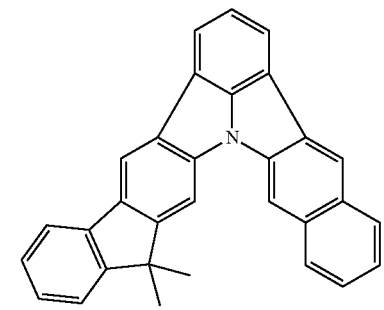
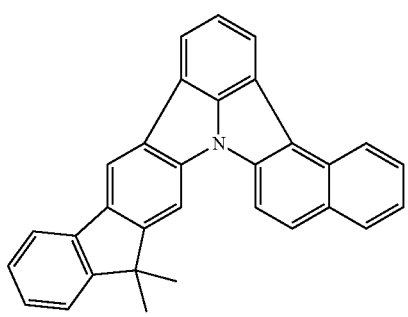

259
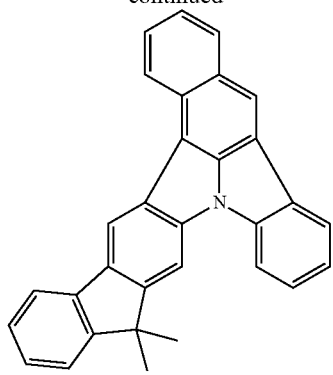
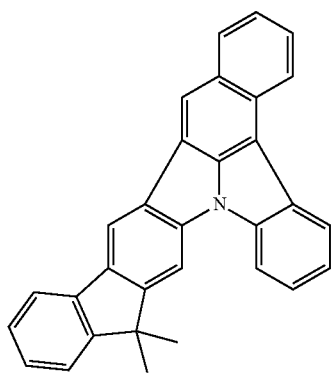
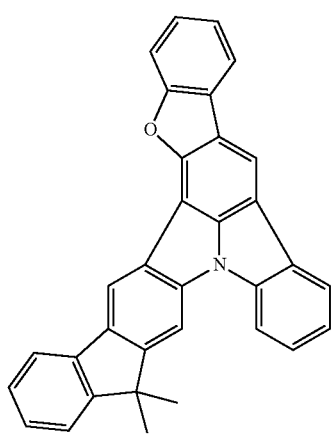
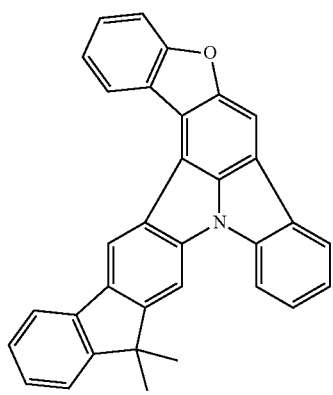
260
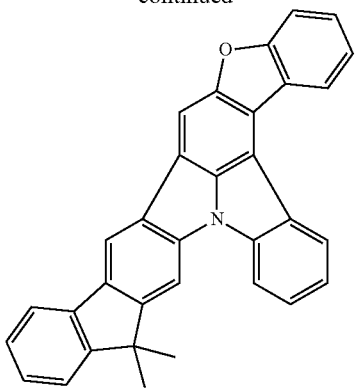
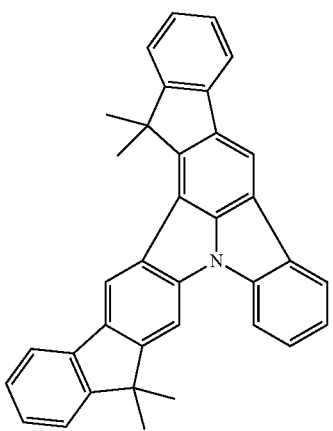
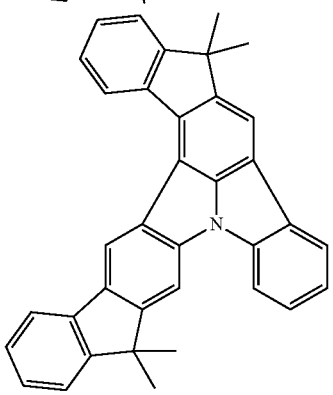

261
-continued
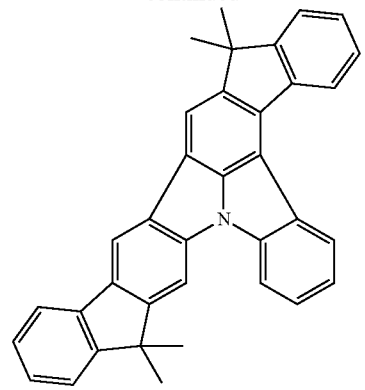
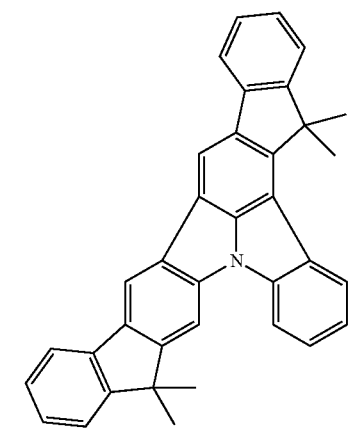
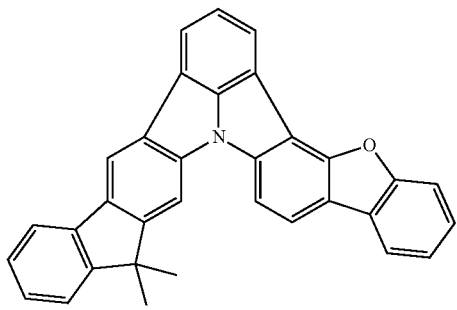
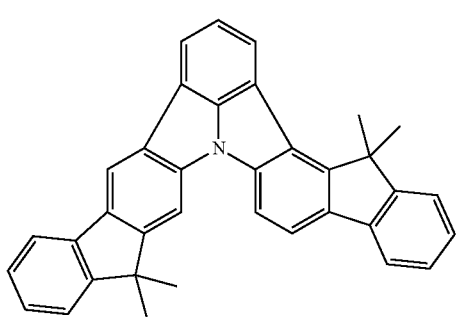
262
-continued
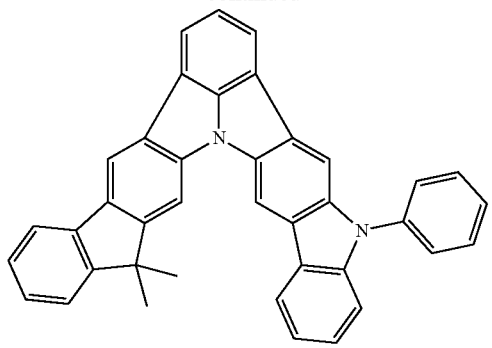
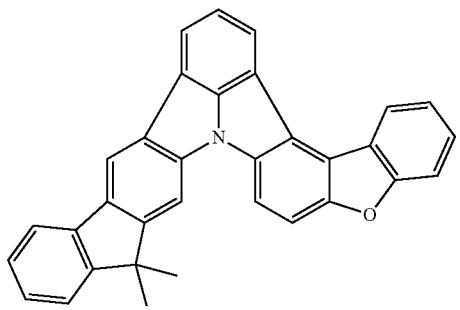
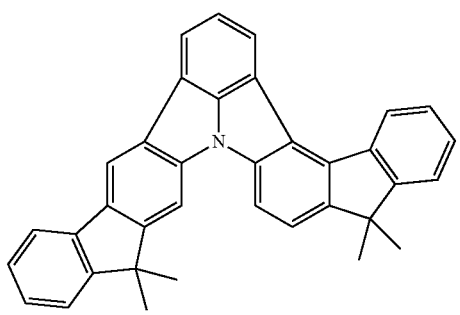
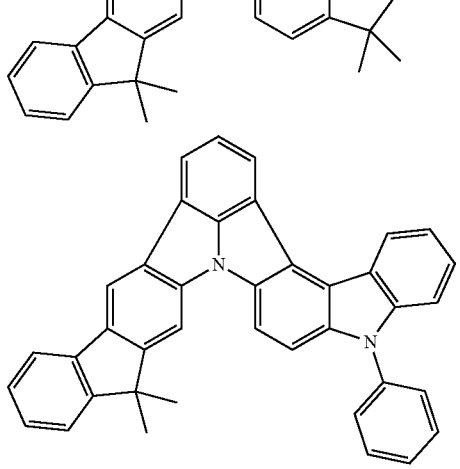
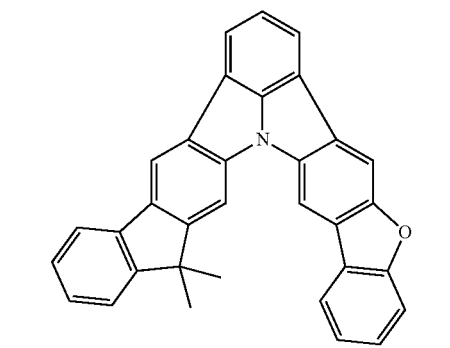

263
-continued
264
-continued
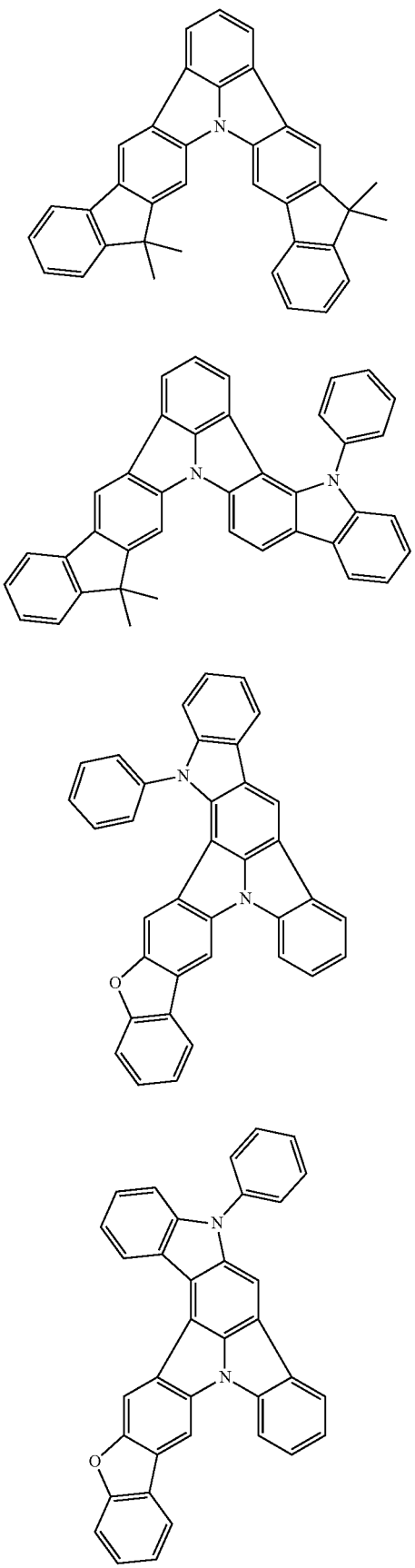

265
-continued
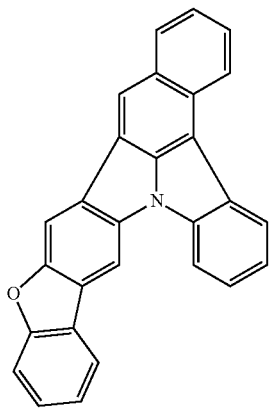
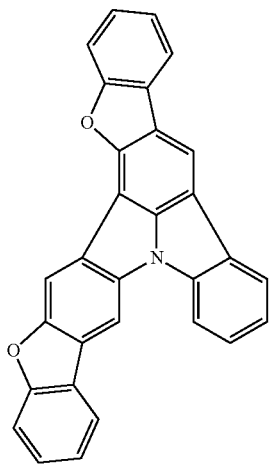
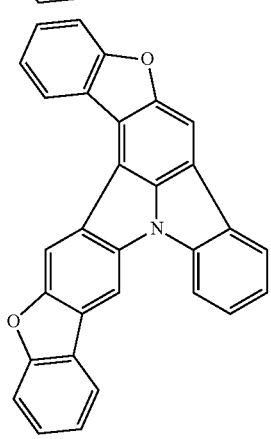
266
-continued
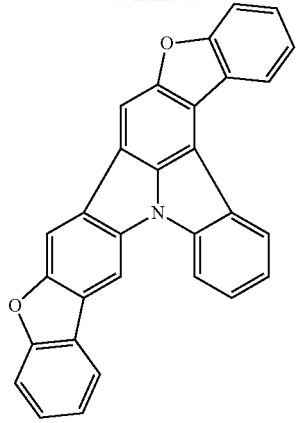
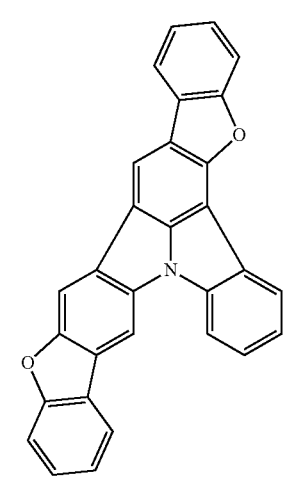
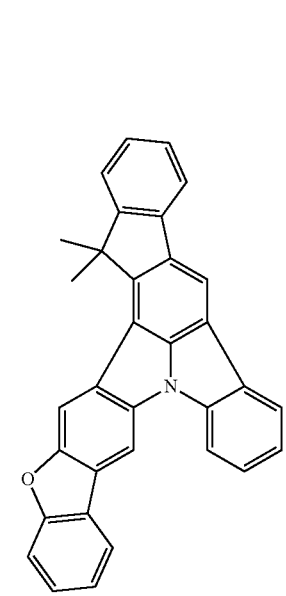

267
-continued
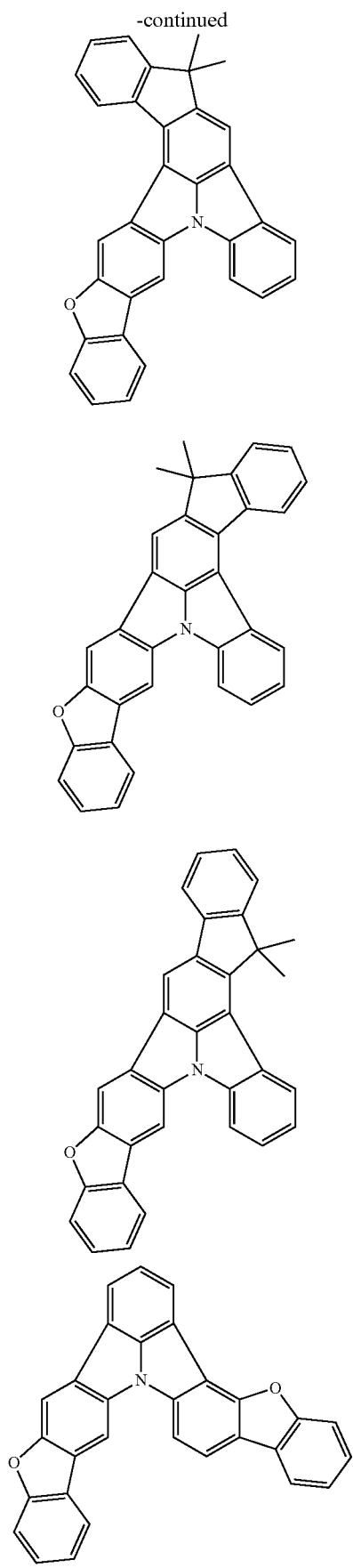
268
-continued
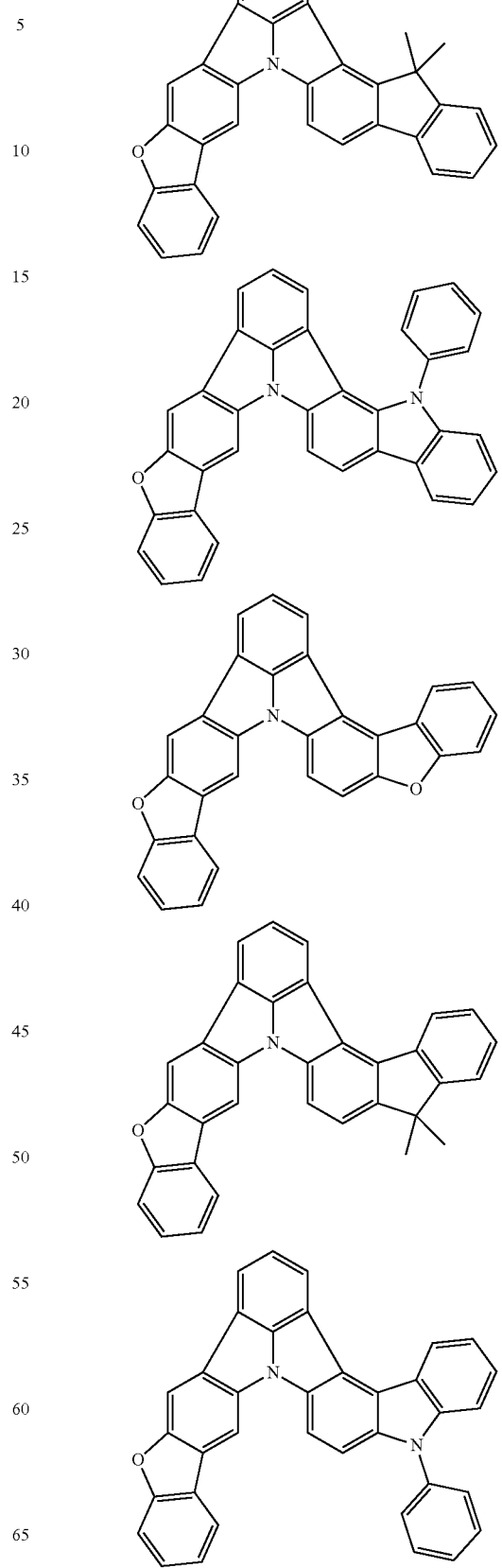

-continued
269
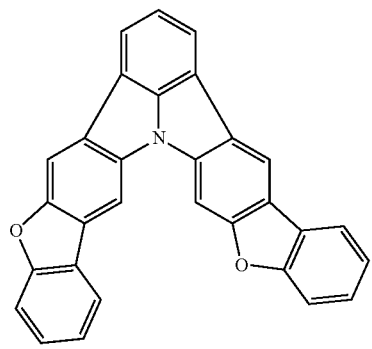
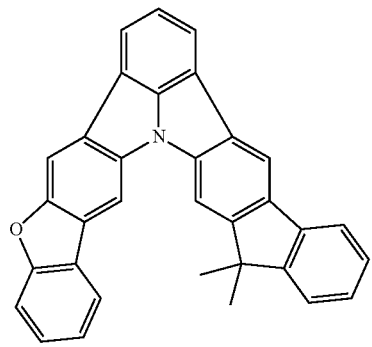
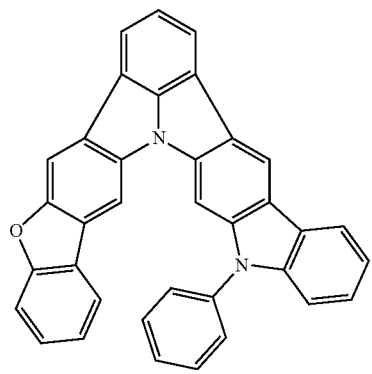
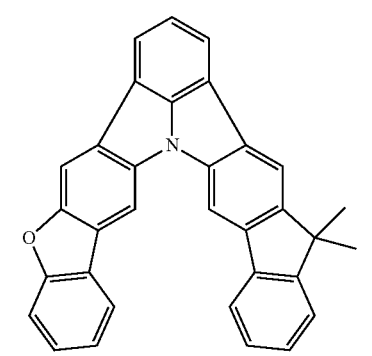
270
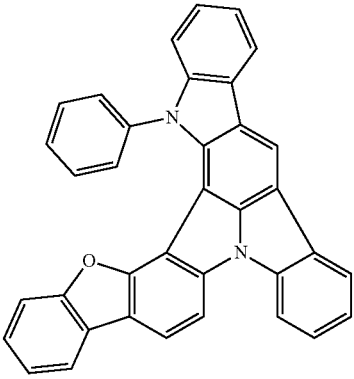
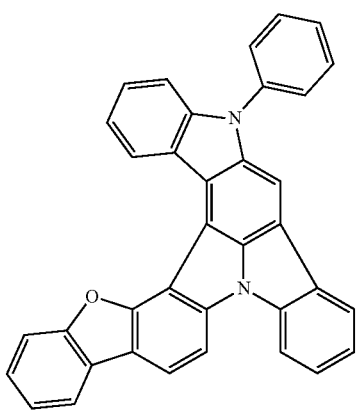
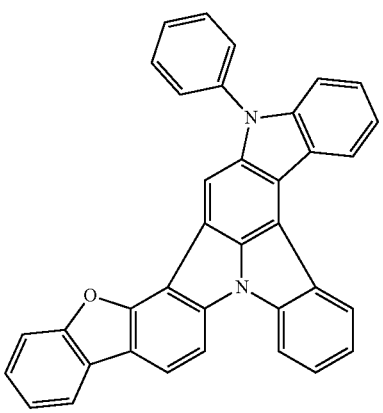
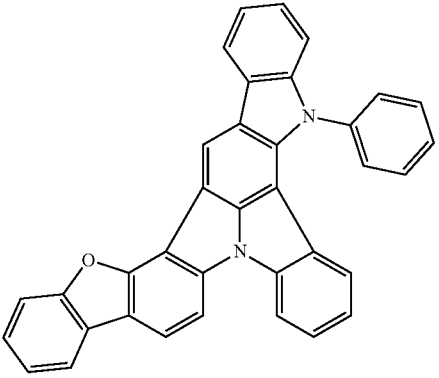

271
-continued
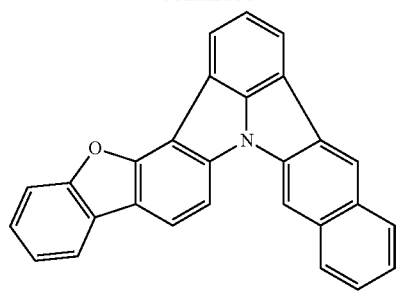
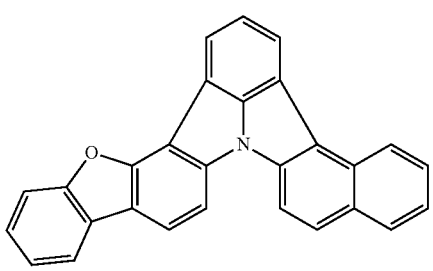
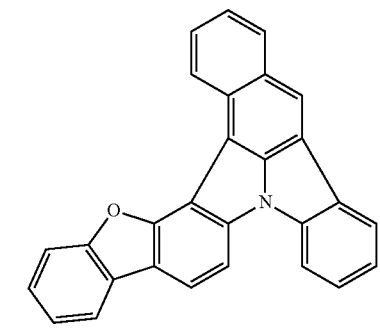
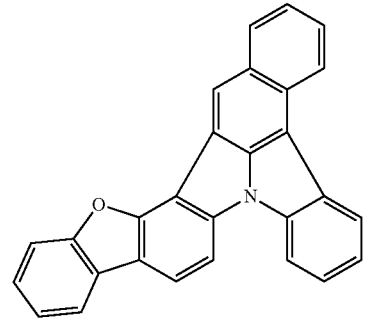
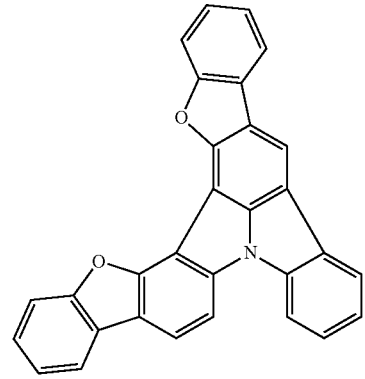
272
-continued
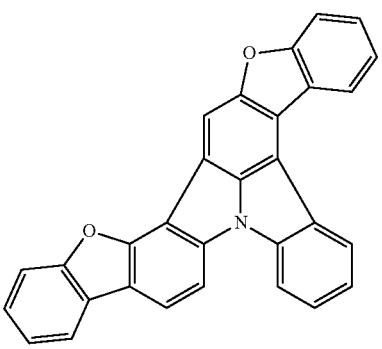
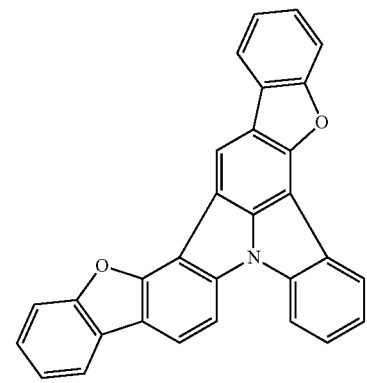
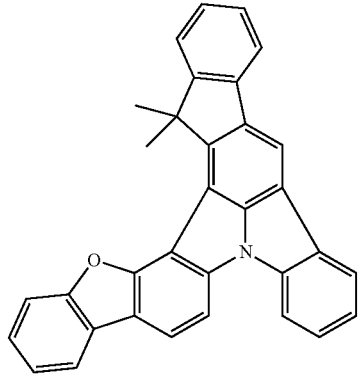

273
-continued
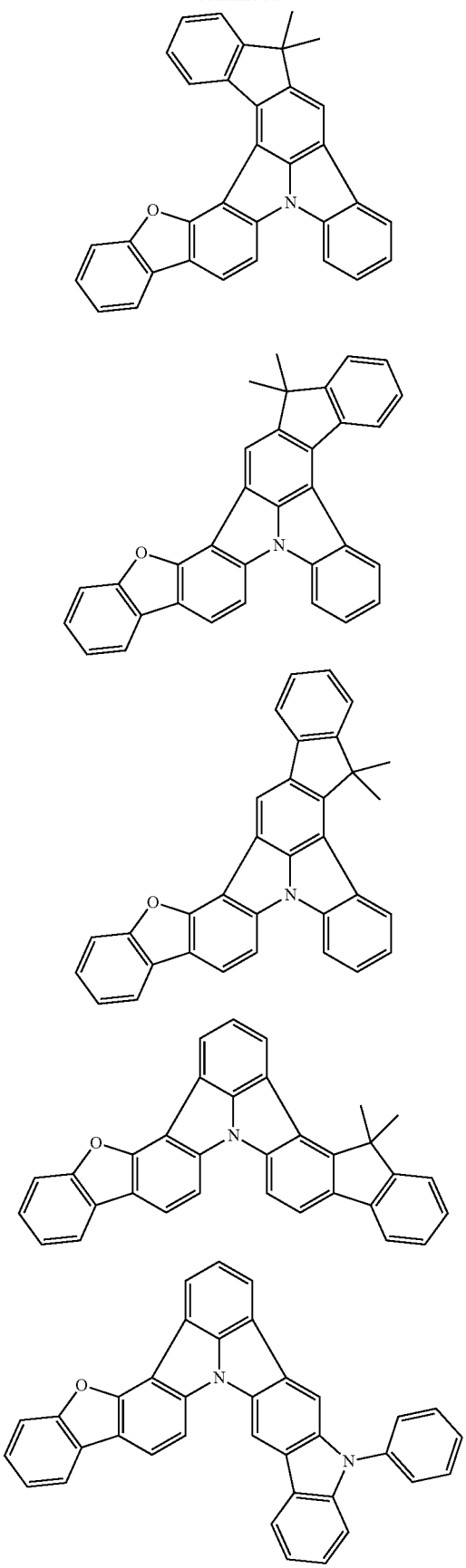
274
-continued
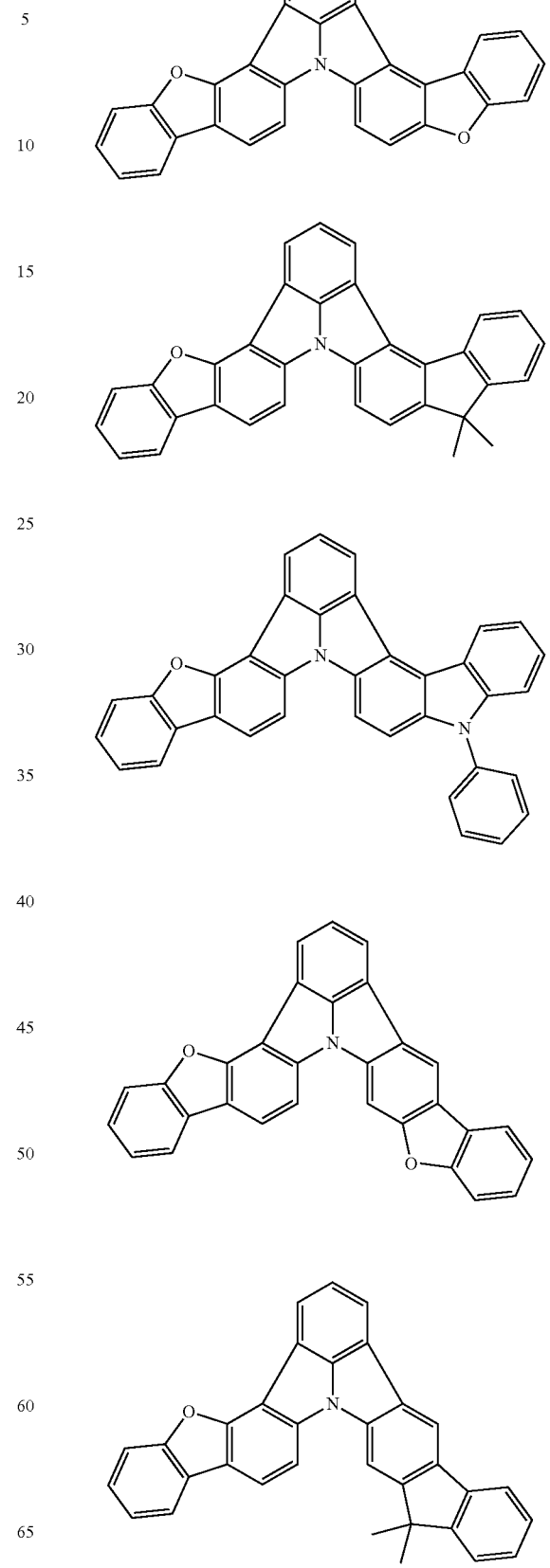

275
-continued
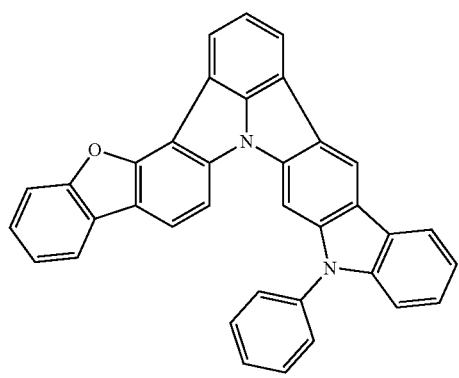
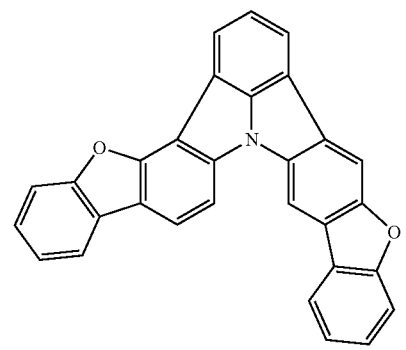
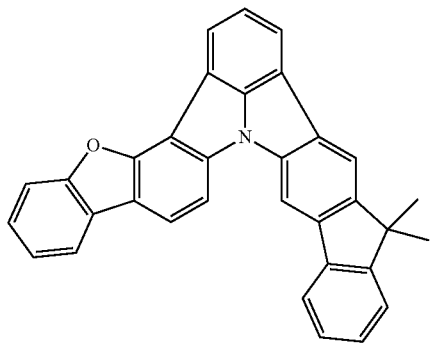
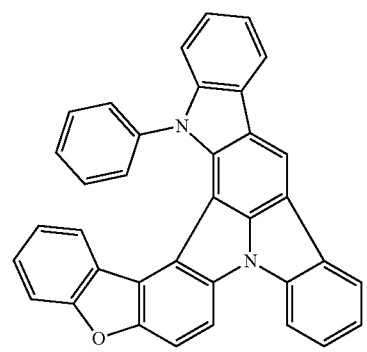
276
-continued
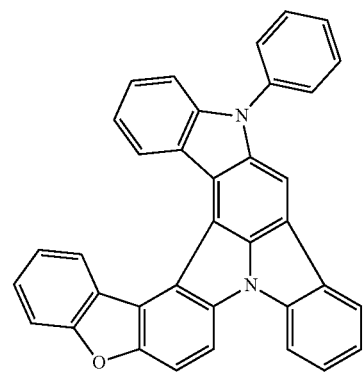
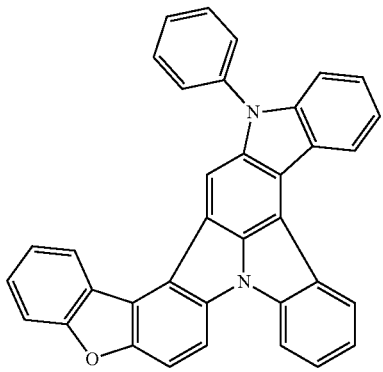
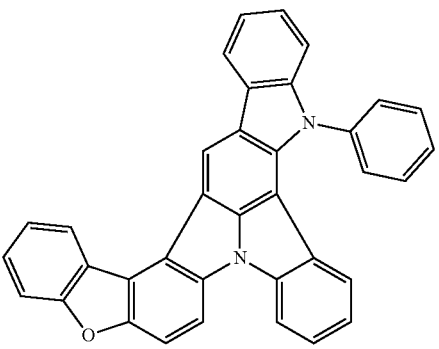
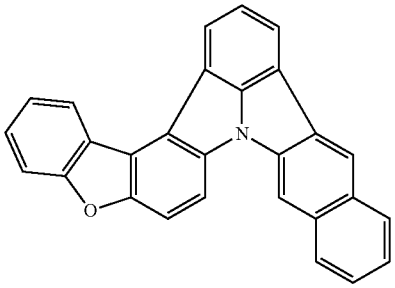
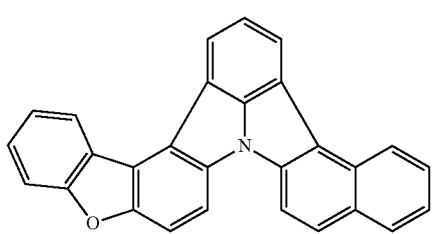

277
-continued
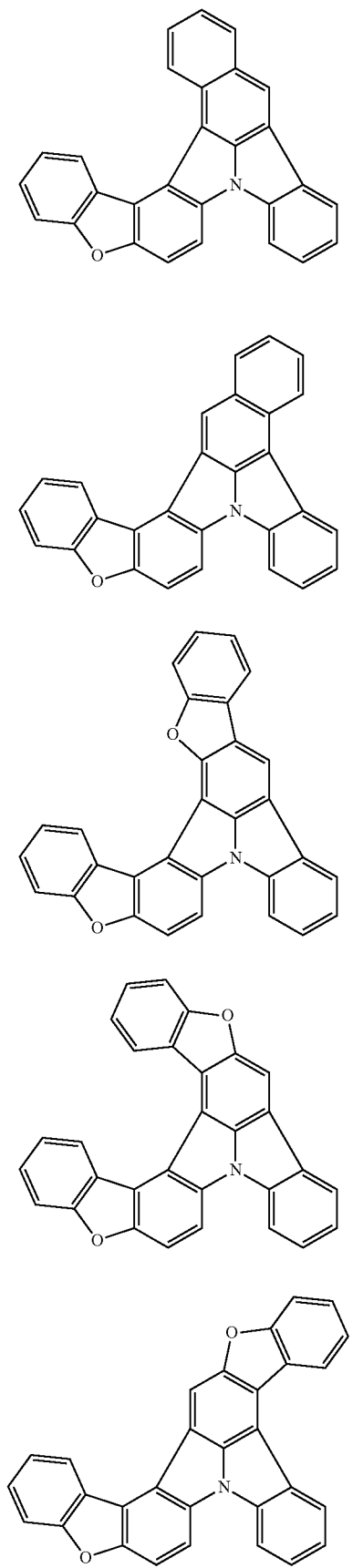
278
-continued
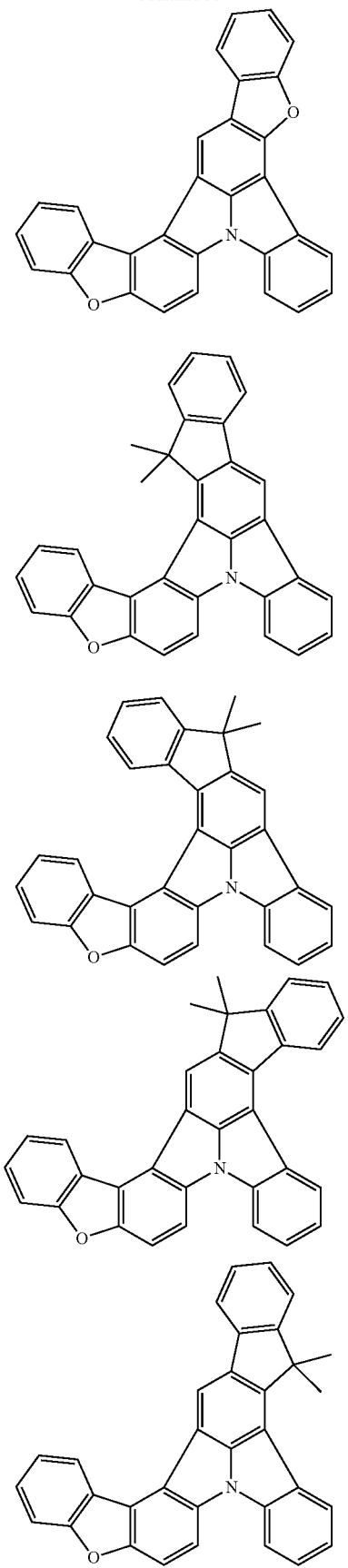

279
-continued
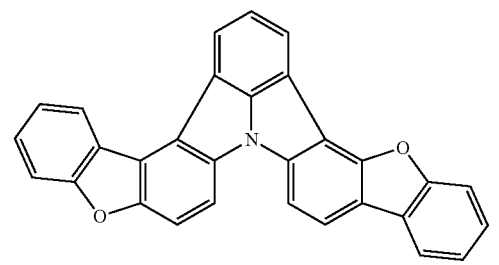
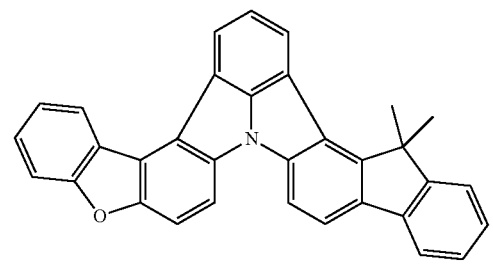
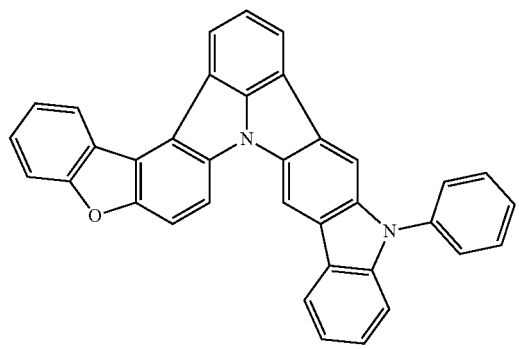
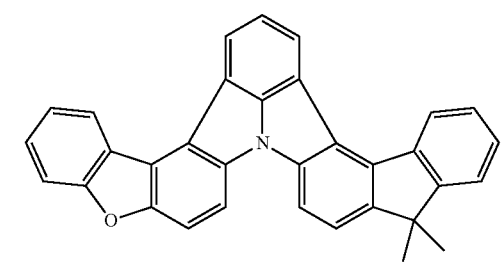
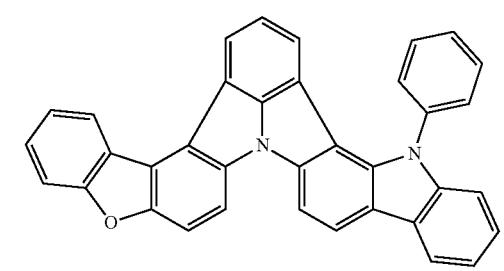
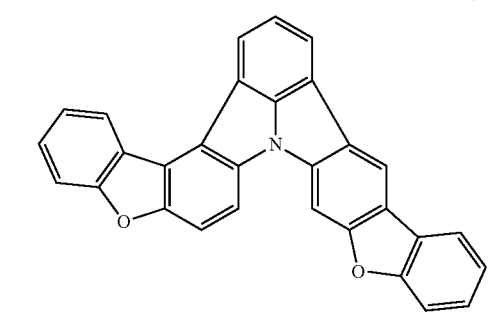
280
-continued
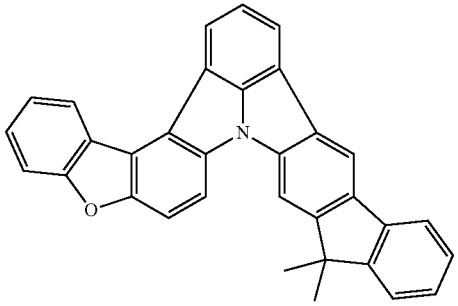
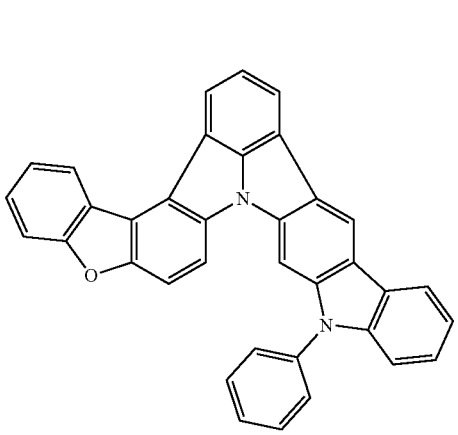
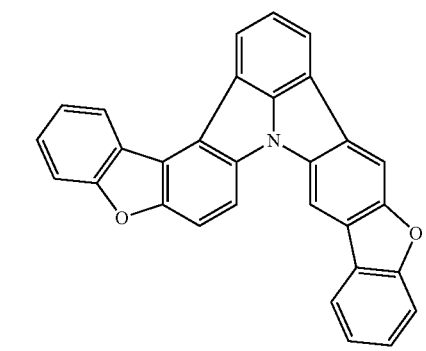
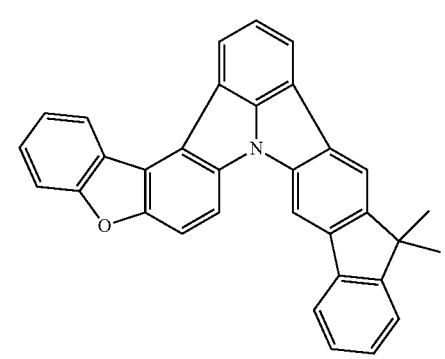 [SMILES: CC1(C)c2ccccc2-c2cc3c(cc21)c1cccc2c4c5c(ccc4n3c12)oc1ccccc15]

281
-continued
282
-continued
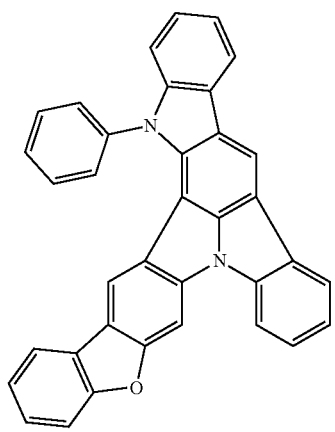
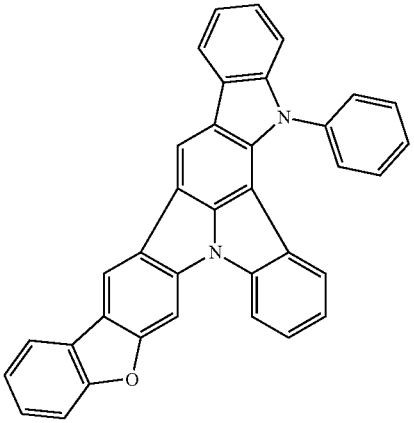
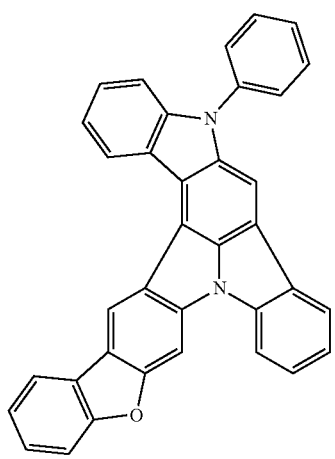
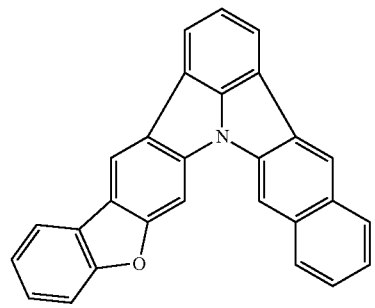
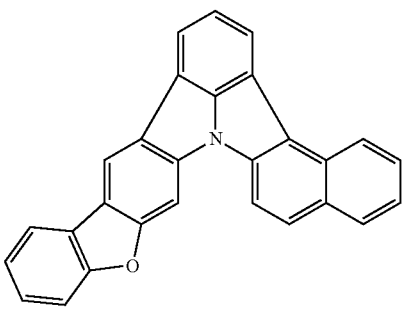
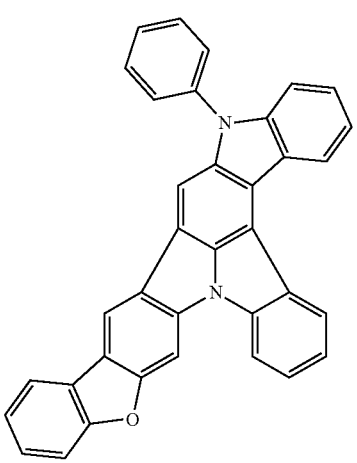
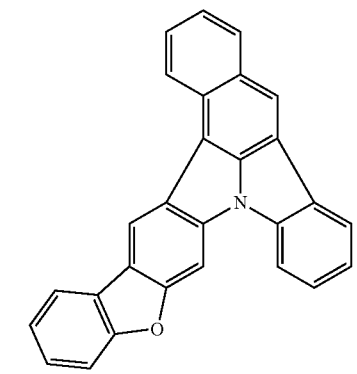

283
-continued
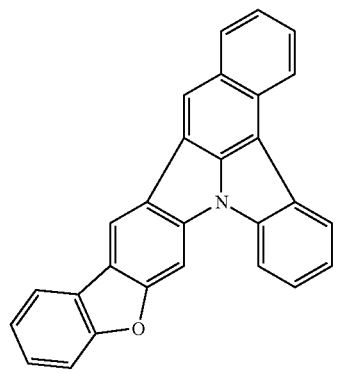
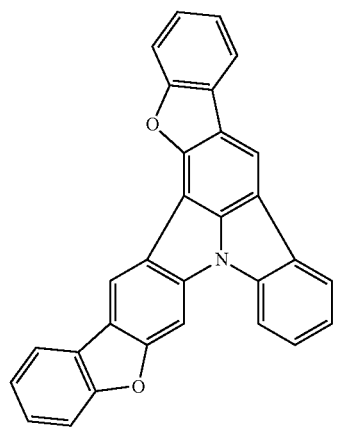
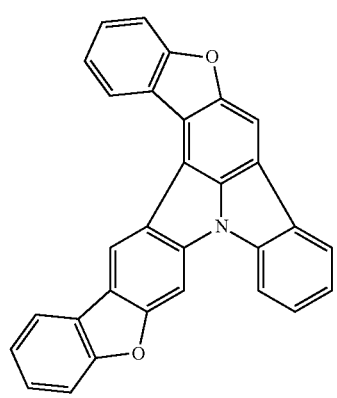
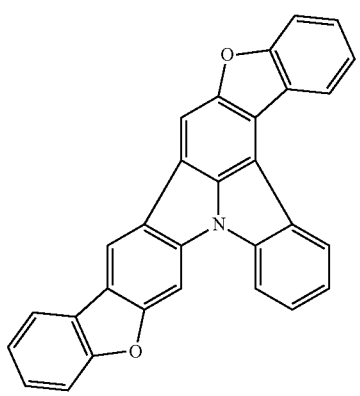
284
-continued
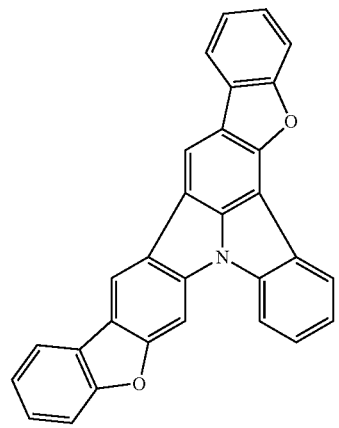
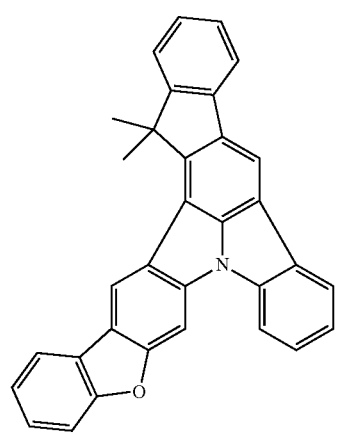
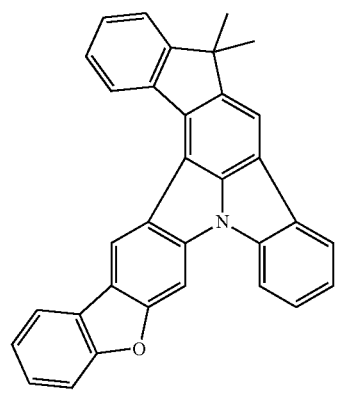
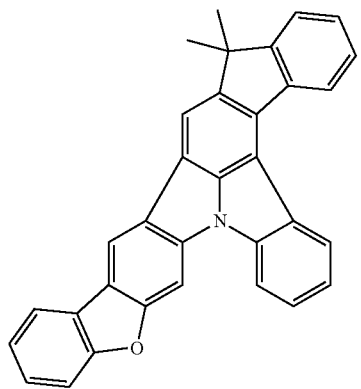

285
-continued
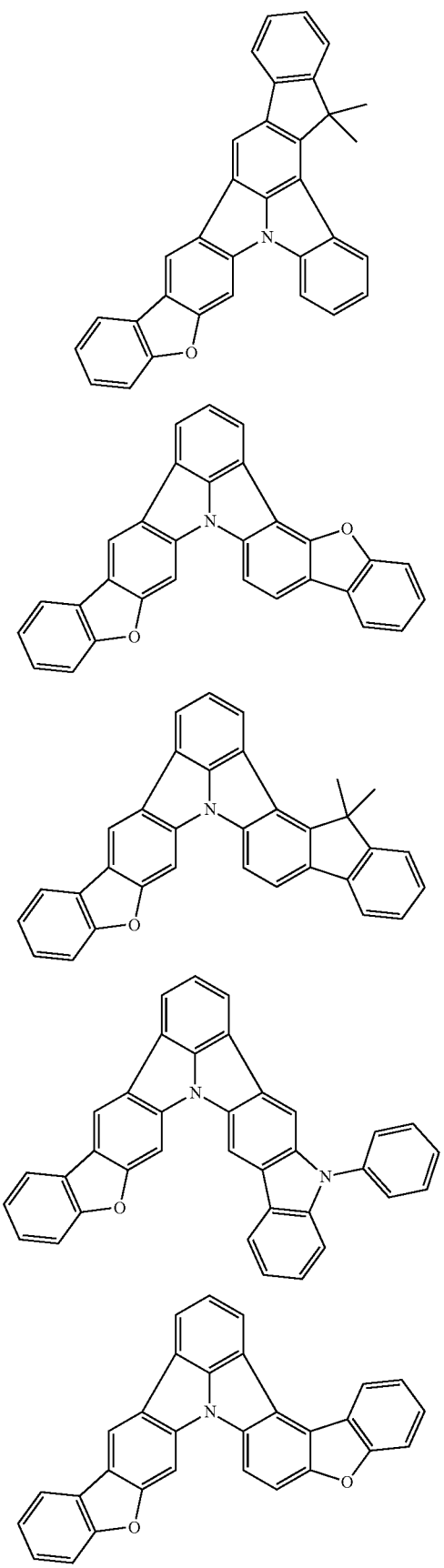
286
-continued
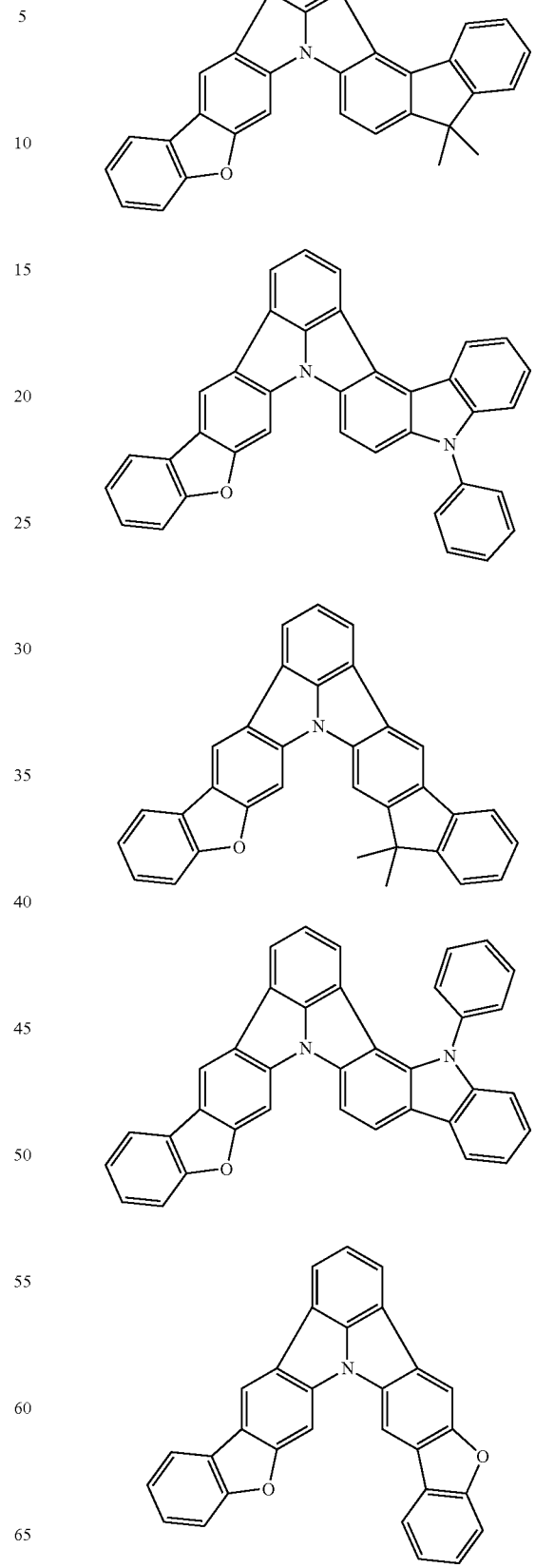

287
-continued
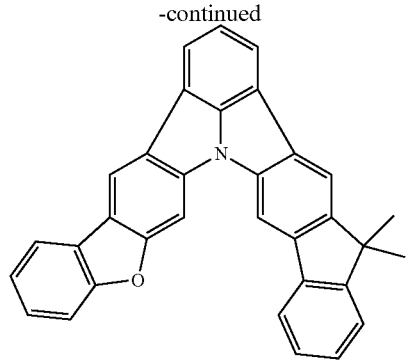
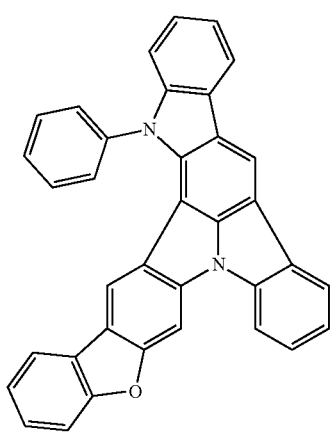
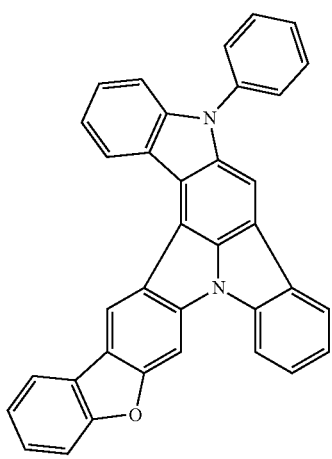
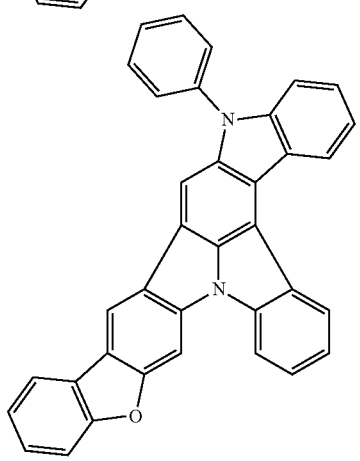
288
-continued
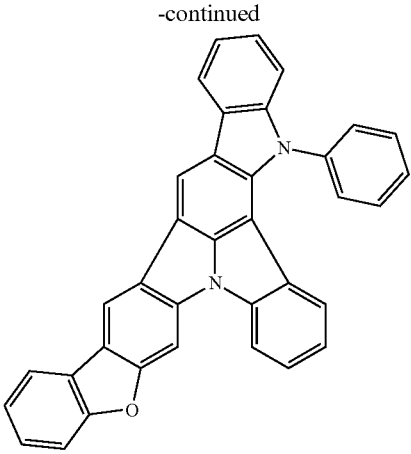
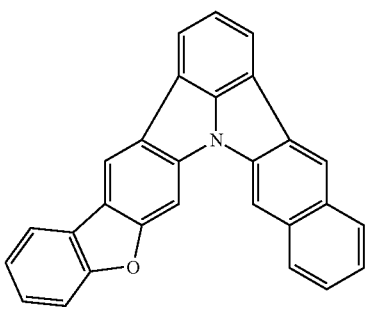
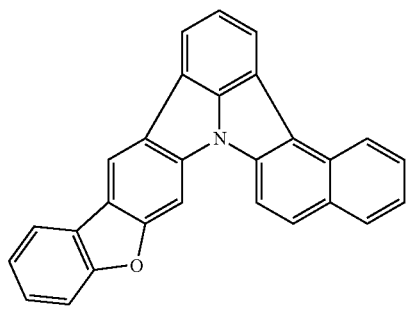
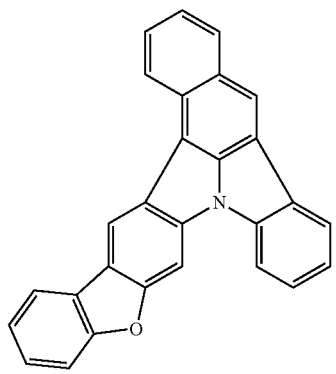

289
-continued
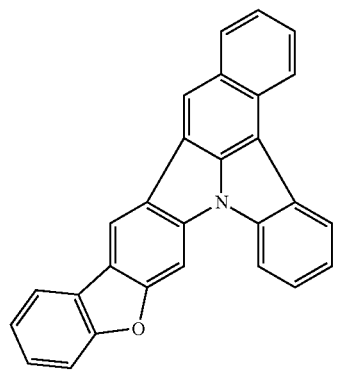
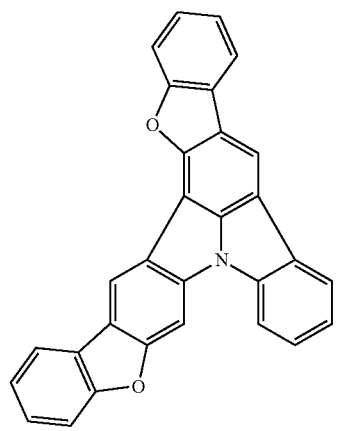
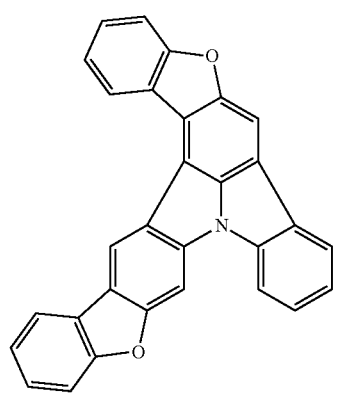
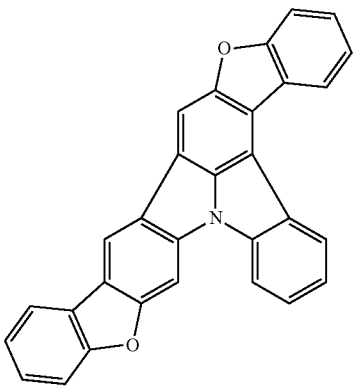
290
-continued
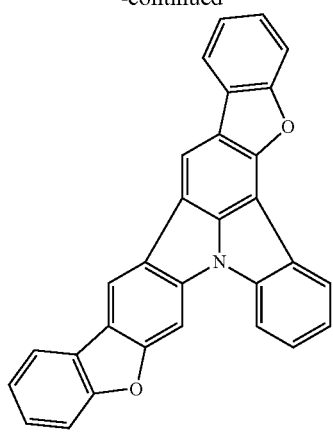
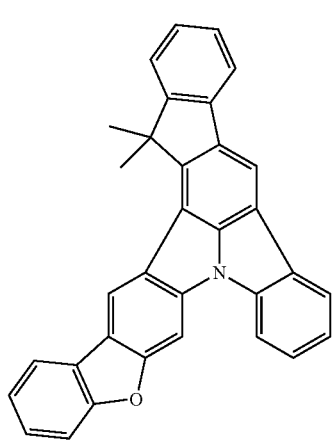
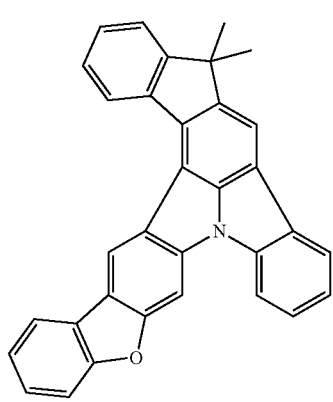
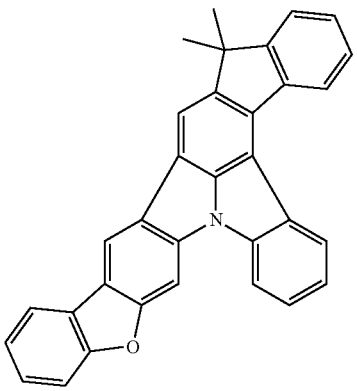

291
-continued
292
-continued
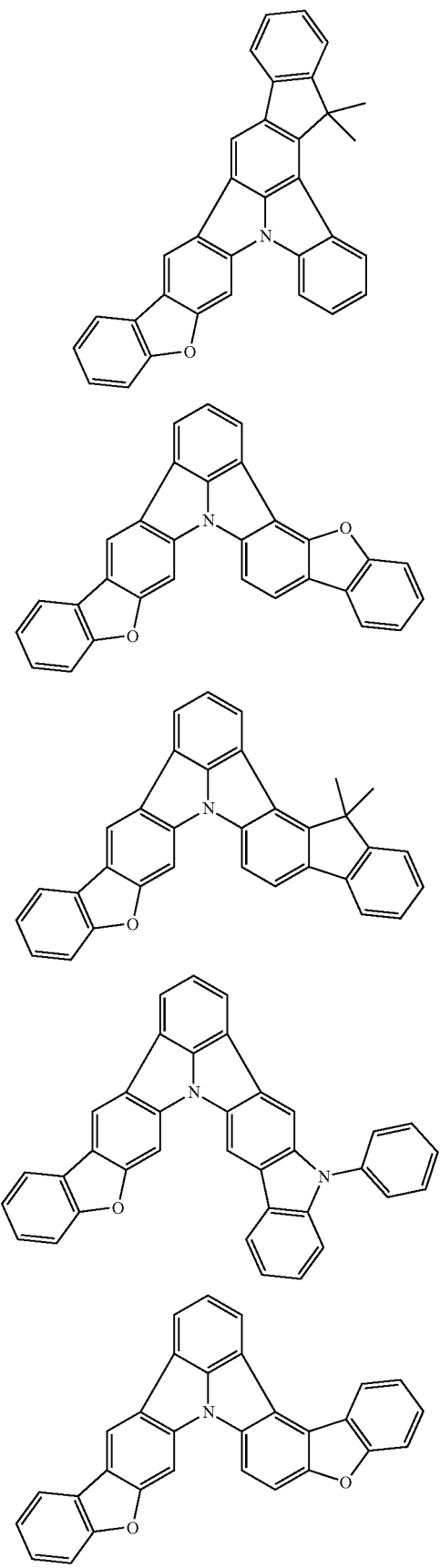
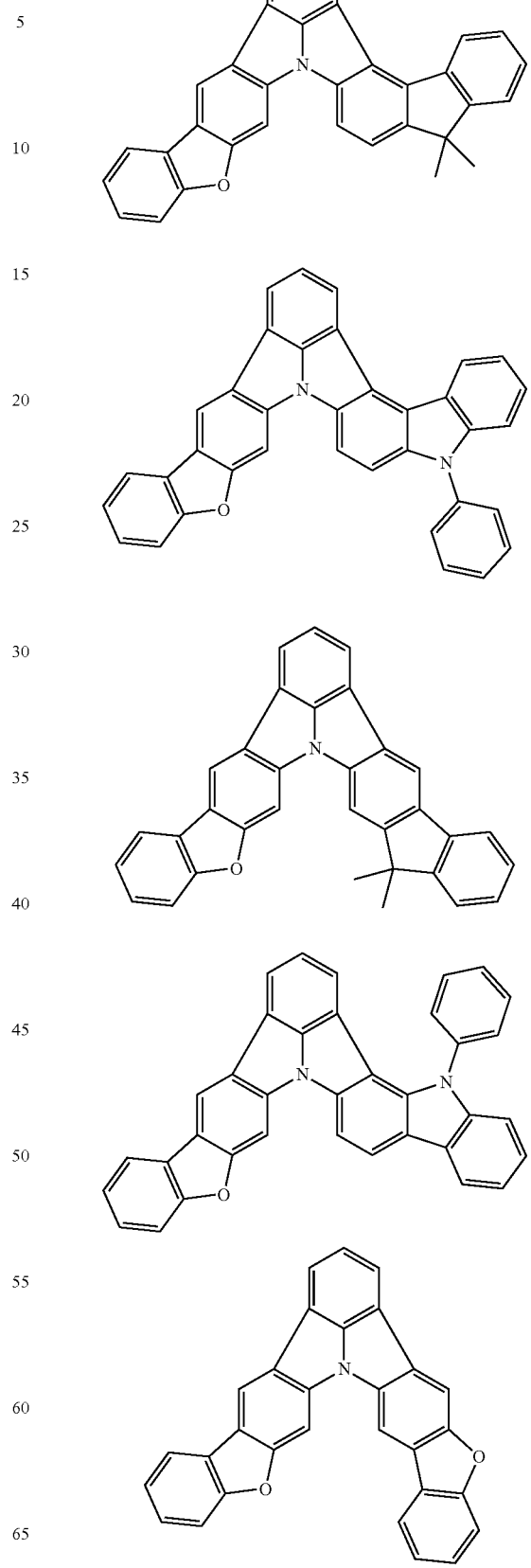

293
-continued
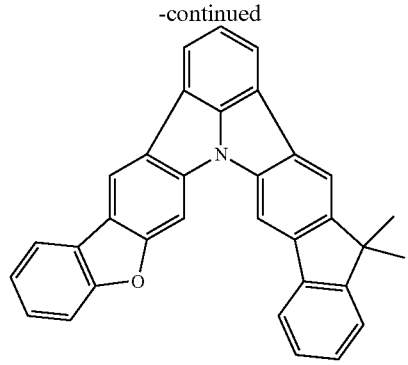
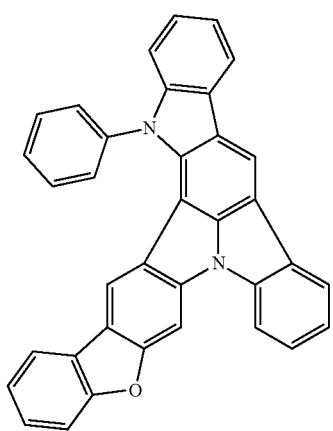
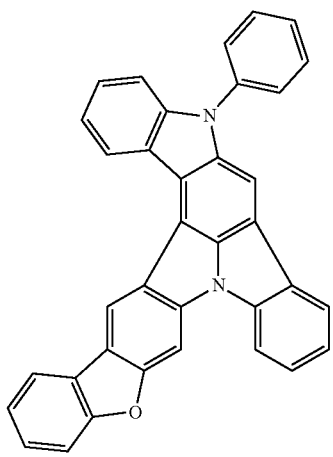
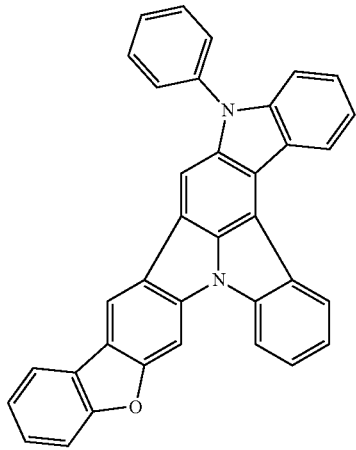
294
-continued
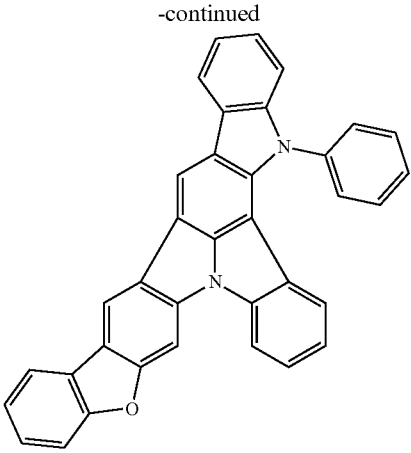
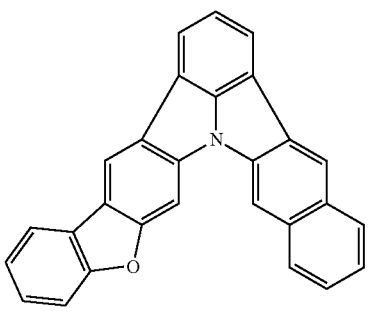
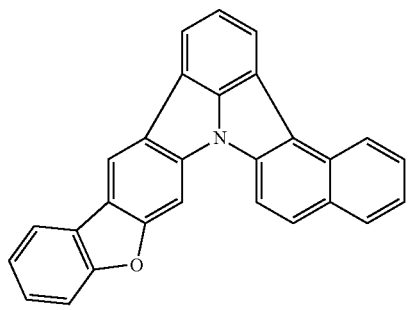
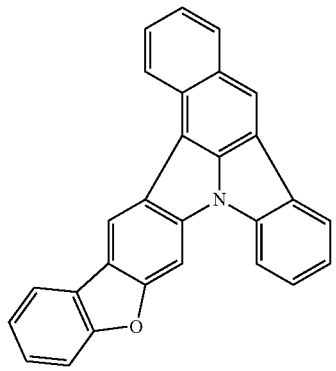

295
-continued
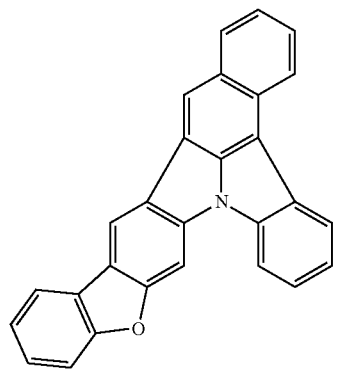
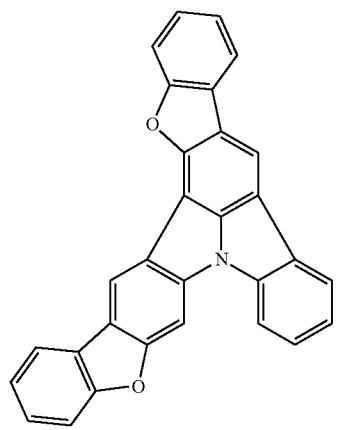
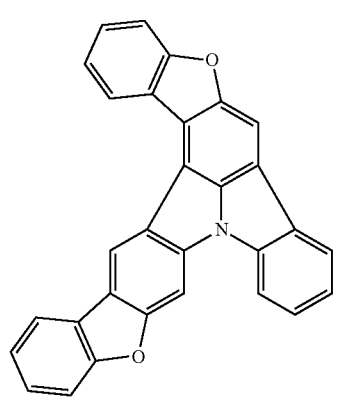
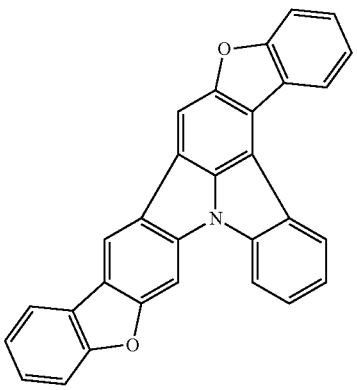
296
-continued
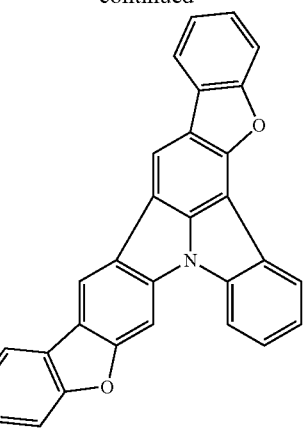
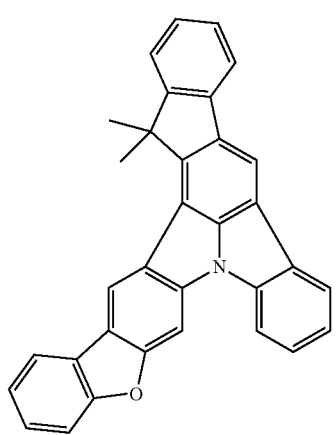

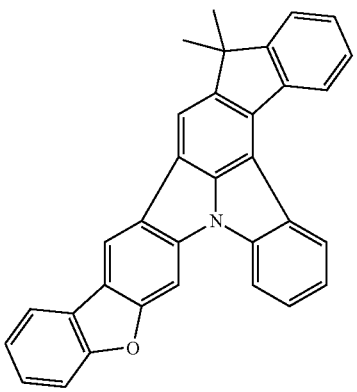

297
-continued
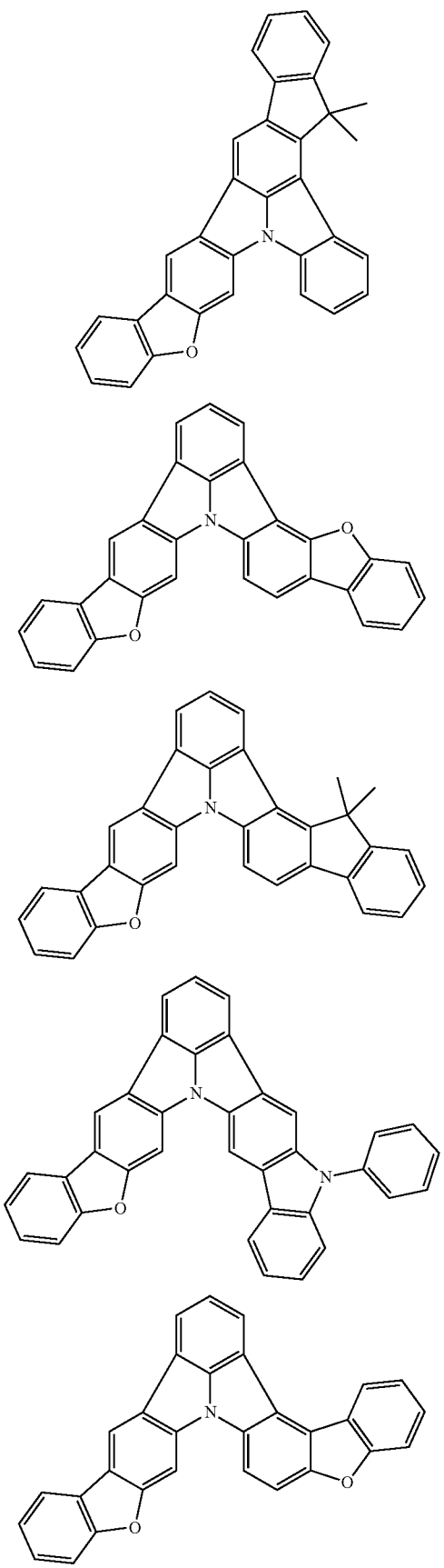
298
-continued
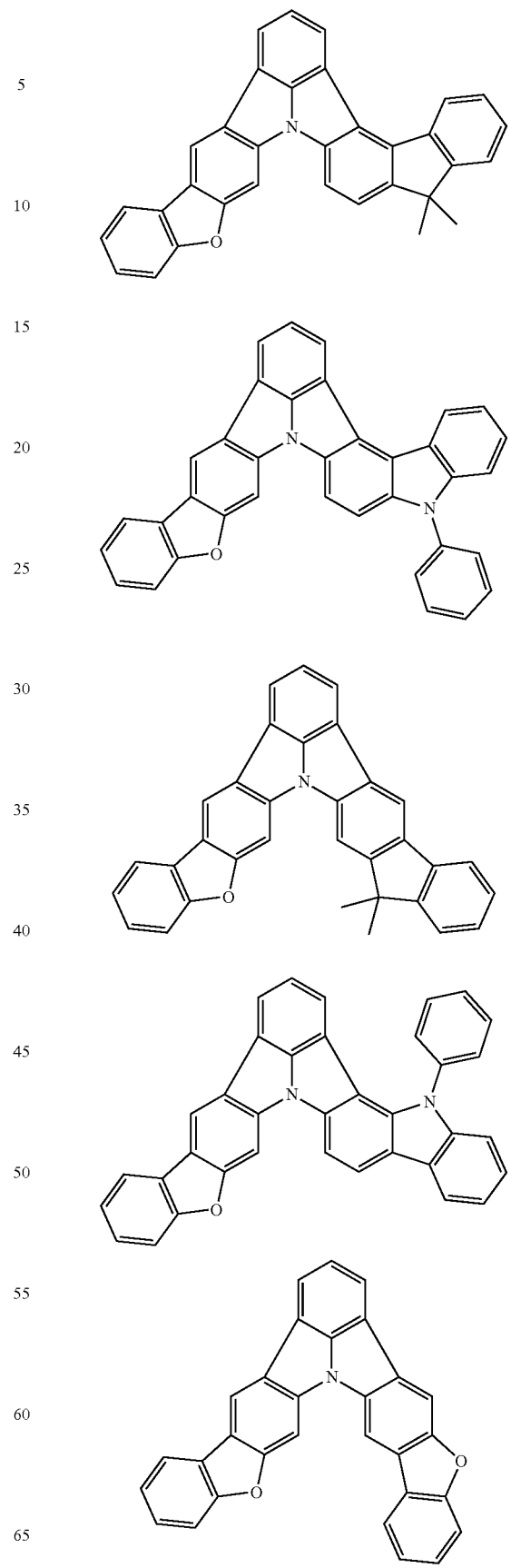

299
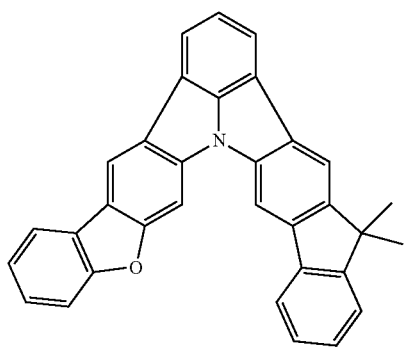
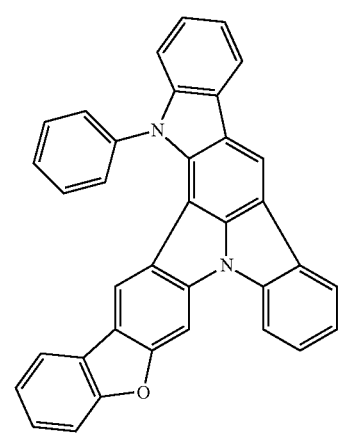
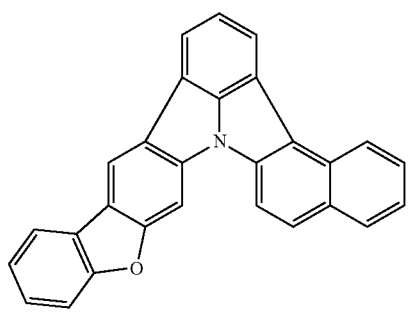
300
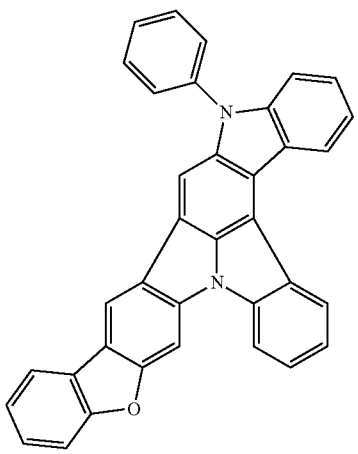
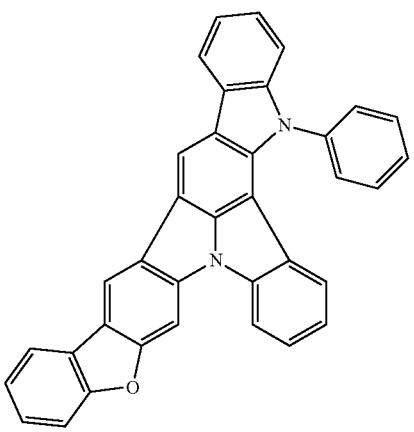
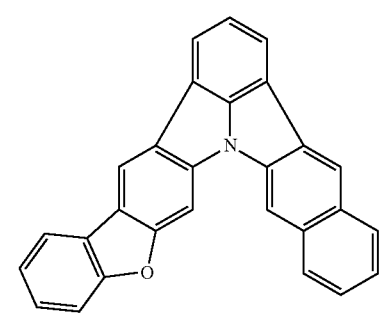
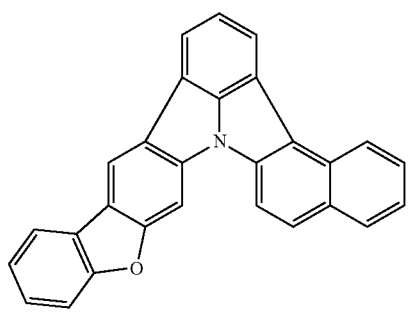

| 301 -continued | 302 -continued |
|---|---|
| 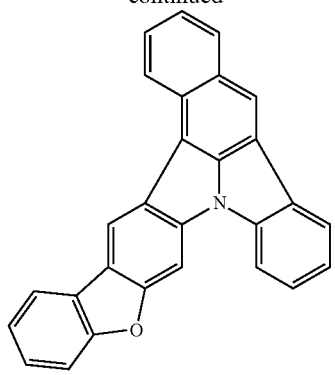 | 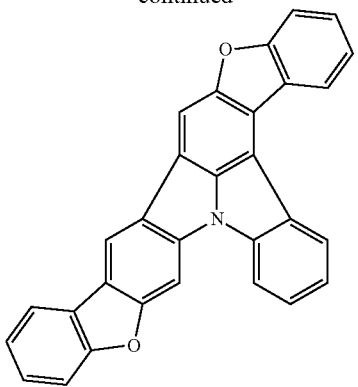 |
| 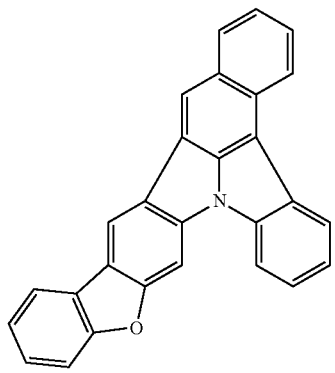 | 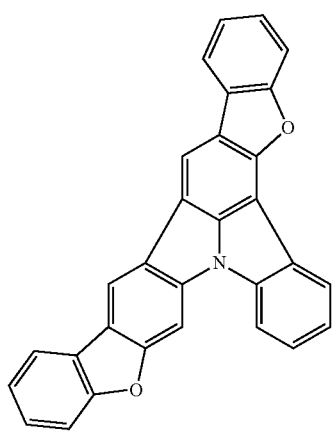 |
| 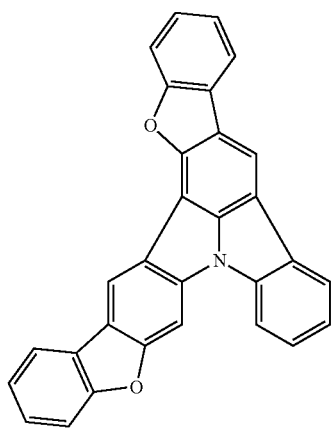 | 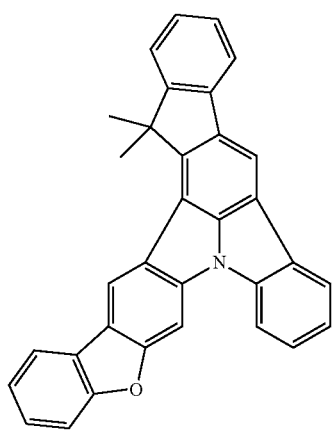 |
| 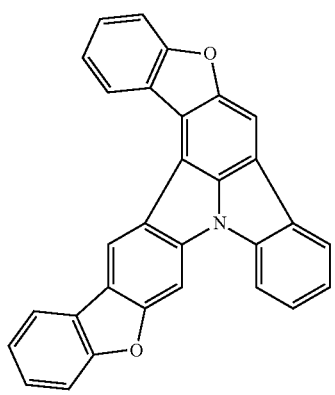 | 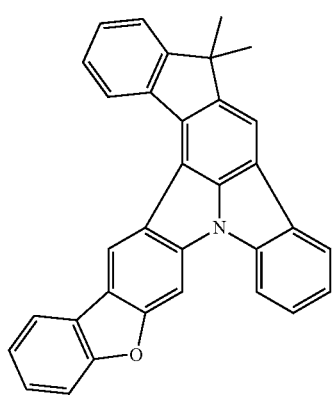 |

303
-continued
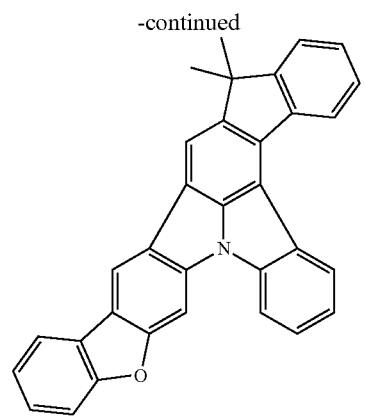
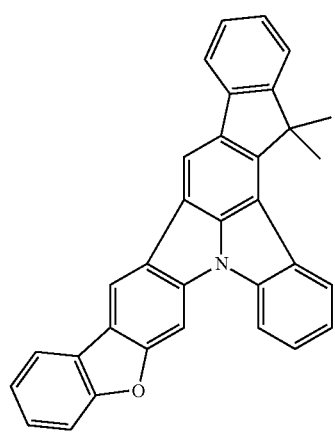
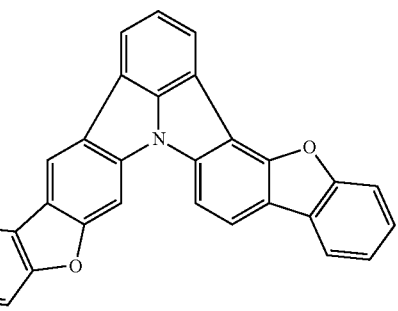
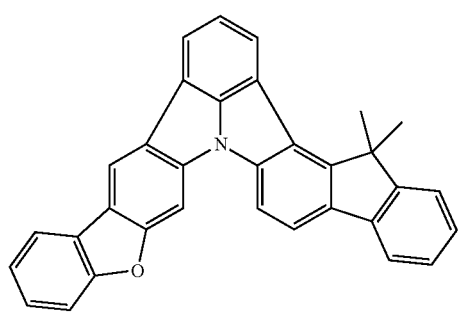
304
-continued
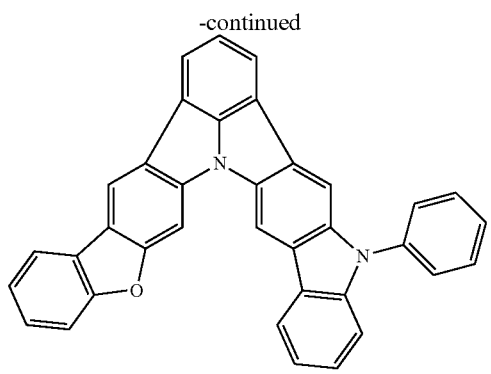
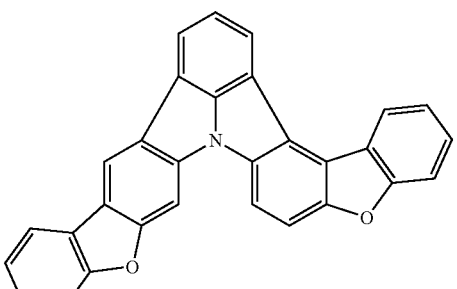
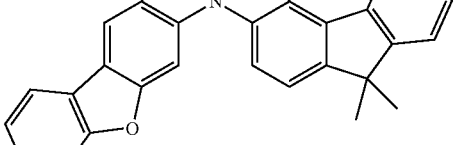
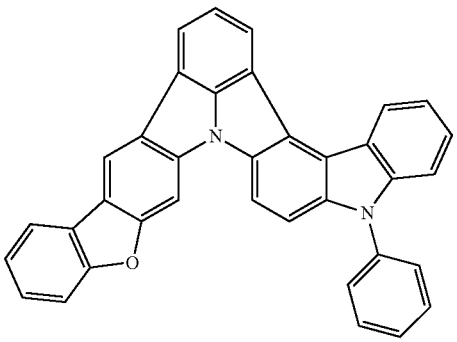
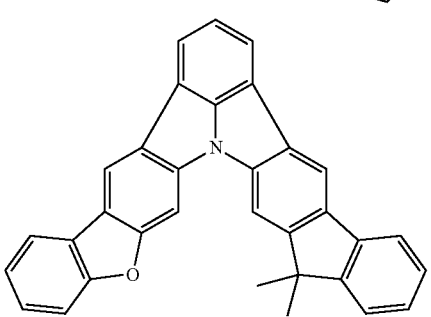

-continued
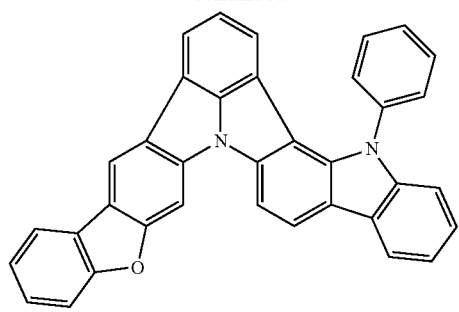
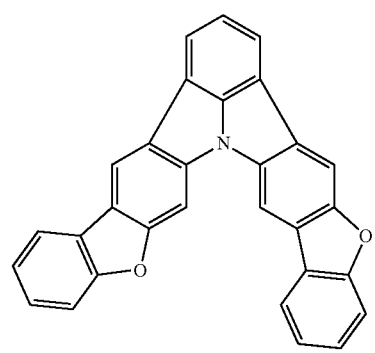
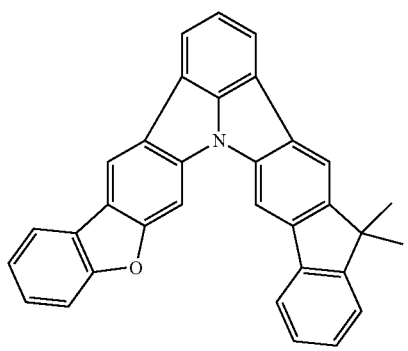
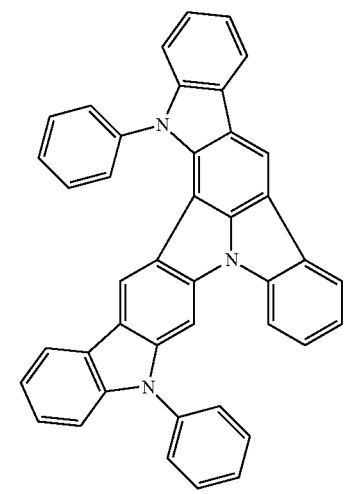
-continued
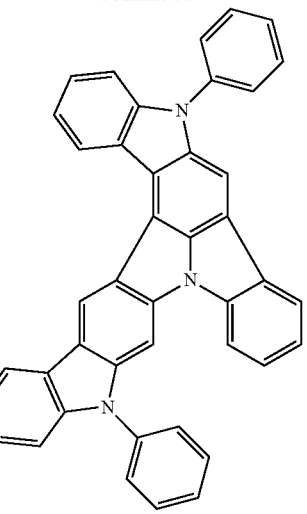
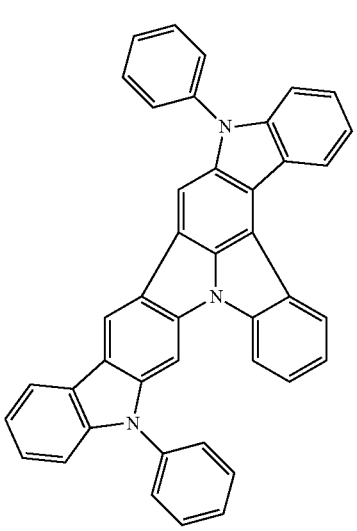
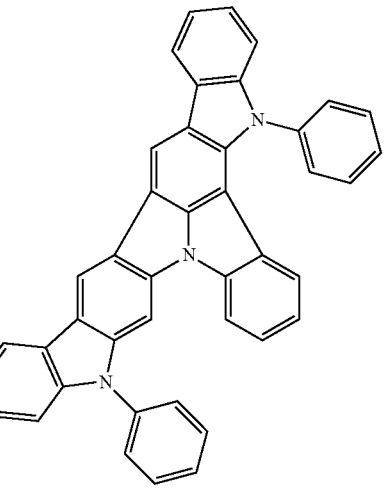

307
-continued
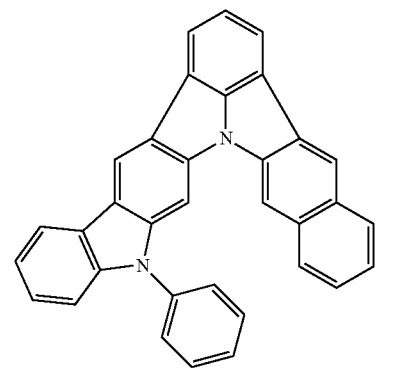
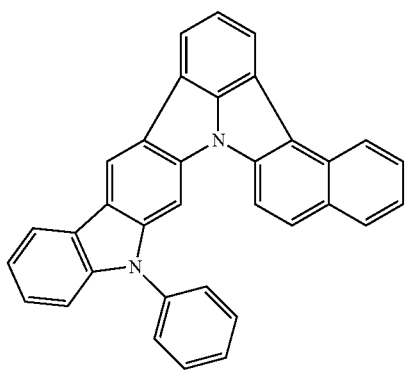
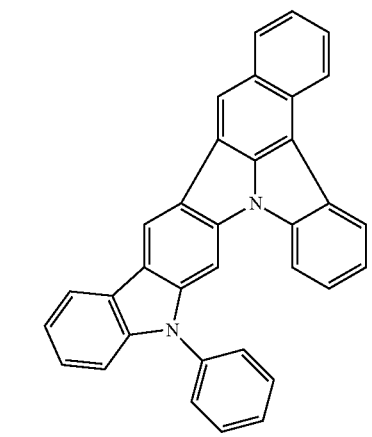

308
-continued
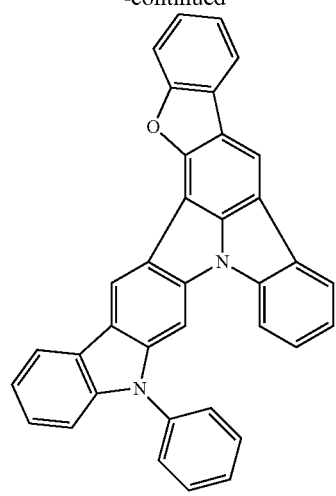
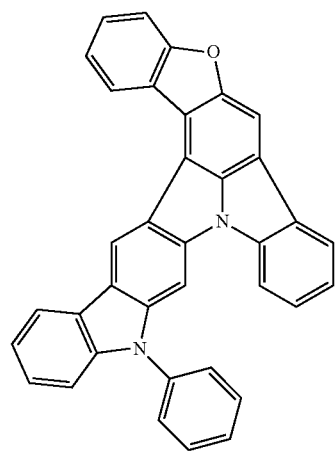
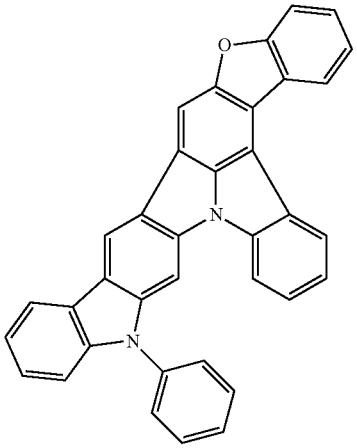

309
-continued
310
-continued
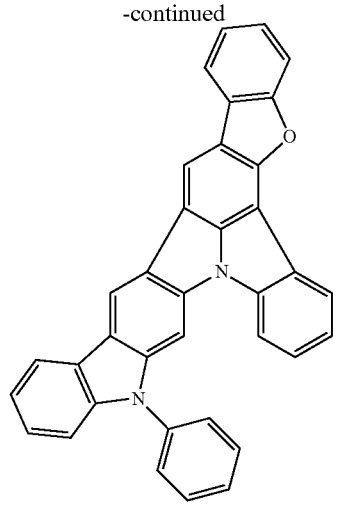
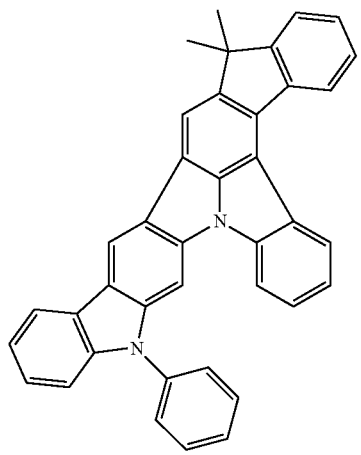
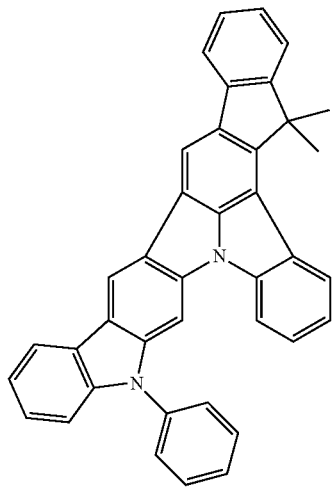
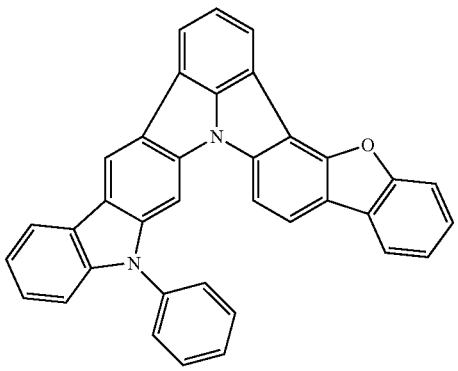
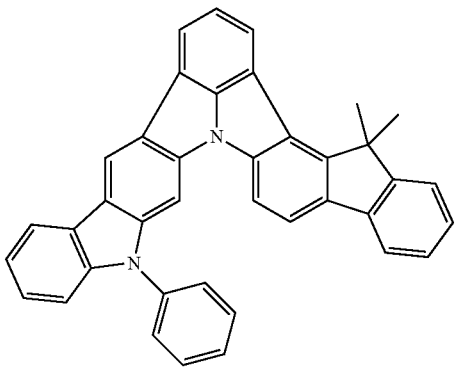

311
-continued
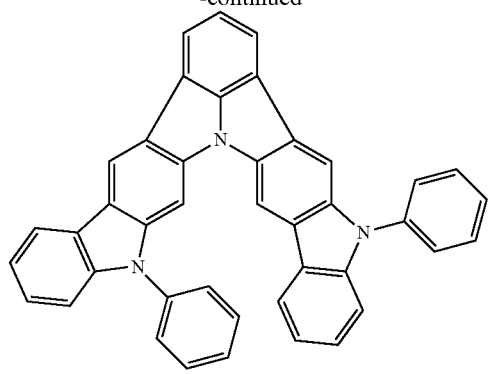
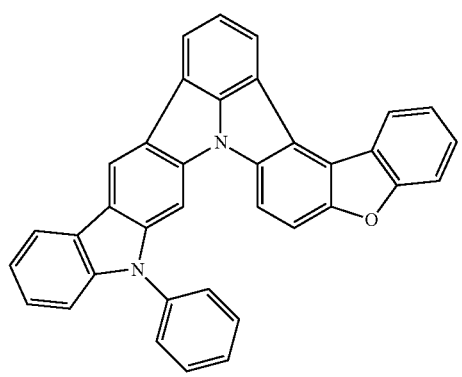
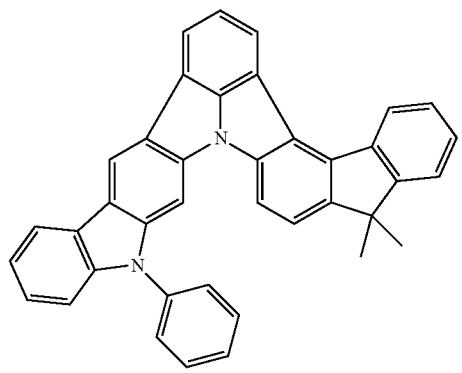
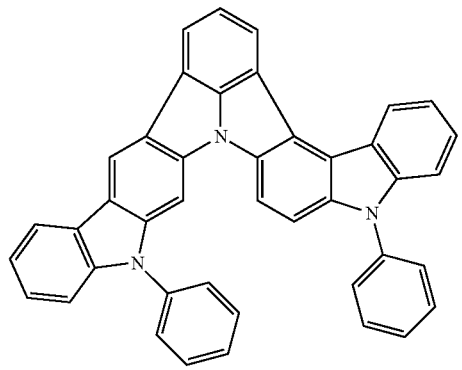
312
-continued
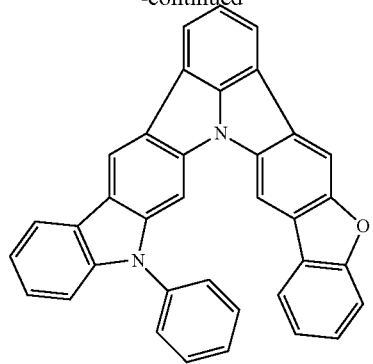
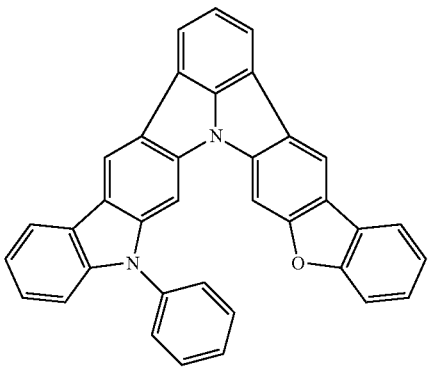
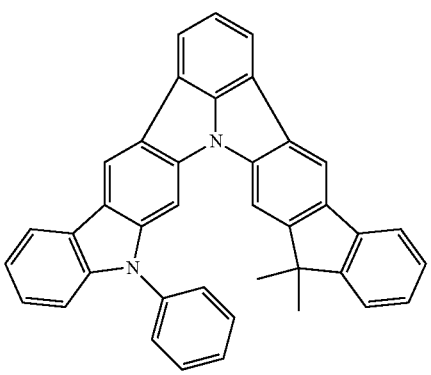
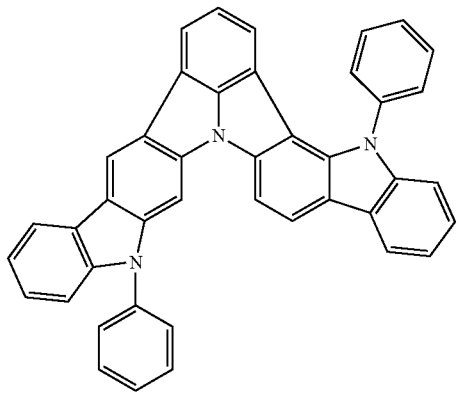

313
-continued
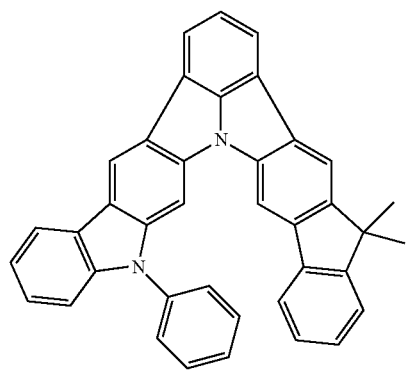
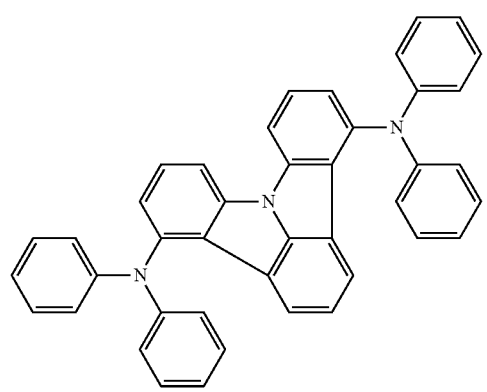
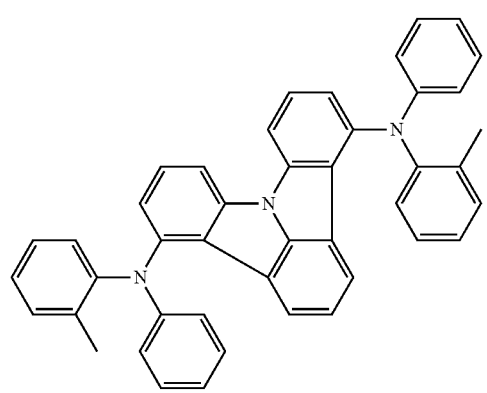
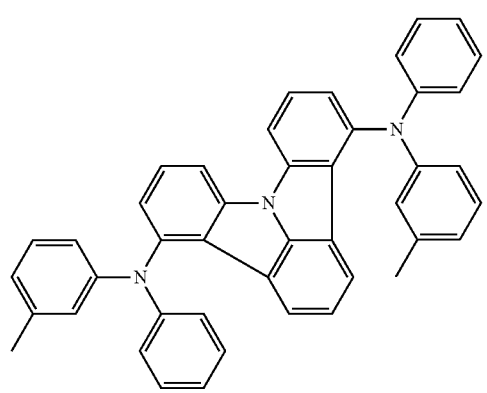
314
-continued
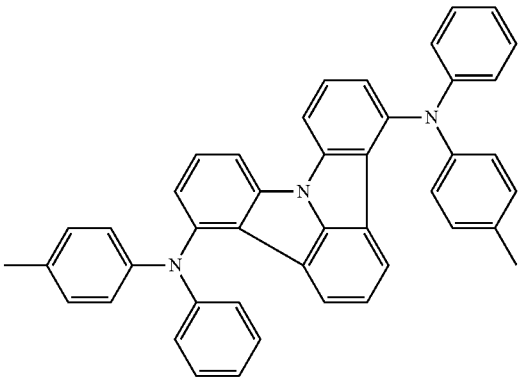
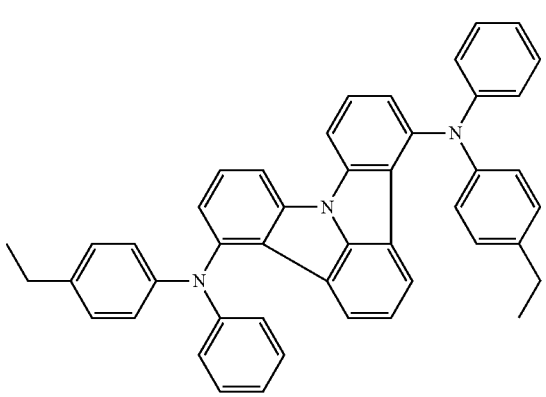
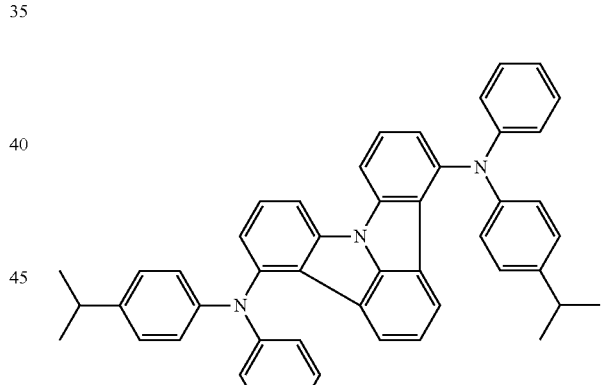
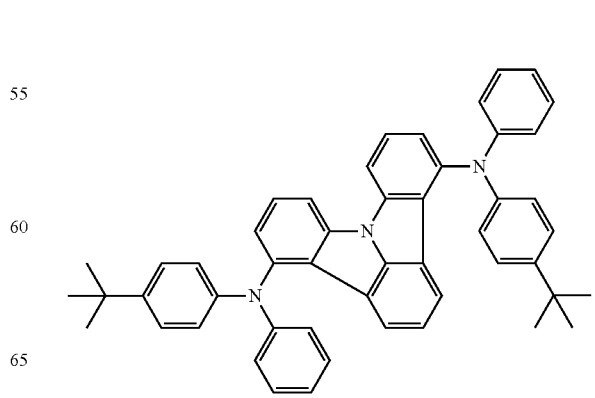

315
-continued
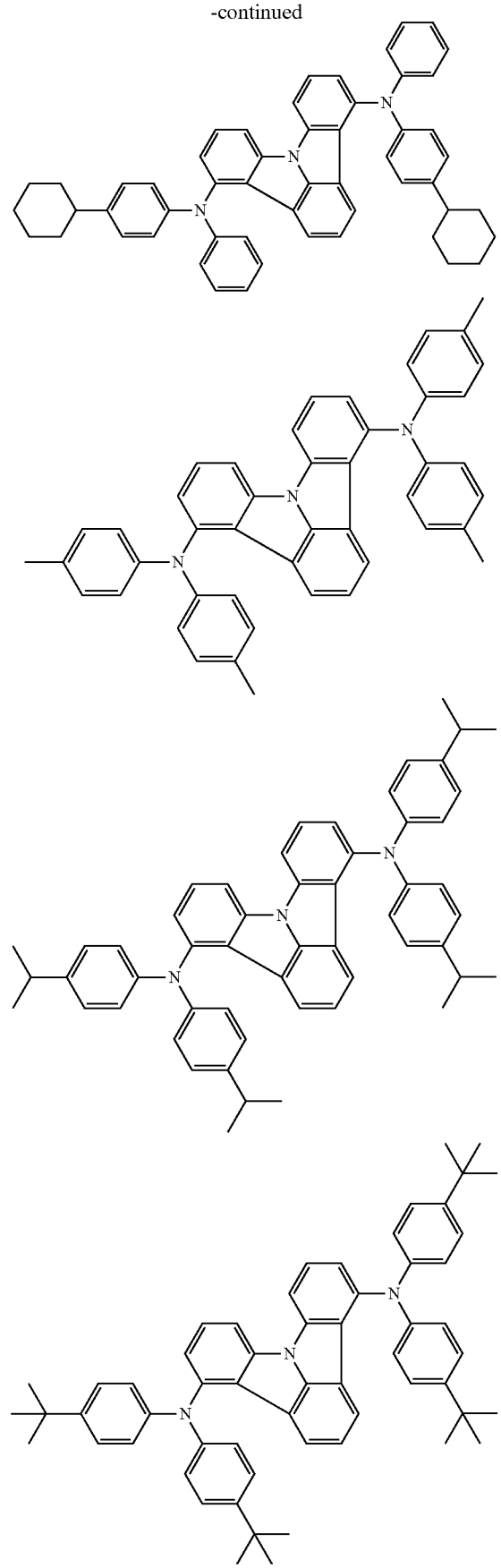
316
-continued
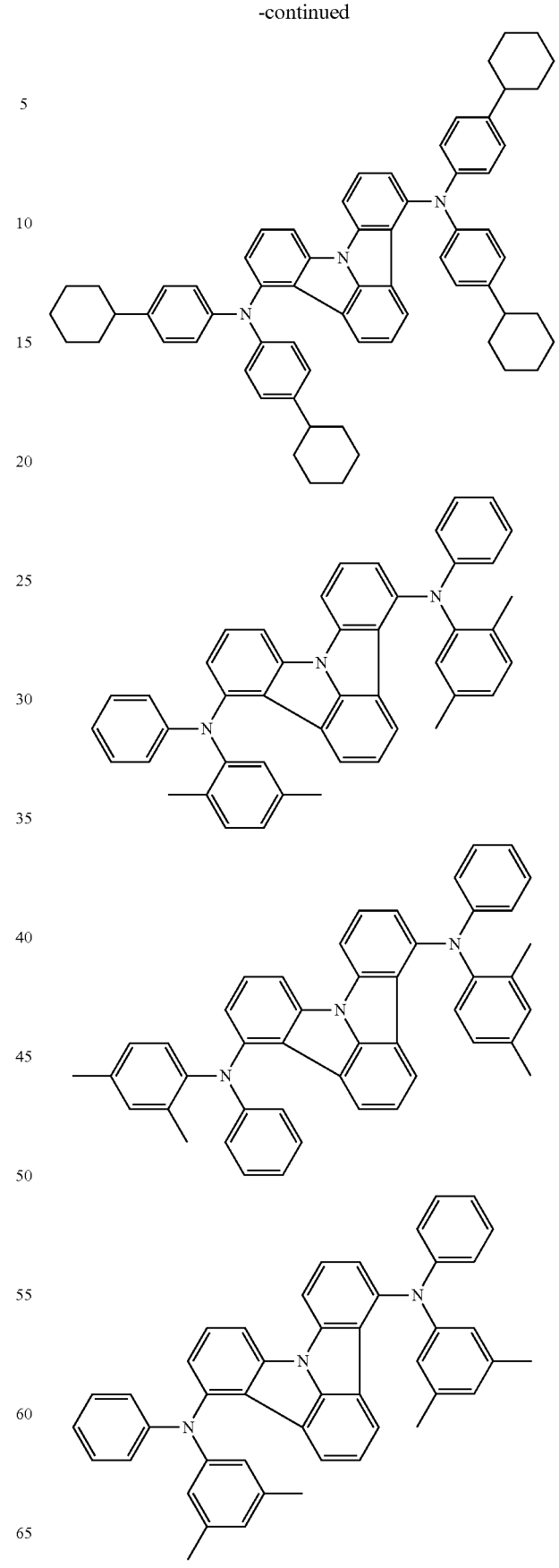

317
-continued
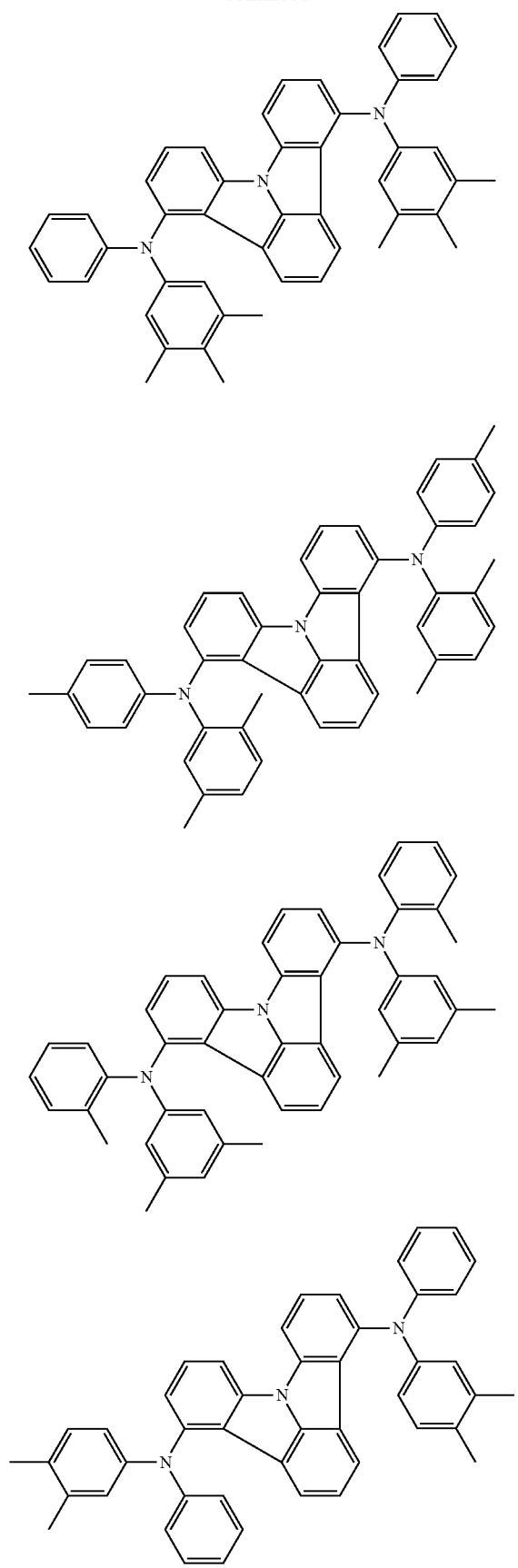
318
-continued
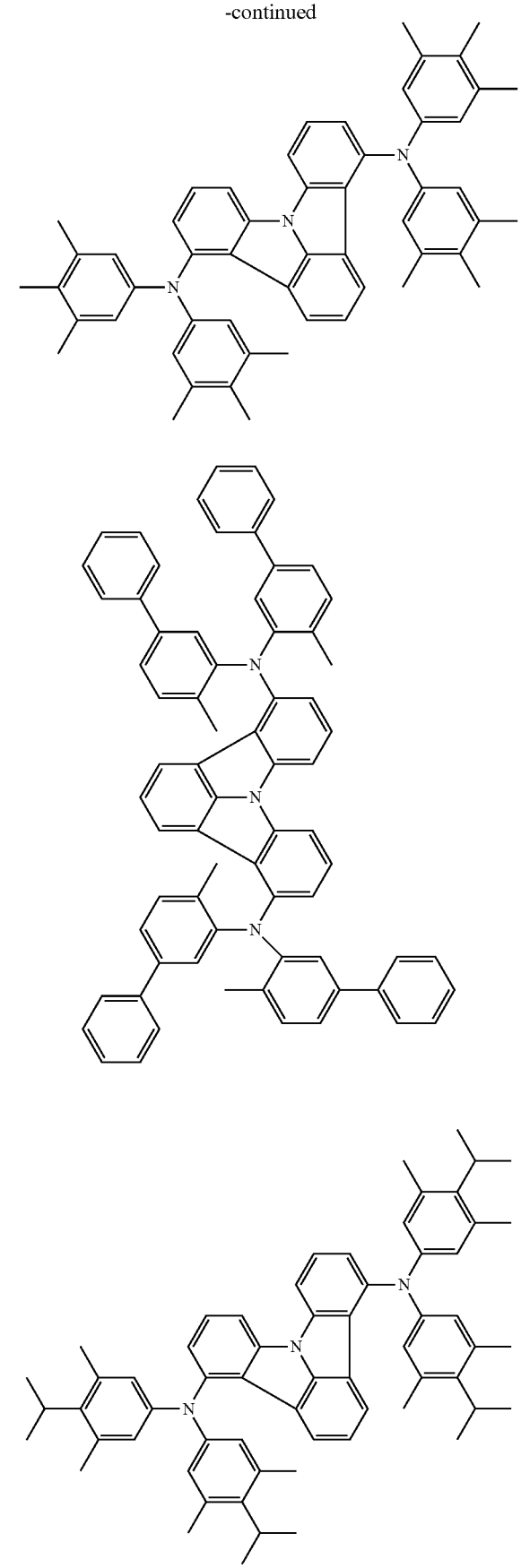

319
-continued
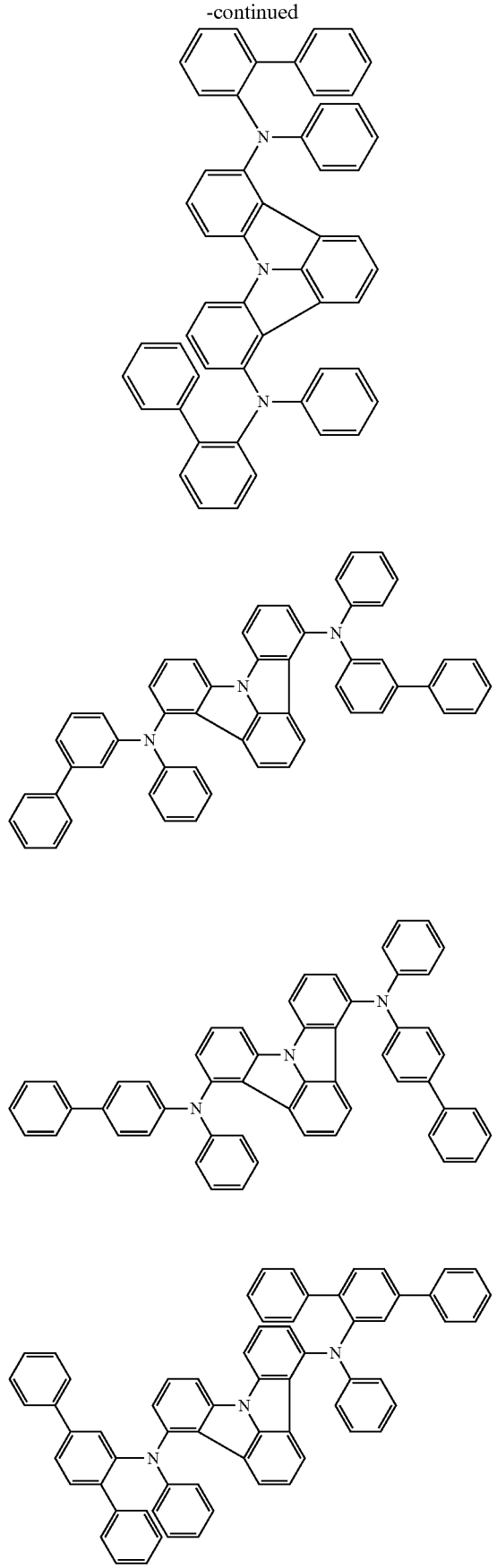
320
-continued
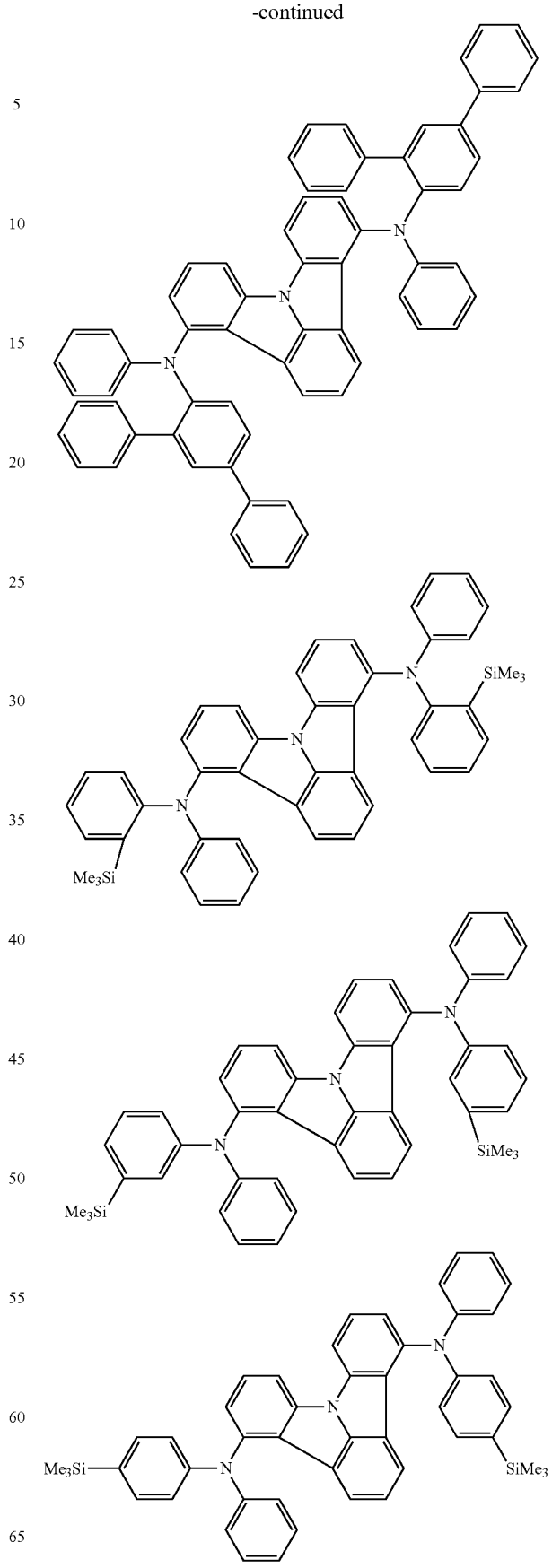

321
-continued
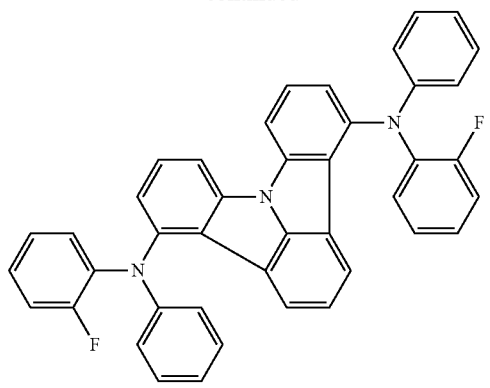
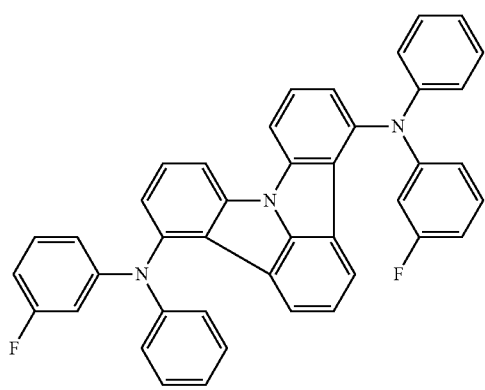
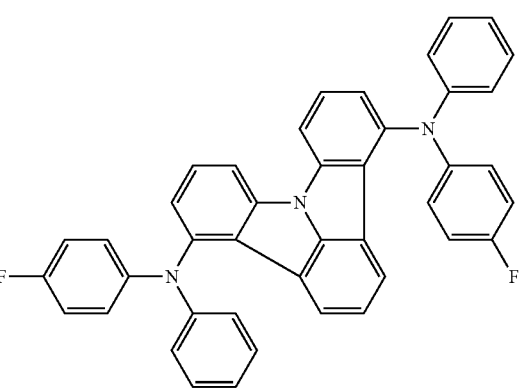
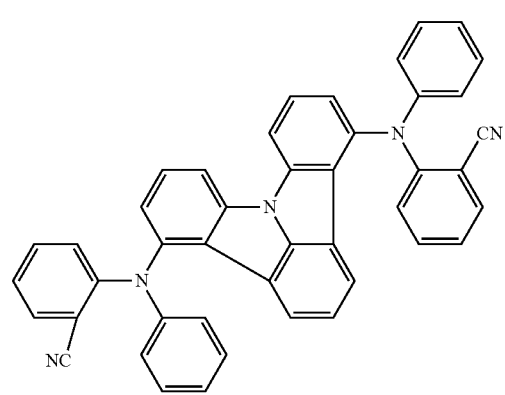
322
-continued
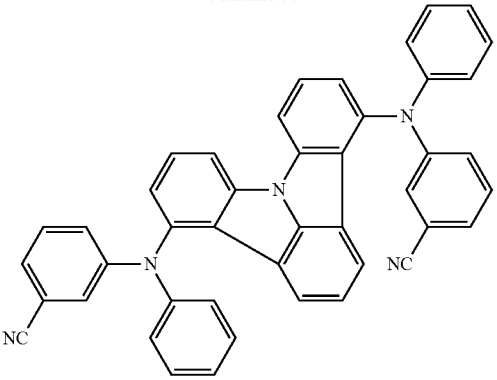
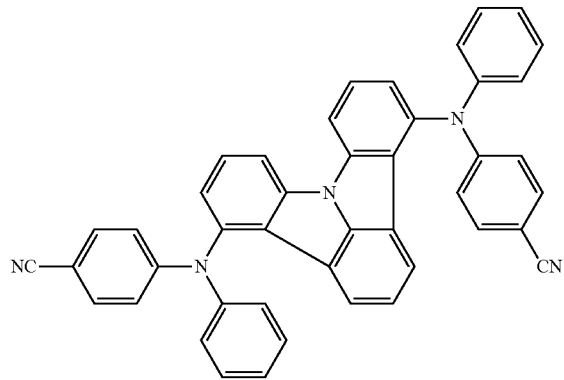
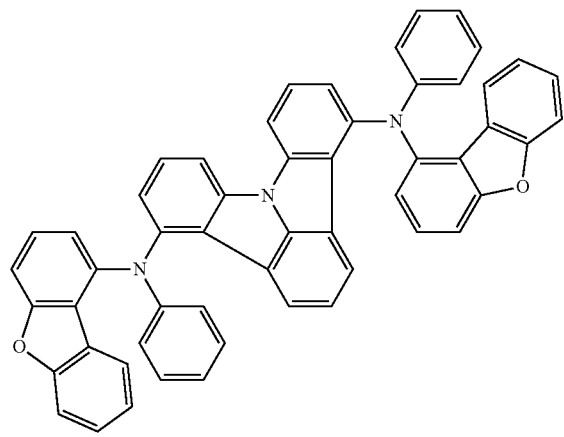
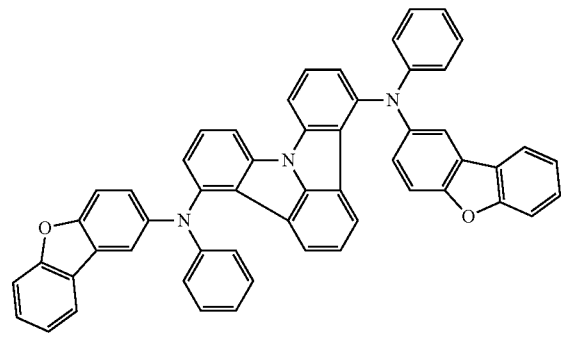

323
-continued
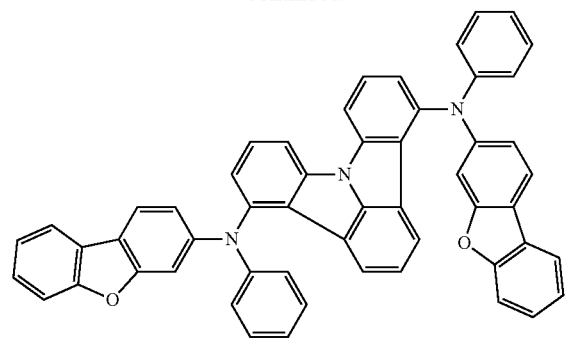
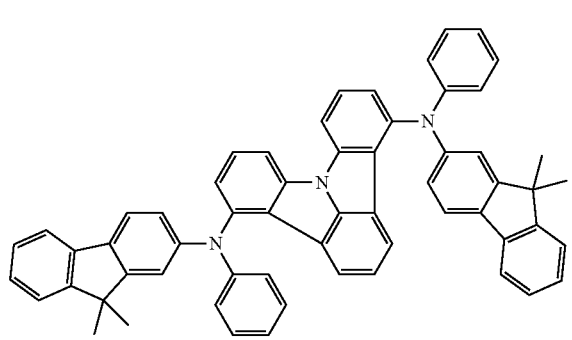
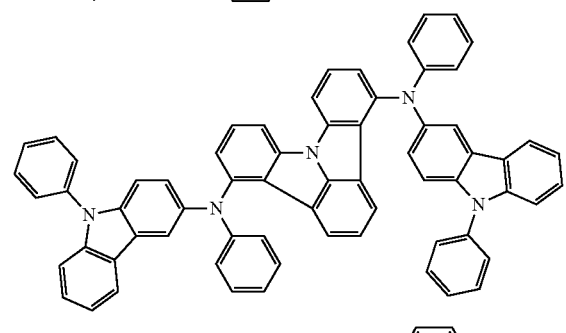
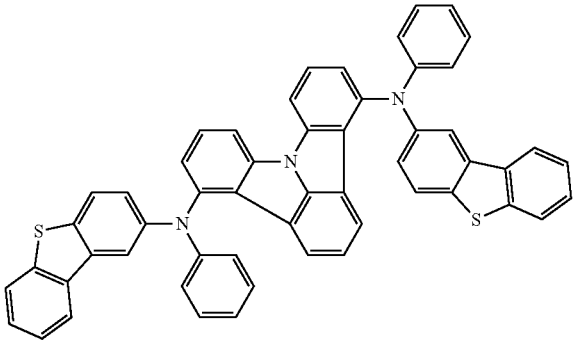

324
-continued
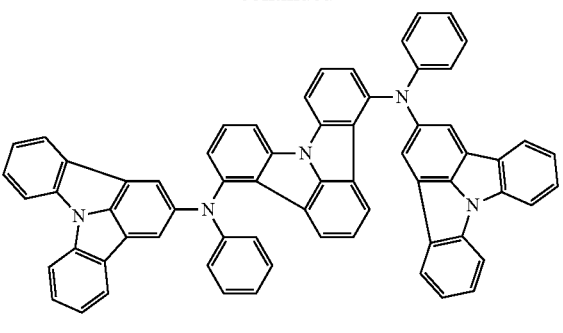
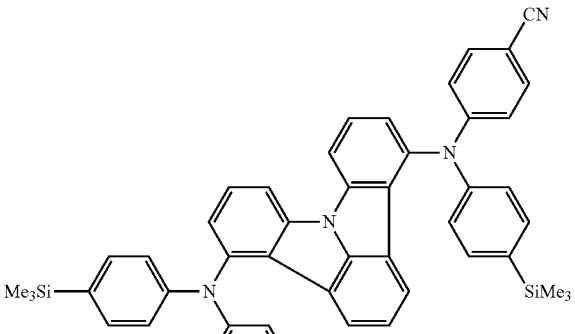
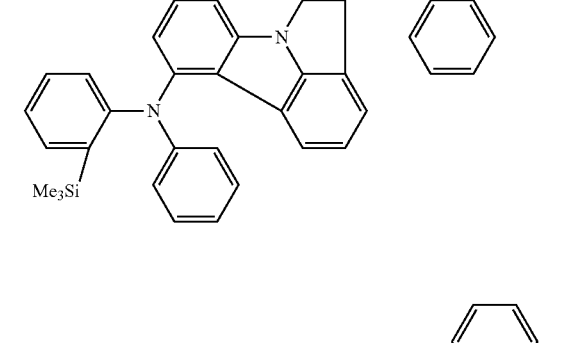
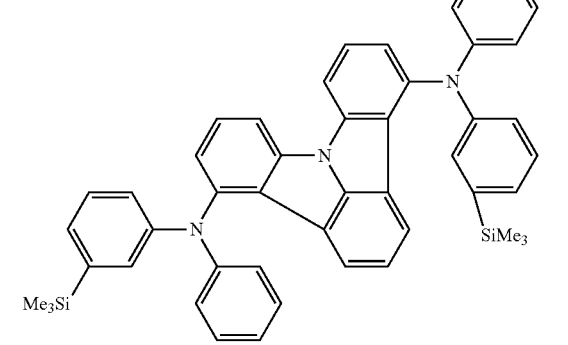

325
-continued
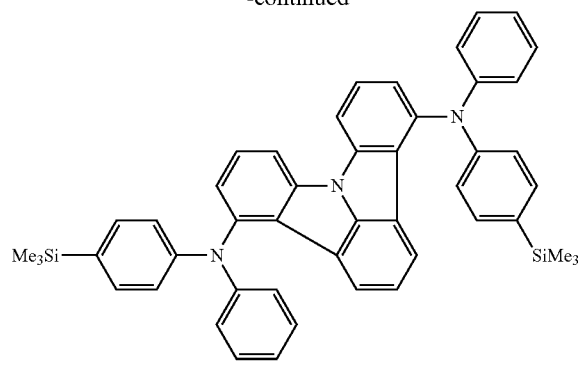
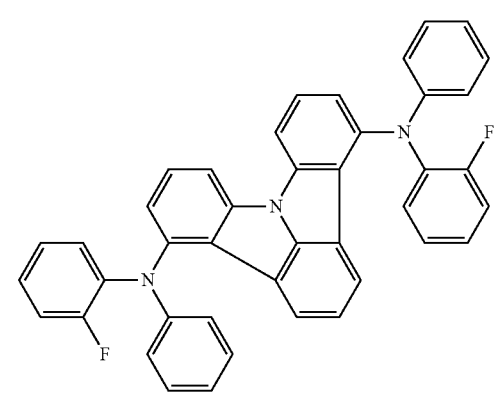
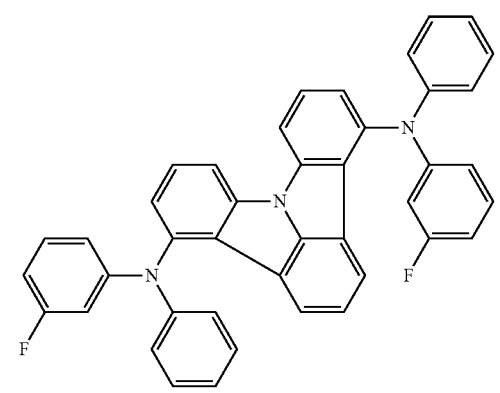
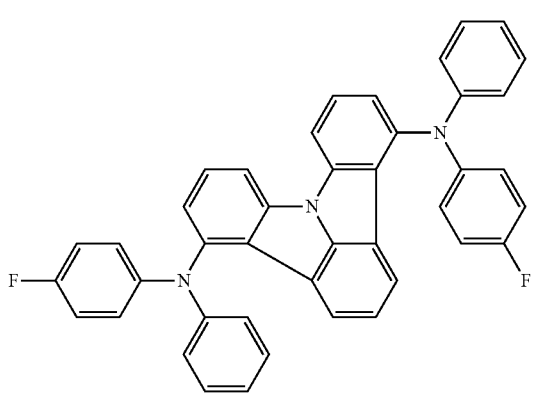
326
-continued
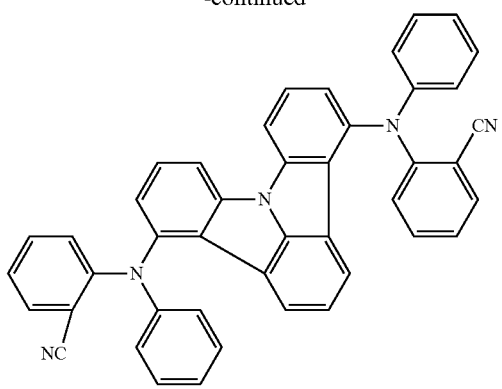
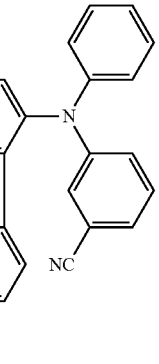
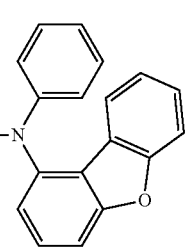

327
-continued
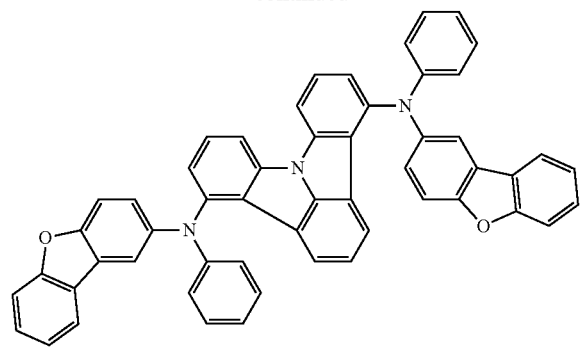
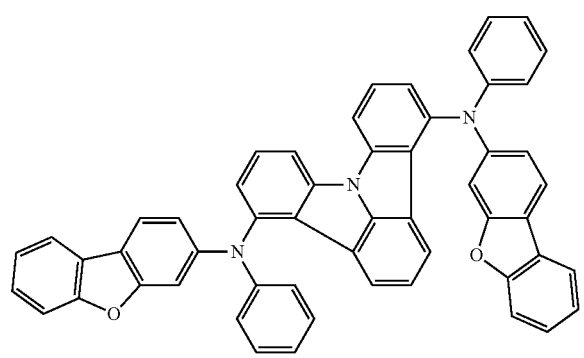
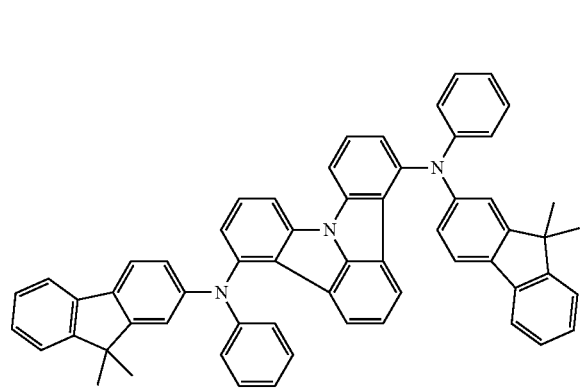
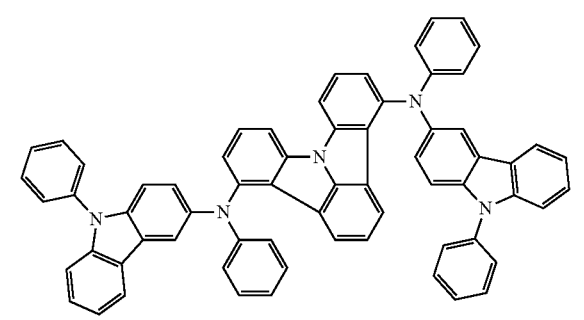
328
-continued
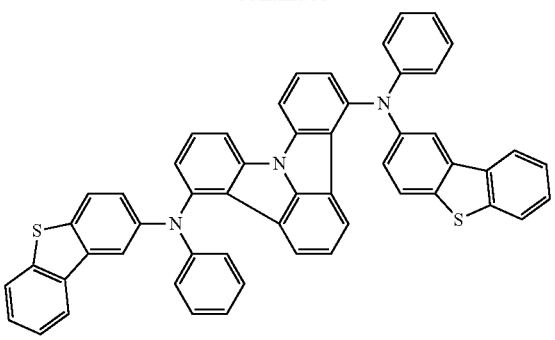
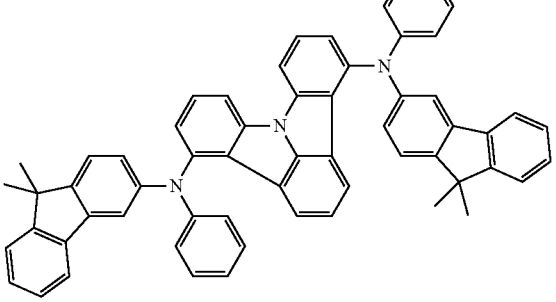
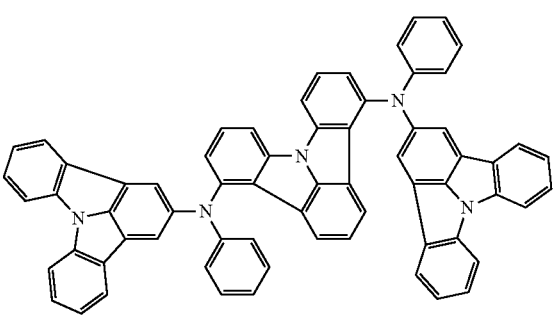
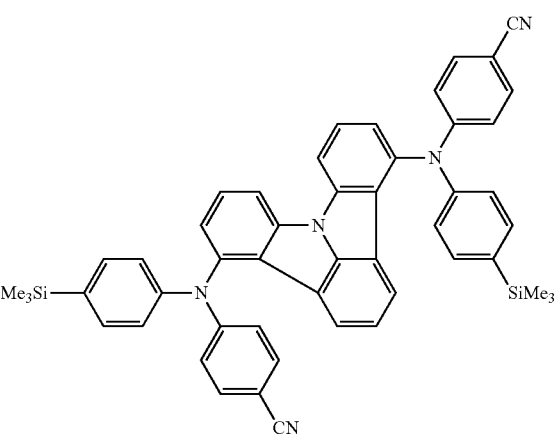 [SMILES: C[Si](C)(C)c1ccc(N(c2ccc(C#N)cc2)c2cccc3c2c2cccc4c5c(N(c6ccc(C#N)cc6)c6ccc([Si](C)(C)C)cc6)cccc5n3c24)cc1]

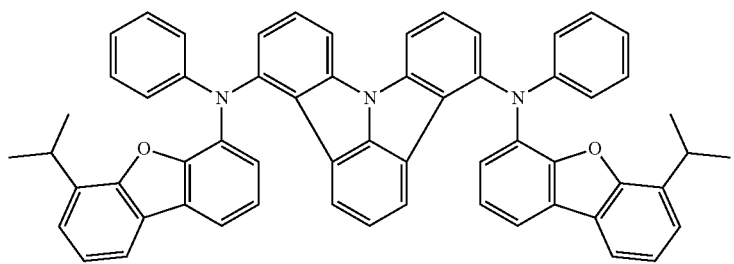
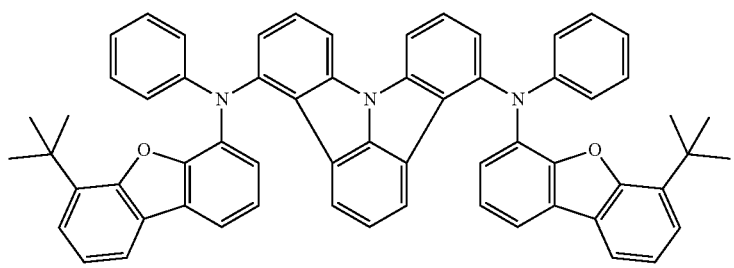
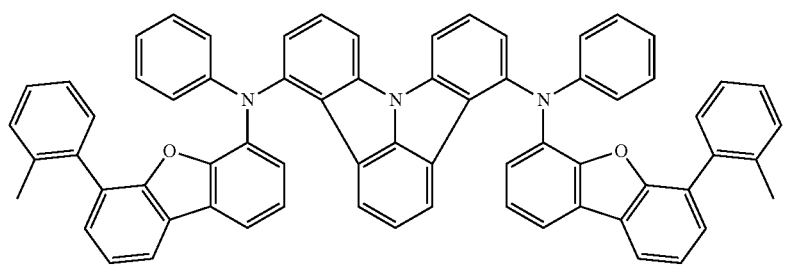
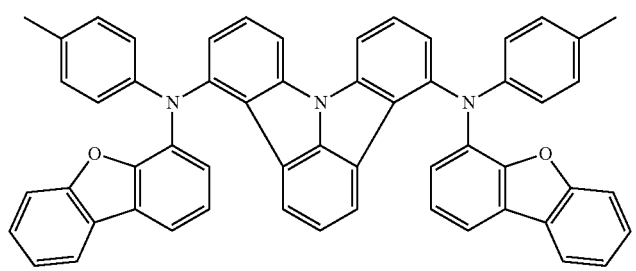

-continued
331
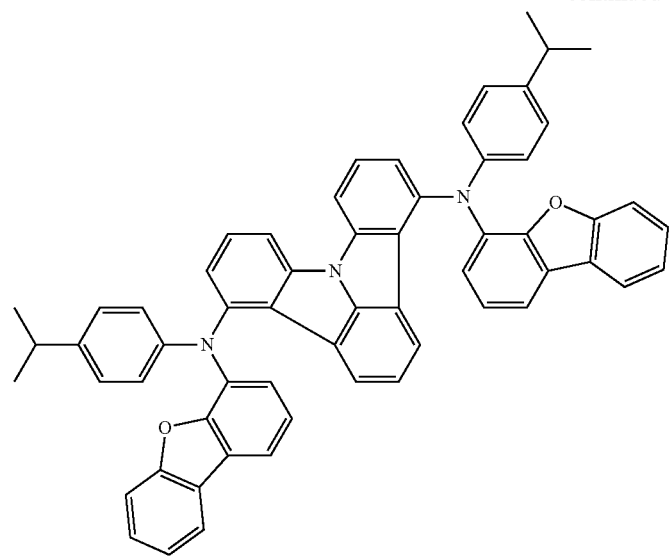
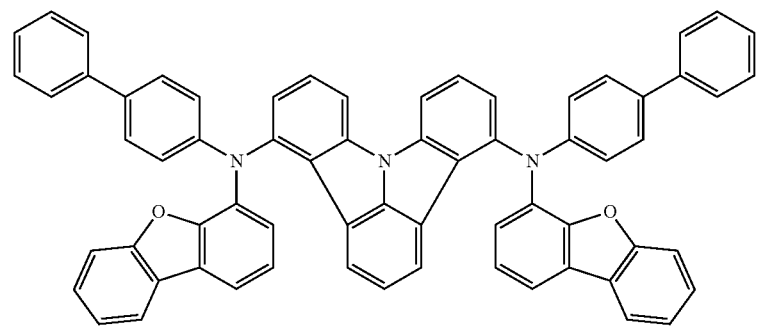
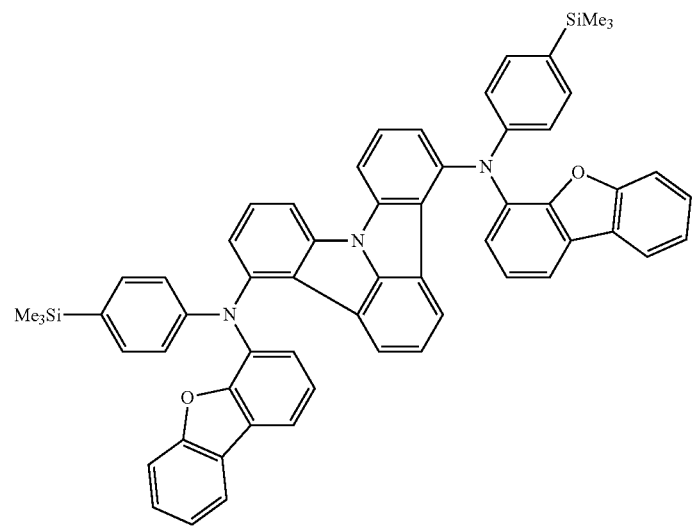
332
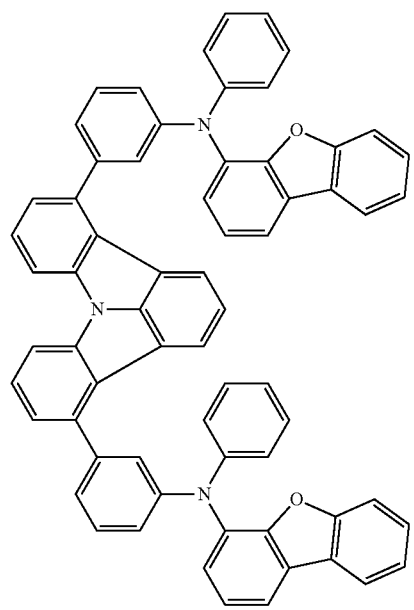

333
-continued
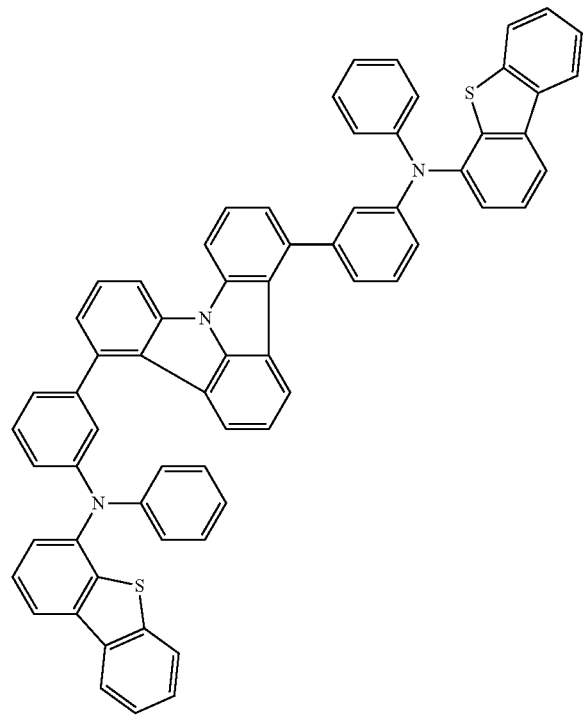
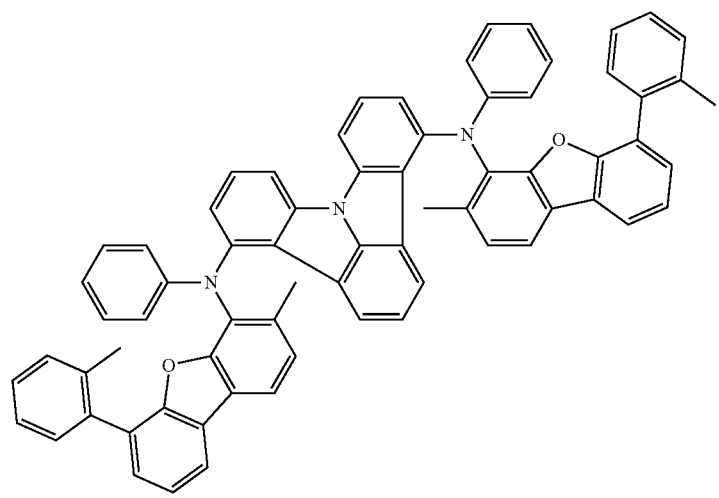
334
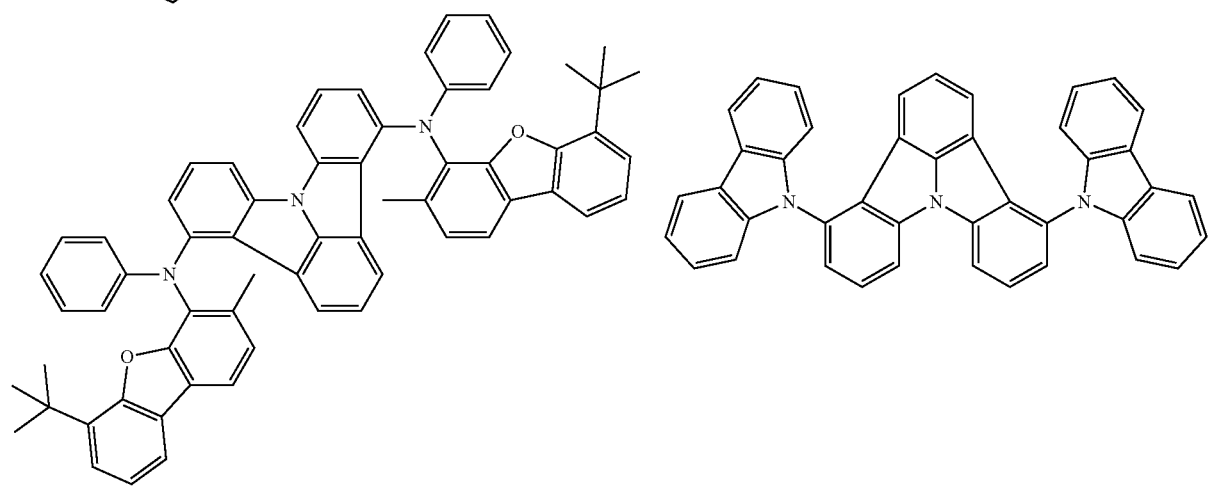

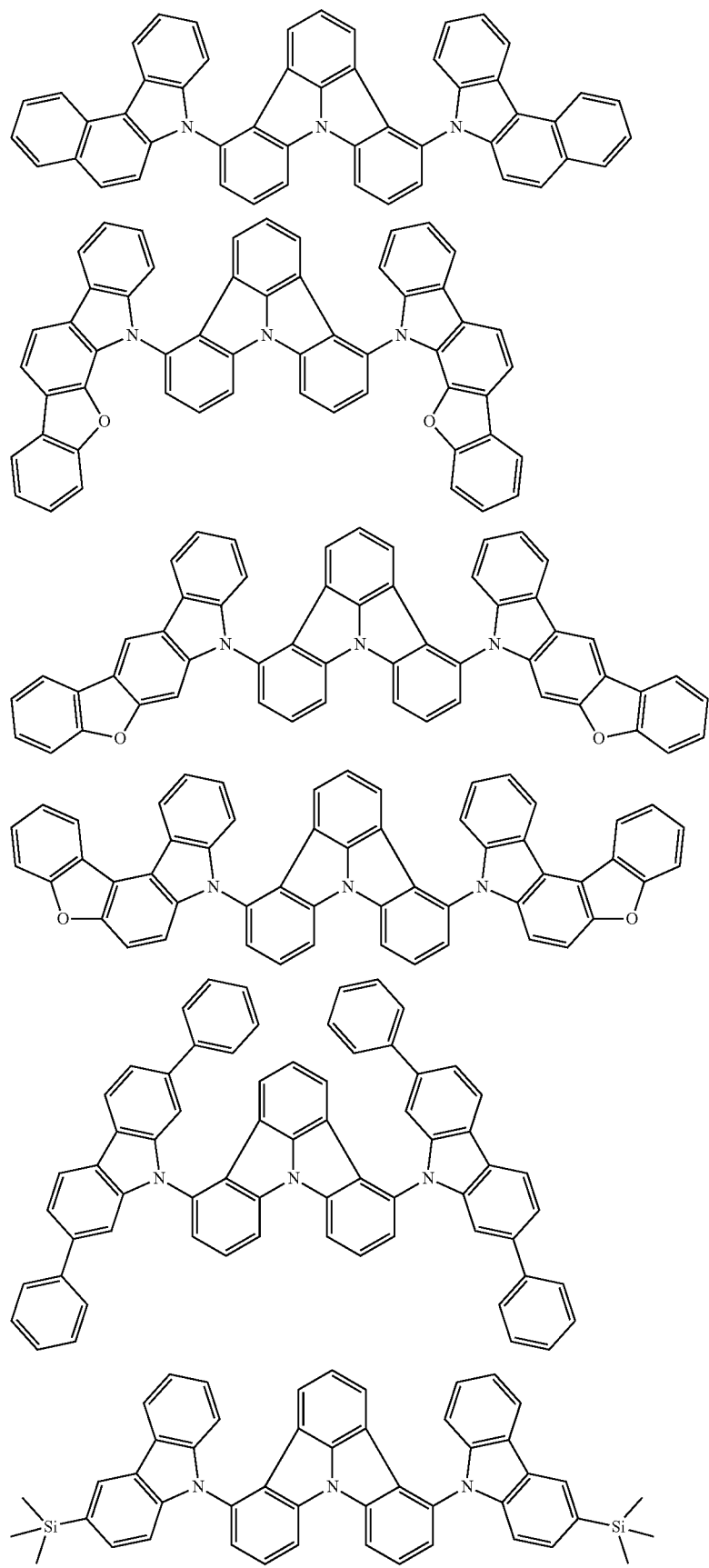

-continued
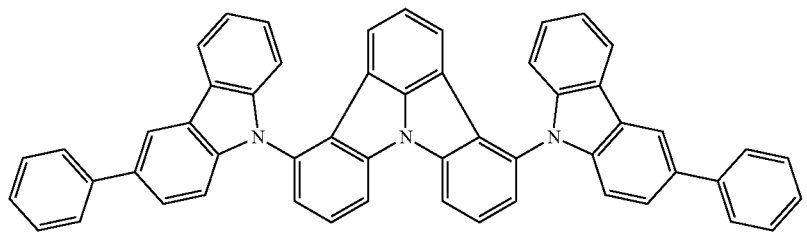
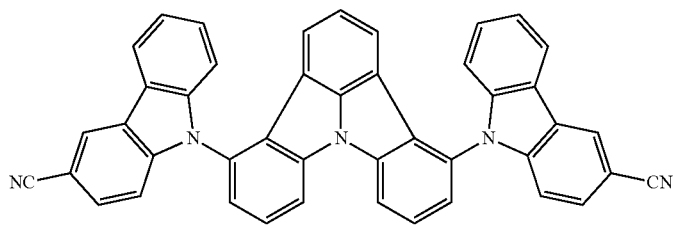
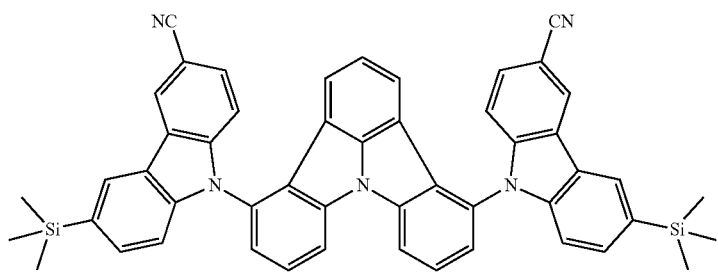
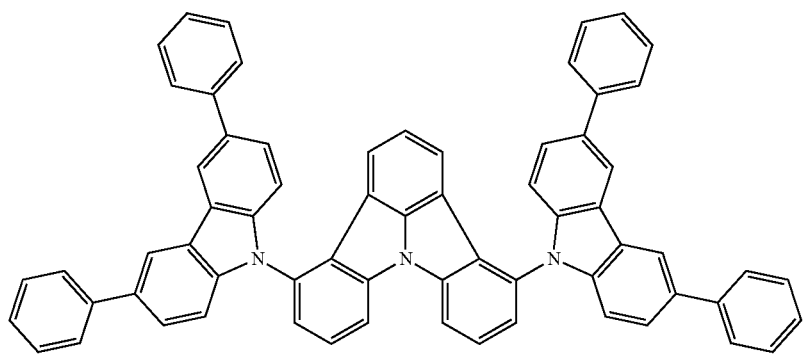
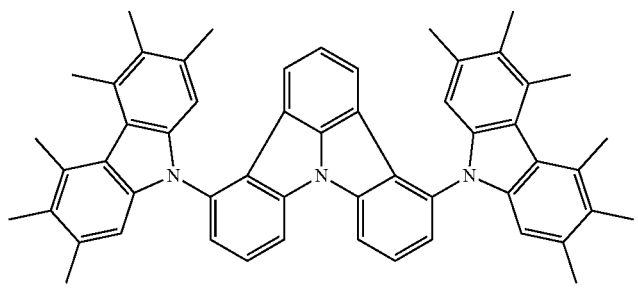
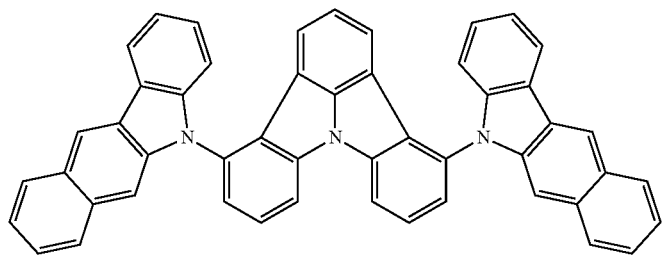

-continued
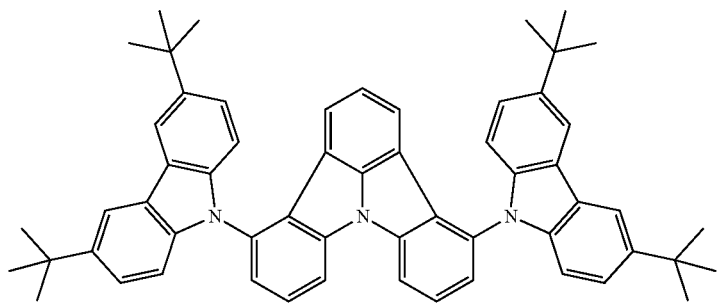
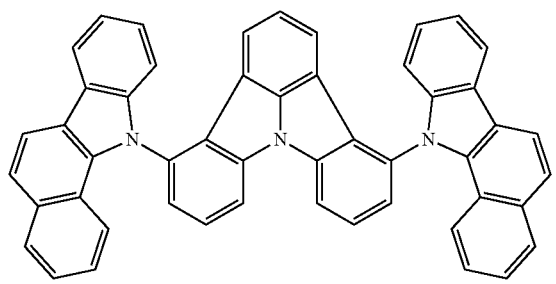
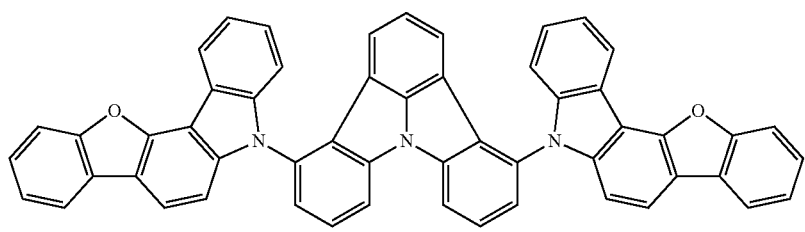
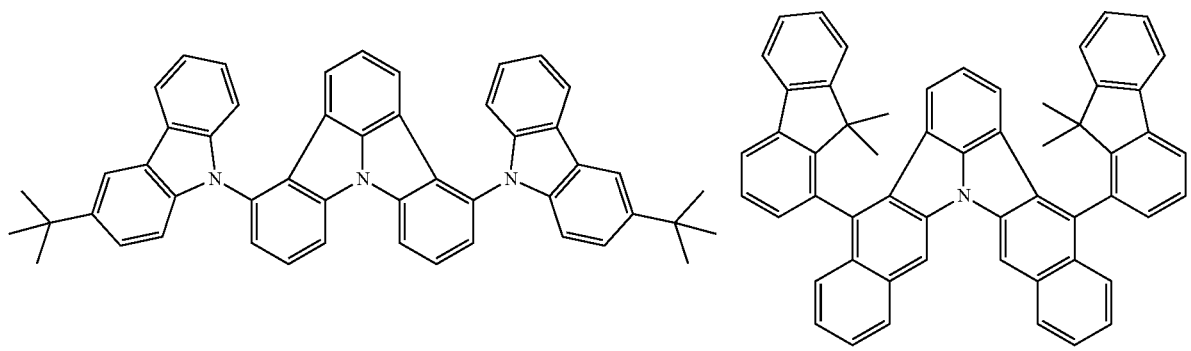
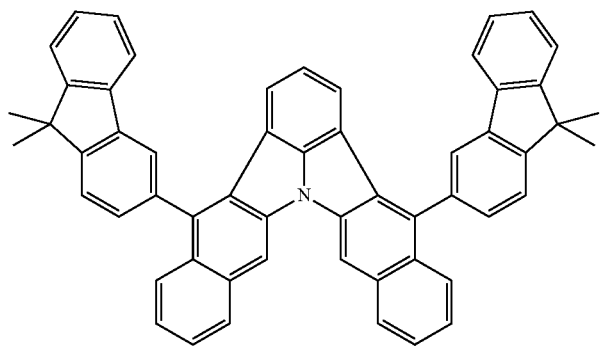

-continued
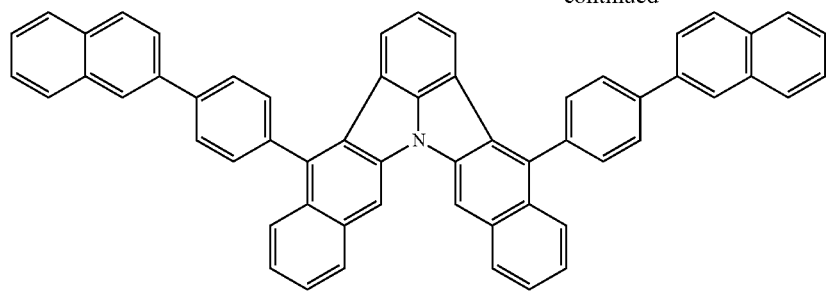
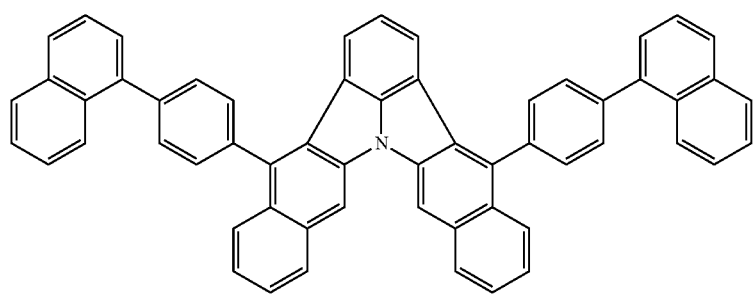
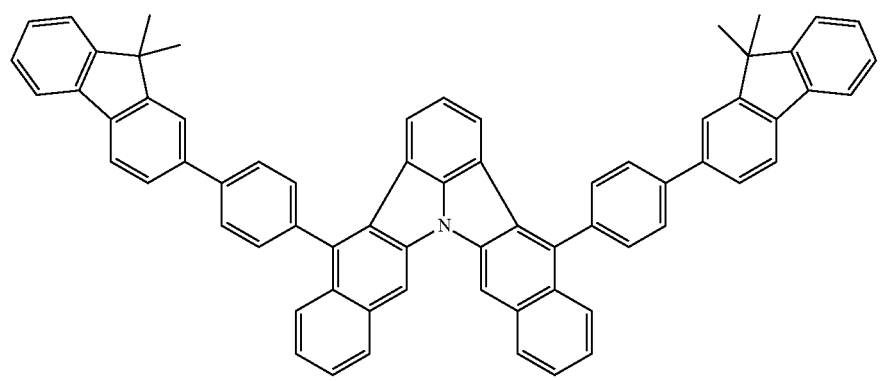
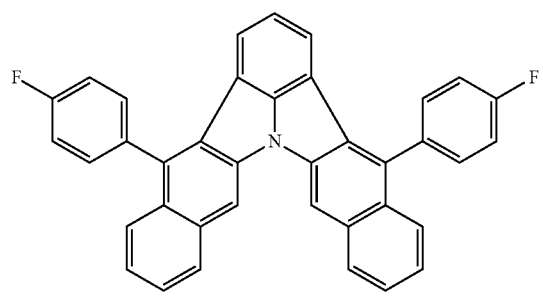
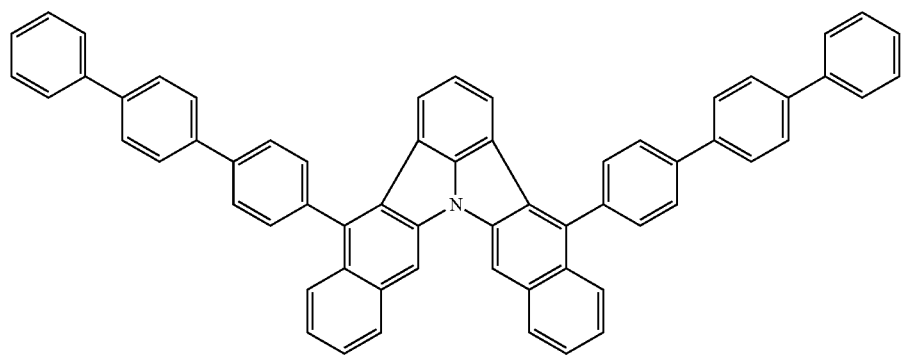

343
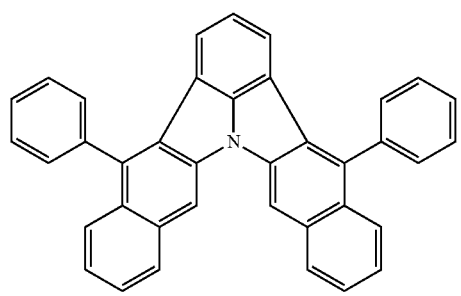
344
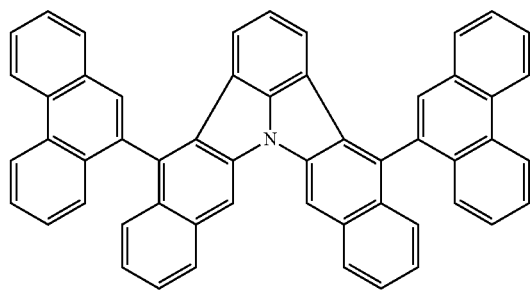
-continued
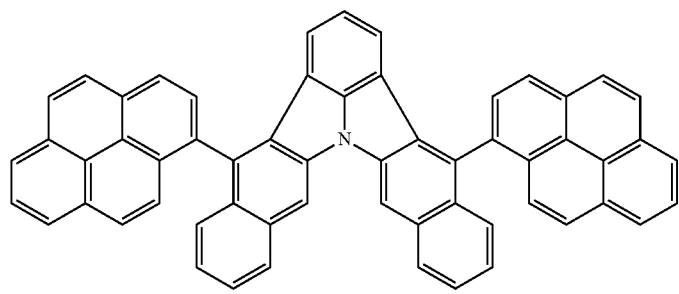
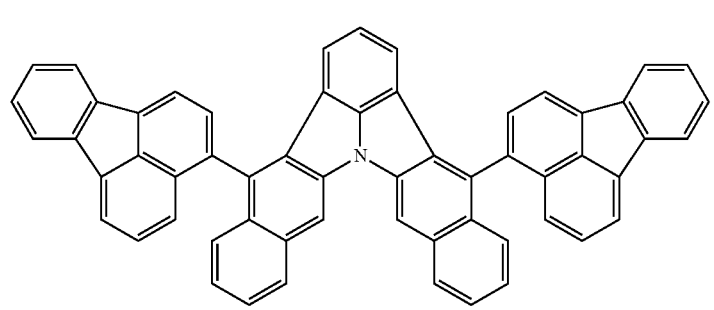
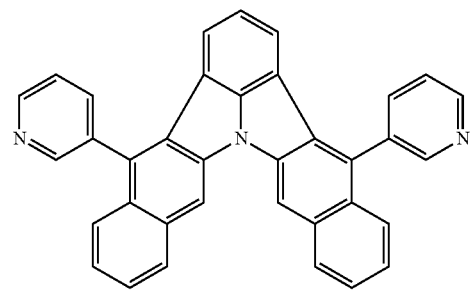
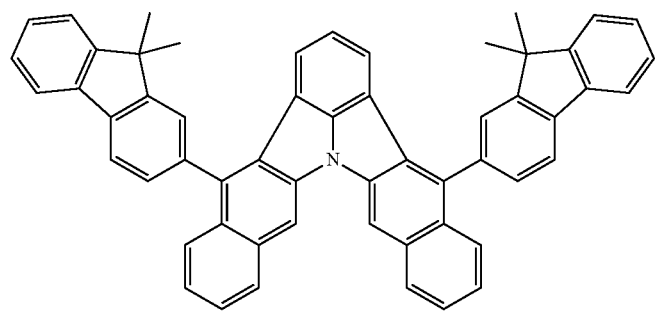
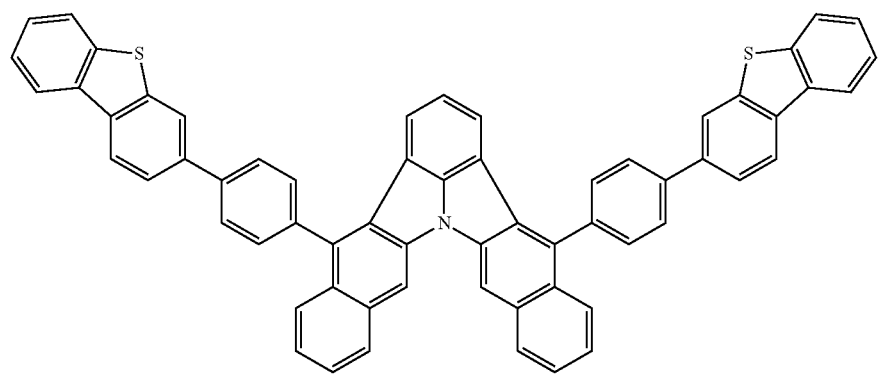

-continued
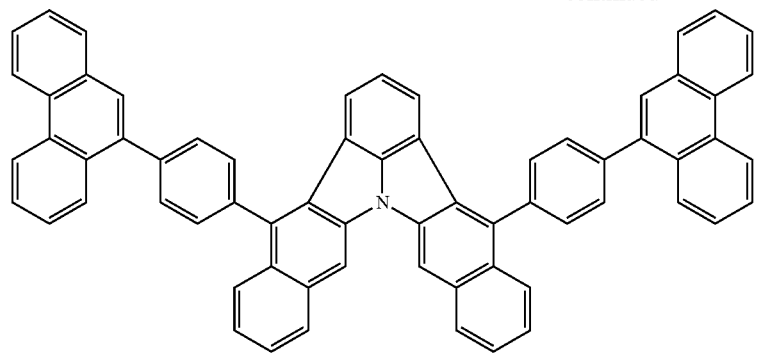
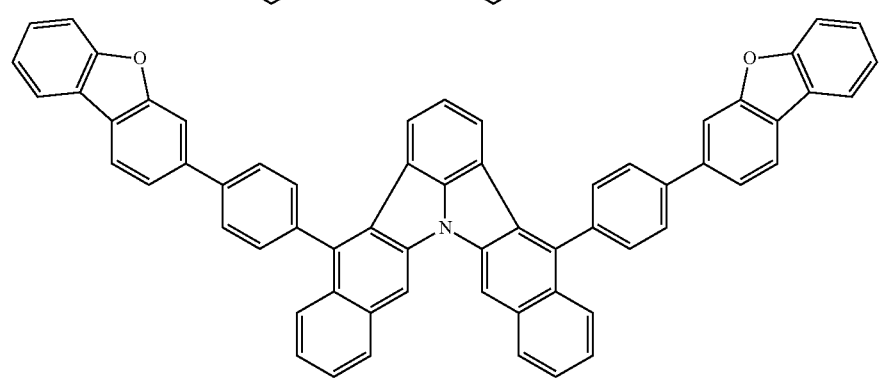
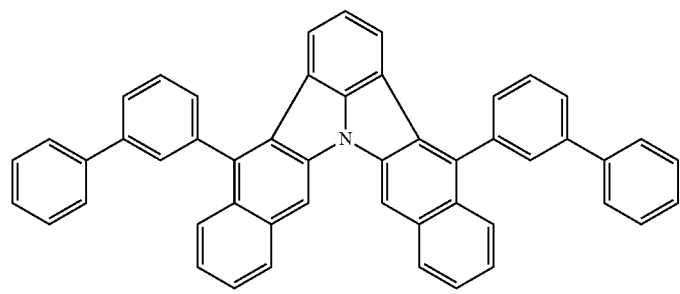
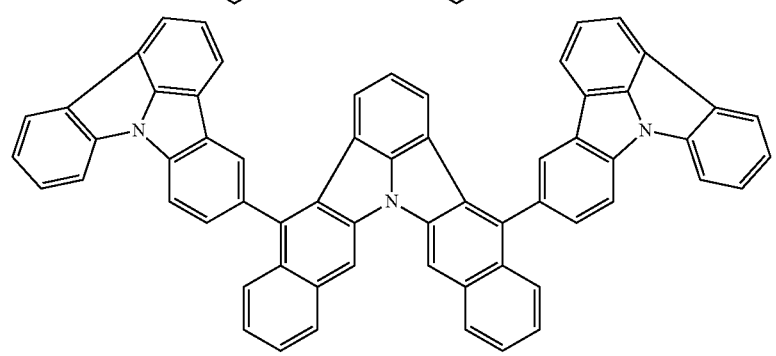
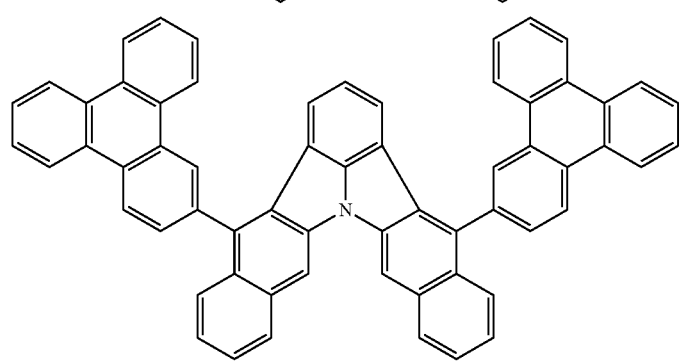

-continued
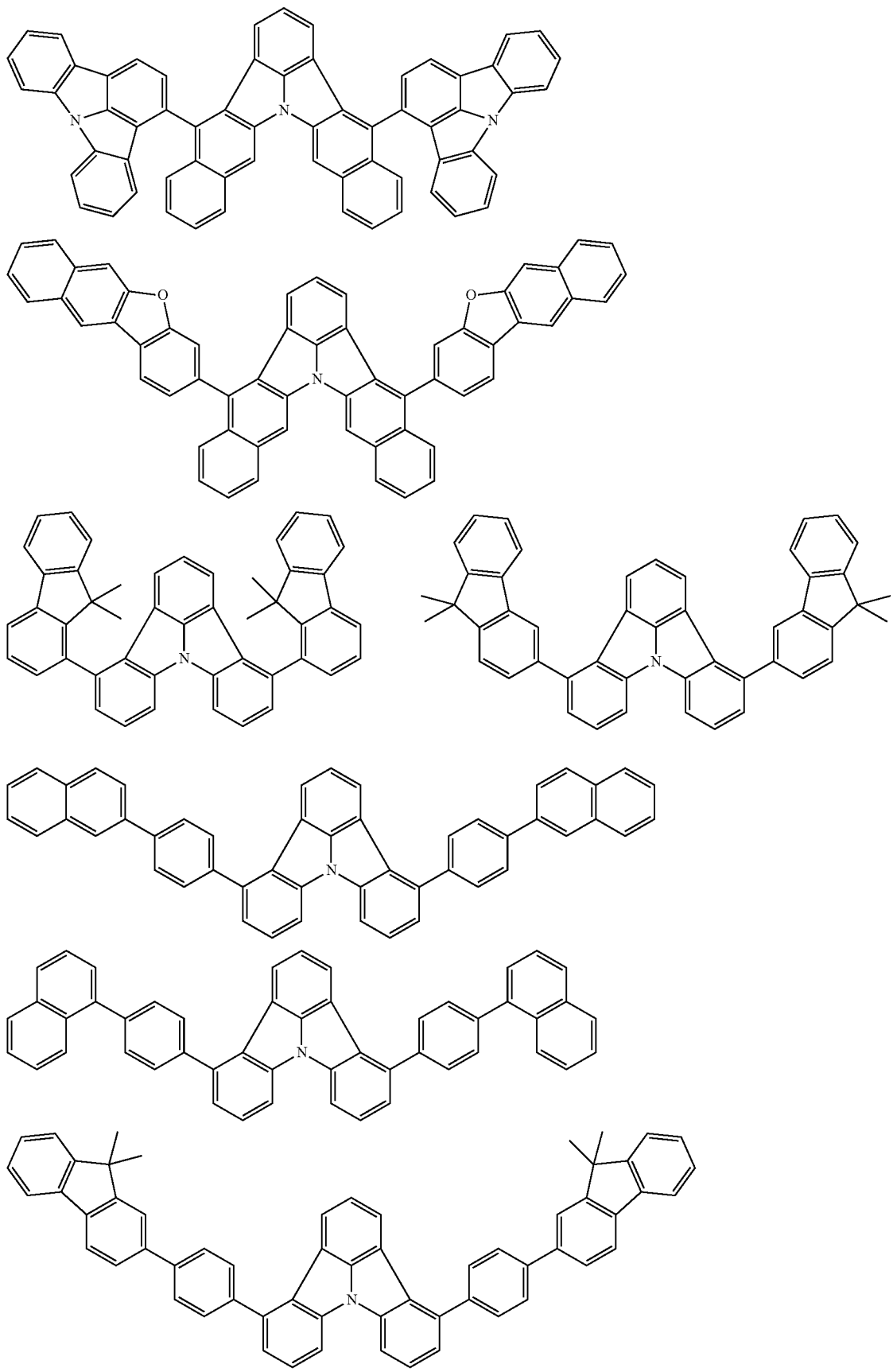

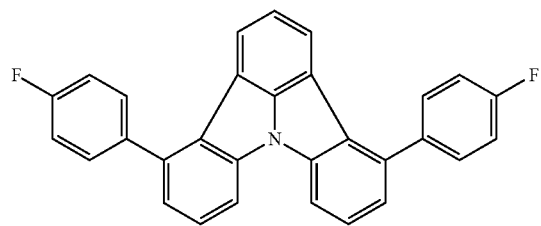
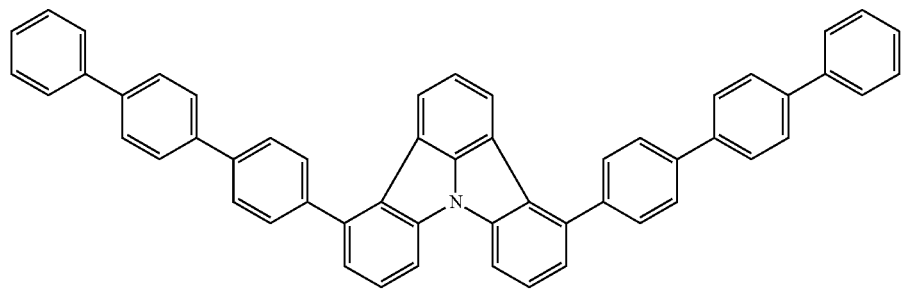
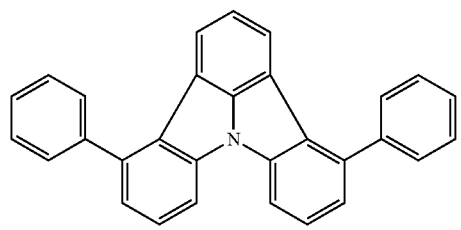
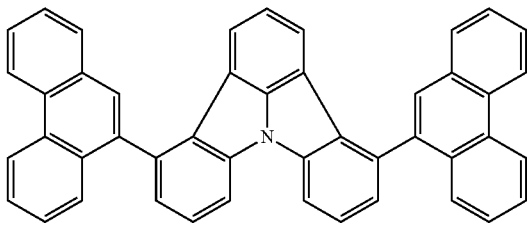
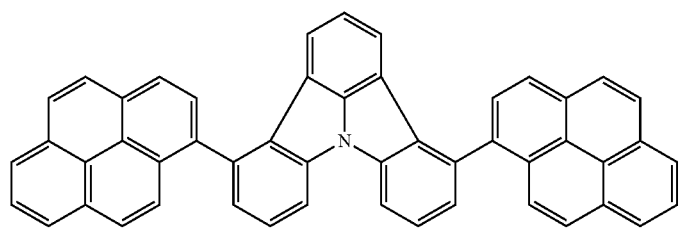
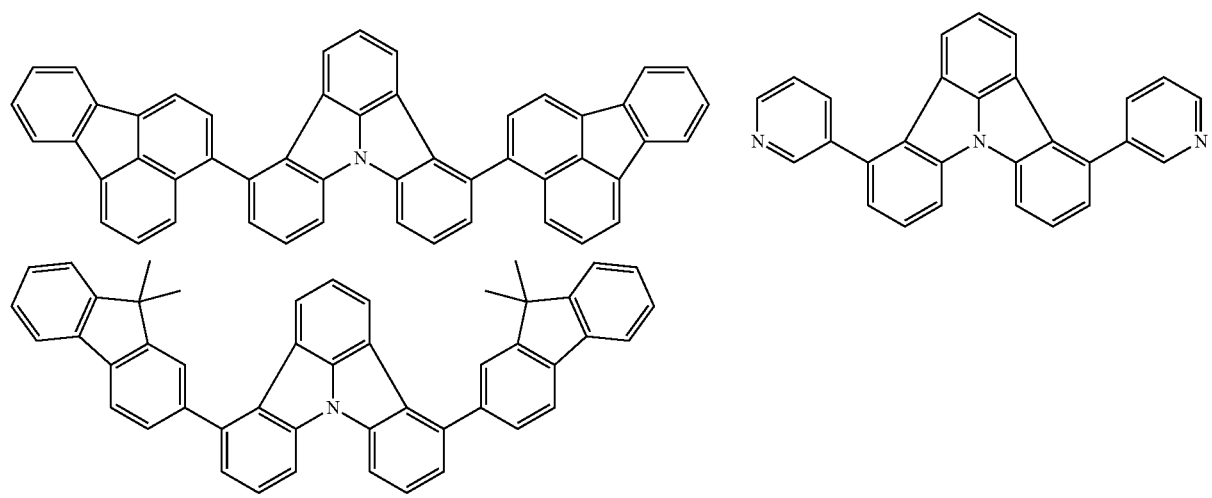

-continued
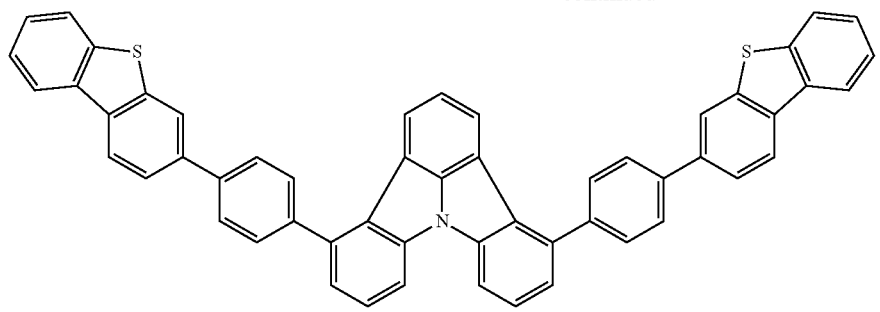
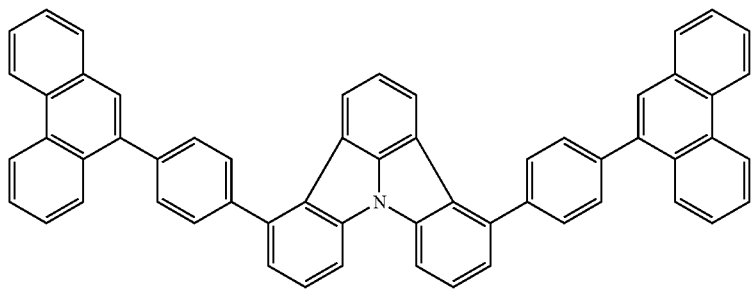
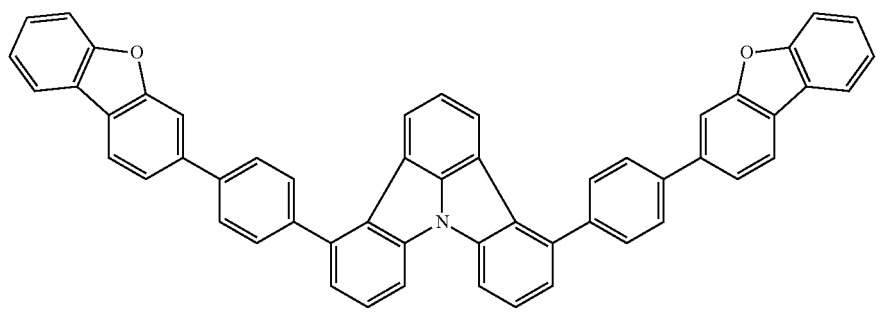
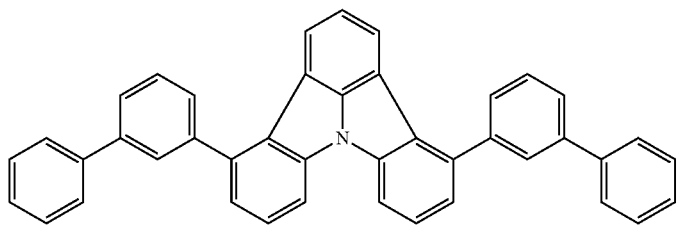
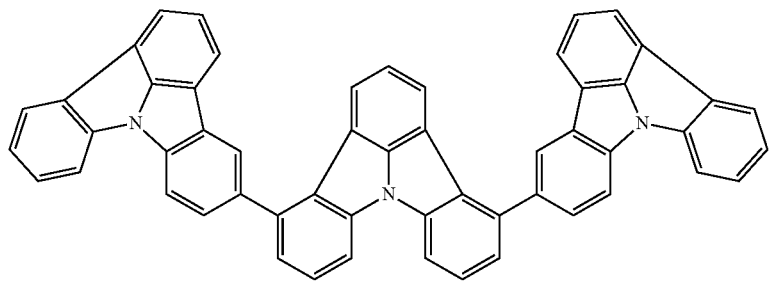
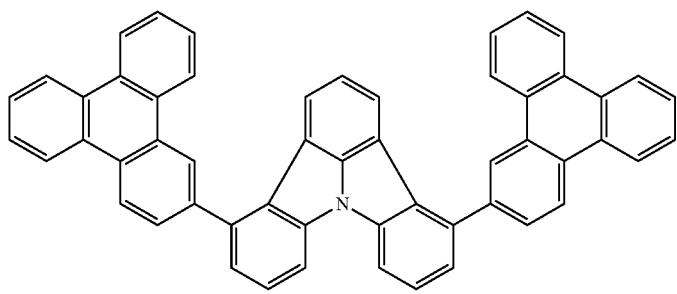

-continued
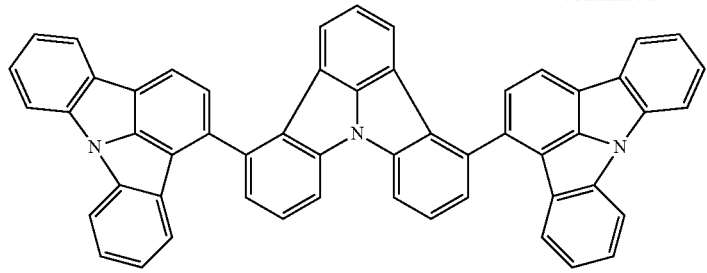
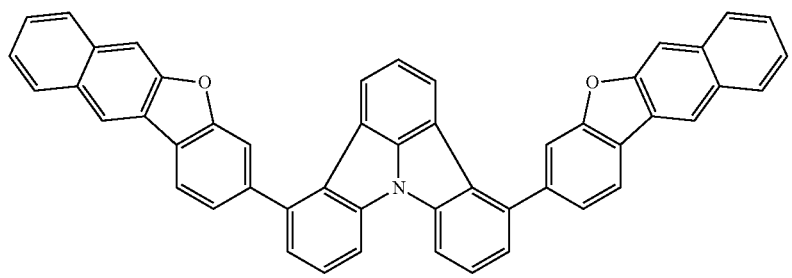
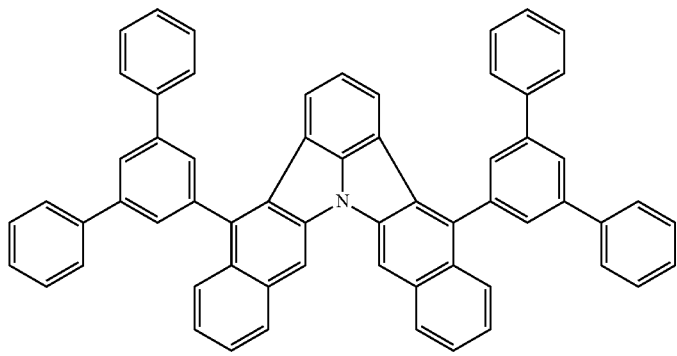
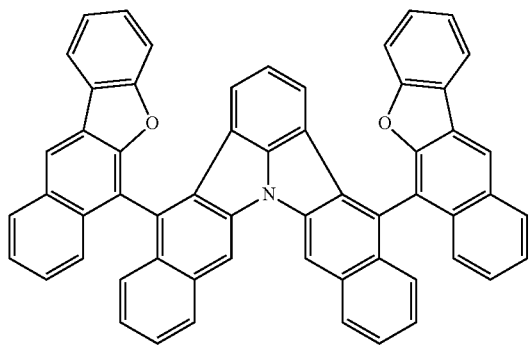
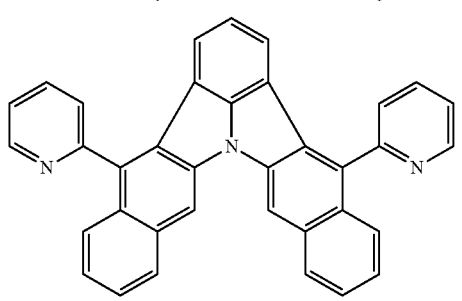
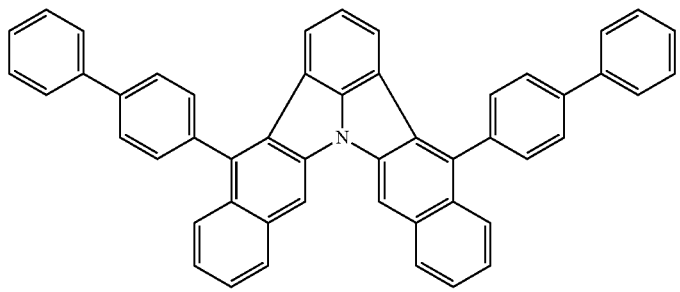

355
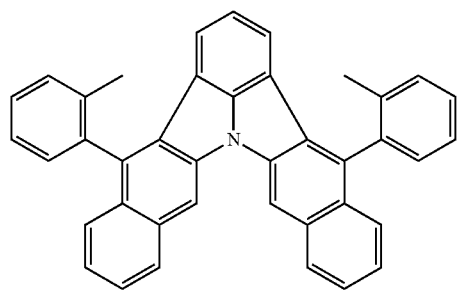
356
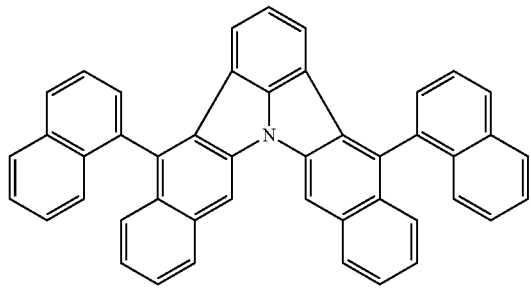
-continued
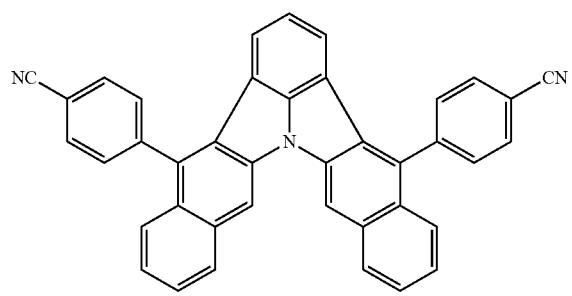
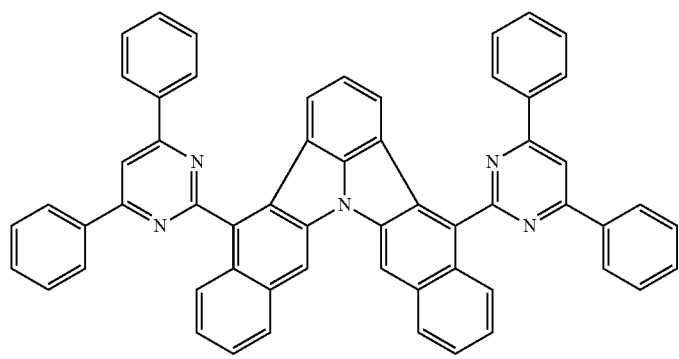
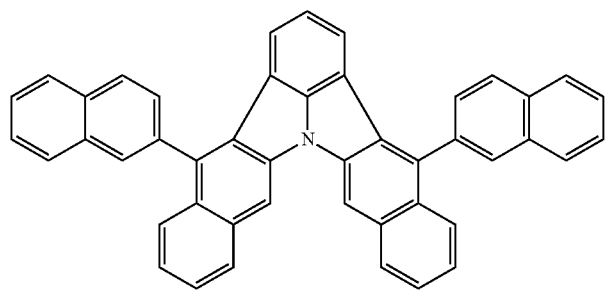
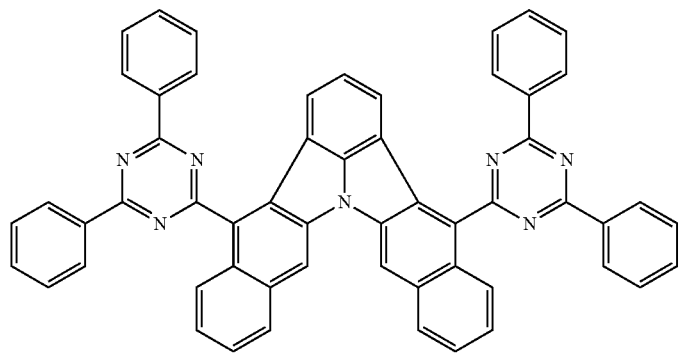

-continued
357
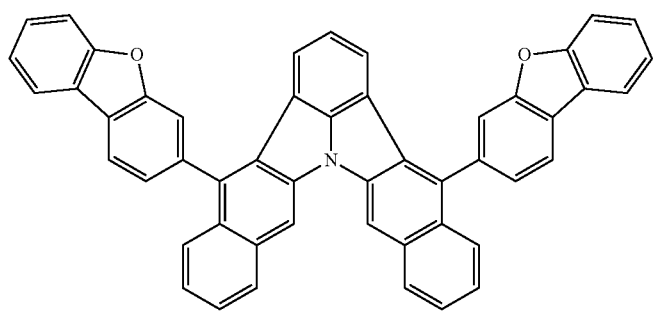
358
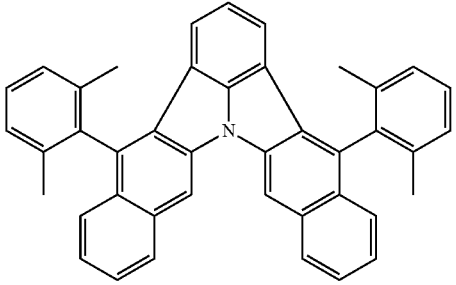
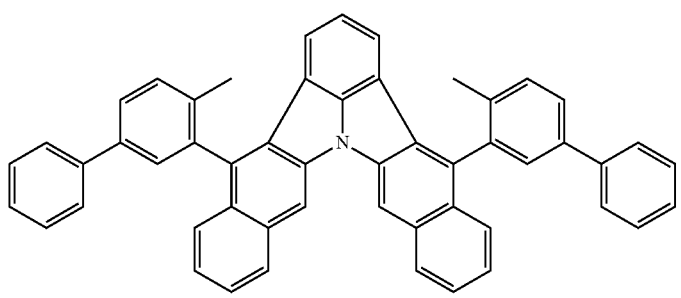
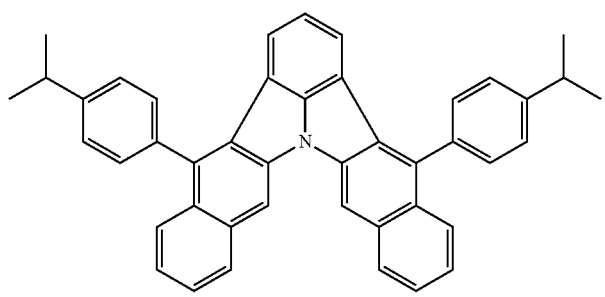
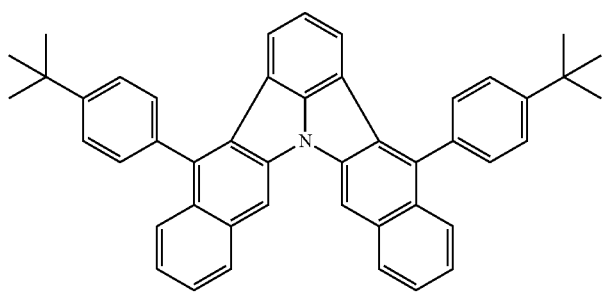
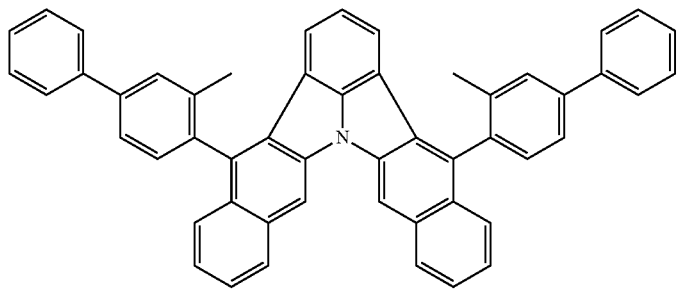

359 360
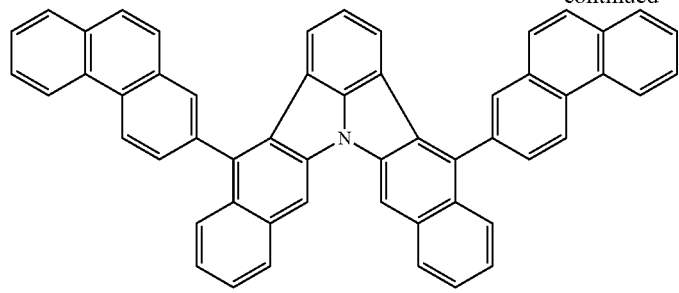
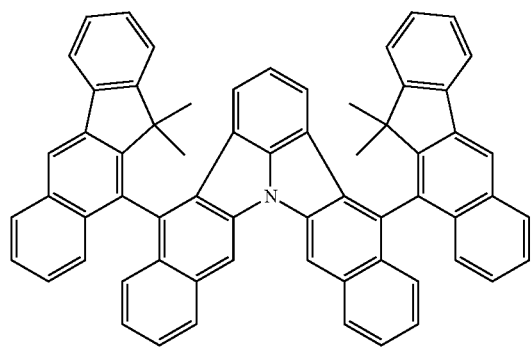
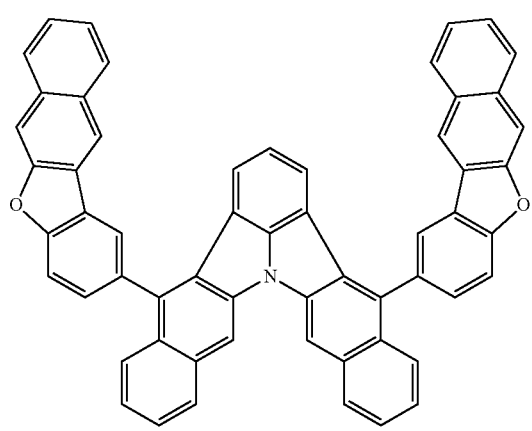
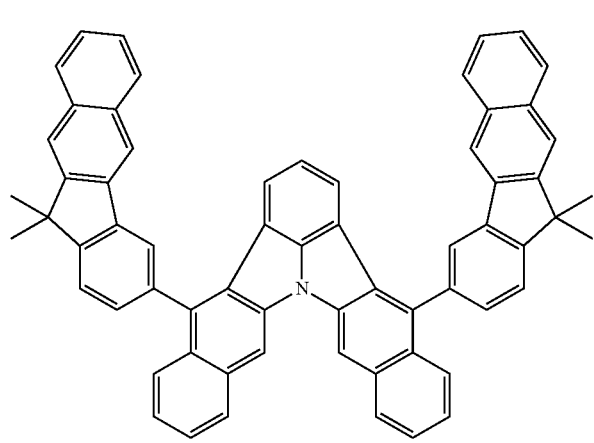
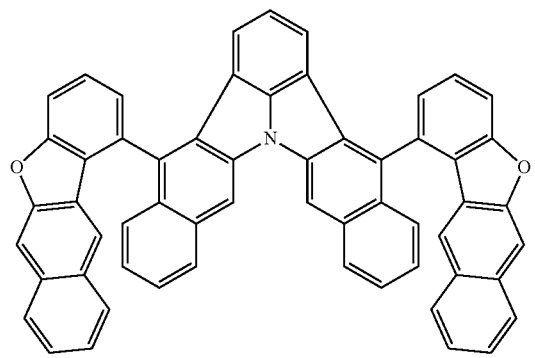
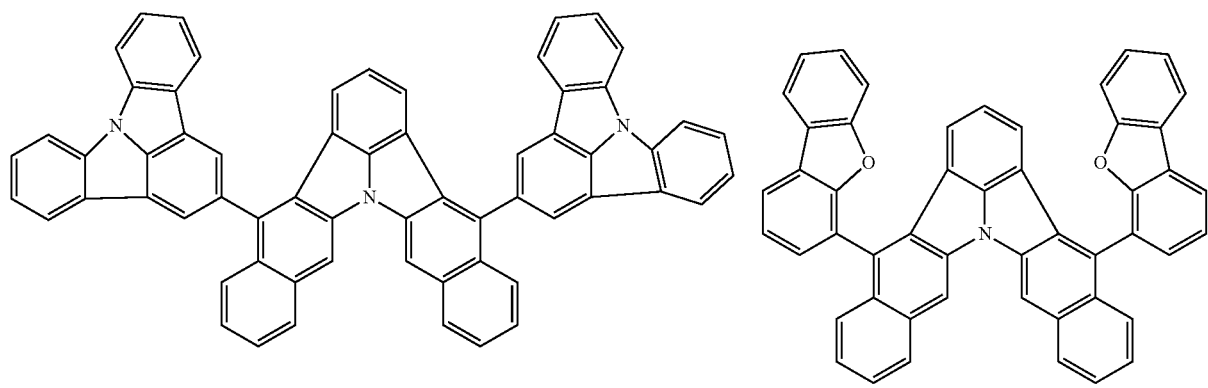

361
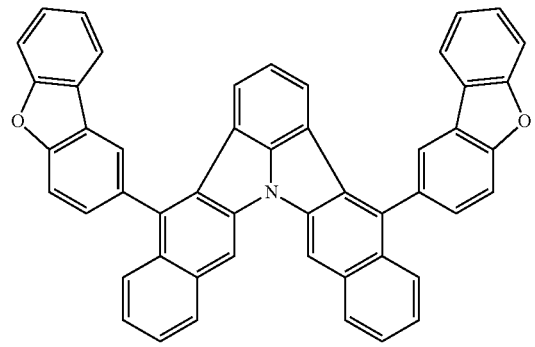
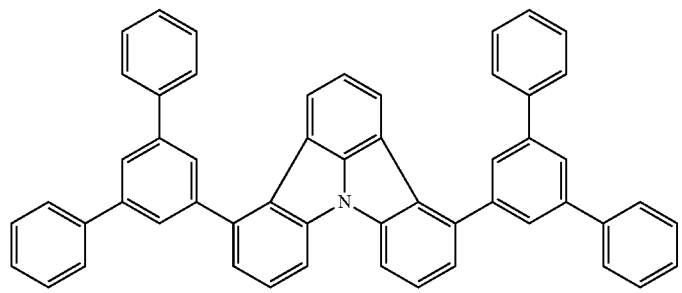
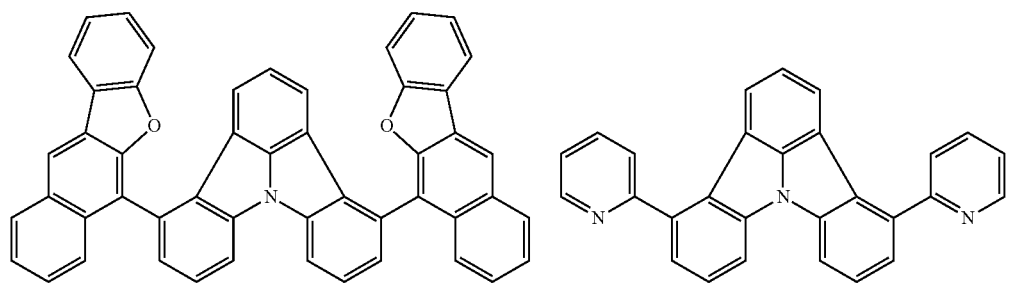
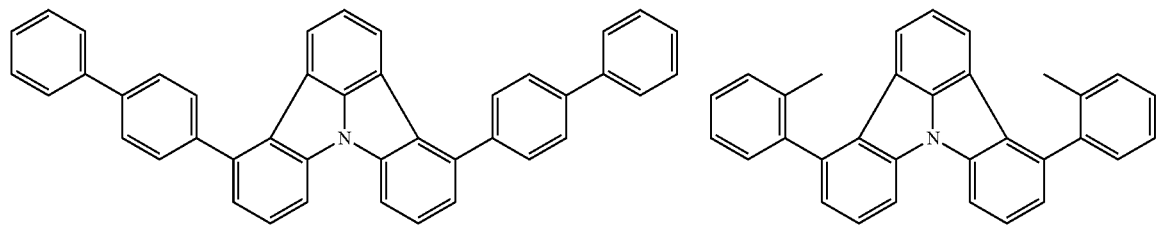
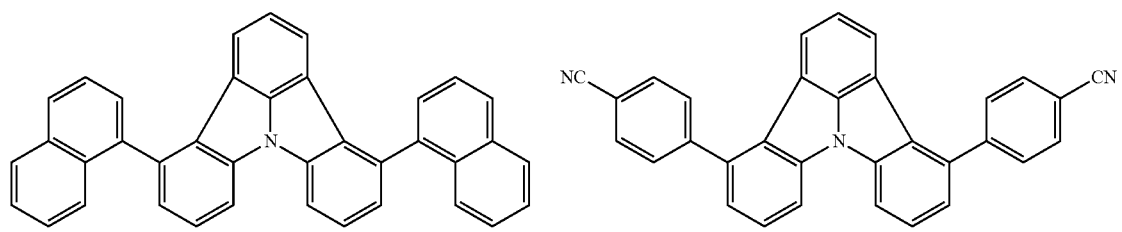

-continued
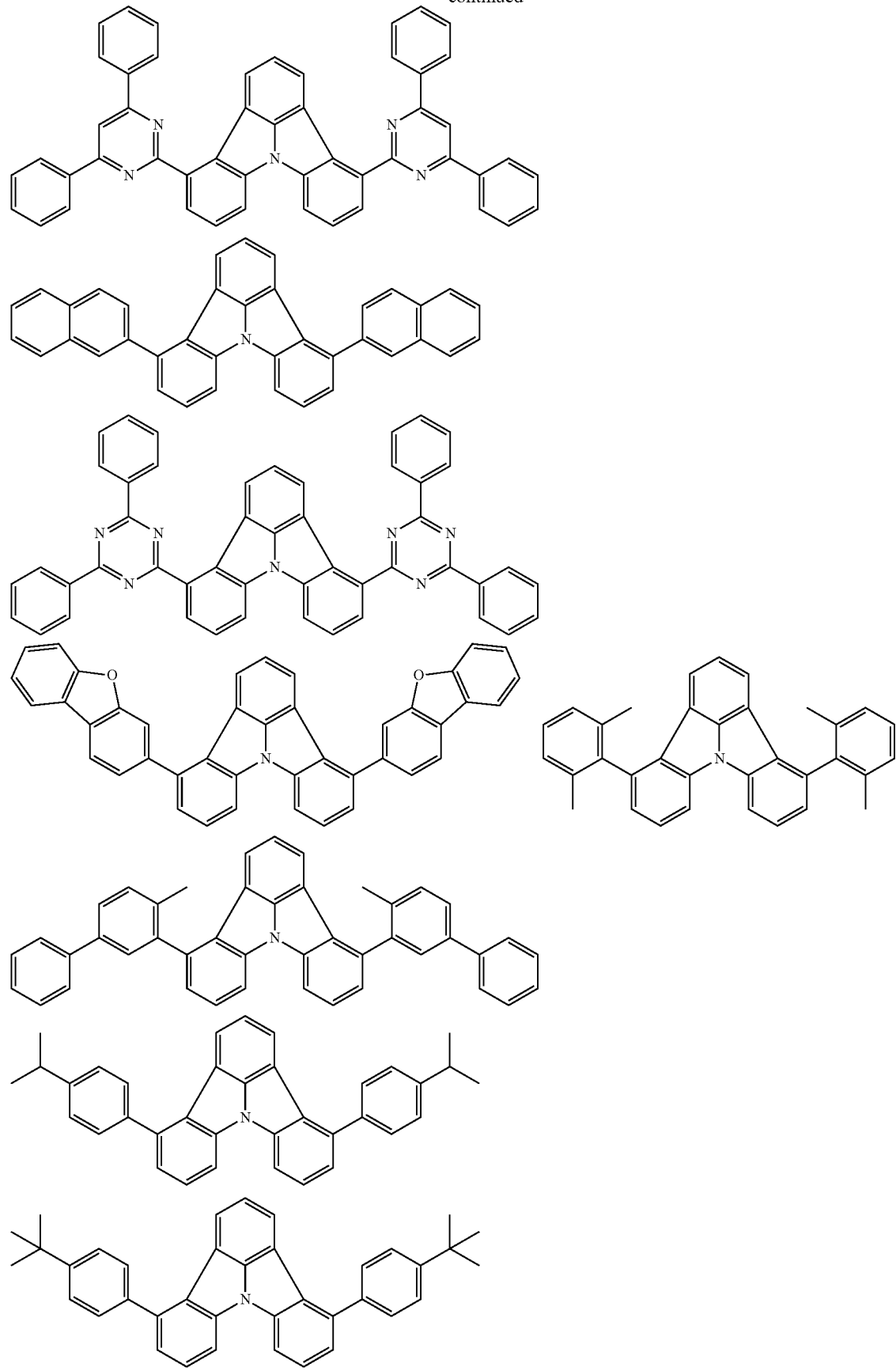

-continued
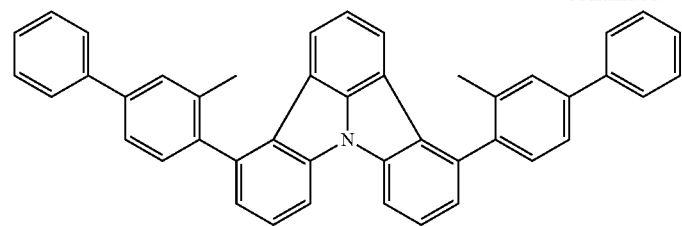
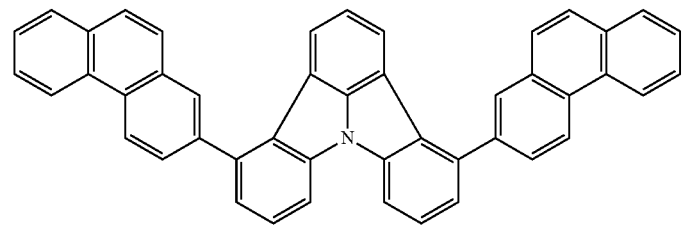
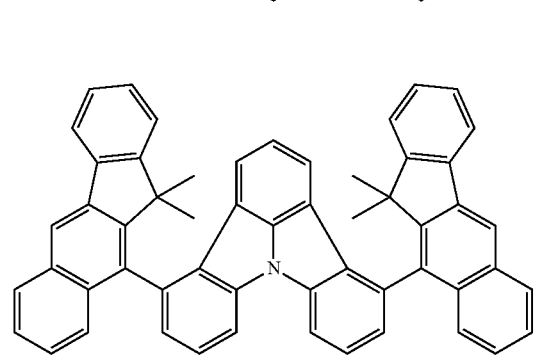
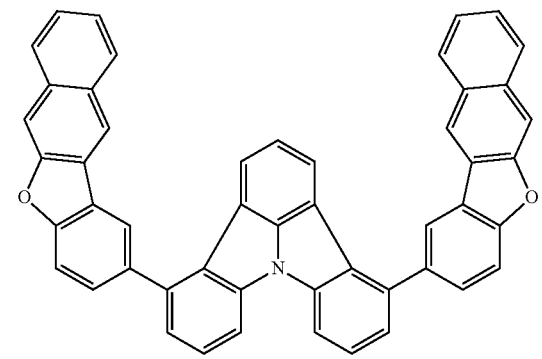
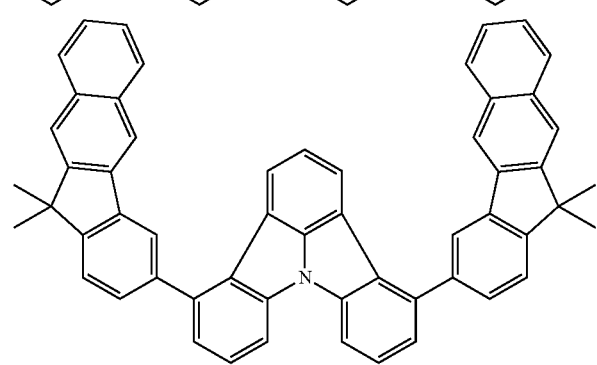
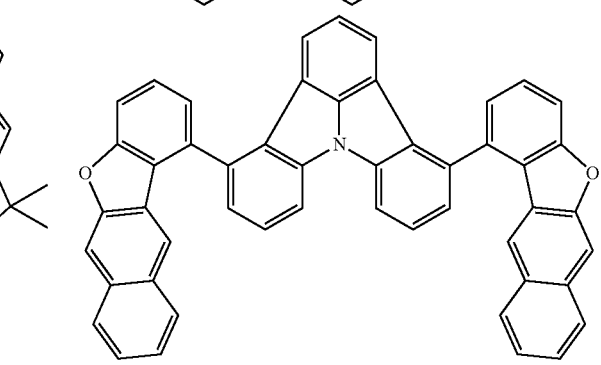
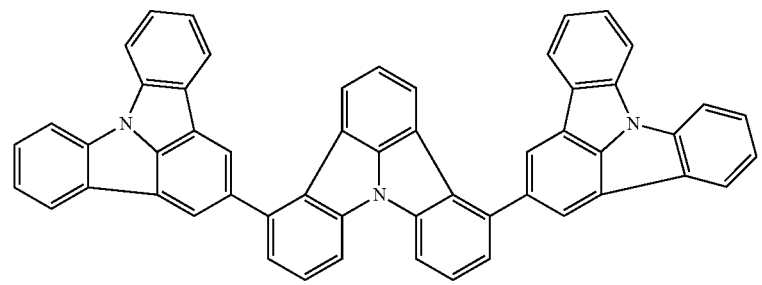
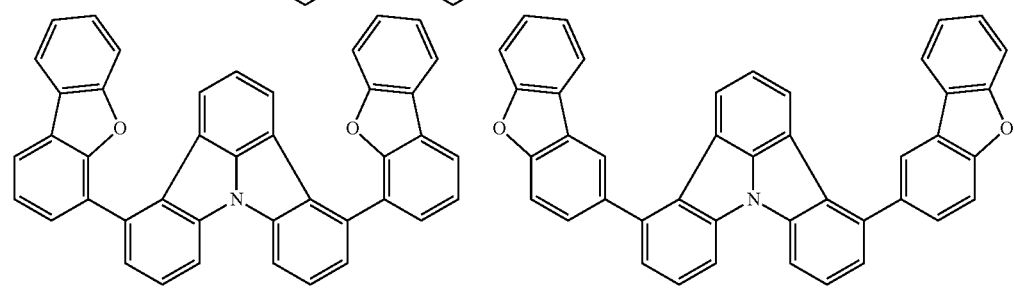

-continued
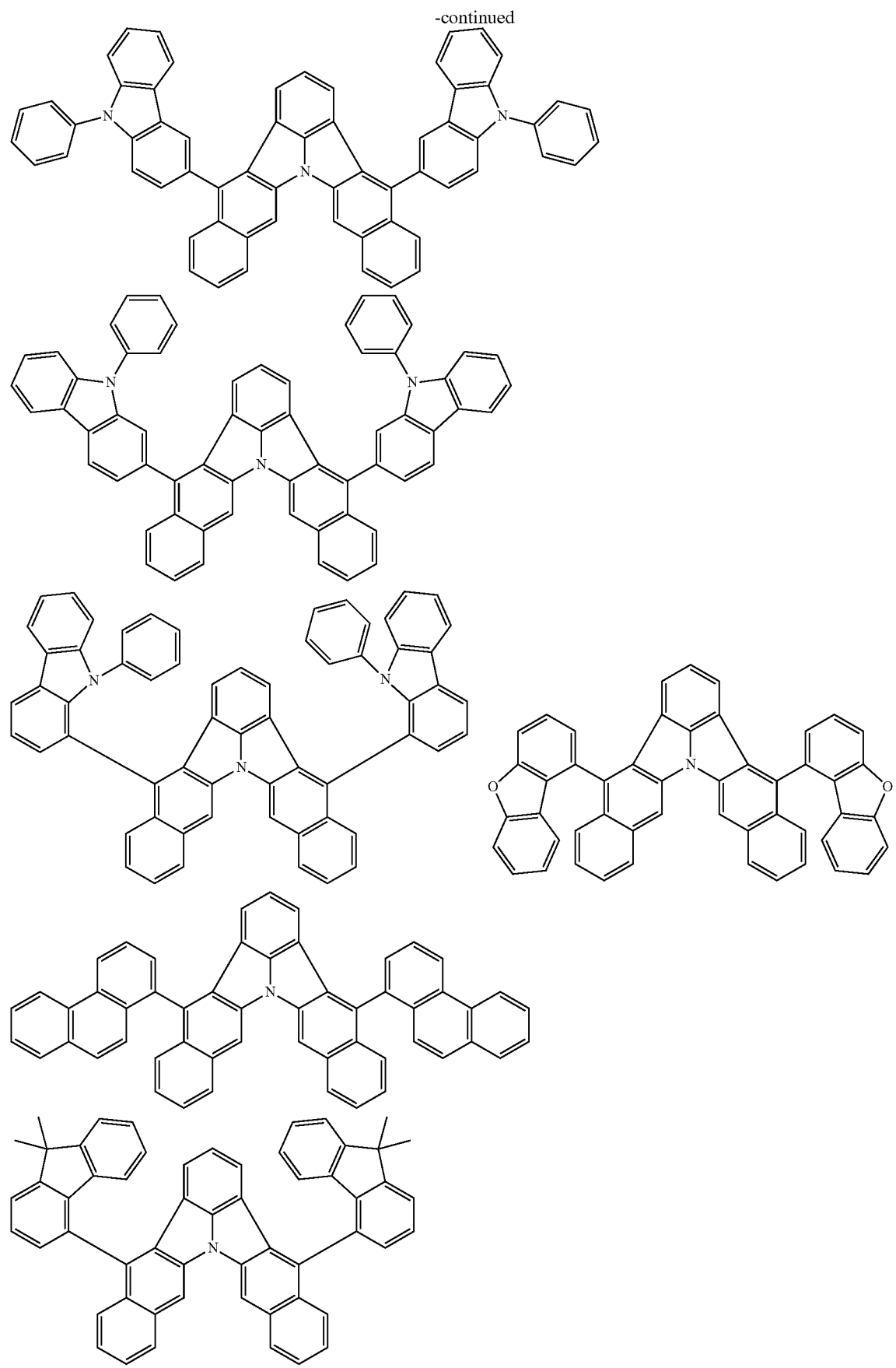

-continued
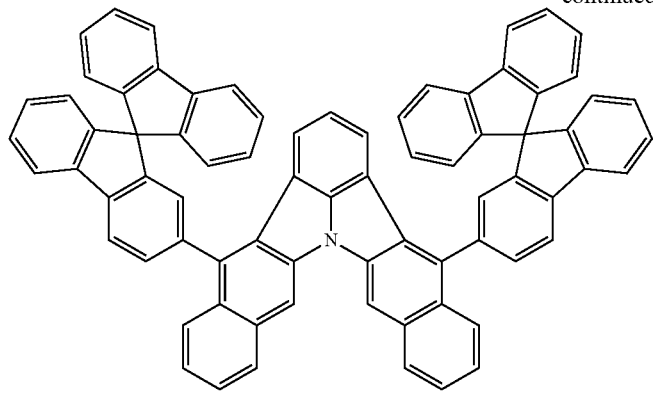
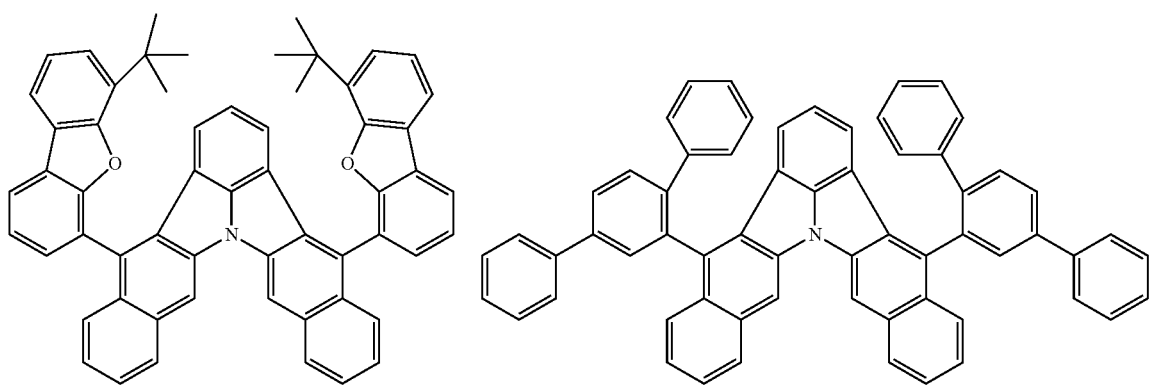

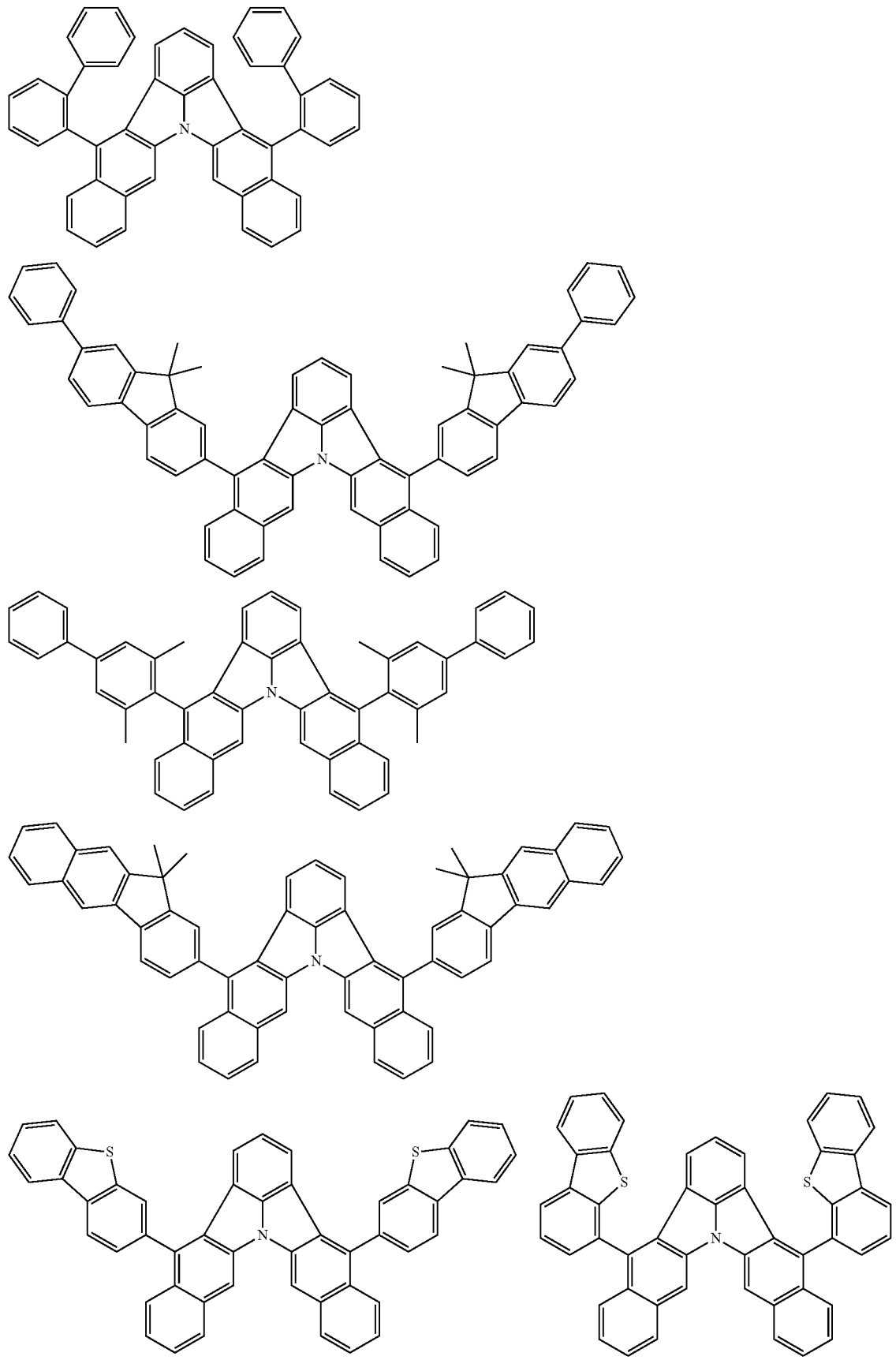

-continued
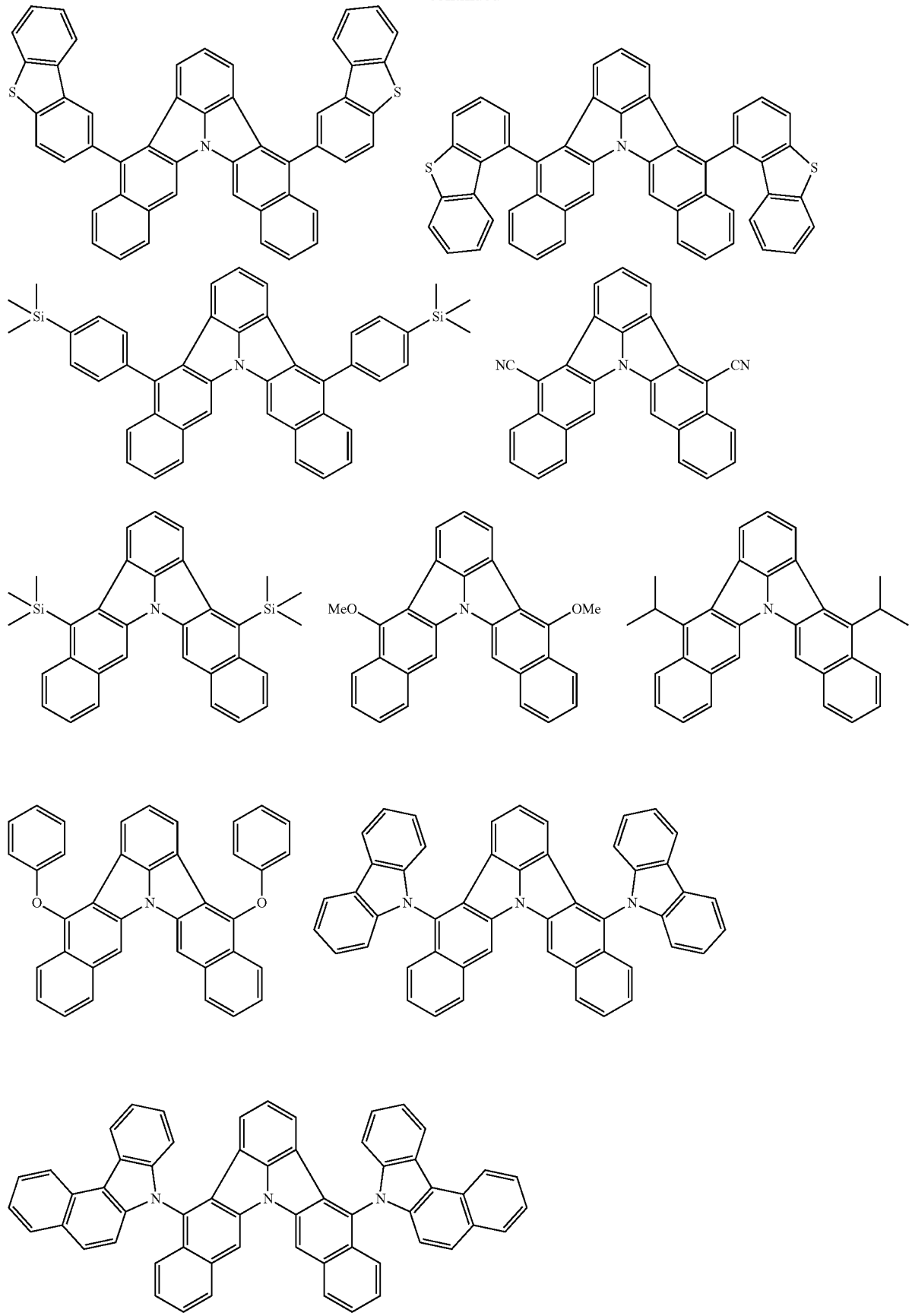

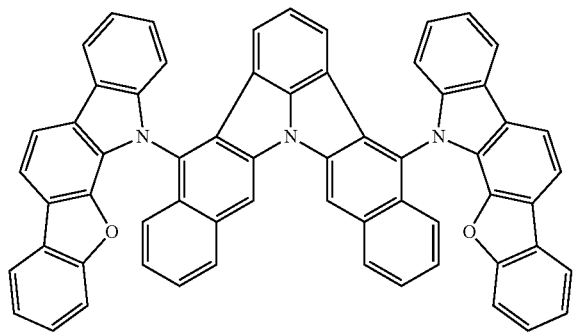
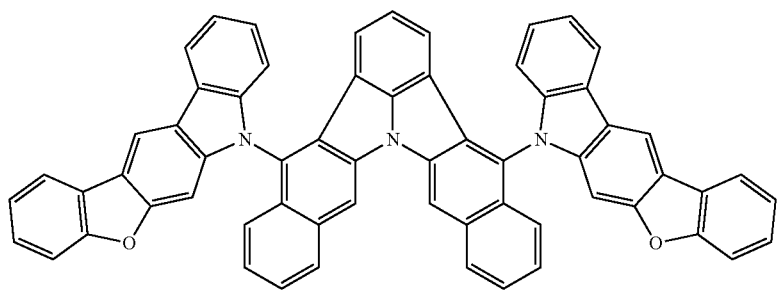
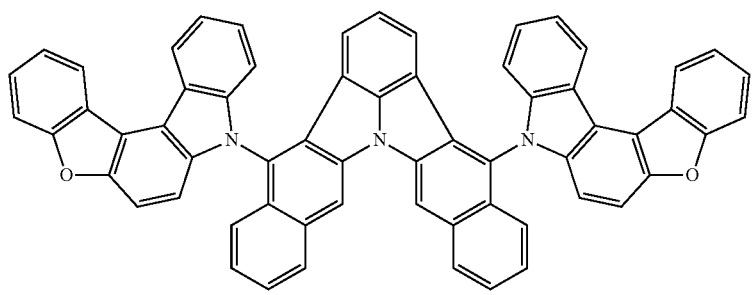
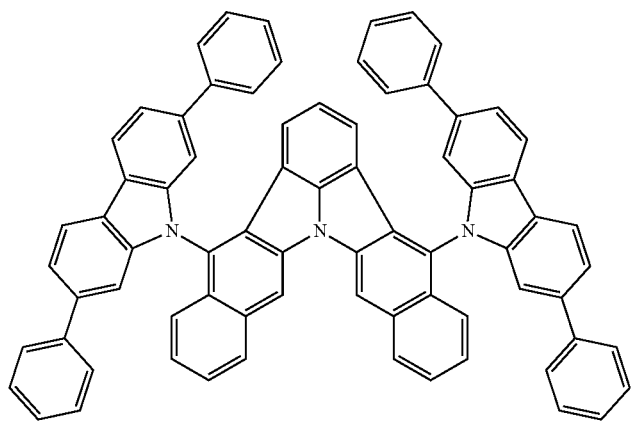
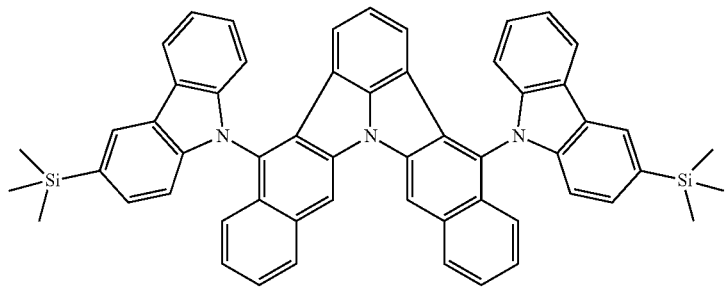

-continued
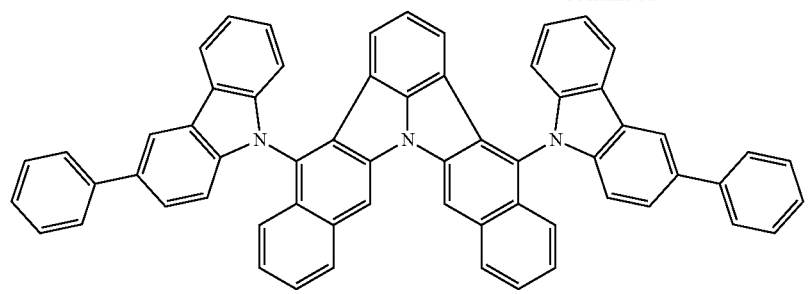
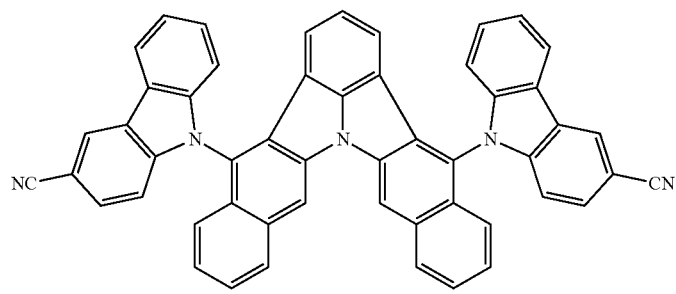
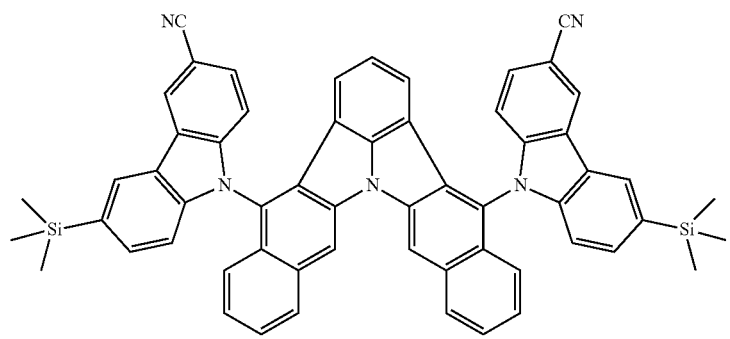
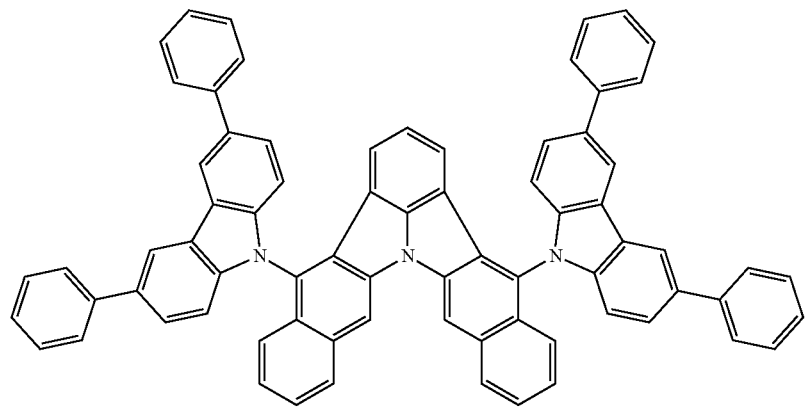
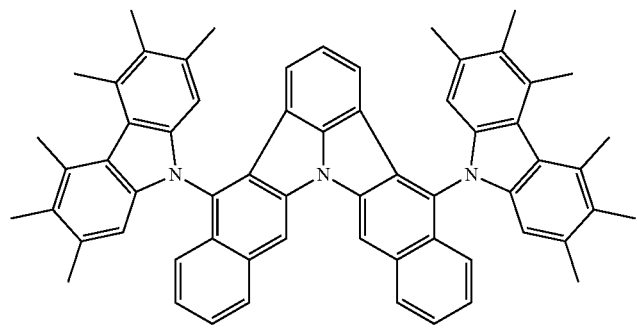

-continued
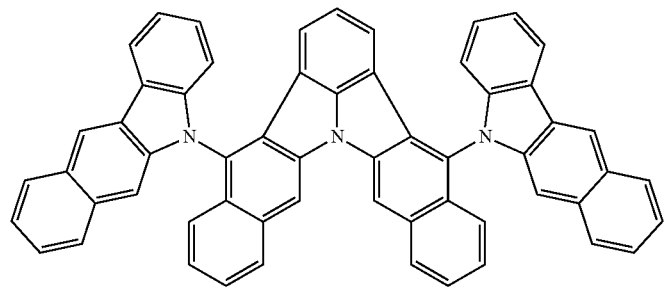
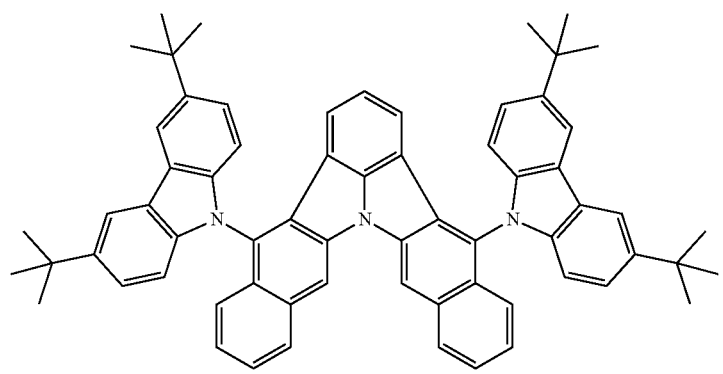
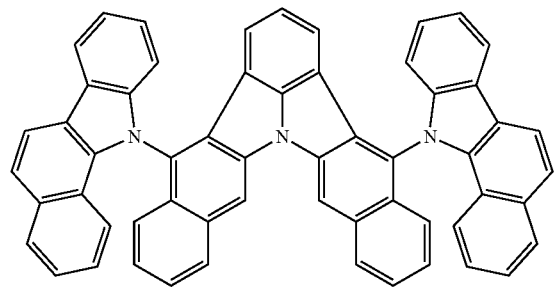
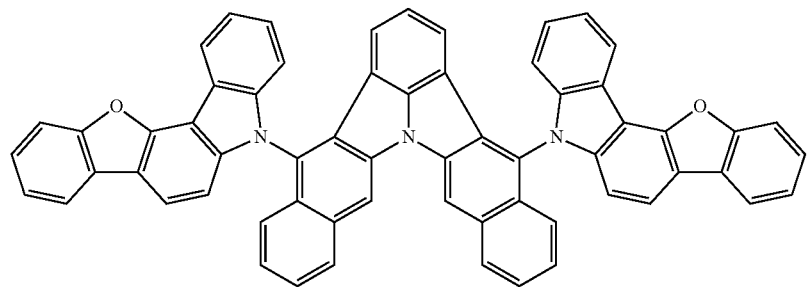
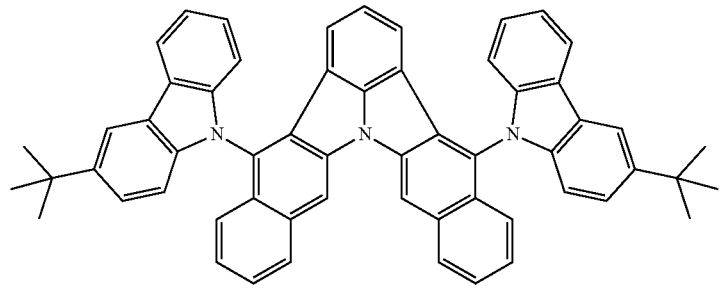

-continued
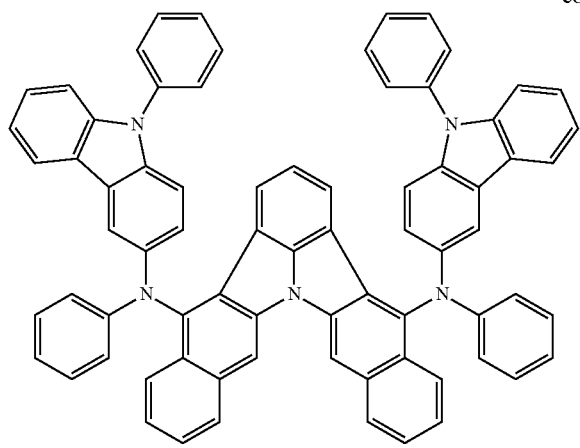
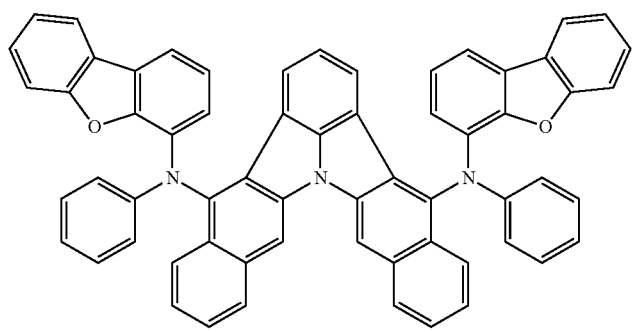
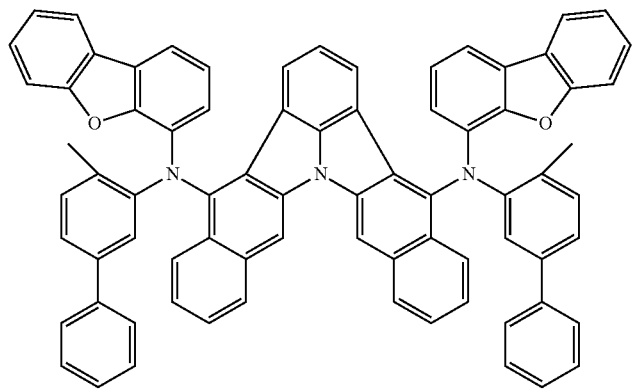
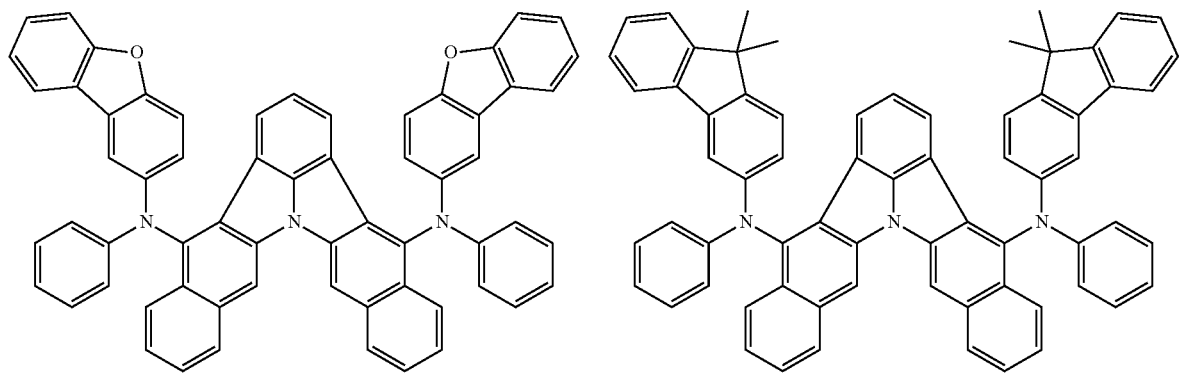

-continued
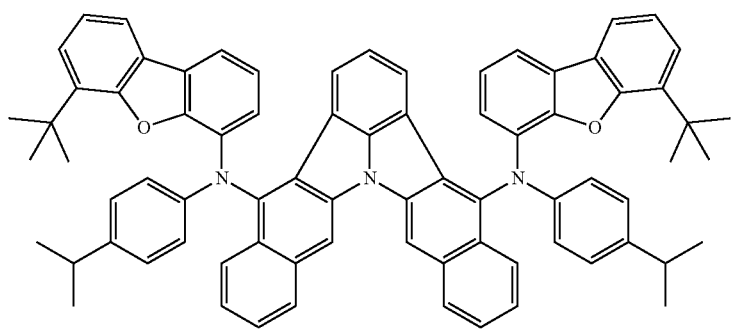
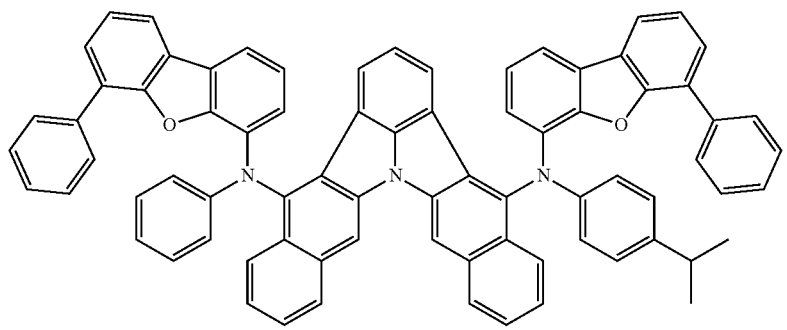
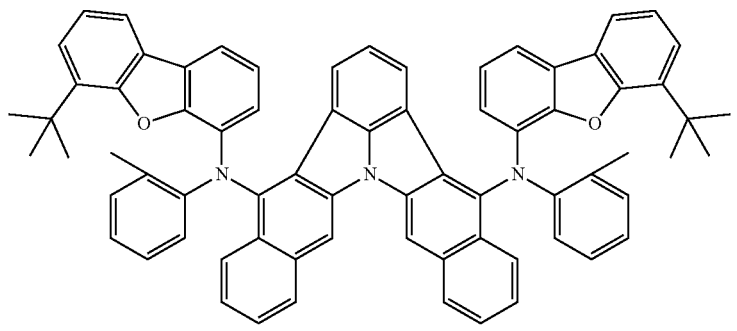
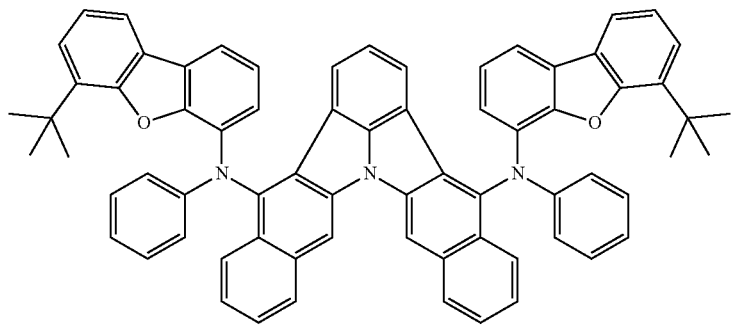
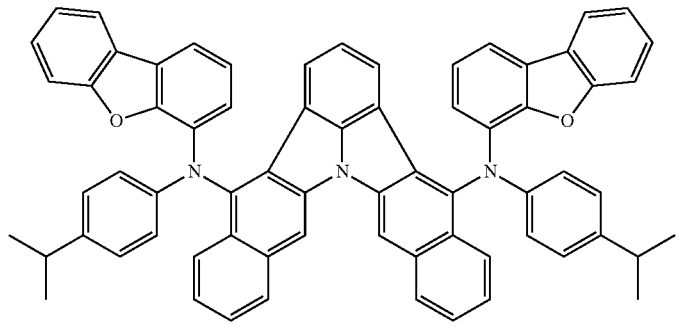

-continued
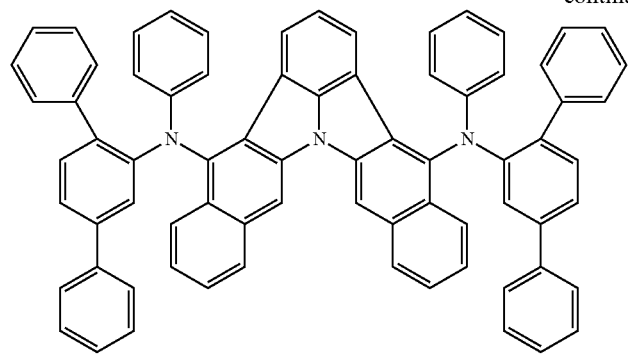
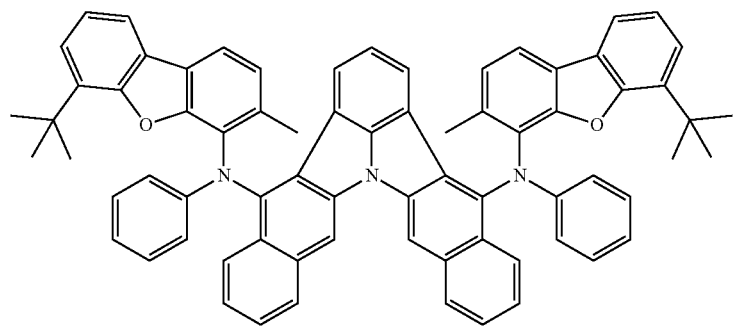
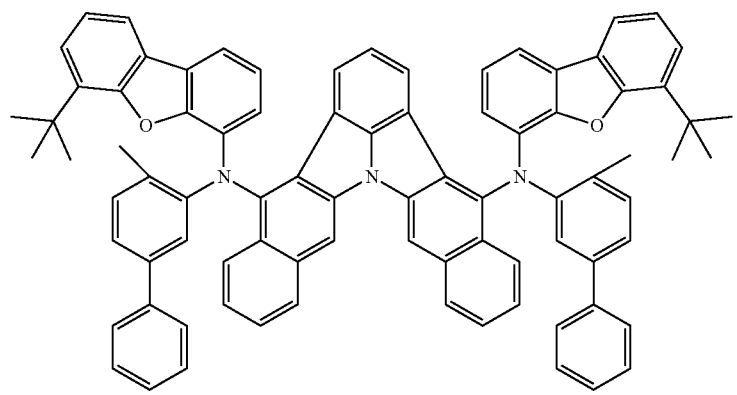
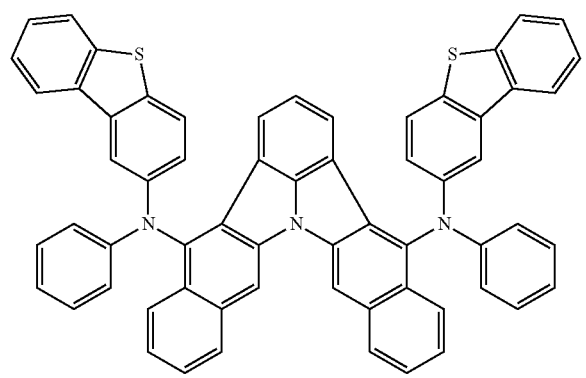

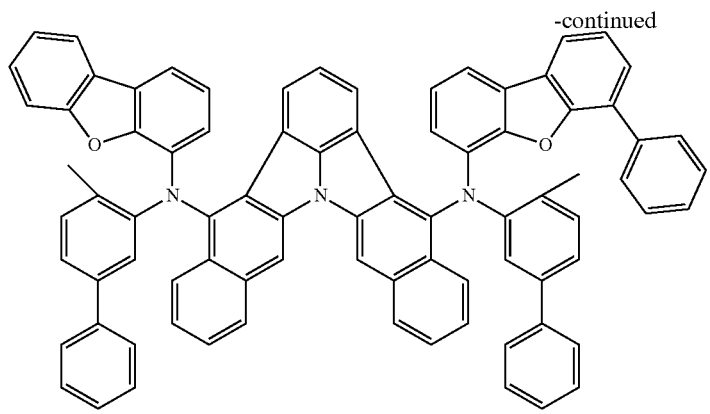
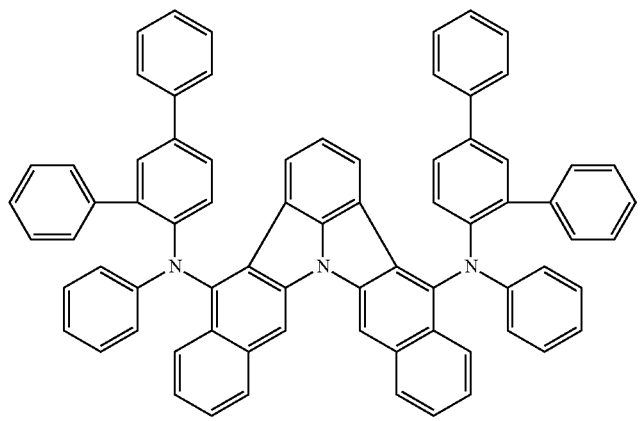
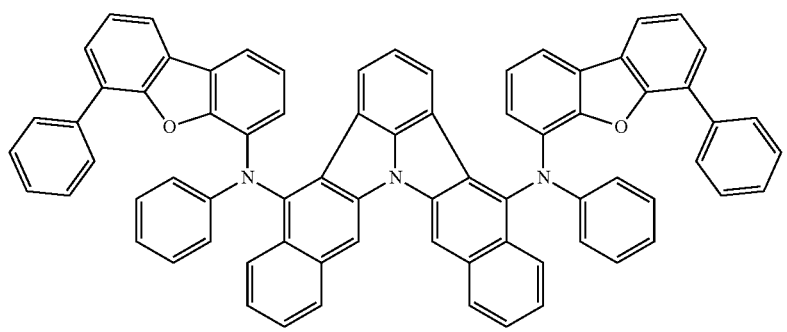
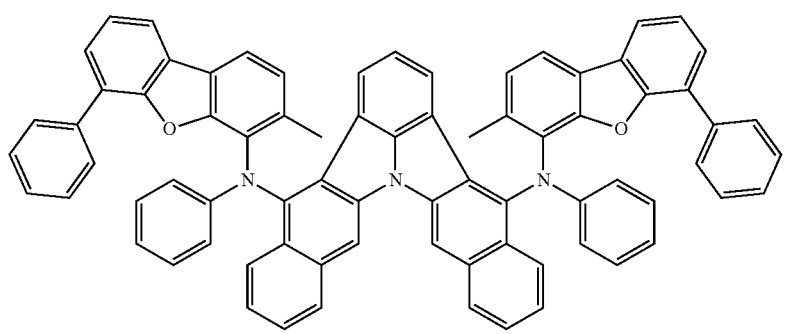

389
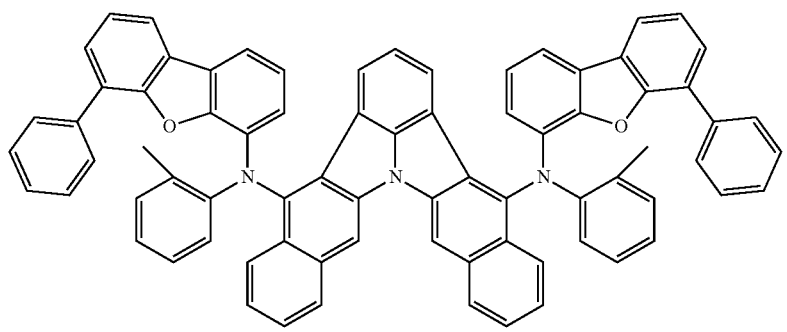
-continued
390
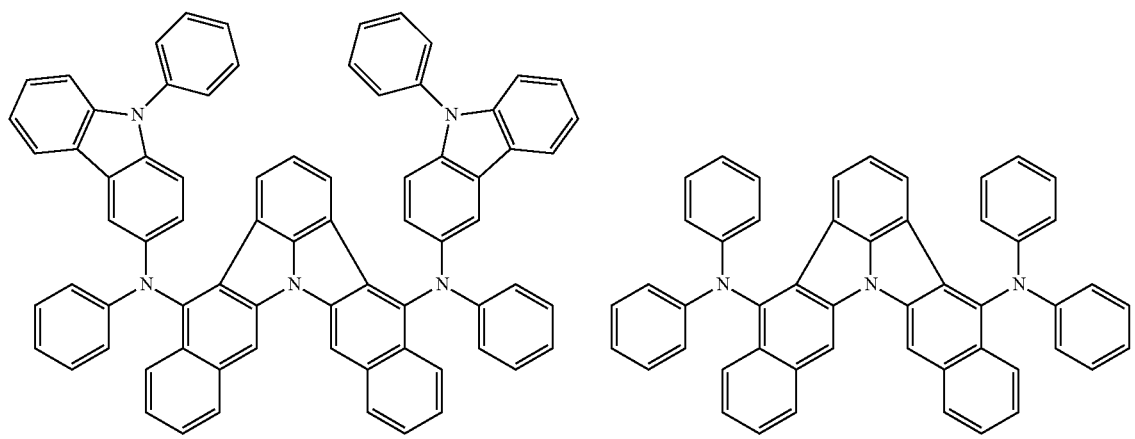
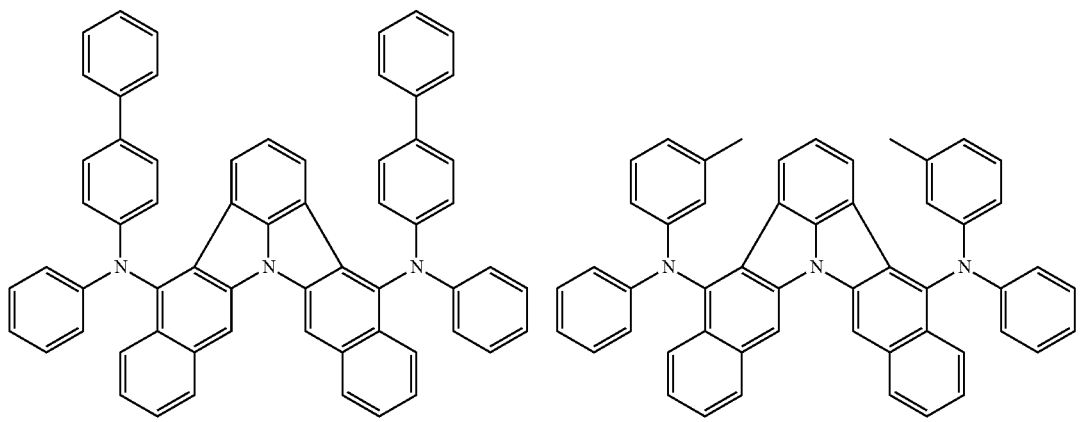
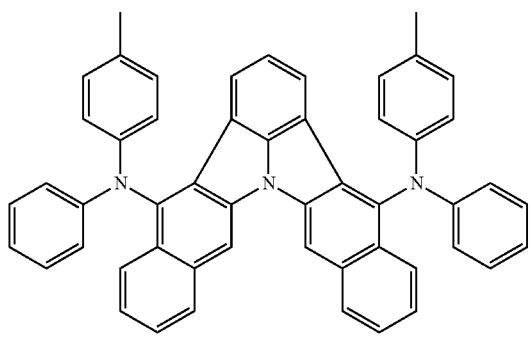

391
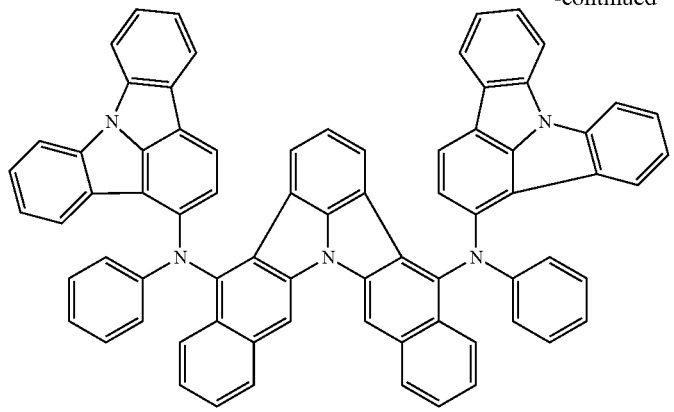
-continued
392
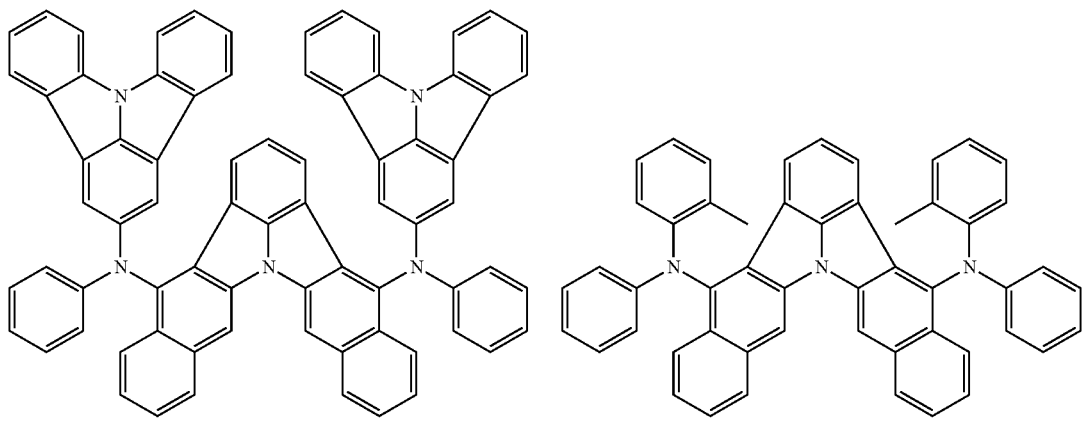
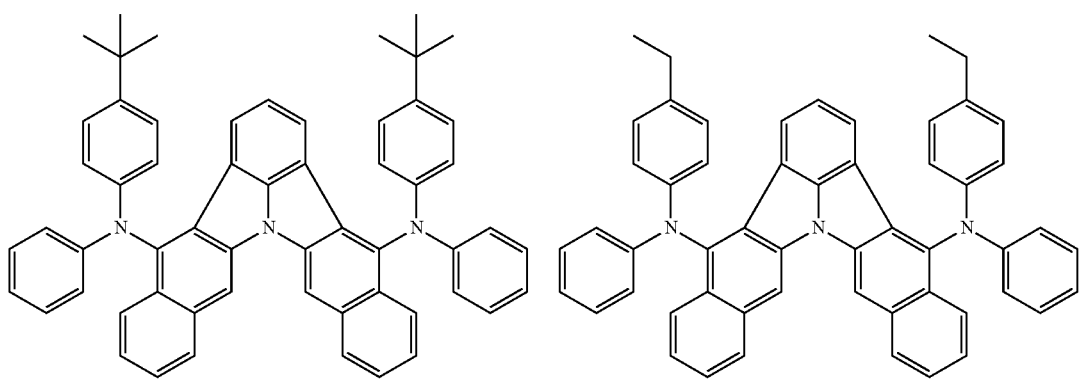
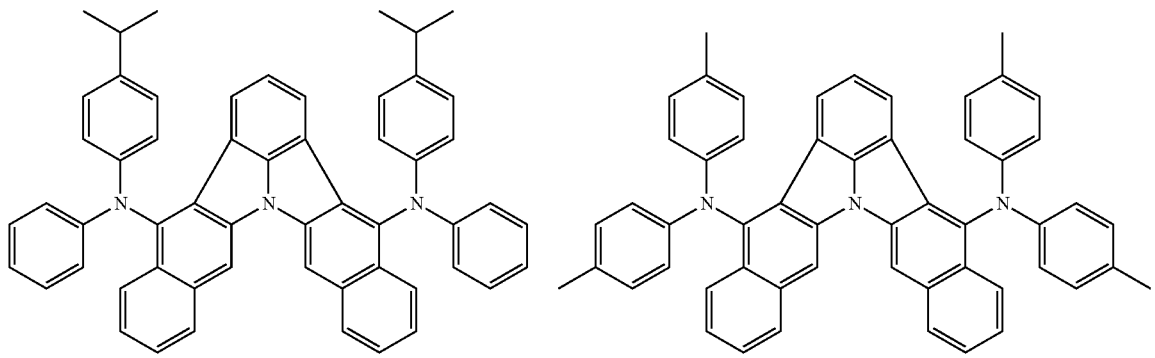

-continued
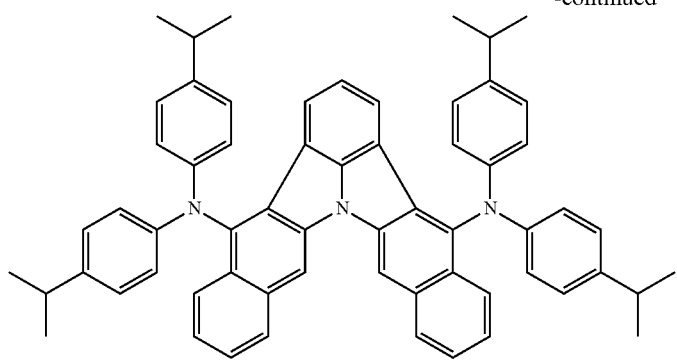
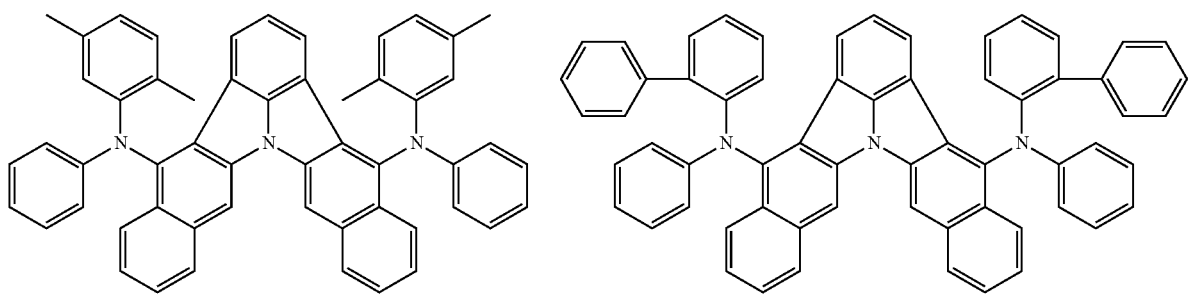
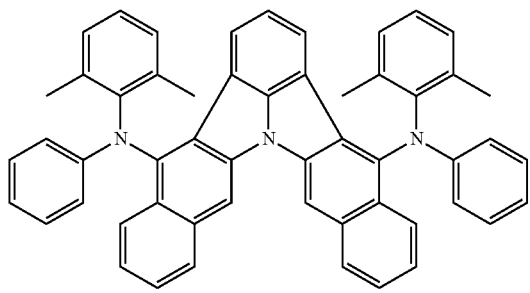
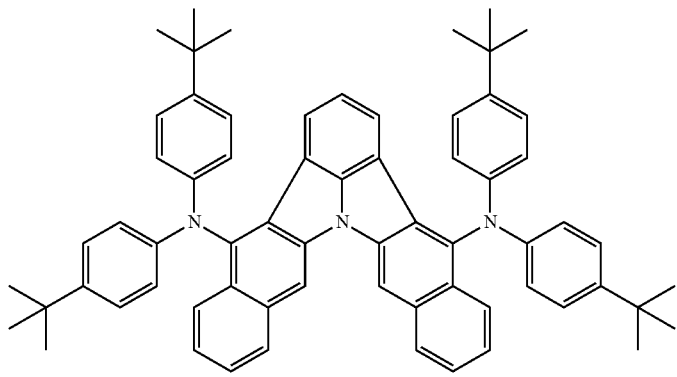
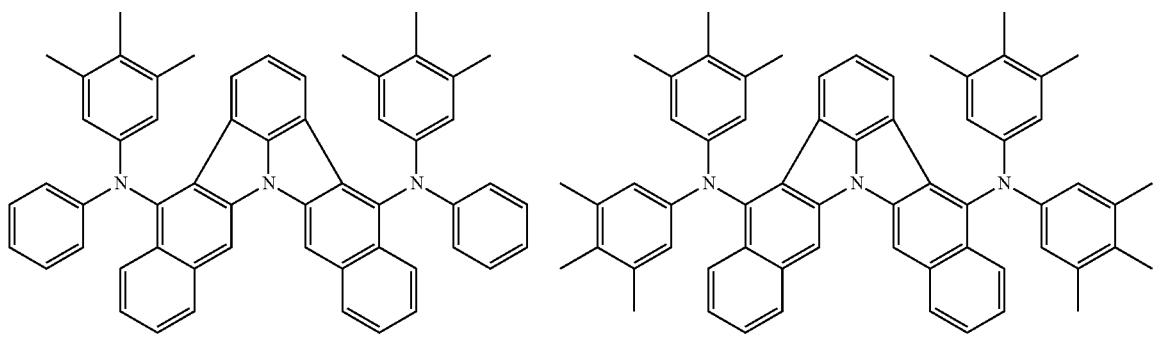

-continued
395
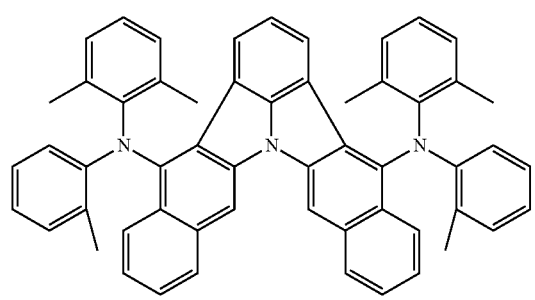
396
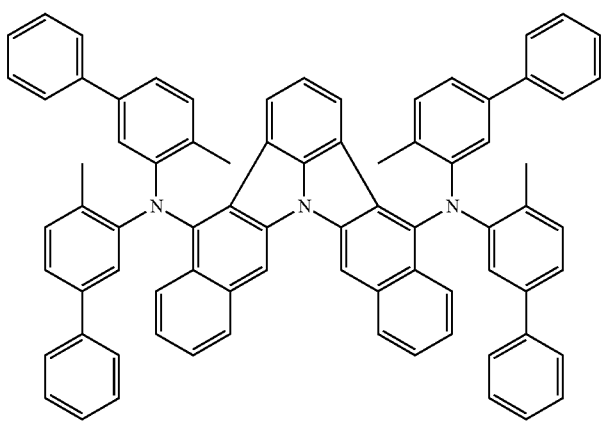
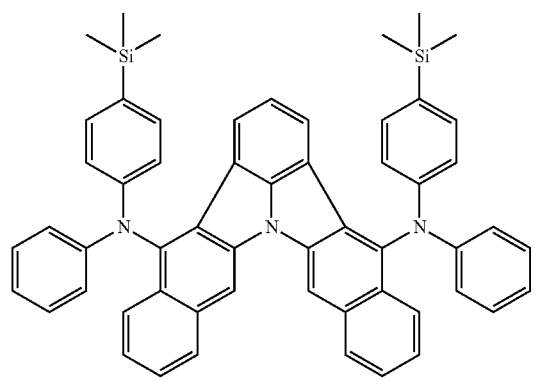
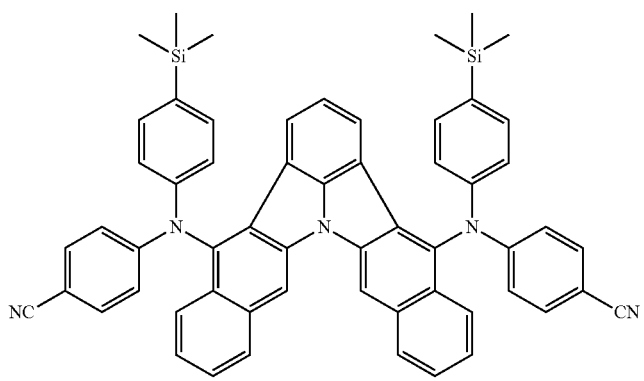
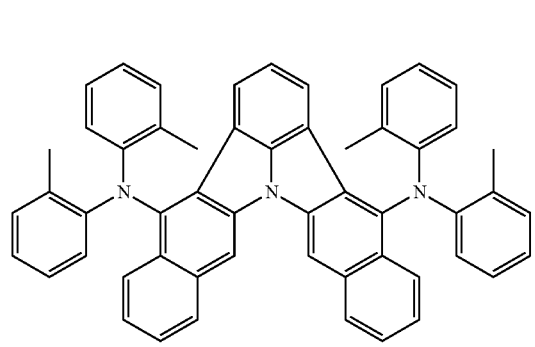
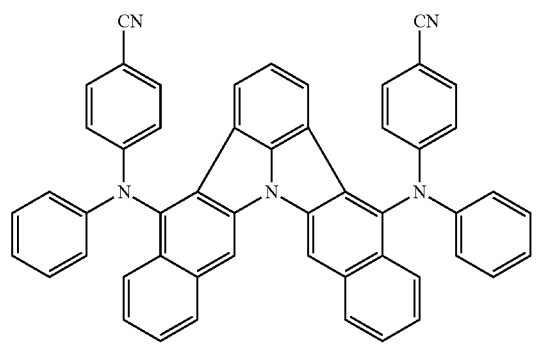
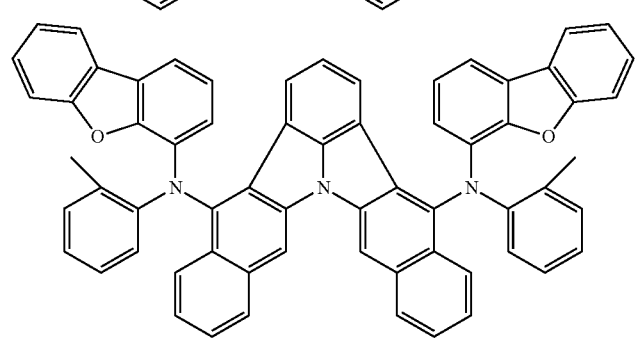

-continued
397
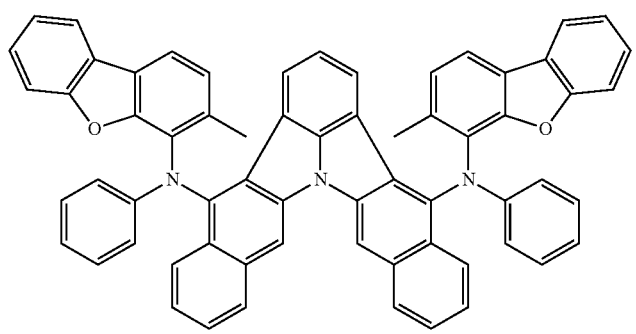
398
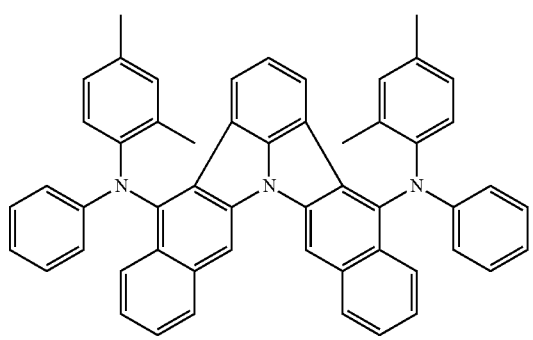
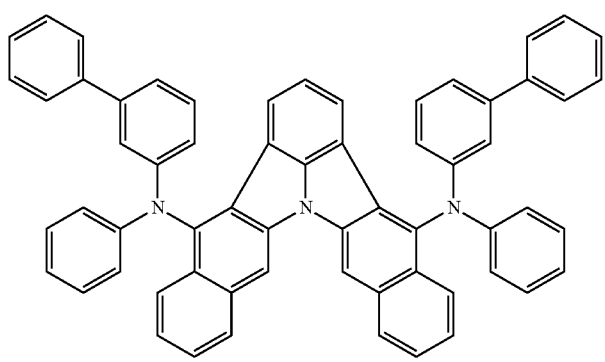
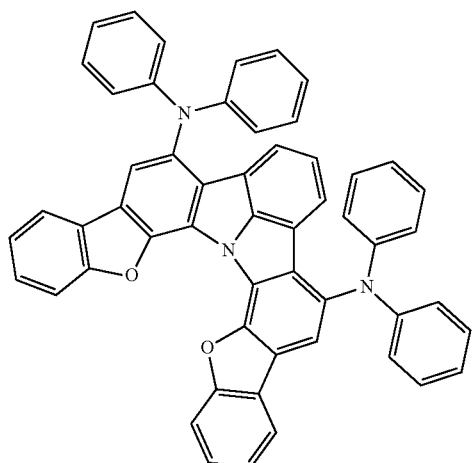
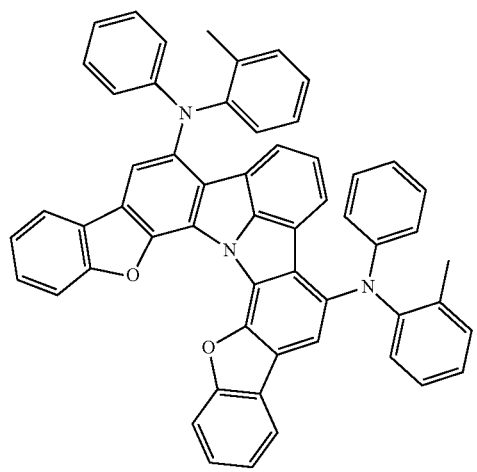
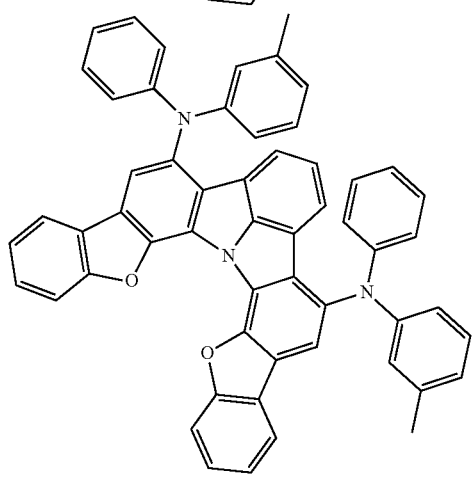
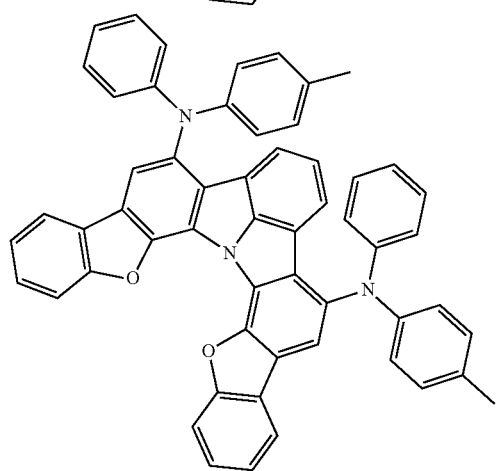

399
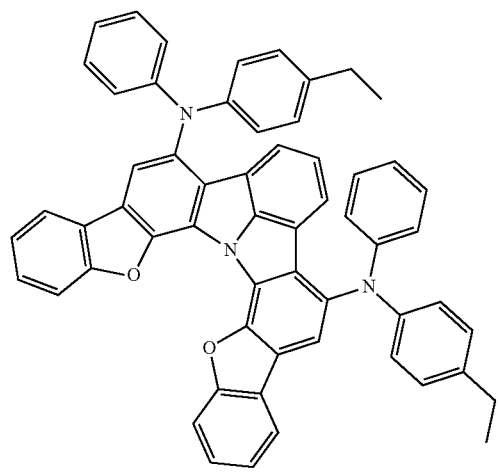
400
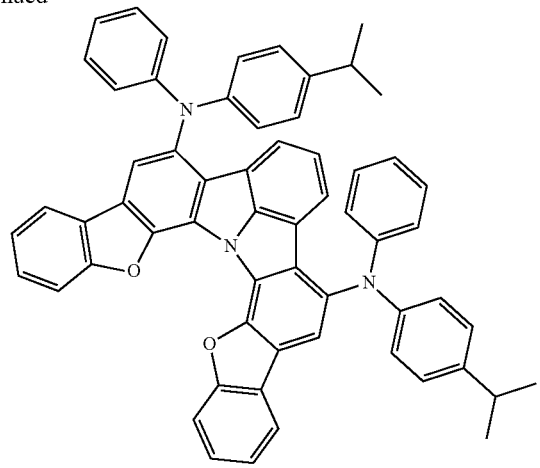
-continued
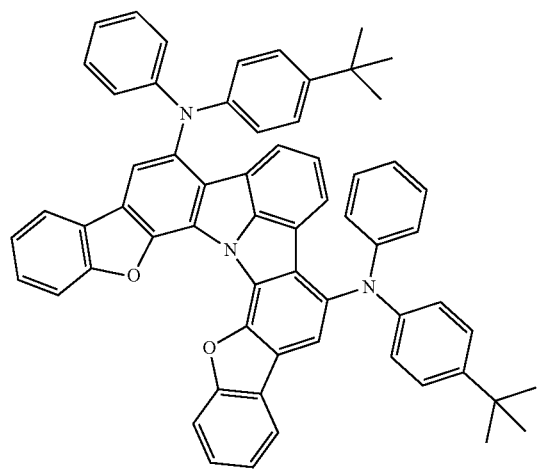
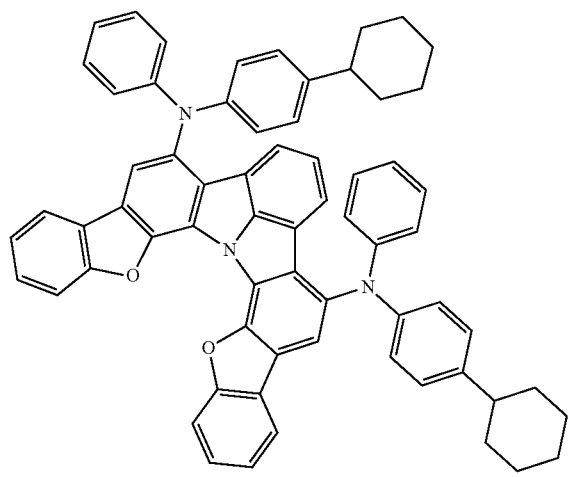
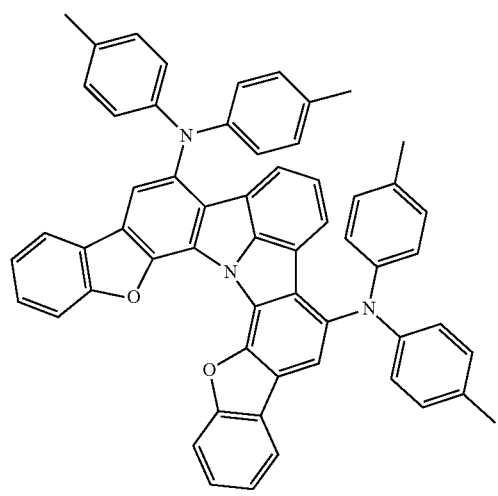
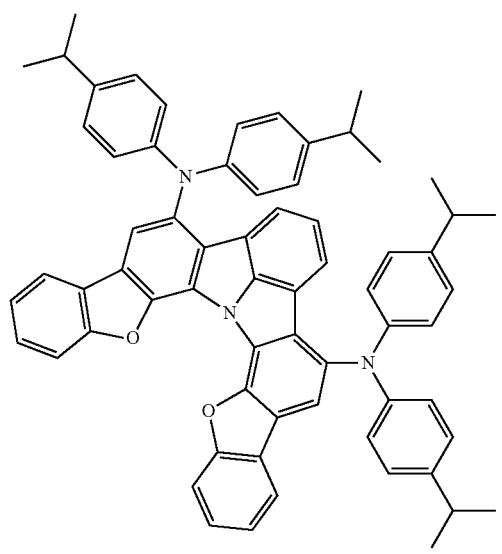

-continued
| 401 | 402 |
|---|---|
| 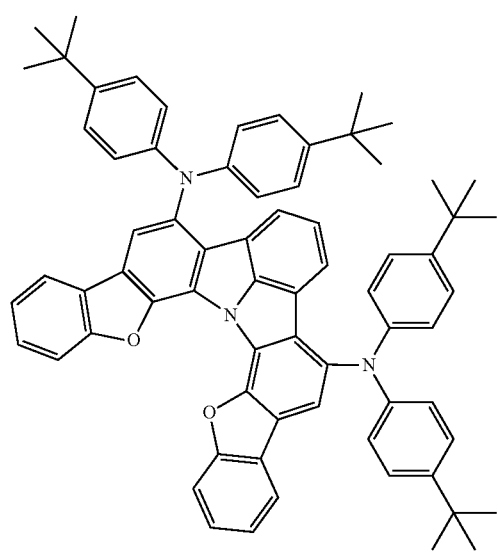 | 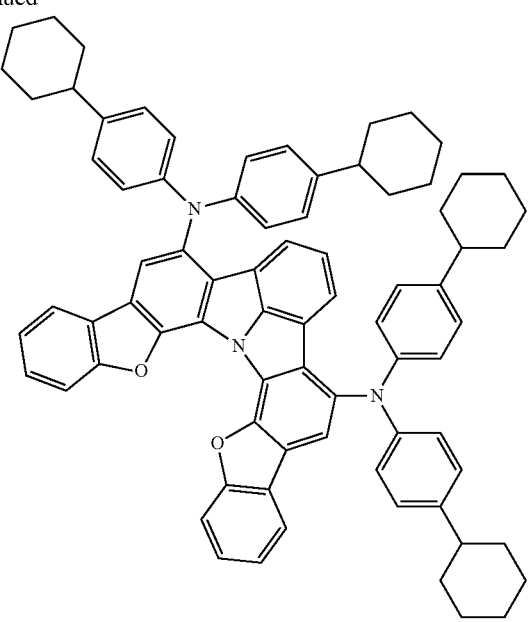 |
| 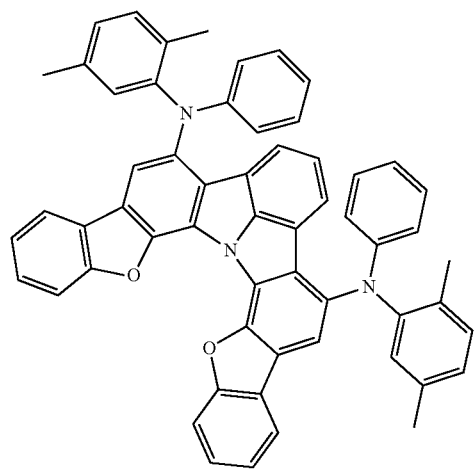 | 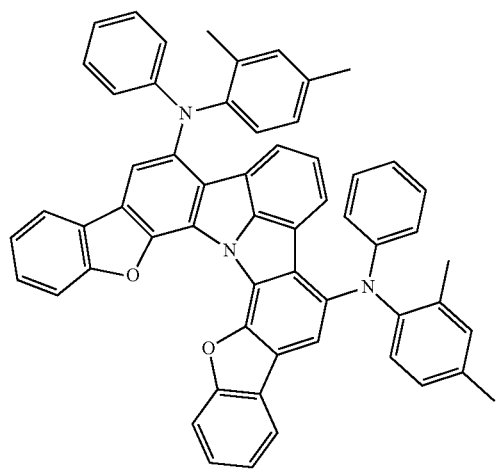 |
| 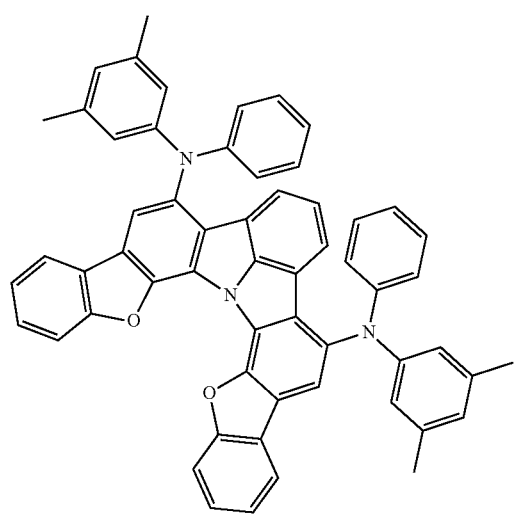 | 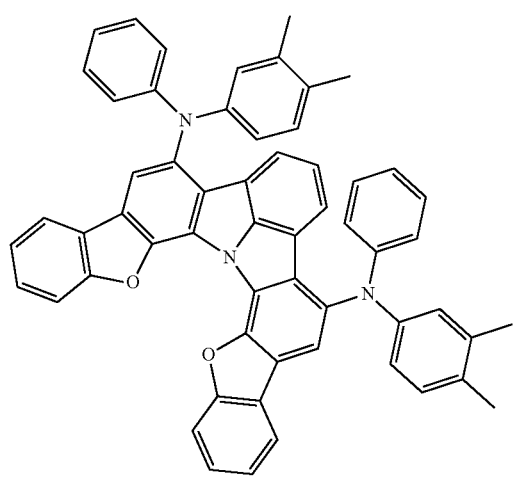 |

-continued
403
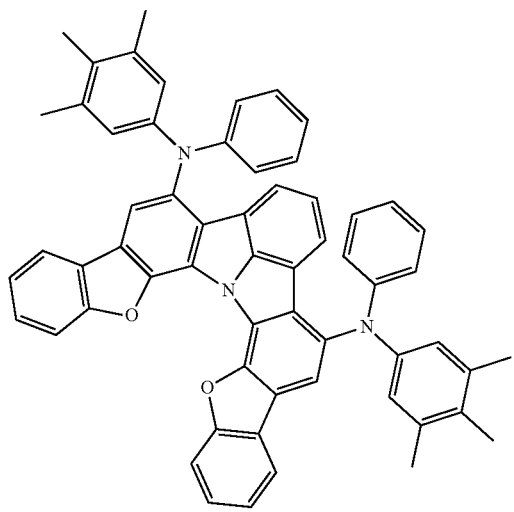
404
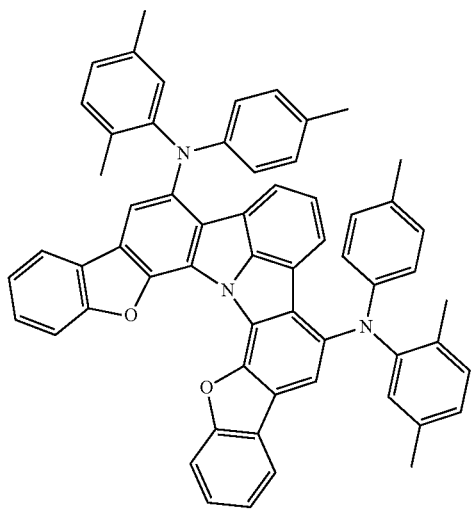
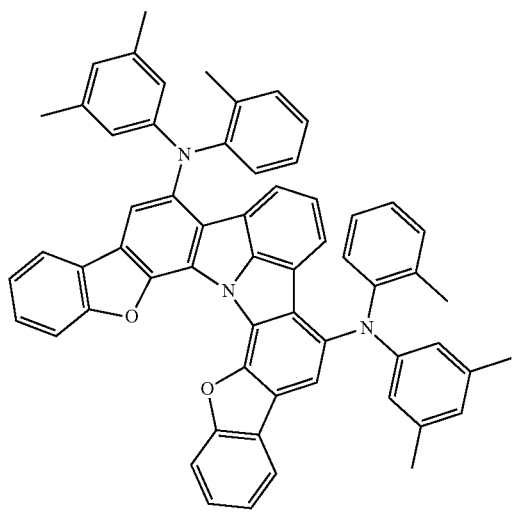
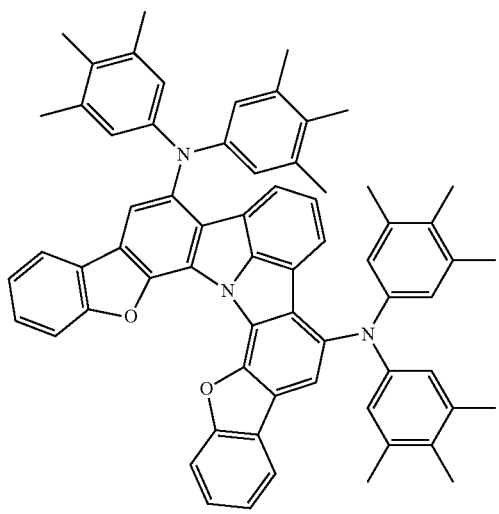
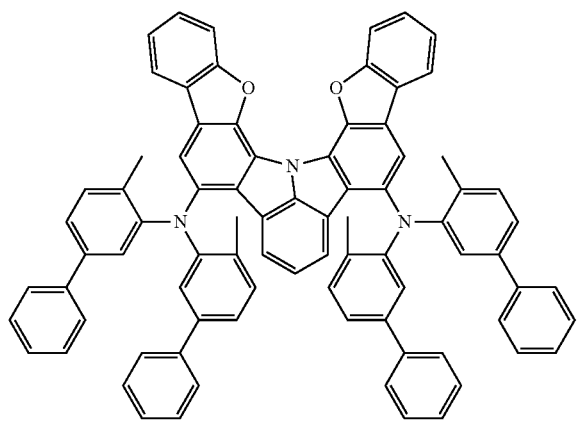
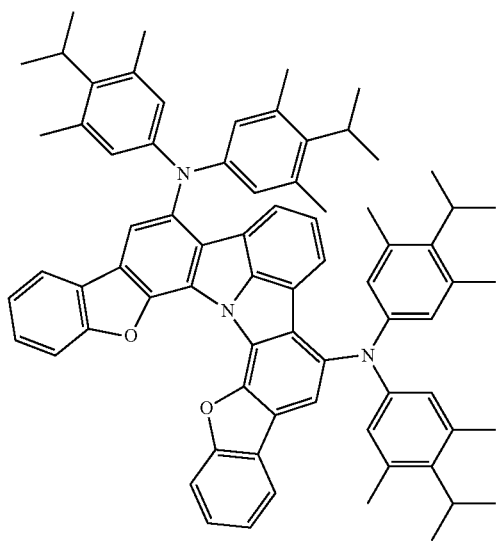

-continued
405
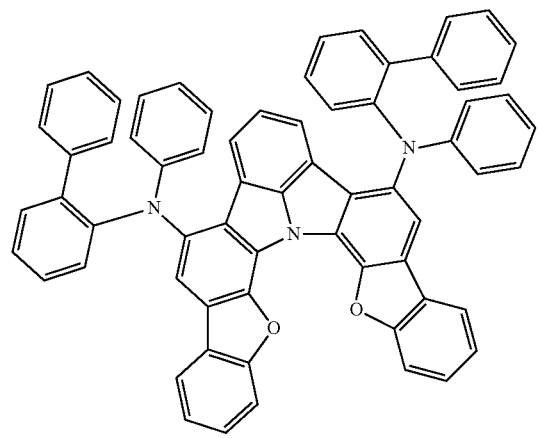
406
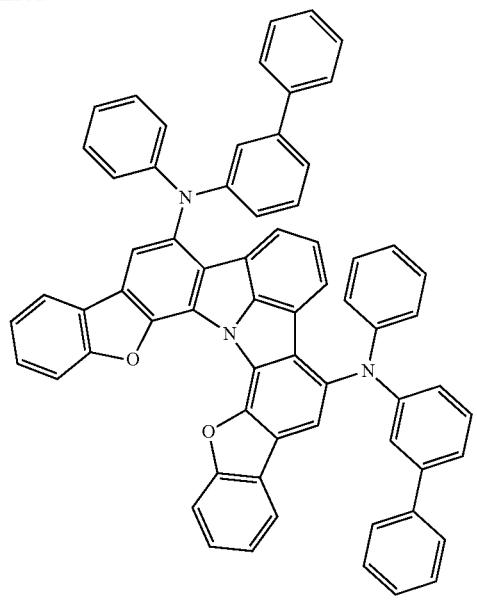
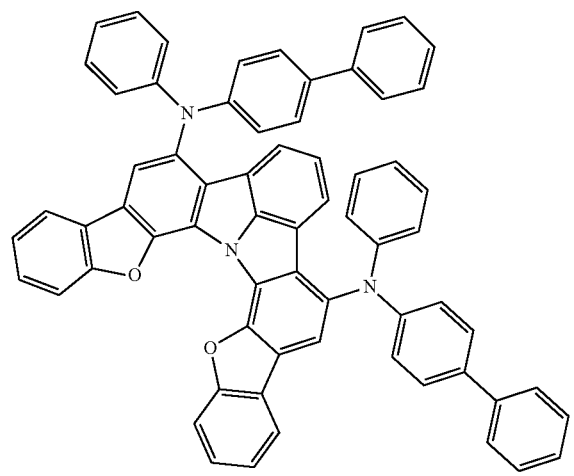
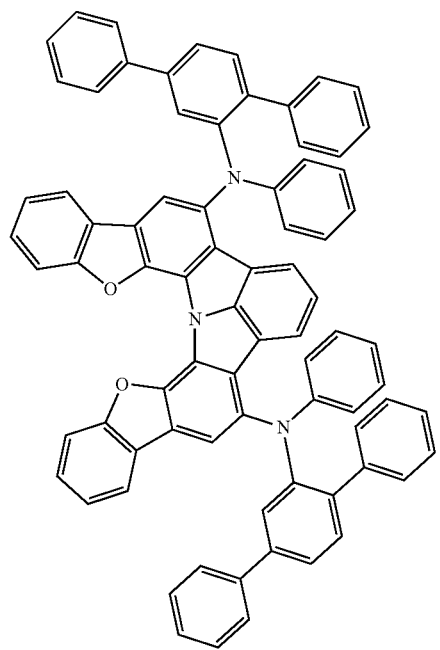

-continued
407
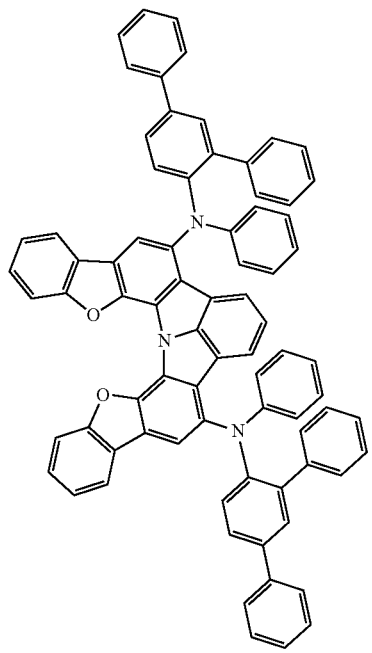
408
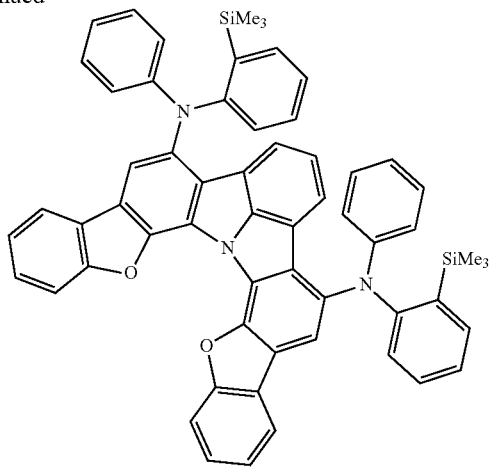
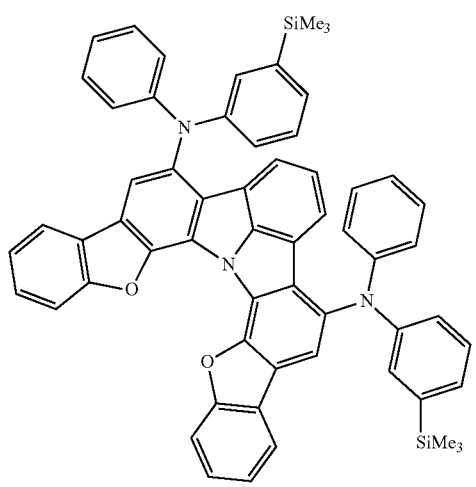
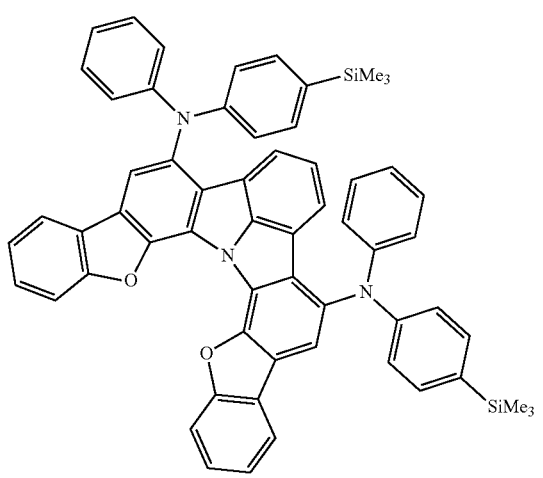
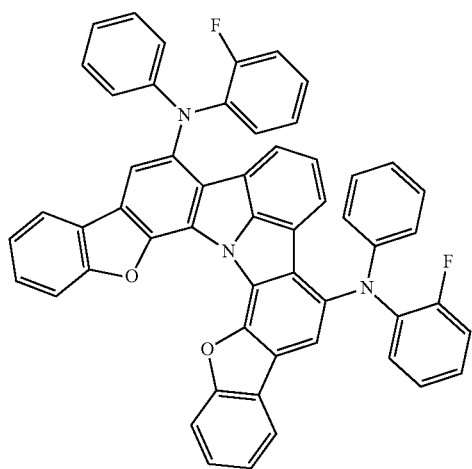
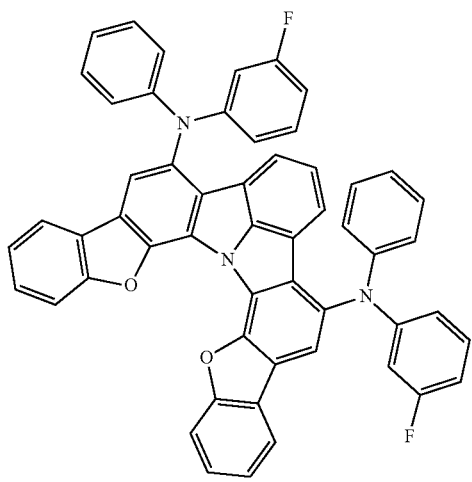

-continued
| 409 | 410 |
|---|---|
| 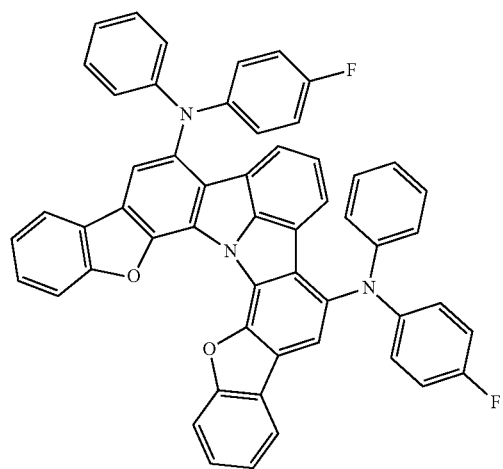 | 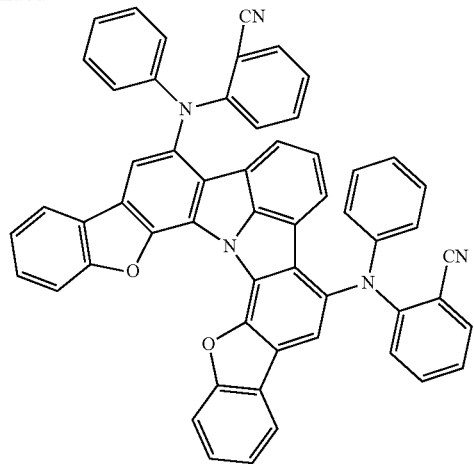 |
| 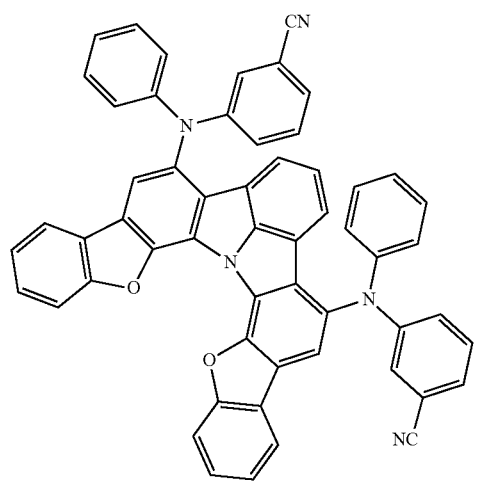 | 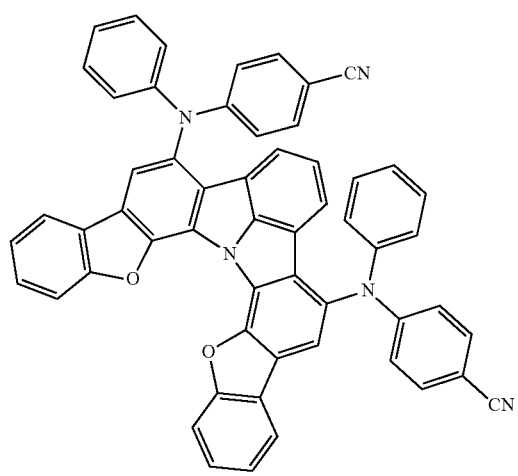 |
| 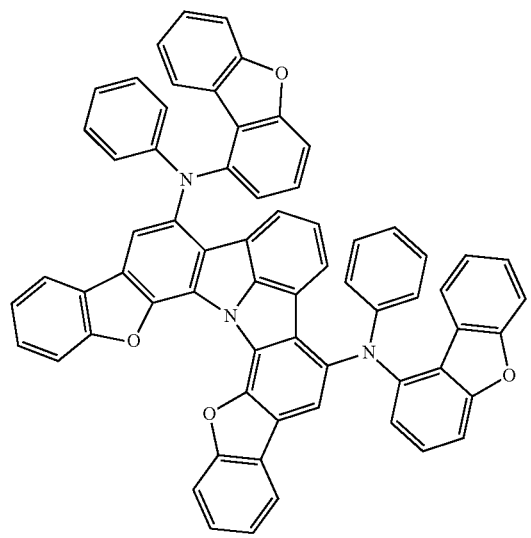 | 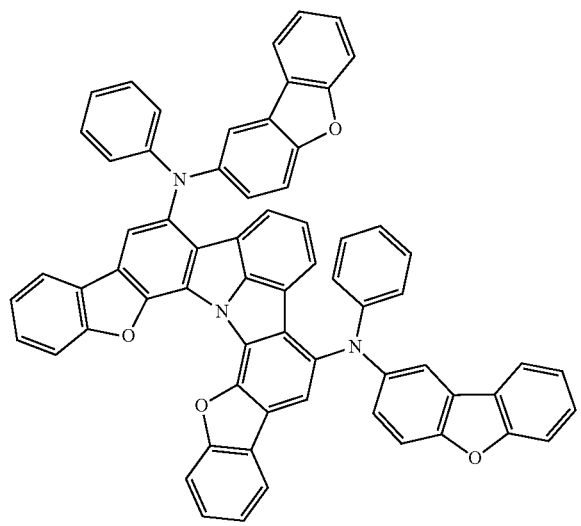 |

411
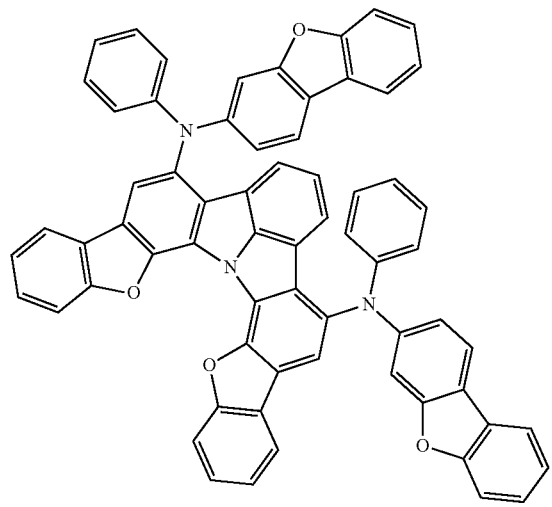
412
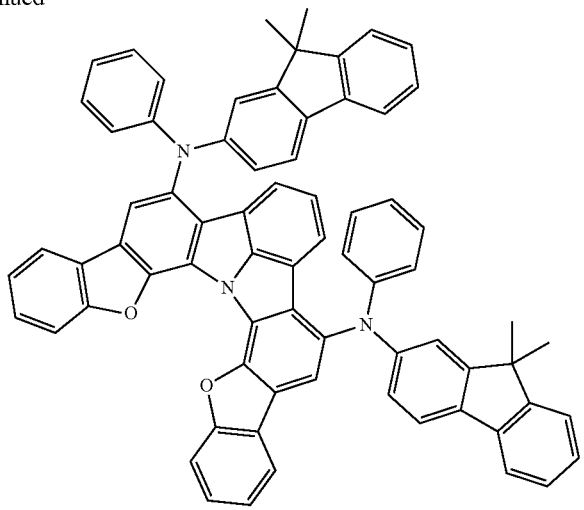
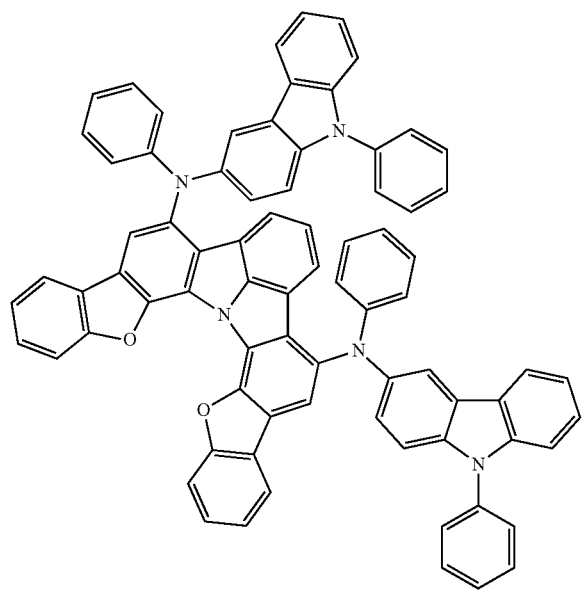
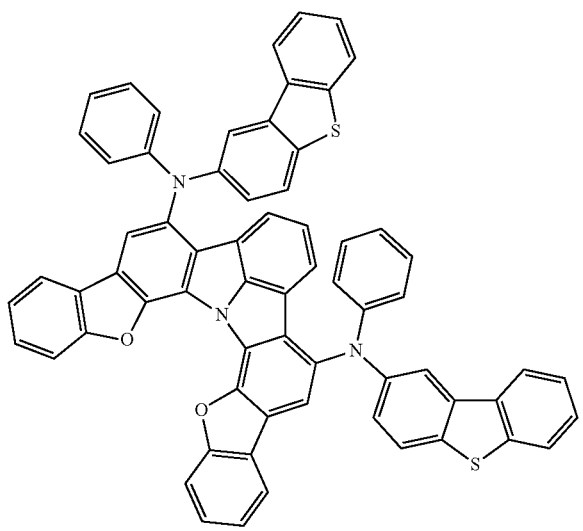
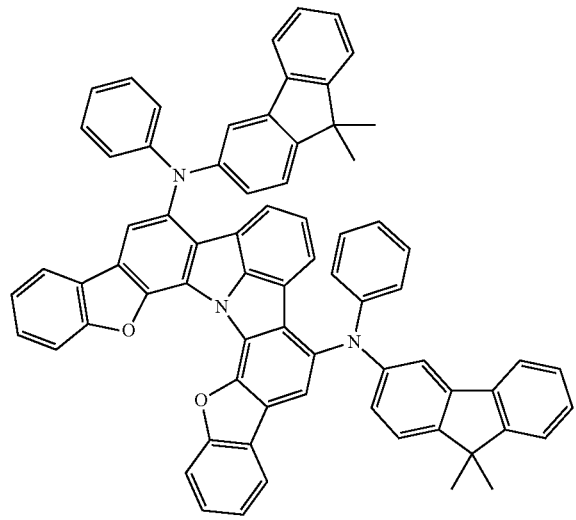
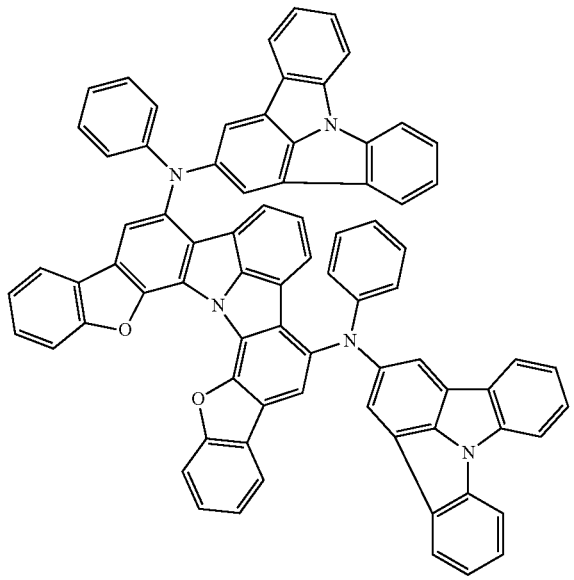

-continued
| 413 | 414 |
|---|---|
| 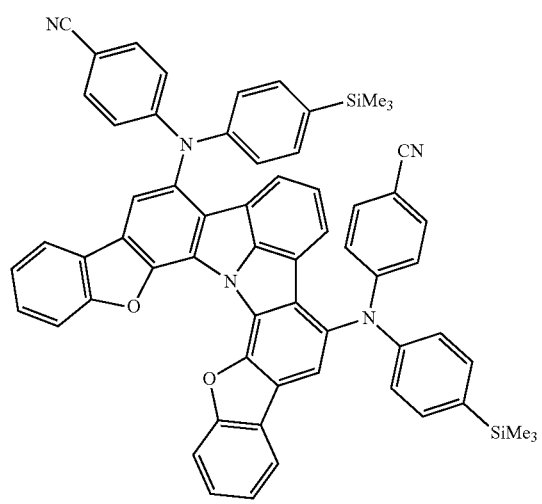 | 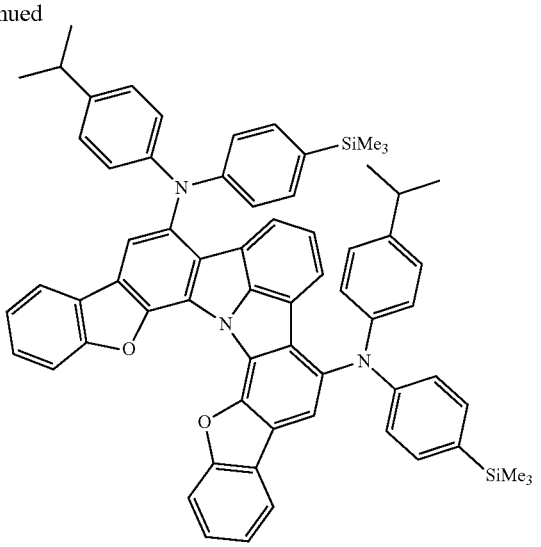 |
| 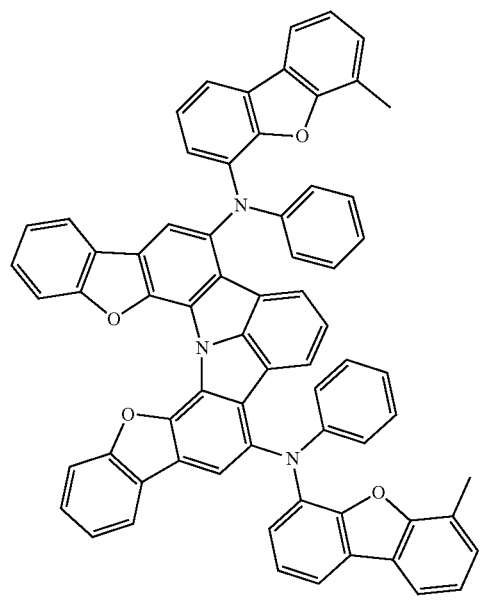 | 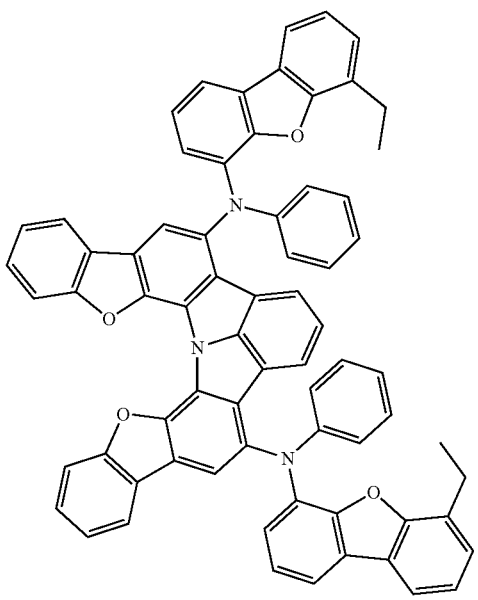 |
| 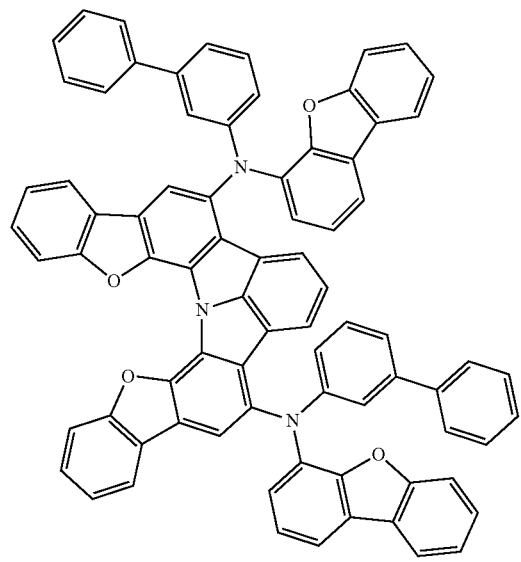 | 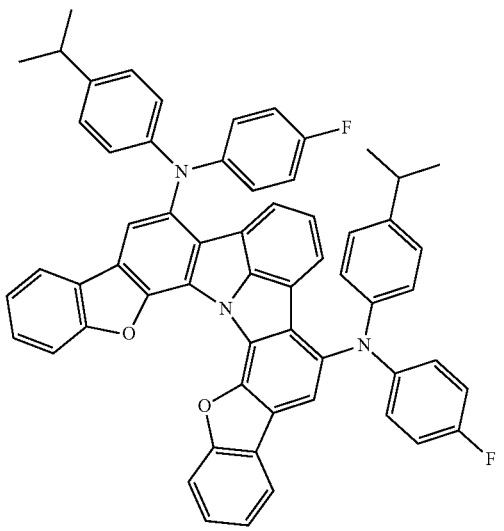 |

415
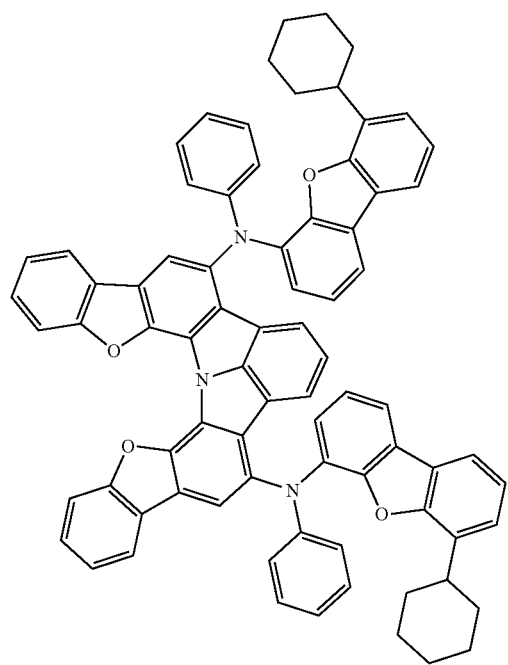
416
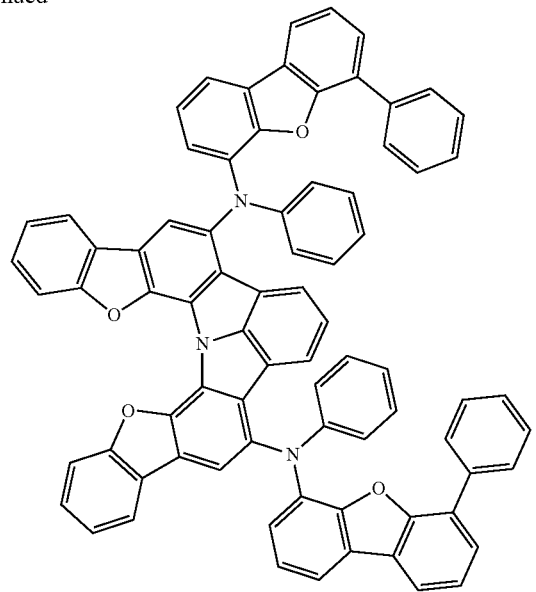
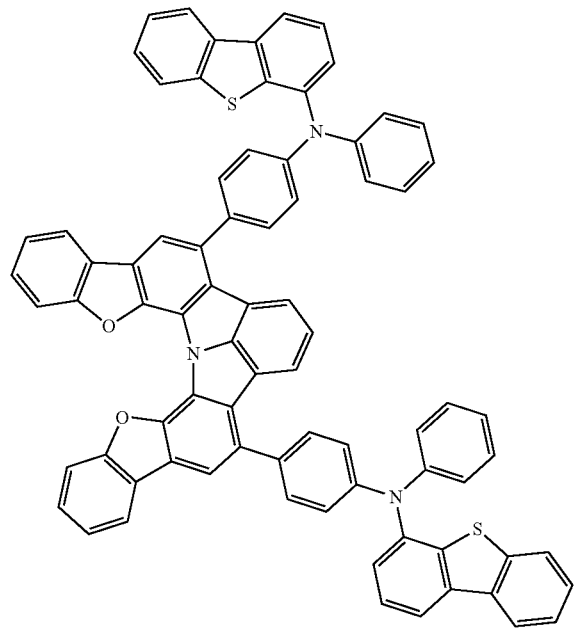
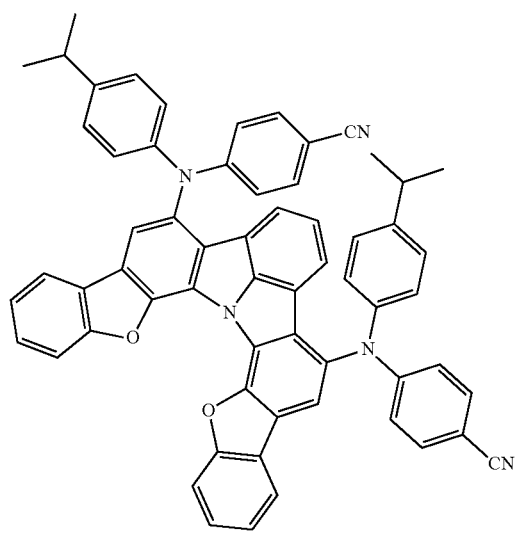

417 418
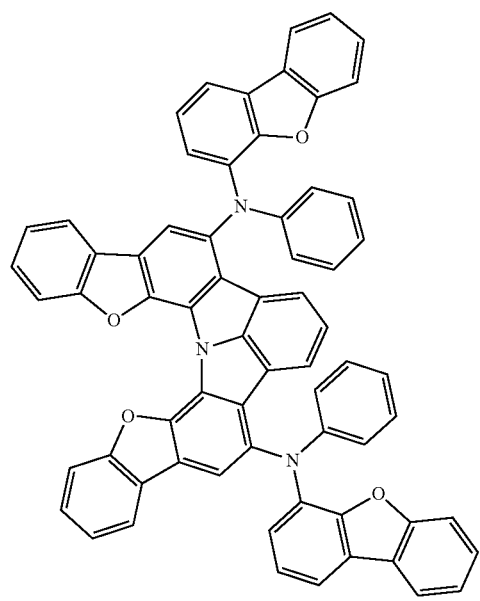 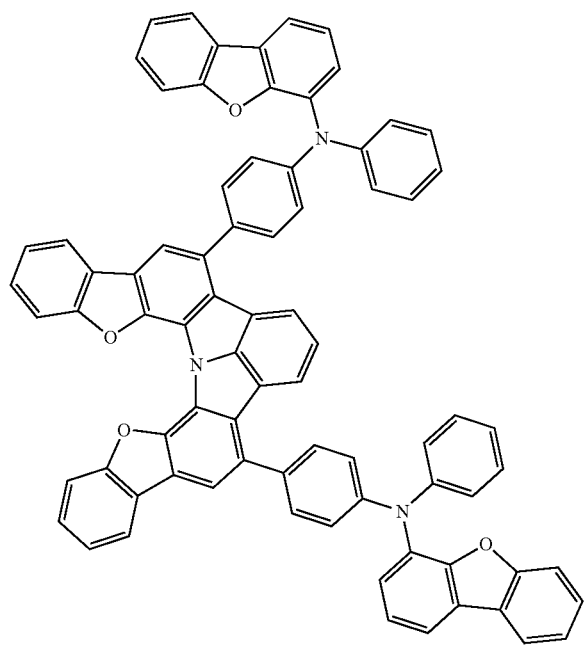
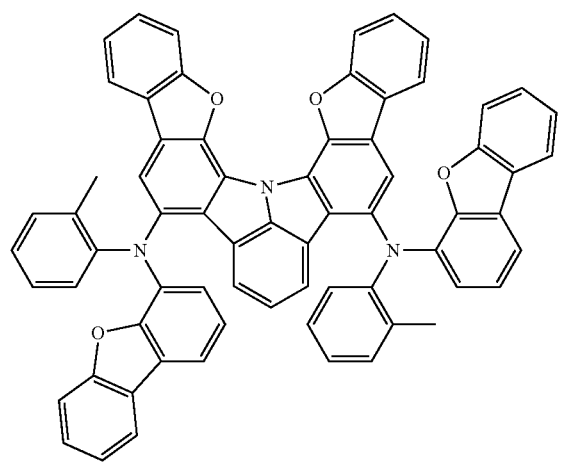 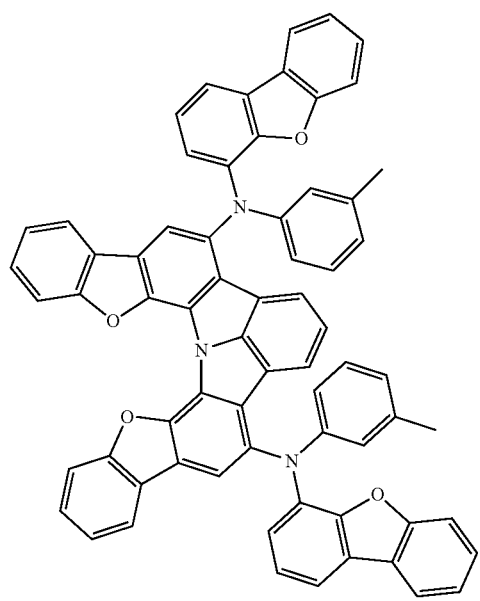

-continued
419
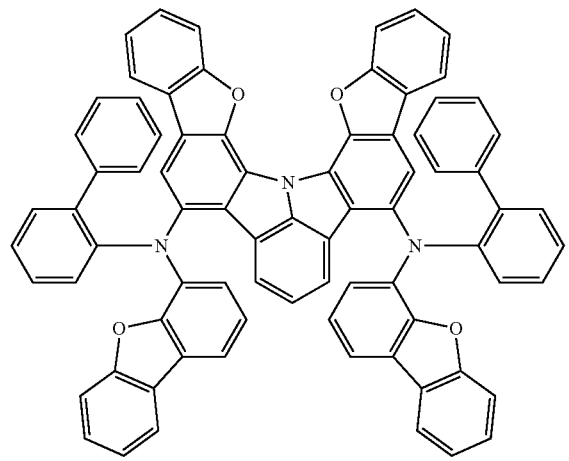
420
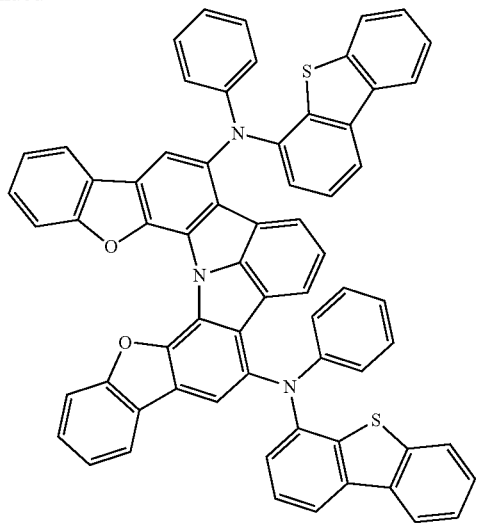
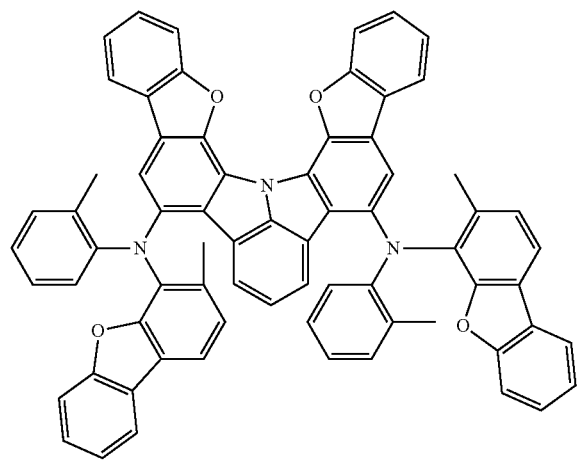
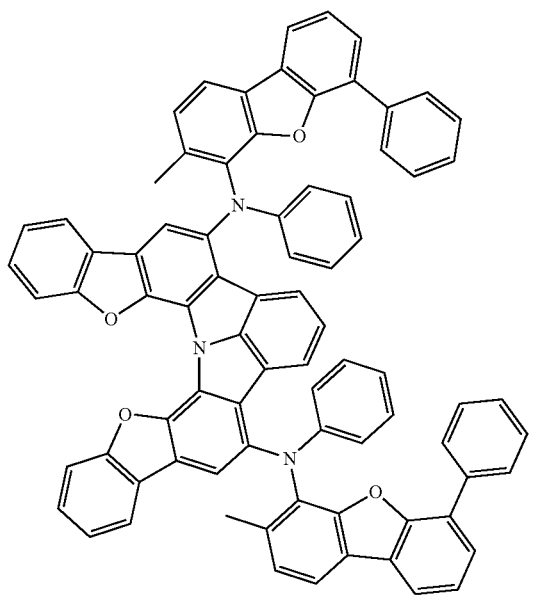

-continued
421 422
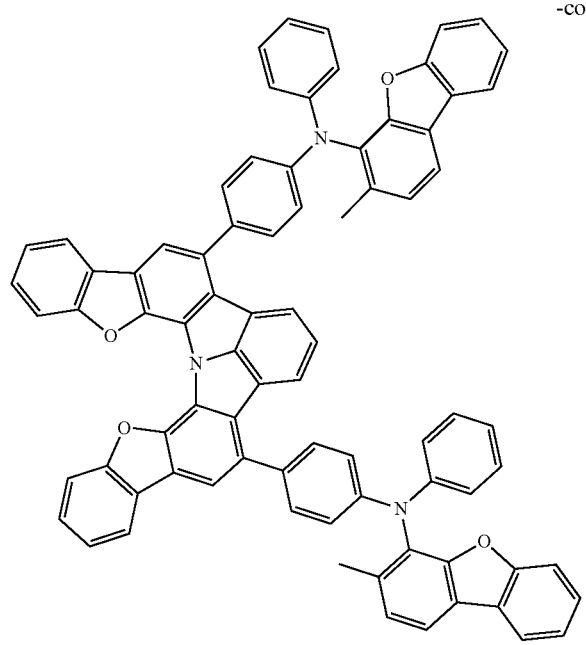 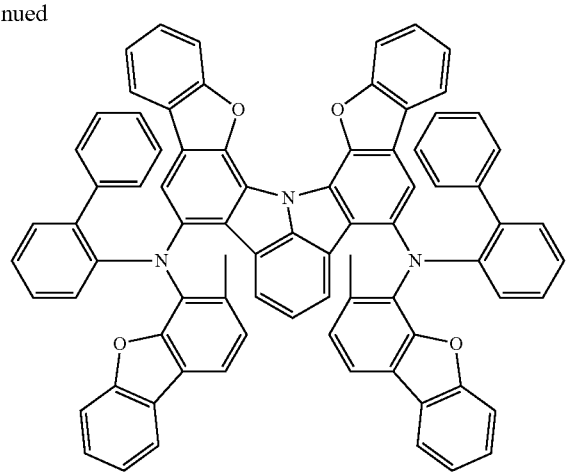
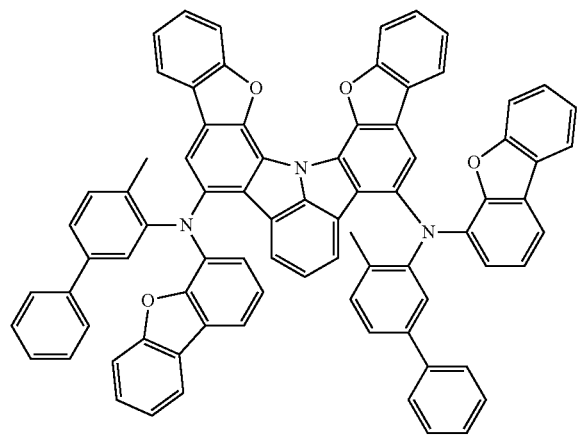 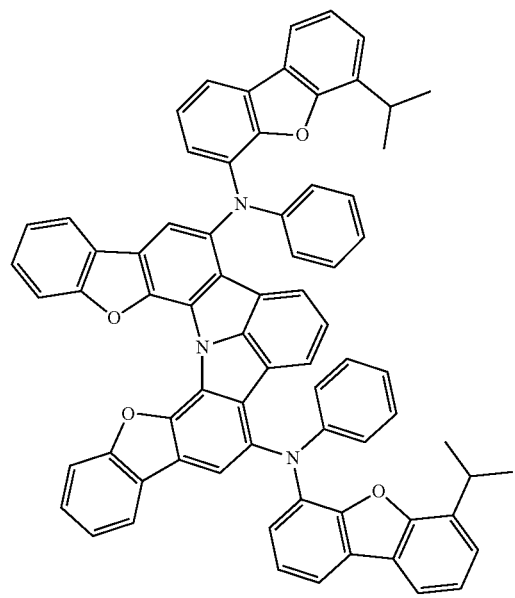

423 424
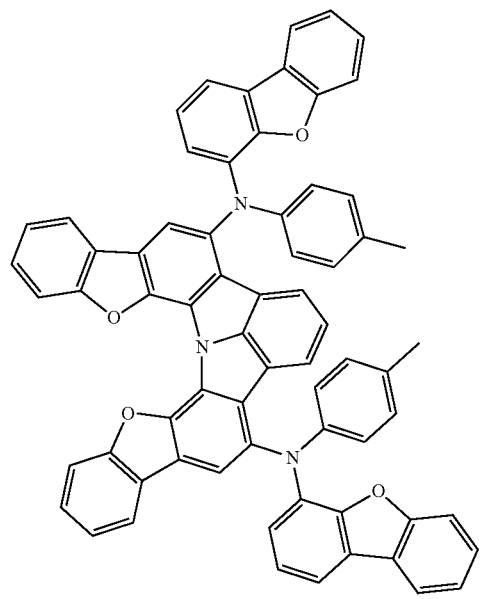 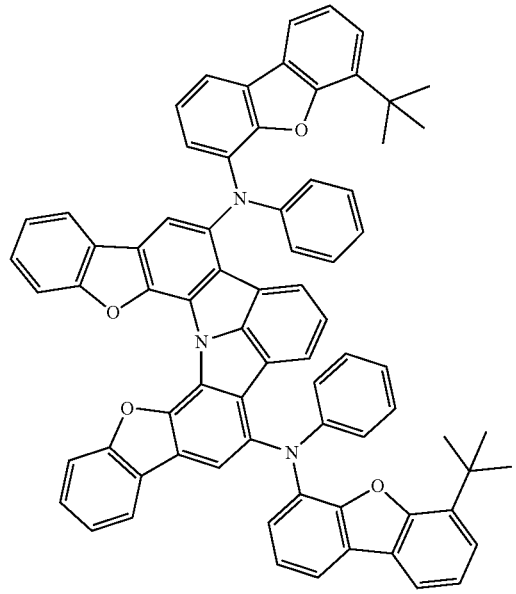
-continued
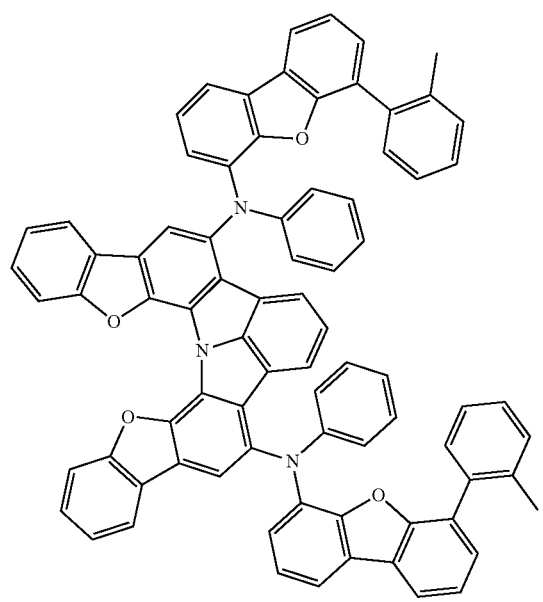 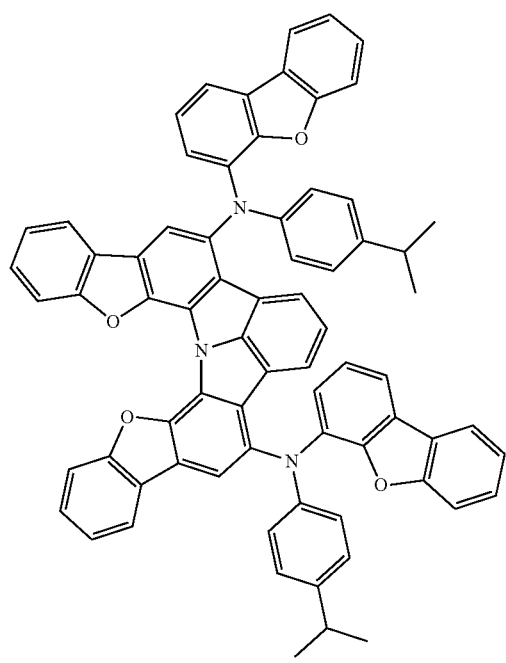

425 426
-continued
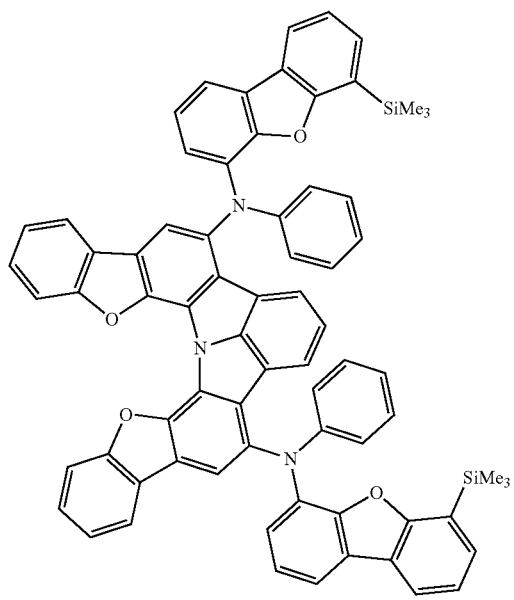
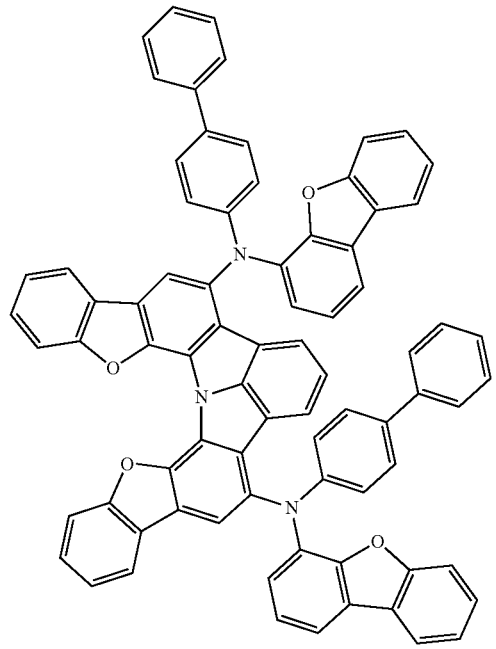
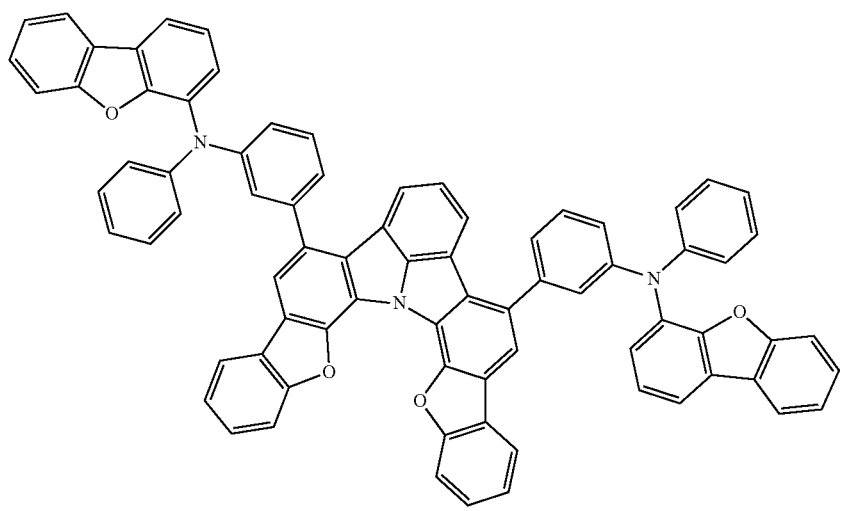

427

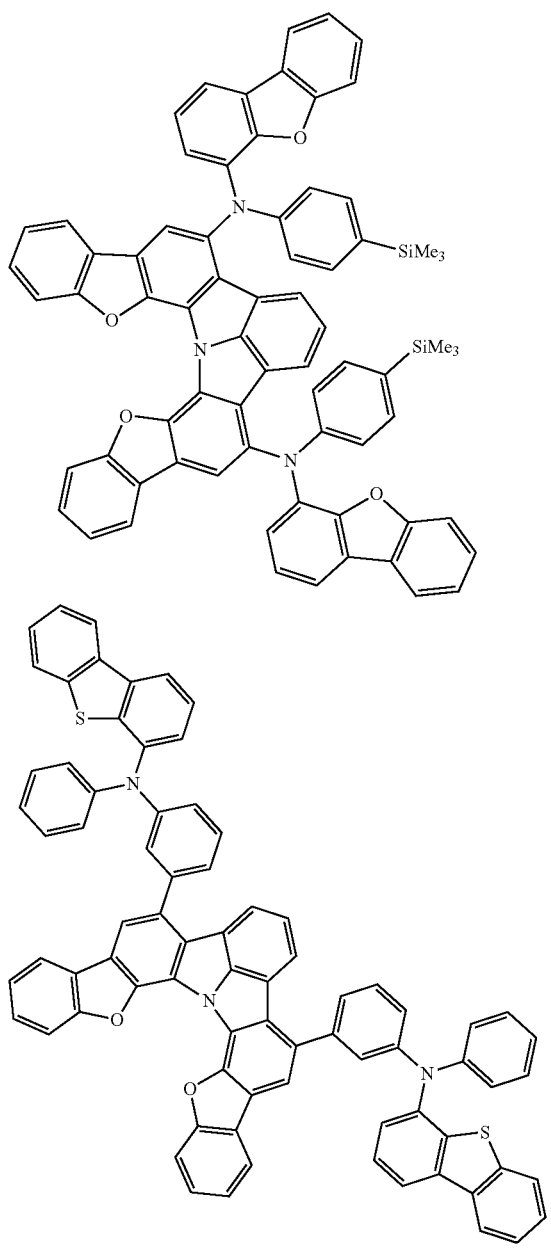

428

-continued

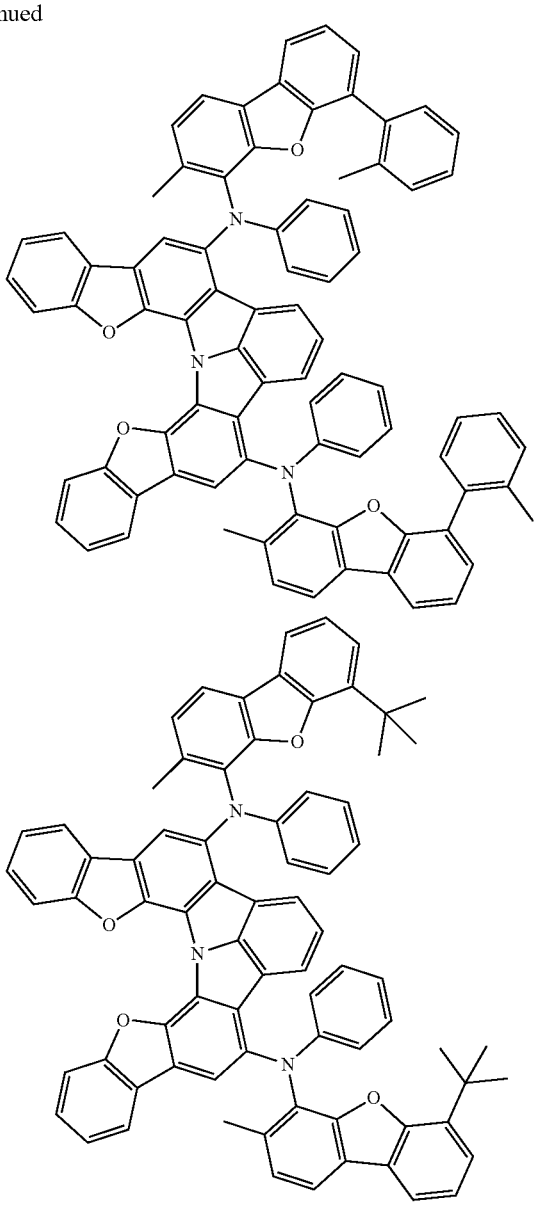

The half width on a photoluminescence spectrum of the first compound is preferably 30 nm or less, more preferably 25 nm or less, and still more preferably 20 nm or less. Within the above ranges, a high color purity is obtained.

The half width on a photoluminescence spectrum of the compound was calculated by measuring the fluorescence intensity using a fluorescence measurement apparatus as described below.

A compound was dissolved in a solvent (toluene) to prepare a fluorescence specimen (5 μmol/mL). After irradiating the fluorescence specimen in a quartz cell with an excitation light at room temperature (300 K), the fluorescence intensity was measured while changing the wavelength, thereby obtaining a photoluminescence spectrum with a vertical coordinate of fluorescence intensity and a horizontal coordinate of wavelength.

As the fluorescence measurement apparatus, for example, Fluorescent Spectrophotometer F-7000 manufactured by Hitachi High-Tech Science Corporation is usable.

Second Compound

The second compound that is not the same as the first compound (hereinafter may be simply referred to as "second compound") is used in the light emitting layer combinedly with the first compound.

In an embodiment, the second compound is used in the light emitting layer combinedly with the first compound as a host material.

The second compound is a compound comprising a polycyclic aromatic skeleton, preferably a compound comprising a fused polycyclic aromatic skeleton, and more preferably a compound comprising a fused polycyclic aromatic skeleton comprising 3 or more fused rings. Examples thereof are preferably a compound comprising an anthracene skeleton, a compound comprising a chrysene skeleton, a compound comprising a pyrene skeleton, and a compound comprising a fluorene skeleton, with a compound comprising an anthracene skeleton being more preferred.

For example, a compound comprising an anthracene skeleton represented by formula (19) is usable as the second compound:

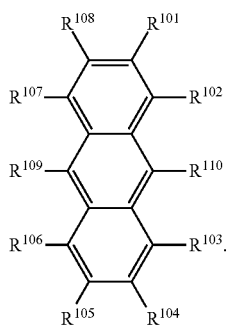

(19)

In formula (19), $R^{101}$ to $R^{110}$ are each independently a hydrogen atom or a substituent, wherein the substituent is the same as described above with respect to $R_1$ to $R_{11}$ or represented by —L—Ar. Examples, preferred numbers of carbon atoms and atoms, and preferred groups thereof are also the same as in $R_1$ to $R_{11}$. Examples of the halogen atom are a fluorine atom, a chlorine atom, a bromine atom, and an iodine atom. Provided that at least one of $R^{101}$ to $R^{110}$ is —L—Ar. L is independently a single bond or a linking group that is a substituted or unsubstituted arylene group having 6 to 30 ring carbon atoms or a substituted or unsubstituted heteroarylene group having 5 to 30 ring atoms. Ar is independently a substituted or unsubstituted single ring group having 5 to 50 ring atoms, a substituted or unsubstituted fused ring group having 8 to 50 ring atoms, or a group wherein the single ring group and the fused ring group are linked to each other.

The single ring group of formula (19) is a group composed of only a ring structure having no fused ring structure.

The single ring group having 5 to 50 ring atoms is preferably an aromatic group, such as a phenyl group, a biphenylyl group, a terphenylyl group, and a quaterphenylyl group, and a heterocyclic group, such as a pyridyl group, a pyrazyl group, a pyrimidyl group, a triazinyl group, a furyl group, and a thienyl group, with a phenyl group, a biphenylyl group, and a terphenylyl group being more preferred.

The fused ring group of formula (19) is a group wherein two or more ring structures are fused together.

The fused ring group having 8 to 50 ring atoms is preferably a fused aromatic ring group, such as a naphthyl group, a phenanthryl group, an anthryl group, a chrysenyl group, a benzanthryl group, a benzophenanthryl group, a triphenylenyl group, a benzochrysenyl group, an indenyl group, a fluorenyl group, a 9,9-dimethylfluorenyl group, a benzofluorenyl group, a dibenzofluorenyl group, a fluoranthenyl group, and a benzofluoranthenyl group, and a fused heterocyclic group, such as a benzofuranyl group, a benzothiophenyl group, an indolyl group, a dibenzofuranyl group, a dibenzothiophenyl group, a carbazolyl group, a quinolyl group, and a phenanthrolinyl group, with a naphthyl group, a phenanthryl group, an anthryl group, a 9,9-dimethylfluorenyl group, a fluoranthenyl group, a benzanthryl group, a dibenzothiophenyl group, a dibenzofuranyl group, and a carbazolyl group being more preferred.

The substituent of Ar is preferably the single ring group or the fused ring group, each described above.

The arylene group of the substituted or unsubstituted arylene group having 6 to 30 ring carbon atoms represented by L is a divalent group derived by removing one hydrogen atom from the aryl group selected from a phenyl group, a naphthylphenyl group, a biphenylyl group, a terphenylyl group, a naphthyl group, an acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, a s-indanyl group, an as-indanyl group, a fluoranthenyl group, a benzo[k]fluoranthenyl group, a triphenylenyl group, a benzo[b]triphenylenyl group, and a perylenyl group. Preferred are a phenylene group, a biphenylenediyl group, a terphenylenediyl group, and a naphthalenediyl group, with a phenylene group, a biphenylenediyl group, and a terphenylenediyl group being more preferred, and a phenylene group being particularly preferred.

The heteroarylene group of the substituted or unsubstituted heteroarylene group having 5 to 30 ring atoms is a divalent group derived by removing two hydrogen atoms from an aromatic heterocyclic compound comprising at least one, preferably 1 to 5 heteroatoms, such as a nitrogen atom, a sulfur atom, and an oxygen atom. Examples of the aromatic heterocyclic compound include pyrrole, furan, thiophene, pyridine, pyridazine, pyrimidine, pyrazine, triazine, imidazole, oxazole, thiazole, pyrazole, isoxazole, isothiazole, oxadiazole, thiadiazole, triazole, tetrazole, indole, isoindole, benzofuran, isobenzofuran, benzothiophene, isobenzothiophene, indolizine, quinolizine, quinoline, isoquinoline, cinnoline, phthalazine, quinazoline, quinoxaline, benzimidazole, benzoxazole, benzothiazole, indazole, benzisoxazole, benzoisothiazole, dibenzofuran, dibenzothiophene, carbazole, phenanthridine, acridine, phenanthroline, phenazine, phenothiazine, phenoxazine, and xanthene. Preferred heteroarylene group is a divalent group derived from furan, thiophene, pyridine, pyridazine, pyrimidine, pyrazine, triazine, benzofuran, benzothiophene, dibenzofuran, or dibenzothiophene by removing two hydrogen atoms, with a divalent group derived from benzofuran, benzothiophene, dibenzofuran, or dibenzothiophene by removing two hydrogen atoms being more preferred.

The compound of formula (19) is preferably an anthracene derivative represented by formula (20):

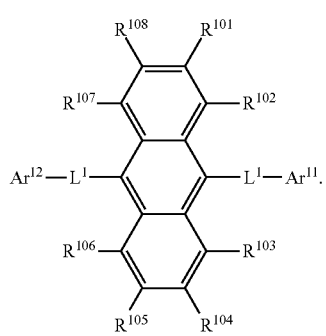

(20)

In formula (20), $R^{101}$ to $R^{108}$ are each independently a hydrogen atom or a substituent. The substituent is the same as described above with respect to $R_1$ to $R_{11}$ and examples, preferred numbers of carbon atoms and atoms, and preferred groups thereof are also the same as in $R_1$ to $R_{11}$. $L^1$ is the same as L of formula (19) and examples, preferred numbers of carbon atoms and atoms, and preferred groups thereof are also the same as in L. Each of $Ar^{11}$ and $Ar^{12}$ is the same as Ar of formula (19).

The anthracene derivative represented by formula (20) is preferably any of the following anthracene derivatives (A), (B), and (C), which are selected according to the structure of the organic EL device and the required properties.

Anthracene Derivative (A)

The anthracene derivative is represented by formula (20), wherein $Ar^{11}$ and $Ar^{12}$ are each independently a substituted or unsubstituted fused ring group having 8 to 50 ring atoms. $Ar^{11}$ and $Ar^{12}$ may be the same or different.

An anthracene derivative wherein $Ar^{11}$ and $Ar^{12}$ of formula (20) are different substituted or unsubstituted fused ring groups (inclusive of difference in the positions bonded to the anthracene ring) is particularly preferred. Examples of preferred fused ring group are described above, with a naphthyl group, a phenanthryl group, a benzanthryl group, a 9,9-dimethylfluorenyl group, and a dibenzofuranyl group being preferred.

Anthracene Derivative (B)

The anthracene derivative (B) is represented by formula (20), wherein one of $Ar^{11}$ and $Ar^{12}$ is a substituted or unsubstituted single ring group having 5 to 50 ring atoms and the other is a substituted or unsubstituted fused ring group having 8 to 50 ring atoms.

In a preferred embodiment, $Ar^{12}$ is a naphthyl group, a phenanthryl group, a benzanthryl group, a 9,9-dimethylfluorenyl group, a dibenzofuranyl group, and $Ar^{11}$ is an unsubstituted phenyl group or a phenyl group substituted by a single ring group or a fused ring group, for example, a phenyl group, a biphenyl group, a naphthyl group, a phenanthryl group, a 9,9-dimethylfluorenyl group, and a dibenzofuranyl group.

Preferred examples of the single ring group and the fused ring group are described above.

In another preferred embodiment, $Ar^{12}$ is a substituted or unsubstituted fused ring group having 8 to 50 ring atoms and $Ar^{11}$ is an unsubstituted phenyl group. In this embodiment, the fused ring group is particularly preferably a phenanthryl group, a 9,9-dimethylfluorenyl group, a dibenzofuranyl group, or a benzanthryl group.

Anthracene Derivative (C)

The anthracene derivative (C) is represented by formula (20), wherein $Ar^{11}$ and $Ar^{12}$ are each independently a substituted or unsubstituted single ring group having 5 to 50 ring atoms.

In a preferred embodiment, both of $Ar^{11}$ and $Ar^{12}$ are substituted or unsubstituted phenyl groups.

In a more preferred embodiment, $Ar^{11}$ is an unsubstituted phenyl group and $Ar^{12}$ is a phenyl group substituted with a single ring group or a fused ring group, or $Ar^{11}$ and $Ar^{12}$ are each independently a phenyl group substituted with a single ring group or a fused ring group.

Preferred examples of the single ring group and the fused ring group as the substituent are described above. More preferred single ring group as the substituent is a phenyl group or a biphenyl group. More preferred fused ring group as the substituent is a naphthyl group, a phenanthryl group, a 9,9-dimethylfluorenyl group, a dibenzofuranyl group, or a benzanthryl group.

The compound represented by formula (19) is more preferably an anthracene derivative represented by any of formulae (21) to (24):

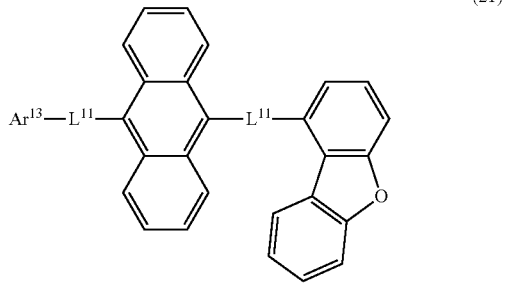

(21)

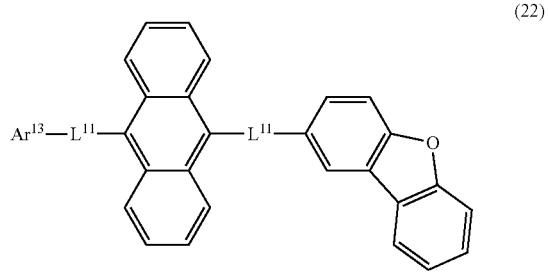

(22)

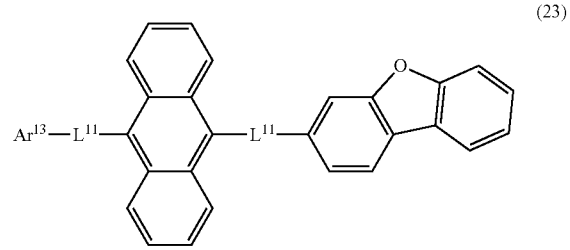

(23)

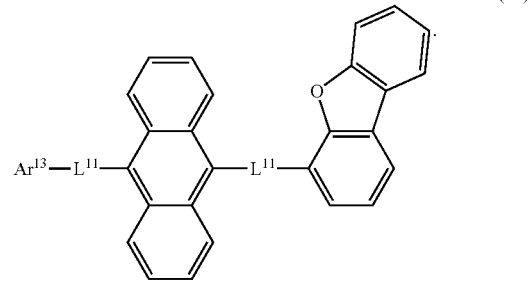

(24)

In formulae (21) to (24), $Ar^{13}$ is an unsubstituted aryl group having 6 to 50 ring carbon atoms. Each $L^{11}$ is independently a single bond or an unsubstituted arylene group having 6 to 30 ring carbon atoms.

Examples of the unsubstituted aryl group having 6 to 50 ring carbon atoms include a phenyl group, a biphenylyl group, a terphenylyl group, a naphthyl group, an acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, a s-indanyl group, an as-indanyl group, a fluoranthenyl group, a benzo[k]fluoranthenyl group, a triphenylenyl group, a benzo[b]triphenylenyl group, and a perylenyl group. Preferred are a phenyl group, a biphenylyl group, a terphenylyl group, a naphthyl group, an anthryl group, a pyrenyl group, and a fluoranthenyl group, with a phenyl group, a biphenylyl group, and a terphenylyl group being more preferred, and a phenyl group being still more preferred.

Examples of the arylene group of the unsubstituted arylene group having 6 to 30 ring carbon atoms represented by $L^{11}$ include a divalent group derived by removing one hydrogen atom from the aryl group selected from a phenyl group, a naphthylphenyl group, a biphenylyl group, a terphenylyl group, a naphthyl group, an acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, a s-indanyl group, an as-indanyl group, a fluoranthenyl group, a benzo[k]fluoranthenyl group, a triphenylenyl group, a benzo[b]triphenylenyl group and a perylenyl group. Preferred are a phenylene group, a biphenylenediyl group, a terphenylenediyl group, and a naphthalenediyl group, with a phenylene group, a biphenylenediyl group, and a terphenylenediyl group being more preferred, and a phenylene group being particularly preferred.

The compound of formula (19) is more preferably an anthracene derivative represented by any of formulae (25) to (32):

(25)
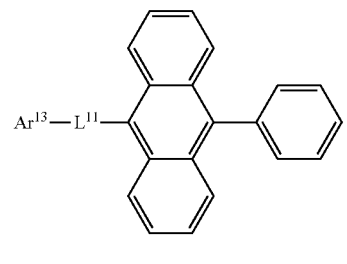

(26)
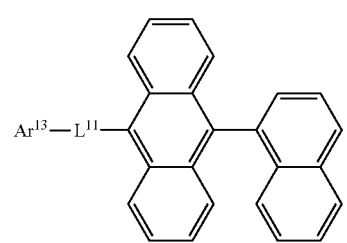

(27)
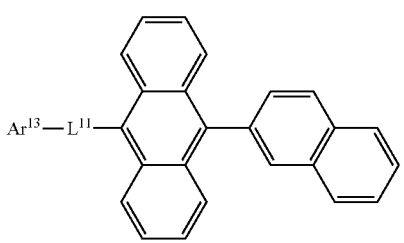

(28)
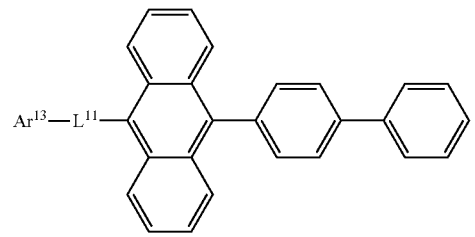

(29)
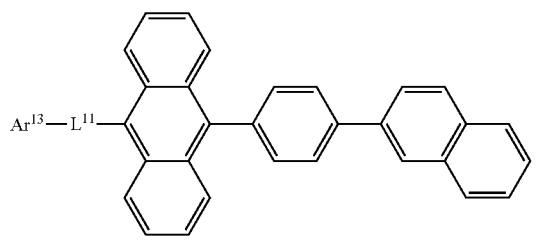

(30)
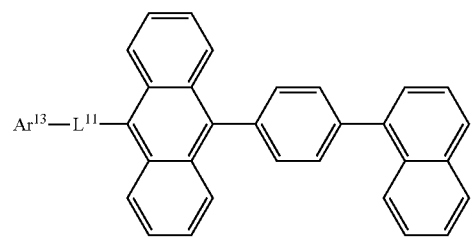

(31)
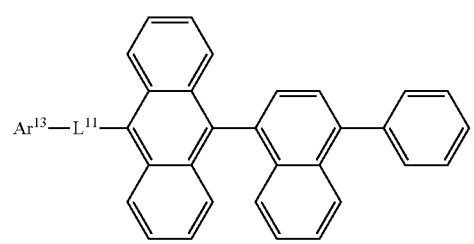

(32)
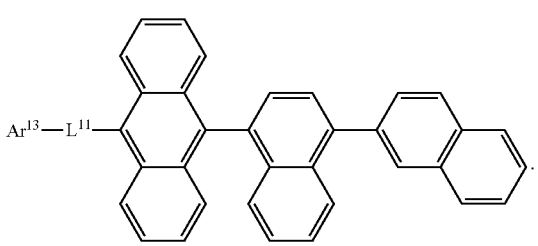

In formula (25) to (32), $Ar^{13}$ and $L^{11}$ are the same as $Ar^{13}$ and $L^{11}$ of formulae (21) to (24).

Examples of the anthracene derivative represented by any of formulae (19), (20), (21) to (24), and (25) to (32) are shown below.

The six membered rings in the following compounds are all benzene rings.

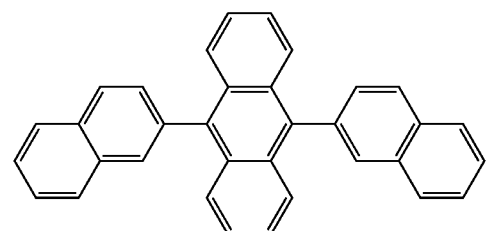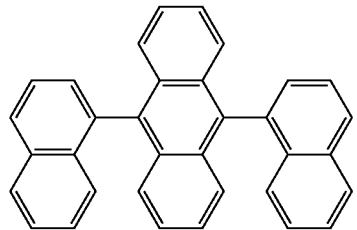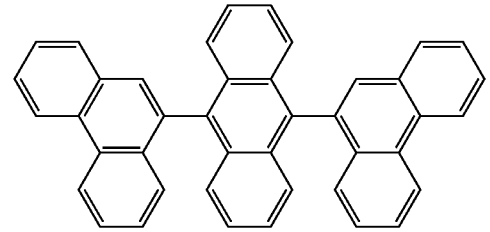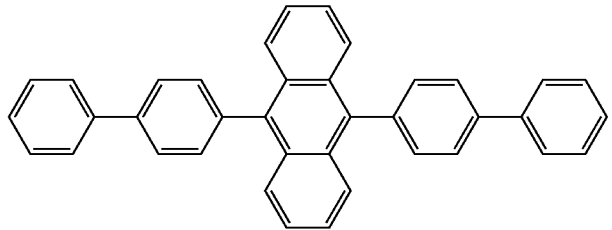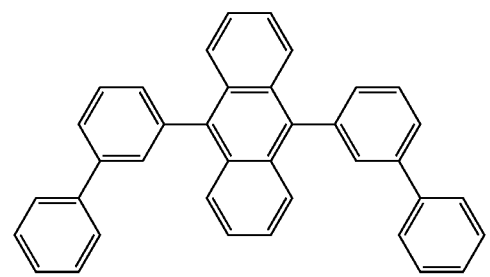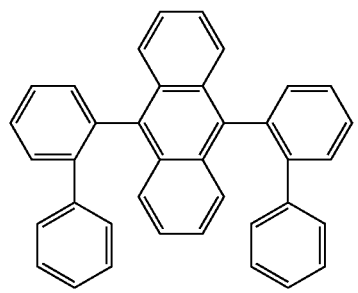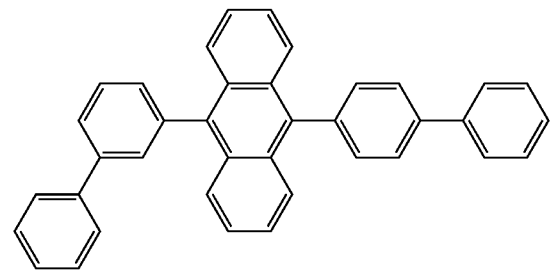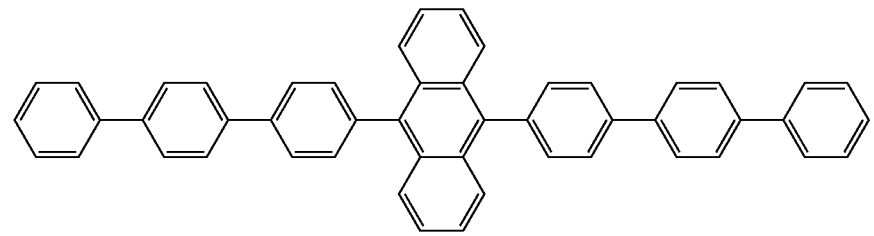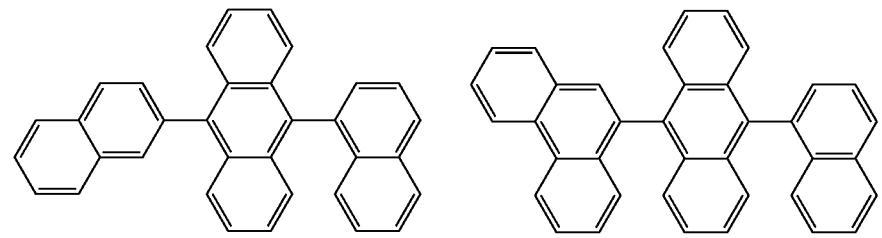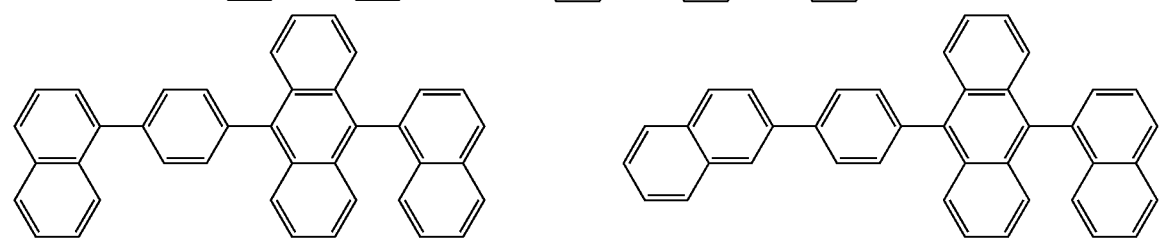

437 438
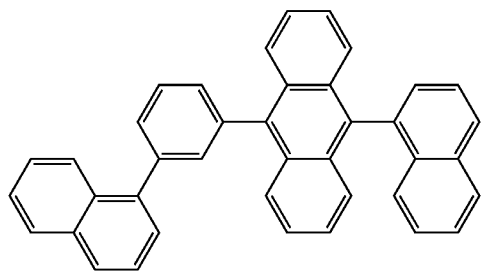 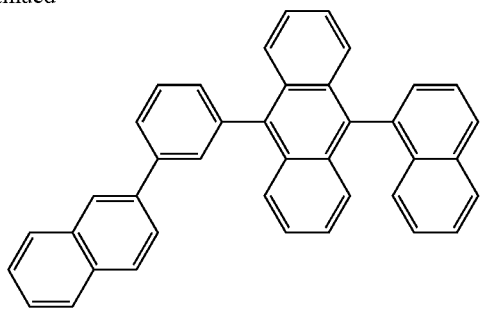
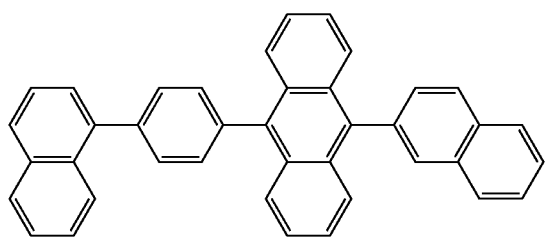 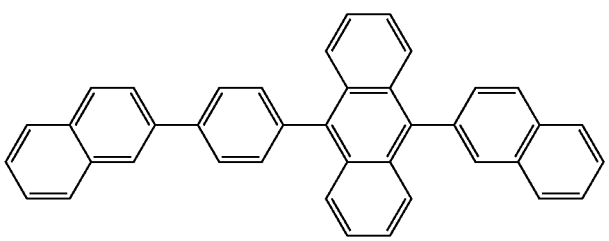
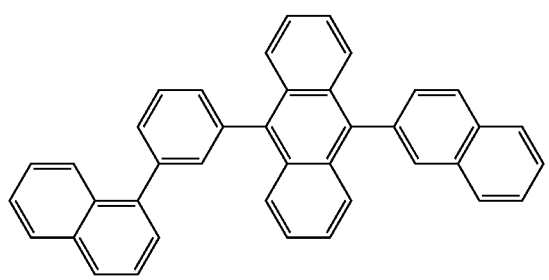 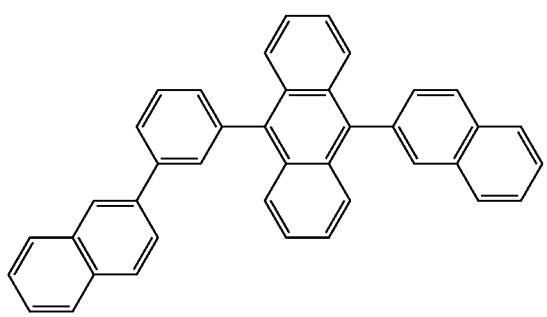
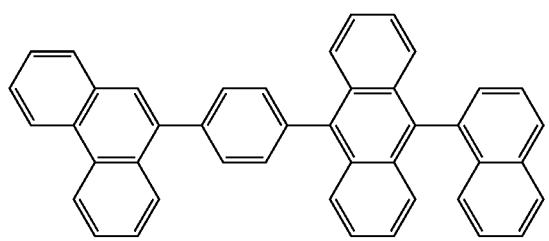 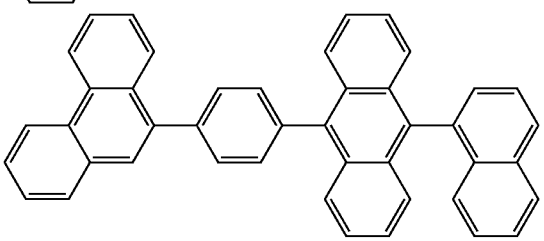
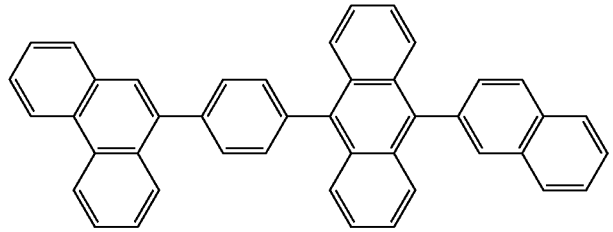 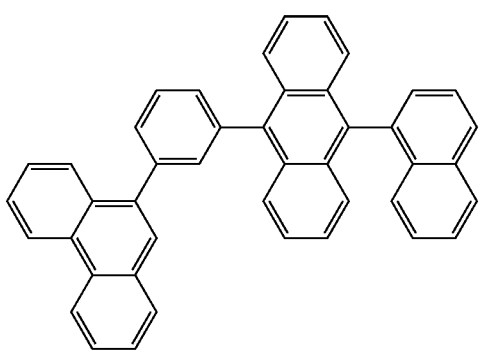

439 440
-continued
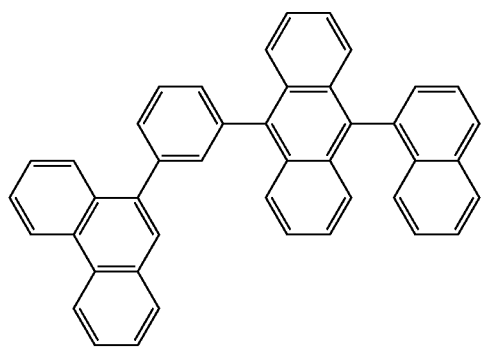 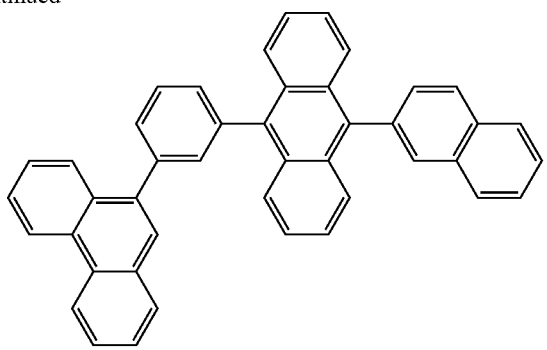
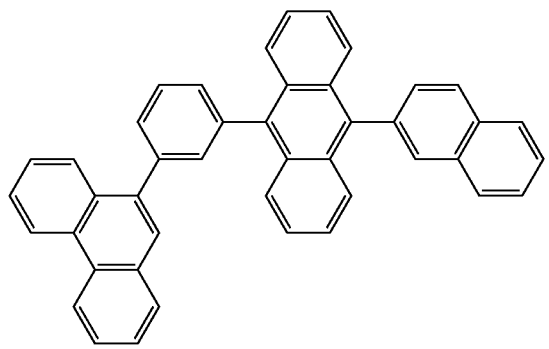 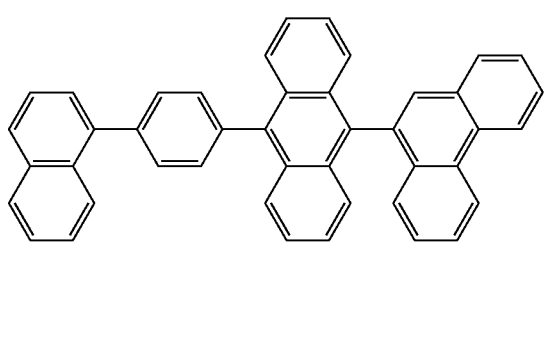
 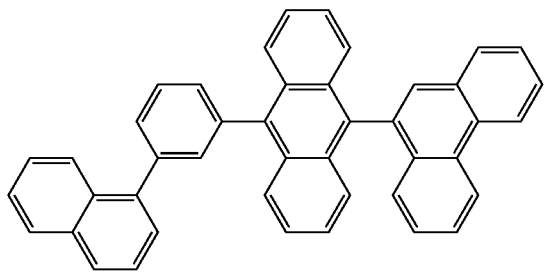
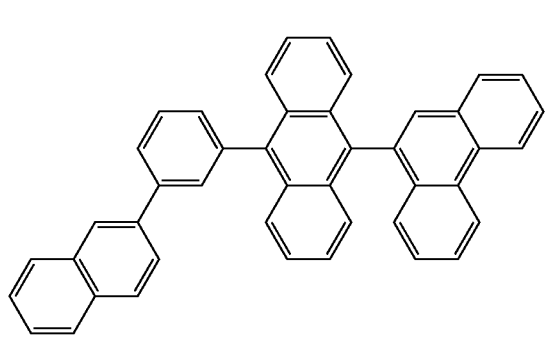 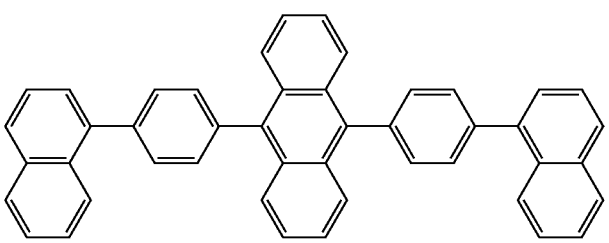
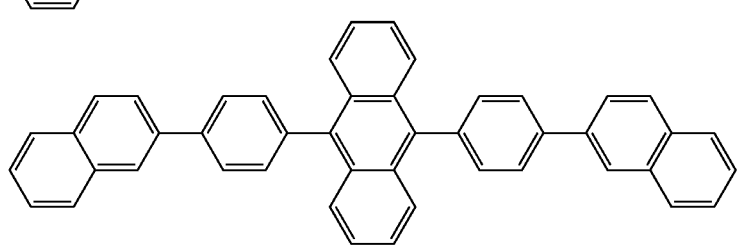

441
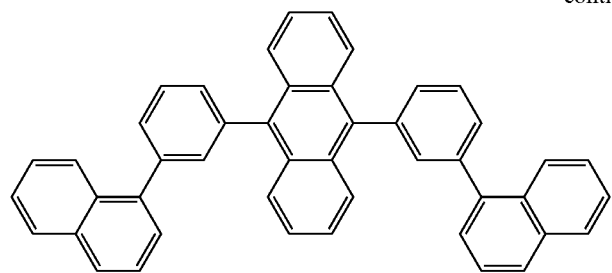
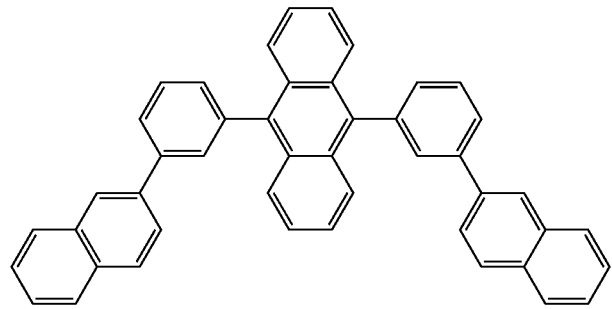
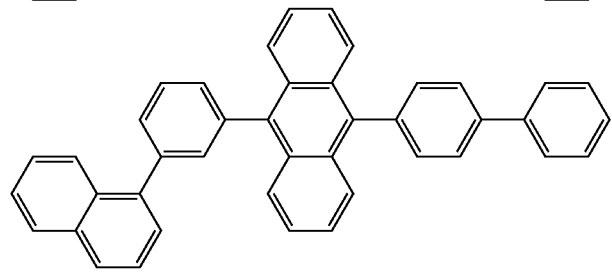
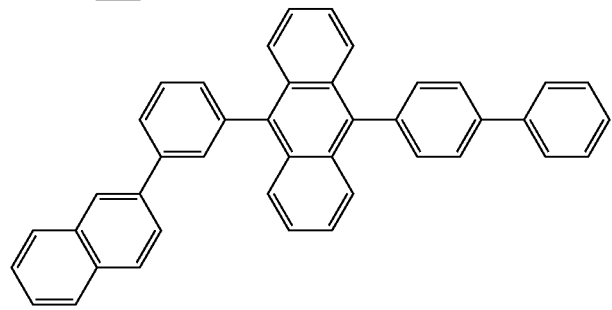
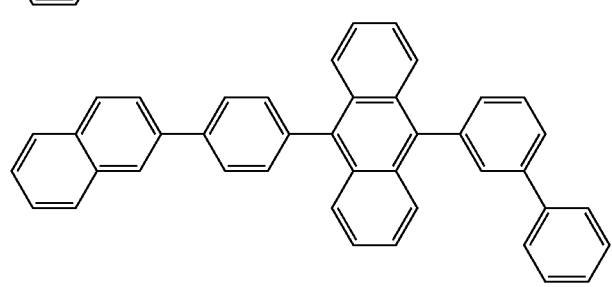
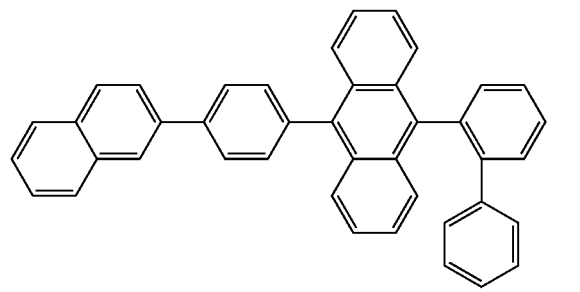
442
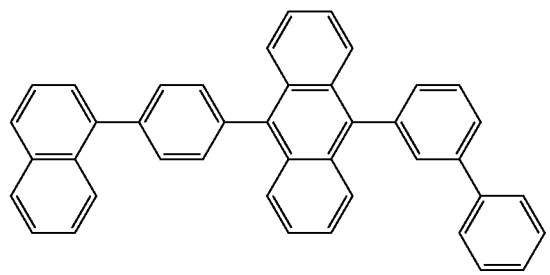
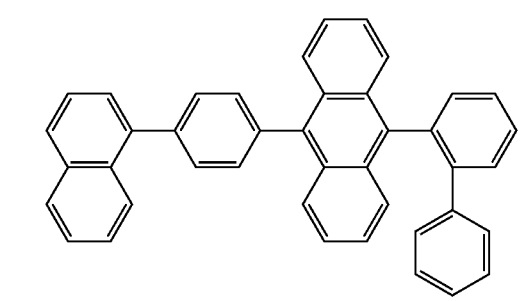
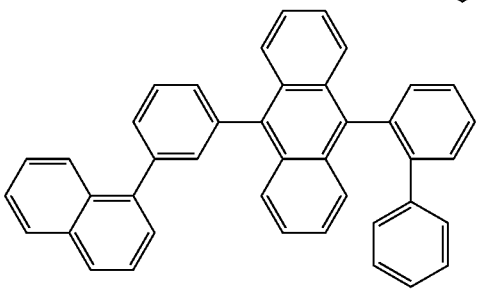

-continued
| 443 | 444 |
|---|---|
| 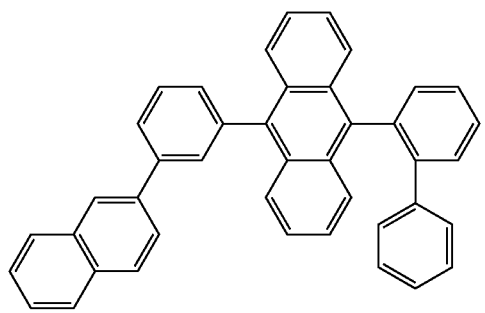 | 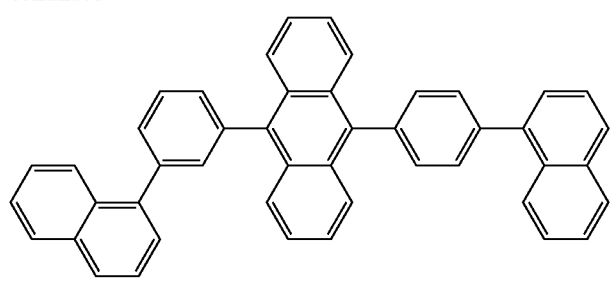 |
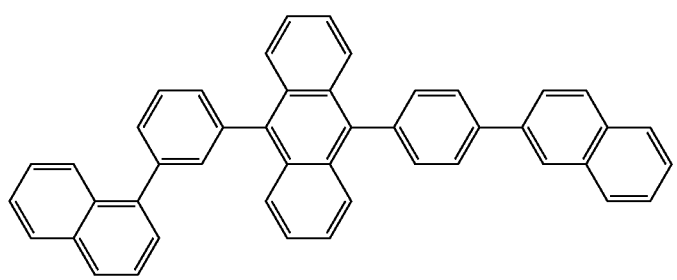
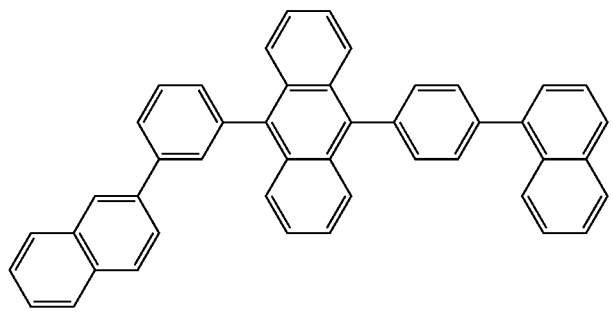
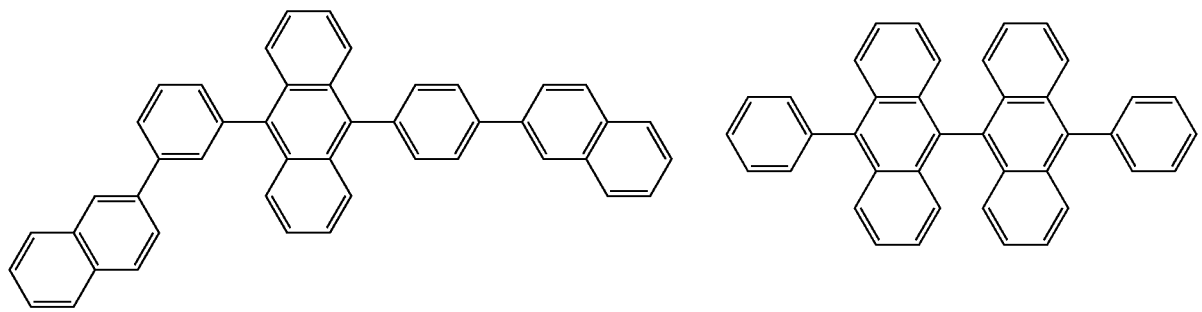
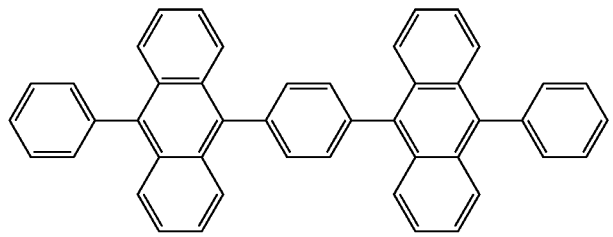 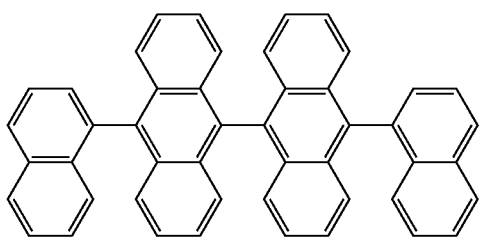
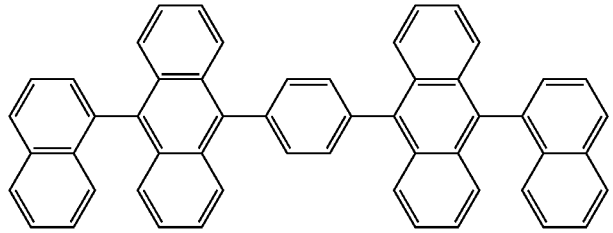

445
446
-continued
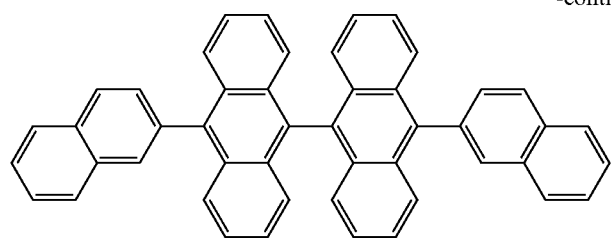
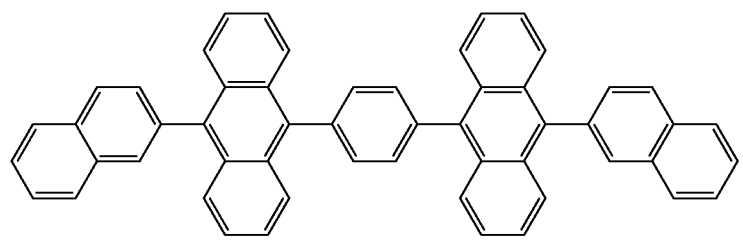
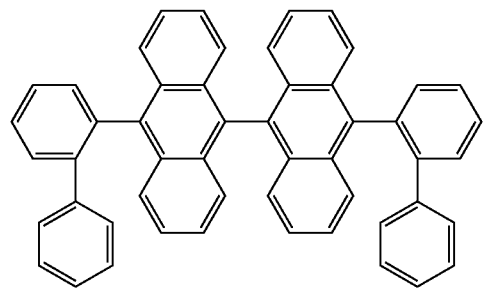
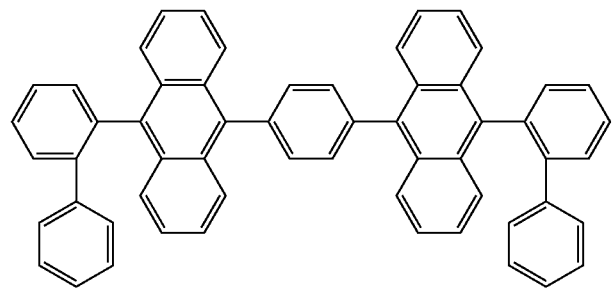
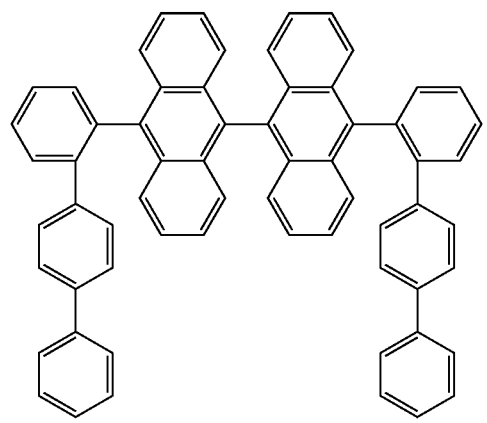
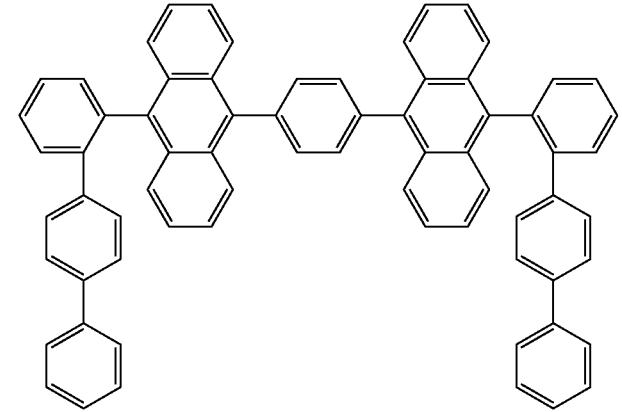

The six membered rings in the following compounds are all benzene rings.
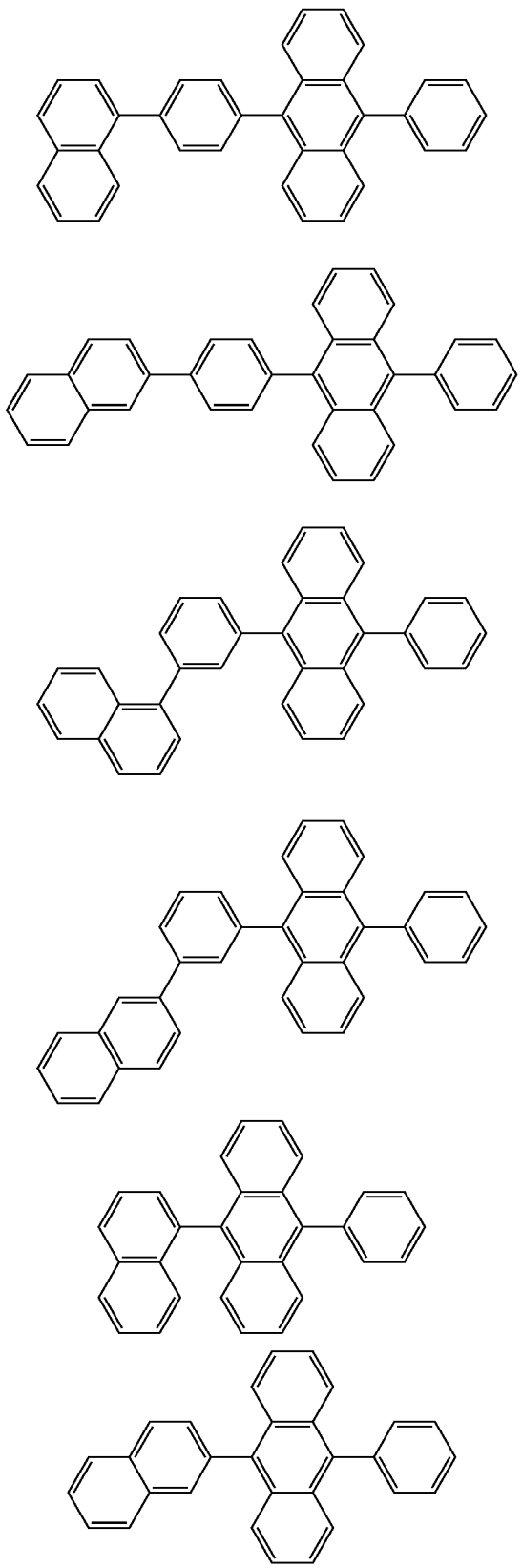
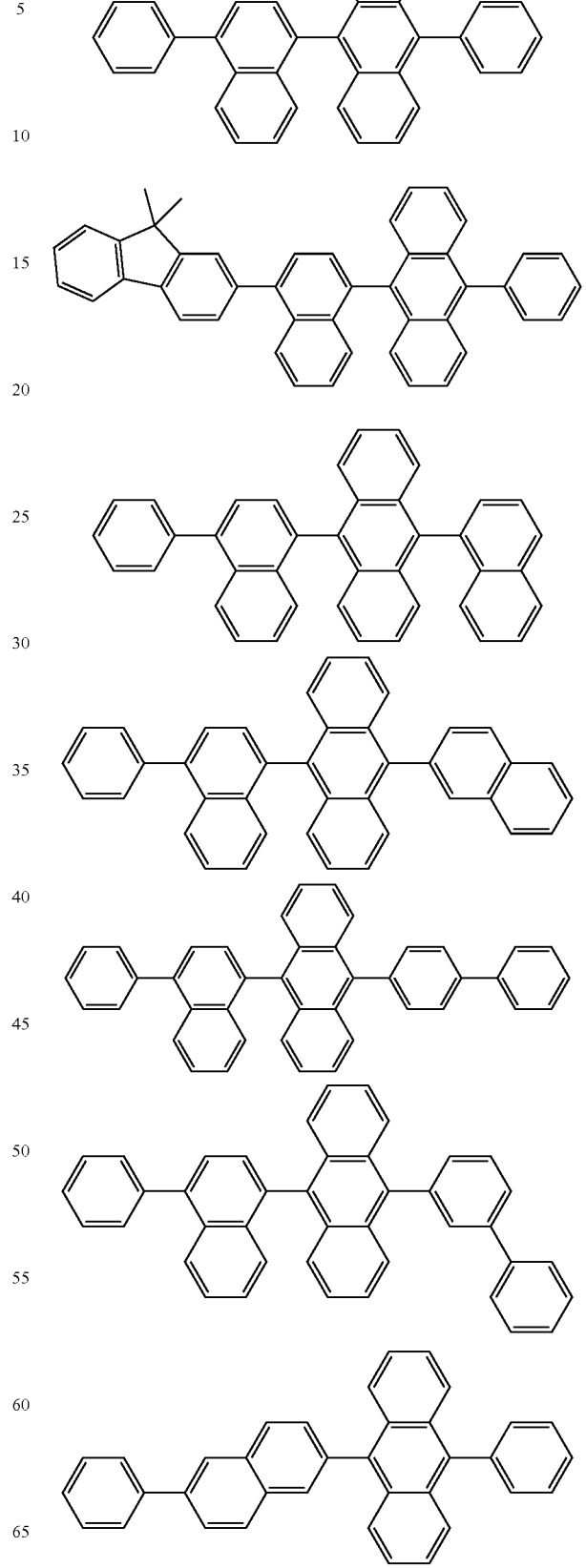

449
-continued
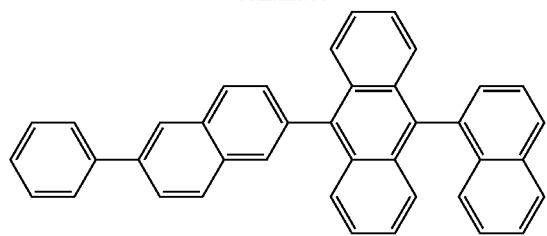
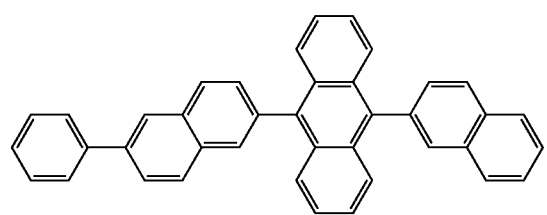
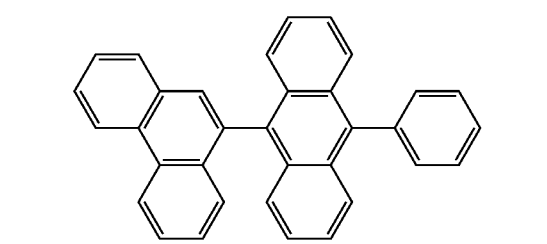
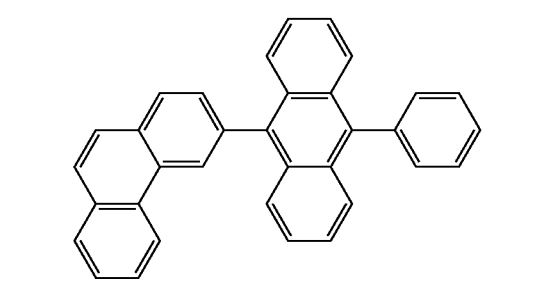
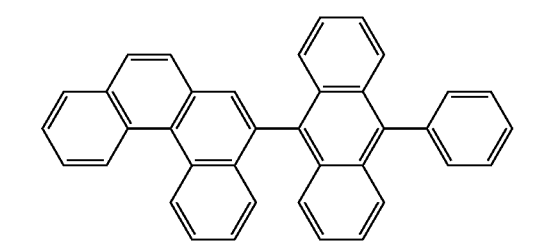
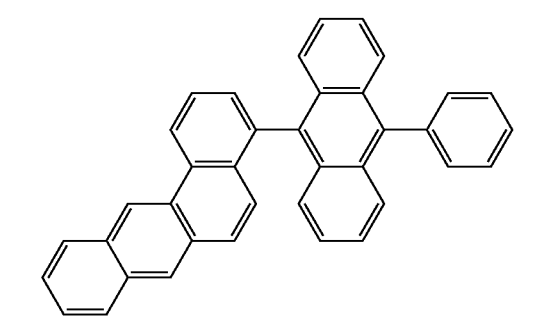
450
-continued
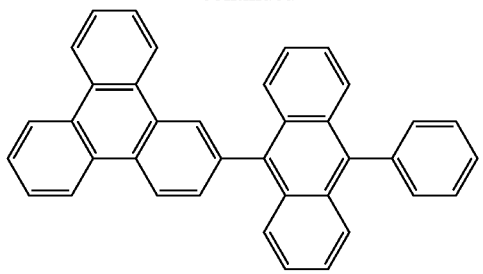
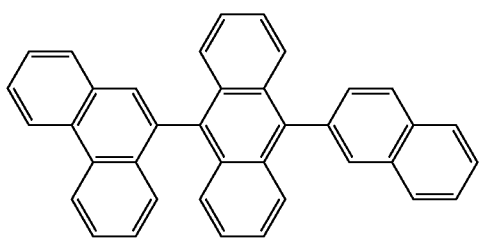
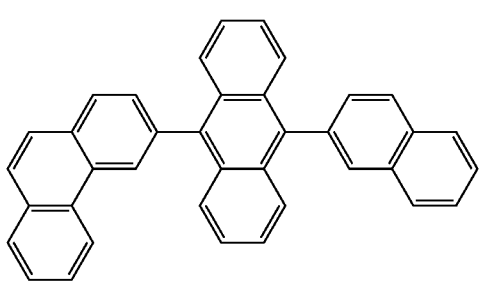
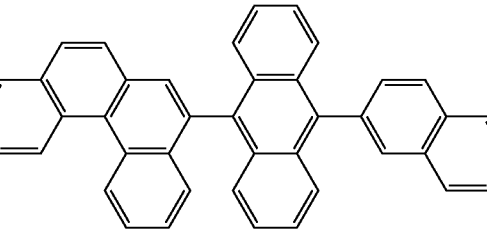
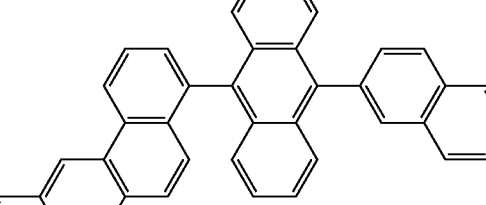
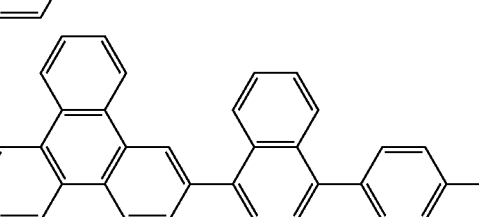

451
-continued
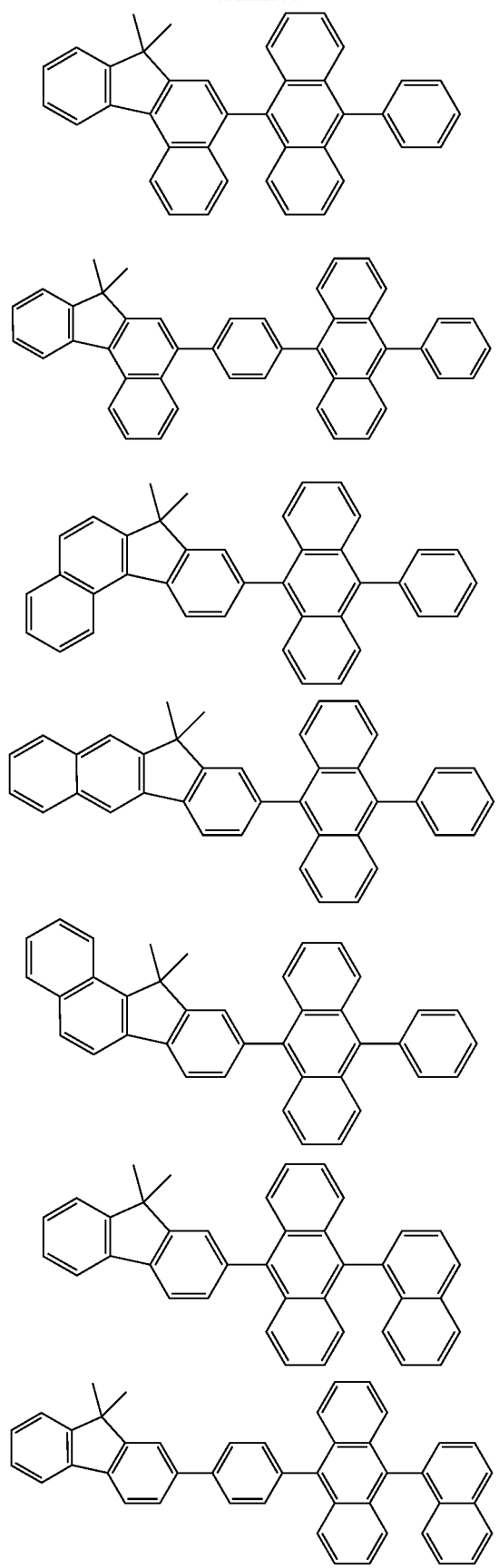
452
-continued
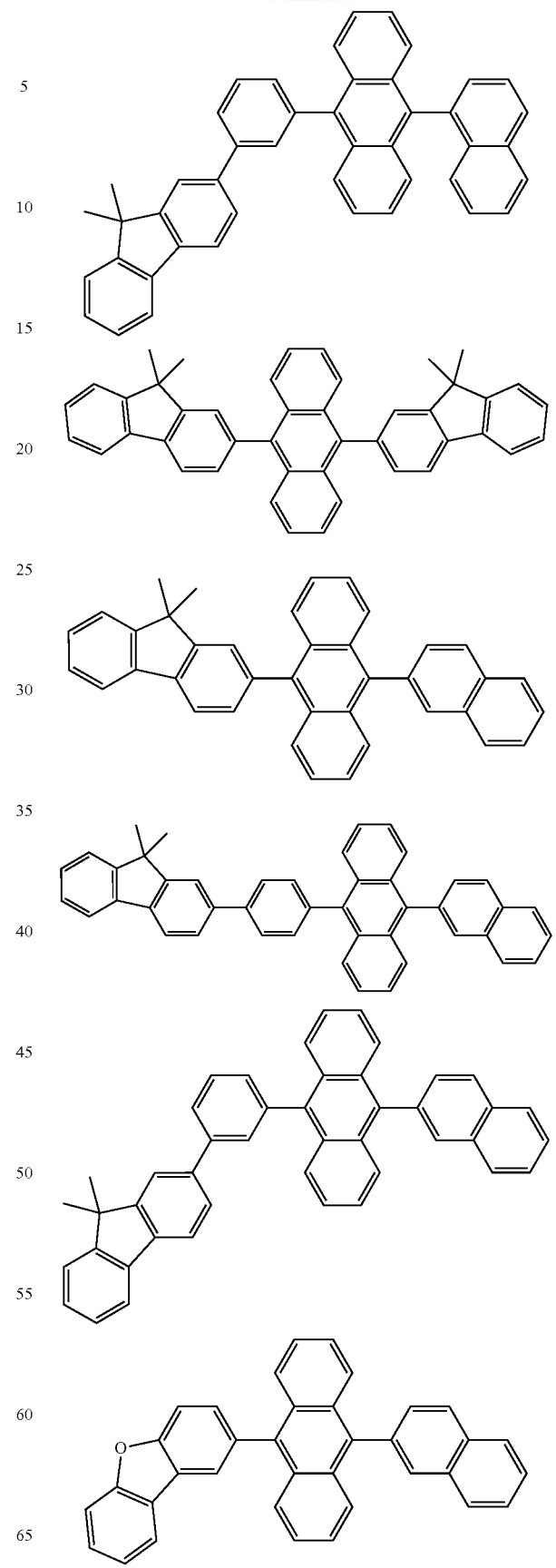

453
-continued
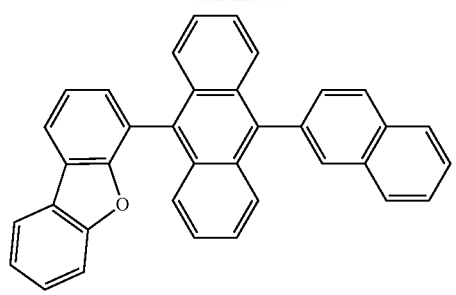
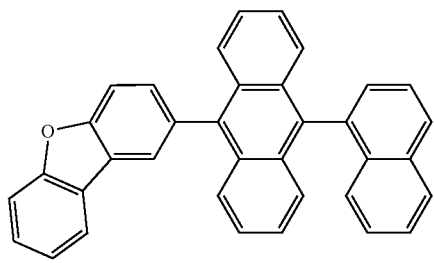
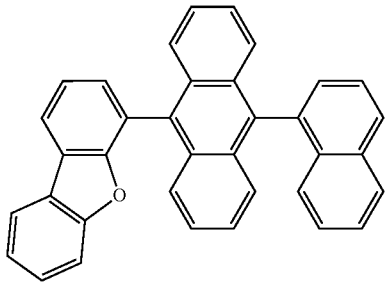
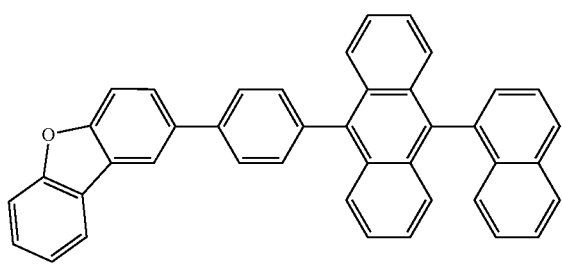
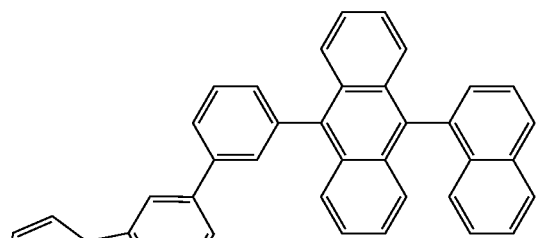
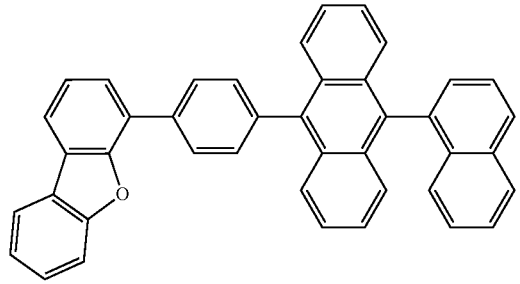
454
-continued
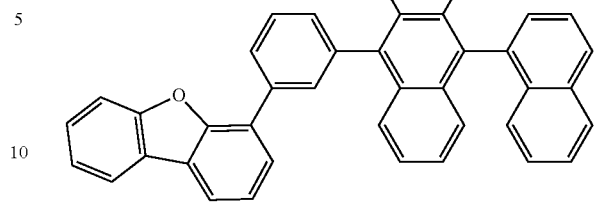
The six membered rings in the following compounds are all benzene rings.
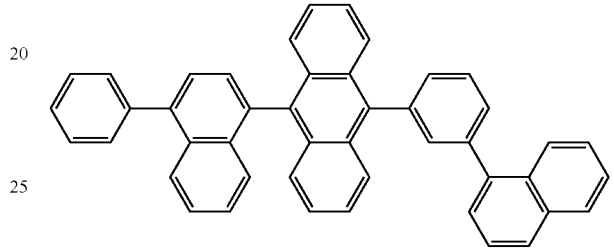
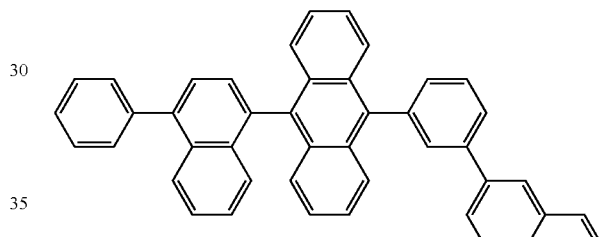
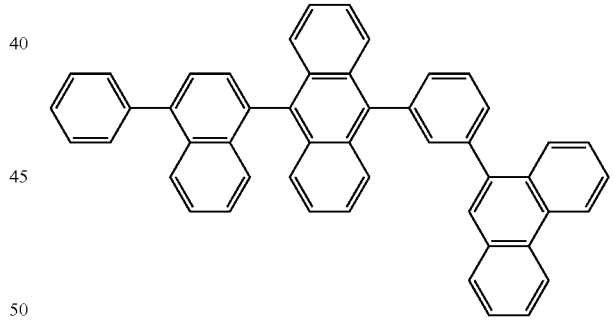
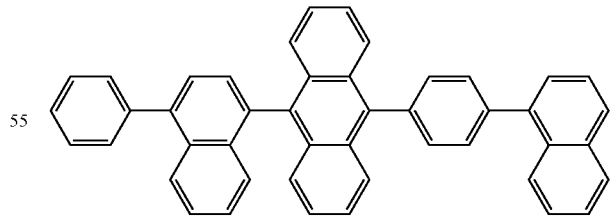
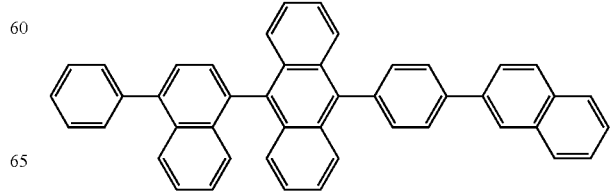

455
-continued
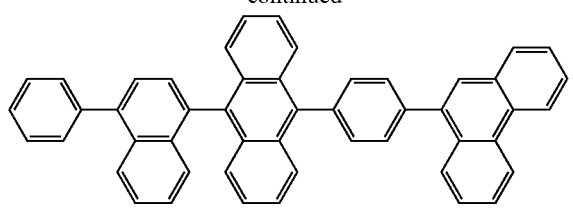
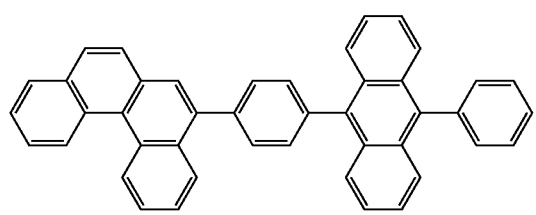
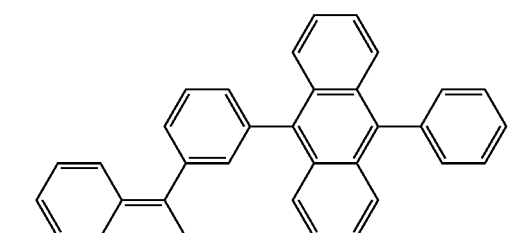
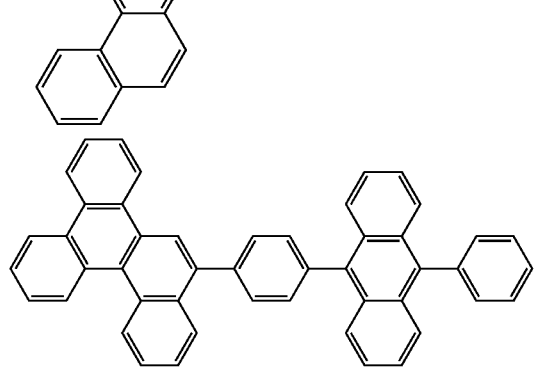
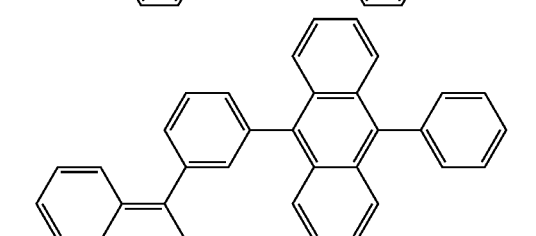
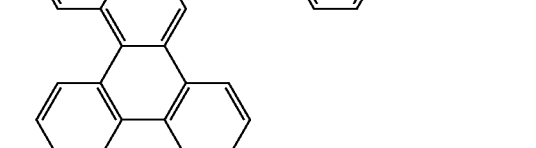
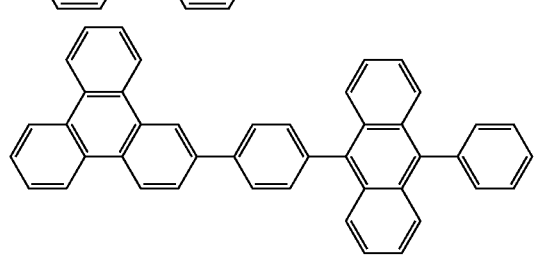
456
-continued
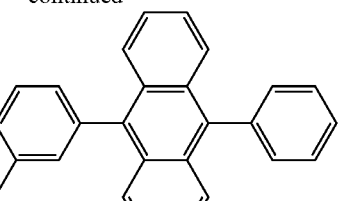
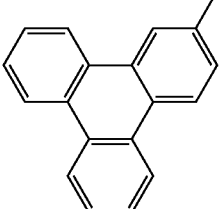
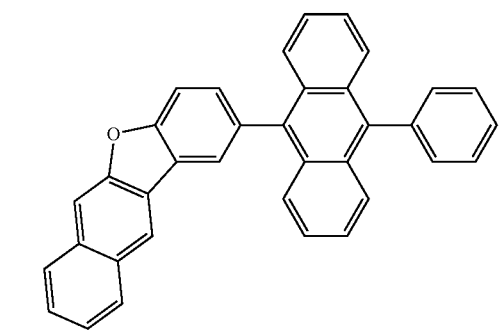
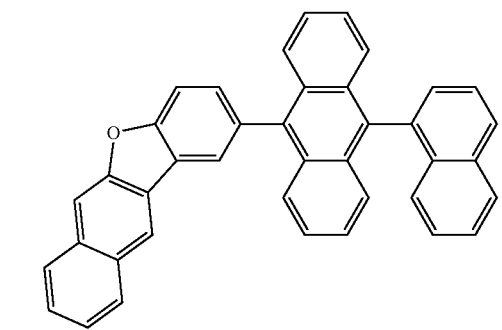
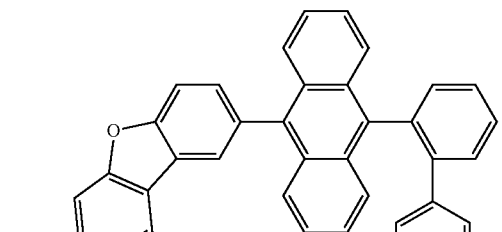
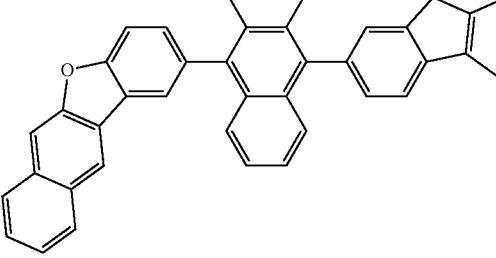

457
-continued
458
-continued
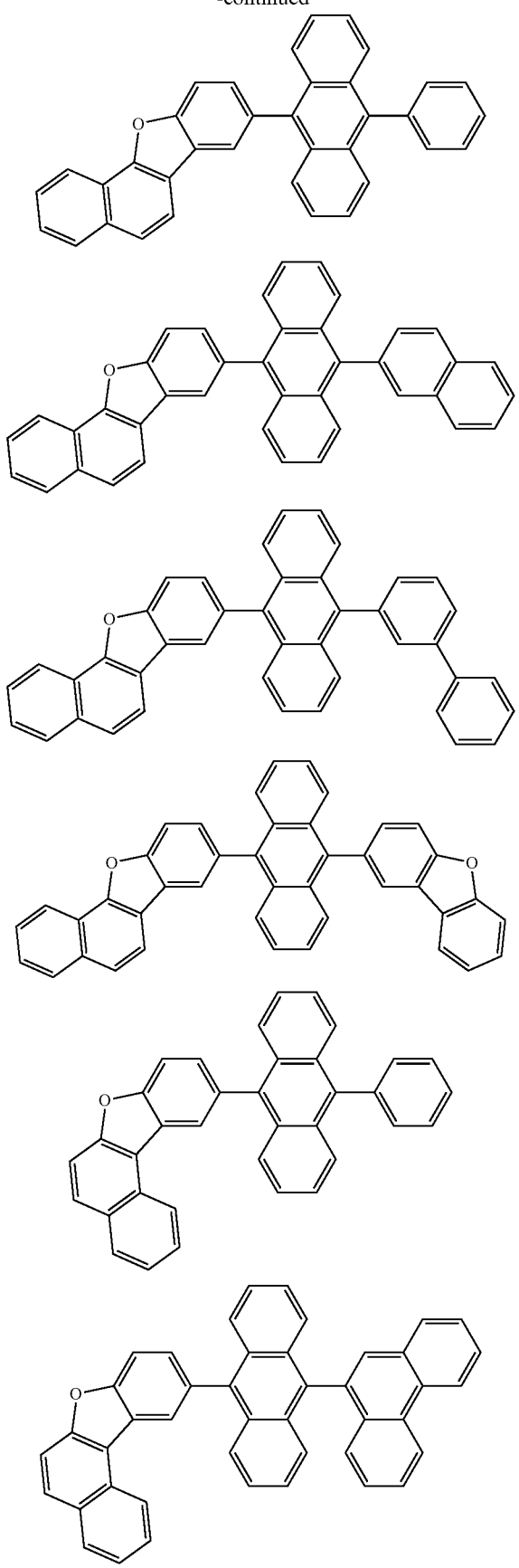
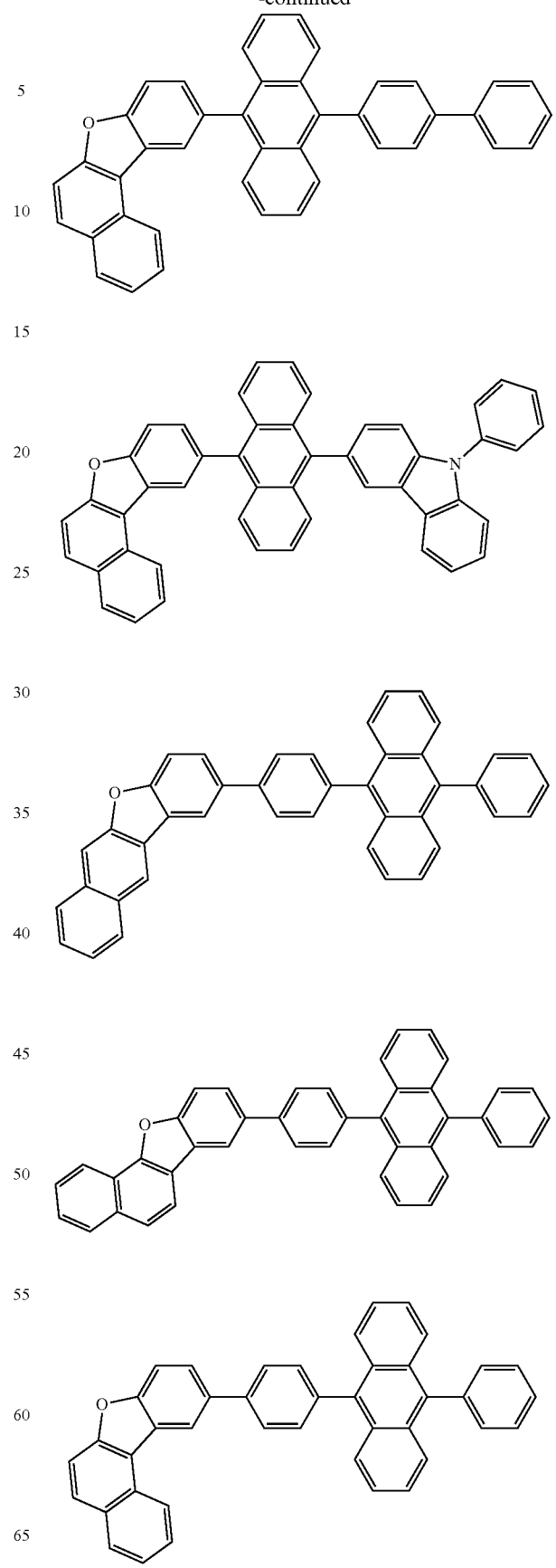

459
-continued
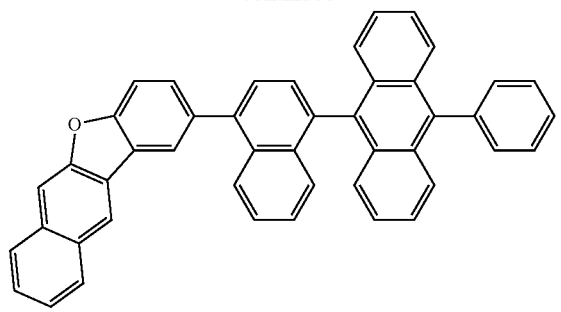
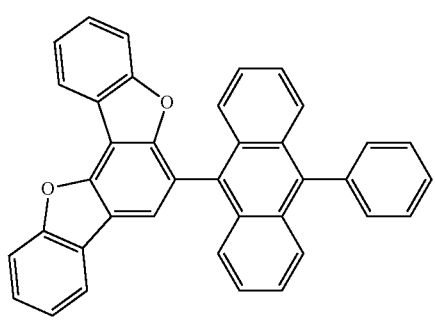
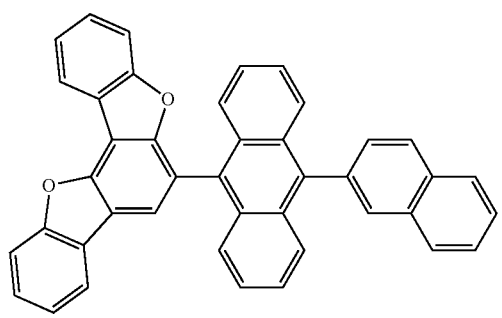
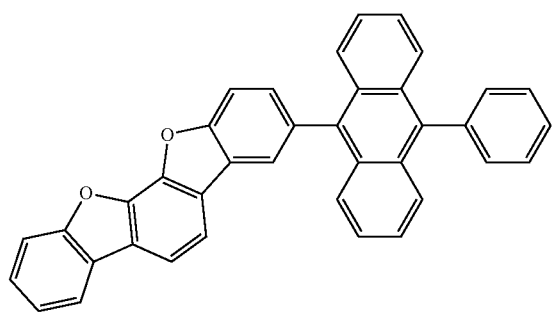
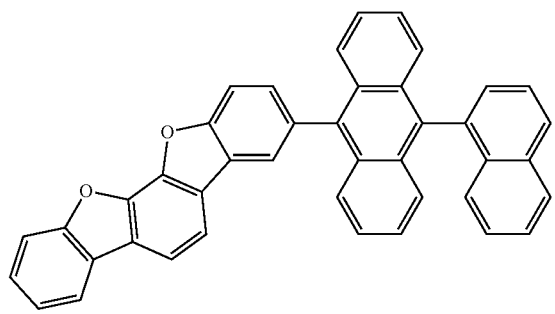
460
-continued
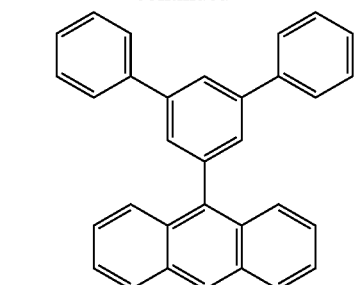
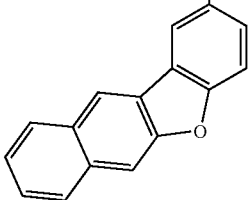
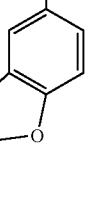

461
-continued
462
-continued
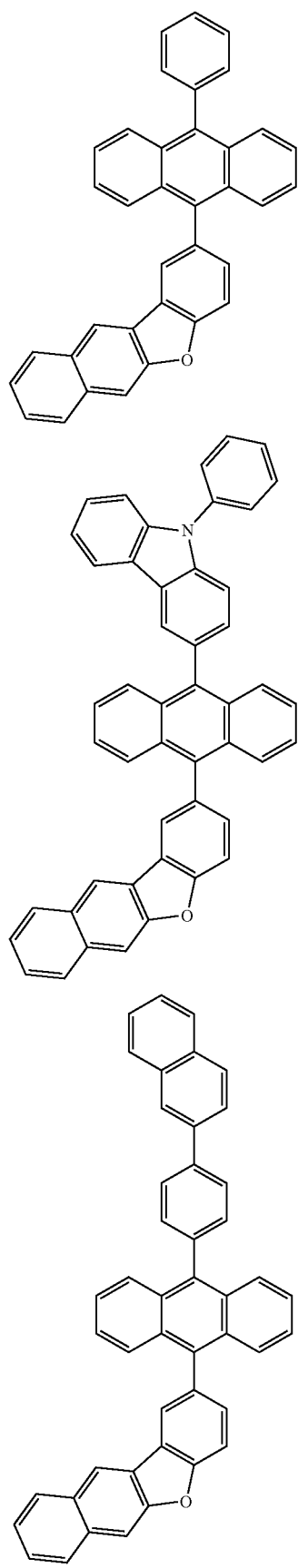
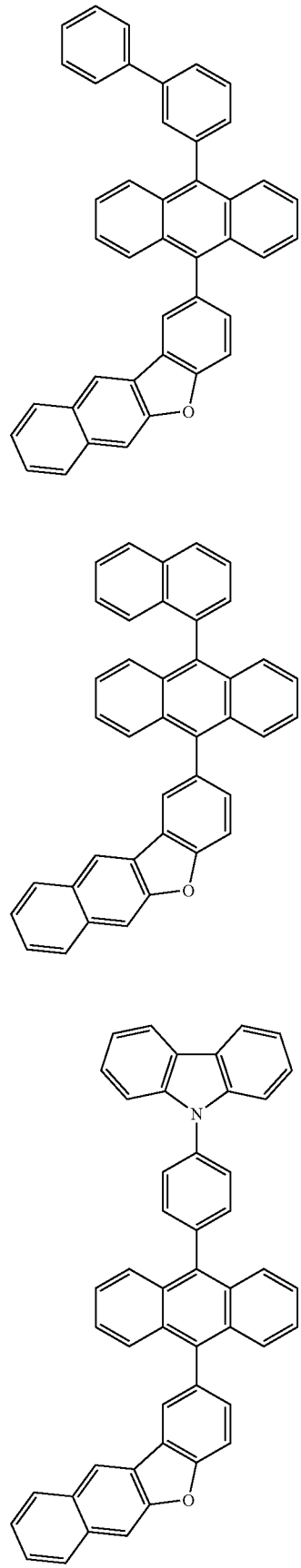

463
-continued
464
-continued
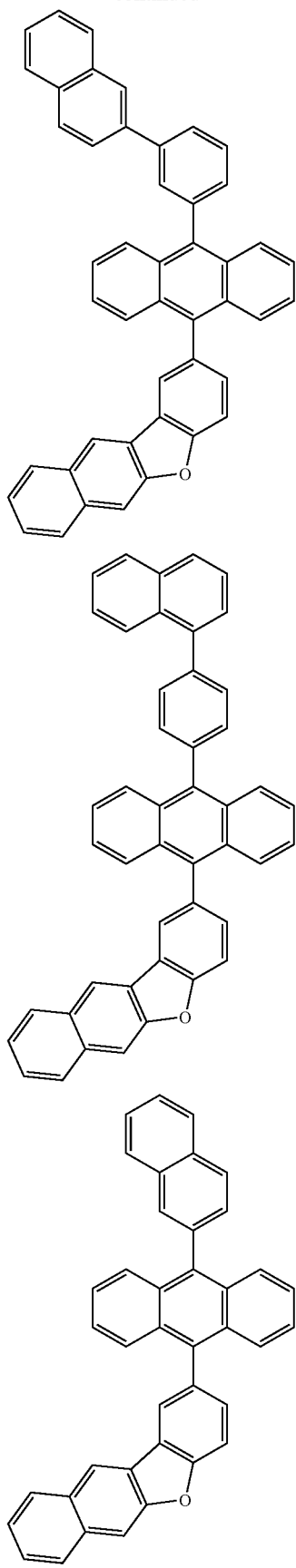

465
-continued
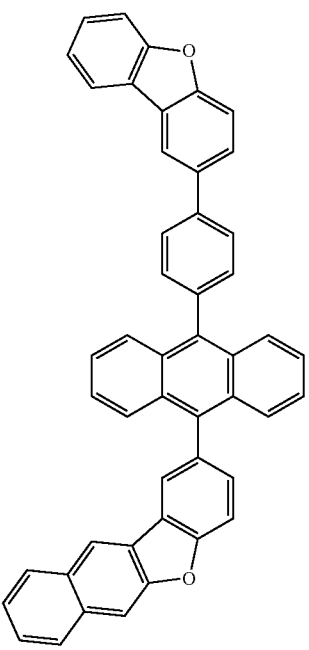
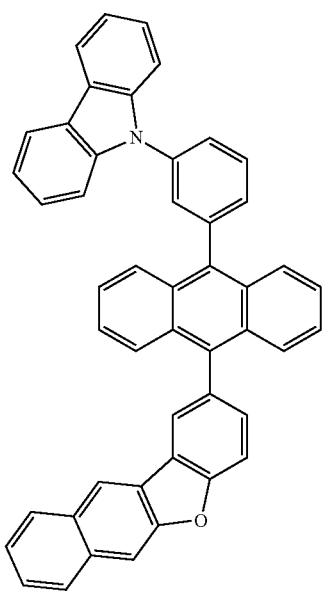
466
-continued
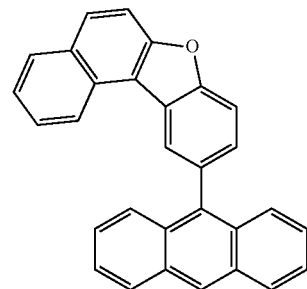
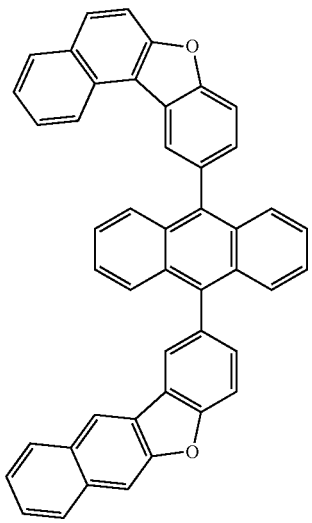
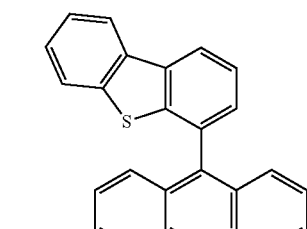
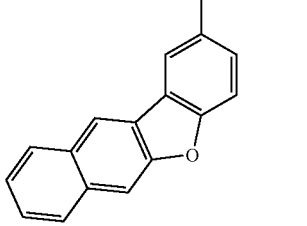
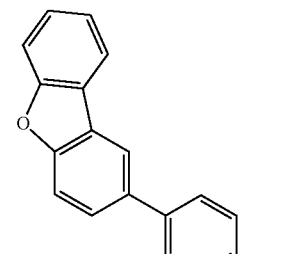
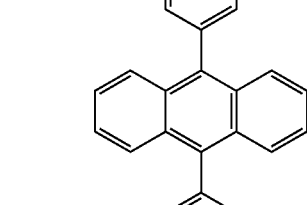
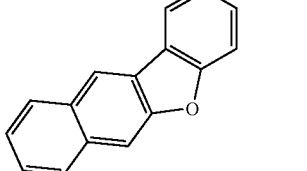

467
-continued
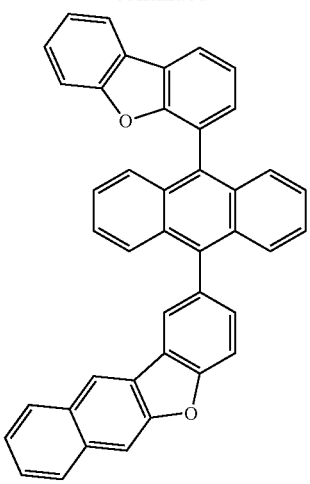
468
-continued
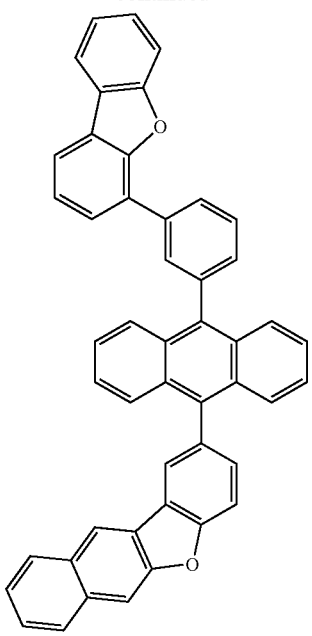
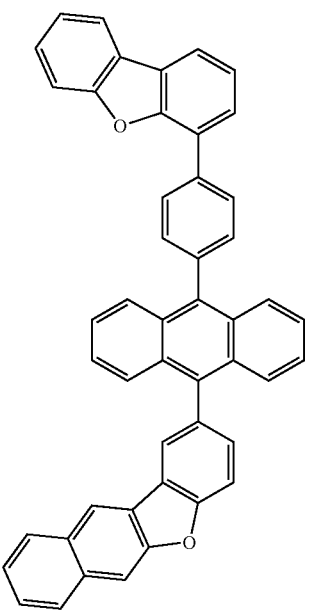

469
-continued
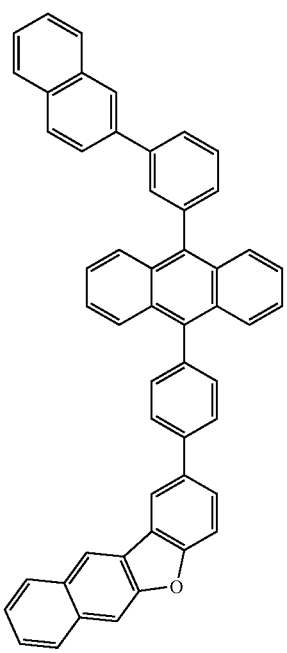
470
-continued
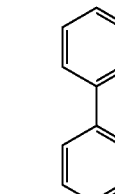
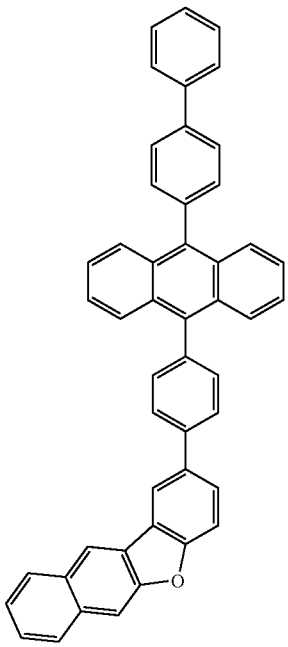
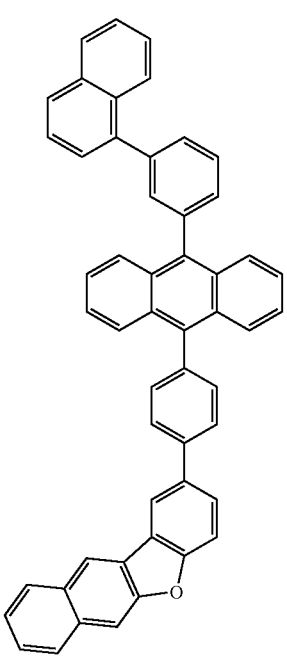
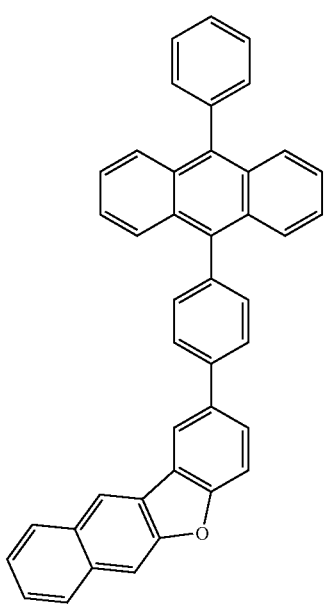

471
-continued
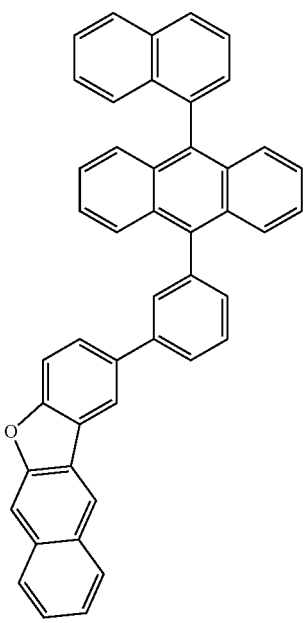
472
-continued
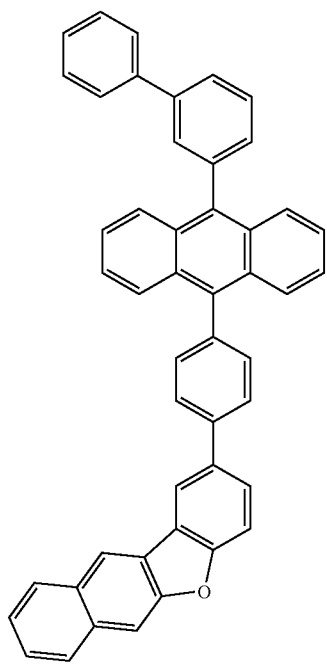
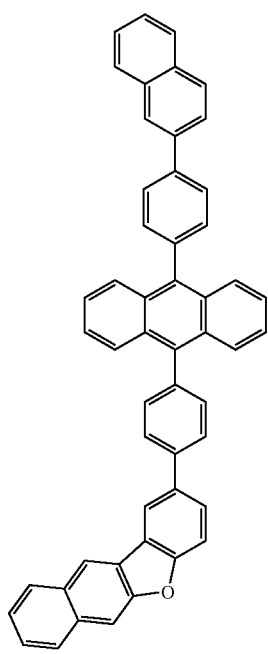
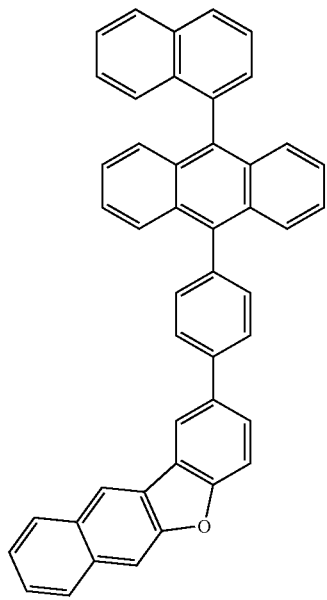

473
-continued
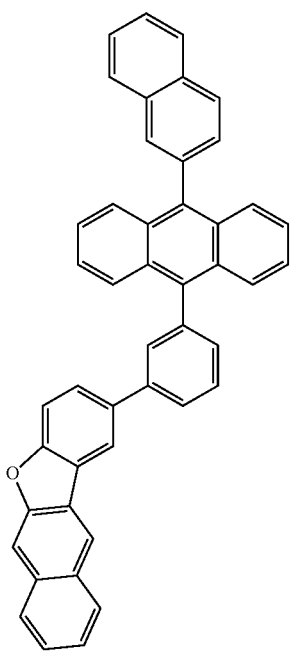
474
-continued
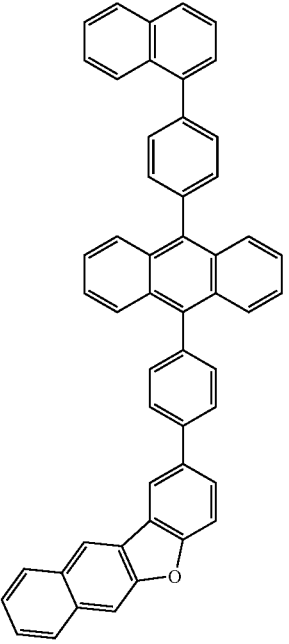
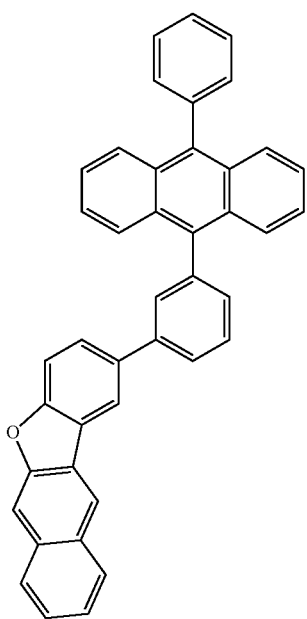
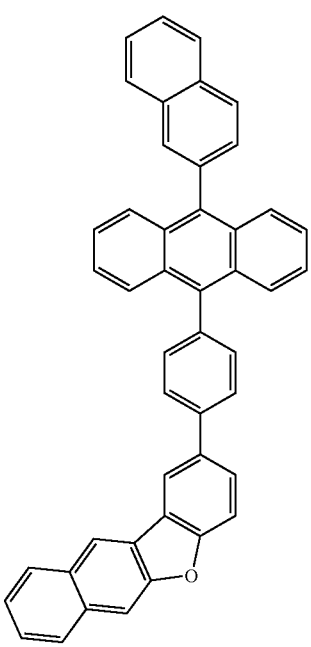

475
-continued
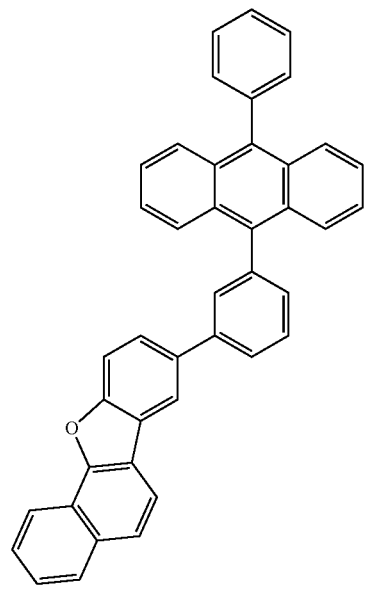
476
-continued
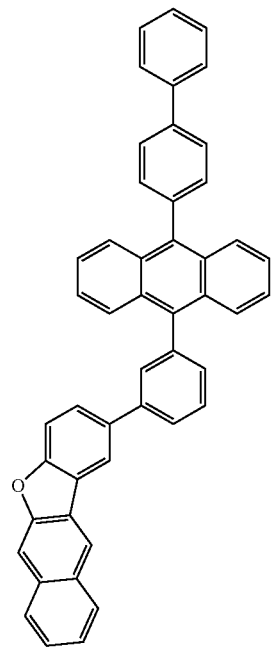
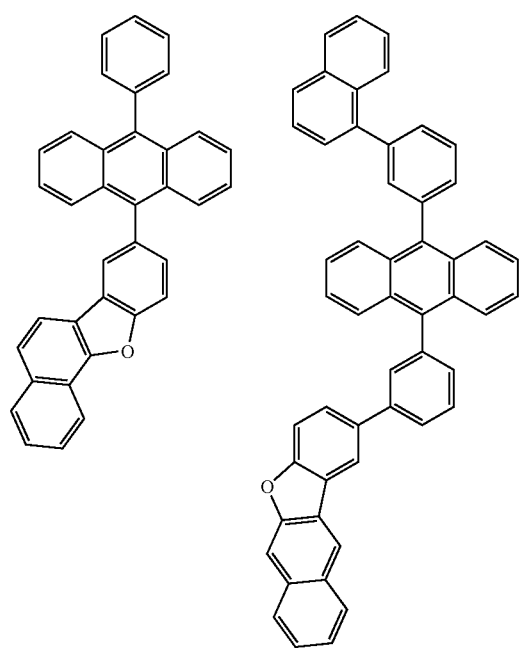
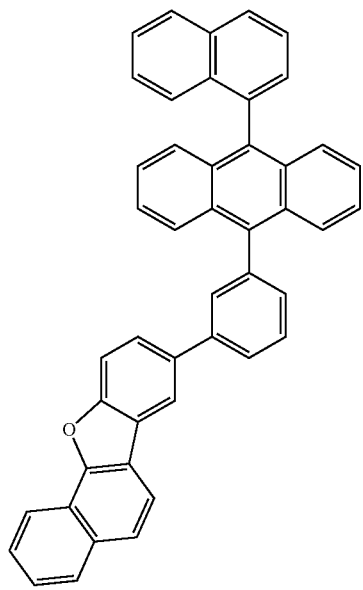

477
-continued
478
-continued
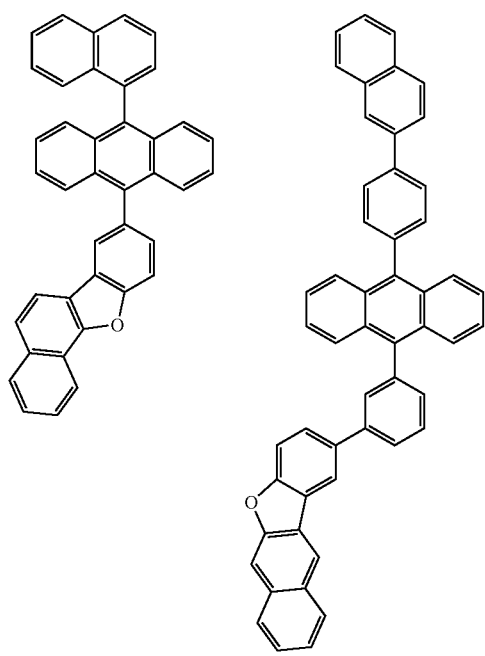

479
-continued
480
-continued
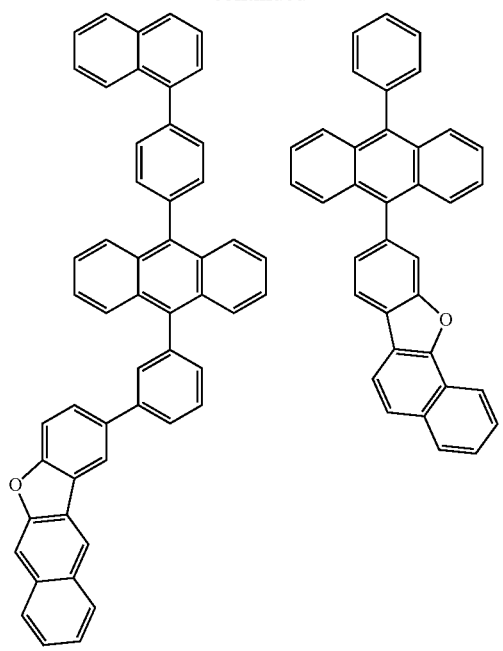
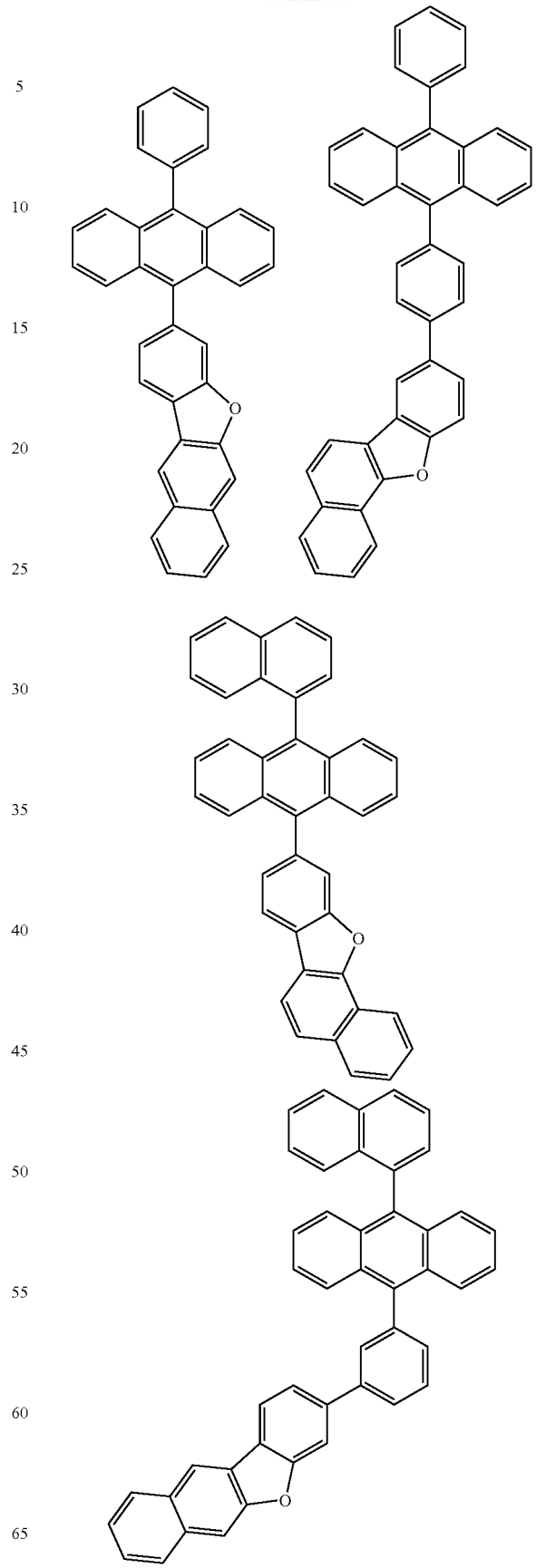

481
-continued
482
-continued
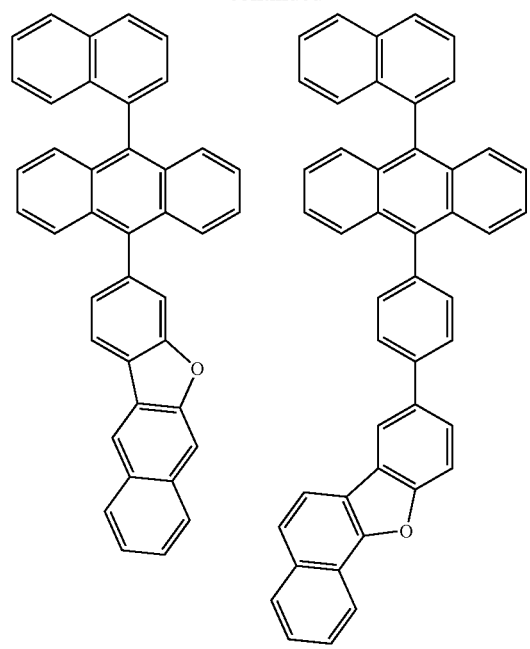
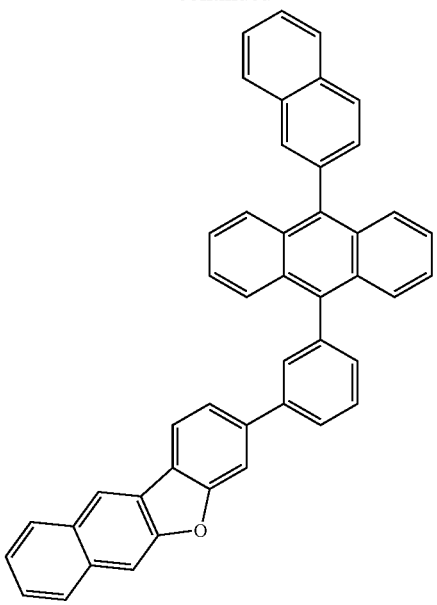
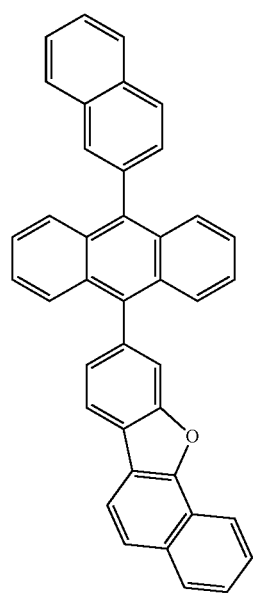
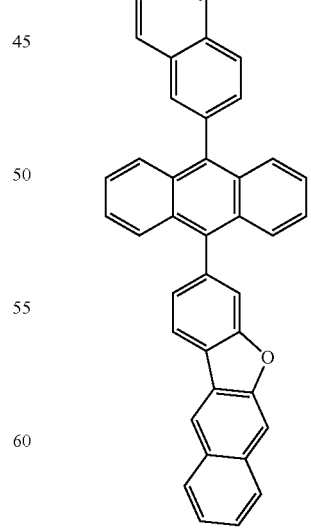
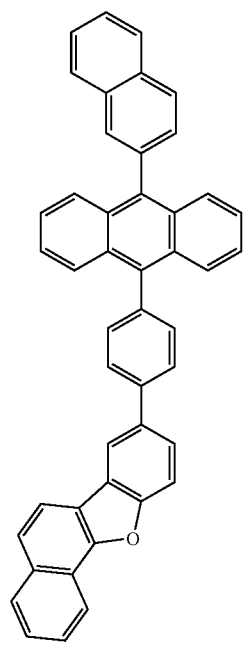

483
-continued
484
-continued
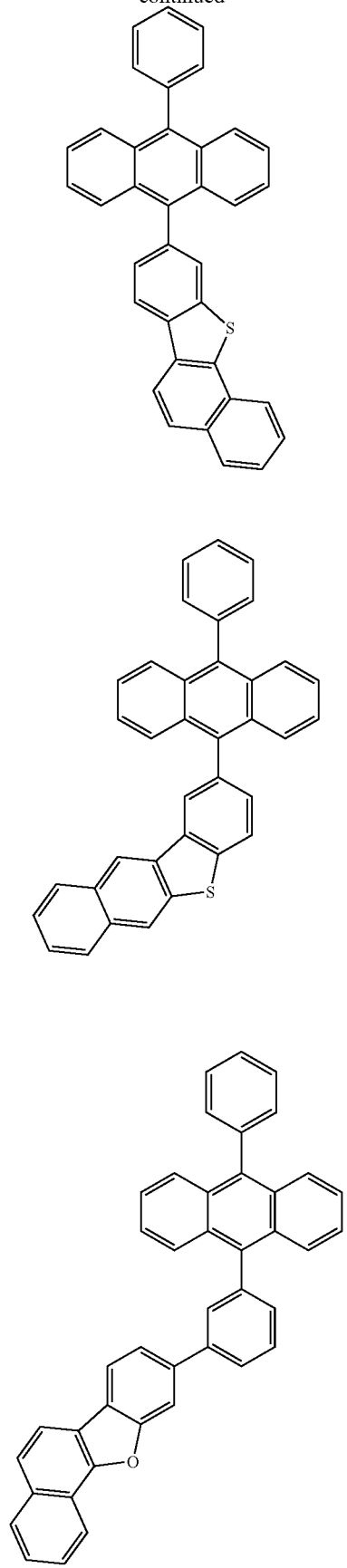
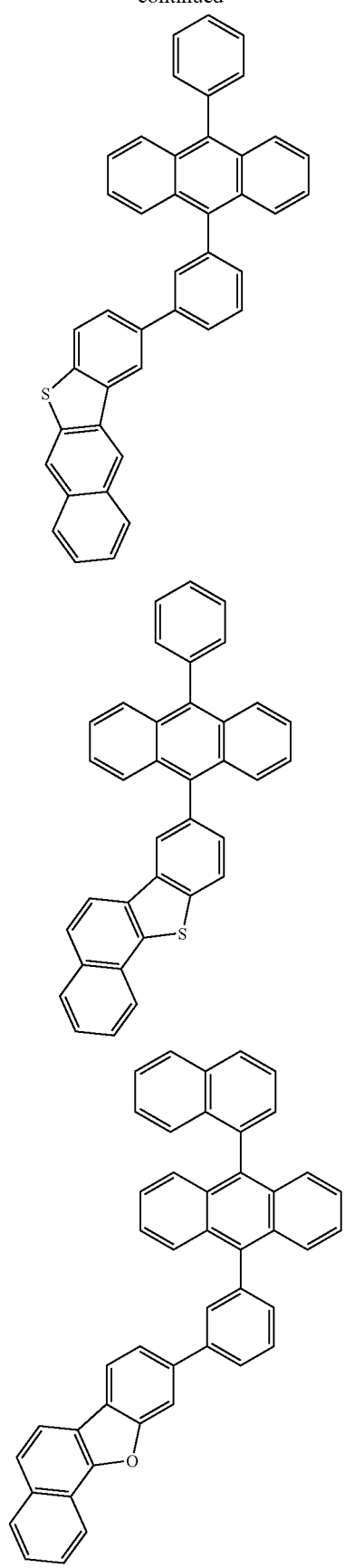

485
-continued
486
-continued
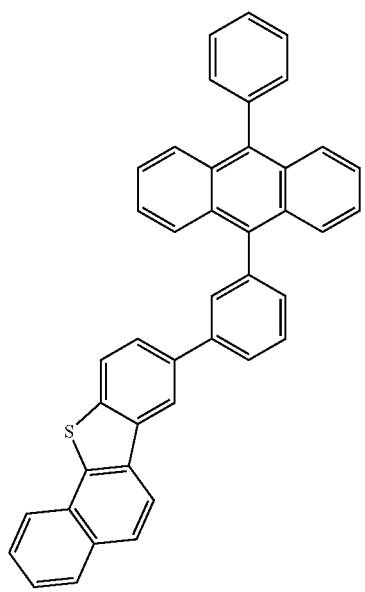
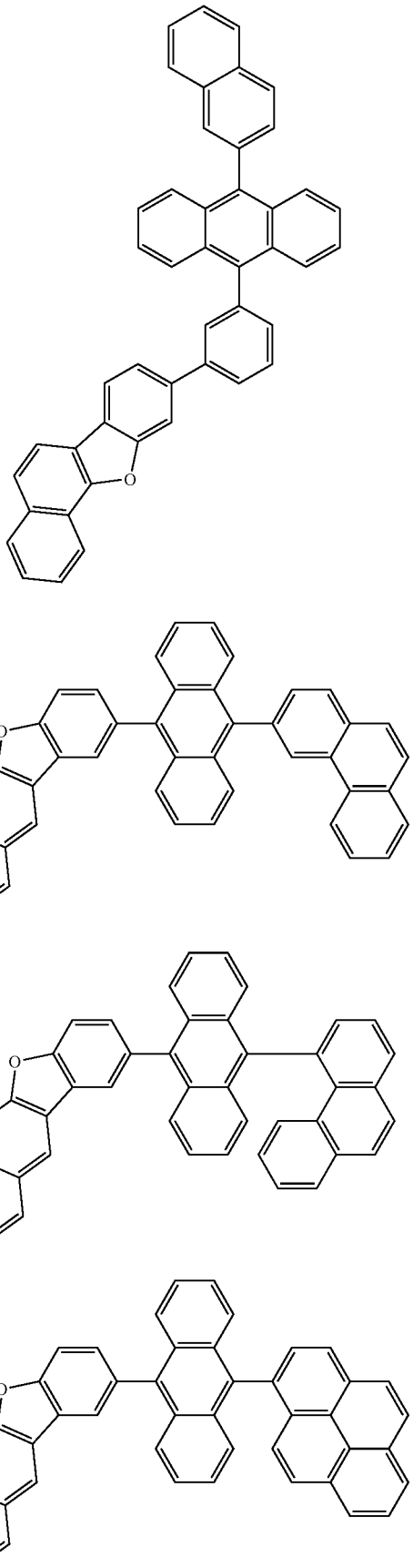
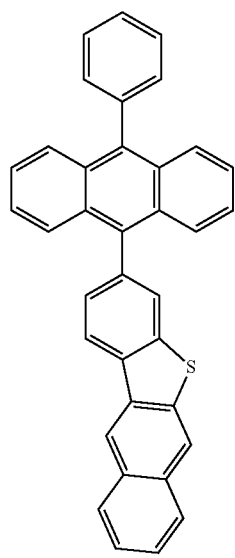

487
-continued
488
-continued
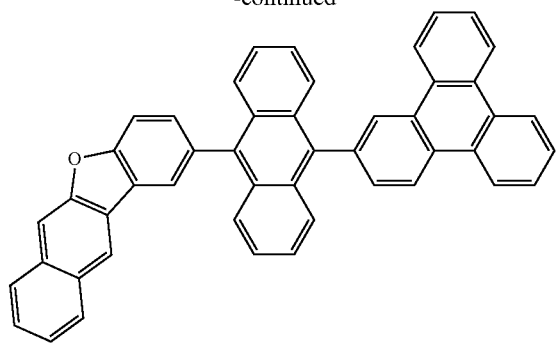
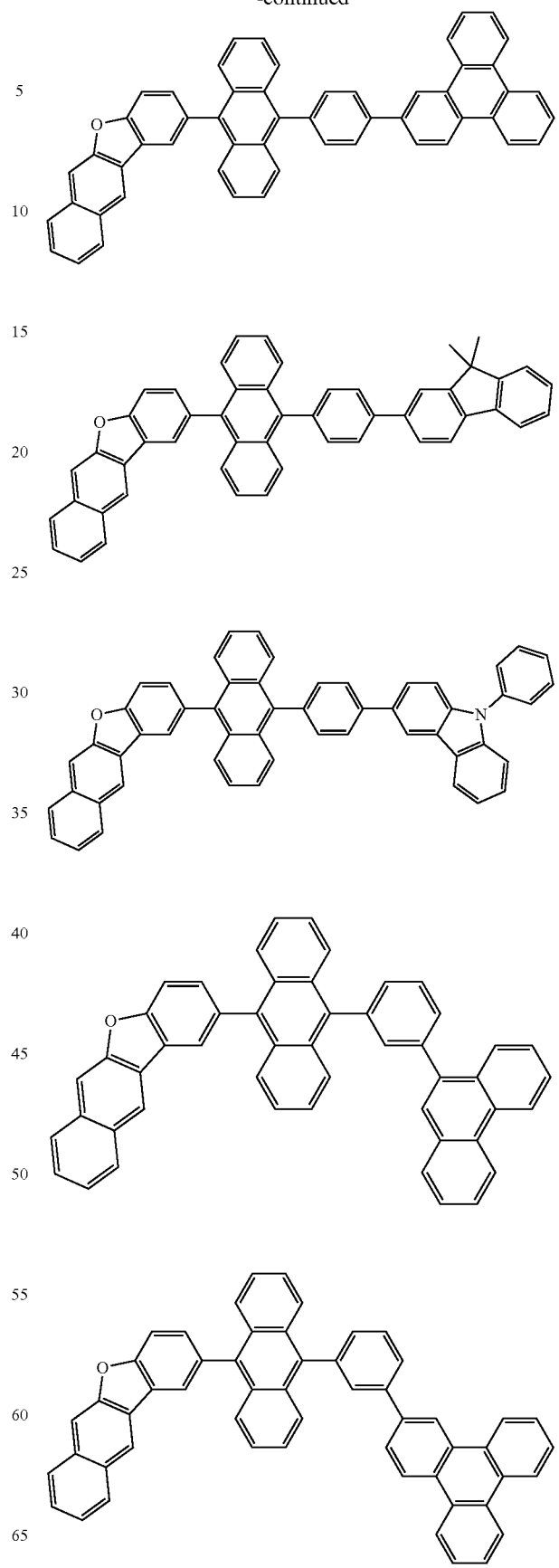

489
-continued
490
-continued
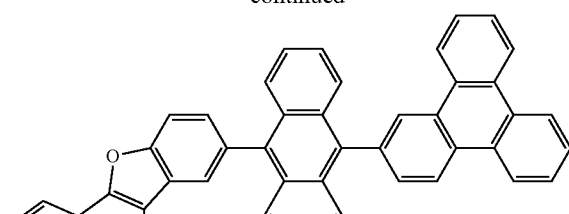
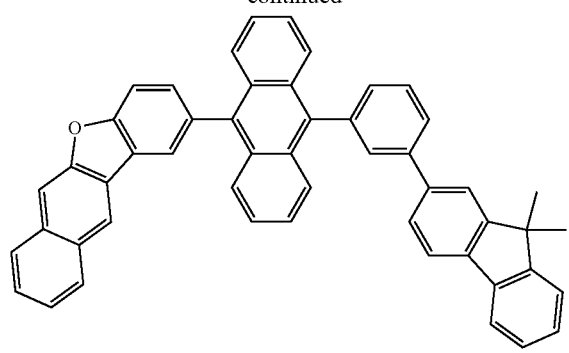
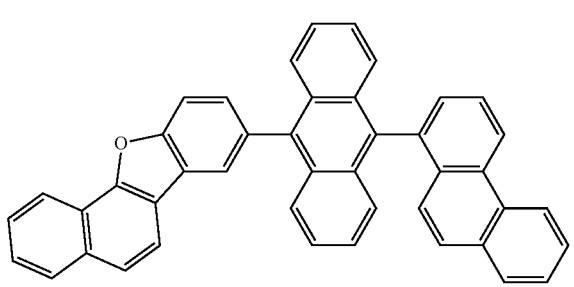
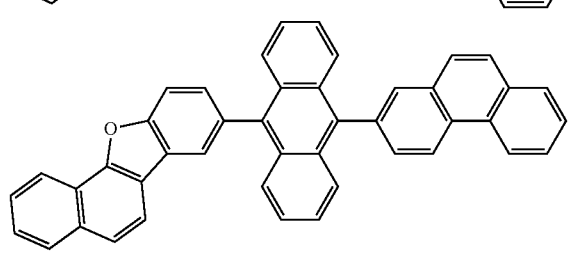
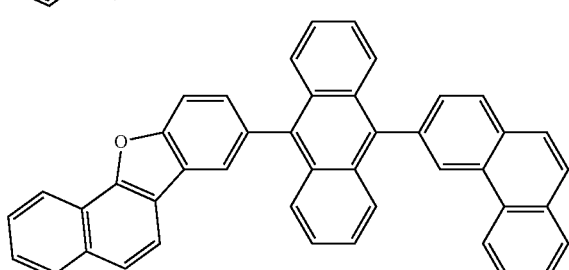
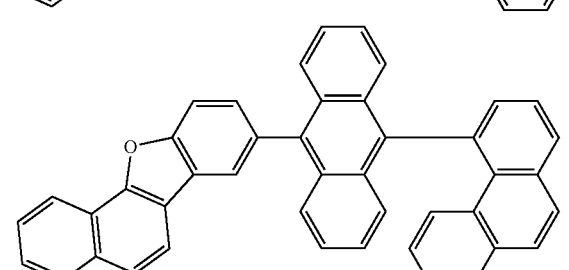
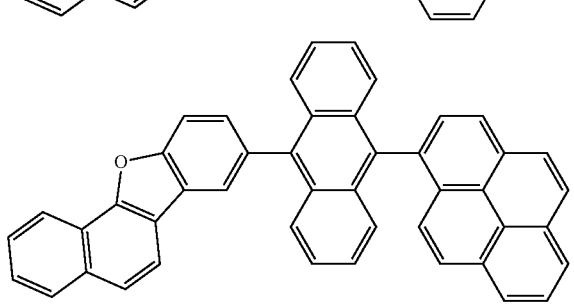
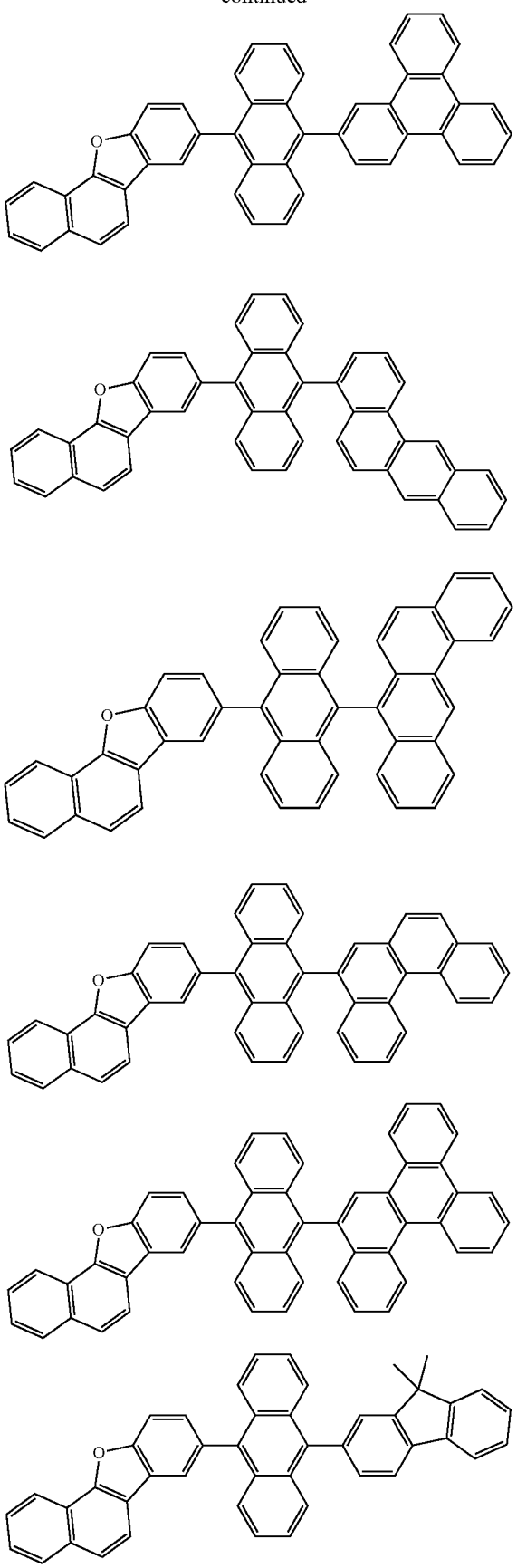

491
-continued
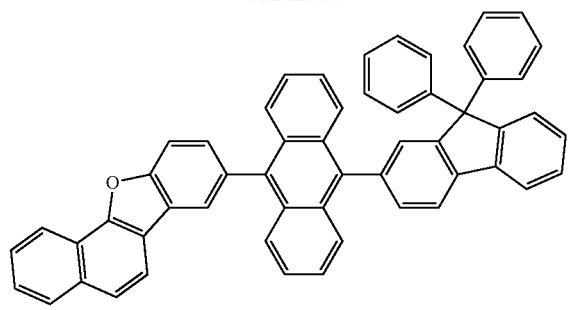
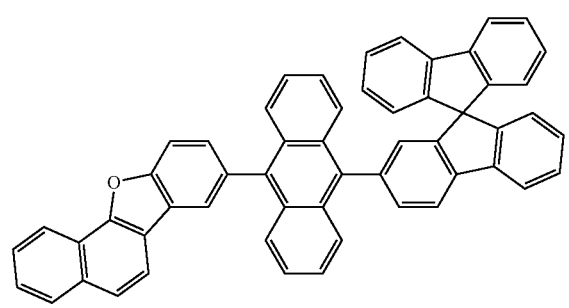
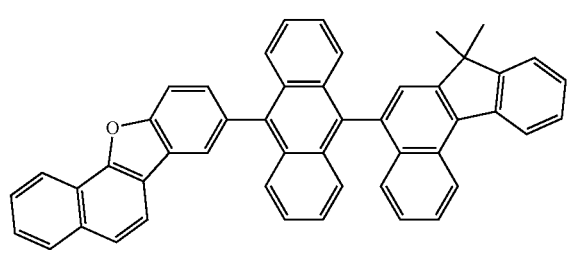
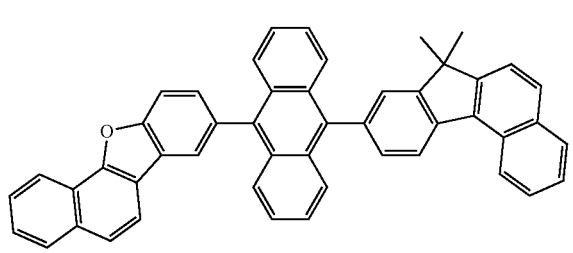
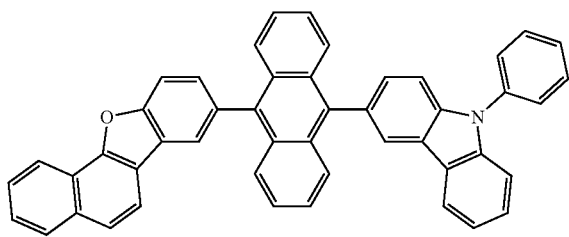
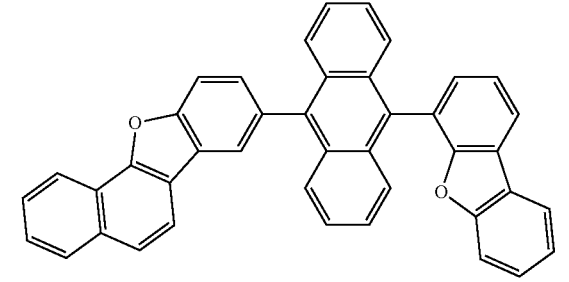
492
-continued
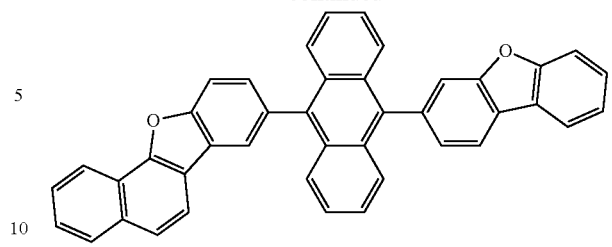
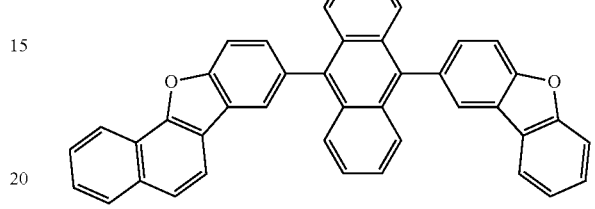
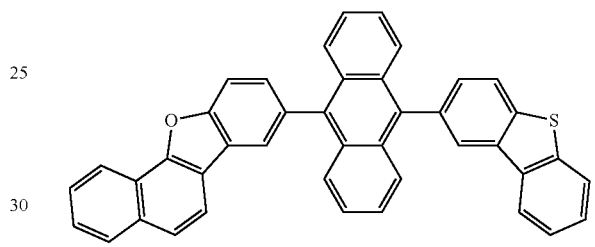
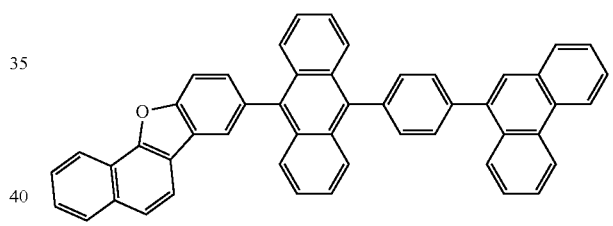
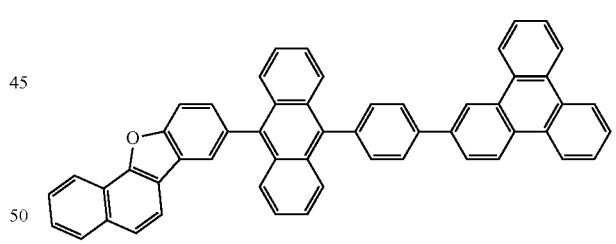
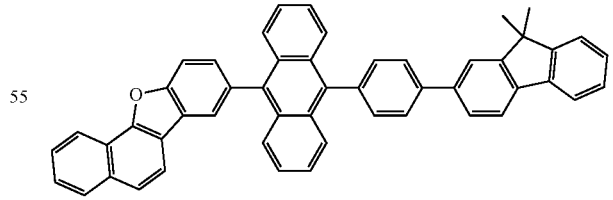
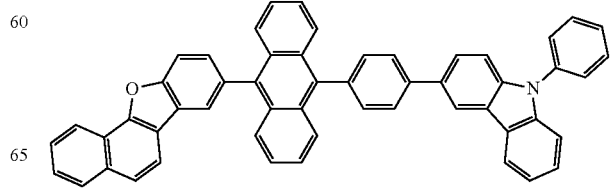

493
-continued
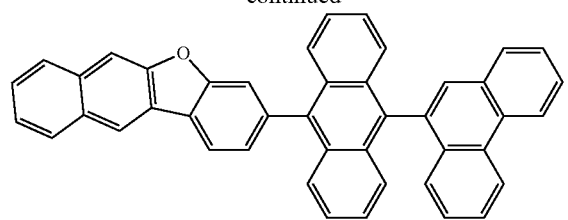
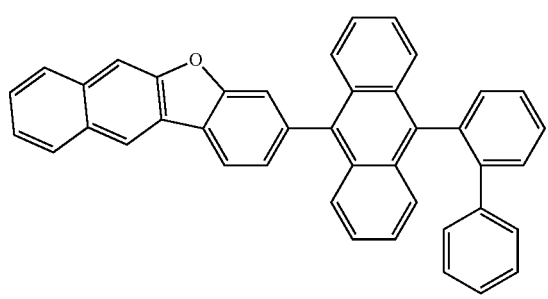
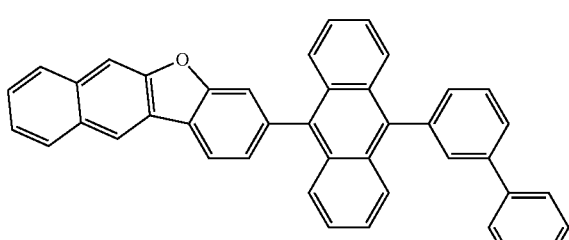
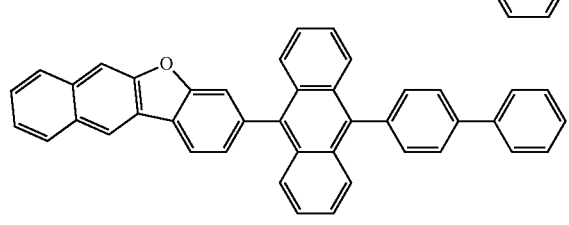
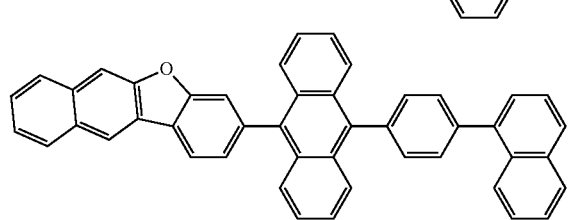
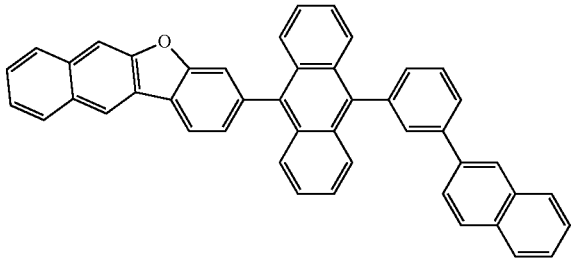
494
-continued
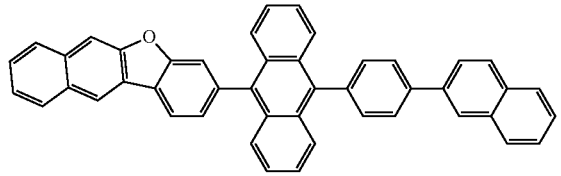
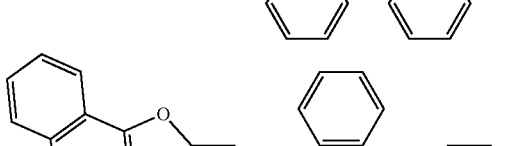
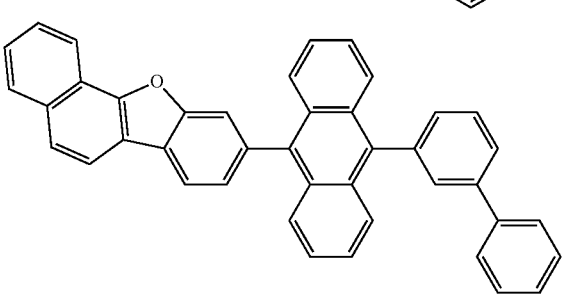
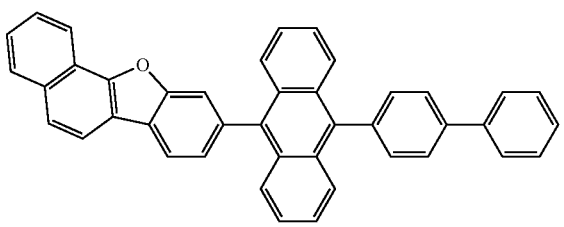
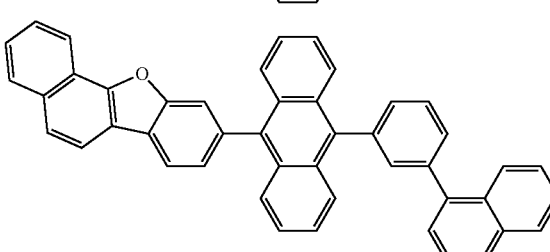
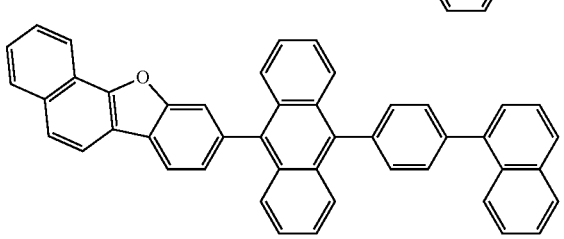

495
-continued
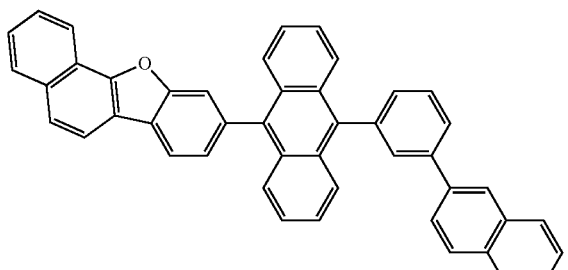
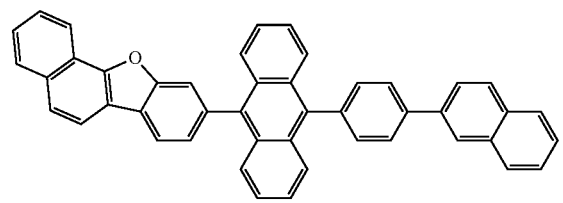
The six membered rings in the following compounds are all benzene rings.
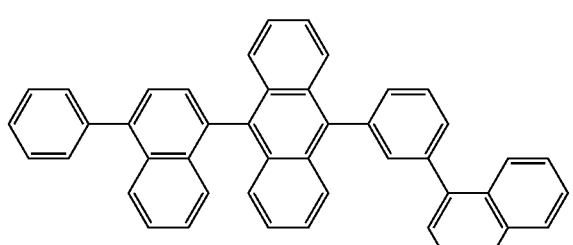
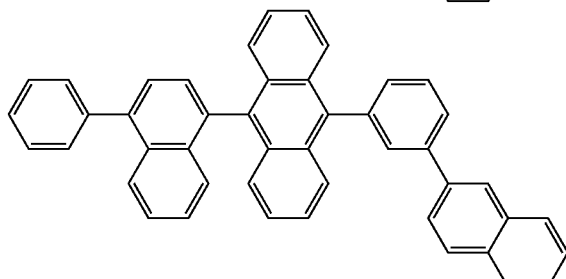
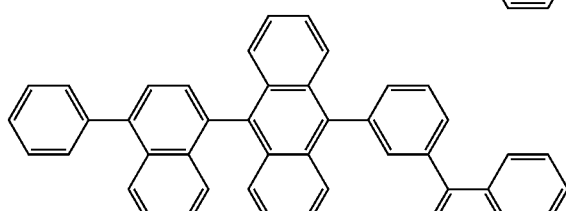
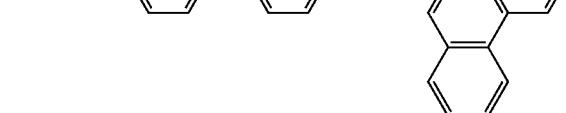
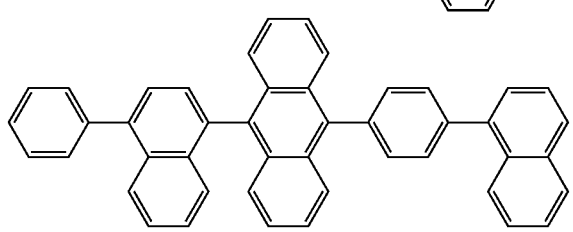
496
-continued
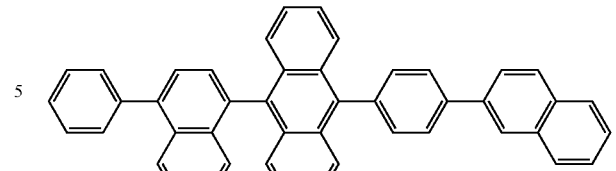
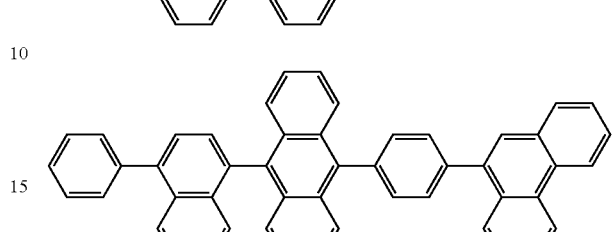
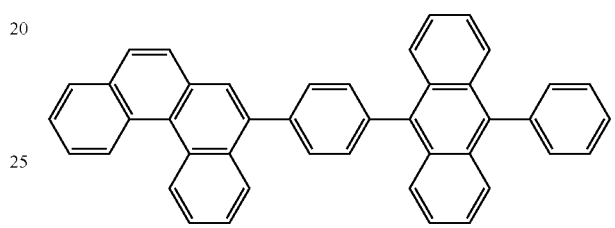
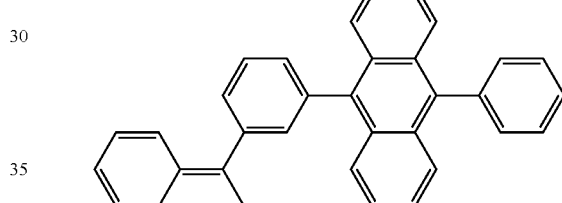
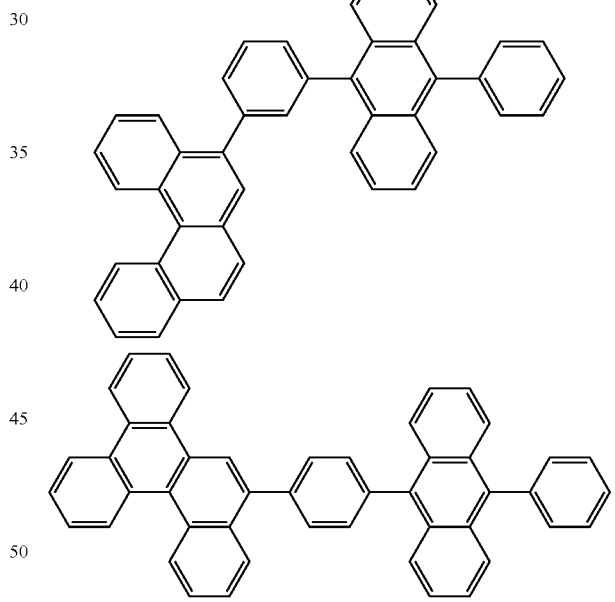
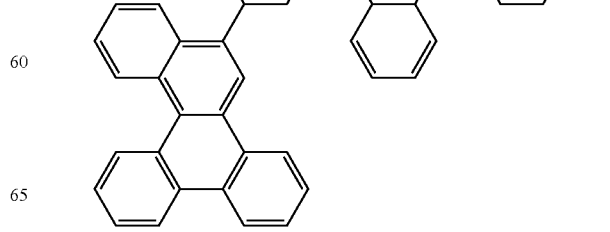

497
-continued
498
-continued
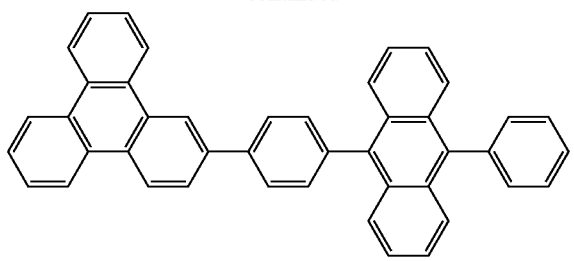
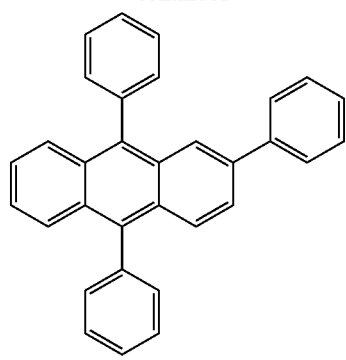
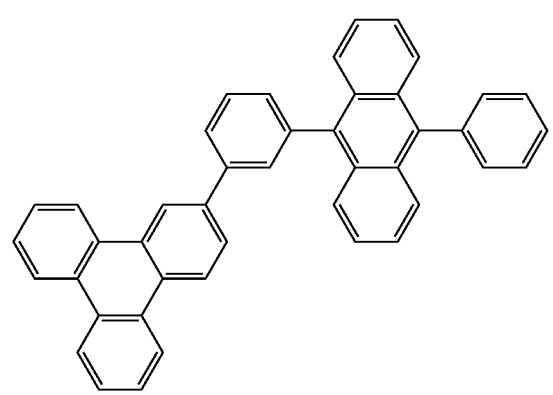
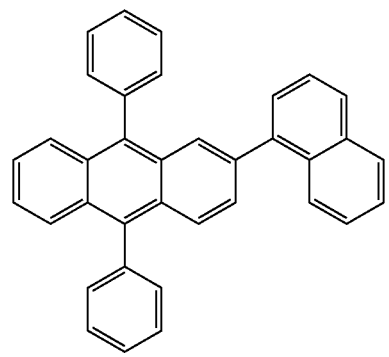
The six membered rings in the following compounds are all benzene rings.
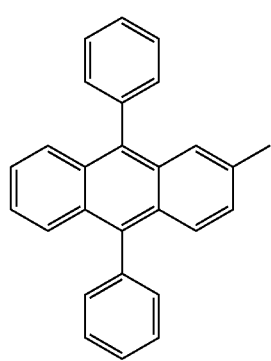
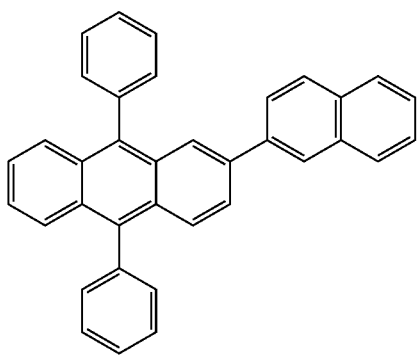
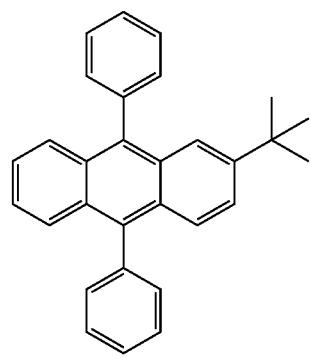
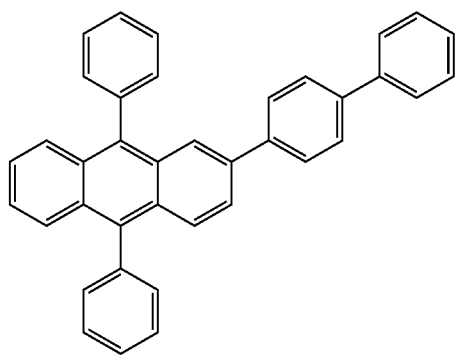

499
-continued
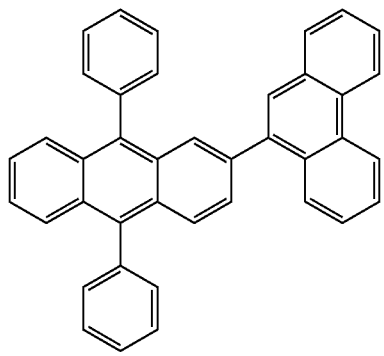
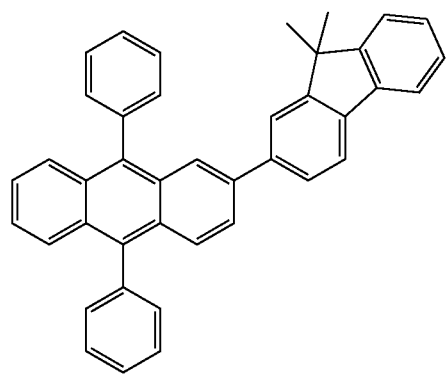
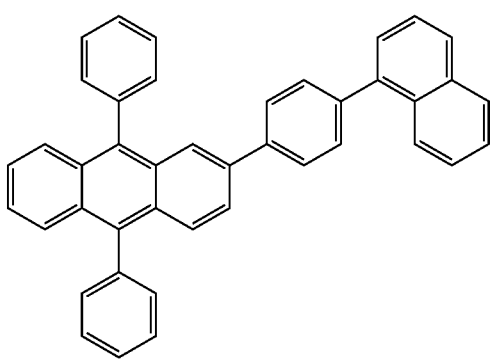
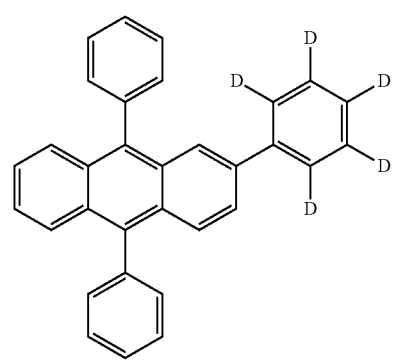
500
-continued
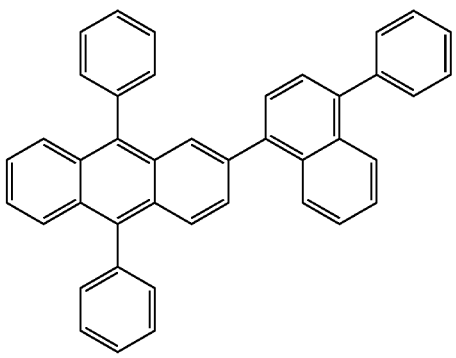
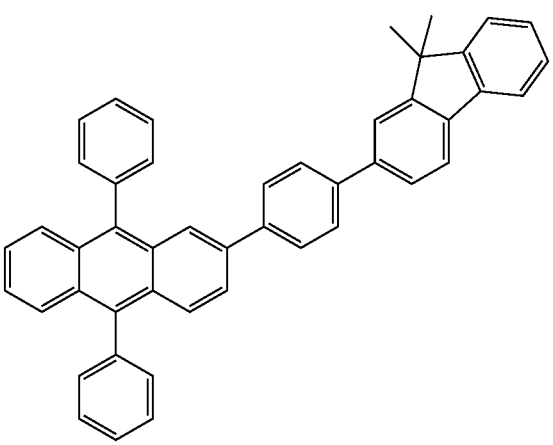
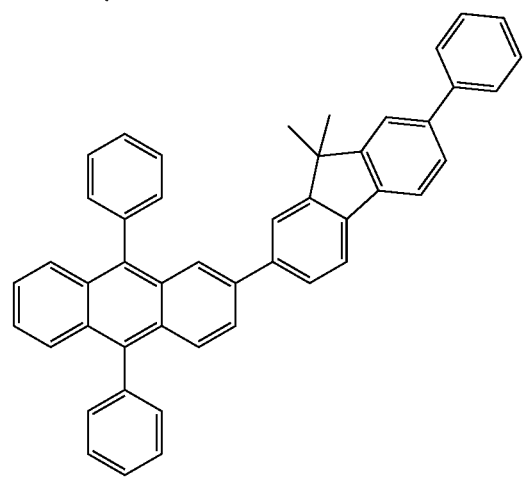
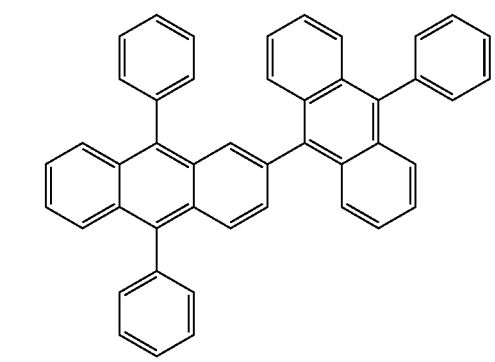

501
-continued
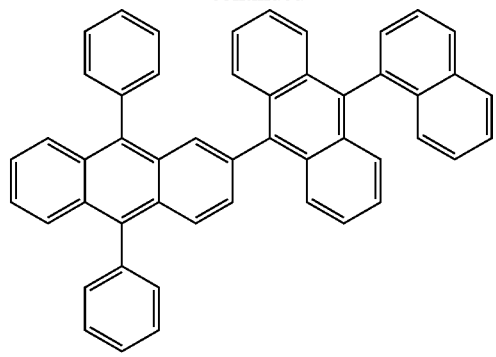
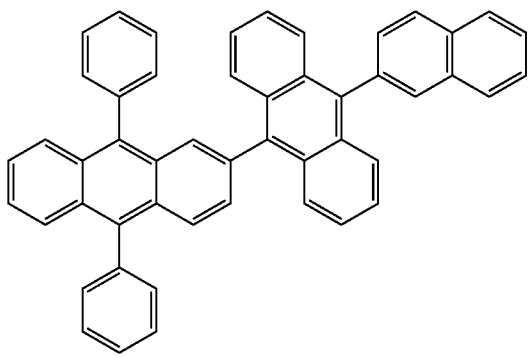
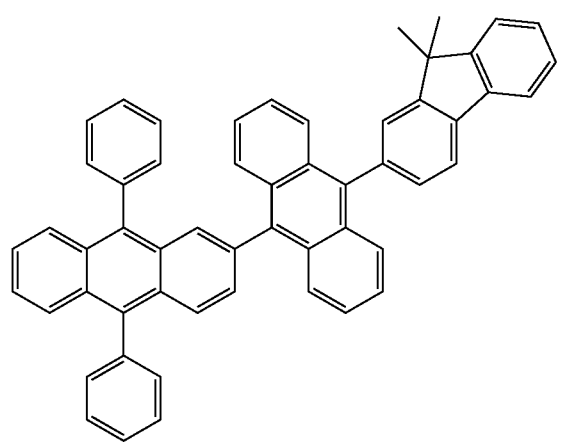
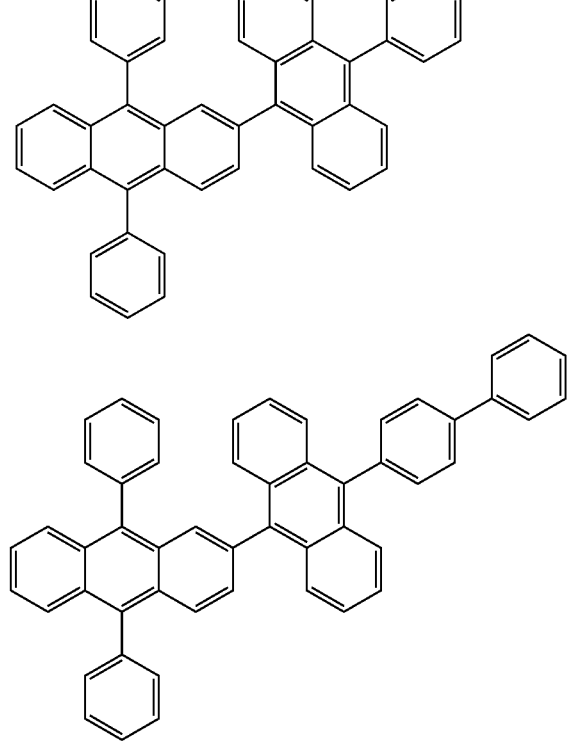
502
-continued
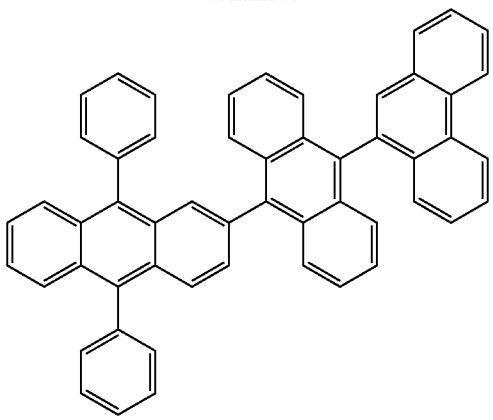
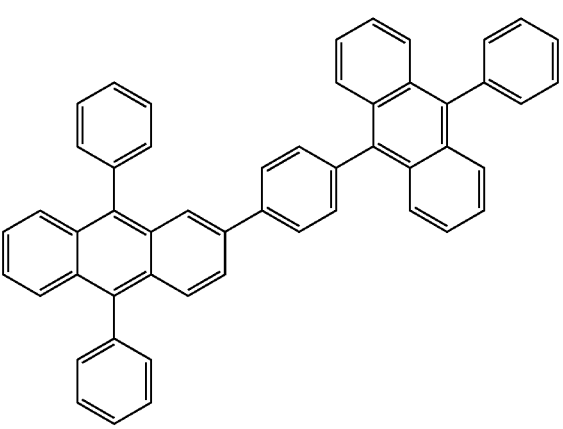
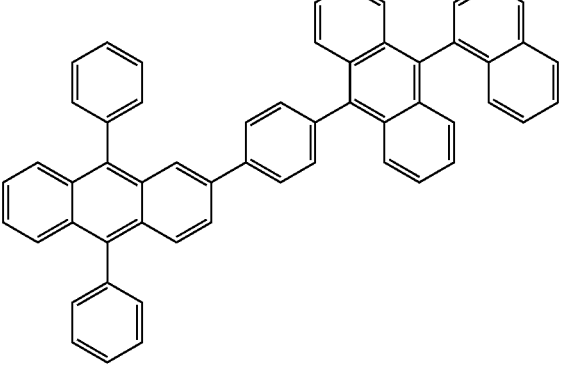
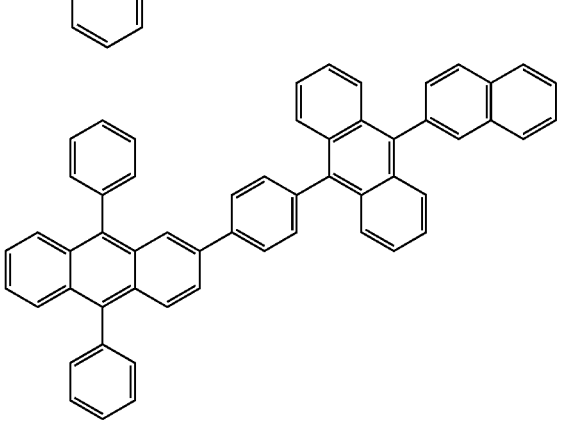

503
-continued
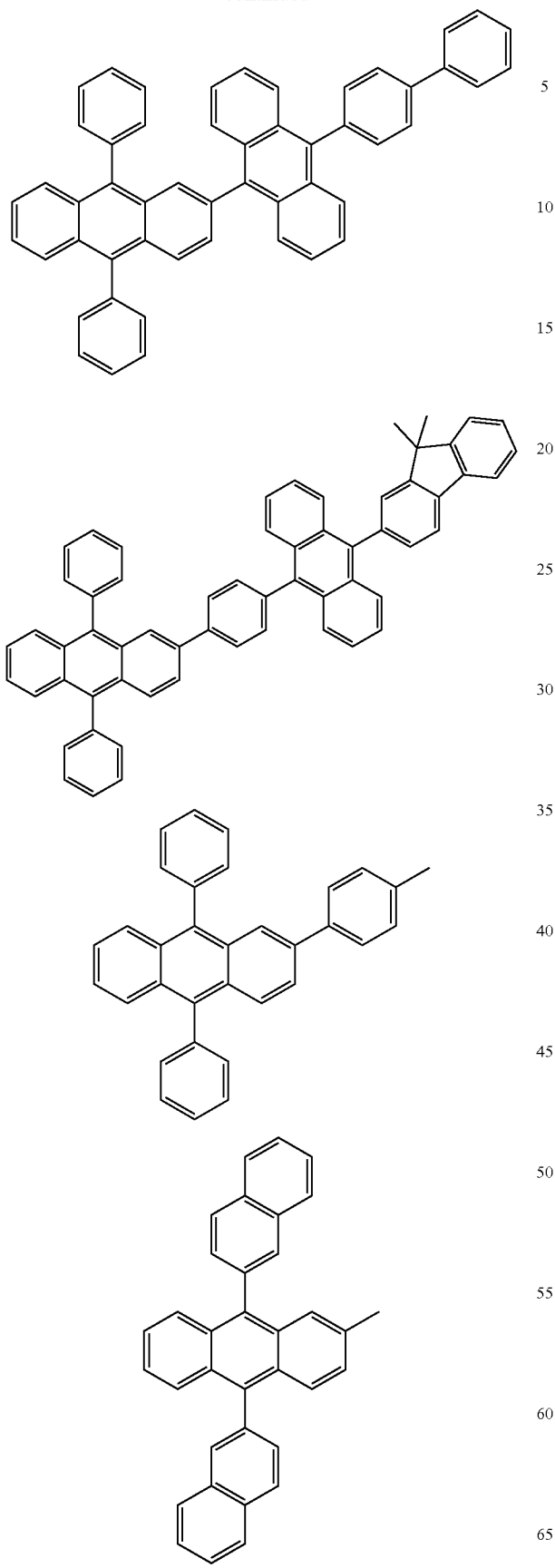
504
-continued
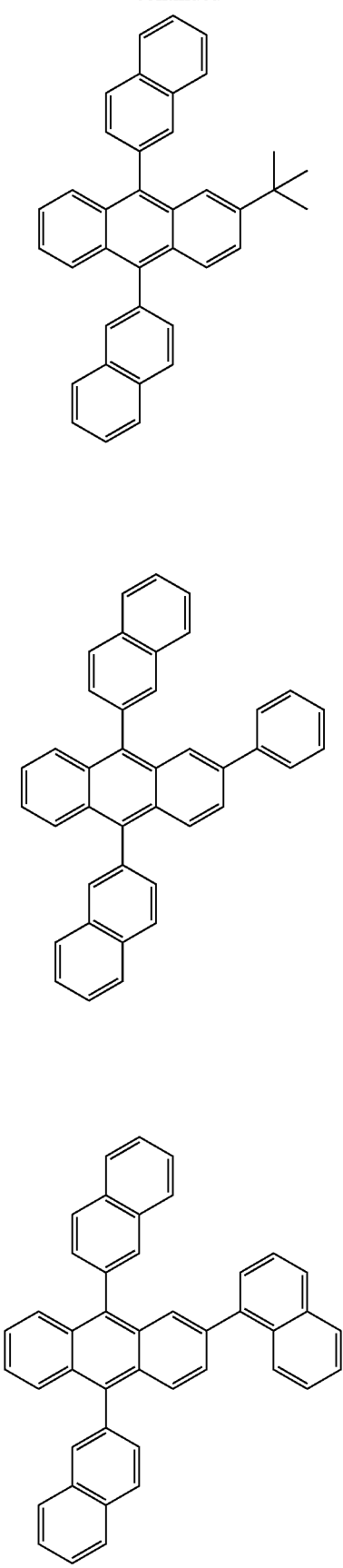

505
-continued
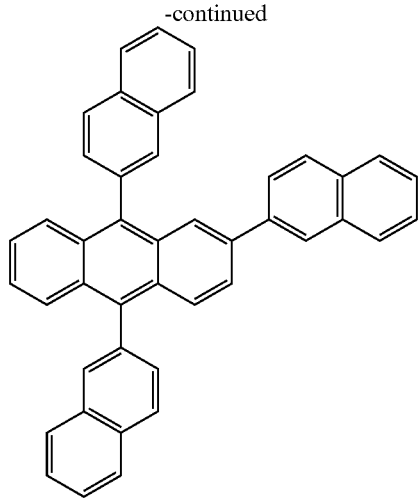
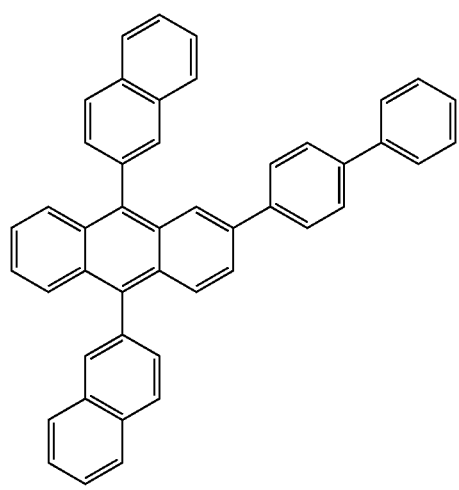
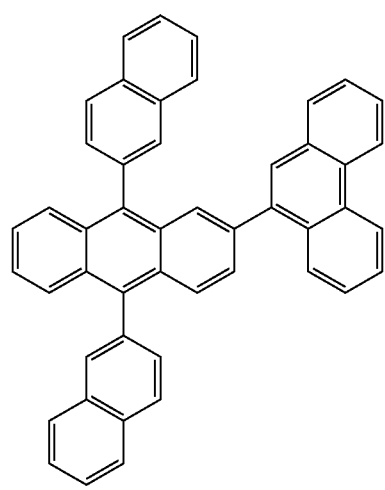
506
-continued
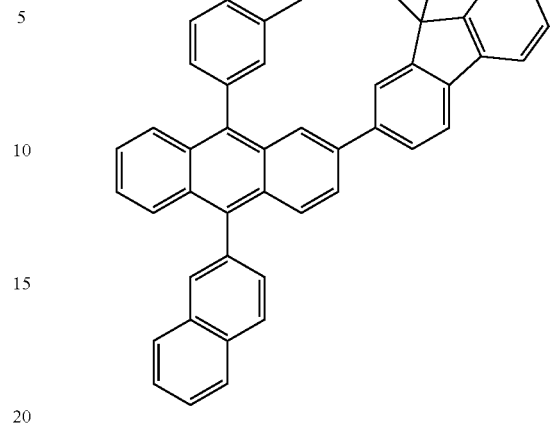
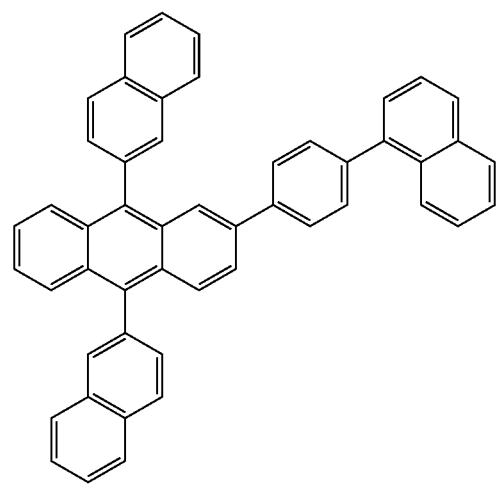
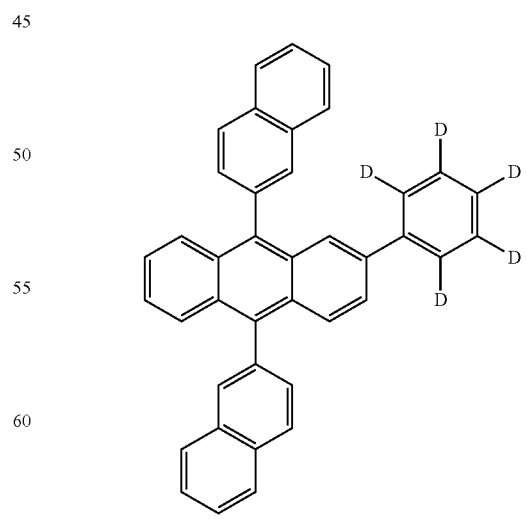
The six membered rings in the following compounds are all benzene rings.

507
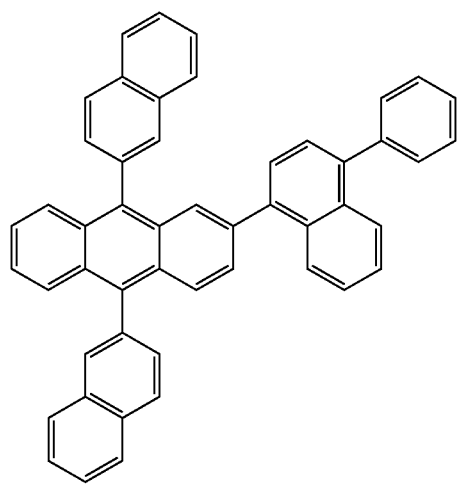
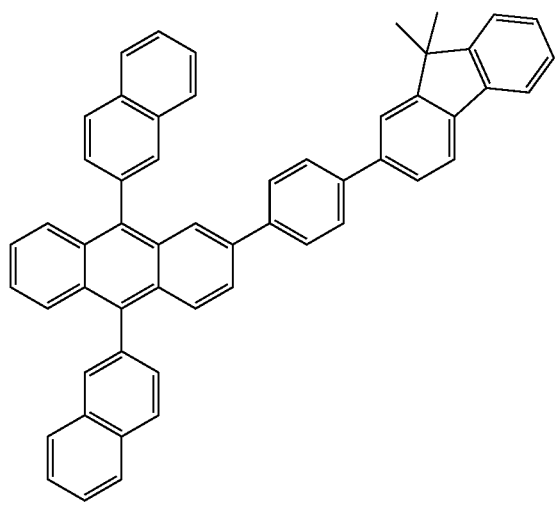
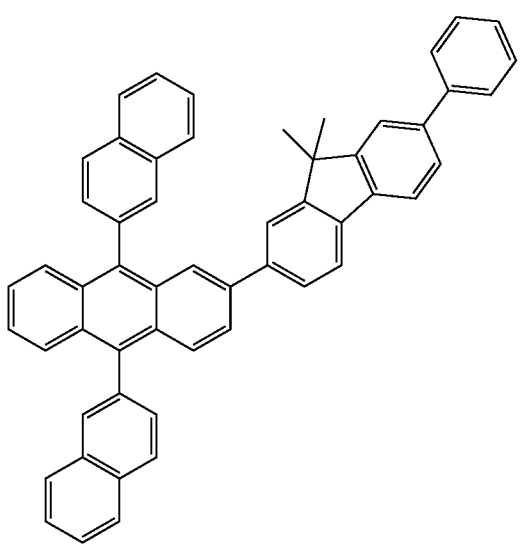
508
-continued
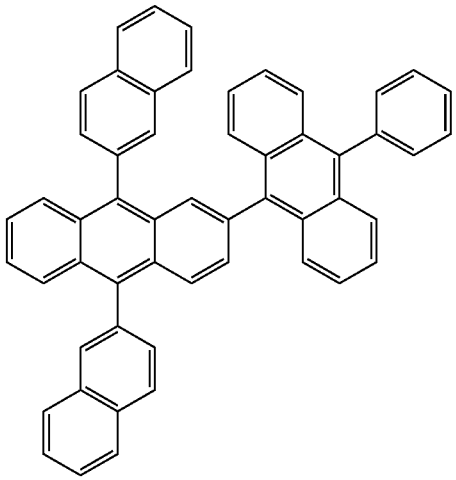
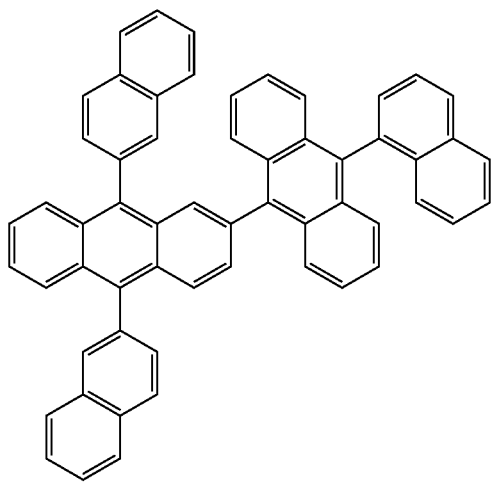
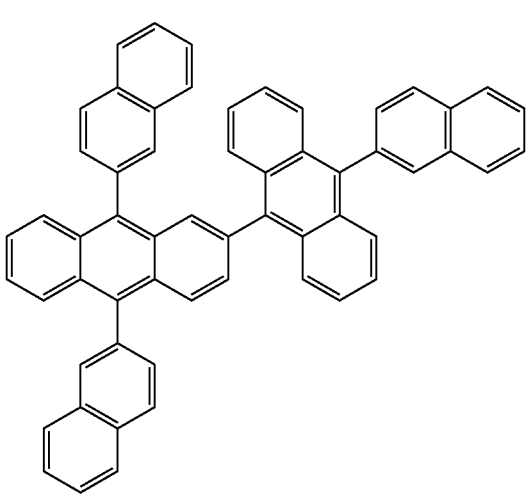

509
-continued
510
-continued
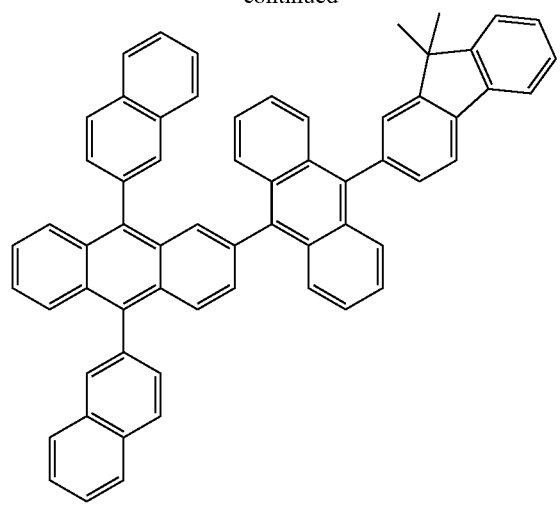
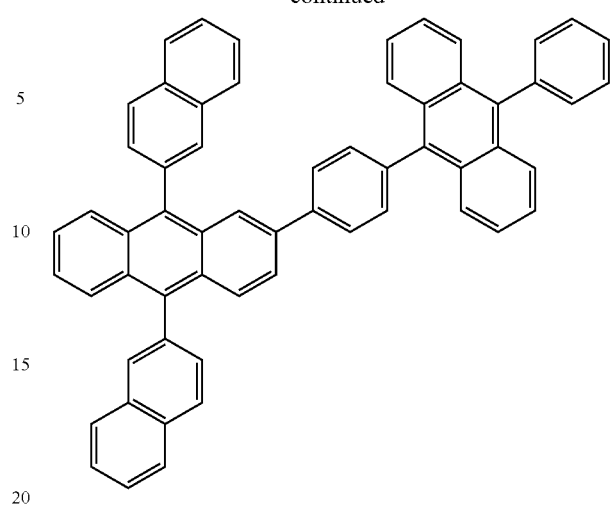
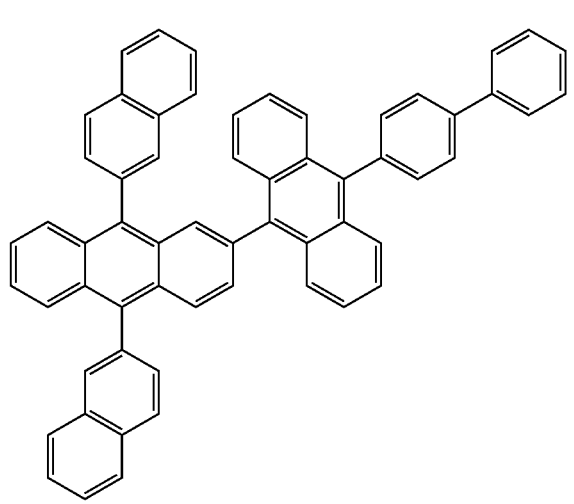
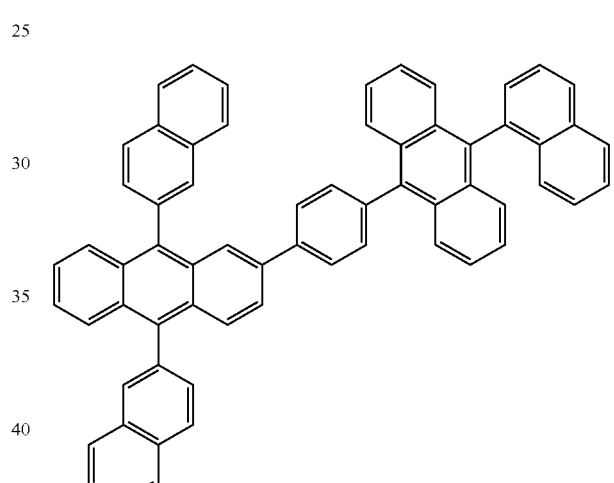
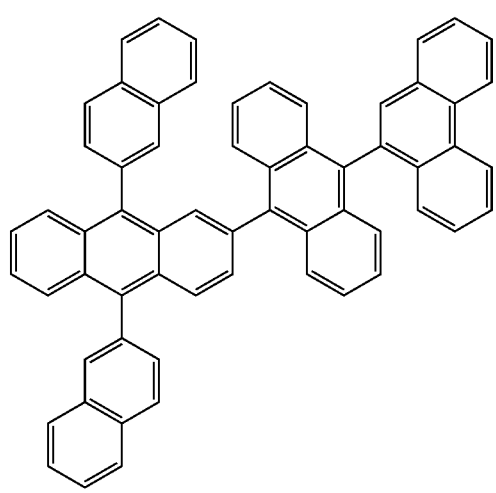
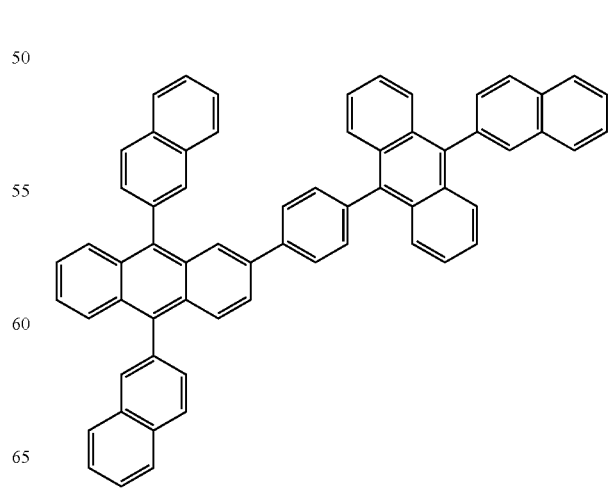

511
-continued
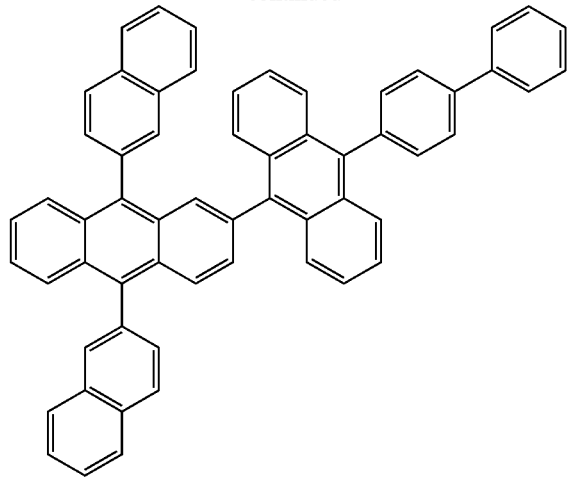
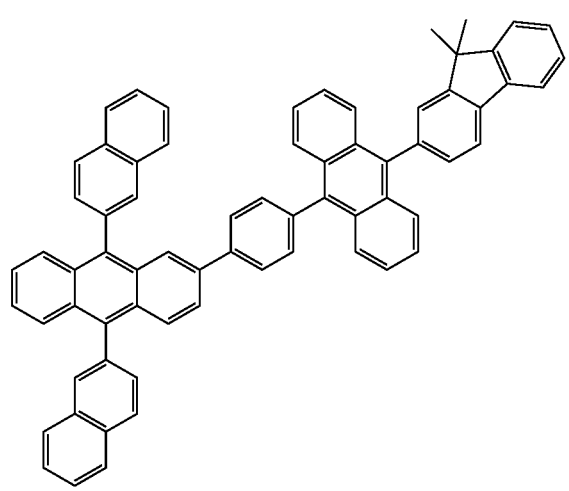
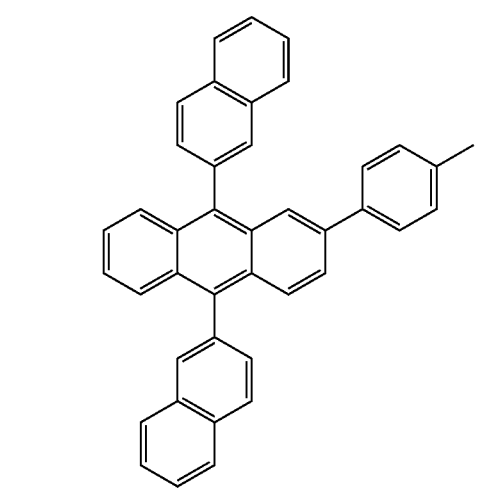 [SMILES: [2H]c1c([2H])c([2H])c(-c2ccc3c(-c4ccc5ccccc5c4)c4ccccc4c(-c4ccc5ccccc5c4)c3c2)c([2H])c1[2H]]
512
-continued
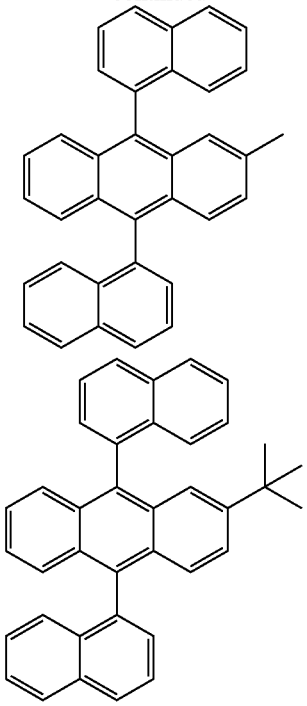
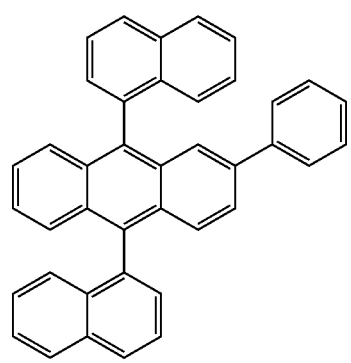
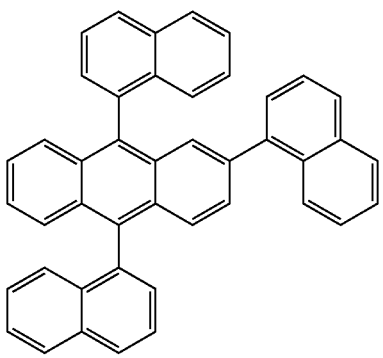

513
-continued
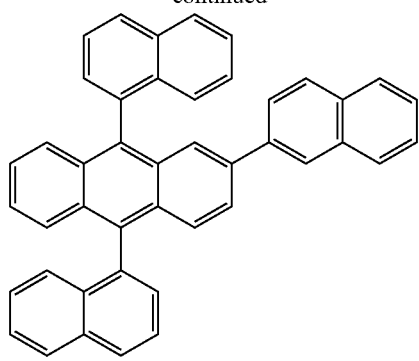
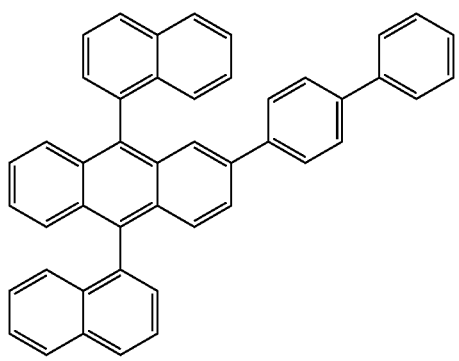
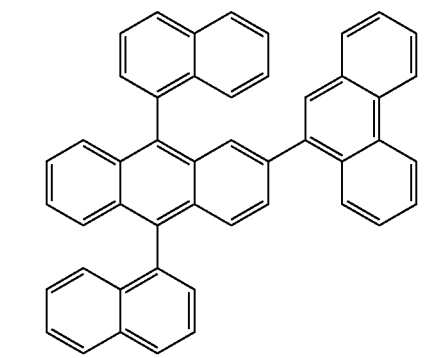
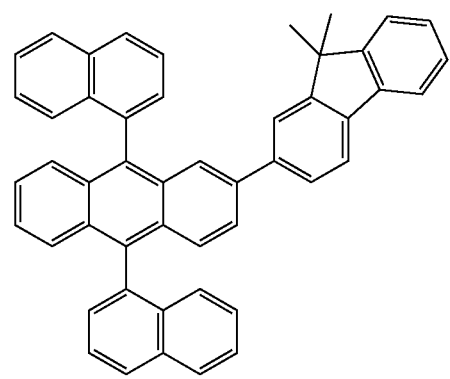
514
-continued
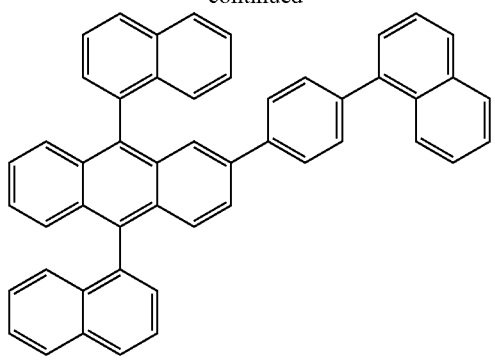
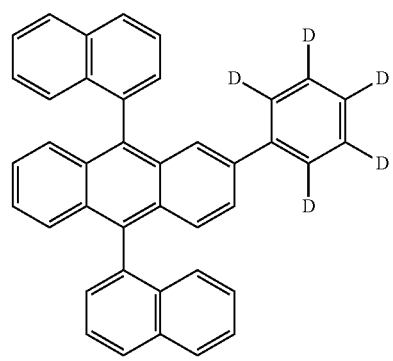
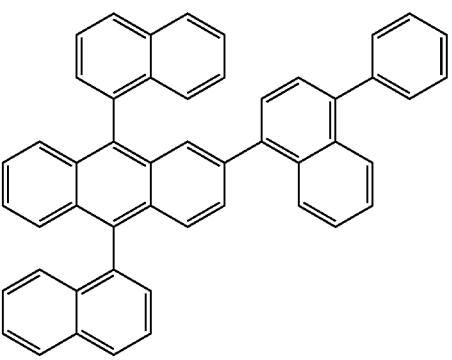
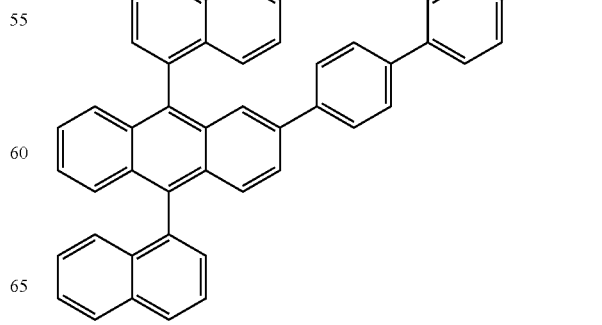

515
-continued
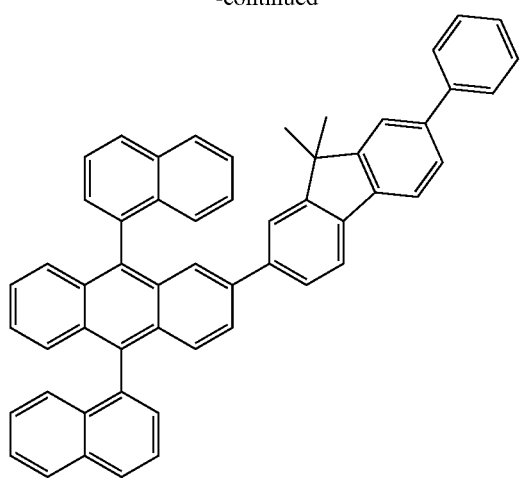
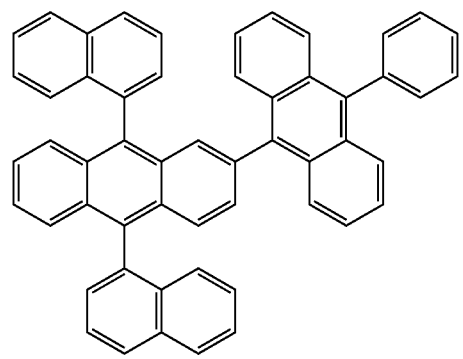
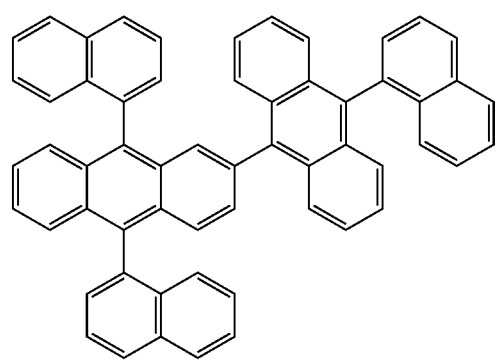
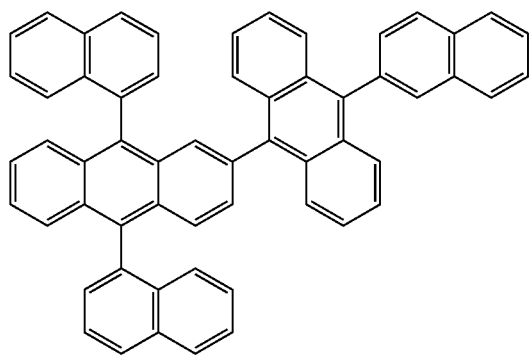
516
-continued
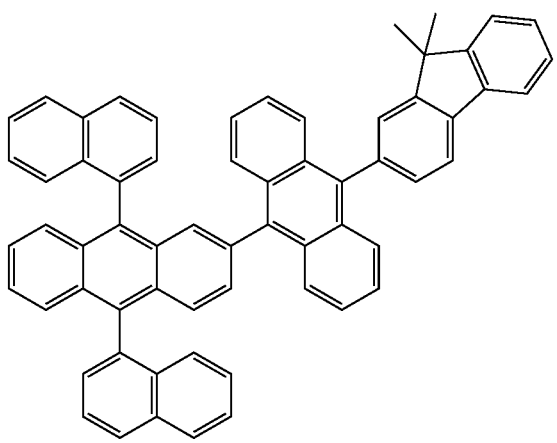
The six membered rings in the following compounds are all benzene rings.
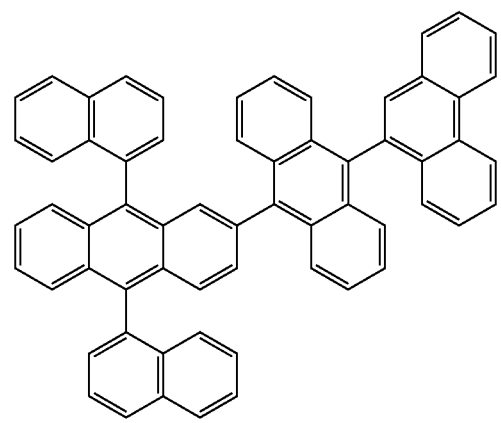

517
-continued
518
-continued
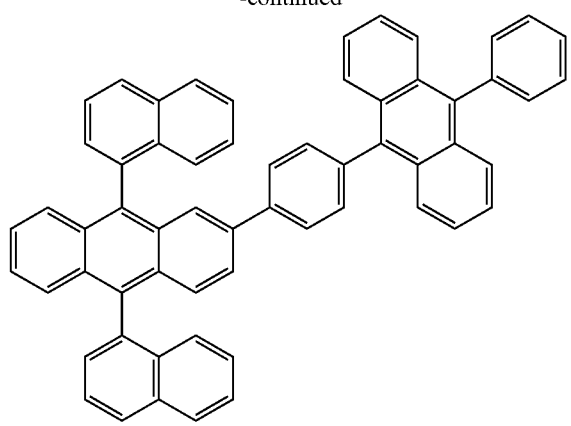
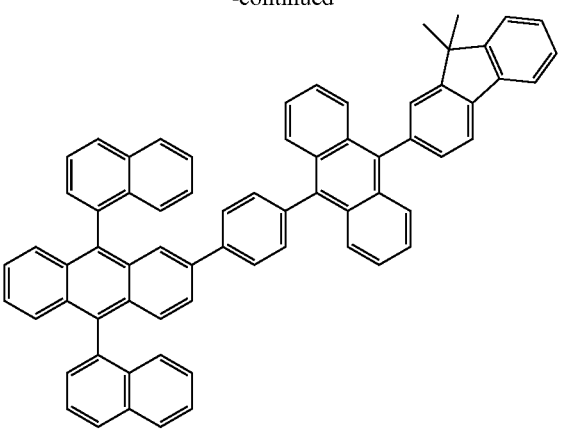
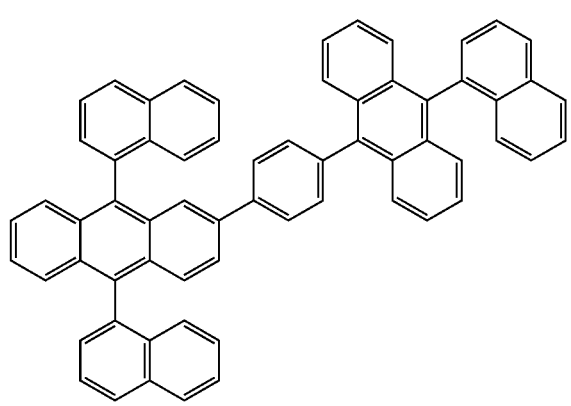
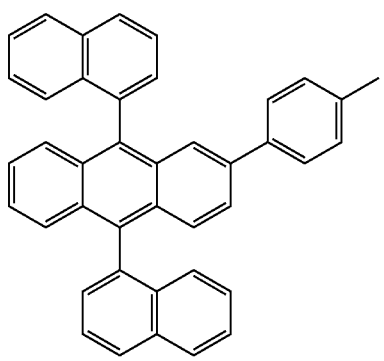
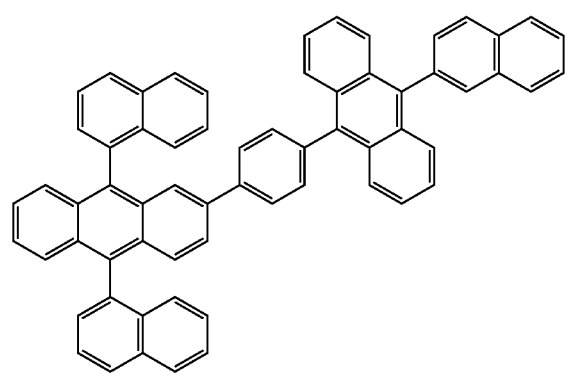
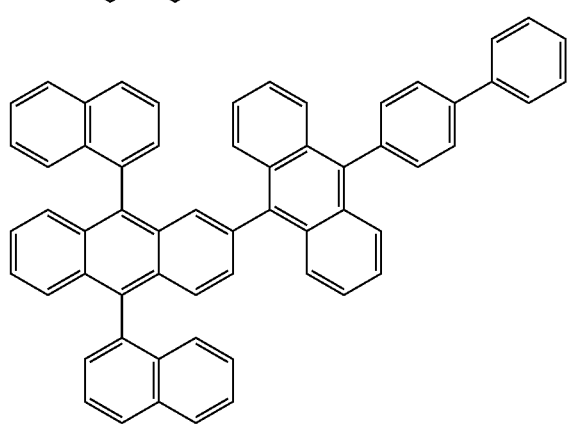
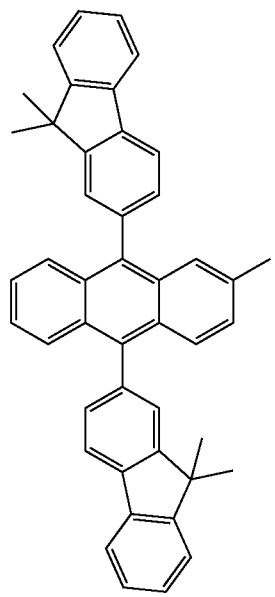

519
-continued
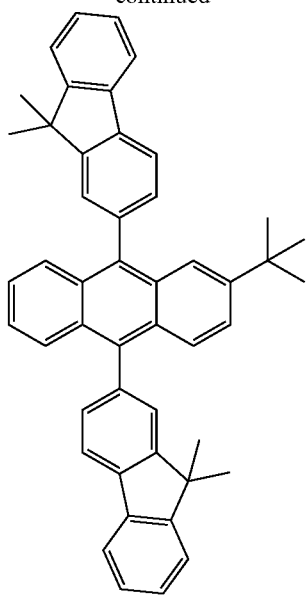
520
-continued
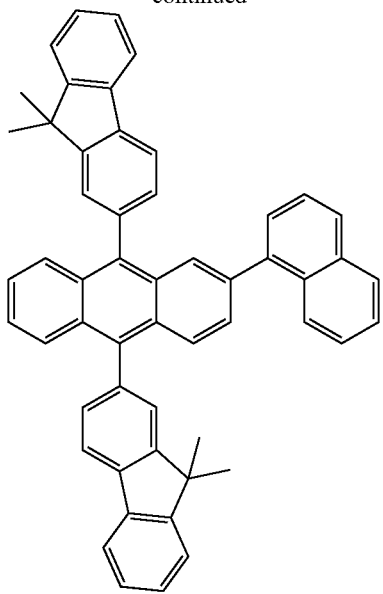
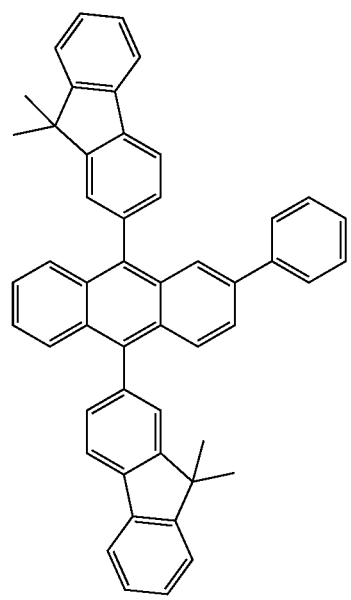
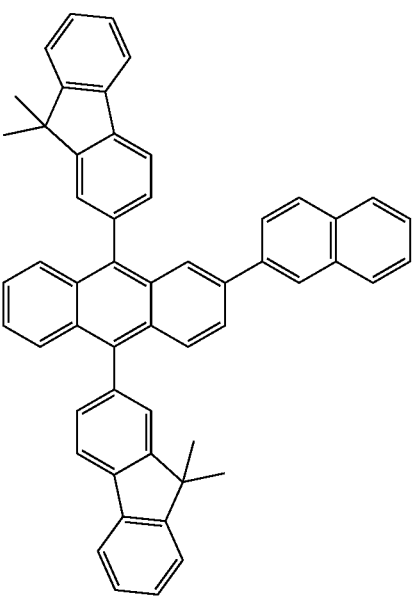

521
-continued
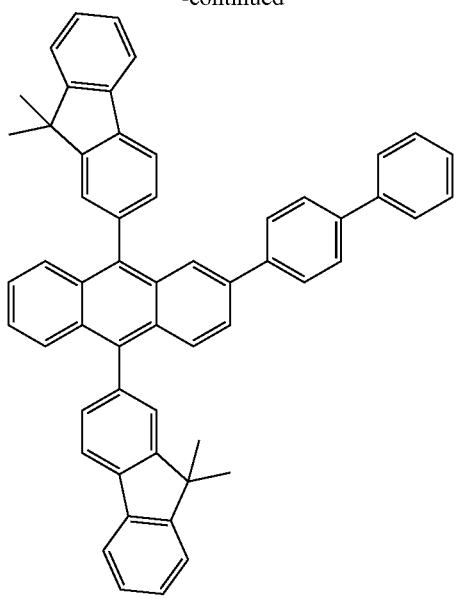
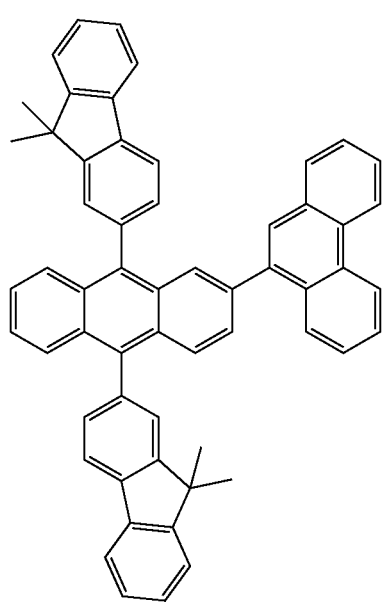
522
-continued
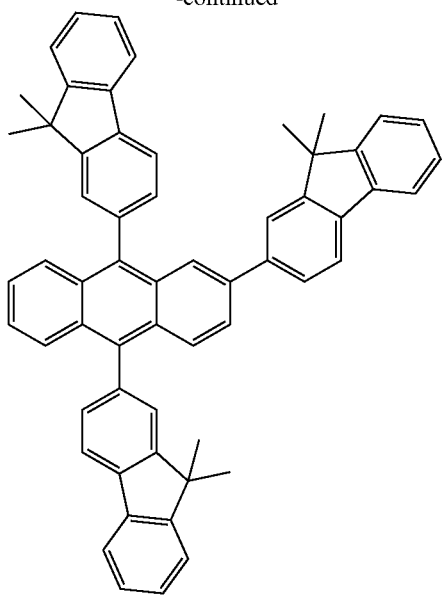
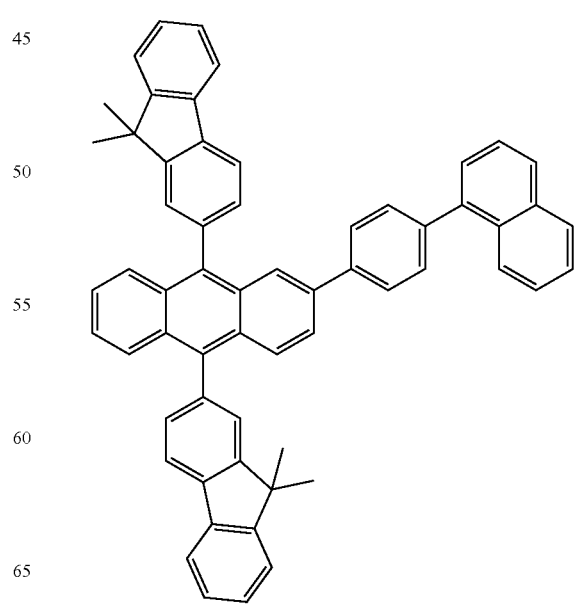

523
-continued
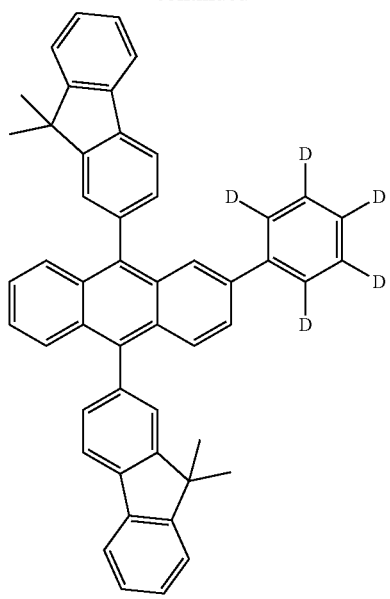
524
-continued
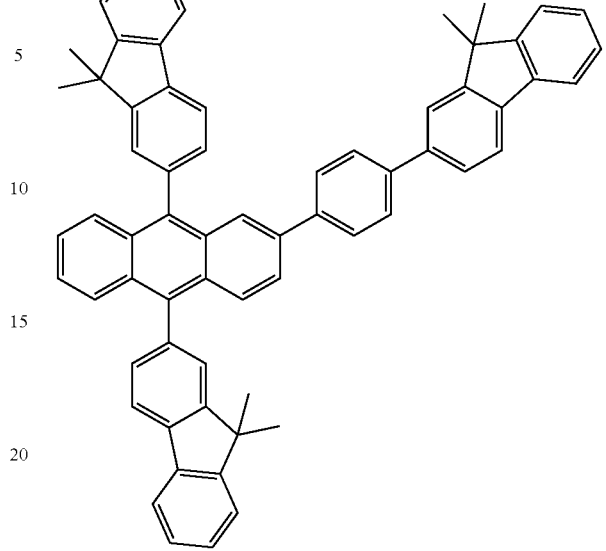
The six membered rings in the following compounds are all benzene rings.
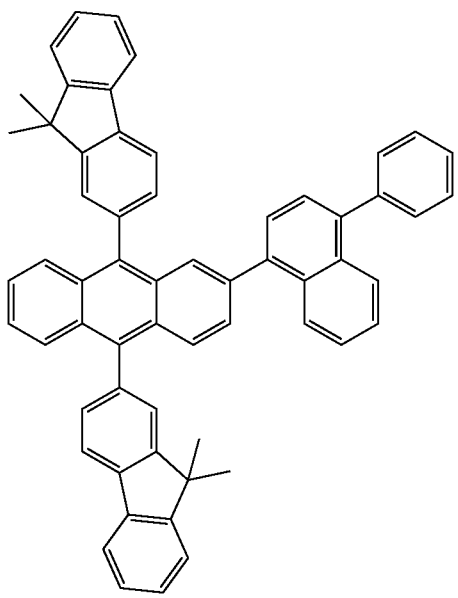
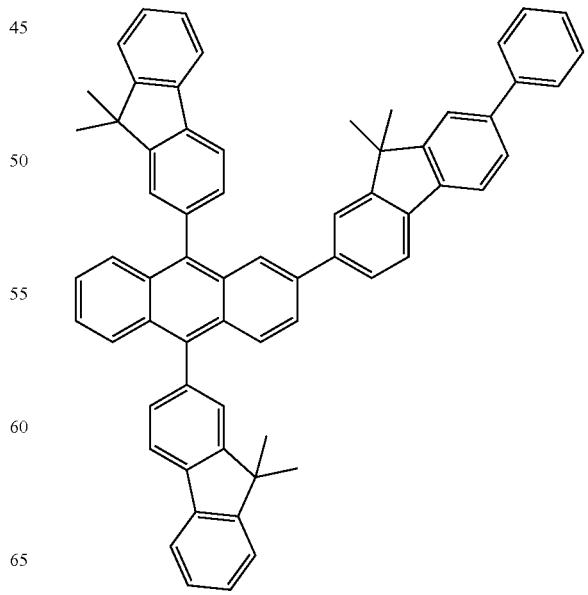

525
-continued
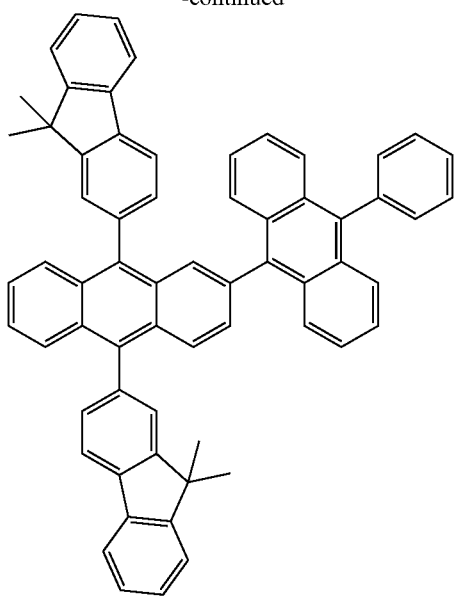
526
-continued
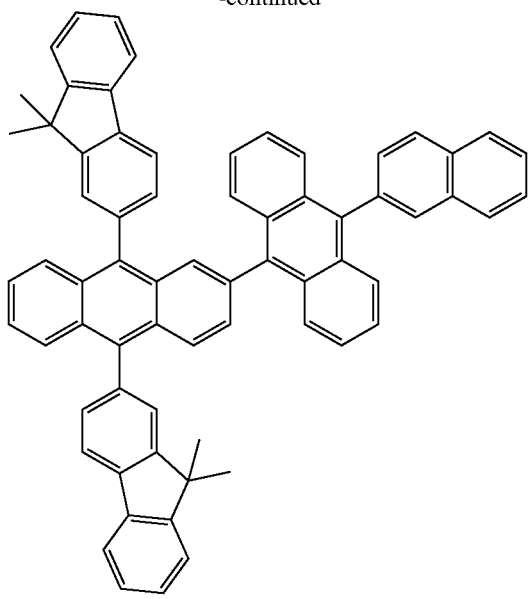
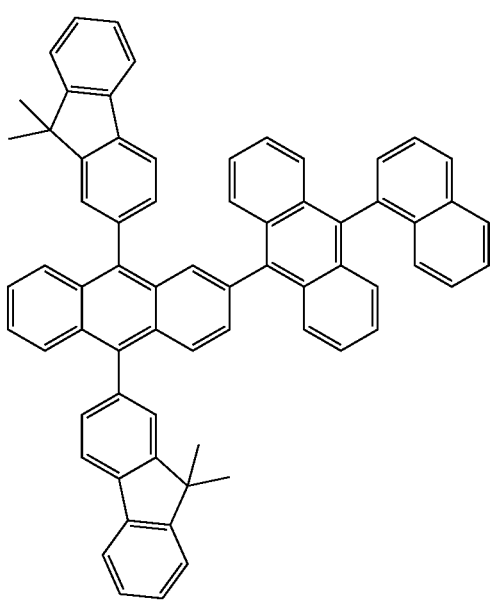
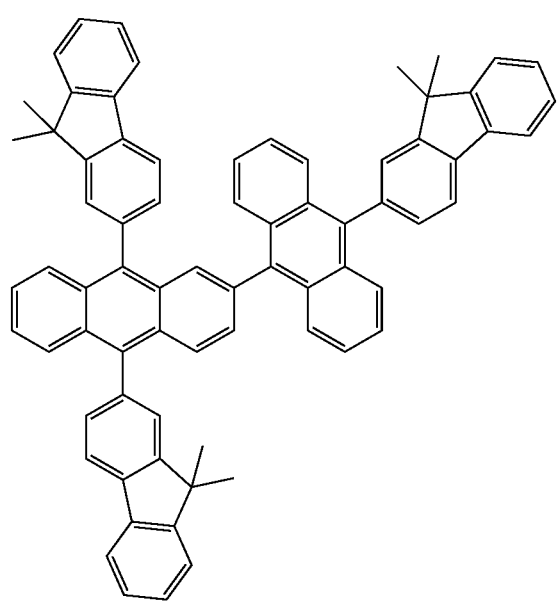

527
-continued
528
-continued
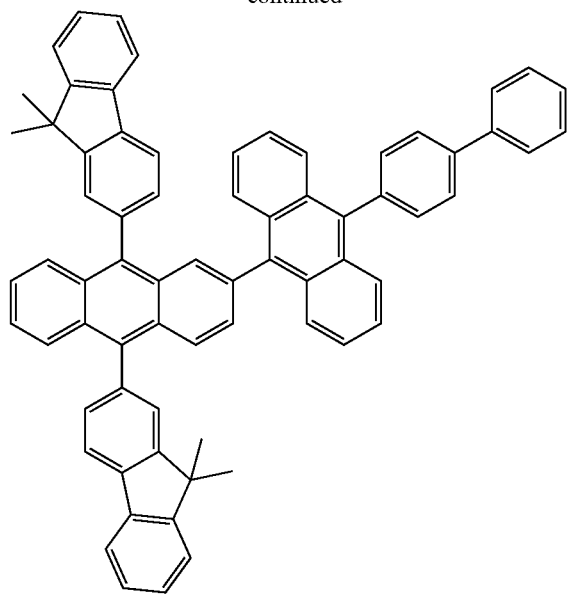
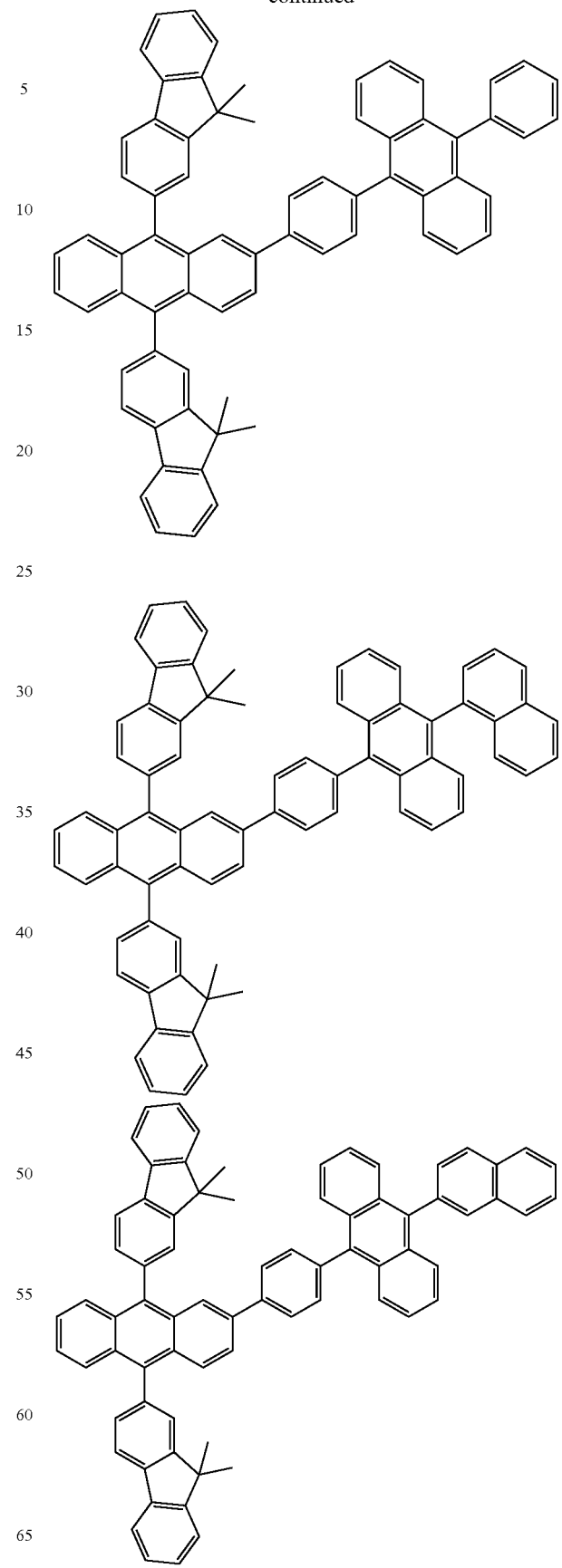

529
-continued
530
-continued
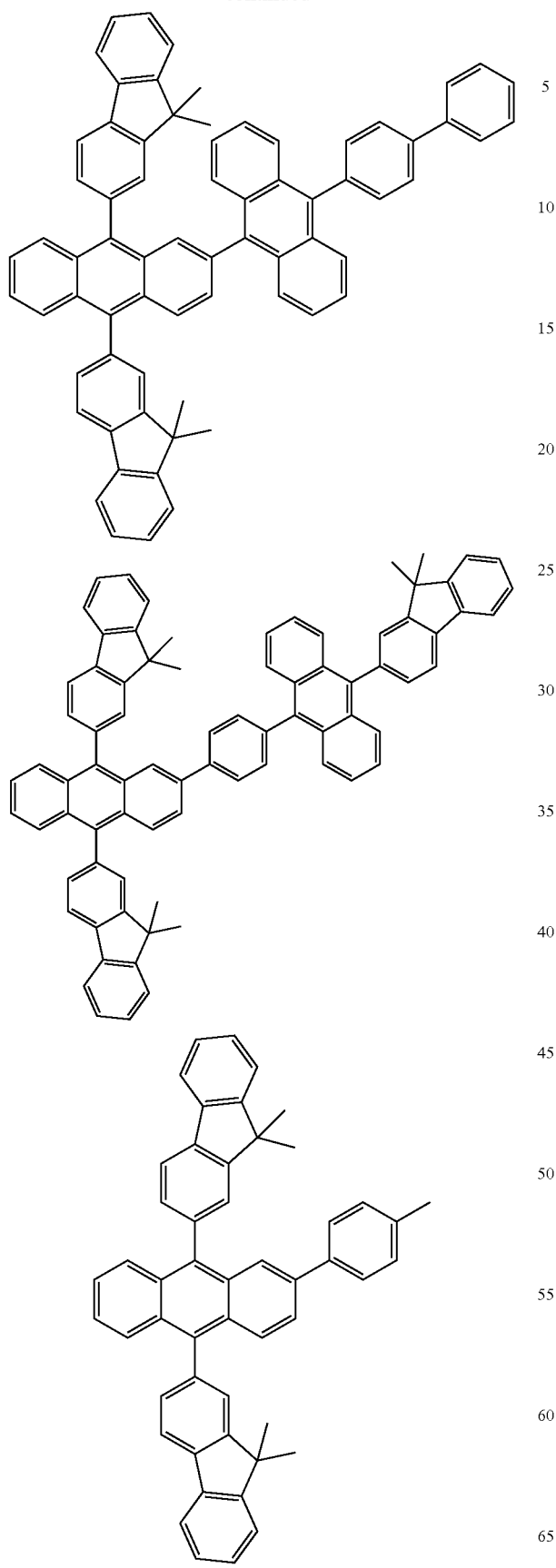

531
-continued
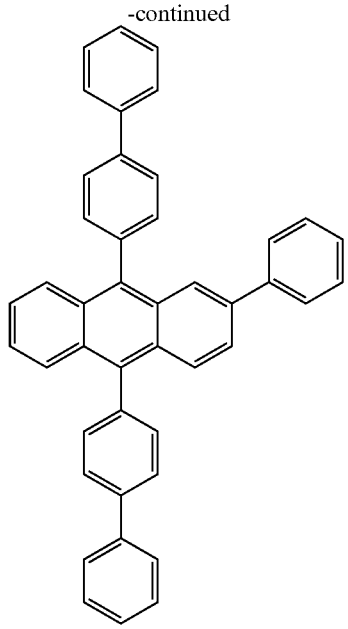
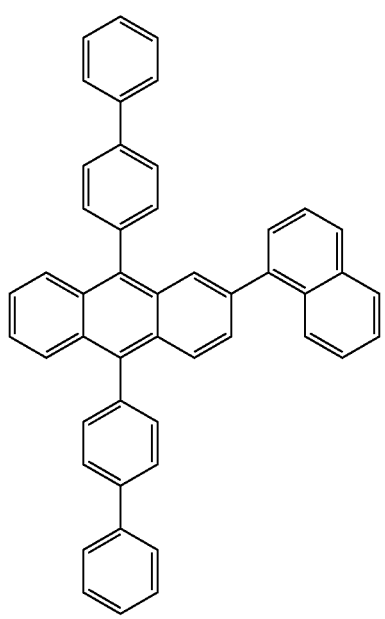
532
-continued
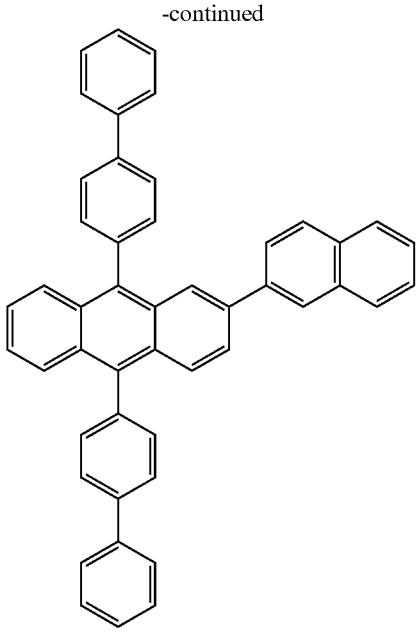
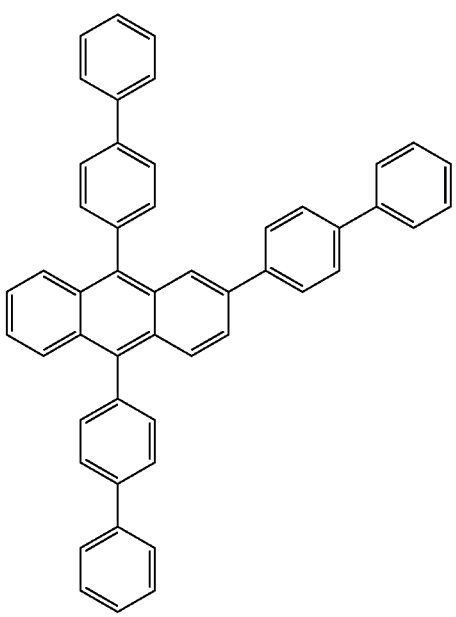

533
-continued
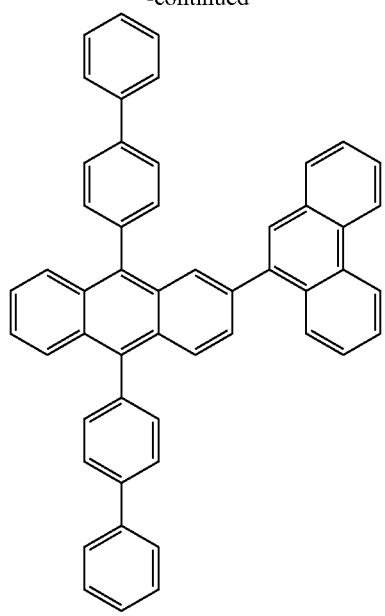
534
-continued
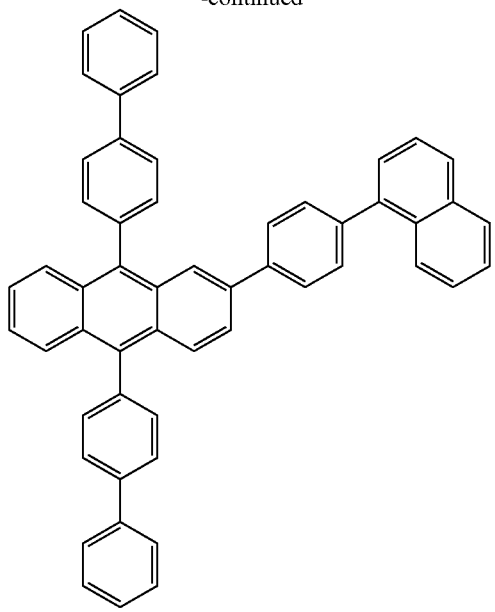
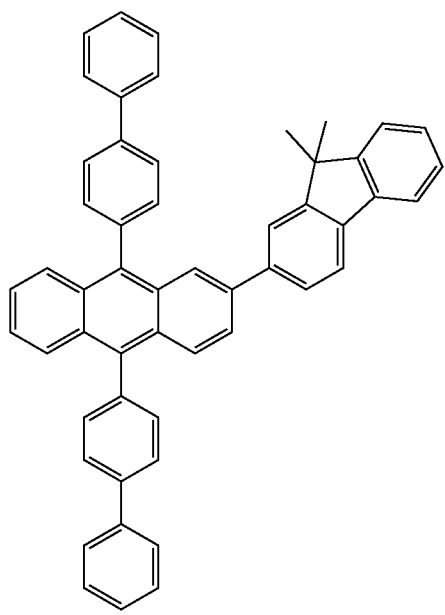
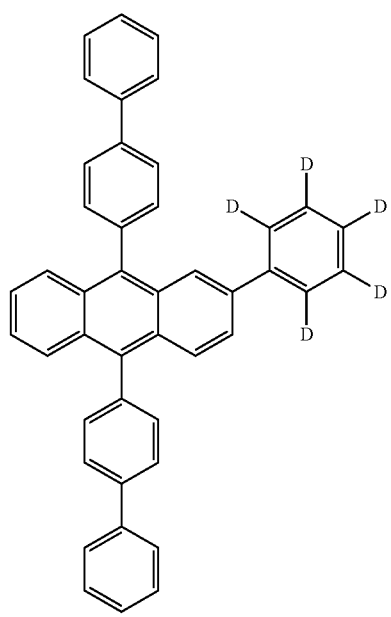

535
-continued
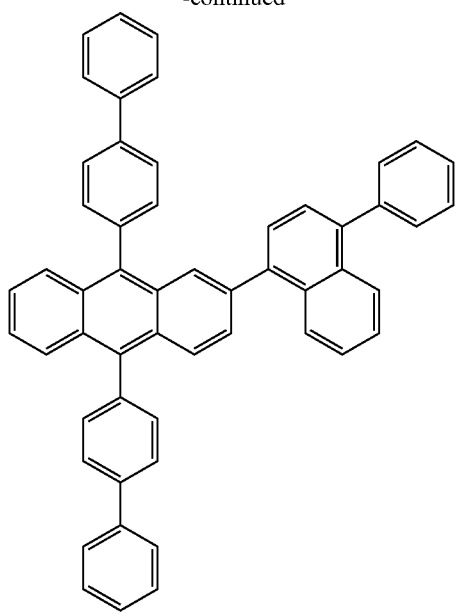
536
-continued
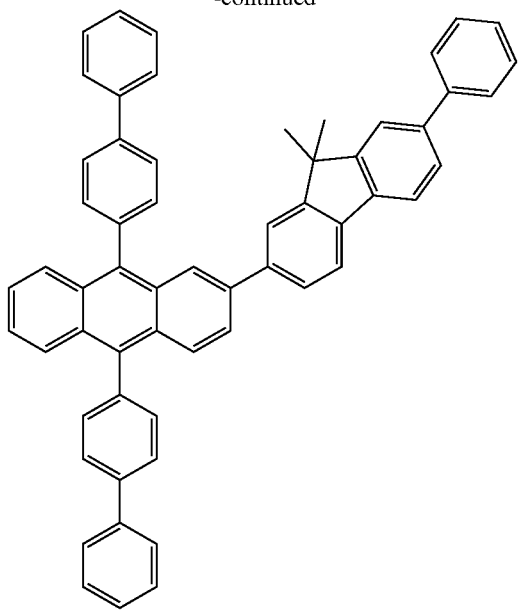
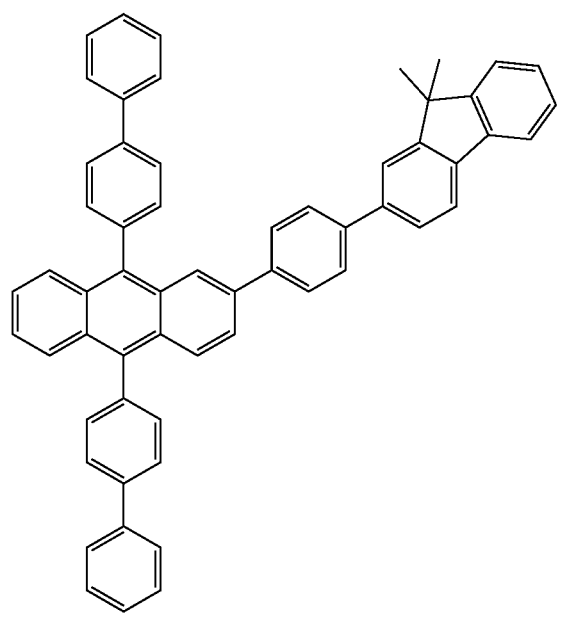
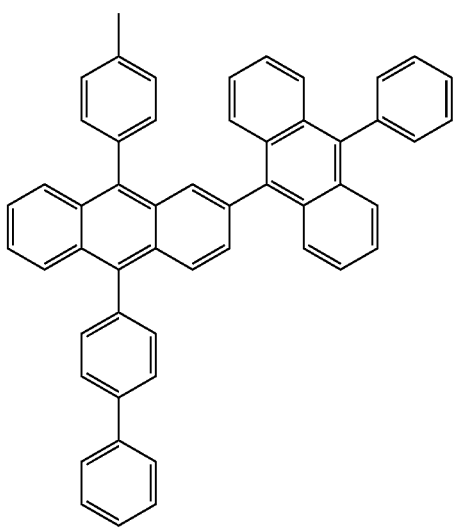

537
-continued
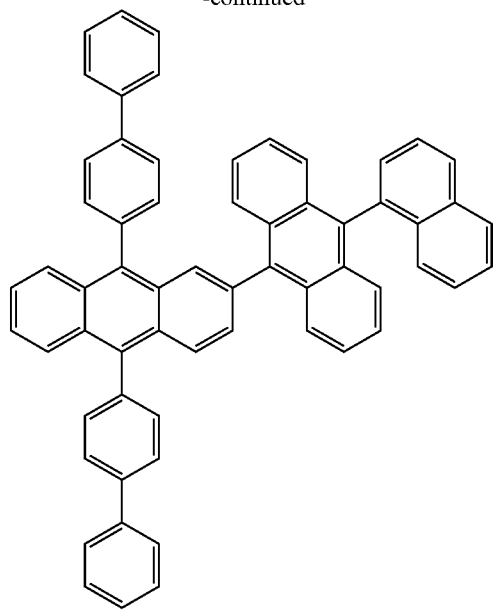
538
-continued
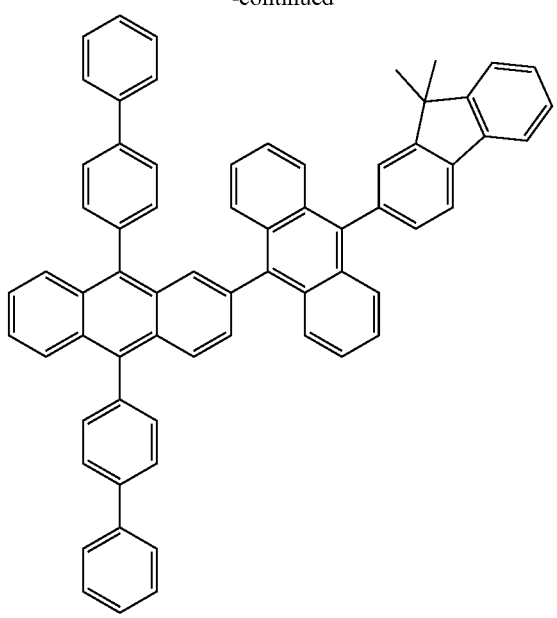
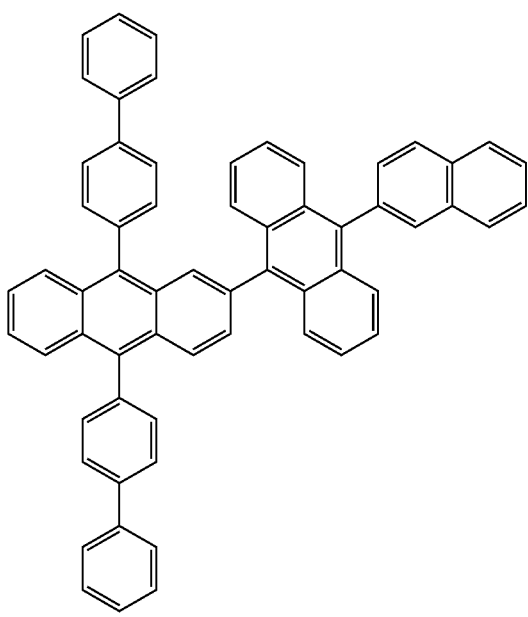
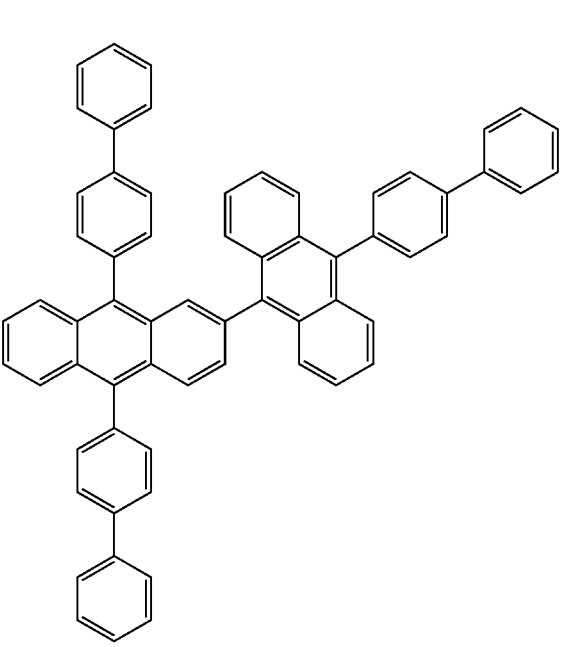
The six membered rings in the following compounds are all benzene rings.

539
540
-continued
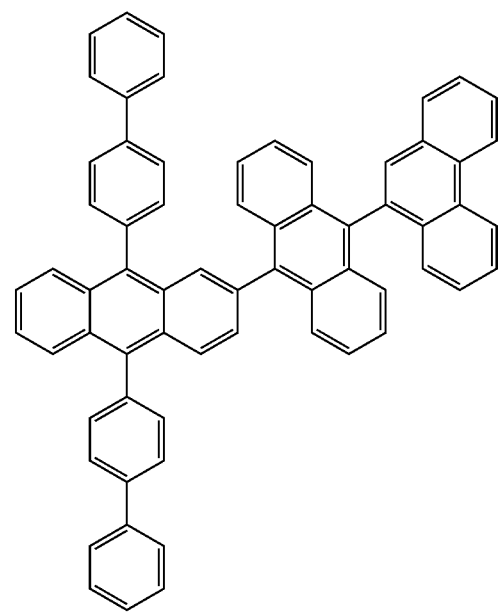
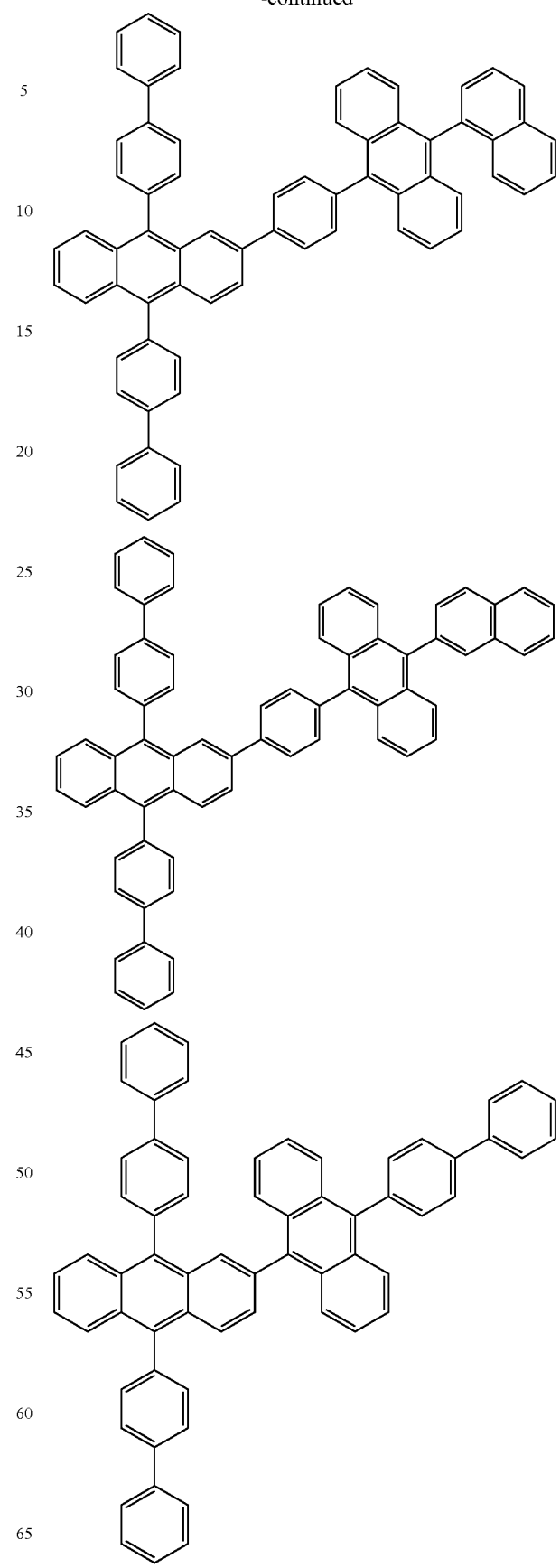

541
-continued
542
-continued
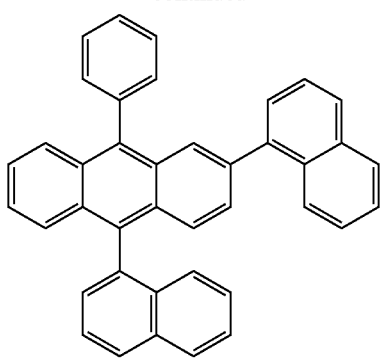
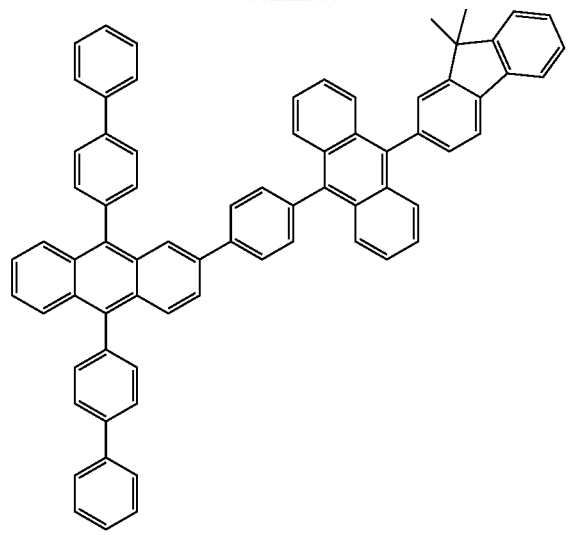

543
-continued
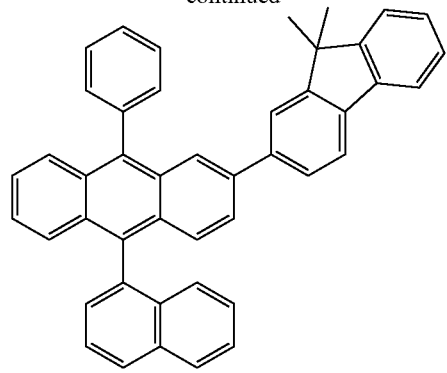
544
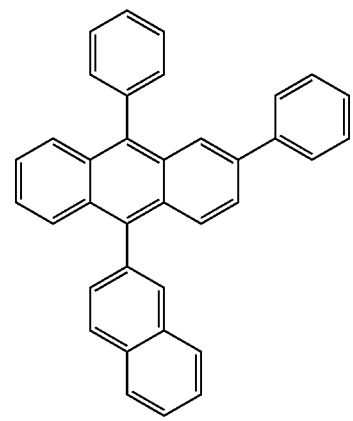
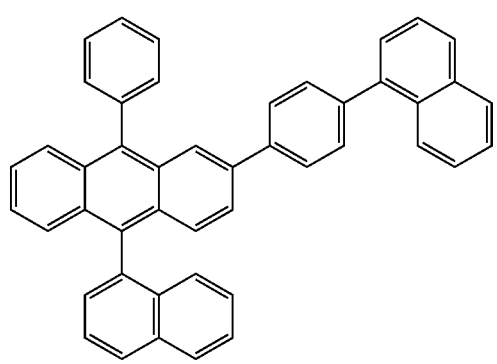
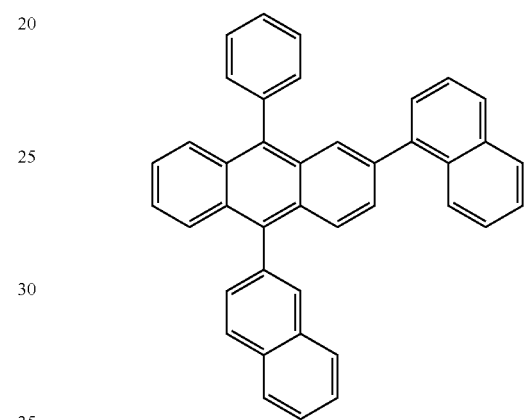
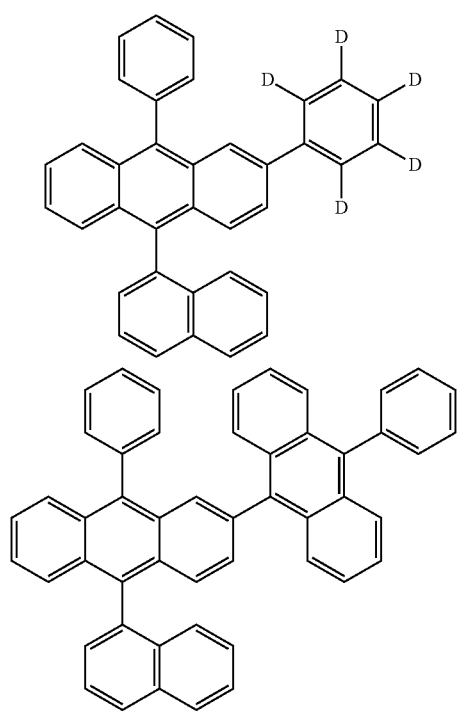
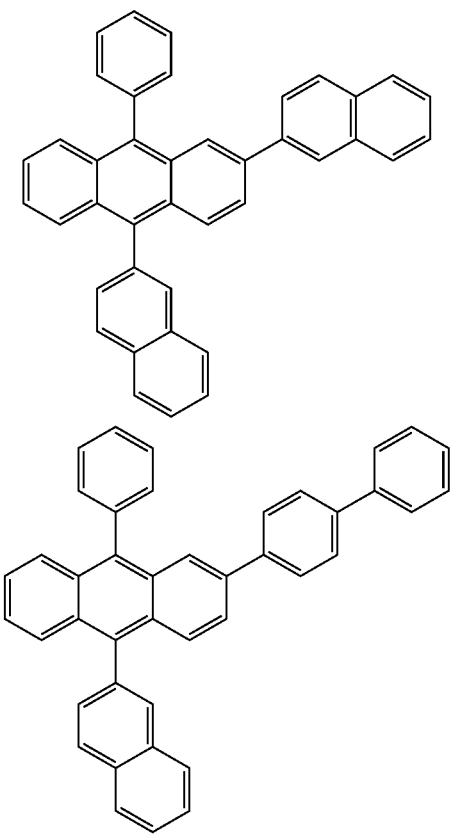
The six membered rings in the following compounds are all benzene rings.

545
-continued
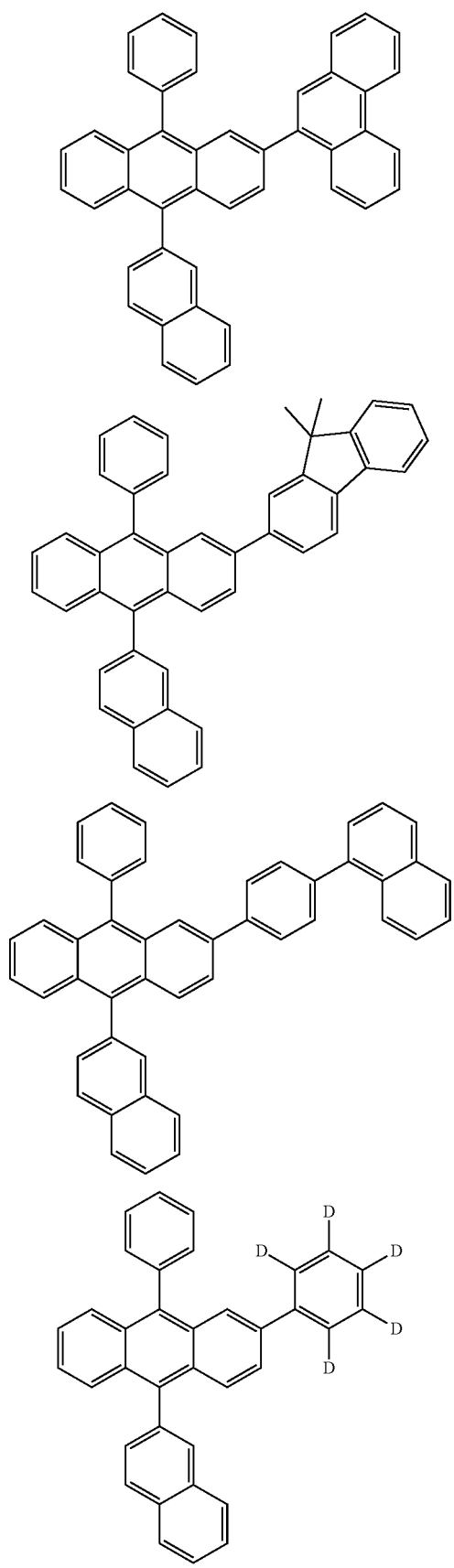
546
-continued
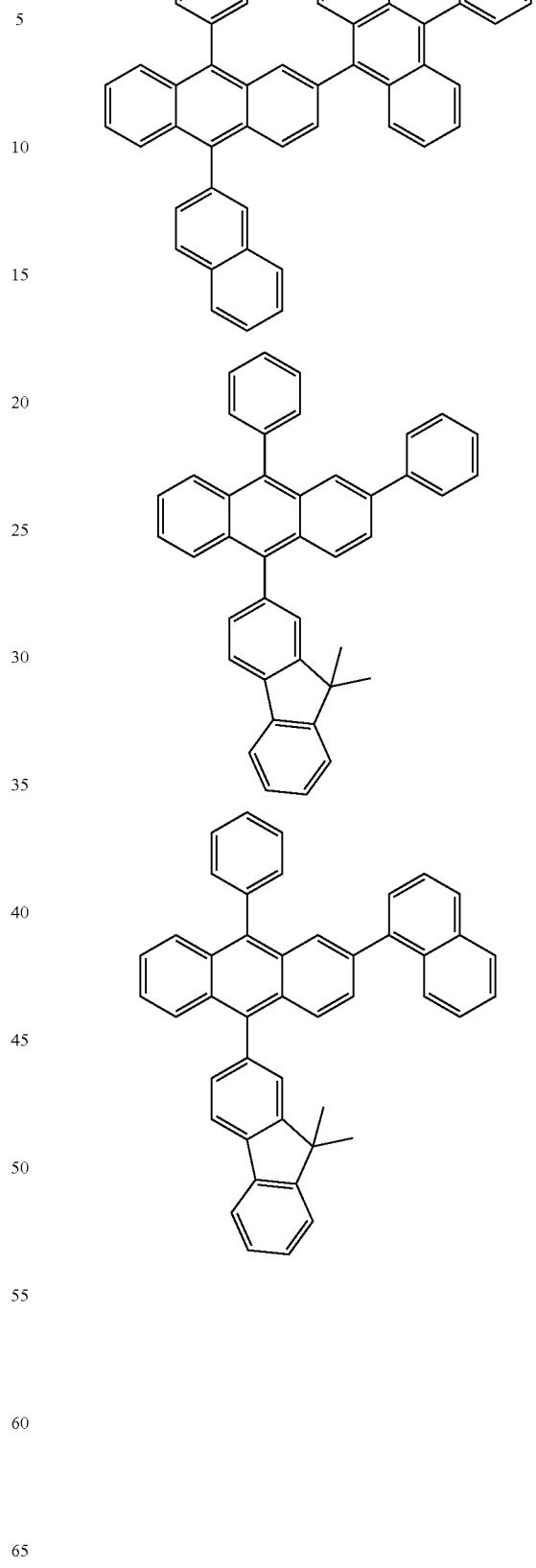

547
-continued
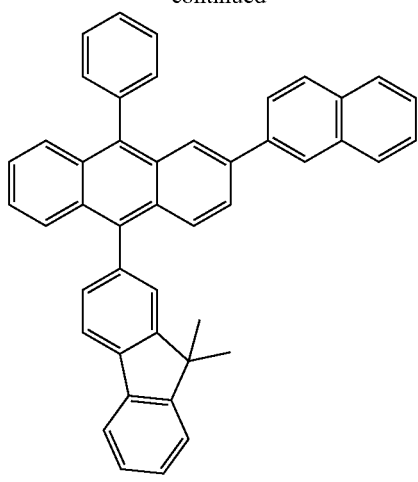
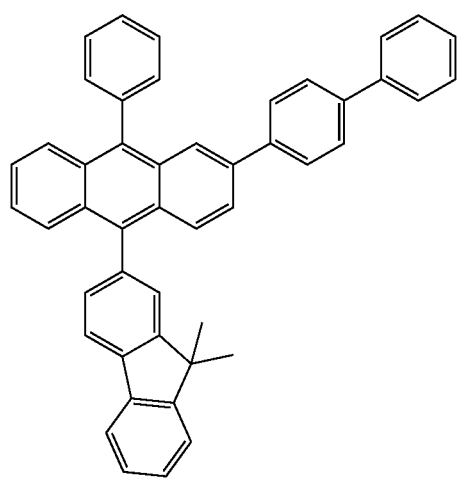
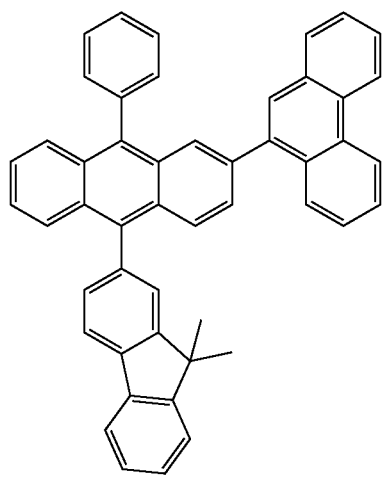
548
-continued
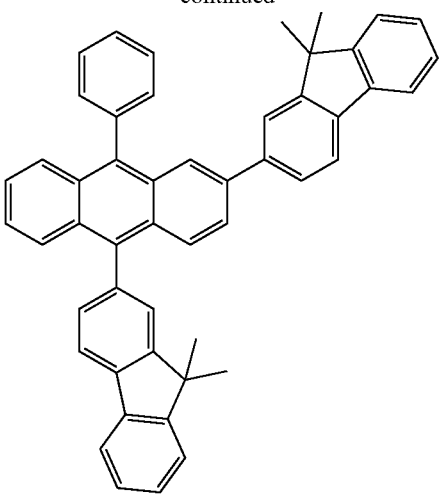
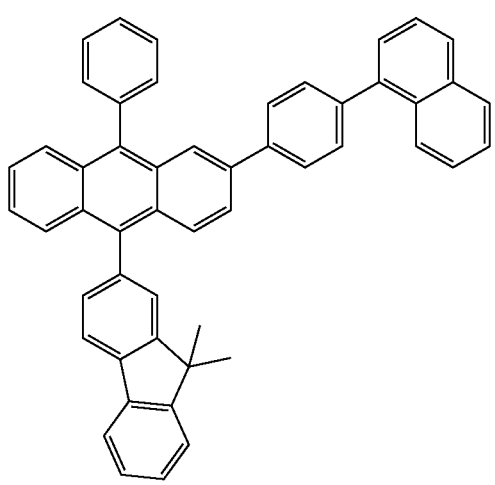
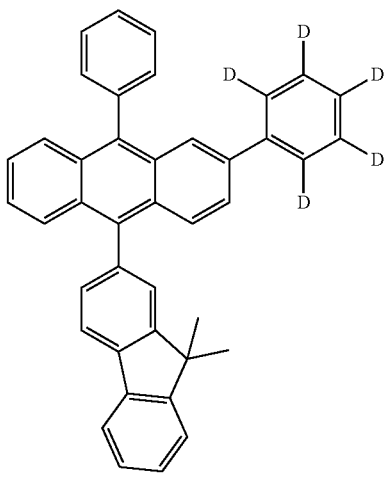

549
-continued
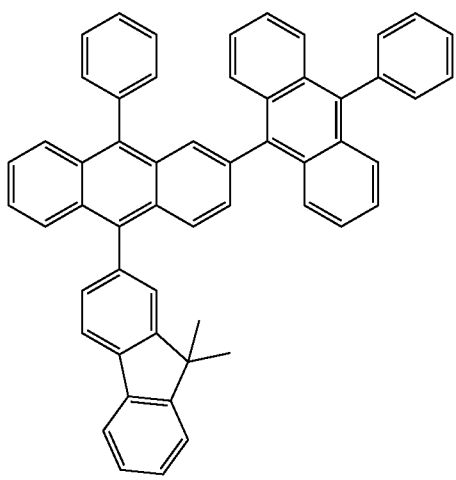
550
-continued
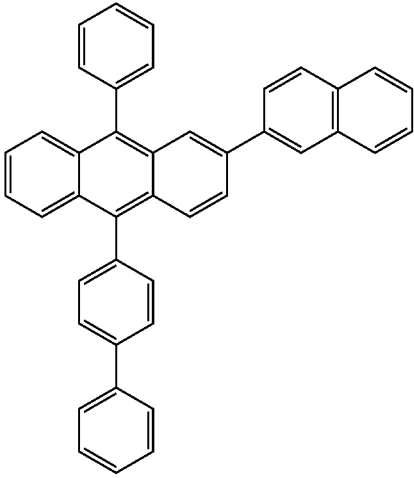
The six membered rings in the following compounds are all benzene rings.
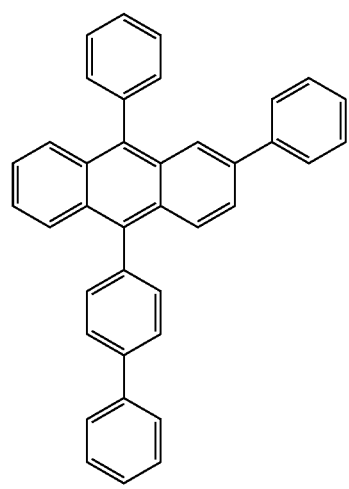
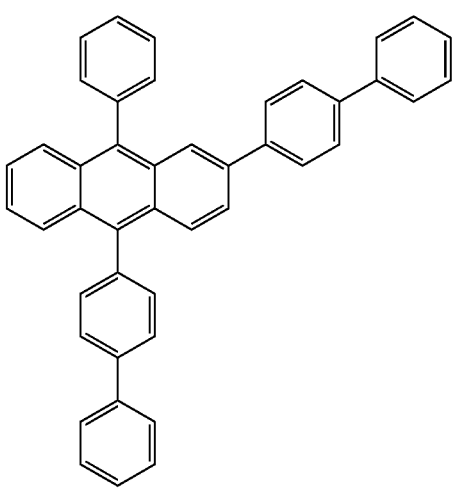
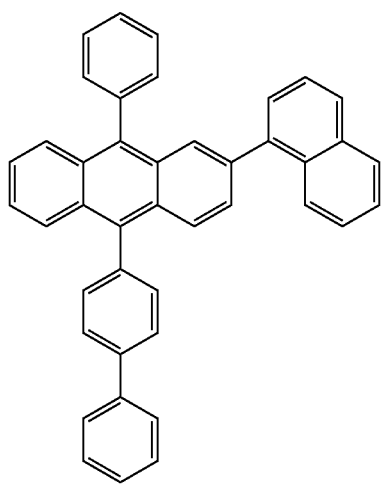
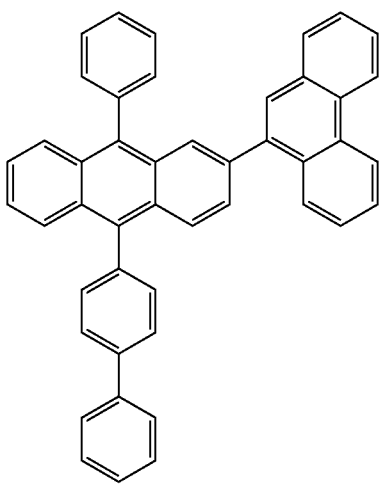

551
-continued
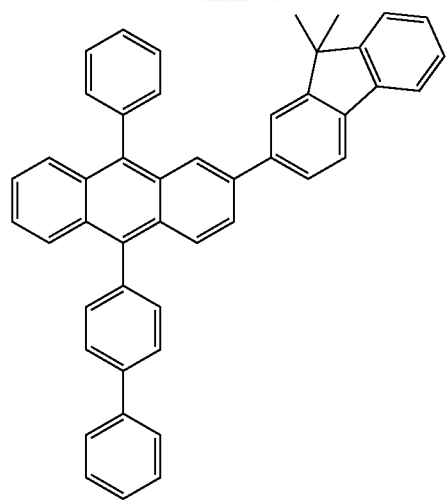
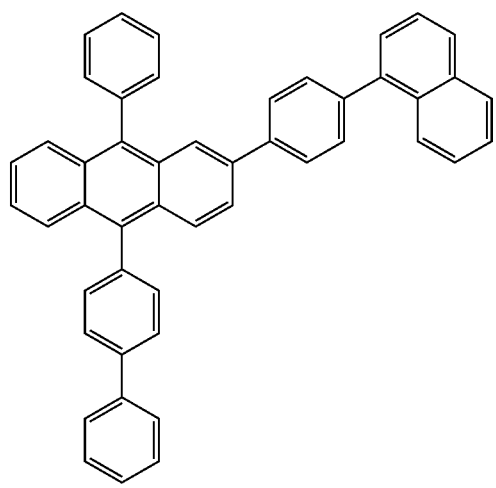
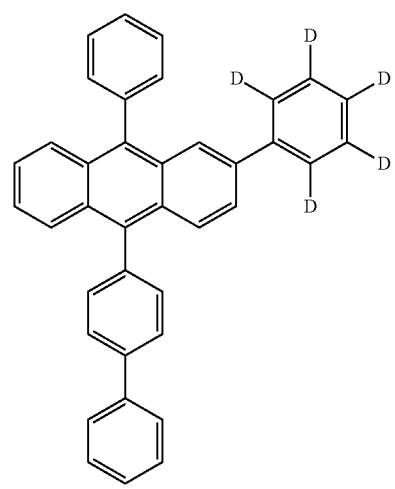
552
-continued
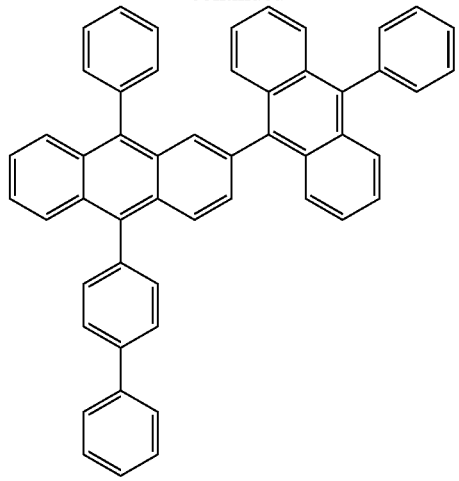
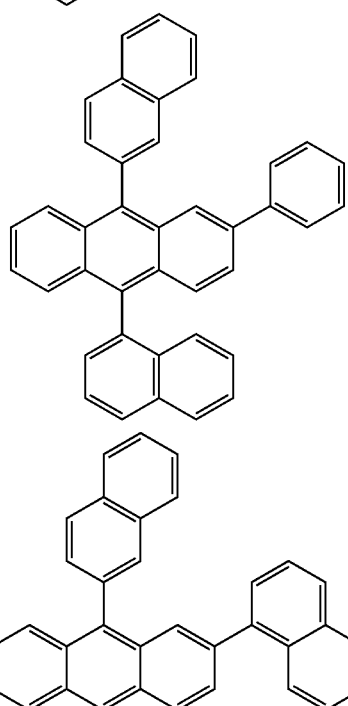
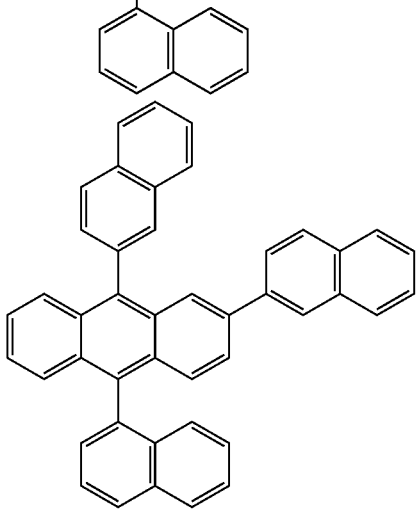

553
-continued
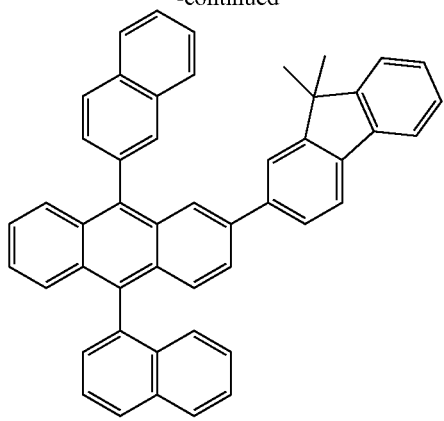
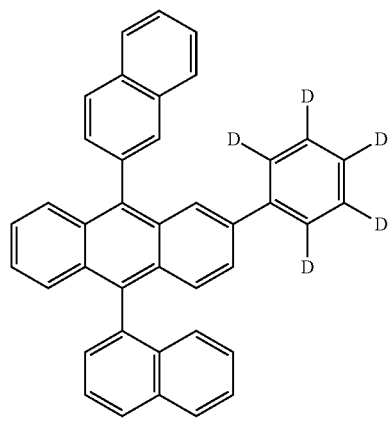
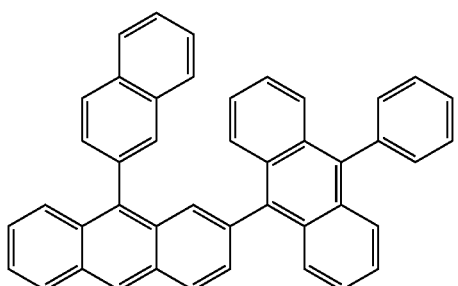
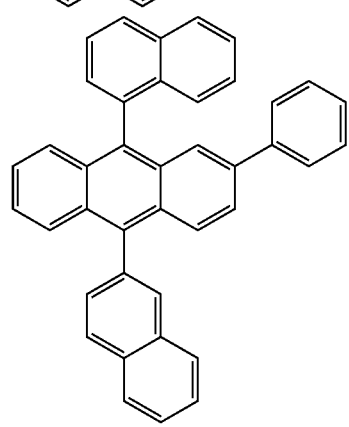
554
-continued
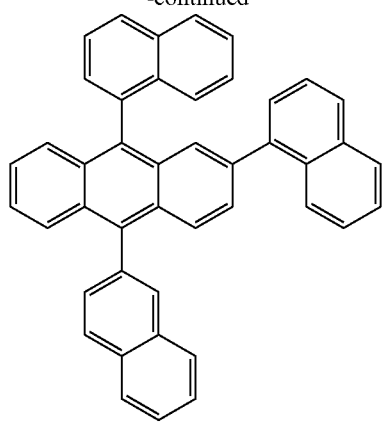
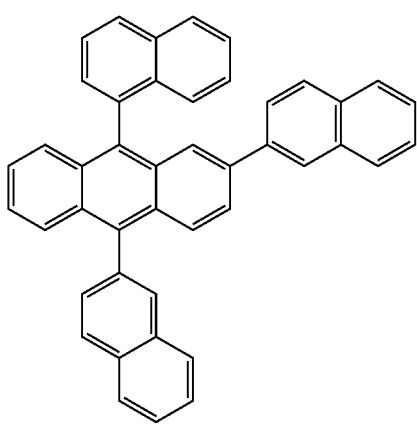
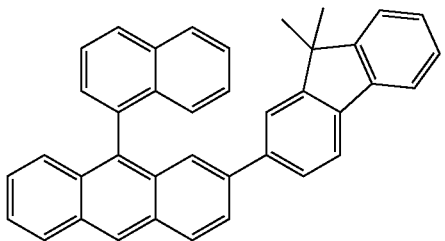
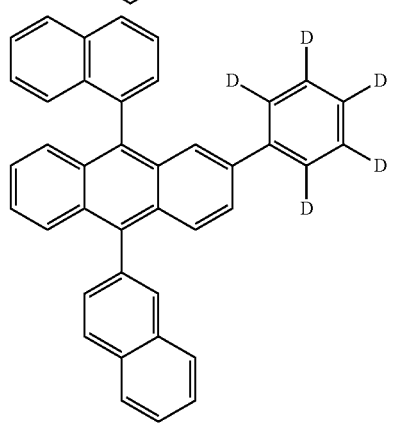

555
-continued
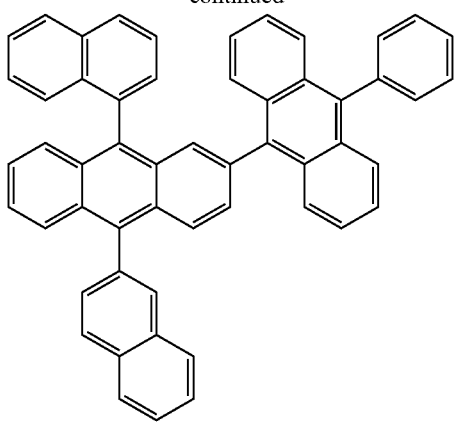
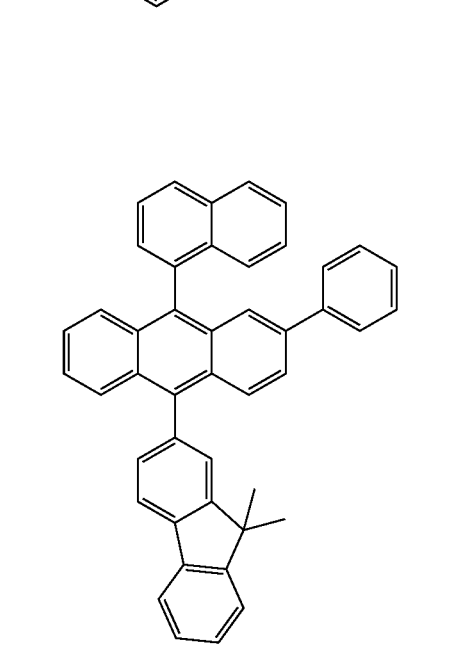
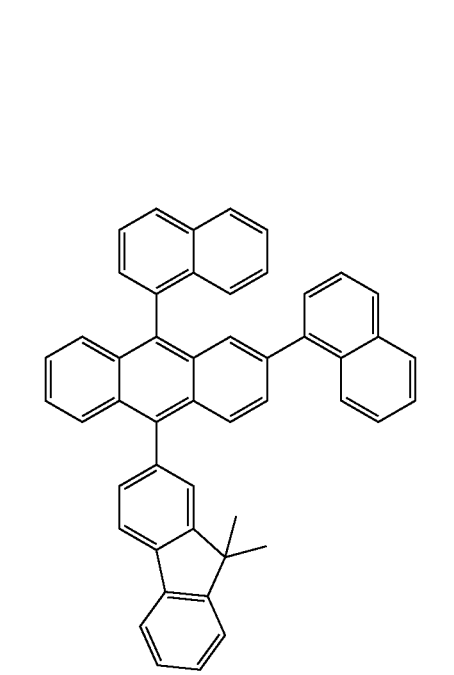
556
-continued
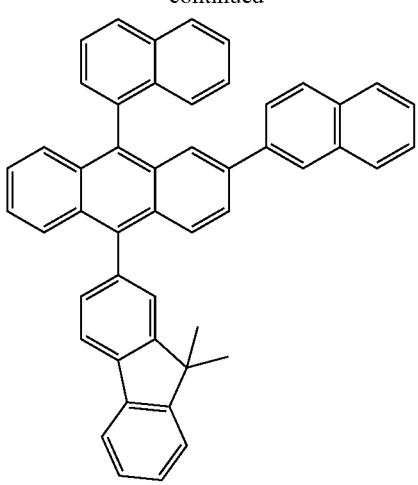
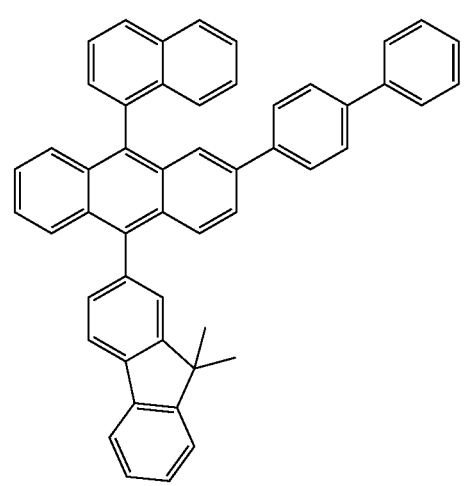
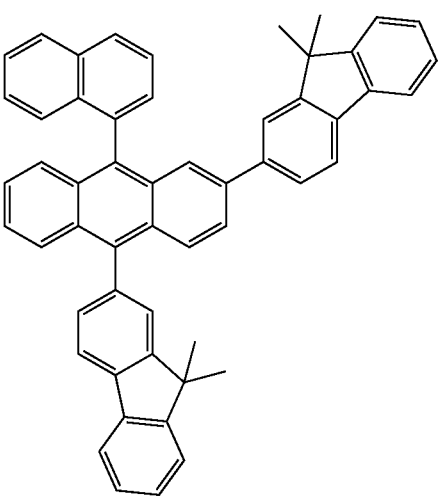

557
-continued
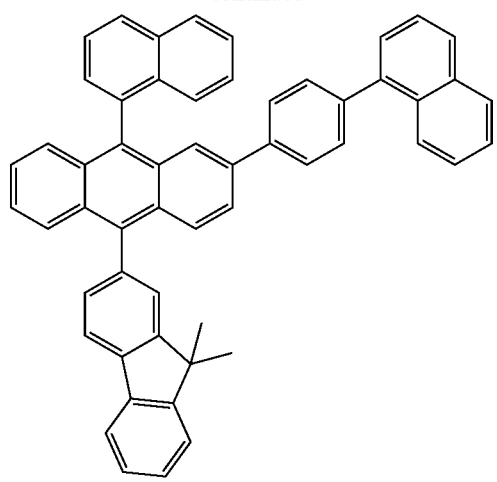
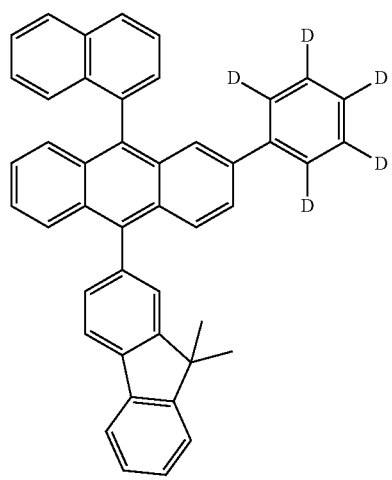
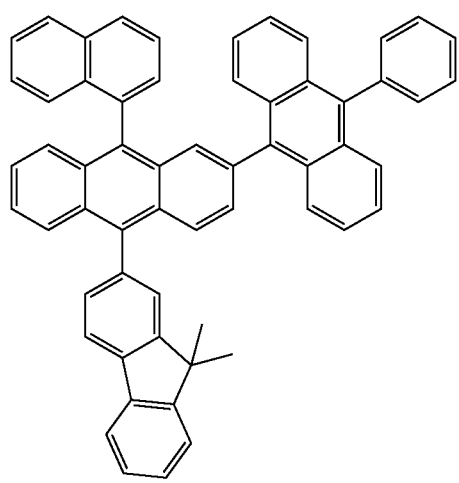
558
-continued
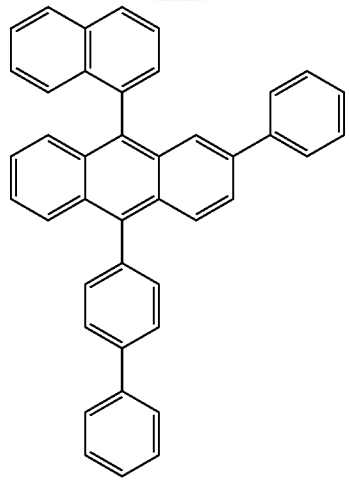
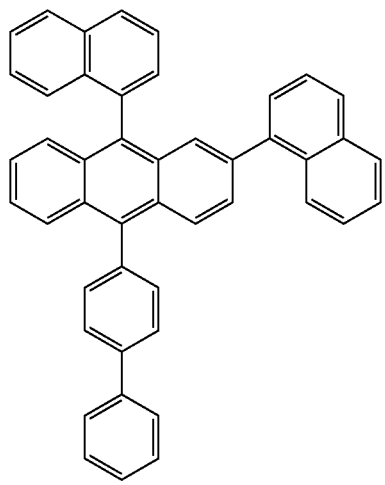
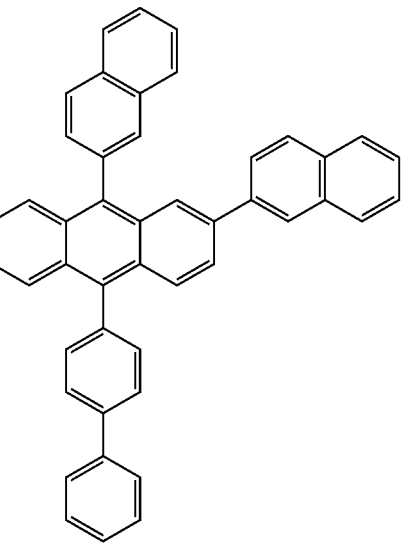

559
-continued
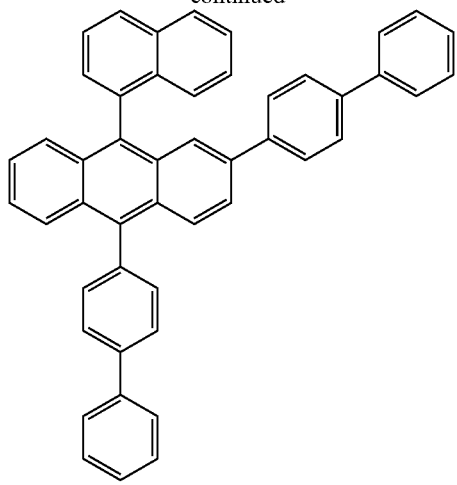
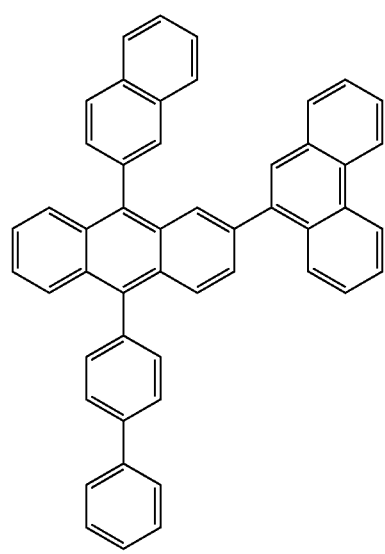
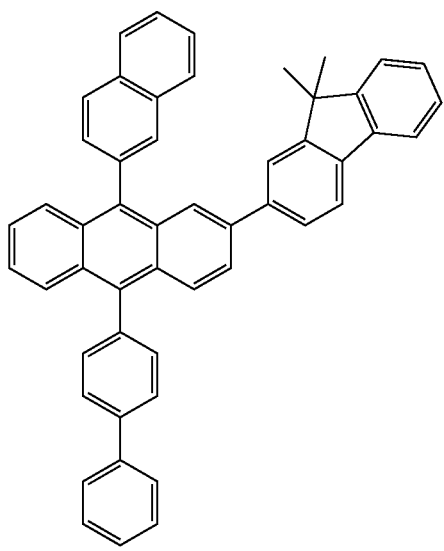
560
-continued
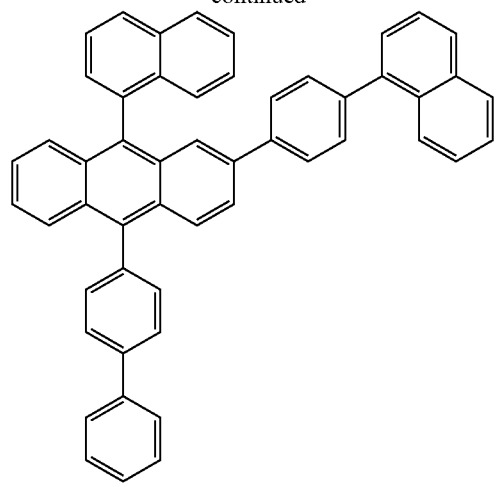
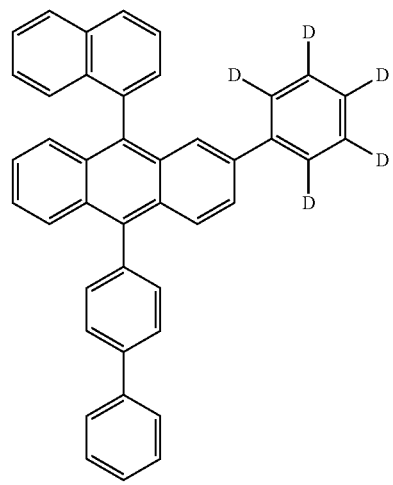
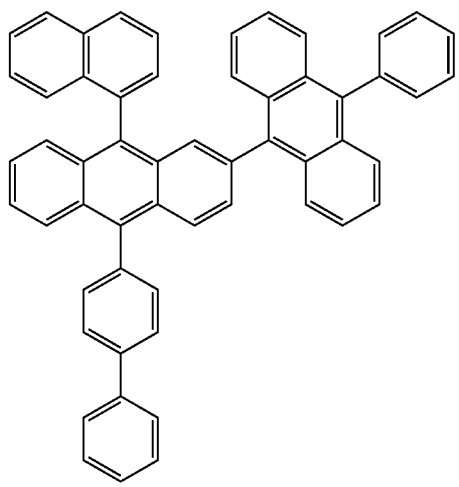

561
-continued
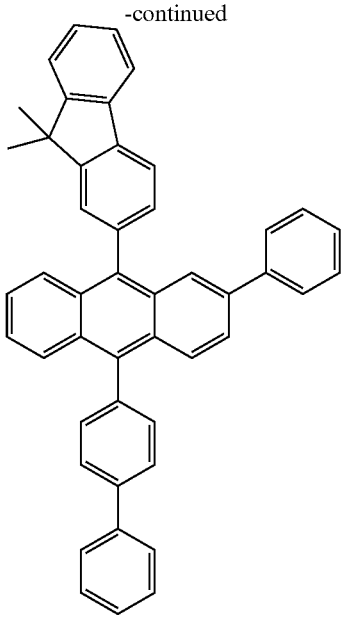
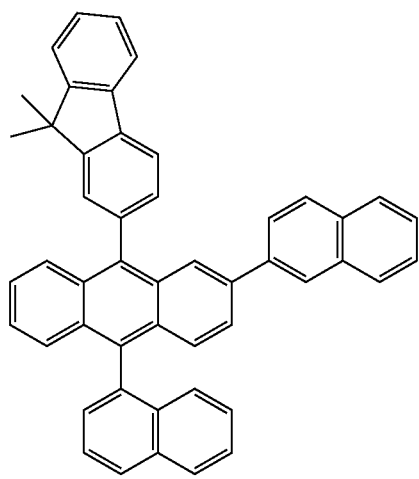
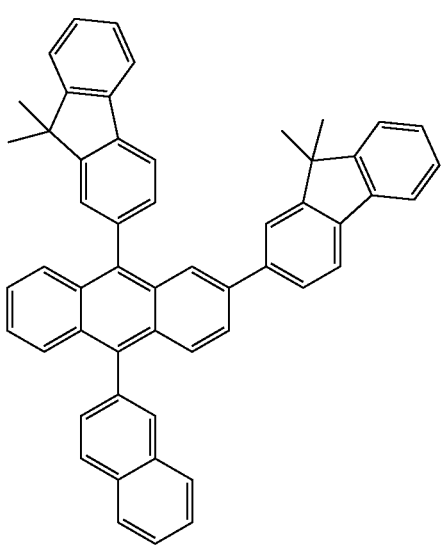
562
-continued
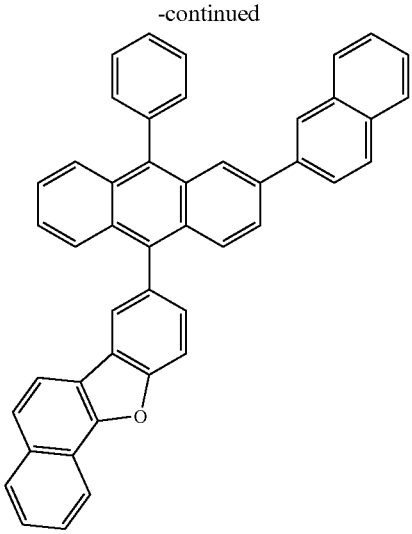
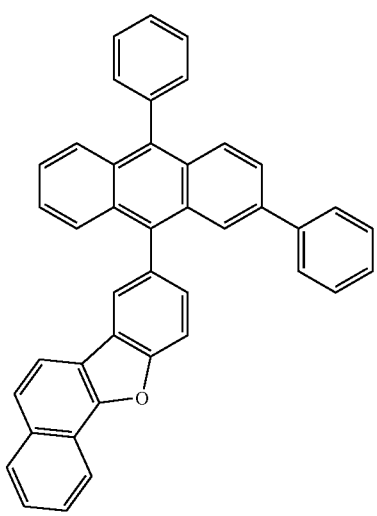
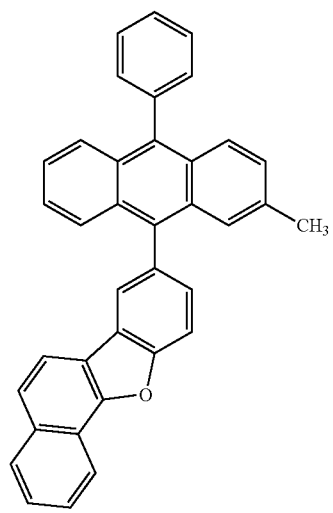

563
-continued
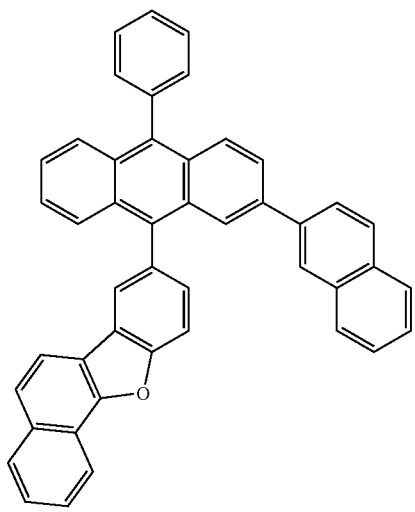
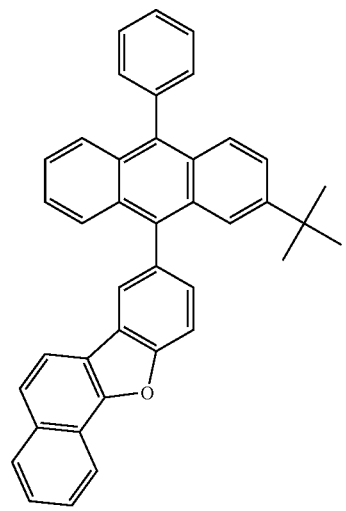
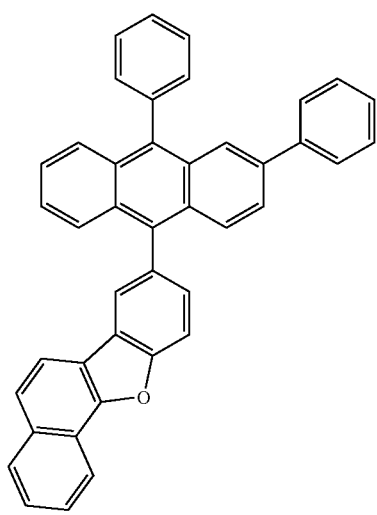
564
-continued
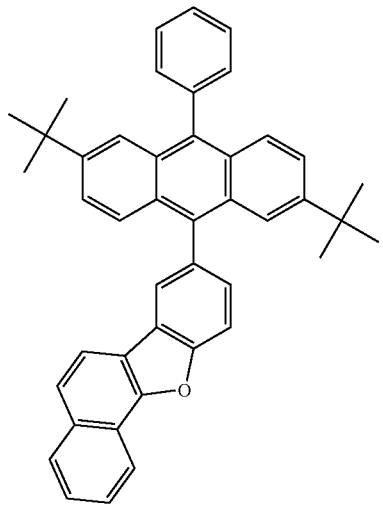
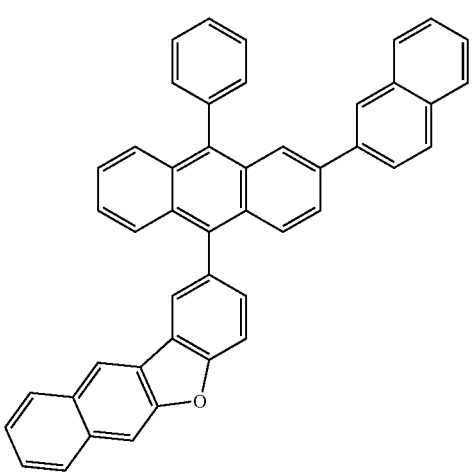
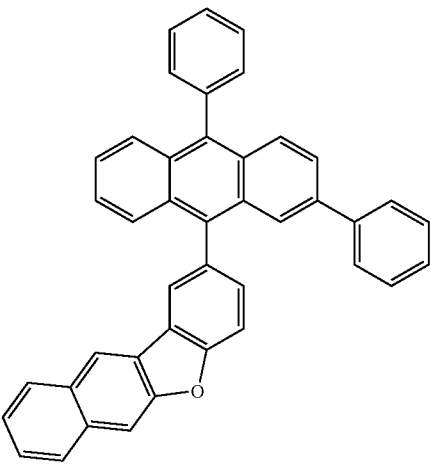

565
-continued

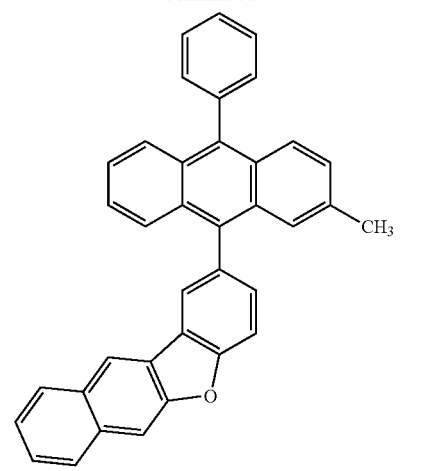

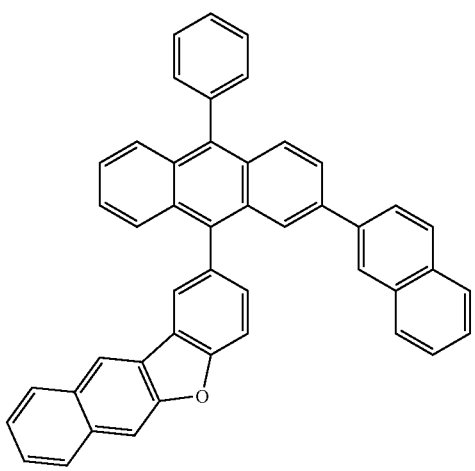

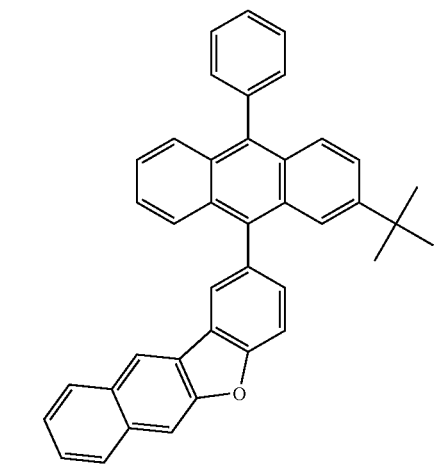

566
-continued

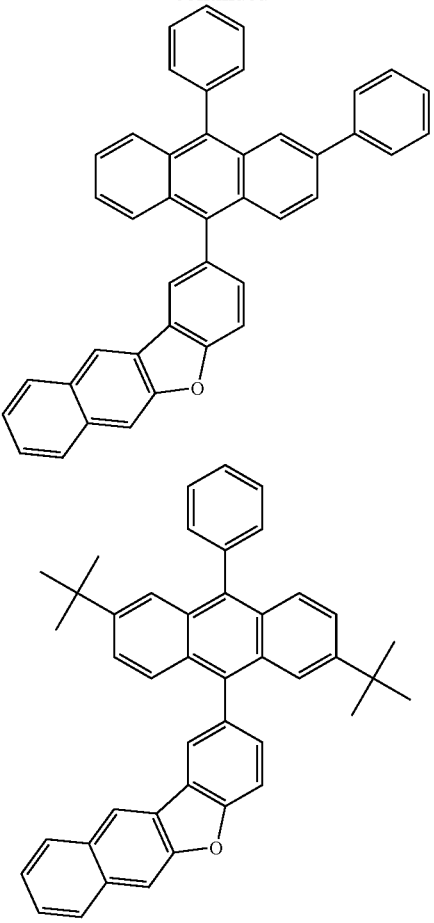

As the compound comprising a chrysene skeleton, for example, a compound represented by formula (21) is preferably used:

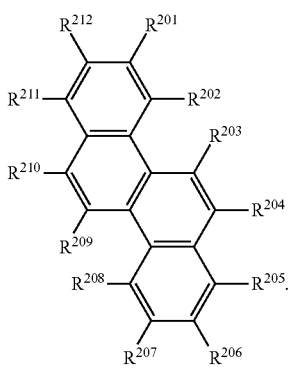

(21)

In formula (21), $R^{201}$ to $R^{212}$ are each independently a hydrogen atom or a substituent, wherein the substituent is the same as described above with respect to $R_1$ to $R_{11}$ or represented by $-L^2-Ar^{21}$. Examples, preferred numbers of carbon atoms and atoms, and preferred groups thereof are also the same as in $R_1$ to $R_{11}$.

Provided that at least one of $R^{201}$ to $R^{212}$ is $-L^2-Ar^{21}$, wherein $L^2$ and $Ar^{21}$ are respectively the same as L and Ar of formula (19) and examples, preferred numbers of carbon atoms and atoms, and preferred groups thereof are also the same as in L and Ar.

One of $R^{204}$ and $R^{210}$ or both of $R^{204}$ and $R^{210}$ are preferably $—L^2-Ar^{21}$. Examples of the chrysene derivative represented by formula (21) are shown below, although not limited thereto.

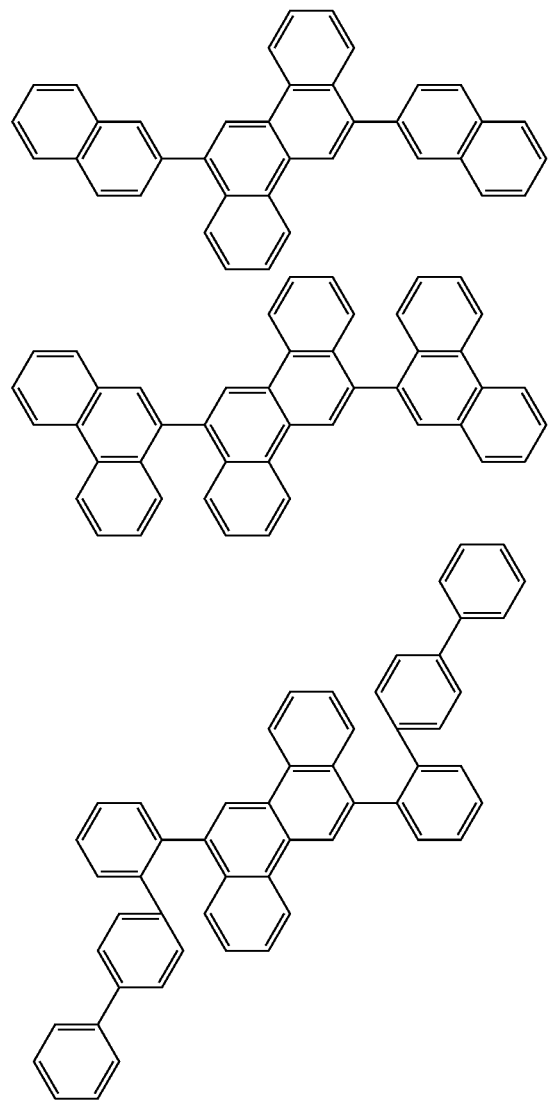

The six membered rings in the following compounds are all benzene rings.

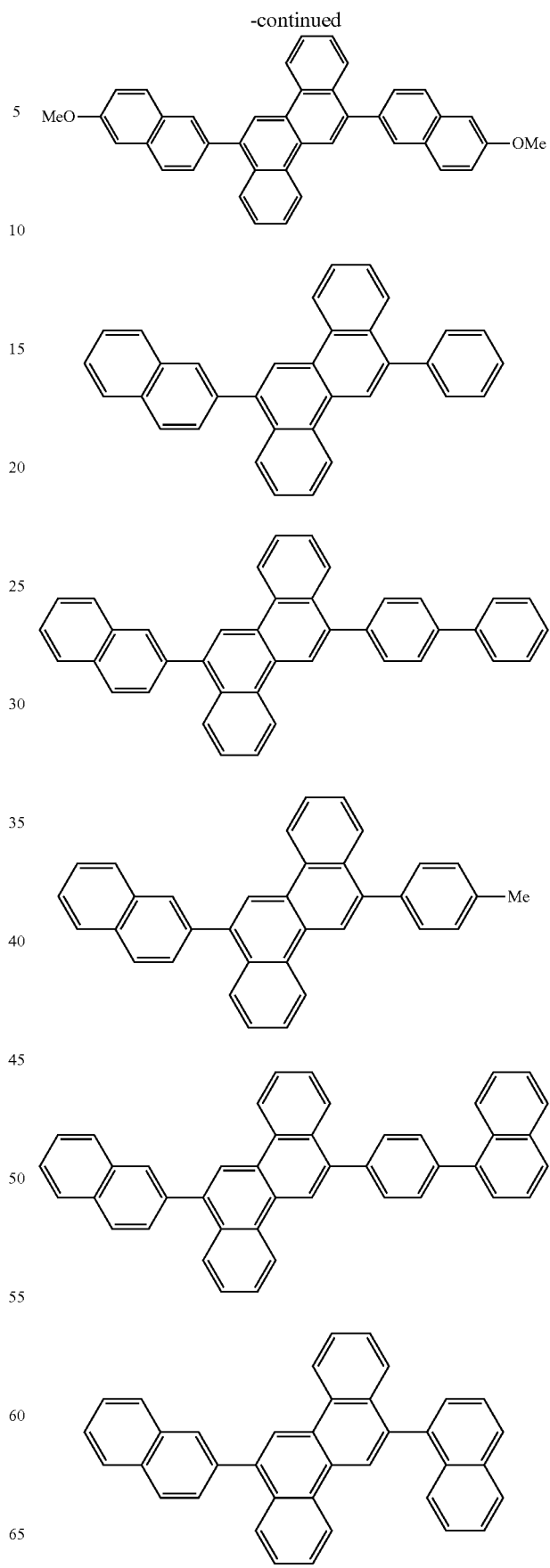

569
-continued
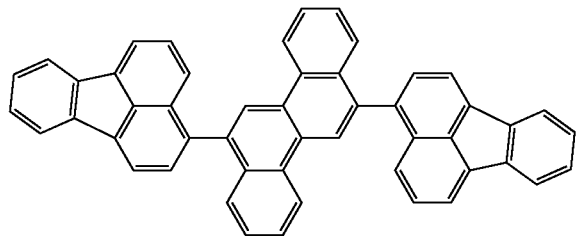
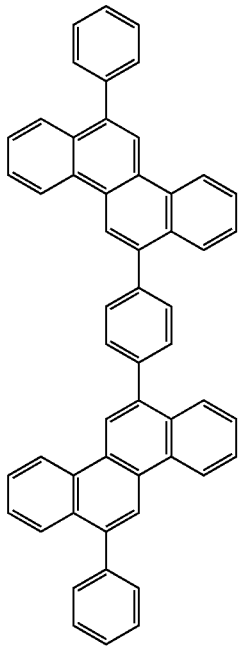
The six membered rings in the following compounds are all benzene rings.
570
-continued
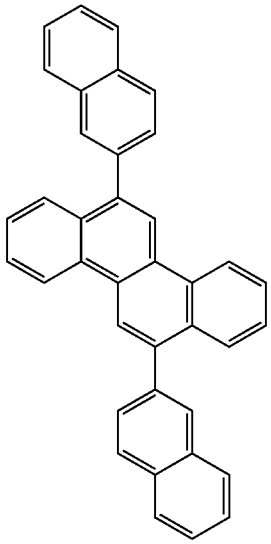
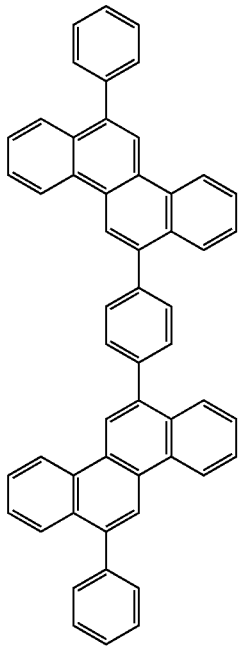

571
-continued
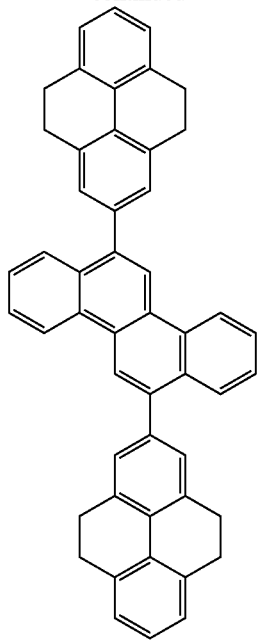
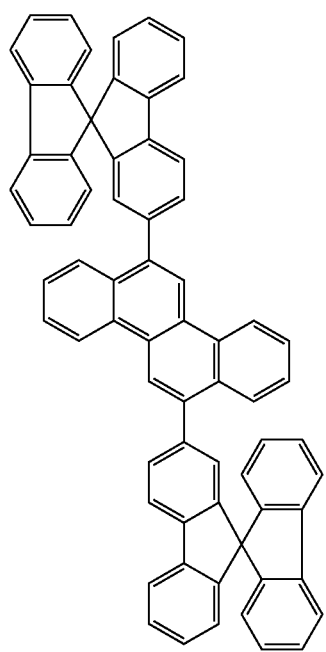
572
-continued
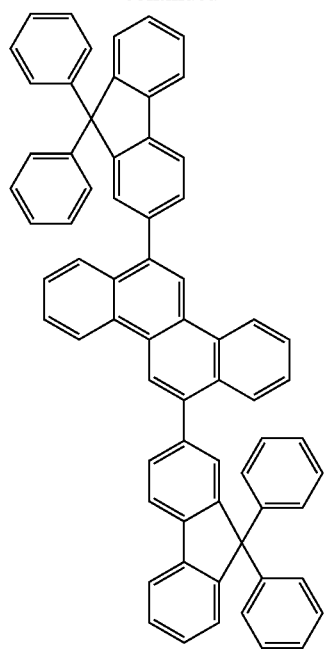
The six membered rings in the following compounds are all benzene rings.
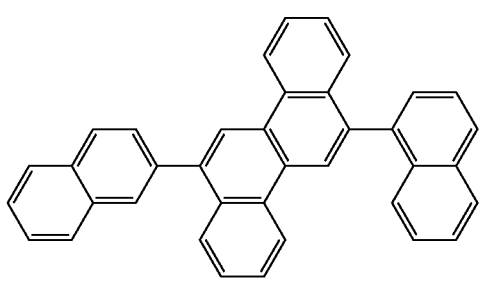

573
-continued
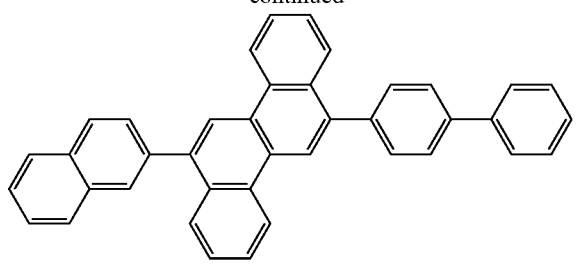
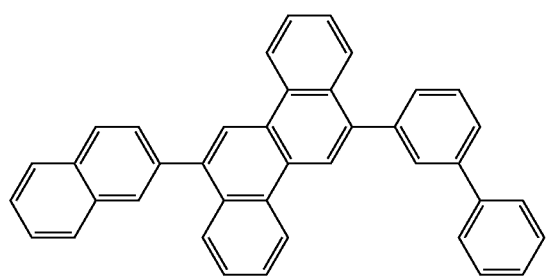
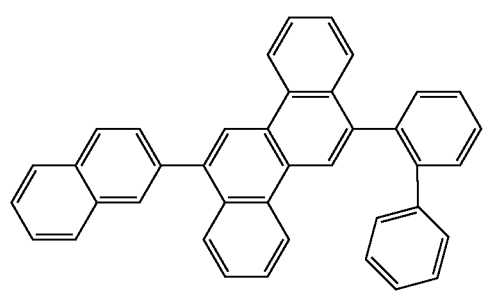
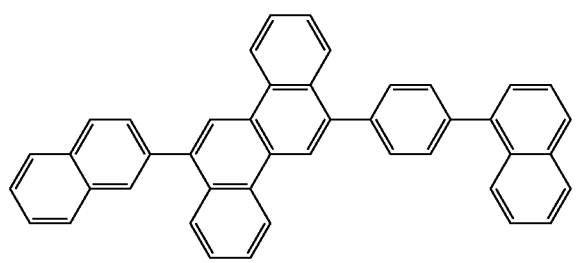
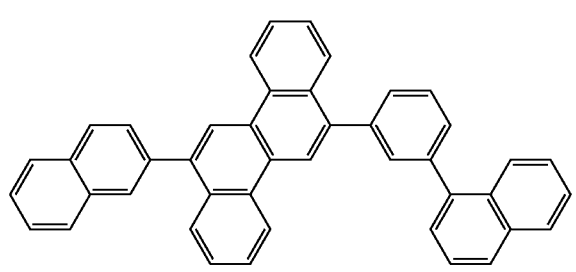
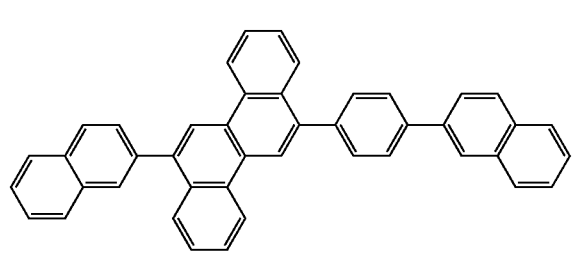
574
-continued
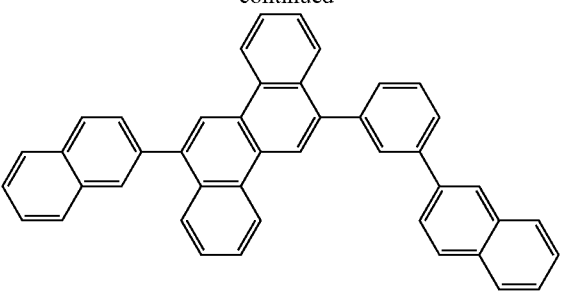
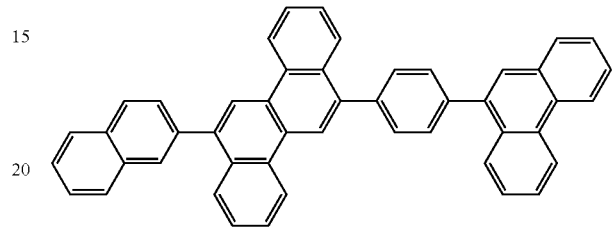
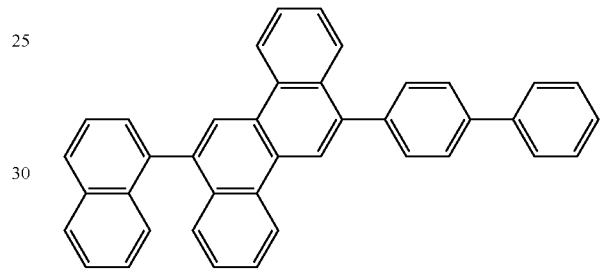
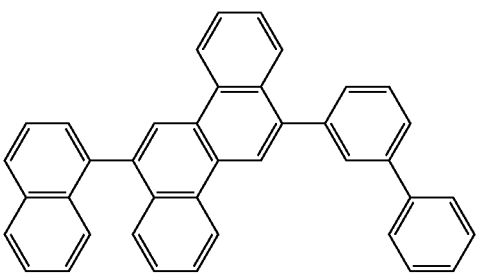
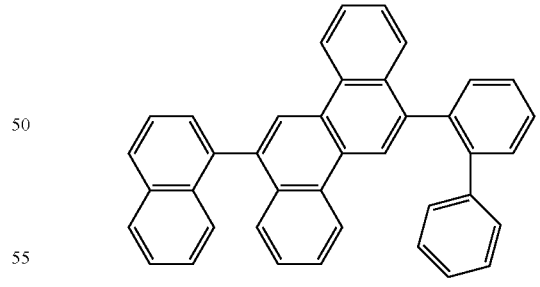
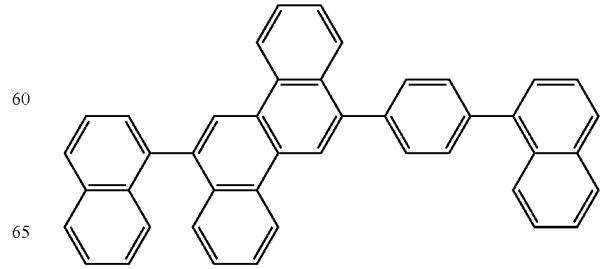

| 575 -continued | 576 -continued |
|---|---|
| 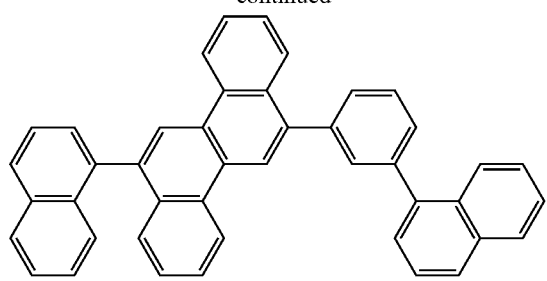 | 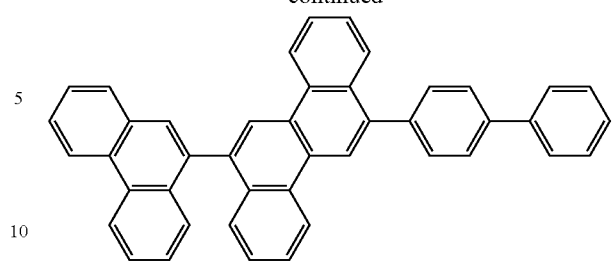 |
| 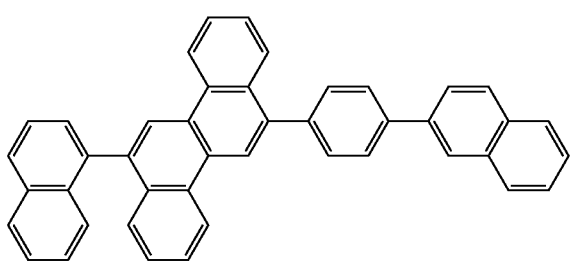 | 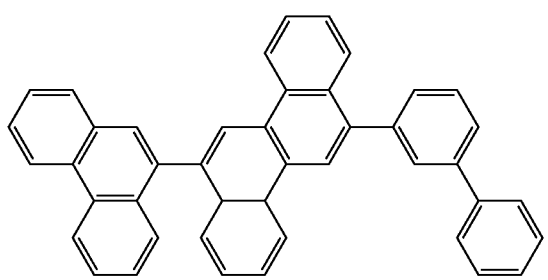 |
| 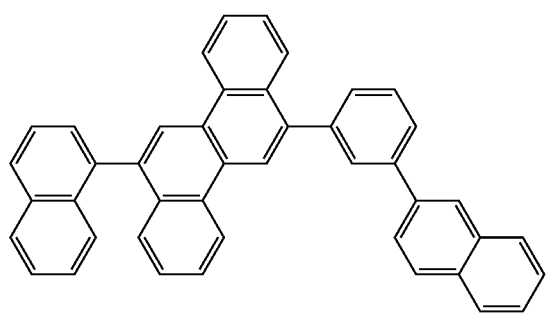 | 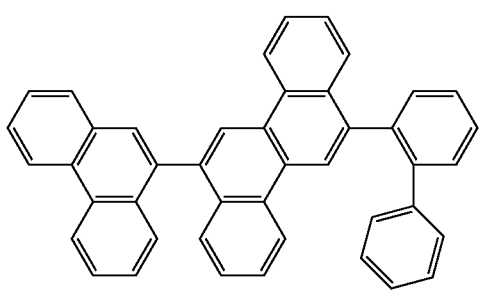 |
| 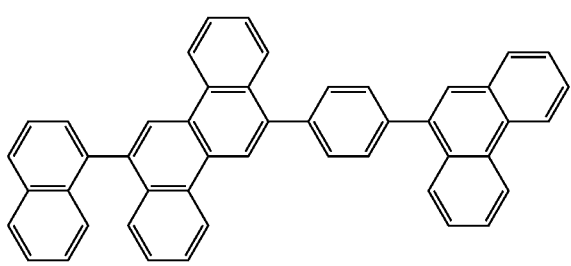 | 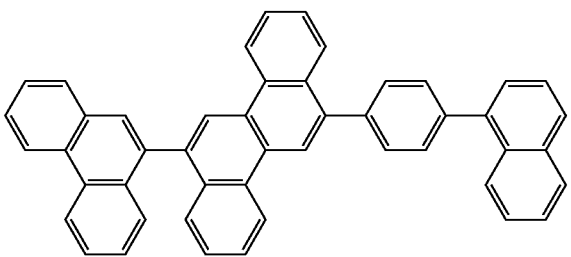 |
| 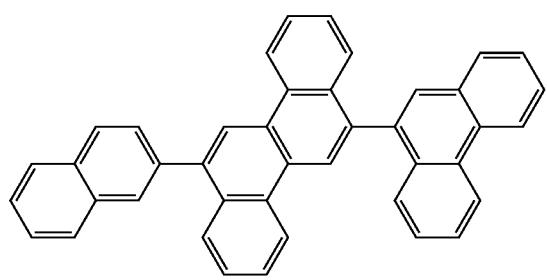 | 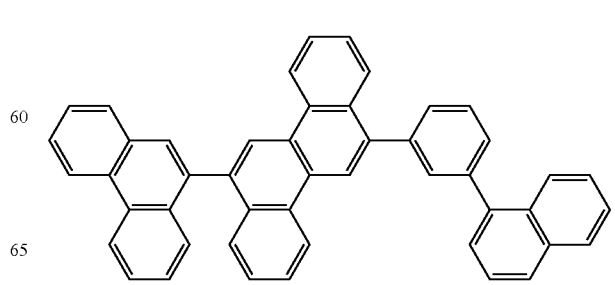 |

577
-continued
578
-continued
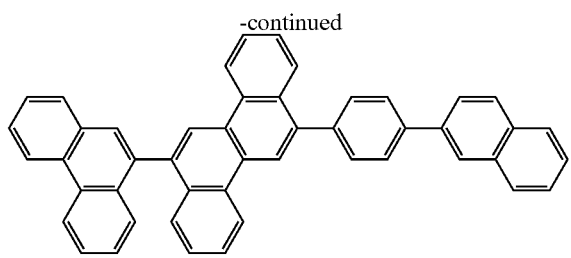
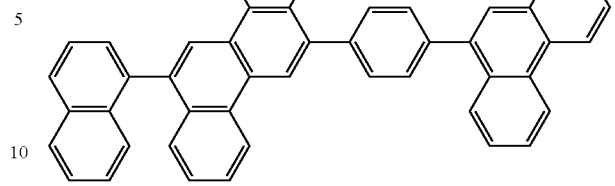
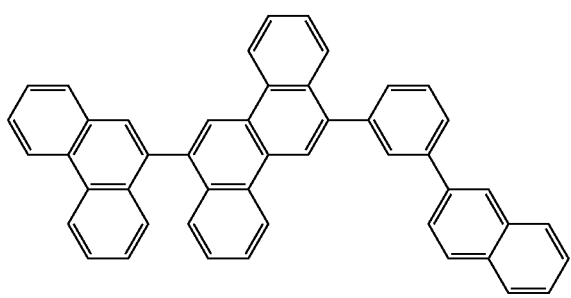
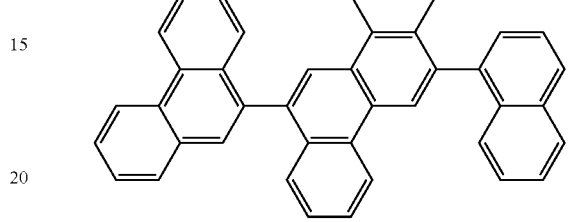
The six membered rings in the following compounds are all benzene rings.
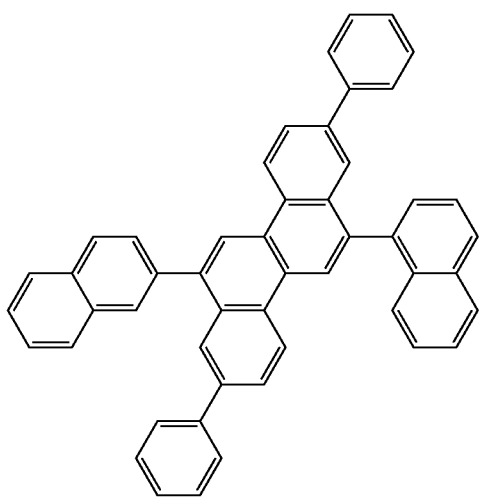
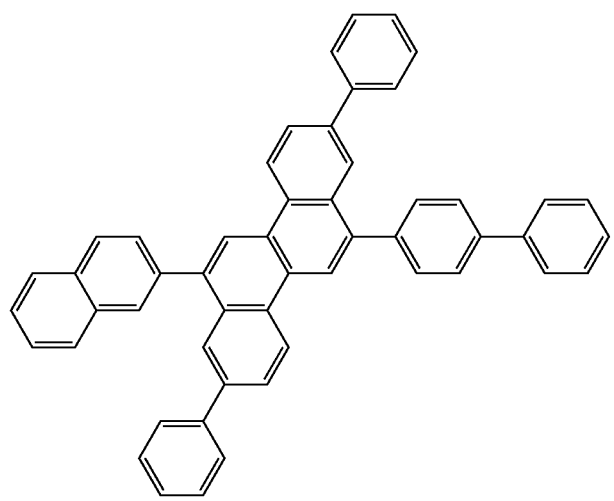
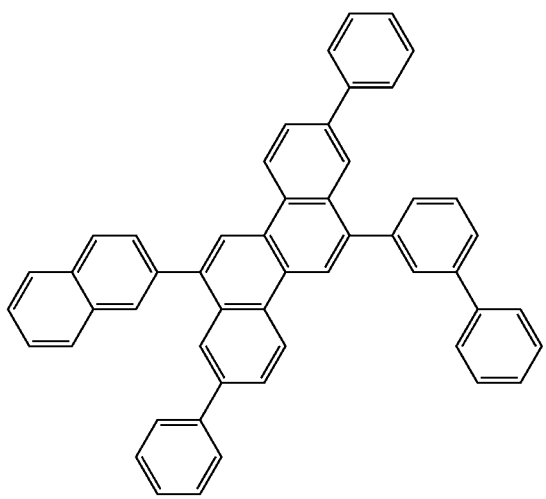
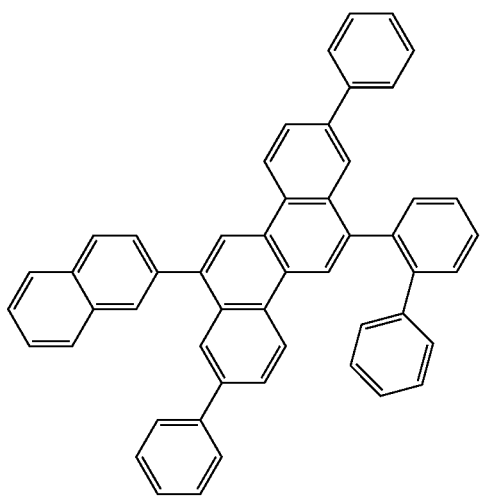

579
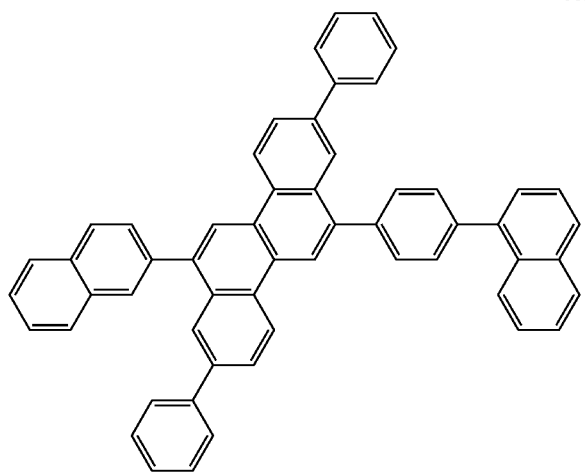
580
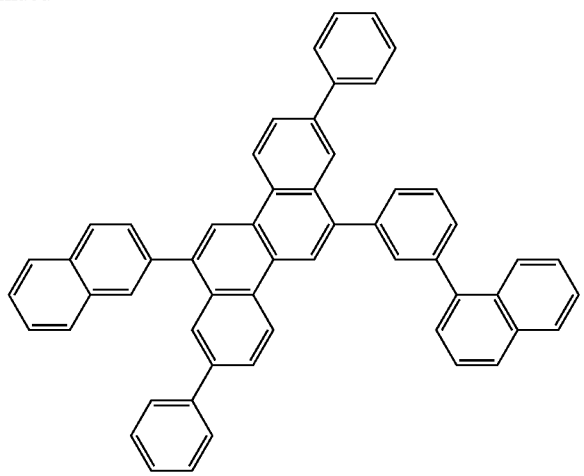
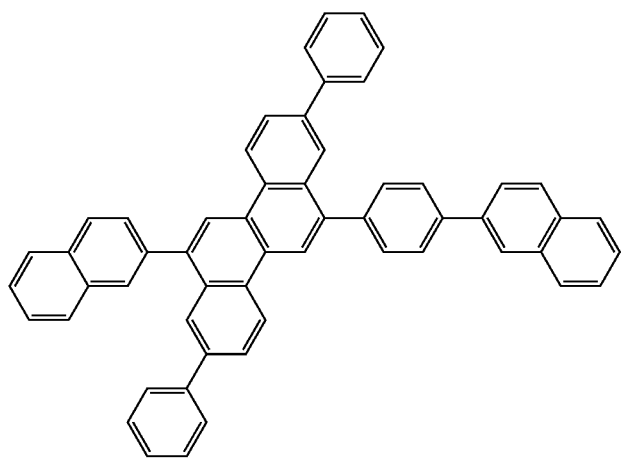
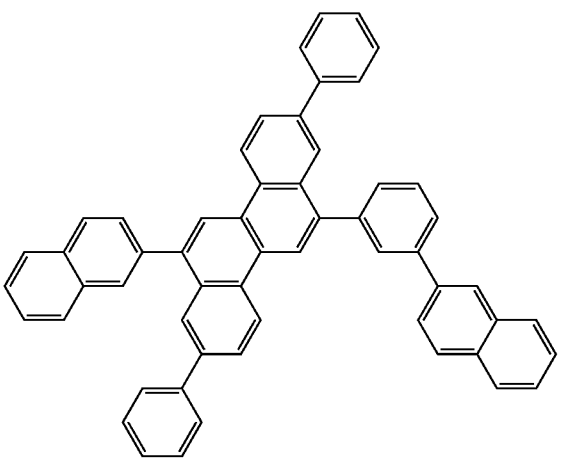
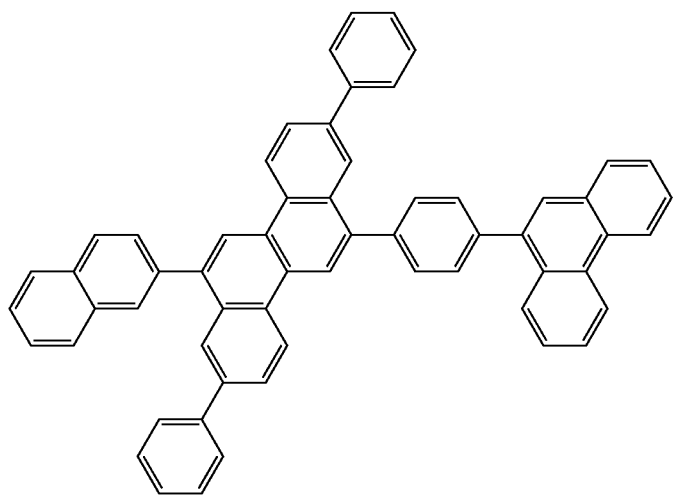
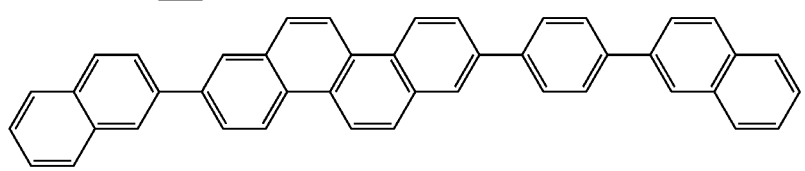

-continued
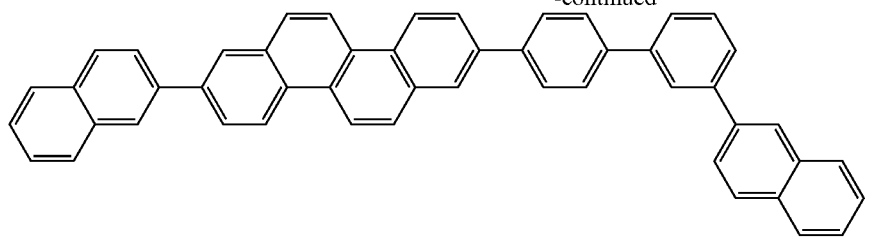
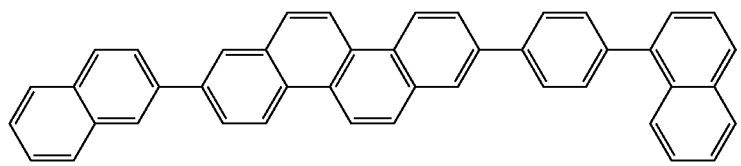
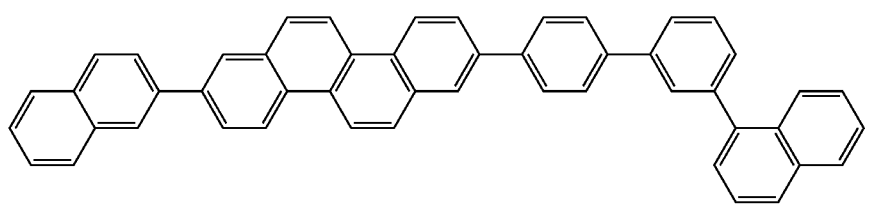
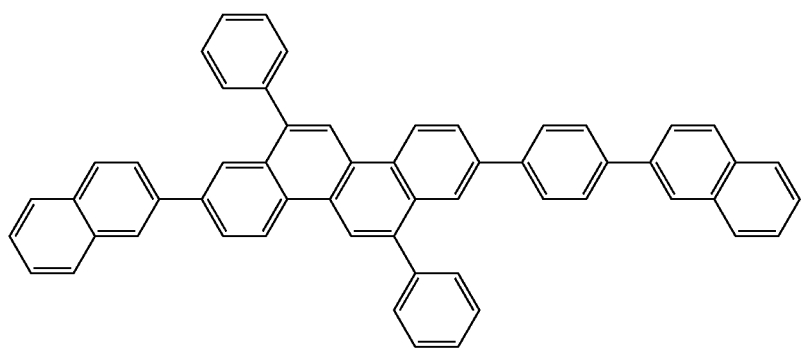
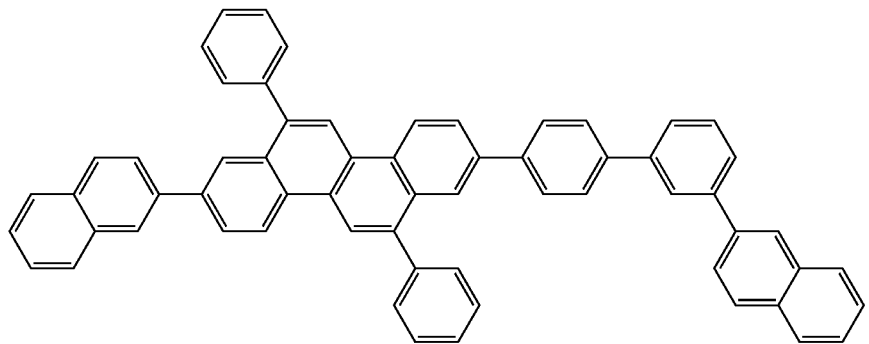
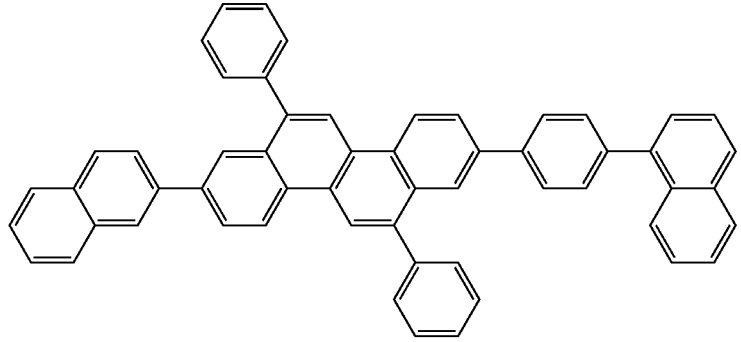

-continued

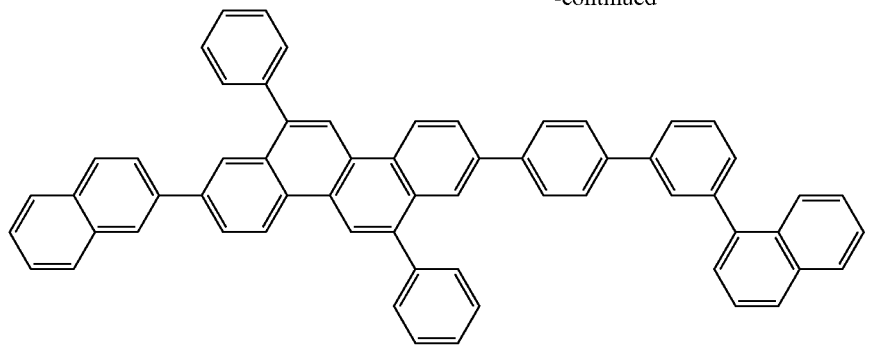

As the pyrene derivative, for example, a compound represented by formula (22) is preferably used:

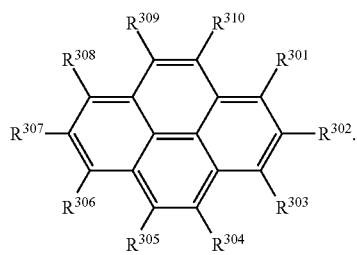

(22)

In formula (22), $R^{301}$ to $R^{310}$ are each independently a hydrogen atom or a substituent, wherein the substituent is the same as described above with respect to $R_1$ to $R_{11}$ or represented by —$L^3$-$Ar^{31}$. Examples, preferred numbers of carbon atoms and atoms, and preferred groups thereof are also the same as in $R_1$ to $R_{11}$.

Provided that at least one of $R^{301}$ to $R^{310}$ is —$L^3$-$Ar^{31}$, wherein $L^3$ and $Ar^{31}$ are respectively the same as L and Ar of formula (19). Examples, preferred numbers of carbon atoms and atoms, and preferred groups thereof are also the same as in L and Ar.

One or more of $R^{301}$, $R^{303}$, $R^{306}$, and $R^{308}$ are preferably —$L^3$-$Ar^{31}$.

Examples of the pyrene derivative represented by formula (22) are shown below, although not limited thereto.

The six membered rings in the following compounds are all benzene rings.

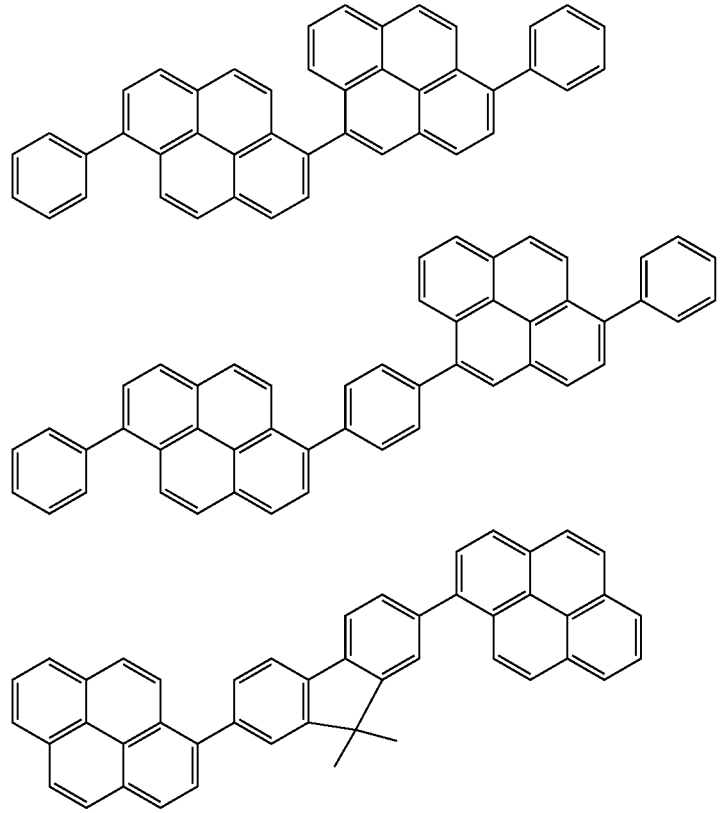

-continued
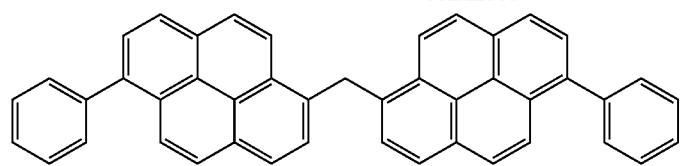
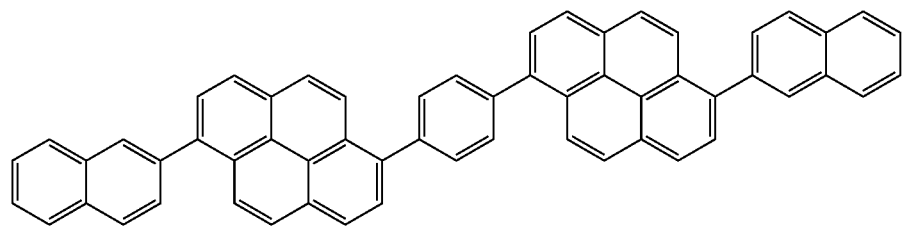
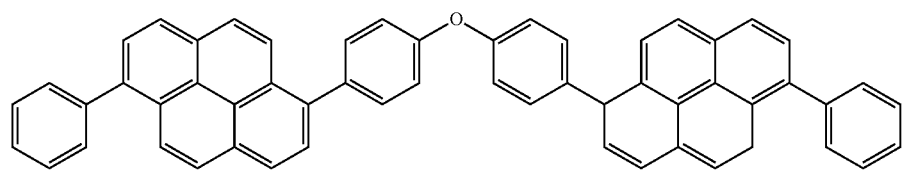
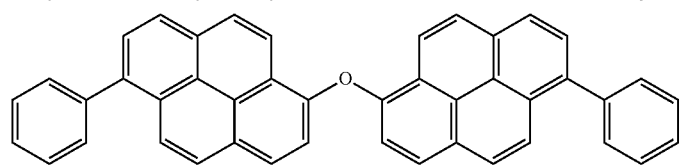
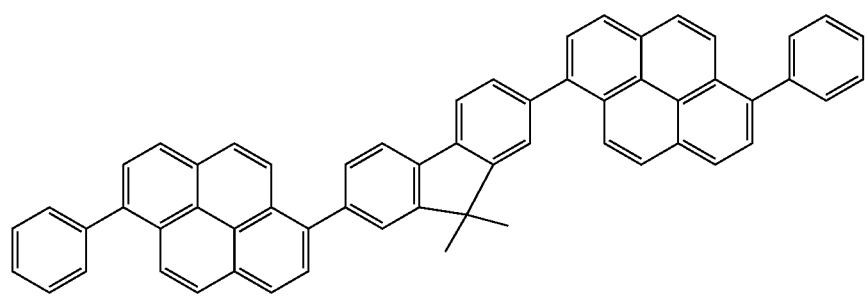
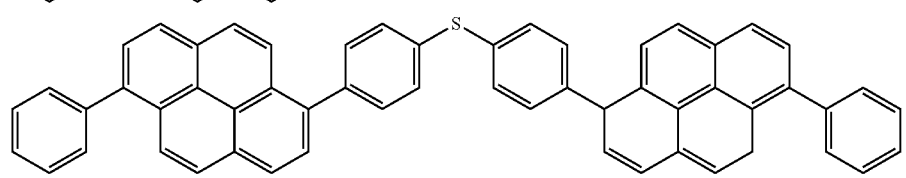
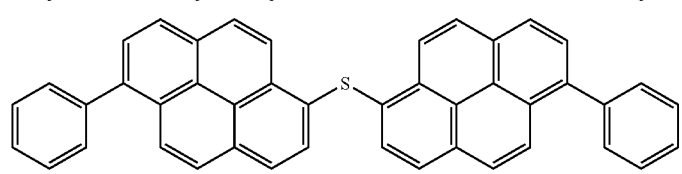
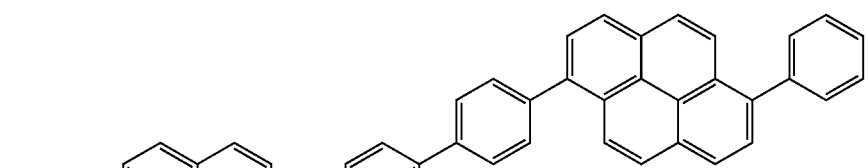
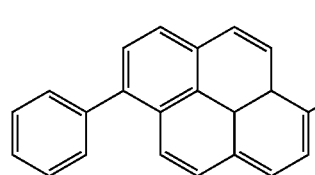

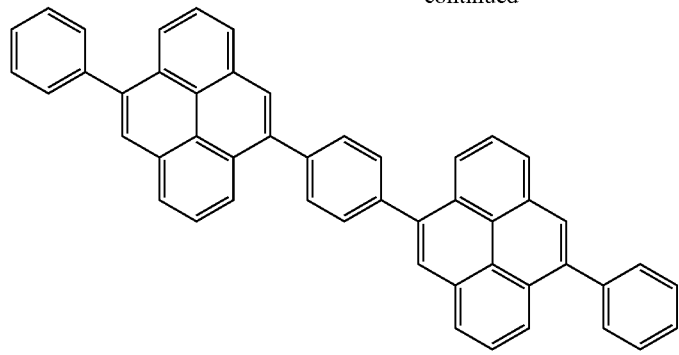
The six membered rings in the following compounds are all benzene rings.
-continued
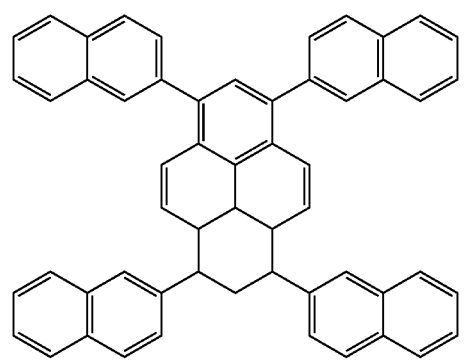
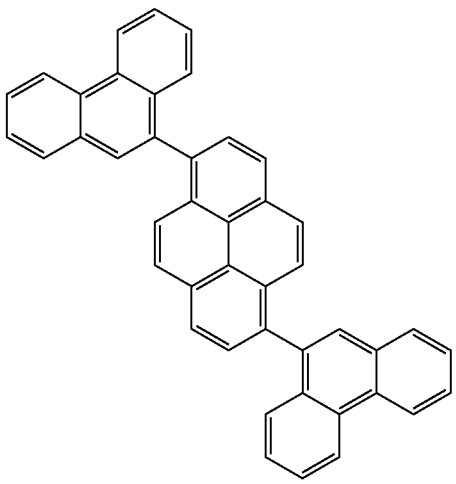
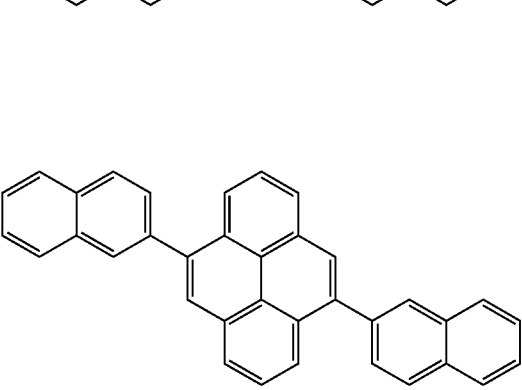
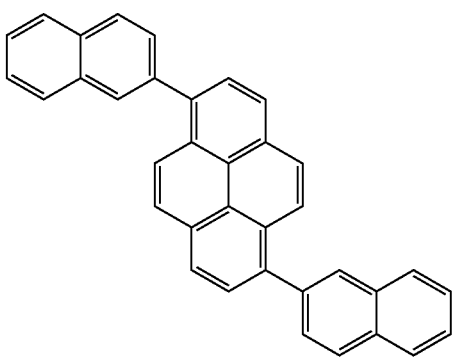
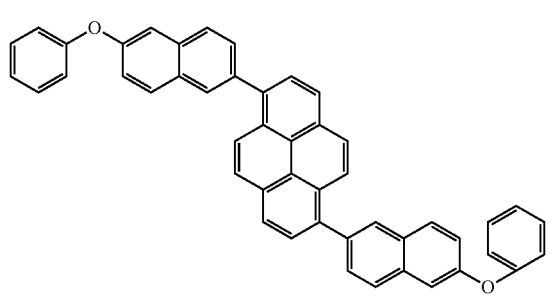
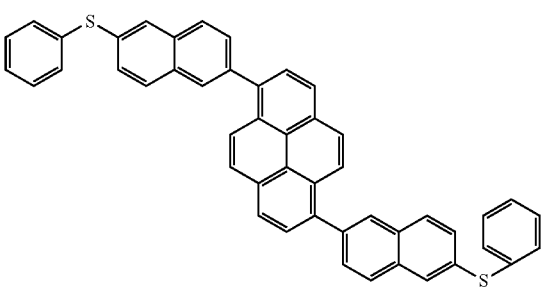

589
-continued
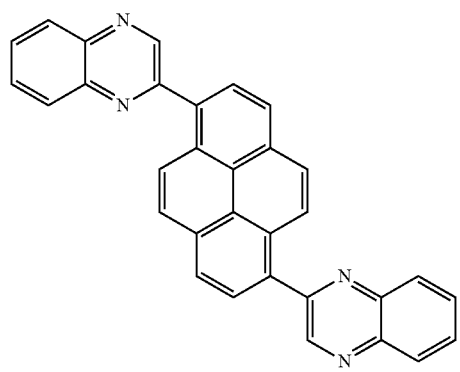
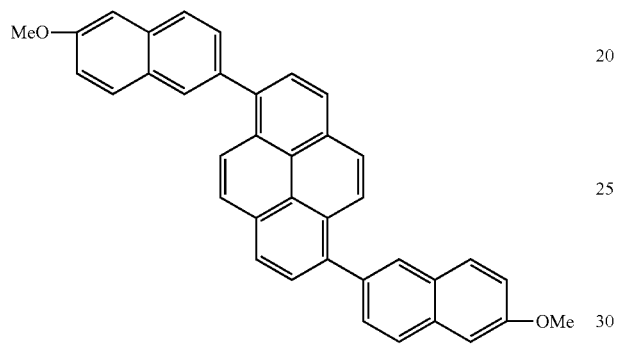
The six membered rings in the following compounds are all benzene rings.
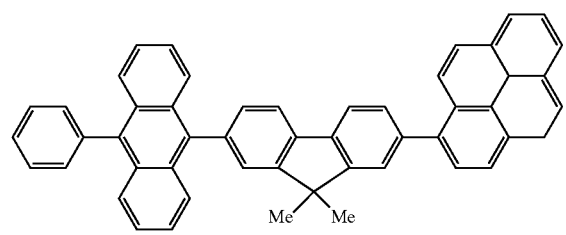
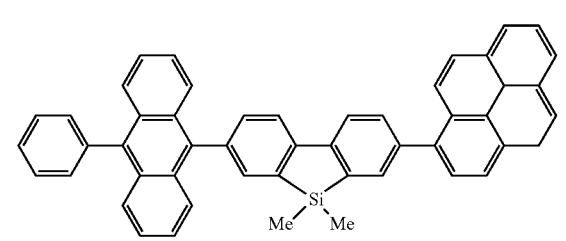
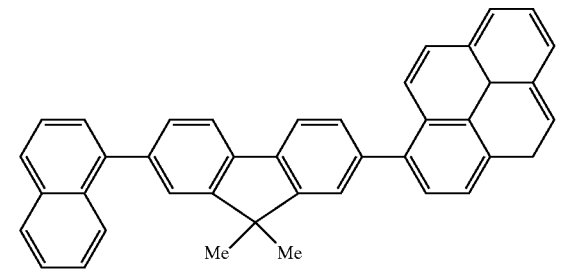
590
-continued
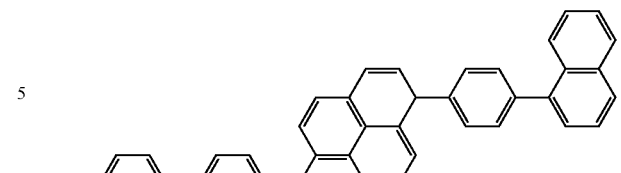
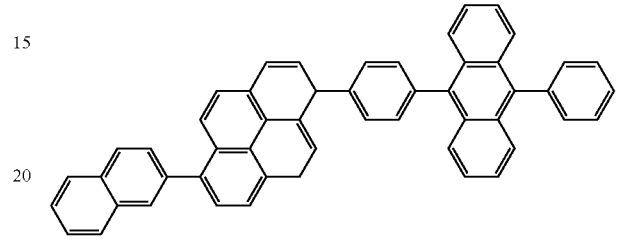
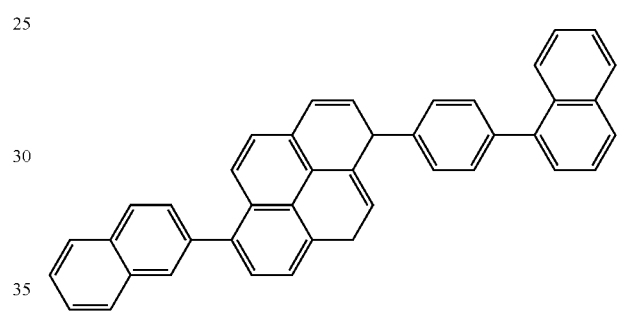
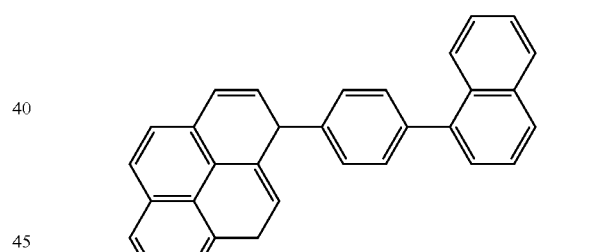
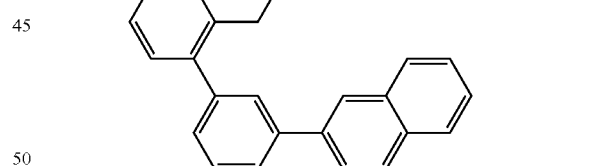
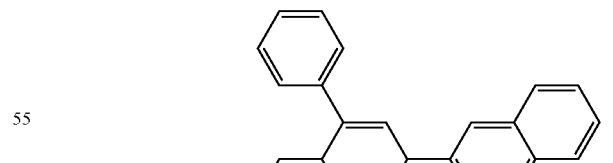
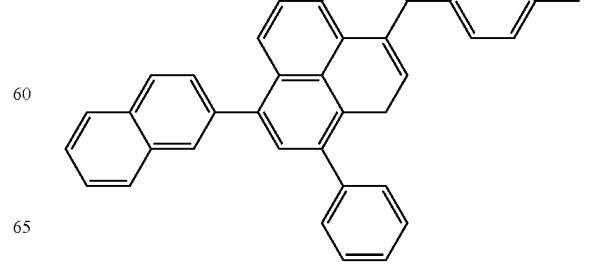

591
-continued
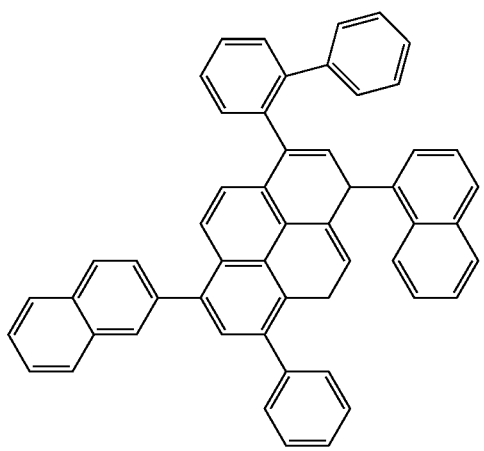
The six membered rings in the following compounds are all benzene rings.
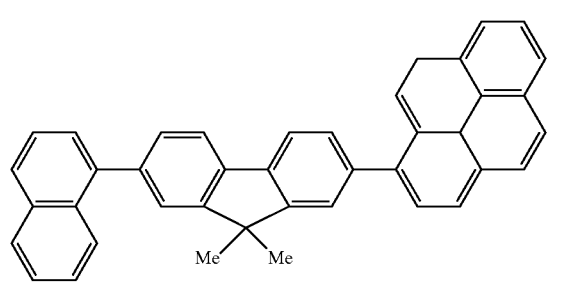
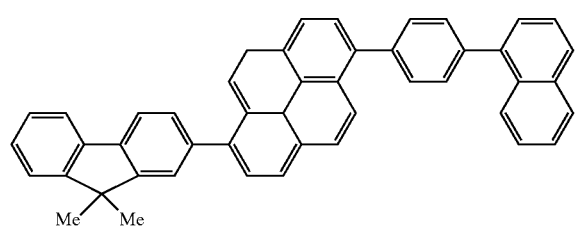
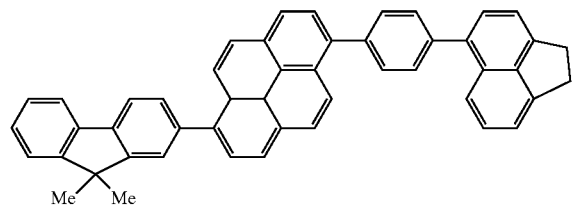
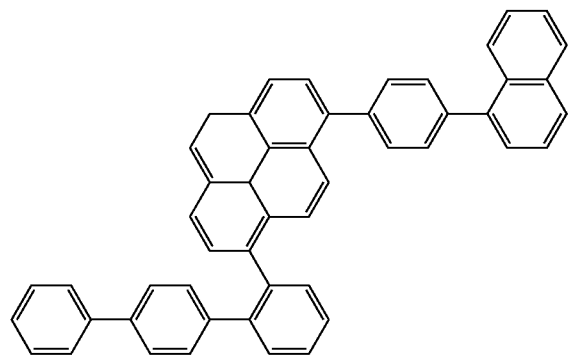
592
-continued
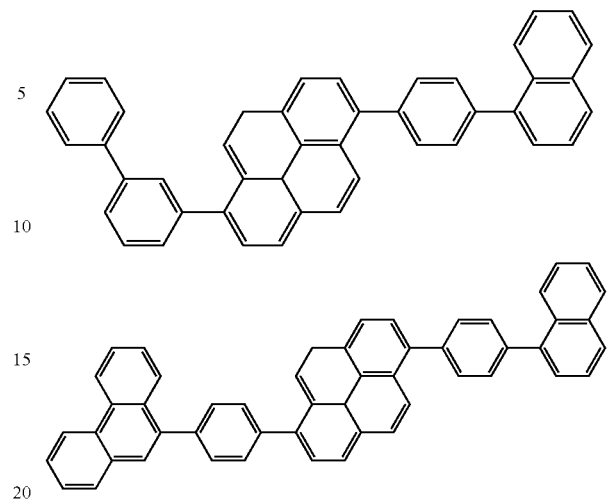
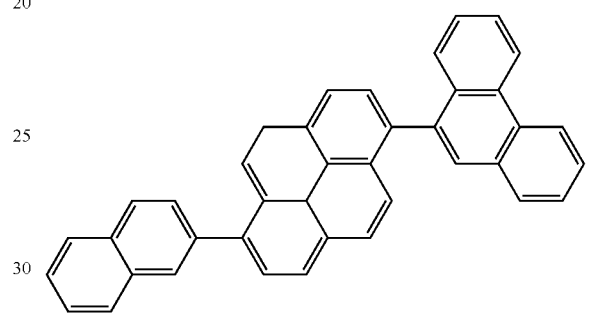
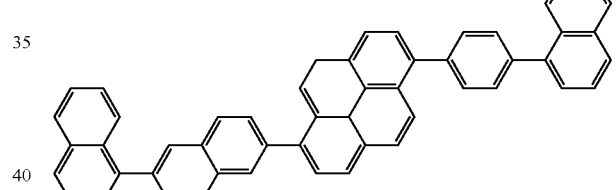
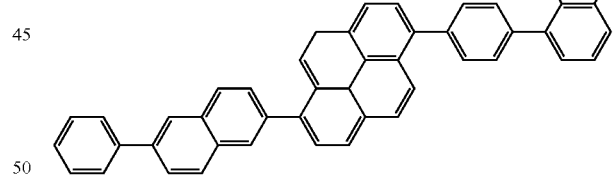
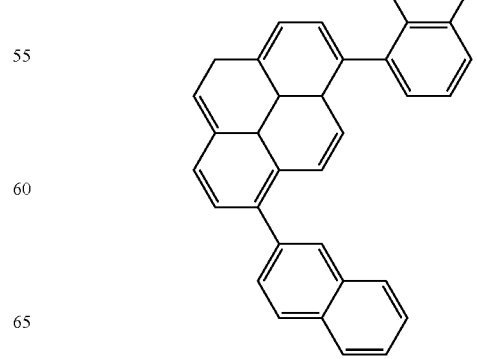

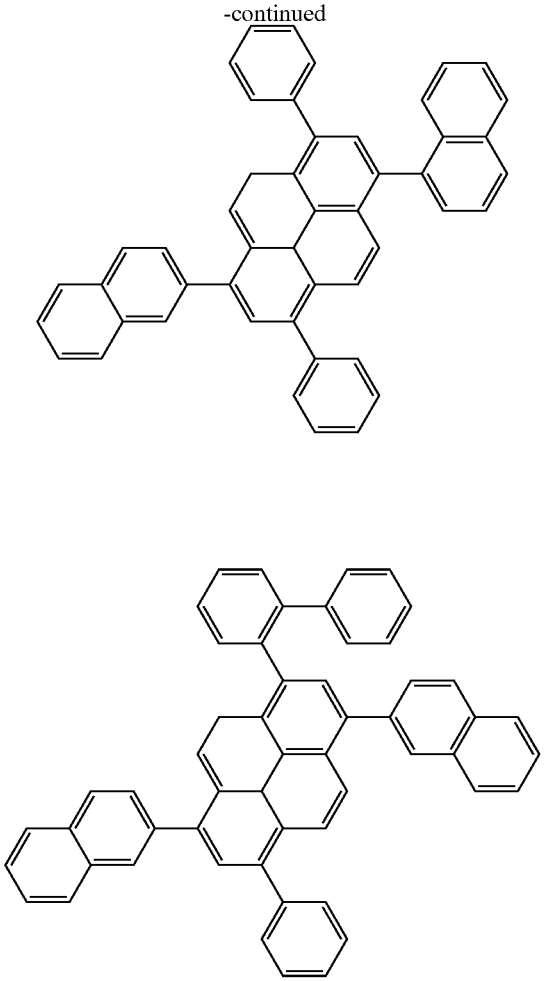
The six membered rings in the following compounds are all benzene rings.
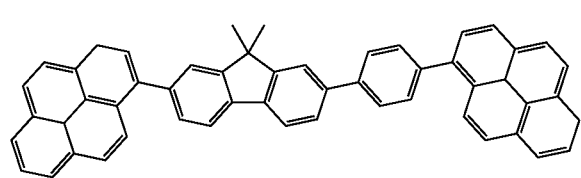
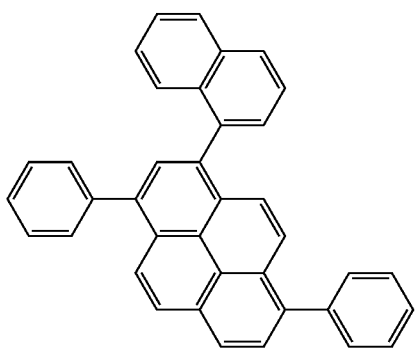
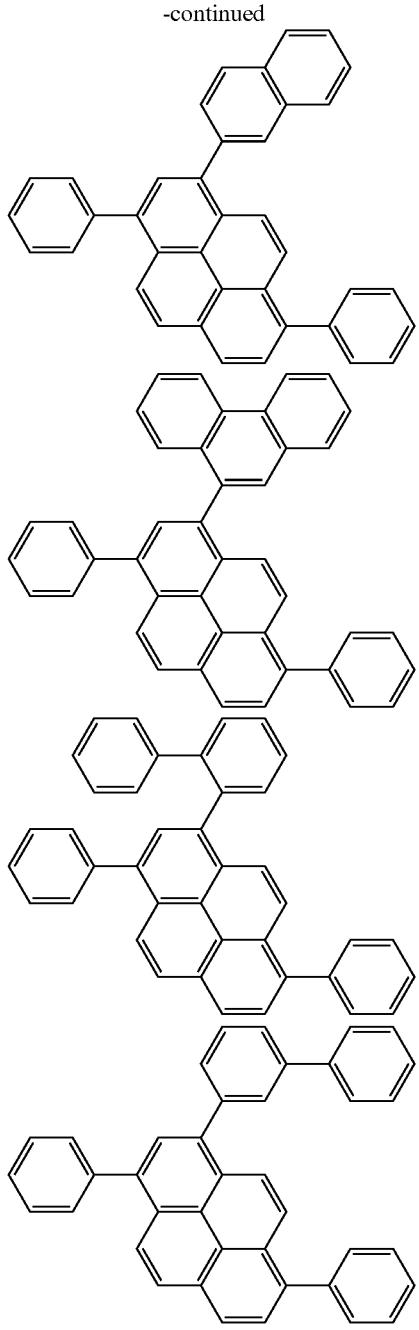

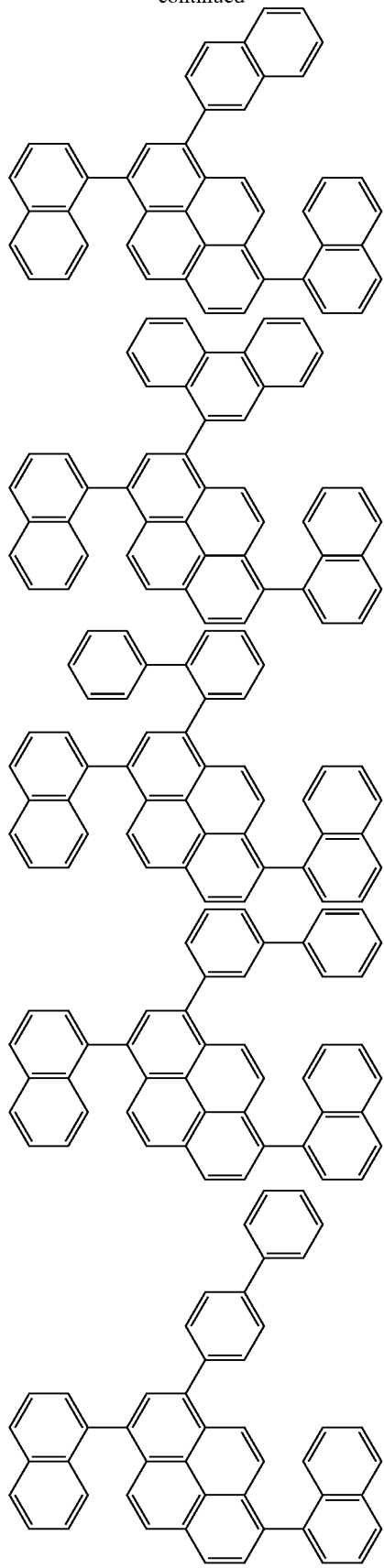
The six membered rings in the following compounds are all benzene rings.
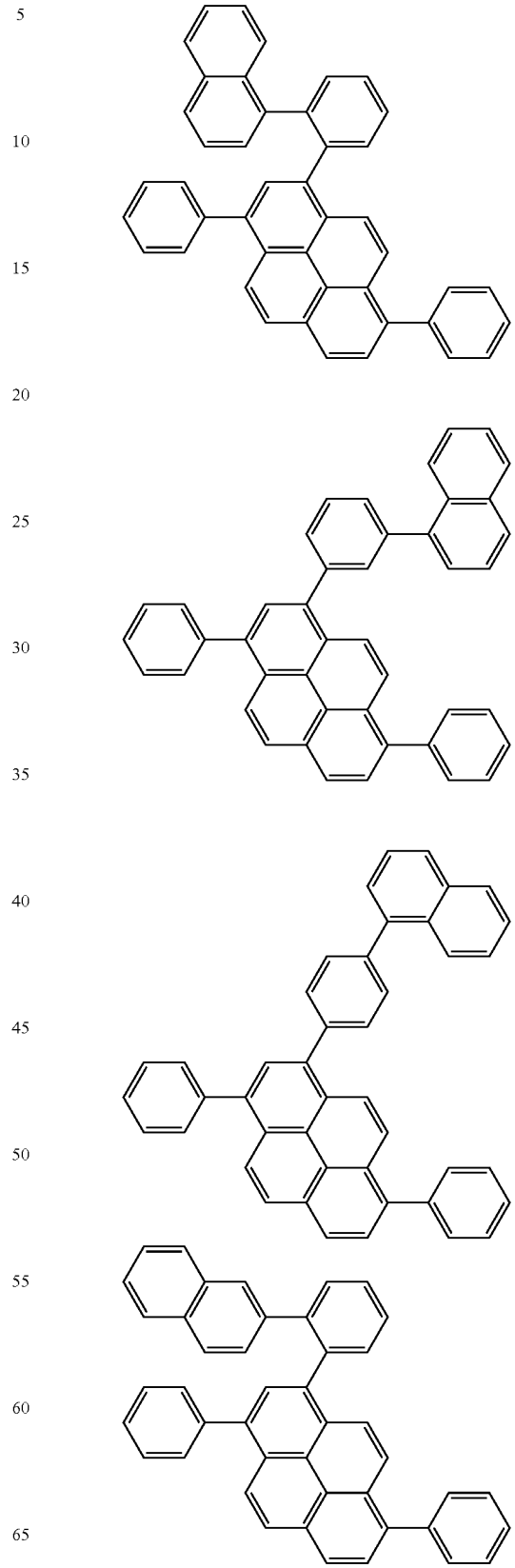

597
-continued
598
-continued
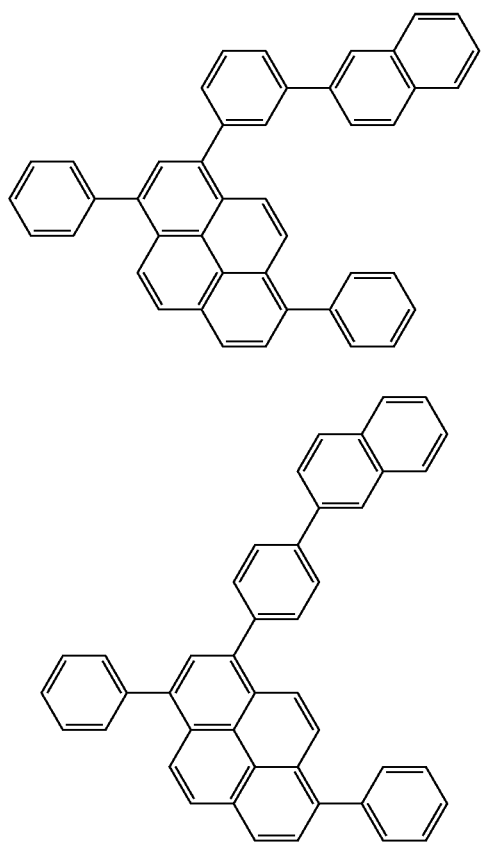
The six membered rings in the following compounds are all benzene rings.
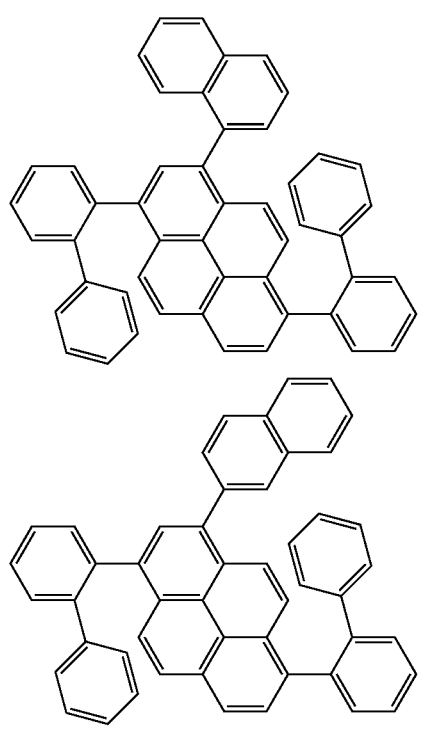
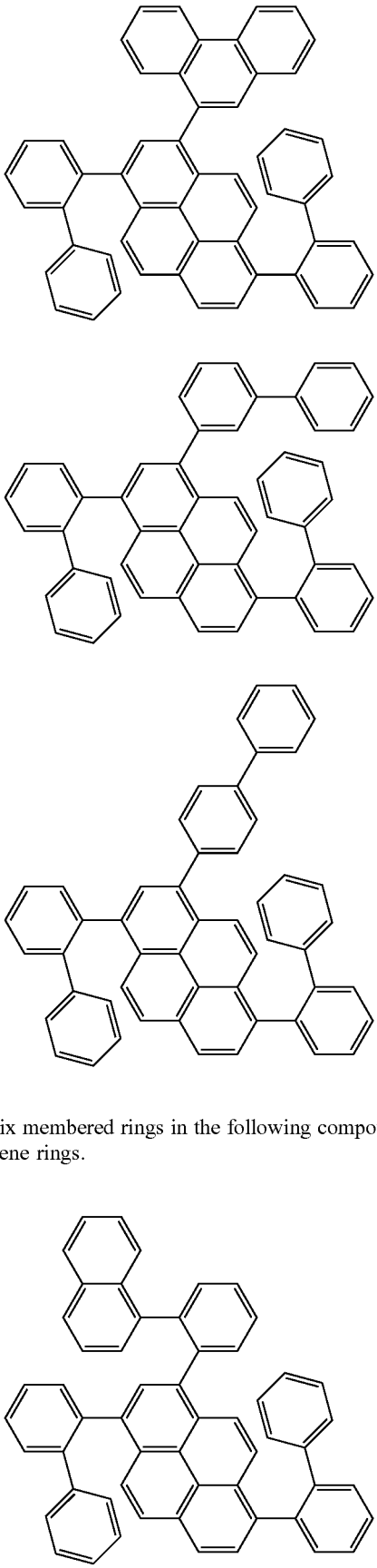
The six membered rings in the following compounds are all benzene rings.

599
-continued
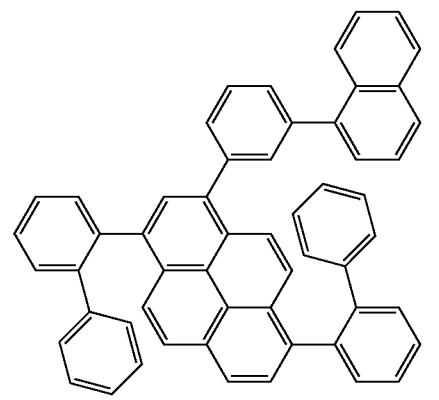
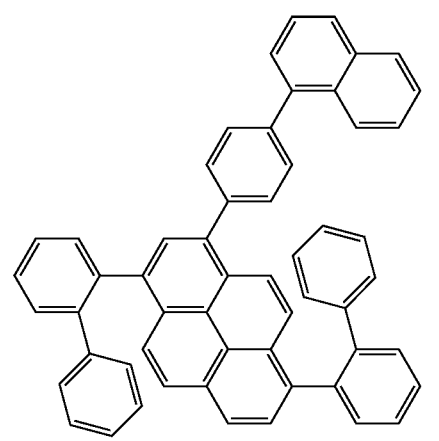
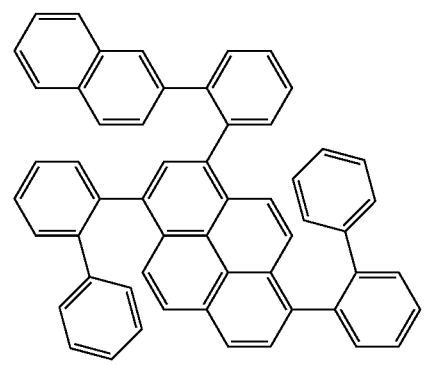
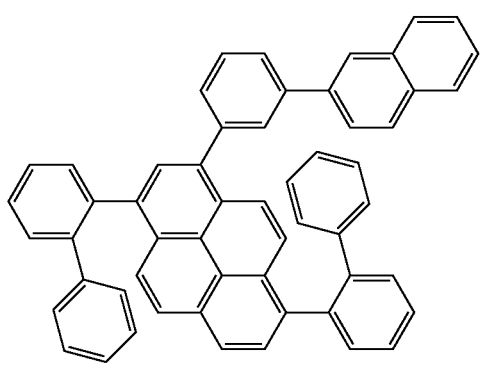
600
-continued
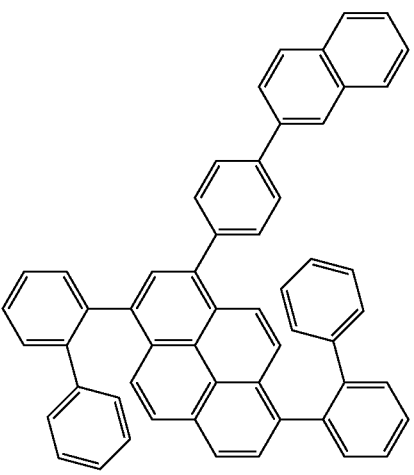
The six membered rings in the following compounds are all benzene rings.
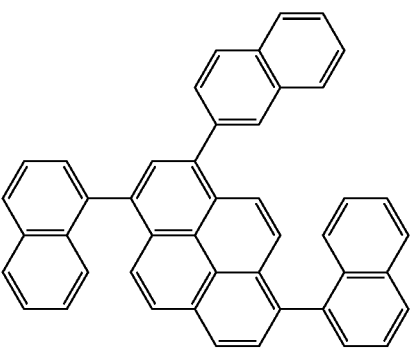
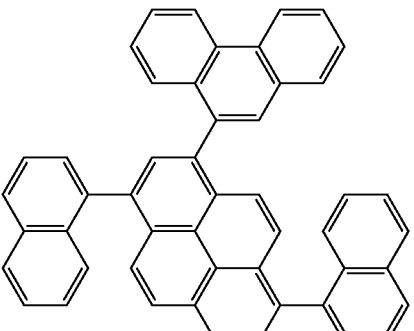
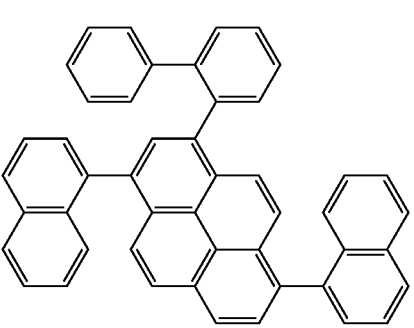

601
-continued
602
-continued
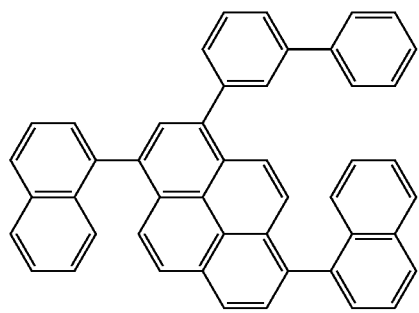
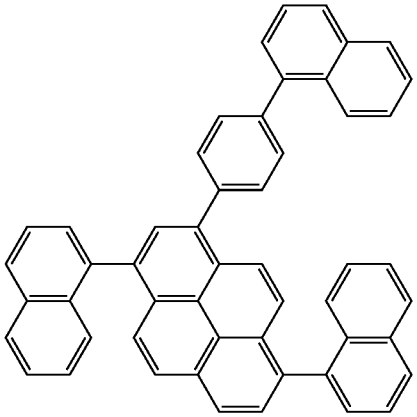
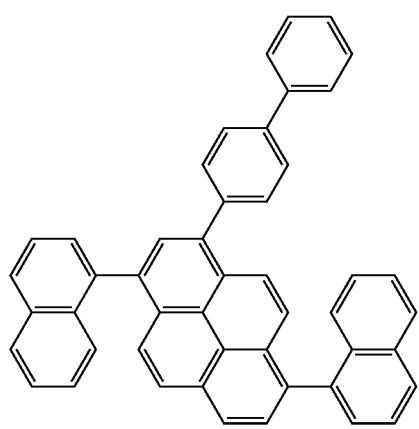 [SMILES: c1ccc(-c2ccc(-c3cc(-c4cccc5ccccc45)c4ccc5ccc(-c6cccc7ccccc67)c6ccc3c4c56)cc2)cc1]
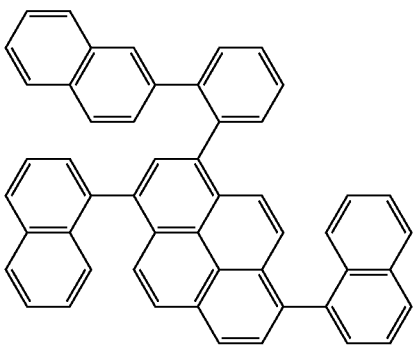
The six membered rings in the following compounds are all benzene rings.
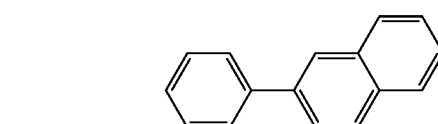
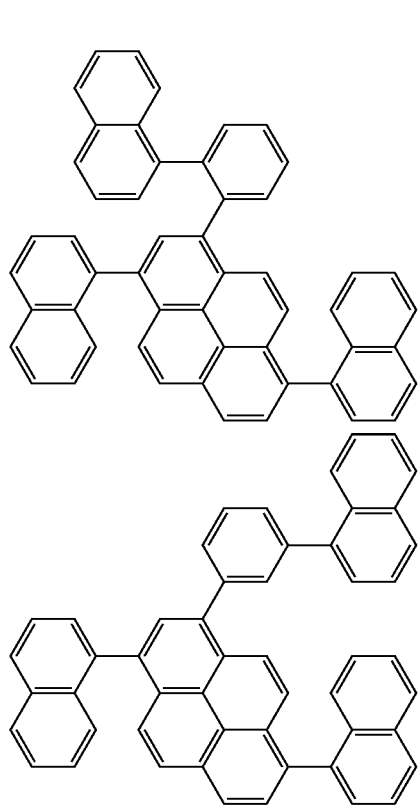
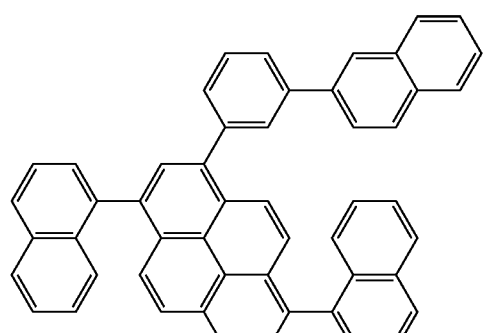
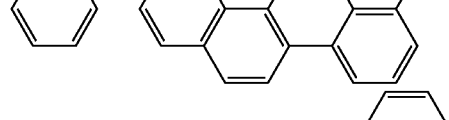
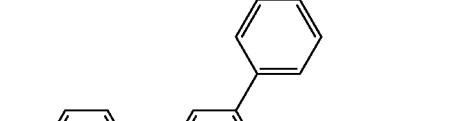
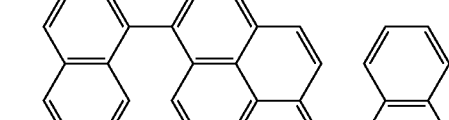
The six membered rings in the following compounds are all benzene rings.

603
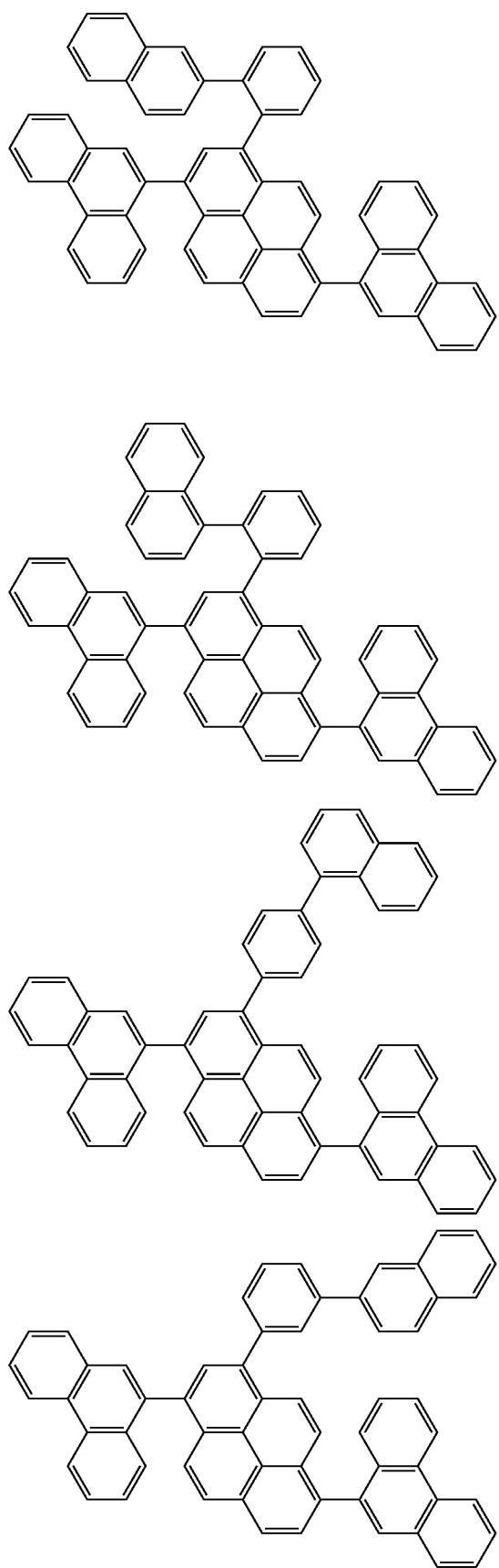
604
-continued
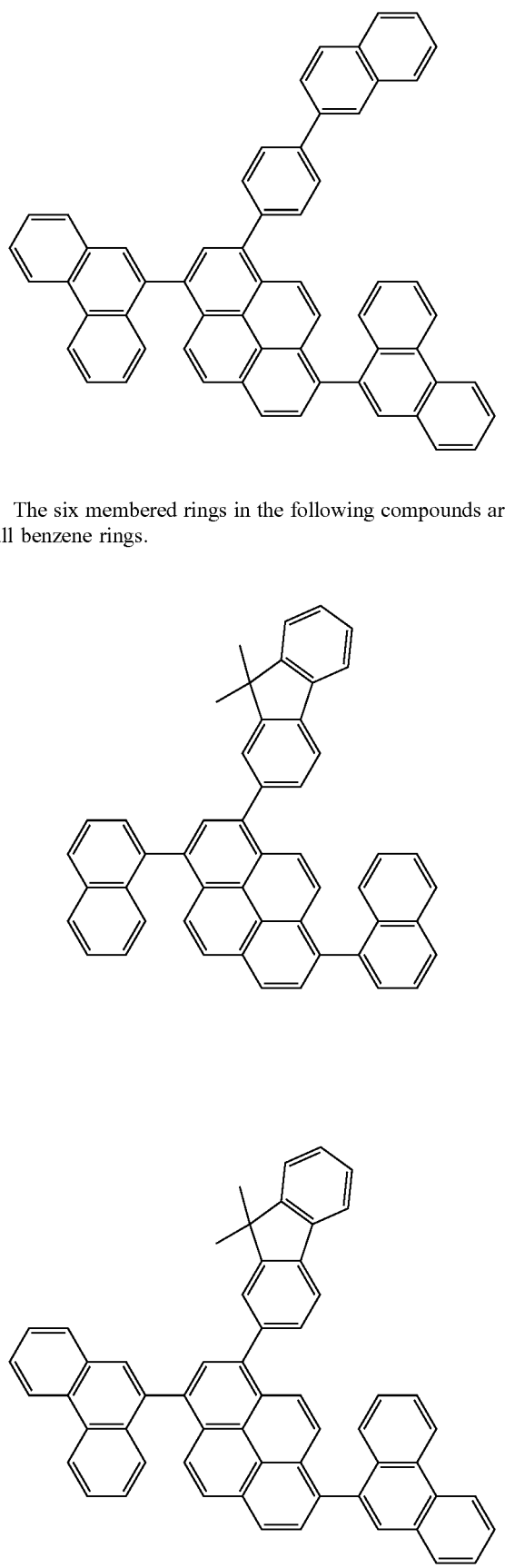
The six membered rings in the following compounds are all benzene rings.

605
-continued
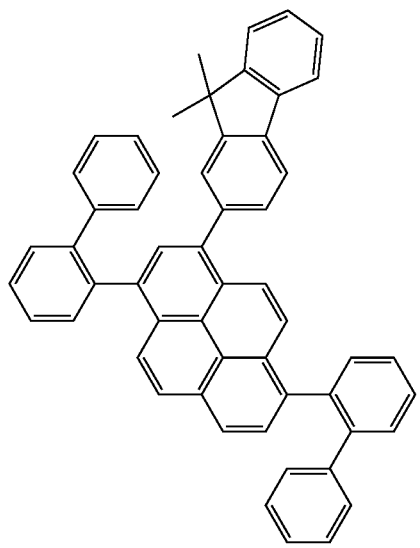
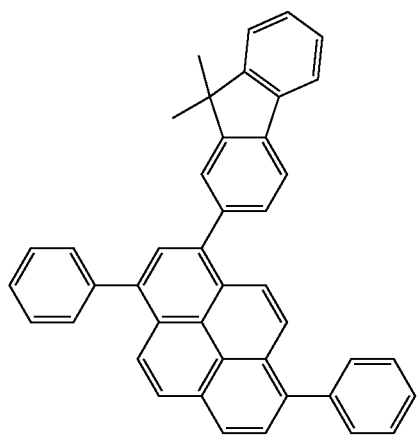 [SMILES: CC1(C)c2ccccc2-c2ccc(-c3cc(-c4ccccc4)c4ccc5ccc(-c6ccccc6)c6ccc3c4c56)cc21]
The six membered rings in the following compounds are all benzene rings.
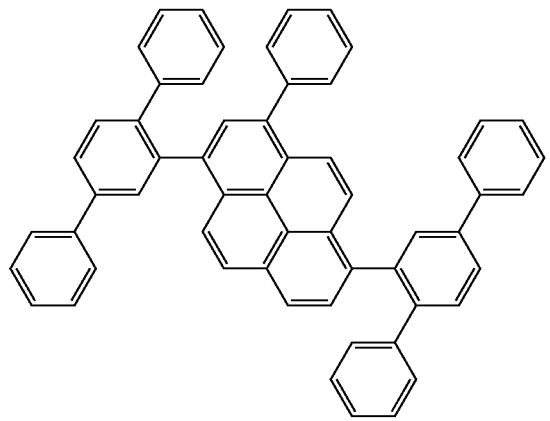
606
-continued
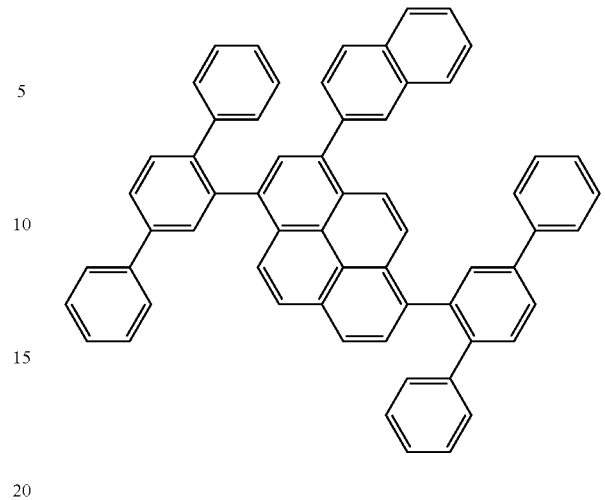
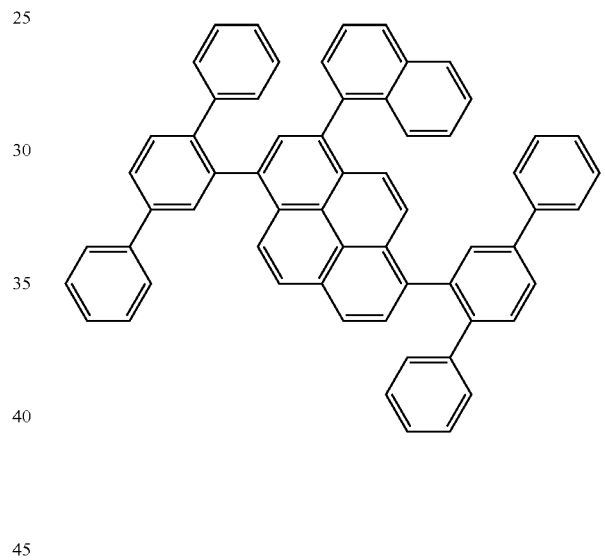
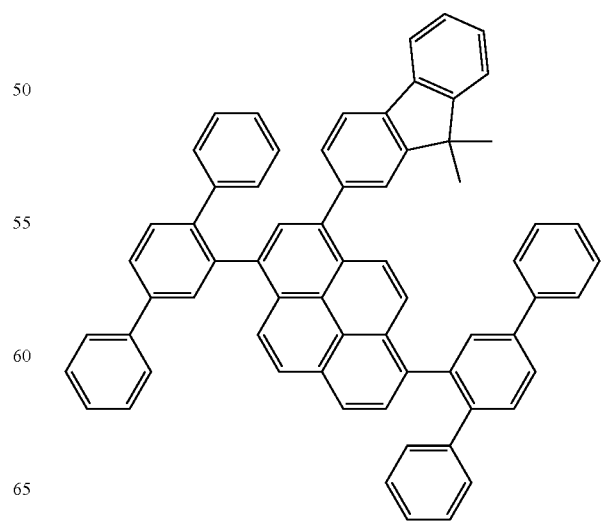

607
-continued
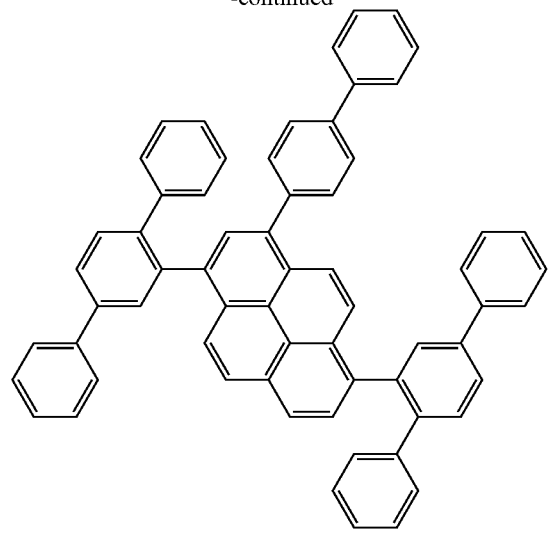
608
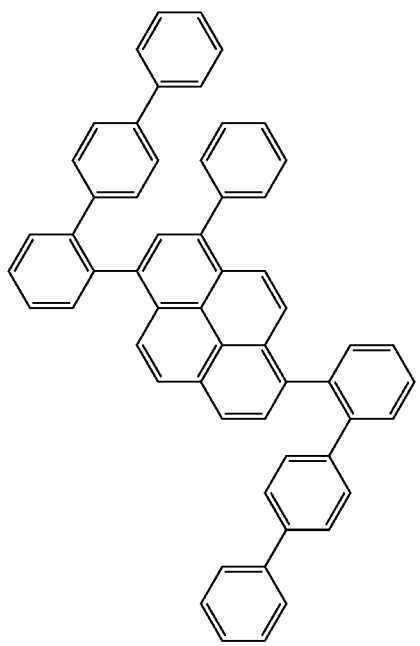
The six membered rings in the following compounds are all benzene rings.
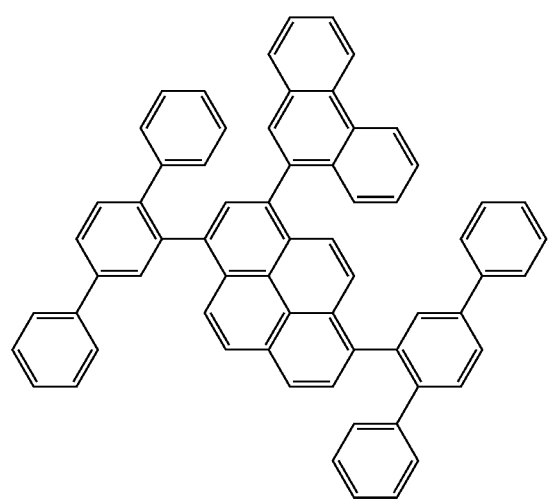
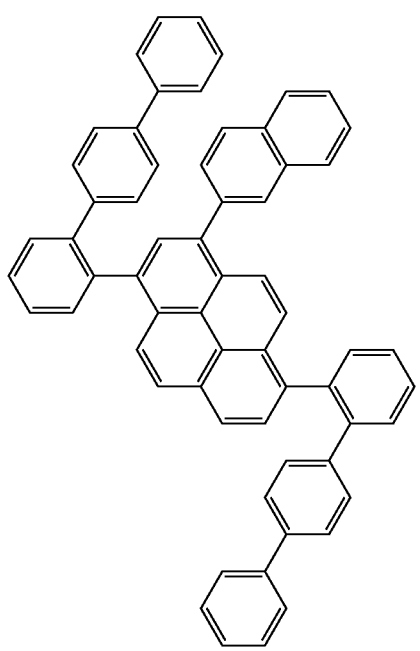

609
-continued
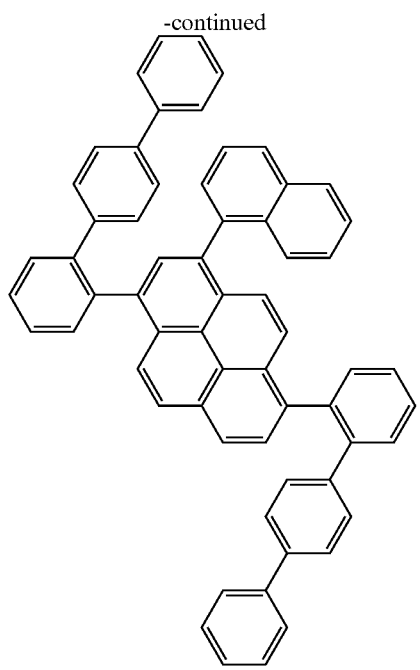
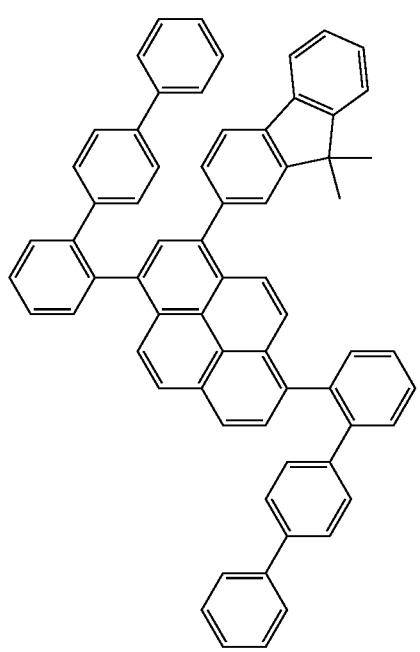
610
-continued
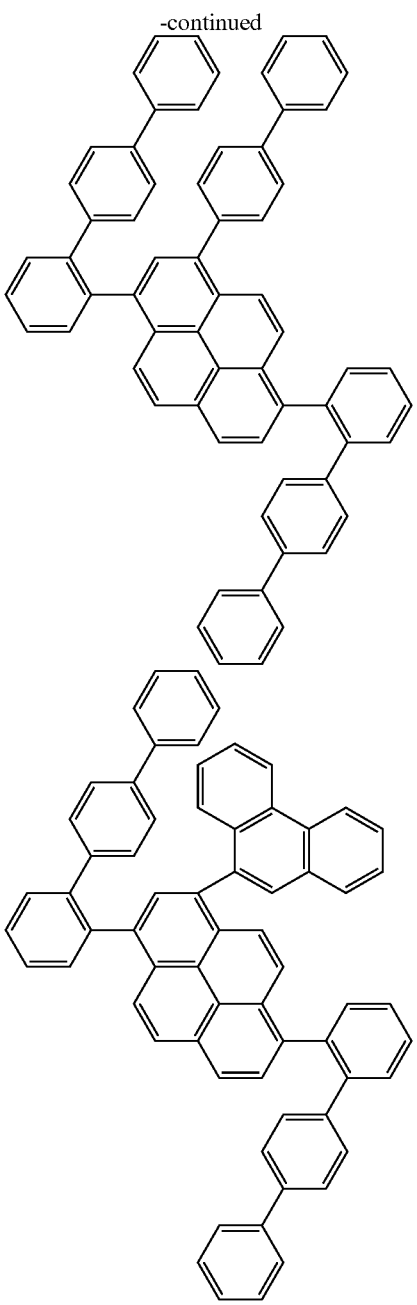
As the fluorene derivative, for example, a compound represented by formula (23) is preferably used:
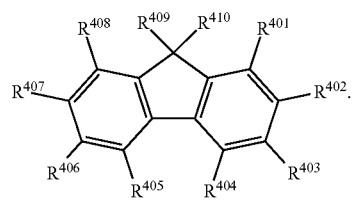
(23)
In formula (23), $R^{401}$ to $R^{410}$ are each independently a hydrogen or a substituent, wherein the substituent is the same as the substituent described above with respect to $R_1$ to $R_{11}$ or represented by —$L^4$-$Ar^{41}$. Examples, preferred numbers of carbon atoms and atoms, and preferred groups thereof are also the same as in $R_1$ to $R_{11}$.

Provided that, at least one of $R^{401}$ to $R^{410}$ is —$L^4$-$Ar^{41}$, wherein $L^4$ and $Ar^{41}$ are respectively the same as L and Ar of formula (19) and examples, preferred numbers of carbon atoms and atoms, and preferred groups thereof are also the same as in L and Ar.

One or more pairs selected from $R^{401}$ and $R^{402}$, $R^{402}$ and $R^{403}$, $R^{403}$ and $R^{404}$, $R^{405}$ and $R^{406}$, $R^{406}$ and $R^{407}$, and $R^{407}$ and $R^{408}$ may be bonded to each other to form a ring.

$R^{402}$ and $R^{407}$ are preferably —$L^4$-$Ar^{41}$. $R^{409}$ and $R^{410}$ are each preferably a substituted or unsubstituted alkyl group or —$L^4$-$Ar^{41}$.

Examples of the fluorene derivative represented by formula (23) are shown below, although not limited thereto.

The six membered rings in the following compounds are all benzene rings.

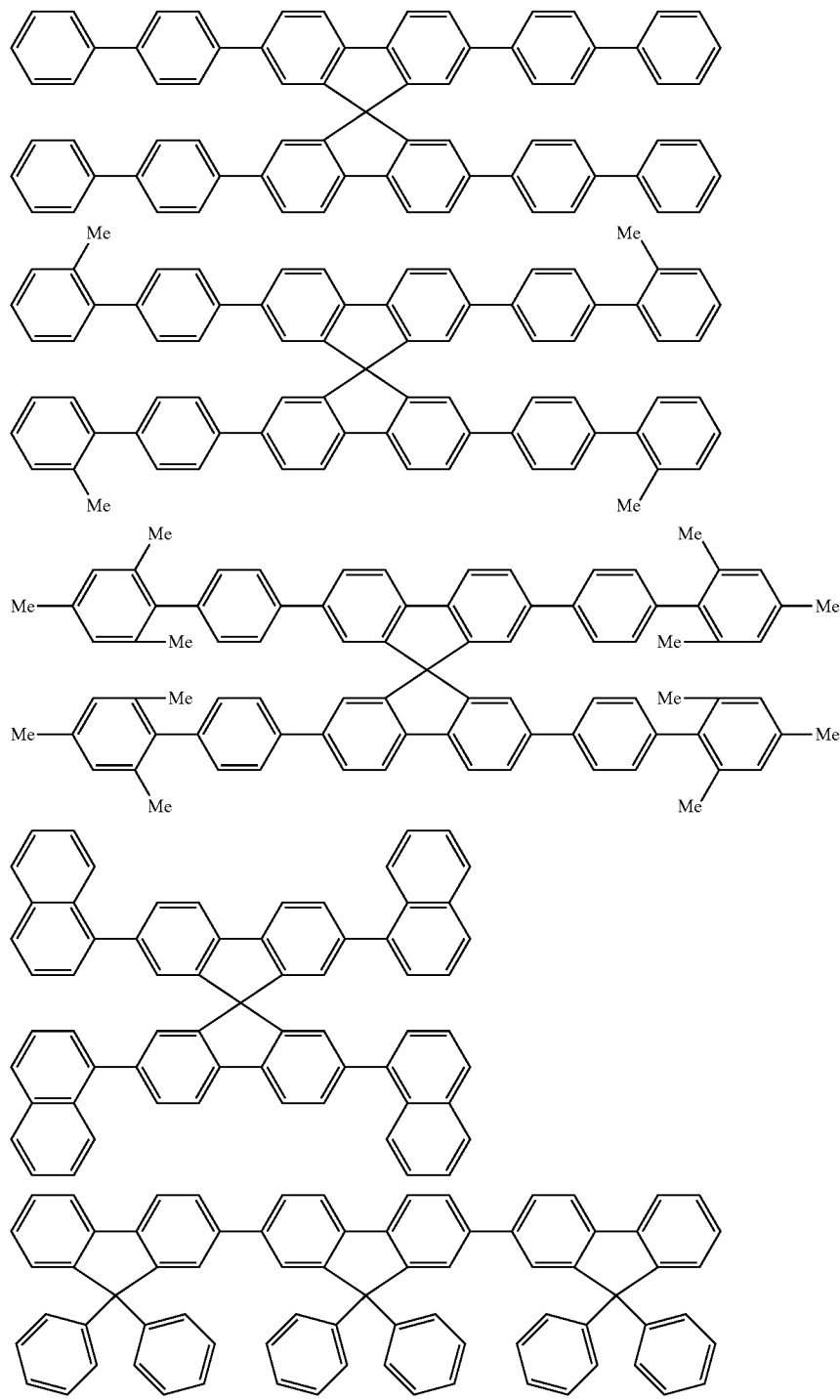

The first compound and the second compound not the same as the first compound in an aspect of the invention are useful as materials for organic EL devices.

The production method of the first compound and the second compound is not particularly limited, and these compounds are easily produced by using or modifying a known synthetic reaction while referring to the examples described below.

In an embodiment of the invention, the first compound is used as a fluorescent dopant material in a light emitting layer of an organic EL device.

In view of the emission efficiency, the fluorescence quantum yield (PLQY) and the shape of fluorescence emission spectrum (half width) are important for the dopant material for use in the light emitting layer of organic EL device.

In a full-color display, to obtain an optimum color gamut, the three primary colors, i.e., red, green and blue light or four or more colors, for example, yellow in addition to the three primary colors are taken out after cutting off through a color filter or after amplifying a light with the intended wavelength and attenuating light with other wavelengths. Thus, the light with a wavelength other than required is removed, this leading to a loss of energy. Therefore, a material showing an emission spectrum with a sharp shape is advantageous for the efficiency, because the range of wavelength to be cut off is small to reduce the loss of energy.

A material little changing its structure between the ground state and the excited state is considered suitable as a dopant material showing an emission spectrum with a sharp shape.

The first compound little changes its structure in the ground state and the excited state because of its rigid structure of the main fused aromatic ring structure.

When the first compound is of a highly symmetric fused ring structure, a sharper emission spectrum may be obtained because the vibrational levels are degenerated. The highly symmetric fused ring structure used herein is, for example, a fused ring structure which is symmetric with respect to a line connecting the nitrogen atom and $R_2$ of formula (1).

The first compound having an asymmetric fused ring structure is effective particularly in controlling the emission wavelength without introducing a substituent. The asymmetric fused ring structure used herein is, for example, a fused ring structure which is asymmetric with respect to a line connecting the nitrogen atom and $R_2$ of formula (1).

The organic EL device of the invention will be described in more detail below.

As described above, the organic EL device of the invention comprises a cathode, an anode, and an organic layer disposed between the cathode and the anode. The organic layer comprises one or more layers that comprise a fluorescent emitting layer. The fluorescent emitting layer comprises the first compound represented by formula (P) described above and the second compound described above which is not the same as the first compound. The organic EL device of the invention includes one capable of operating at low driving voltage, one having a long lifetime, and one capable of emitting blue light with high color purity.

The first compound and the second compound are combinedly used in the light emitting layer, particularly in the light emitting layer as a dopant material, and preferably in the fluorescent emitting layer as a dopant material. Also preferably, the first compound and the second compound are combinedly used as a dopant material in a light emitting layer using thermally activated delayed fluorescence.

The fluorescent emitting layer of the invention does not include a phosphorescent emitting heavy metal complex comprising a heavy metal, such as iridium, platinum, osmium, rhenium, and ruthenium.

The organic EL device of the invention may be any of a single color emitting device using fluorescence or thermally activated delayed fluorescence; a white-emitting hybrid device comprising the above single color emitting devices; an emitting device of a simple type having a single emission unit; and an emitting device of a tandem type having two or more emission units. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below. In the following emission units, one including no fluorescent emitting layer is excluded.

(1) Anode/Emission Unit/Cathode

The emission unit may be a layered structure comprising two or more light emitting layers selected from a phosphorescent light emitting layer, a fluorescent light emitting layer, and a light emitting layer using thermally activated delayed fluorescence. A space layer may be disposed between the light emitting layers to prevent the diffusion of excitons generated in the phosphorescent emitting layer into the fluorescent emitting layer. Representative layered structures of the emission unit are shown below:

(a) Hole transporting layer/Light emitting layer(/Electron transporting layer);

(b) Hole transporting layer/First fluorescent emitting layer/Second fluorescent emitting layer(/Electron transporting layer);

(c) Hole transporting layer/Phosphorescent emitting layer/Space layer/Fluorescent emitting layer(/Electron transporting layer);

(d) Hole transporting layer/First phosphorescent emitting layer/Second phosphorescent emitting layer/Space layer/Fluorescent emitting layer(/Electron transporting layer);

(e) Hole transporting layer/First phosphorescent emitting layer/Space layer/Second phosphorescent emitting layer/Space layer/Fluorescent emitting layer(/Electron transporting layer); and (f) Hole transporting layer/Phosphorescent emitting layer/Space layer/First fluorescent emitting layer/Second fluorescent emitting layer(/Electron transporting layer).

The emission colors of the phosphorescent emitting layers and the fluorescent emitting layer may be different. For example, the layered structure (d) may be Hole transporting layer/First phosphorescent emitting layer (red)/Second phosphorescent emitting layer (green)/Space layer/Fluorescent emitting layer (blue)/Electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to facilitate the charge recombination in the light emitting layer, thereby improving the emission efficiency.

Representative device structure of the tandem-type organic EL device is shown below.

(2) Anode/First Emission Unit/Intermediate Layer/Second Emission Unit/Cathode

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

A schematic structure of an example of the organic EL device of the invention is shown in FIG. 1 wherein the organic EL device 1 comprises a substrate 2, an anode 3, a cathode 4, and an emission unit (organic thin film layer) 10 disposed between the anode 3 and the cathode 4. The emission unit 10 comprises a light emitting layer 5 which comprises at least one fluorescent emitting layer comprising a fluorescent host material and a fluorescent dopant material. A hole injecting layer/hole transporting layer 6 may be disposed between the light emitting layer 5 and the anode 3, and an electron injecting layer/electron transporting layer 7 may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to facilitate the exciton generation in the light emitting layer 5.

In the present invention, a host material is referred to as a fluorescent host material when combinedly used with a fluorescent dopant material and as a phosphorescent host material when combinedly used with a phosphorescent dopant material. Therefore, the fluorescent host material and the phosphorescent host material are not distinguished from each other merely by the difference in their molecular structures. Namely, in the present invention, the term "fluorescent host material" means a material for constituting a fluorescent emitting layer which contains a fluorescent dopant material and does not mean a material that cannot be used as a material for a phosphorescent emitting layer. The same applies to the phosphorescent host material.

Substrate

The organic EL device of the invention is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective. Examples of the material for anode include an indium tin oxide alloy (ITO), tin oxide (NESA), an indium zinc oxide alloy, gold, silver, platinum, and cupper. The anode is formed by making the electrode material into a thin film by a method, such as a vapor deposition method or a sputtering method. When getting the light emitted from the light emitting layer through the anode, the transmittance of anode to visible light is preferably 10% or more. The sheet resistance of anode is preferably several hundreds Ω/or less. The film thickness of anode depends upon the kind of material and generally 10 nm to 1 µm, preferably 10 to 200 nm.

Cathode

The cathode injects electrons to the electron injecting layer, the electron transporting layer or the light emitting layer, and is formed preferably by a material having a small work function. Examples of the material for cathode include, but not limited to, indium, aluminum, magnesium, a magnesium-indium alloy, a magnesium-aluminum alloy, an aluminum-lithium alloy, an aluminum-scandium-lithium alloy, and a magnesium-silver alloy. Like the anode, the cathode is formed by making the material into a thin film by a method, such as the vapor deposition method and the sputtering method. The emitted light may be taken through the cathode, if necessary.

The material other than the compounds described above which is usable in each layer will be described below. However, the light emitting layer includes a fluorescent emitting layer comprising the first compound and the second compound described above.

Light Emitting Layer

The light emitting layer is an organic layer having a light emitting function and contains a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

The light emitting layer may be made into a double dopant layer, in which two or more kinds of dopant materials having high quantum yield are combinedly used and each dopant material emits light with its own color. For example, a yellow-emitting layer is obtained by co-depositing a host material, a red-emitting dopant material and a green-emitting dopant material into a single emitting layer.

In a layered structure comprising two or more light emitting layers, electrons and holes are accumulated in the interface between the light emitting layers, and therefore, the recombination region is localized in the interface between the light emitting layers to improve the quantum efficiency The easiness of hole injection to the light emitting layer and the easiness of electron injection to the light emitting layer may be different from each other. Also, the hole transporting ability and the electron transporting ability in the light emitting layer, each expressed by hole mobility and electron mobility, may be different from each other.

The light emitting layer is formed, for example, by a known method, such as a vapor deposition method, a spin coating method, and LB method. The light emitting layer can be formed also by making a solution of a binder, such as resin, and a material for the light emitting layer in a solvent into a thin film by a method such as spin coating.

The light emitting layer is preferably a molecular deposit film. The molecular deposit film is a thin film formed by depositing a vaporized material or a film formed by solidifying a material in the form of solution or liquid. The molecular deposit film can be distinguished from a thin film formed by LB method (molecular build-up film) by the differences in the assembly structures and higher order structures and the functional difference due to the structural differences.

The thickness of the light emitting layer is preferably 5 to 50 nm, more preferably 7 to 50 nm, and still more preferably 10 to 50 nm. If being 5 nm or more, the light emitting layer is formed easily. If being 50 nm or less, the driving voltage is prevented from increasing.

Dopant Material

The fluorescent dopant material (fluorescent emitting material) for forming the light emitting layer is not particularly limited as long as emitting light by releasing the energy of excited singlet state. Examples thereof include a fluoranthene derivative, a styrylarylene derivative, a pyrene derivative, an arylacetylene derivative, a fluorene derivative, a boron complex, a perylene derivative, an oxadiazole derivative, an anthracene derivative, a styrylamine derivative, and an arylamine derivative, with an anthracene derivative, a fluoranthene derivative, a styrylamine derivative, an arylamine derivative, a styrylarylene derivative, a pyrene derivative, and a boron complex being preferred, and an anthracene derivative, a fluoranthene derivative, a styrylamine derivative, an arylamine derivative, and a boron complex compound being more preferred.

The content of the fluorescent dopant in the light emitting layer is not particularly limited and selected according to the use of the device, and preferably 0.1 to 70% by mass, more preferably 1 to 30% by mass, still more preferably 1 to 20% by mass, and particularly preferably 1 to 10% by mass. If being 0.1% by mass or more, the amount of light emission is sufficient. If being 70% by mass or less, the concentration quenching is avoided.

Electron-Donating Dopant

The organic EL device of the invention preferably comprises an electron-donating dopant at an interfacial region between the cathode and the emitting unit. With such a construction, the organic EL device has an improved luminance and an elongated lifetime. The electron-donating dopant comprises a metal having a work function of 3.8 eV or less and examples thereof include at least one selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and mixture thereof, such as $Ba_xSr_{1-x}O$ (0<x<1) and $Ba_xCA^1_{-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from an alkali metal ion, an alkaline earth metal ion, and a rare earth metal ion, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The electron-donating dopant material is added to the interfacial region preferably into a form of layer or island, which is formed by co-depositing the electron-donating dopant material with an organic compound (light emitting material, electron injecting material) for forming the interfacial region by a resistance heating deposition method, thereby dispersing the electron-donating dopant material into the organic material. The disperse concentration expressed by the ratio of organic material:electron-donating dopant material is 100:1 to 1:100 by mole.

When the electron-donating dopant material is formed into a form of layer, a light emitting material or an electron injecting material is formed into an interfacial organic layer, and then, the electron-donating dopant material alone is deposited by a resistance heating deposition method into a layer having a thickness of preferably 0.1 to 15 nm. When the electron-donating dopant material is formed into a form of island, a light emitting material or an electron injecting material is made into an interfacial island, and then, the electron-donating dopant material alone is deposited by a resistance heating deposition method into a form of island having a thickness of preferably 0.05 to 1 nm.

The molar ratio of the main component and the electron-donating dopant in the organic EL device of the invention is preferably 5:1 to 1:5.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently.

An aromatic heterocyclic compound having one or more heteroatoms in its molecule is preferably used as an electron transporting material used in the electron transporting layer, and a nitrogen-containing ring derivative is particularly preferred. In addition, the nitrogen-containing ring derivative is preferably an aromatic ring compound having a nitrogen-containing, 6- or 5-membered ring, or a fused aromatic ring compound having a nitrogen-containing, 6- or 5-membered ring.

The nitrogen-containing ring derivative is preferably, for example, a metal chelate complex of a nitrogen-containing ring represented by formula (A):

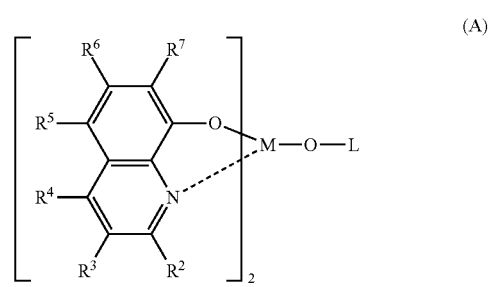

wherein each of $R^2$ to $R^7$ independently represents a hydrogen atom, a halogen atom, a hydroxyl group, an amino group, a hydrocarbon group having 1 to 40, preferably 1 to 20, more preferably 1 to 10, and still more preferably 1 to 6 carbon atoms, an alkoxy group having 1 to 40, preferably 1 to 20, more preferably 1 to 10, and still more preferably 1 to 6 carbon atoms, an aryloxy group having 6 to 40, preferably 6 to 20, and more preferably 6 to 12 ring carbon atoms, an alkoxycarbonyl group having 2 to 40, preferably 2 to 20, more preferably 2 to 10, and still more preferably 2 to 5 carbon atoms, or an aromatic heterocyclic group having 9 to 40, preferably 9 to 30, and more preferably 9 to 20 ring atoms, each optionally having a substituent.

M is aluminum (Al), gallium (Ga), or indium (In), with In being preferred.

L is a group represented by formula (A') or (A"):

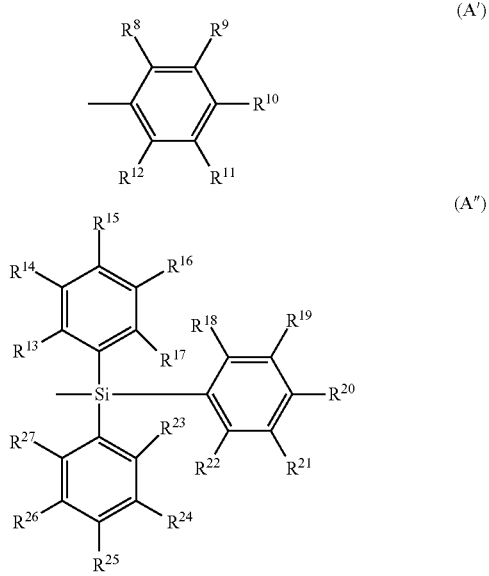

Each $R^8$ to $R^{12}$ in formula (A') independently represents a hydrogen atom or a substituted or unsubstituted hydrocarbon group having 1 to 40, preferably 1 to 20, more preferably 1 to 10, and still more preferably 1 to 6 carbon atoms. Two adjacent groups may form a ring structure. Each of $R^{13}$ to $R^{27}$ in formula (A") independently represents a hydrogen atom or a substituted or unsubstituted hydrocarbon group having 1 to 40, preferably 1 to 20, more preferably 1 to 10, and still more preferably 1 to 6 carbon atoms. Two adjacent groups may form a ring structure.

Examples of the hydrocarbon group having 1 to 40 carbon atoms for $R^8$ to $R^{12}$ and $R^{13}$ to $R^{27}$ in formulae (A') and (A") are the same as those described above with respect to $R^2$ to $R^7$ of formula (A).

Examples of the divalent group formed by two adjacent groups of $R^8$ to $R^{12}$ and $R^{13}$ to $R^{27}$ which completes the ring structure include a tetramethylene group, a pentamethylene group, a hexamethylene group, a diphenylmethane-2,2'-diyl group, a diphenylethane-3,3'-diyl group, and a diphenylpropane-4,4'-diyl group.

The electron transporting compound for use in the electron transporting layer is preferably a metal complex including 8-hydroxyquinoline or its derivative, an oxadiazole derivative, or a nitrogen-containing heterocyclic derivative.

The electron transporting compound is preferably good in the thin film-forming property. Examples of the electron transporting compound are shown below.

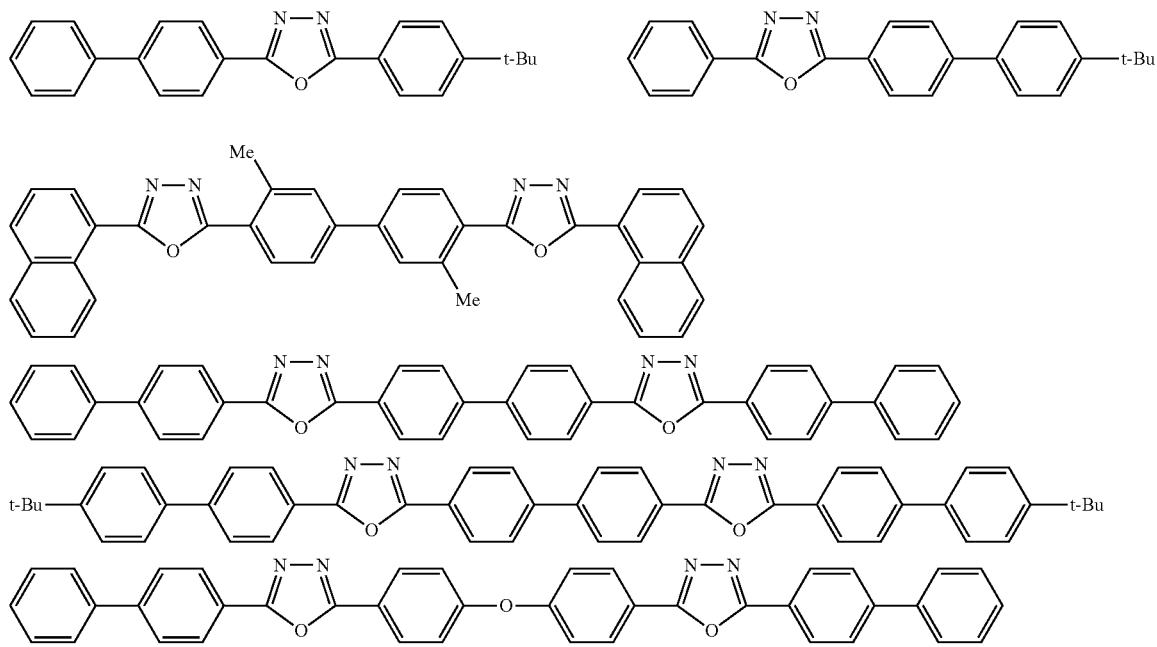

Example of the nitrogen-containing heterocyclic derivative for use as the electron transporting compound also includes a nitrogen-containing compound other than the metal complex, for example, a compound having a nitrogen-containing heterocyclic group selected from the following formulae is preferred.

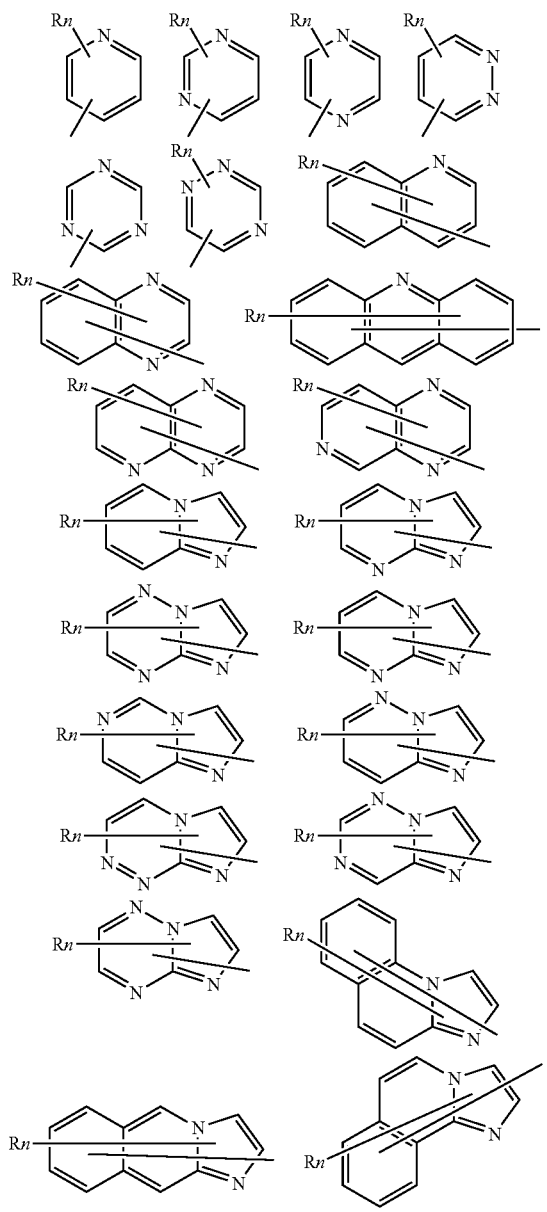

wherein R is an aromatic hydrocarbon group or a fused aromatic hydrocarbon group each having 6 to 40 carbon atoms, an aromatic heterocyclic group or a fused aromatic heterocyclic group each having 3 to 40 carbon atoms, an alkyl group having 1 to 20 carbon atoms, or an alkoxy group having 1 to 20 carbon atoms; and n is an integer of 0 to 5. If n is an integer of 2 or more, groups R may be the same or different.

The electron transporting layer in the organic EL device of the invention preferably comprises at least one compound selected from the nitrogen-containing heterocyclic derivatives represented by formulae (60) to (62):

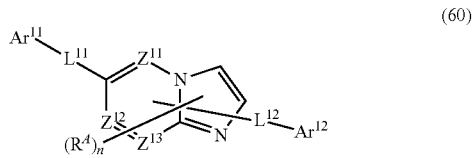
(60)

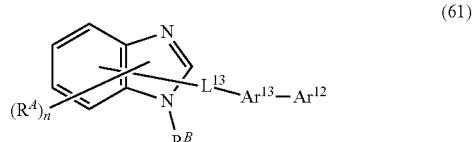
(61)

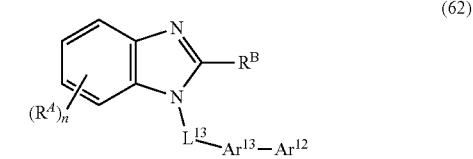
(62)

wherein:

$Z^{11}$, $Z^{12}$, and $Z^{13}$ each independently represent a nitrogen atom or a carbon atom;

$R^A$ and $R^B$ each independently represent a substituted or unsubstituted aryl group having 6 to 50, preferably 6 to 30, more preferably 6 to 20, and still more preferably 6 to 12 ring carbon atoms, a substituted or unsubstituted heterocyclic group having 5 to 50, preferably 5 to 30, more preferably 5 to 20, and still more preferably 5 to 12 ring atoms, a substituted or unsubstituted alkyl group having 1 to 20, preferably 1 to 10, and more preferably 1 to 6 carbon atoms, a substituted or unsubstituted haloalkyl group having 1 to 20, preferably 1 to 10, and more preferably 1 to 6 carbon atoms, or a substituted or unsubstituted alkoxyl group having 1 to 20, preferably 1 to 10, and more preferably 1 to 6 carbon atoms;

n is an integer of 0 to 5, when n is an integer of 2 or more, groups $R^A$ may be the same or different, and adjacent two groups $R^A$ may bond to each other to form a substituted or unsubstituted hydrocarbon ring;

$Ar^{11}$ represents a substituted or unsubstituted aryl group having 6 to 50, preferably 6 to 30, more preferably 6 to 20, and still more preferably 6 to 12 ring carbon atoms or a substituted or unsubstituted heterocyclic group having 5 to 50, preferably 5 to 30, more preferably 5 to 20, and still more preferably 5 to 12 ring atoms;

$Ar^{12}$ represents a hydrogen atom, a substituted or unsubstituted alkyl group having 1 to 20, preferably 1 to 10, and more preferably 1 to 6 carbon atoms, a substituted or unsubstituted haloalkyl group having 1 to 20, preferably 1 to 10, and more preferably 1 to 6 carbon atoms, a substituted or unsubstituted alkoxyl group having 1 to 20, preferably 1 to 10, and more preferably 1 to 6 carbon atoms, a substituted or unsubstituted aryl group having 6 to 50, preferably 6 to 30, more preferably 6 to 20, and still more preferably 6 to 12 ring carbon atoms, or a substituted or unsubstituted heteroaryl group having 5 to 50, preferably 5 to 30, more preferably 5 to 20, and still more preferably 5 to 12 ring atoms;

provided that one of $Ar^{11}$ and $Ar^{12}$ is a substituted or unsubstituted fused aromatic hydrocarbon group having 10 to 50, preferably 10 to 30, more preferably 10 to 20, and still more preferably 10 to 14 ring carbon atoms or a substituted or unsubstituted fused aromatic heterocyclic group having 9 to 50, preferably 9 to 30, more preferably 9 to 20, and still more preferably 9 to 14 ring atoms;

$Ar^{13}$ represents a substituted or unsubstituted arylene group having 6 to 50, preferably 6 to 30, more preferably 6 to 20, and still more preferably 6 to 12 ring carbon atoms or a substituted or unsubstituted heteroarylene group having 5 to 50, preferably 5 to 30, more preferably 5 to 20, and still more preferably 5 to 12 ring atoms; and $L^{11}$, $L^{12}$, and $L^{13}$ each independently represent a single bond, a substituted or unsubstituted arylene group having 6 to 50, preferably 6 to 30, more preferably 6 to 20, and still more preferably 6 to 12 ring carbon atoms or a substituted or unsubstituted divalent fused aromatic heterocyclic group having 9 to 50, preferably 9 to 30, more preferably 9 to 20, and still more preferably 9 to 14 ring atoms.

Examples of the nitrogen-containing heterocyclic derivative represented by formulae (60) to (62) are shown below.

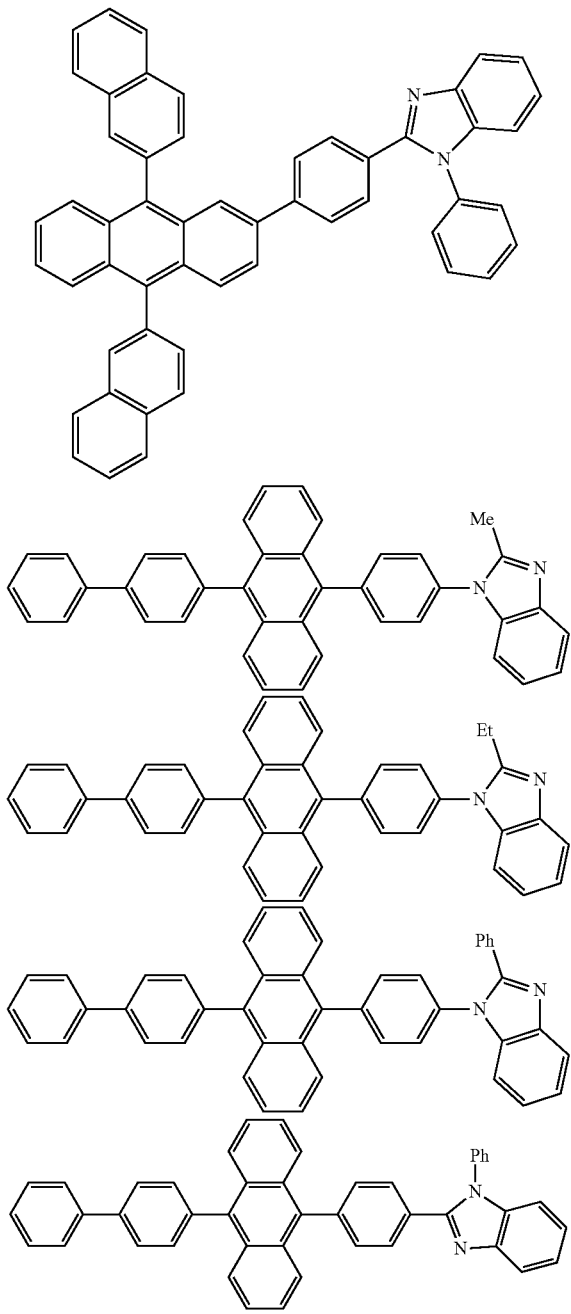

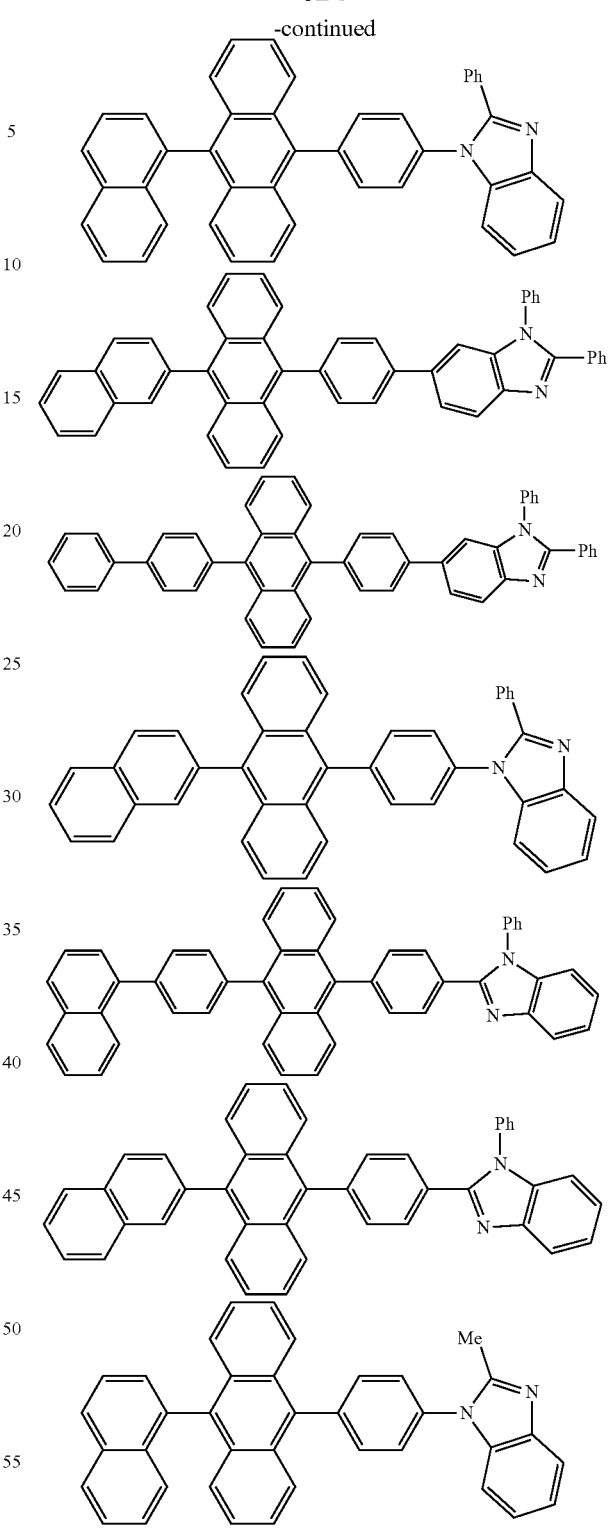

The electron transporting layer of the organic EL device of the invention may be made into two-layered structure of a first electron transporting layer (anode side) and a second electron transporting layer (cathode side).

The thickness of the electron transporting layer is preferably 1 to 100 nm, although not particularly limited thereto. If the electron transporting layer is of a two-layered structure of a first electron transporting layer (anode side) and a second electron transporting layer (cathode side), the thickness is preferably 5 to 60 nm and more preferably 10 to 40 nm for the first electron transporting layer, and preferably 1 to 20 nm and more preferably 1 to 10 nm for the second electron transporting layer.

Preferred example of the material for an electron injecting layer optionally formed adjacent to the electron transporting layer include, in addition to the nitrogen-containing ring derivative, an inorganic compound, such as an insulating material and a semiconductor. The electron injecting layer formed by the insulating material or the semiconductor effectively prevents the leak of electric current to enhance the electron injecting properties.

The insulating material is preferably at least one metal compound selected from the group consisting of an alkali metal chalcogenide, an alkaline earth metal chalcogenide, an alkali metal halide and an alkaline earth metal halide. The alkali metal chalcogenide, etc. mentioned above are preferred because the electron injecting properties of the electron injecting layer are further enhanced. Example of preferred alkali metal chalcogenide includes $Li_2O$, $K_2O$, $Na_2S$, $Na_2Se$ and $Na_2O$, and example of preferred alkaline earth metal chalcogenide includes CaO, BaO, SrO, BeO, BaS and CaSe. Example of preferred alkali metal halide includes LiF, NaF, KF, LiCl, KCl and NaCl. Example of the alkaline earth metal halide includes a fluoride, such as $CaF_2$, $BaF_2$, $SrF_2$, $MgF_2$ and $BeF_2$, and a halide other than the fluoride.

Example of the semiconductor includes an oxide, a nitride or an oxynitride of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound in the electron injecting layer preferably forms a microcrystalline or amorphous insulating thin film. If the electron injecting layer is formed from such an insulating thin film, the pixel defects, such as dark spots, can be decreased because a more uniform thin film is formed. Example of such an inorganic compound includes the alkali metal chalcogenide, the alkaline earth metal chalcogenide, the alkali metal halide and the alkaline earth metal halide.

The thickness of the layer of the insulating material or the semiconductor is preferably about 0.1 to 15 nm. The electron injecting layer preferably contains the electron-donating dopant mentioned above.

Hole Transporting Layer

The hole transporting layer is an organic layer formed between the light emitting layer and the anode and transports holes from the anode to the light emitting layer. When the hole transporting layer is formed by two or more layers, the layer closer to the anode may be defined as a hole injecting layer in some cases. The hole injecting layer injects holes from the anode to the organic layer unit efficiently.

An aromatic amine compound, for example, the aromatic amine derivative represented by formula (I) is preferably used as a material for the hole transporting layer:

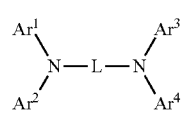

(I)

wherein:
each of $Ar^1$ to $Ar^4$ represents a substituted or unsubstituted aromatic hydrocarbon group having 6 to 50, preferably 6 to 30, more preferably 6 to 20, and still more preferably 6 to 12 ring carbon atoms, a substituted or unsubstituted fused aromatic hydrocarbon group having 6 to 50, preferably 6 to 30, more preferably 6 to 20, and still more preferably 6 to 12 ring carbon atoms, a substituted or unsubstituted aromatic heterocyclic group having 5 to 50, preferably 5 to 30, more preferably 5 to 20, and still more preferably 5 to 12 ring carbon atoms, a substituted or unsubstituted fused aromatic heterocyclic group having 5 to 50, preferably 5 to 30, more preferably 5 to 20, and still more preferably 5 to 12 ring atoms, or a group wherein the aromatic hydrocarbon group or the fused aromatic hydrocarbon group is bonded to the aromatic heterocyclic group or the fused aromatic heterocyclic group;

$Ar^1$ and $Ar^2$ or $Ar^3$ and $Ar^4$ may form a ring; and

L represents a substituted or unsubstituted aromatic hydrocarbon group having 6 to 50, preferably 6 to 30, more preferably 6 to 20, and still more preferably 6 to 12 ring carbon atoms, a substituted or unsubstituted fused aromatic hydrocarbon group having 6 to 50, preferably 6 to 30, more preferably 6 to 20, and still more preferably 6 to 12 ring carbon atoms, a substituted or unsubstituted aromatic heterocyclic group having 5 to 50, preferably 5 to 30, more preferably 5 to 20, and still more preferably 5 to 12 ring carbon atoms, or a substituted or unsubstituted fused aromatic heterocyclic group having 5 to 50, preferably 5 to 30, more preferably 5 to 20, and still more preferably 5 to 12 ring atoms.

Examples of the compound represented by formula (I) are shown below.

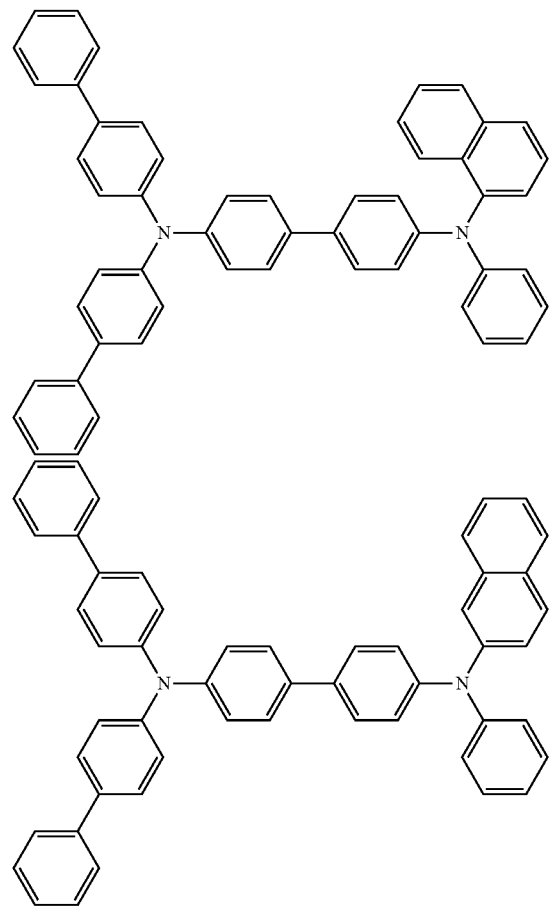

627
-continued
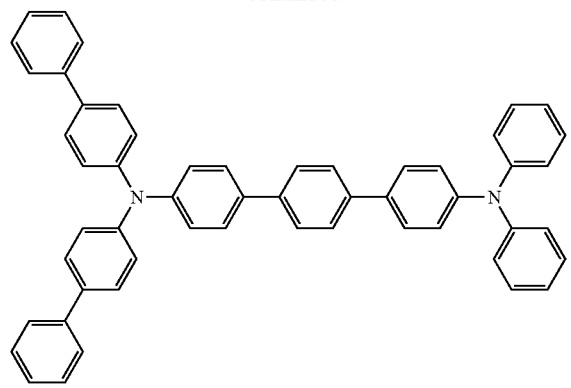
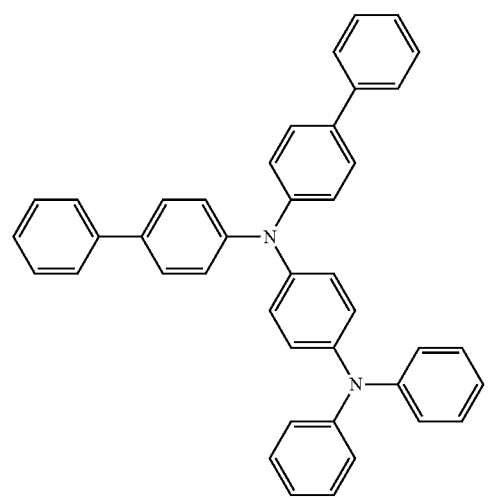
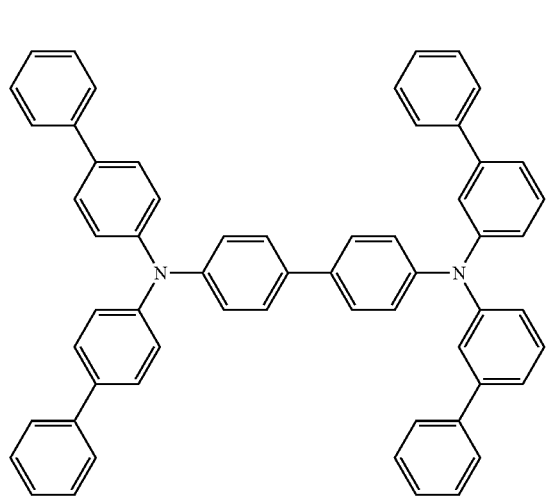
628
-continued
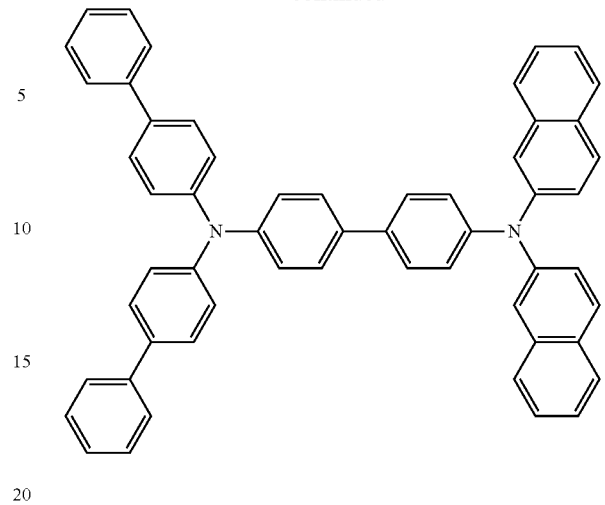
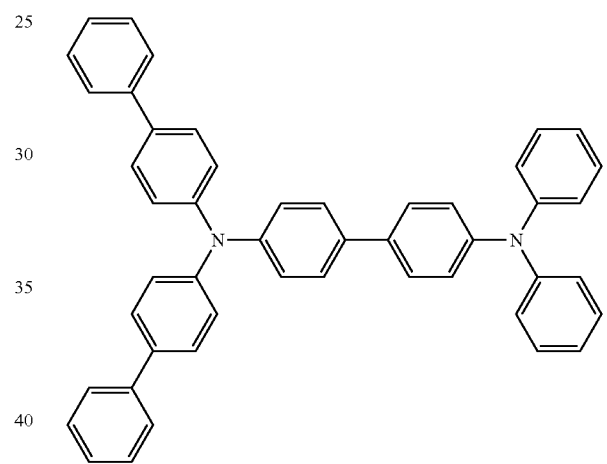
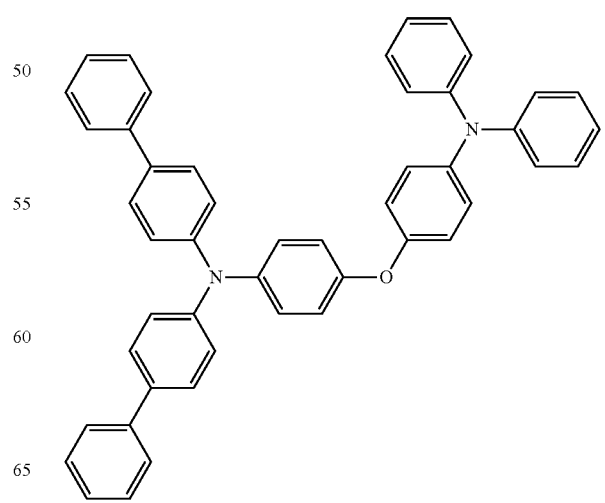

629
-continued
630
-continued
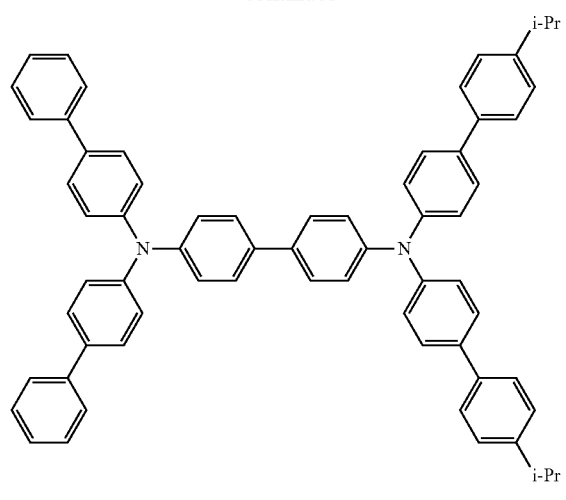
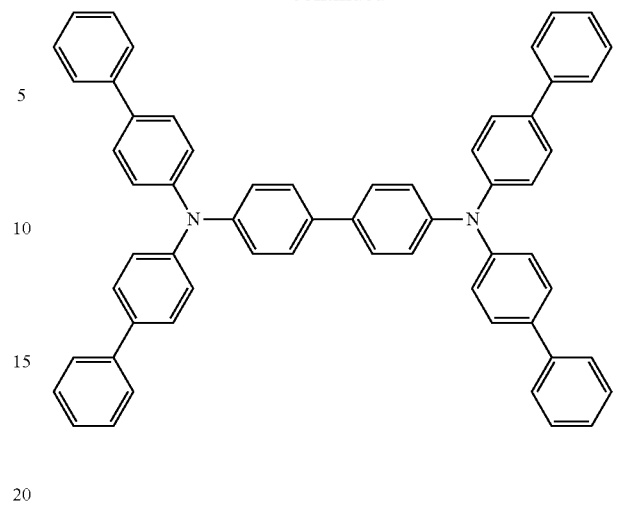
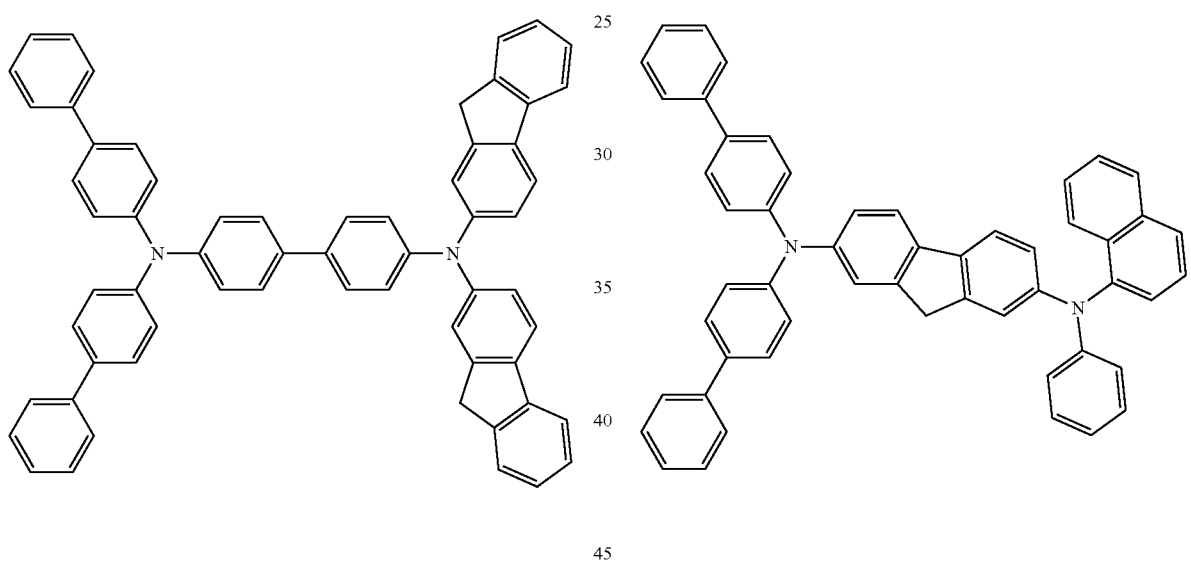
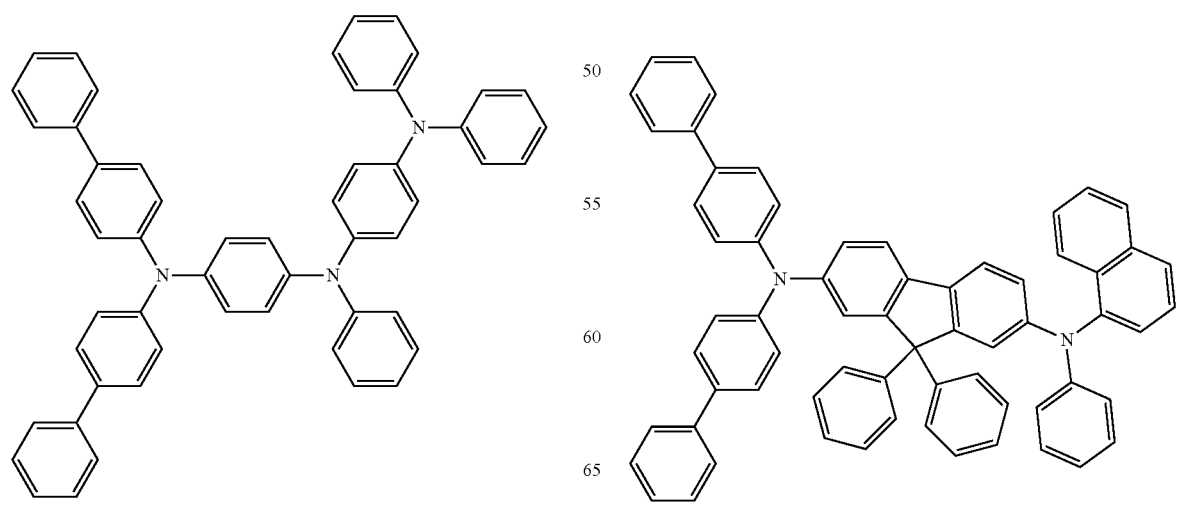

631
-continued
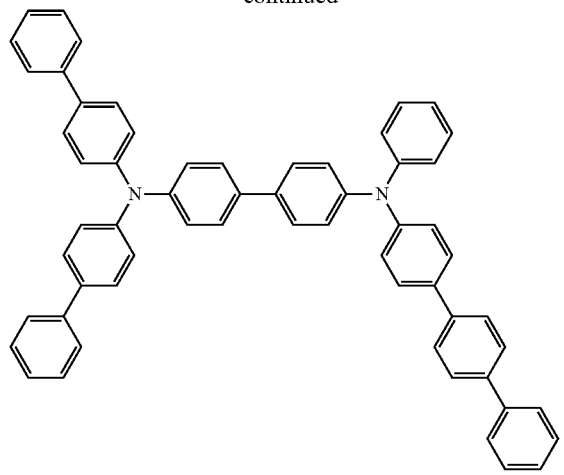
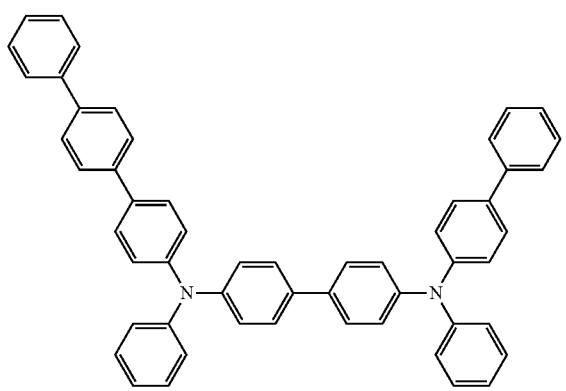
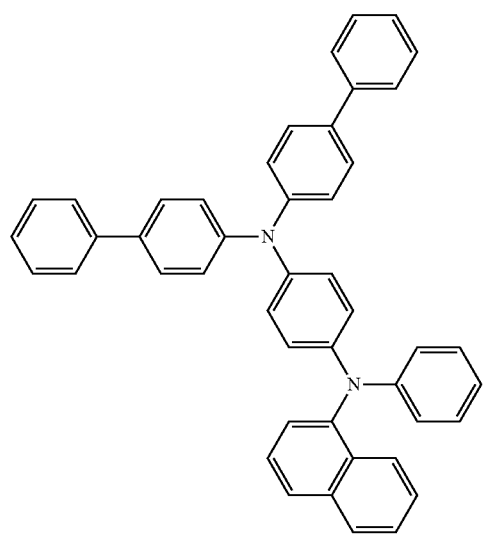
632
-continued
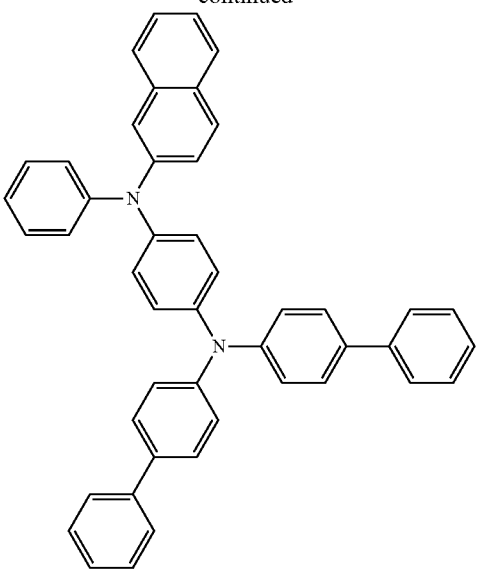
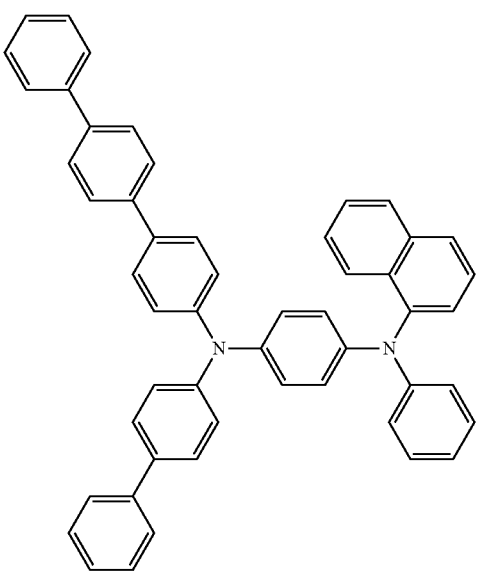
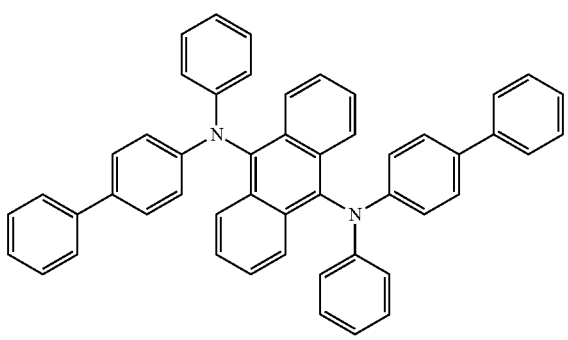

633
-continued
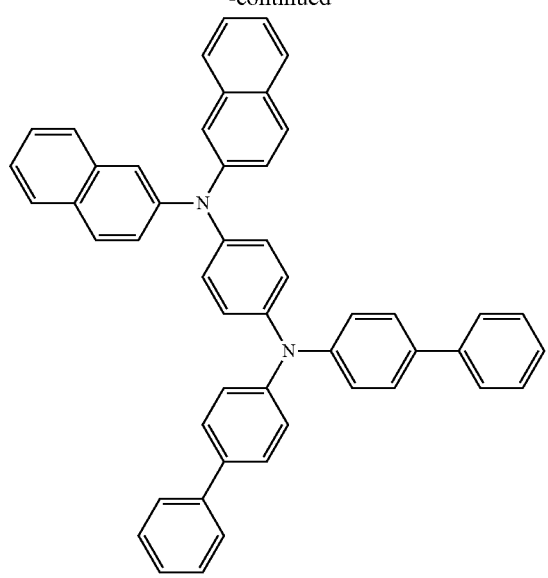
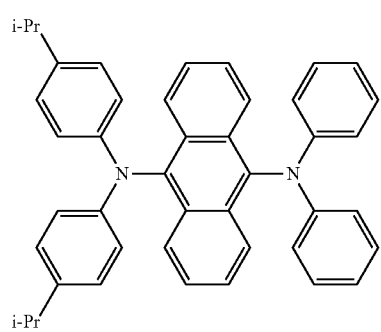
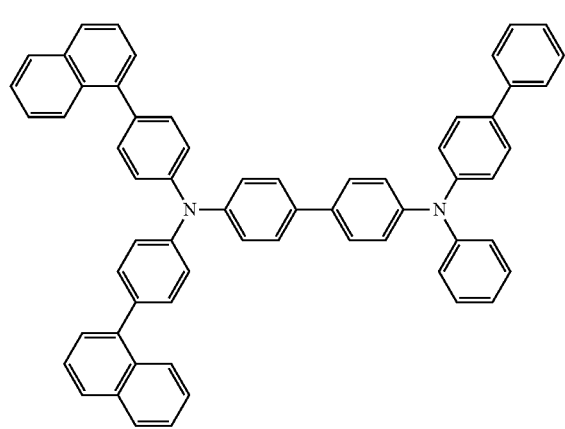
634
-continued
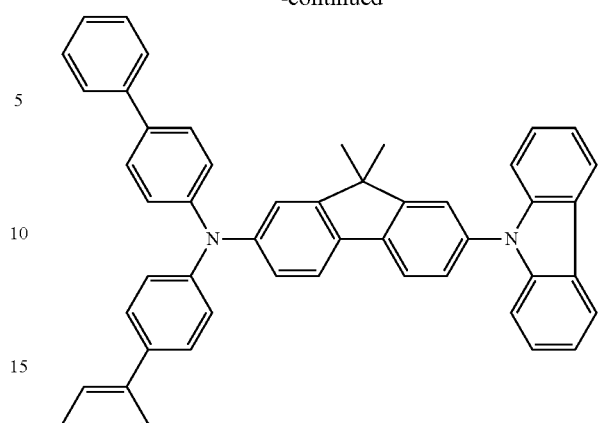
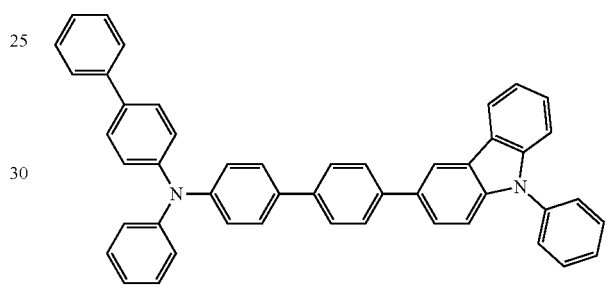
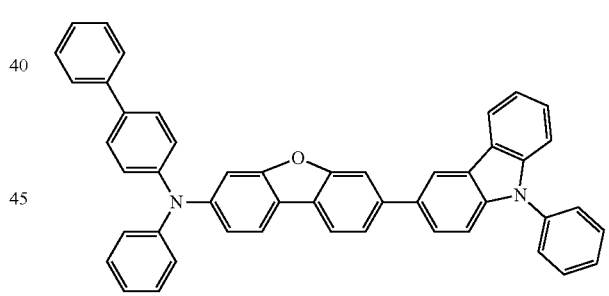

635
-continued
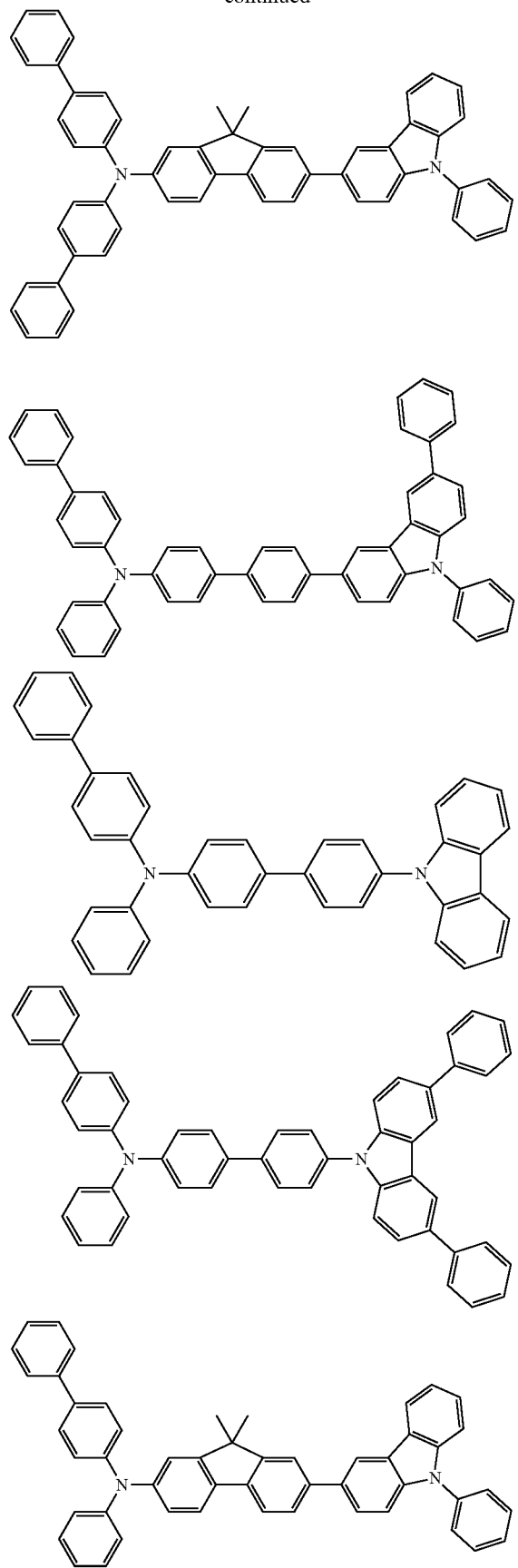
636
-continued
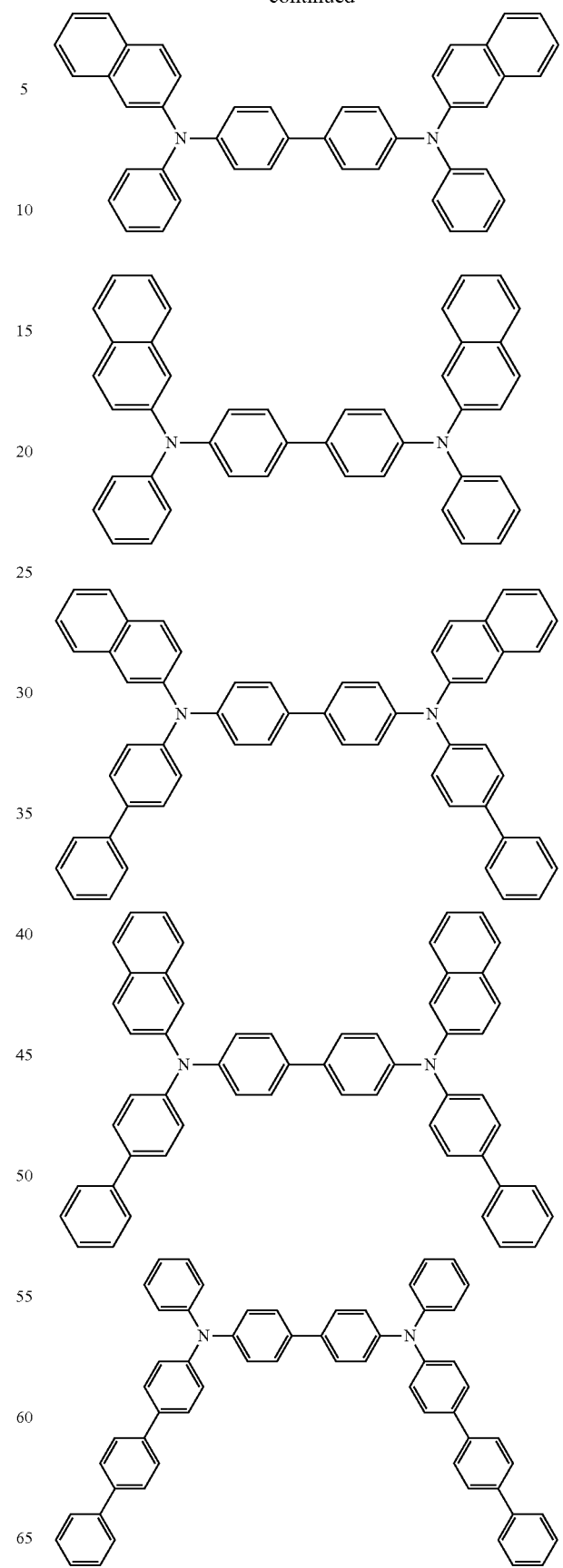

637
-continued
638
-continued
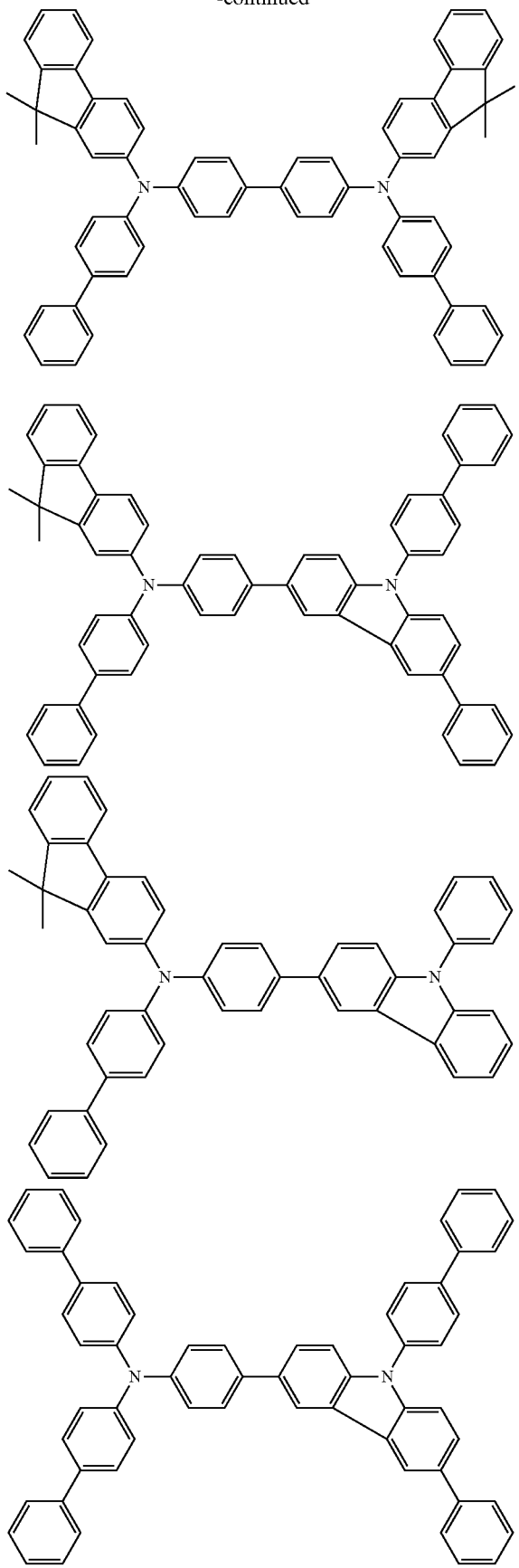
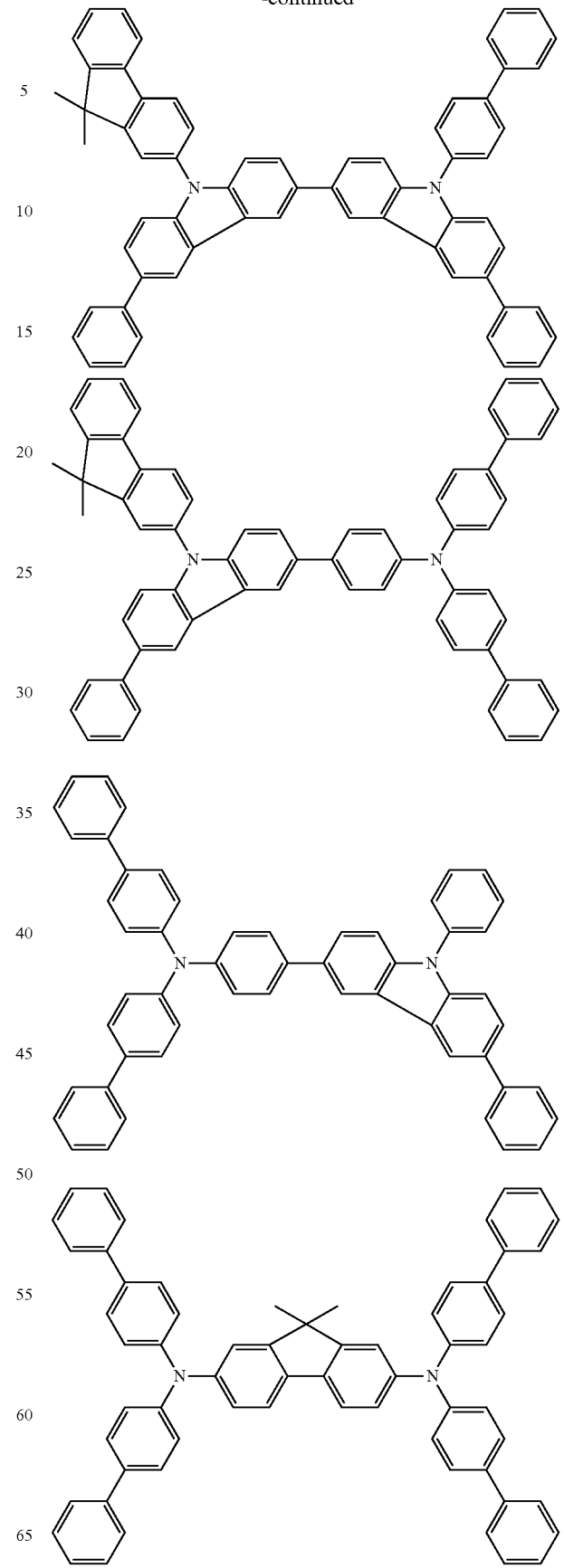

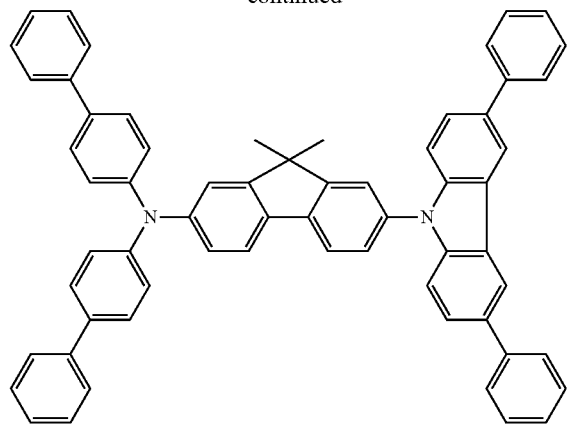
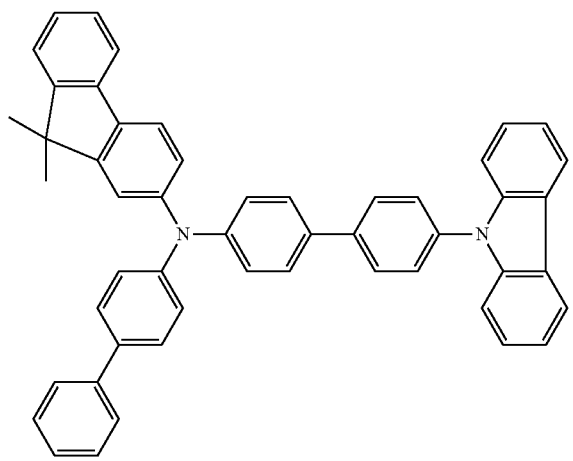
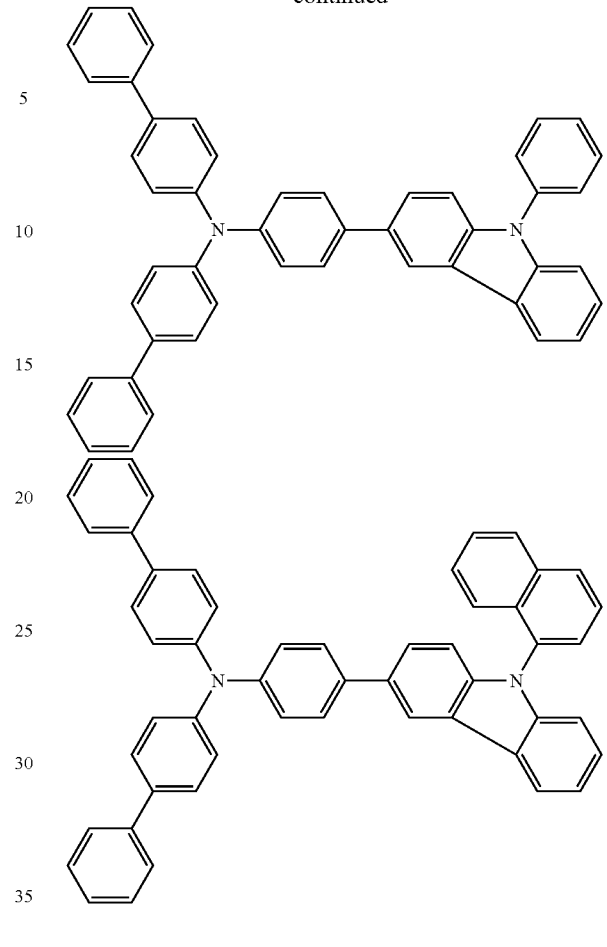
An aromatic amine represented by formula (II) is also preferably used to form the hole transporting layer:
(II)
wherein $Ar^1$ to $Ar^3$ are the same as defined above with respect to $Ar^1$ to $Ar^4$ of formula (I).
Examples of the compound represented by formula (II) are shown below, although not limited thereto.
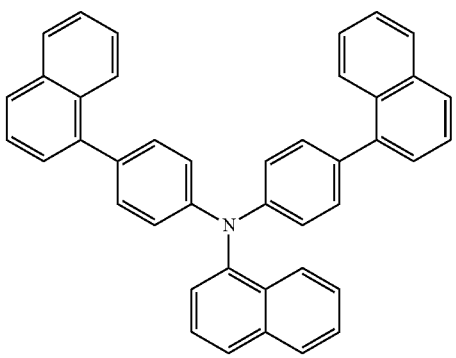

641
-continued
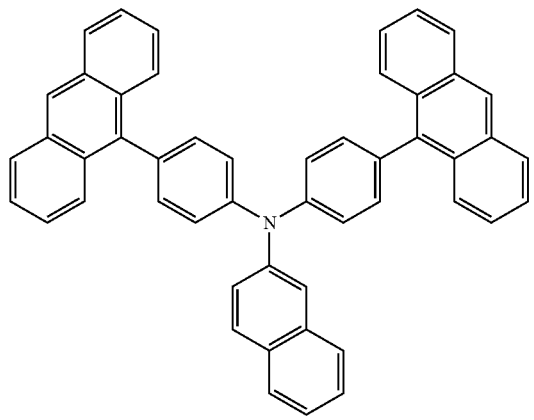
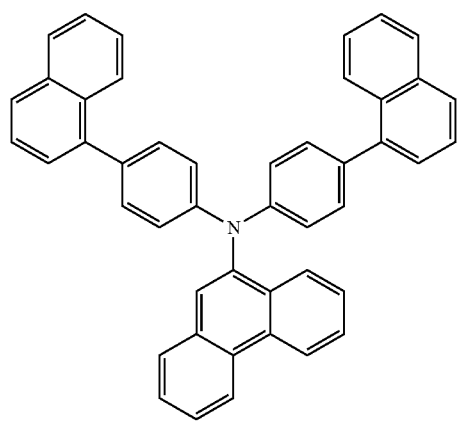
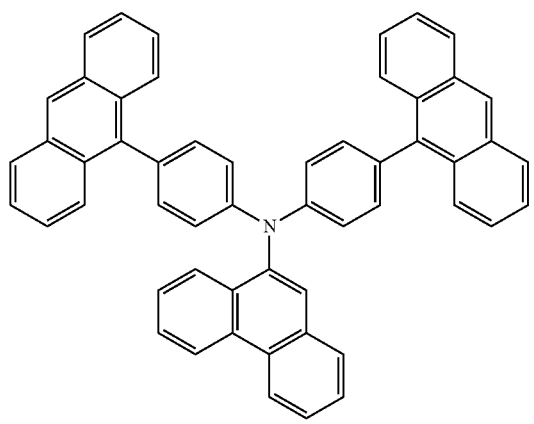
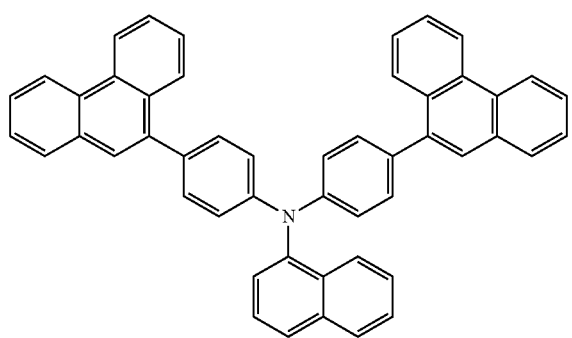
642
-continued
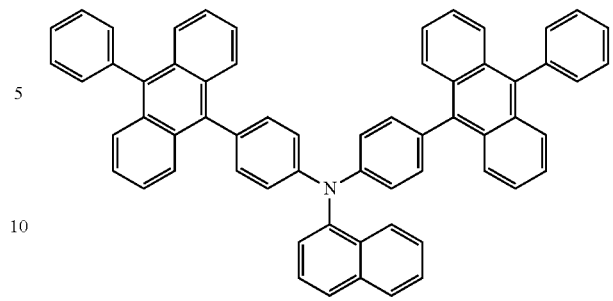
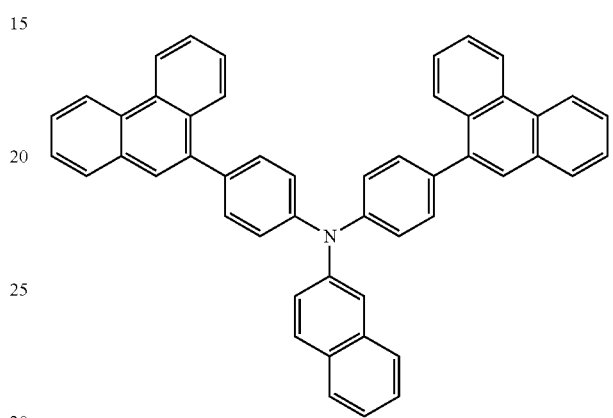
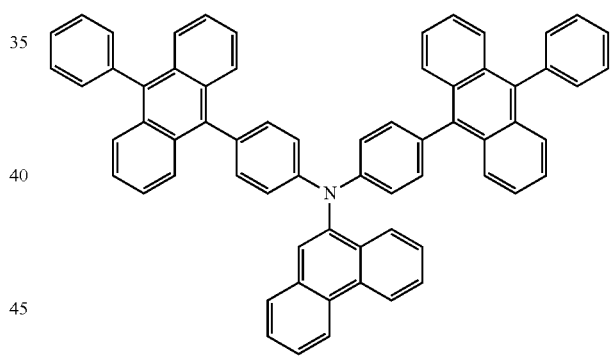
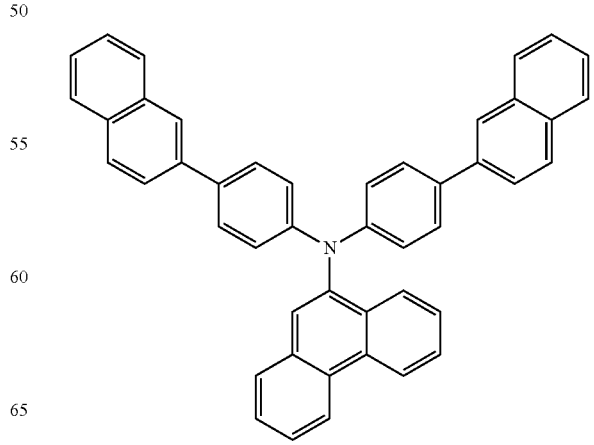

643
-continued
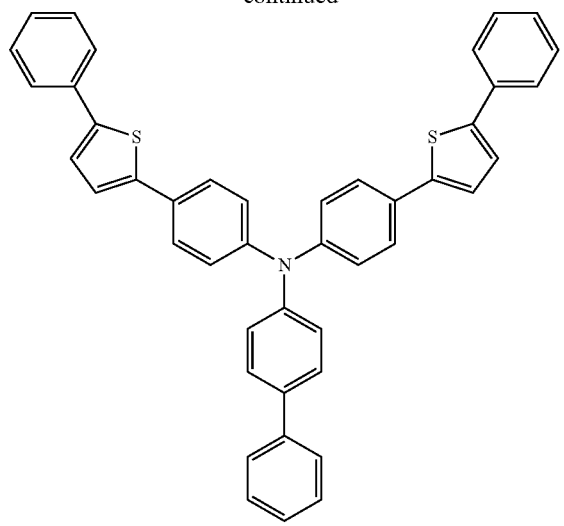
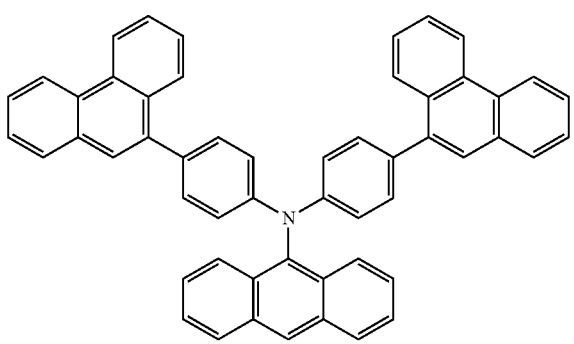
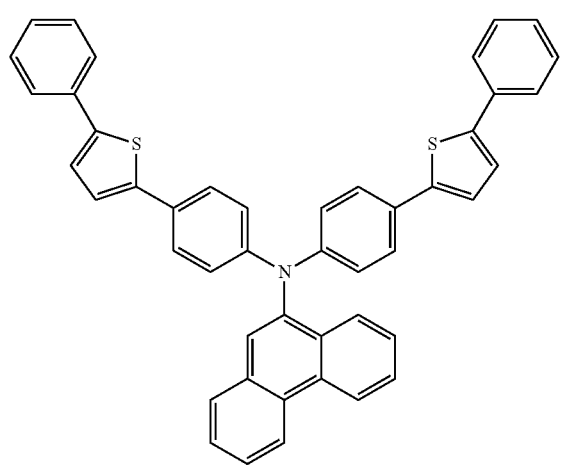
644
-continued
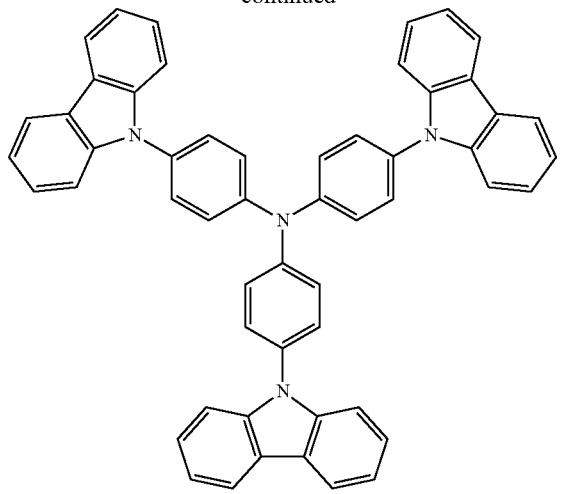
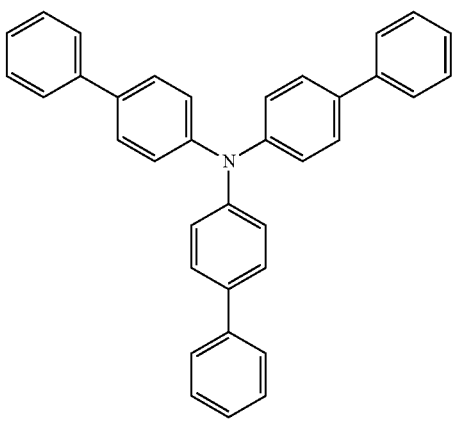
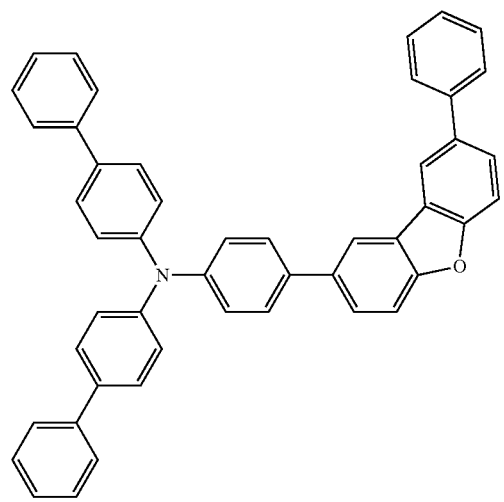

645
-continued
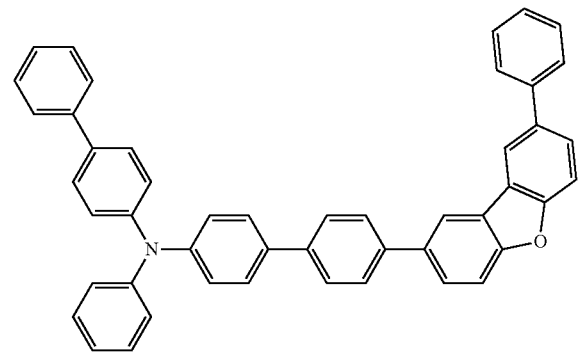
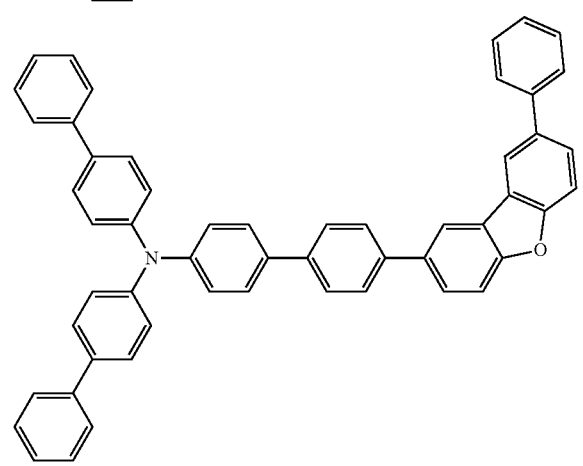
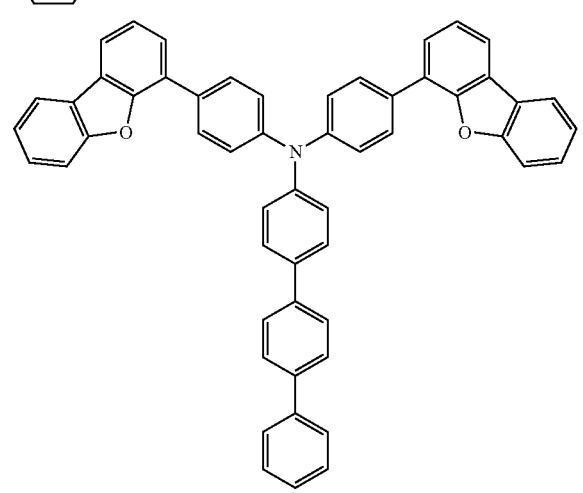
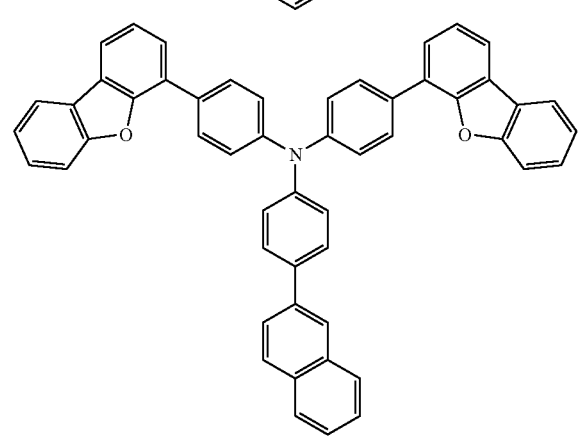
646
-continued
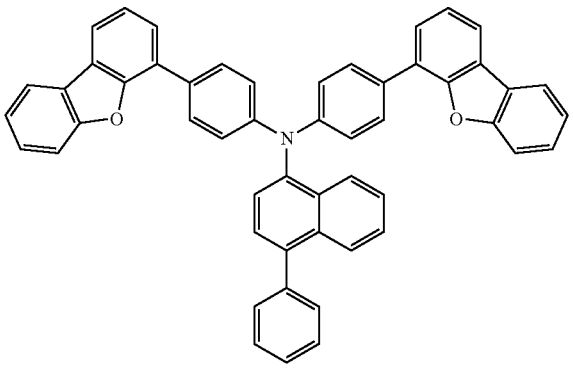
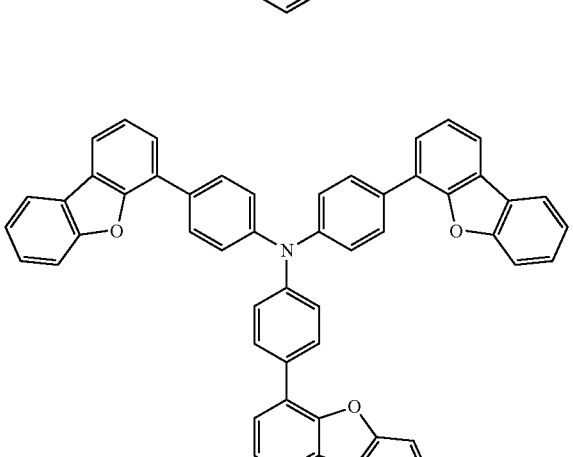
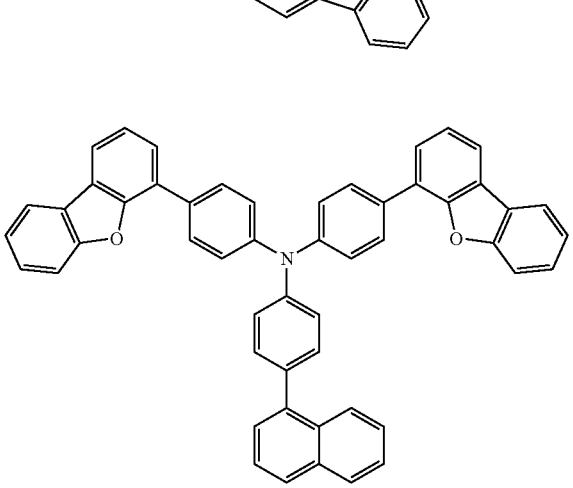
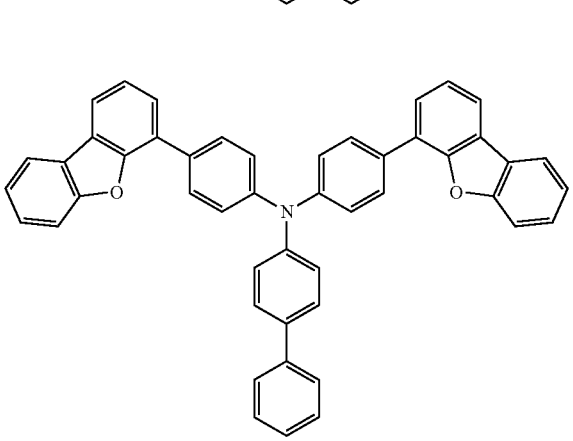

-continued

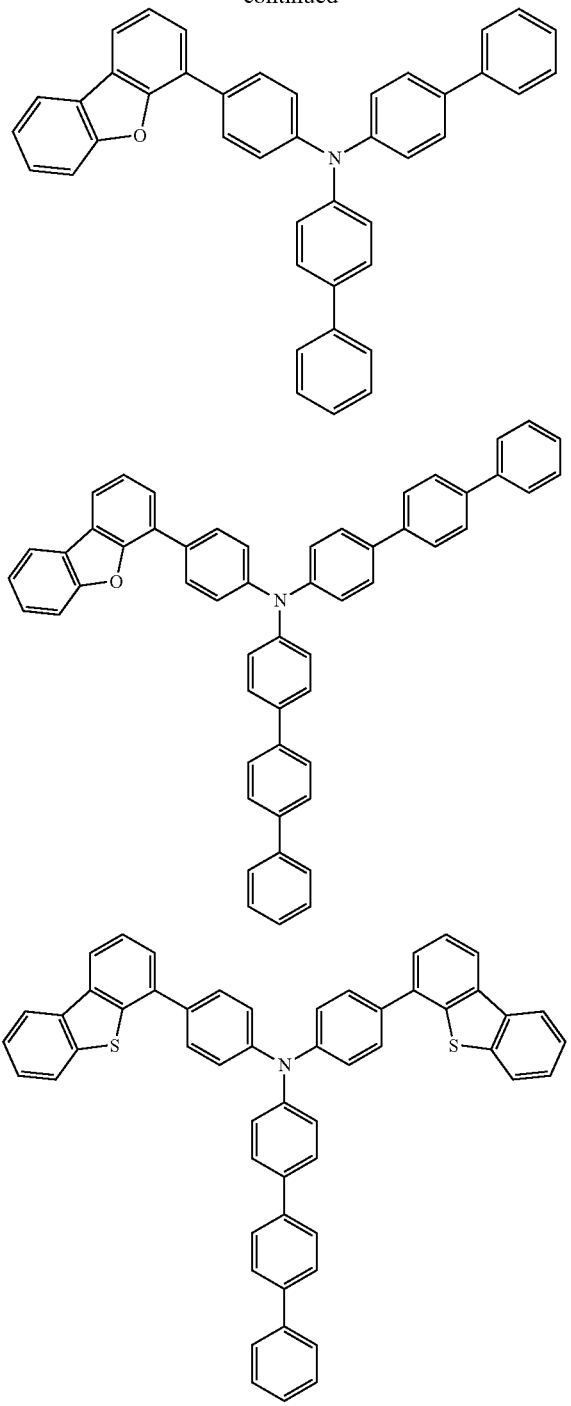

The hole transporting layer of the organic EL device of the invention may be made into two-layered structure of a first hole transporting layer (anode side) and a second hole transporting layer (cathode side).

The thickness of the hole transporting layer is preferably 10 to 200 nm, although not particularly limited thereto. If the hole transporting layer is of a two-layered structure of a first hole transporting layer (anode side) and a second hole transporting layer (cathode side), the thickness is preferably 50 to 150 nm and more preferably 50 to 110 nm for the first hole transporting layer, and preferably 5 to 50 nm and more preferably 5 to 30 nm for the second hole transporting layer.

The organic EL device of the invention may have a layer comprising an acceptor material which is disposed in contact with the anode side of the hole transporting layer or the first hole transporting layer. With such a layer, it is expected that the driving voltage is lowered and the production cost is reduced.

The acceptor material is preferably a compound represented by the following formula.

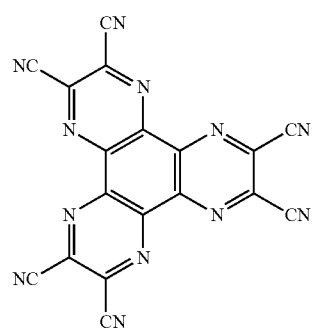 [SMILES: N#Cc1nc2c3nc(C#N)c(C#N)nc3c3nc(C#N)c(C#N)nc3c2nc1C#N]

The thickness of the layer comprising the acceptor material is preferably 5 to 20 nm, although not particularly limited thereto.

N/P Doping

The carrier injecting properties of the hole transporting layer and the electron transporting layer can be controlled, as described in JP 3695714B, by the doping (n) with a donor material or the doping (p) with an acceptor material.

A typical example of the n-doping is an electron transporting material doped with a metal, such as Li and Cs, and a typical example of the p-doping is a hole transporting material doped with an acceptor material, such as $F_4TCNQ$.

Space Layer

For example, in an organic EL device wherein a fluorescent emitting layer and a phosphorescent emitting layer are laminated, a space layer is disposed between the fluorescent emitting layer and the phosphorescent emitting layer to prevent the diffusion of excitons generated in the phosphorescent emitting layer to the fluorescent emitting layer or to control the carrier balance. The space layer may be disposed between two or more phosphorescent emitting layers. Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

The organic EL device of the invention preferably comprises a blocking layer, such as an electron blocking layer, a hole blocking layer, and a triplet blocking layer, which is disposed adjacent to the light emitting layer. The electron blocking layer is a layer for preventing the diffusion of electrons from the light emitting layer to the hole transporting layer and disposed between the light emitting layer and the hole transporting layer. The hole blocking layer is a layer for preventing the diffusion of holes from the light emitting layer to the electron transporting layer and disposed between the light emitting layer and the electron transporting layer.

The triplet blocking layer prevents the diffusion of triplet excitons generated in the light emitting layer to adjacent layers and confines the triplet excitons in the light emitting layer, thereby preventing the energy of the triplet excitons from being deactivated on the molecules other than the emitting dopant, i.e., on the molecules in the electron transporting layer.

The electron mobility of the electron injecting layer is preferably $10^{-6}$ cm$^2$/Vs or more at an electric field strength of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

Electronic Device

The organic EL device comprising the compound of the invention is of high performance and is usable in electronic device, for example, as display parts, such as organic EL panel module, display devices of television sets, mobile phones, personal computer, etc., and light emitting sources of lighting equipment and vehicle lighting equipment.

EXAMPLES

The present invention will be described below in more details with reference to the examples. However, it should be noted that the scope of the invention is not limited to the examples.

Synthesis Example 1 (Synthesis of Compound 2)

(1) Synthesis of Intermediate 1

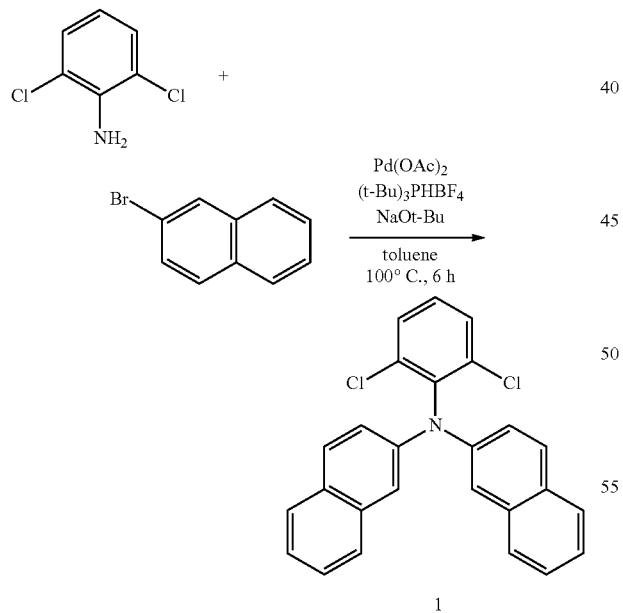

Under argon atmosphere, 2,6-dichloroaniline (1.0 g, 6.17 mmol), 2-bromonaphthalene (2.68 g, 13.0 mmol), palladium acetate (28 mg, 0.123 mmol), tri-t-butylphosphine tetrafluoroborate (72 mg, 0.247 mmol), and sodium t-butoxide (1.78 g, 18.5 mmol) were dissolved in toluene (15 mL). The resultant solution was stirred at 100° C. for 6 h. After the reaction, water was added to the reaction solution, which was then extracted with dichloromethane. The organic layers were collected and concentrated. The obtained solid was purified by column chromatography to obtain a white solid (1.8 g), which was identified as the target Intermediate 1 by the result of mass spectrometric analysis (m/e=414 to the molecular weight of 414.32). (yield: 71%)

(2) Synthesis of Compound 2

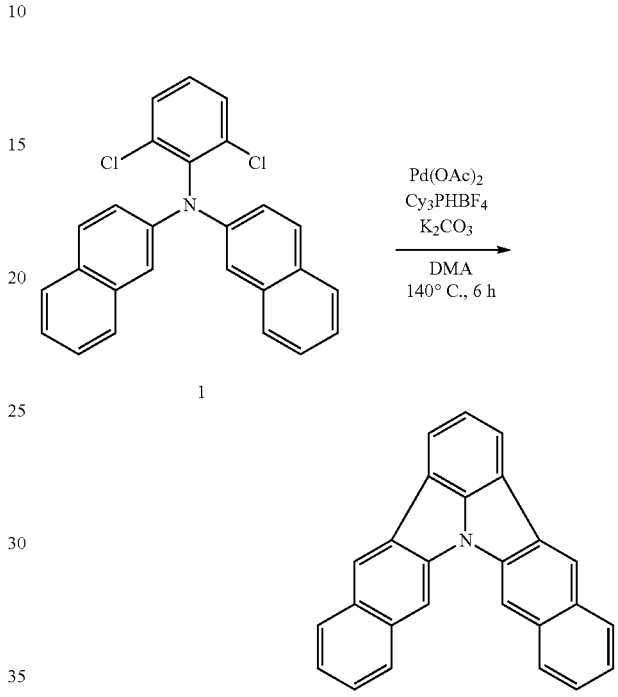

Under argon atmosphere, Intermediate 1 (100 mg, 0.241 mmol), palladium acetate (2.7 mg, 0.0121 mmol), tricyclohexylphosphine tetrafluoroborate (9.0 mg, 0.0241 mmol), and potassium carbonate (133 mg, 0.964 mmol) were dissolved in dimethylacetamide (3 mL). The resultant solution was heated at 140° C. for 6 h. After the reaction, water was added to the reaction solution, which was then extracted with dichloromethane. The organic layers were collected and concentrated. The obtained solid was purified by flash column chromatography to obtain a yellow solid (32 mg), which was identified as the target Compound 2 by the result of mass spectrometric analysis (m/e=341 to the molecular weight of 341.40). (yield: 39%)

Synthesis Example 2 (Synthesis of Compound 5)

(1) Synthesis of Intermediate 3

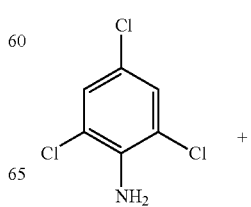

-continued

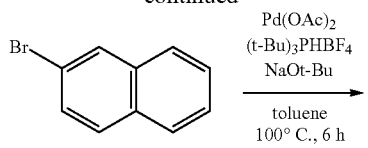

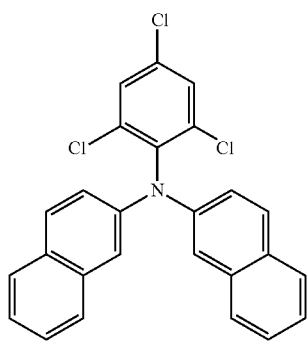

3

Under argon atmosphere, 2,4,6-trichloroaniline (1.0 g, 5.09 mmol), 2-bromonaphthalene (2.21 g, 10.7 mmol), palladium acetate (22 mg, 0.102 mmol), tri-t-butylphosphine tetrafluoroborate (59 mg, 0.204 mmol), and sodium t-butoxide (1.38 g, 15.3 mmol) were dissolved in toluene (15 mL). The resultant solution was stirred at 100° C. for 6 h. After the reaction, water was added to the reaction solution, which was then extracted with dichloromethane. The organic layers were collected and concentrated. The obtained solid was purified by column chromatography to obtain a white solid (1.5 g), which was identified as the target Intermediate 3 by the result of mass spectrometric analysis (m/e=448 to the molecular weight of 448.77). (yield: 66%)

(2) Synthesis of Intermediate 4

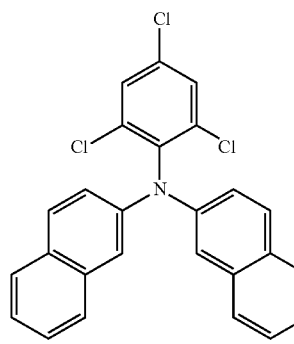

3

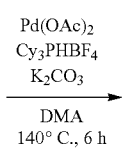

-continued

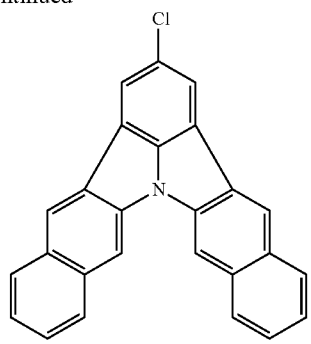

4

Under argon atmosphere, Intermediate 3 (100 mg, 0.223 mmol), palladium acetate (2.5 mg, 0.0111 mmol), tricyclohexylphosphine tetrafluoroborate (6.4 mg, 0.0222 mmol), and potassium carbonate (92 mg, 0.669 mmol) were dissolved in dimethylacetamide (3 mL). The resultant solution was heated at 140° C. for 6 h.

After the reaction, water was added to the reaction solution, which was then extracted with dichloromethane. The organic layers were collected and concentrated. The obtained solid was purified by flash column chromatography to obtain a yellow solid (26 mg), which was identified as the target Intermediate 4 by the result of mass spectrometric analysis (m/e=375 to the molecular weight of 375.85). (yield: 30%)

(3) Synthesis of Compound 5

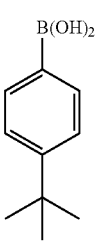

4

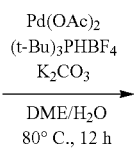

653

-continued

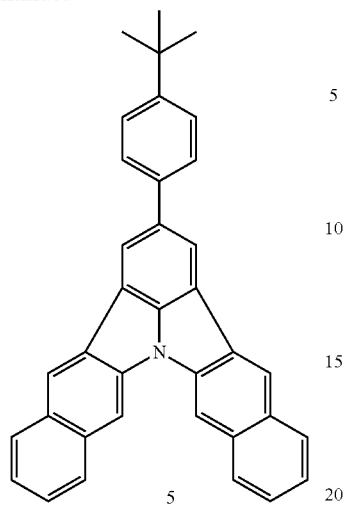

5

Under argon atmosphere, into a mixture of Intermediate 4 (20 mg, 0.0532 mmol), 4-tert-butylphenylboronic acid (9.3 mg, 0.0639 mmol), palladium acetate (1.2 mg, 0.00532 mmol), tri-t-butylphosphine tetrafluoroborate (3.1 mg, 0.0106 mmol), and potassium carbonate (14.7 mg, 0.106 mmol), dimethoxyethane (2 mL) and water (0.5 mL) were added. The resultant mixture was stirred at 80° C. for 12 h. After the reaction, water was added to the reaction solution, which was then extracted with dichloromethane. The organic layers were collected and concentrated. The obtained solid was purified by column chromatography to obtain a yellow solid (16 mg), which was identified as the target Compound 5 by the result of mass spectrometric analysis (m/e=473 to the molecular weight of 473.61). (yield: 64%)

Synthesis Example 3 (Synthesis of Compound 7)

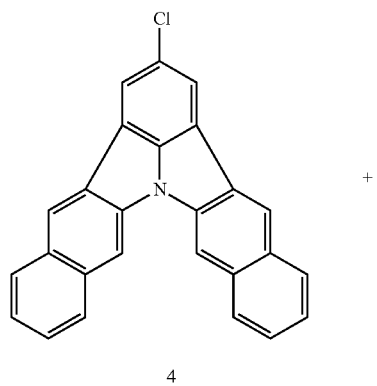

4

+

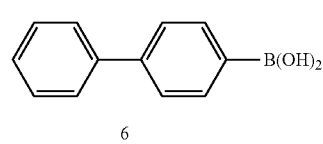

6

$\xrightarrow[\text{toluene}]{\text{Pd}_2(\text{dba})_3,\text{SPhos}}$
$\xrightarrow[\text{160° C., 7 min}]{\text{K}_3\text{PO}_4}$

654

-continued

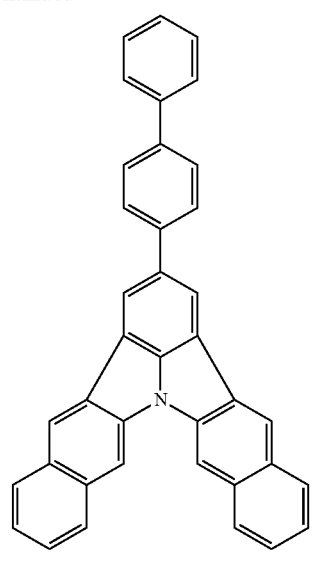

7

Under argon atmosphere, into a mixture of Intermediate 4 (150 mg, 0.399 mmol), boronic acid 6 (395 mg, 1.995 mmol), tris(dibenzylideneacetone) dipalladium (15 mg, 0.016 mmol), 2-dicyclohexylphosphino-2',6'-dimethoxybiphenyl (SPhos) (26 mg, 0.064 mmol), and potassium phosphate (847 mg, 3.99 mmol), toluene (2 mL) was added. The resultant mixture was stirred at 160° C. for 7 min. After the reaction, the precipitated solid was collected by filtration and washed with toluene and methanol to obtain a yellow solid (167 mg), which was identified as the target Compound 7 by the result of mass spectrometric analysis (m/e=493 to the molecular weight of 493.6). (yield: 83%)

Synthesis Example 4 (Synthesis of Compound 9)

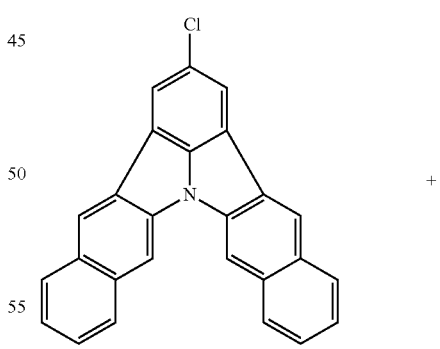

4

+

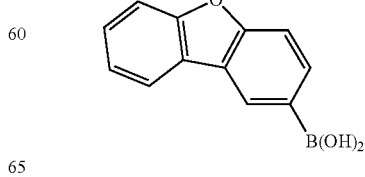

8

$\xrightarrow[\text{toluene}]{\text{Pd}_2(\text{dba})_3,\text{SPhos}}$
$\xrightarrow[\text{60° C., 7 min}]{\text{K}_3\text{PO}_4}$

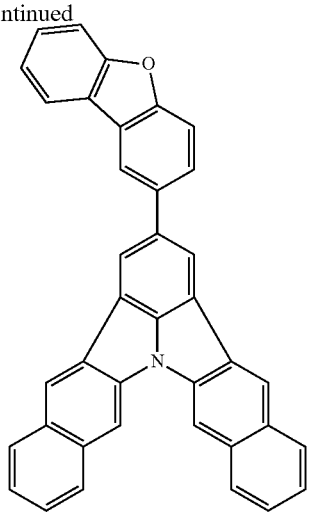

9

Under argon atmosphere, into a mixture of Intermediate 4 (150 mg, 0.399 mmol), boronic acid 8 (423 mg, 1.995 mmol), tris(dibenzylideneacetone) dipalladium (15 mg, 0.016 mmol), SPhos (26 mg, 0.064 mmol), and potassium phosphate (847 mg, 3.99 mmol), toluene (2 mL) was added. The resultant mixture was stirred at 160° C. for 7 min. After the reaction, the precipitated solid was collected by filtration and washed with toluene and methanol to obtain a yellow solid (188 mg), which was identified as the target Compound 9 by the result of mass spectrometric analysis (m/e=507 to the molecular weight of 507.58). (yield: 93%)

Synthesis Example 5 (Synthesis of Compound 11)

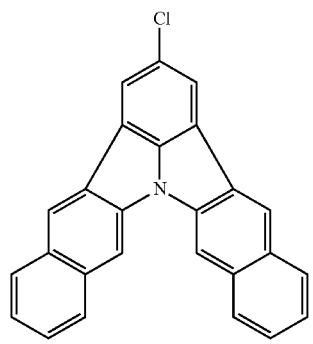

4

+

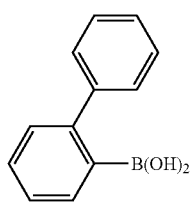

10

Pd$_2$(dba)$_3$, SPhos
K$_3$PO$_4$
→
toluene
160° C., 5 min

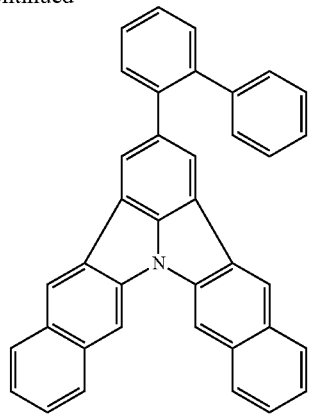

11

Under argon atmosphere, into a mixture of Intermediate 4 (150 mg, 0.399 mmol), boronic acid 10 (395 mg, 1.995 mmol), tris(dibenzylideneacetone) dipalladium (15 mg, 0.016 mmol), SPhos (26 mg, 0.064 mmol), and potassium phosphate (847 mg, 3.99 mmol), toluene (2 mL) was added. The resultant mixture was stirred at 160° C. for 5 min. After the reaction, the precipitated solid was collected by filtration and washed with toluene and methanol to obtain a yellow solid (142 mg), which was identified as the target Compound 11 by the result of mass spectrometric analysis (m/e=493 to the molecular weight of 493.6). (yield: 72%)

Synthesis Example 6 (Synthesis of Compound 17)

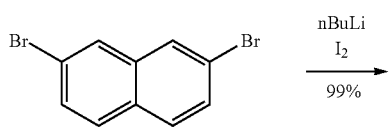

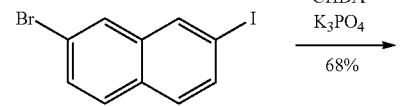

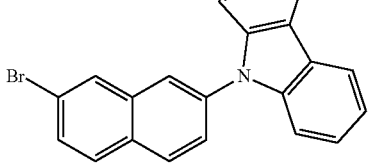

14

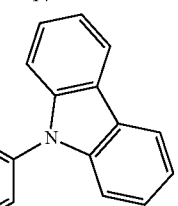

15

-continued

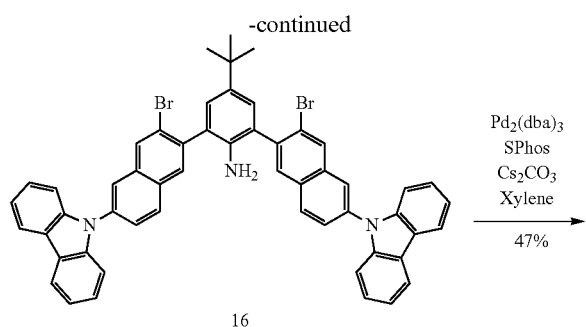

16

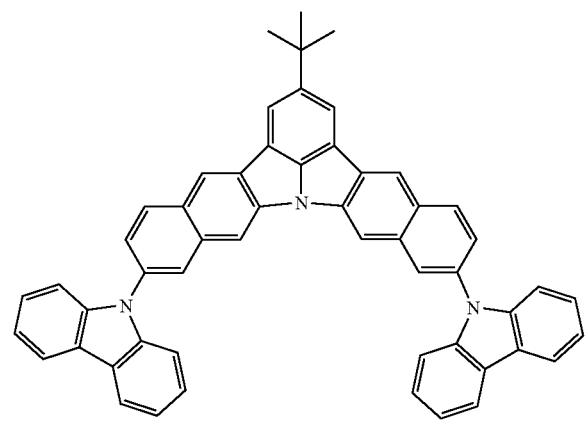

17

(1) Synthesis of 2-bromo-7-iodonaphthalene

Under argon atmosphere, a solution of 2,7-dibromonaphthalene (5.0 g, 17 mmol) in a mixed solvent of anhydrous tetrahydrofuran (80 mL) and anhydrous toluene (40 mL) was cooled to −48° C. in a dry ice/acetone bath. Into the solution, 10.6 mL of a n-butyllithium/hexane solution (1.64 mol/L, 17 mmol) was added and the solution was stirred at −45° C. for 20 min and further at −72° C. for 30 min. After adding a solution of iodine (4.9 g, 19 mmol) in tetrahydrofuran, the reaction mixture was stirred at −72° C. for one hour and then at room temperature for 2.5 h. The reaction mixture was deactivated by a 10% by mass aqueous solution of sodium sulfite (60 mL) and then extracted with toluene (150 mL). The organic layer was washed with a saturated brine (30 mL) and dried over magnesium sulfate. The solvent was evaporated off and the residue was dried under reduced pressure to obtain a pale yellow solid (5.66 g), which was identified as the target 2-bromo-7-iodonaphthalene by the result of mass spectrometric analysis (m/e=339 to the molecular weight of 339). (yield: 99%)

(2) Synthesis of Intermediate 14

Under argon atmosphere, into a suspension of 9H-carbazole (2.55 g, 15 mmol), 2-bromo-7-iodonaphthalene (5.7 g, 17 mmol), copper iodide (30 mg, 0.16 mmol), and tripotassium phosphate (7.5 g, 35 mmol) in anhydrous 1,4-dioxane (20 mL), trans-1,2-diaminocyclohexane (0.19 mL, 1.6 mmol) was added. The resultant mixture was refluxed for 10 h. After the reaction, toluene (200 mL) was added and the inorganic substance was removed by filtration. The brown solid (6.5 g) obtained by concentrating the filtrate was purified by column chromatography to obtain a white acicular crystal (3.8 g), which was identified as the target Intermediate 14 by the result of mass spectrometric analysis (m/e=332 to the molecular weight of 332). (yield: 68%)

(3) Synthesis of Intermediate 15

Under argon atmosphere, a solution of 2,2,6,6-tetramethylpiperidine (2.9 g, 20.6 mmol) in anhydrous tetrahydrofuran (30 mL) was cooled to −43° C. in a dry ice/acetone bath. After adding 12.5 mL of a n-butyllithium/hexane solution (1.64 mol/L, 20.5 mmol), the solution was stirred at −36° C. for 20 min and then cooled to −70° C. After adding triisopropoxyborane (7 mL, 30 mmol) dropwise and then adding a solution of Intermediate 14 (3.8 g, 10.2 mmol) in tetrahydrofuran (20 mL), the resultant solution was stirred from 10 h in a cooling bath. After the reaction, a 5% by mass hydrochloric acid (100 mL) was added, and the solution was stirred at room temperature for 30 min and then extracted with ethyl acetate (150 mL). The organic layer was washed with a saturated brine (30 mL) and dried over magnesium sulfate. The solvent was evaporated off to obtain a yellow amorphous solid (4.9 g). The obtained solid was purified by column chromatography to obtain a yellow solid (2.9 g), which was identified as the target Intermediate 15 by the result of mass spectrometric analysis (m/e=415 to the molecular weight of 415). (yield: 68%)

(4) Synthesis of Intermediate 16

Under argon atmosphere, into a suspension of 2,6-diiodo-4-tert-butylaniline (1.27 g, 3.2 mmol), Intermediate 15 (2.9 g, 7.0 mmol), tetrakis(triphenylphosphine)palladium (0.36 g, 0.31 mmol), and sodium hydrogen carbonate (2.1 g, 25 mmol) in 1,2-dimethoxyethane (40 mL), water (21 mL) was added and the resultant mixture was refluxed for 11 h. After the reaction, the mixture was extracted with dichloromethane (200 mL), the organic layer was dried over magnesium sulfate, and the solvent was evaporated off to obtain a yellow amorphous solid (3.5 g). The obtained solid was purified by column chromatography to obtain a white solid (2.0 g), which was identified as the target Intermediate 16 by the result of mass spectrometric analysis (m/e=887 to the molecular weight of 887). (yield: 70%)

(5) Synthesis of Compound 17

Under argon atmosphere, a suspension of Intermediate 16 (1.0 g, 1.1 mmol), tris(dibenzylideneacetone) dipalladium (0) (41 mg, 45 μmol), SPhos (5 mg, 0.18 mmol), and cesium carbonate (2.2 g, 6.7 mmol) in anhydrous xylene (100 mL) was refluxed for 10 h. After the reaction, the reaction mixture was filtered, and the residue was washed with water and methanol and then dried under reduced pressure to obtain a pale green solid (0.427 g). The obtained solid was purified by column chromatography to obtain a yellow solid (0.37 g), which was identified as the target Compound 17 by the result of mass spectrometric analysis (m/e=727 to the molecular weight of 727). (yield: 47%)

Synthesis Example 7 (Synthesis of Compound 22)
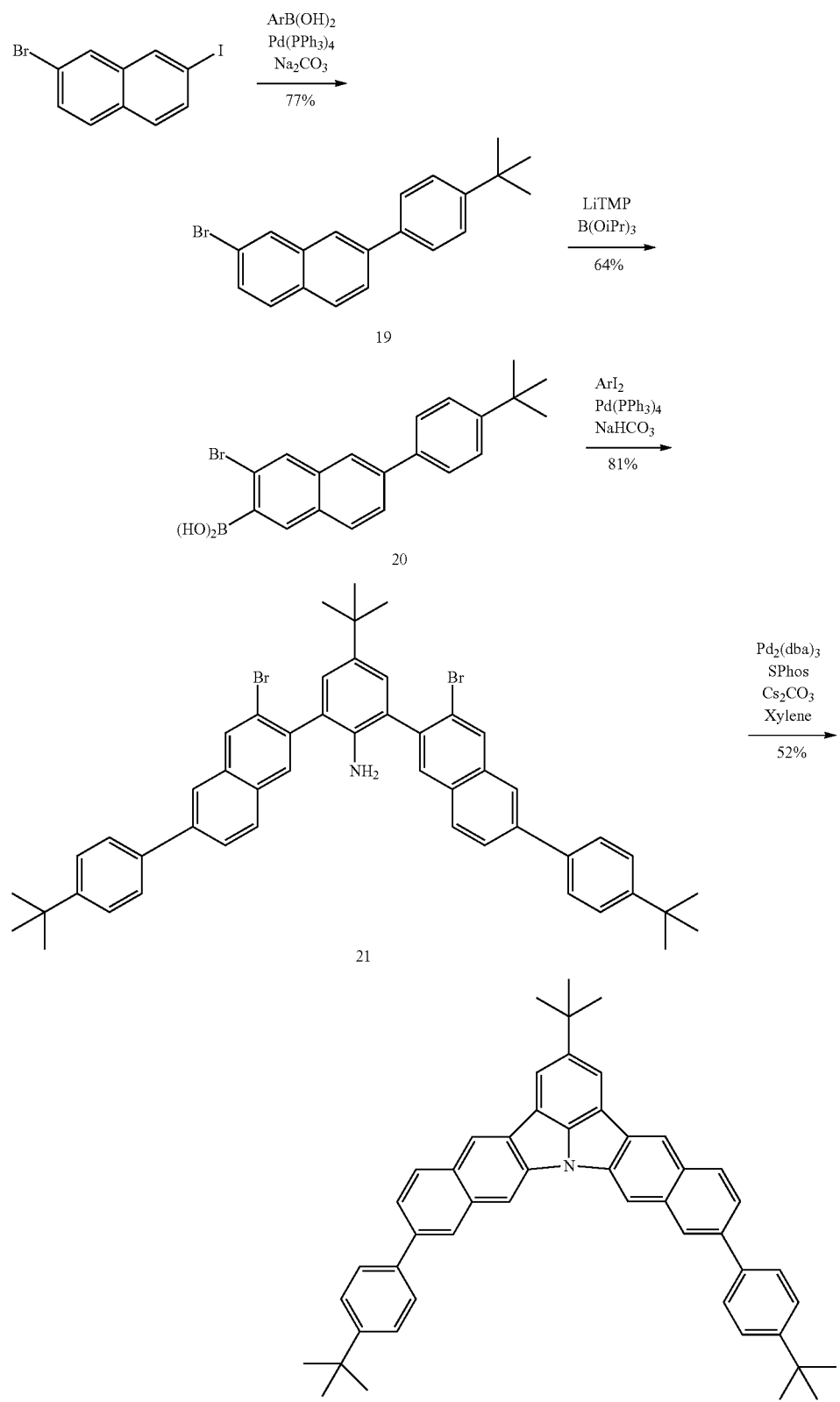

(1) Synthesis of Intermediate 19

Under argon atmosphere, into a solution of 4-tert-butylphenylboronic acid (3.0 g, 17 mmol), 2-bromo-7-iodonaphthalene (5.66 g, 17 mmol), and tetrakis(triphenylphosphine)palladium (0.35 g, 0.30 mmol) in 1,2-dimethoxyethane (45 mL), a 2 M aqueous solution of sodium carbonate (23 mL, 45 mmol) was added and the resultant solution was refluxed for 11 h. After the reaction, the reaction mixture was extracted with toluene (150 mL). The organic layer was washed with a saturated brine (30 mL) and dried over magnesium sulfate. The solvent was evaporated off to obtain a brown solid (9.2 g). The obtained solid was purified by column chromatography to obtain a white solid (4.45 g), which was identified as the target Intermediate 19 by the result of mass spectrometric analysis (m/e=338 to the molecular weight of 338). (yield: 77%)

(2) Synthesis of Intermediate 20

Under argon atmosphere, a solution of 2,2,6,6-tetramethylpiperidine (2.8 g, 20 mmol) in anhydrous tetrahydrofuran (30 mL) was cooled to −40° C. in a dry ice/acetone bath. After adding a 12 mL of a n-butyllithium/hexane solution (1.64 mol/L, 20 mmol), the solution was stirred at −54° C. for 20 min. After the reaction, the solution was cooled to −65° C., triisopropoxyborane (6 mL, 26 mmol) was added dropwise, then a solution of Intermediate 19 (4.45 g, 13 mmol) in tetrahydrofuran (20 mL) was added, and then the solution was stirred for 10 h in a cooling bath. After the reaction, a 5% by mass hydrochloric acid (70 mL) was added. The solution was stirred at room temperature for 30 min and then extracted with ethyl acetate (200 mL). The organic layer was washed with a saturated brine (30 mL) and dried over magnesium sulfate. The solvent was evaporated off to obtain a yellow amorphous solid (5.5 g). The obtained solid was purified by column chromatography to obtain a white solid (3.19 g), which was identified as the target Intermediate 20 by the result of mass spectrometric analysis (m/e=382 to the molecular weight of 382). (yield: 64%)

(3) Synthesis of Intermediate 21

Under argon atmosphere, into a suspension of Intermediate 20 (3.19 g, 8.3 mmol), 2,6-diiodo-4-tert-butylaniline (1.5 g, 3.7 mmol), tetrakis(triphenylphosphine)palladium (0.43 g, 0.37 mmol), and sodium hydrogen carbonate (2.5 g, 30 mmol) in 1,2-dimethoxyethane (50 mL), water (25 mL) was added and the resultant mixture was refluxed for 11 h. The reaction mixture was extracted with dichloromethane (200 mL). The organic layer was dried over magnesium sulfate and the solvent was evaporated off to obtain a yellow amorphous solid (4.14 g). The obtained solid was purified by column chromatography to obtain a white solid (2.47 g), which was identified as the target Intermediate 21 by the result of mass spectrometric analysis (m/e=821 to the molecular weight of 821). (yield: 81%)

(4) Synthesis of Compound 22

Under argon atmosphere, a suspension of Intermediate 21 (2.47 g, 3.0 mmol), tris(dibenzylideneacetone) dipalladium (0) (0.11 g, 0.12 mmol), SPhos (0.20 g, 0.49 mmol), and cesium carbonate (5.9 g, 18 mmol) in anhydrous xylene (250 mL) was refluxed for 11 h. After the reaction, the reaction mixture was filtered. The residue was washed with water and then methanol and dried under reduced pressure to obtain a pale yellow acicular crystal (1.88 g). The obtained crystal was purified by column chromatography to obtain a yellow solid (1.03 g), which was identified as the target Compound 22 by the result of mass spectrometric analysis (m/e=661 to the molecular weight of 661). (yield: 52%)

Synthesis Example 8 (Synthesis of Compound 38)

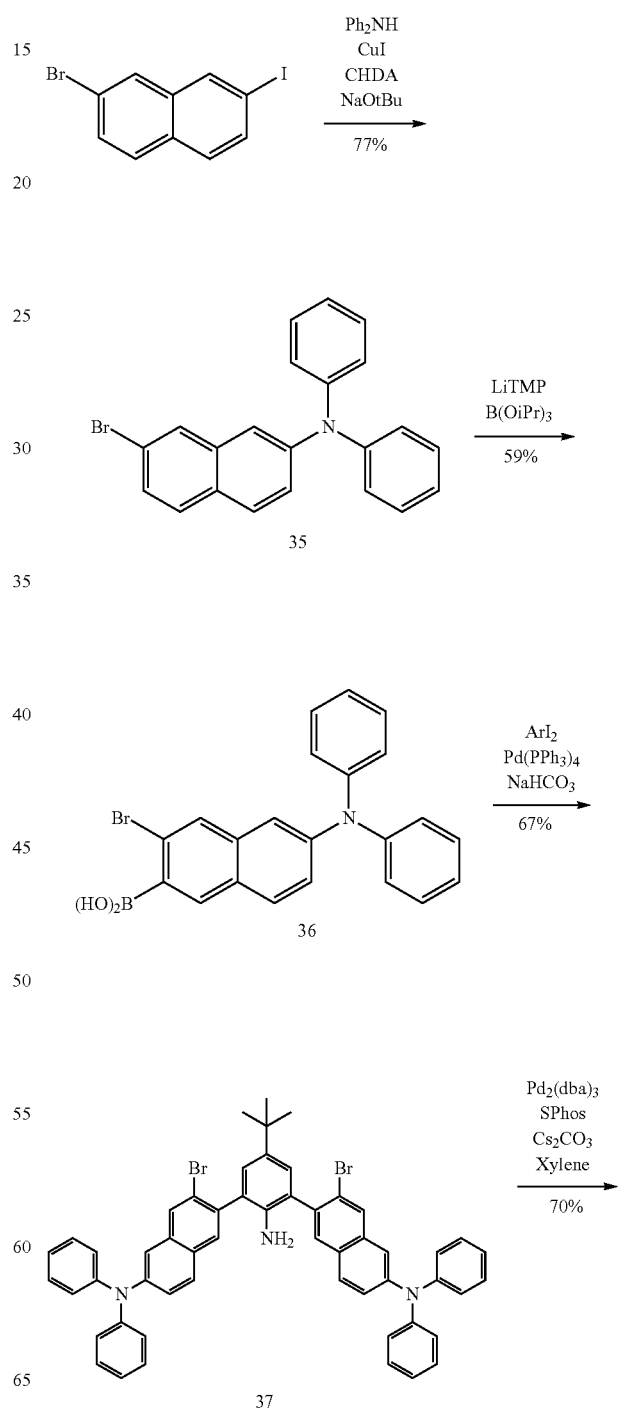

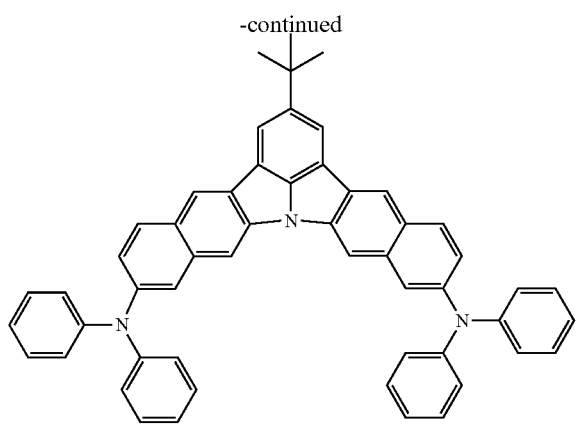

38

(1) Synthesis of Intermediate 35

Under argon atmosphere, into a suspension of 2-bromo-7-iodonaphthalene (2.83 g, 16.7 mmol), diphenylamine (5.57 g, 16.7 mmol), copper iodide (30 mg, 0.16 mmol), and sodium t-butoxide (2.2 g, 23 mmol) in anhydrously, 4-dioxane (20 mL), trans-1,2-diaminocyclohexane (0.19 mL, 1.6 mmol) was added, and the resultant mixture was stirred at 110° C. for 10 h. The reaction mixture was filtered through a silica pad and the residue was washed with toluene (100 mL). The solvent of the filtrate was evaporated off and the residue was dried under reduced pressure to obtain a dark brown oil (6.7 g). The obtained oil was purified by column chromatography to obtain a white solid (4.56 g), which was identified as the target Intermediate 35 by the result of mass spectrometric analysis (m/e=373 to the molecular weight of 373). (yield: 68%)

(2) Synthesis of Intermediate 36

Under argon atmosphere, a solution of 2,2,6,6-tetramethylpiperidine (3.4 g, 24 mmol) in anhydrous tetrahydrofuran (35 mL) was cooled to −30° C. in a dry ice/acetone bath. After adding 14.7 mL of a n-butyllithium/hexane solution (1.64 mol/L, 24 mmol), the solution was stirred at −20° C. for 20 min and then cooled to −75° C. Then, triisopropoxyborane (8.3 mL, 36 mmol) was added dropwise. After 5 min, a solution of Intermediate 35 (4.5 g, 12 mmol) in tetrahydrofuran (20 mL) was added. The resultant solution was stirred for 10 h in a cooling bath. After the reaction, a 5% by mass hydrochloric acid (100 mL) was added and the resultant solution was stirred at room temperature for 30 min and extracted with ethyl acetate (150 mL). The organic layer was washed with a saturated brine (30 mL) and dried over magnesium sulfate. The solvent was evaporated off to obtain a reddish brown amorphous solid (5.8 g). The obtained solid was purified by column chromatography to obtain a pale yellow solid (2.94 g), which was identified as the target Intermediate 36 by the result of mass spectrometric analysis (m/e=417 to the molecular weight of 417). (yield: 59%)

(3) Synthesis of Intermediate 37

Under argon atmosphere, into a suspension of 2,6-diiodo-4-tert-butylaniline (1.28 g, 3.19 mmol), Intermediate 36 (2.94 g, 7.0 mmol), tetrakis(triphenylphosphine)palladium (0.37 g, 0.32 mmol), and sodium hydrogen carbonate (2.1 g, 25 mmol) in 1,2-dimethoxyethane (45 mL), water (22 mL) was added and the resultant mixture was refluxed for 11 h. After the reaction, the reaction mixture was extracted with dichloromethane (150 mL) and the organic layer was dried over magnesium sulfate. The solvent was evaporated off to obtain a yellow amorphous solid (3.8 g). The obtained solid was purified by column chromatography to obtain a yellow solid (1.92 g), which was identified as the target Intermediate 37 by the result of mass spectrometric analysis (m/e=891 to the molecular weight of 891). (yield: 67%)

(4) Synthesis of Compound 38

Under argon atmosphere, a suspension of Intermediate 37 (1.92 g, 2.1 mmol), tris(dibenzylideneacetone) dipalladium (0) (0.14 g, 0.34 mmol), and cesium carbonate (4.1 g, 12.6 mmol) in anhydrous xylene (200 mL) was refluxed for 11 h. After the reaction, the reaction mixture was filtered, the solvent of the filtrate was evaporated off, and the residue was dried under reduced pressure to obtain a yellow solid. The obtained solid was purified by column chromatography to obtain a yellow solid (1.6 g). The obtained solid was recrystallized from toluene (40 mL) to obtain a yellow acicular crystal (1.07 g), which was identified as the target Compound 38 by the result of mass spectrometric analysis (m/e=731 to the molecular weight of 731). (yield: 70%)

Synthesis Example 9 (Synthesis of Compound 41)

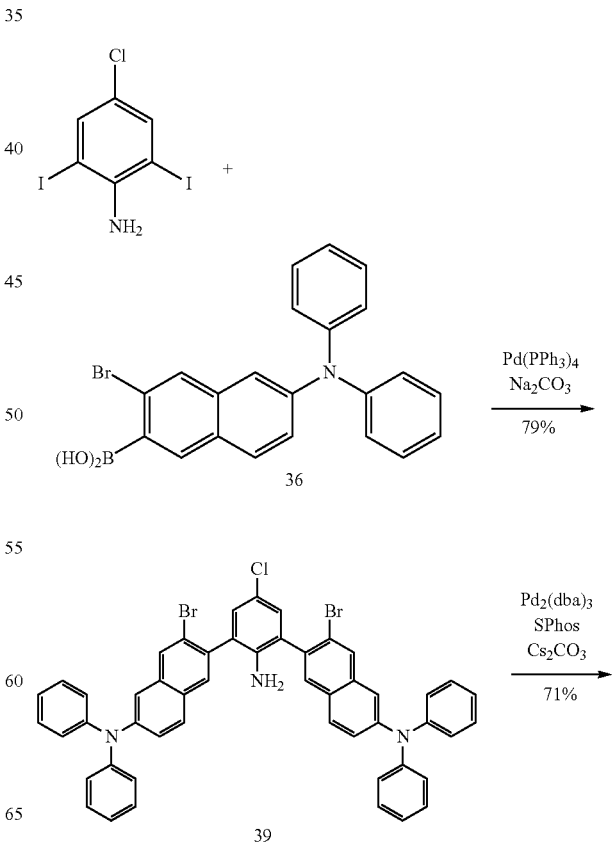

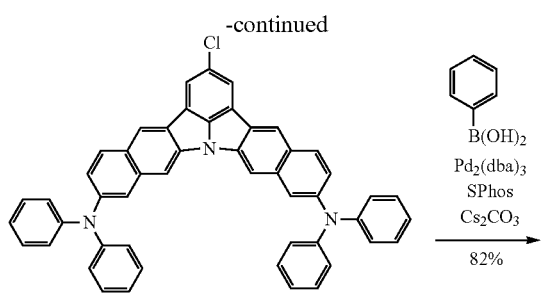

40

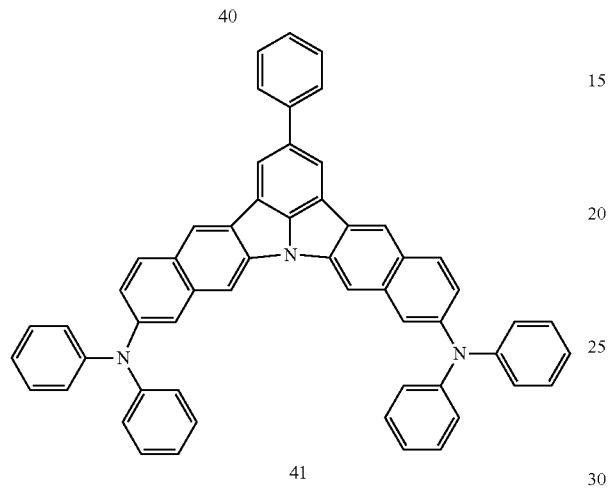

41

(1) Synthesis of Intermediate 39

Under argon atmosphere, into a suspension of Intermediate 36 (9.3 g, 22.4 mmol, 2.2 eq), 4-chloro-2,6-diiodoaniline (3.87 g, 10.2 mmol), Pd(PPh$_3$)$_4$ (0.589 g, 0.510 mmol, 5% Pd), and Na$_2$CO$_3$ (8.00 g, 75 mmol) in 1,2-toluene (230 mL) and dioxane (230 mL), H$_2$O (40 mL) was added and the resultant mixture was refluxed for 13 h. The reaction mixture was diluted with H$_2$O (150 mL) and filtered to remove the solid matter. The filtrate was washed successively with water and methanol and dried under reduced pressure to obtain a yellow solid. The obtained solid was purified by column chromatography to obtain a white solid (7.02 g, 79% yield), which was identified as the target Intermediate 39 by the result of mass spectrometric analysis (m/e=872 to the molecular weight of 872.09).

(2) Synthesis of Intermediate 40

Under argon atmosphere, a suspension of Intermediate 39 (5.62 g, 6.44 mmol), Pd$_2$(dba)$_3$ (0.236 g, 0.258 mmol, 4% Pd), SPhos (0.423 g, 1.03 mmol), and Cs$_2$CO$_3$ (12.6 g, 38.7 mmol, 6 eq) in anhydrous xylene (330 mL) was refluxed for 10 h. The reaction mixture was filtered and the filtrate was washed with water and then methanol and dried under reduced pressure to obtain a dark yellow solid. The obtained solid was purified by column chromatography to obtain a yellow solid (3.25 g, 71% yield), which was identified as the target Intermediate 40 by the result of mass spectrometric analysis (m/e=710 to the molecular weight of 710.26).

(3) Synthesis of Compound 41

Under argon atmosphere, a suspension of Intermediate 40 (0.83 g, 6.44 mmol), phenylboronic acid (1.43 g, 11.7 mmol), Pd$_2$(dba)$_3$ (430 mg, 0.047 mmol, 4% Pd), SPhos (770 mg, 0.187 mmol), and K$_3$PO$_4$ (4.96 g, 23.4 mmol) in anhydrous xylene (60 mL) was refluxed for two days. The reaction mixture was filtered, and the filtrate was washed with water and then methanol and dried under reduced pressure to obtain a dark yellow solid. The obtained solid was purified by column chromatography to obtain a yellow solid (0.72 g, 82% yield), which was identified as the target Compound 41 by the result of mass spectrometric analysis (m/e=751 to the molecular weight of 751.91).

Synthesis Example 10 (Synthesis of Compound 43)

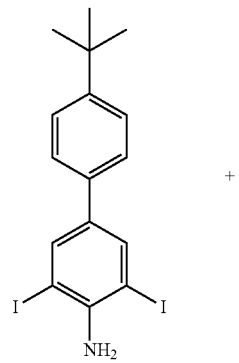

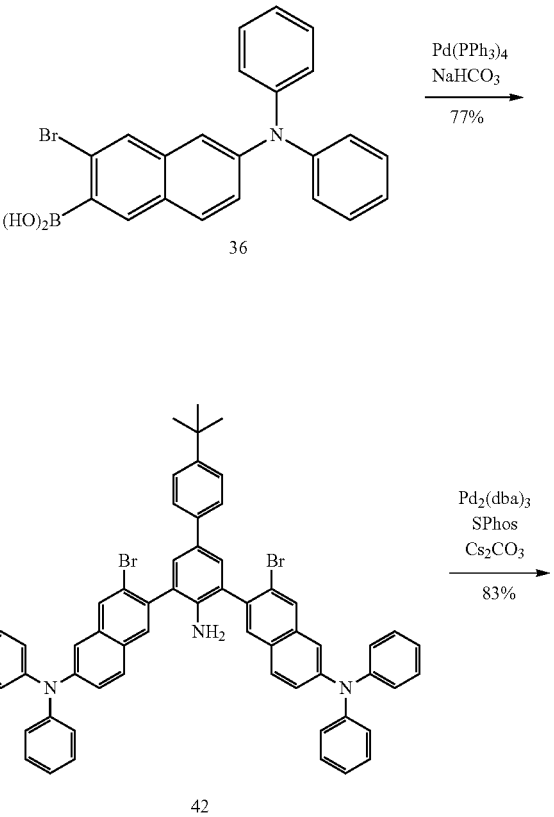

36

42

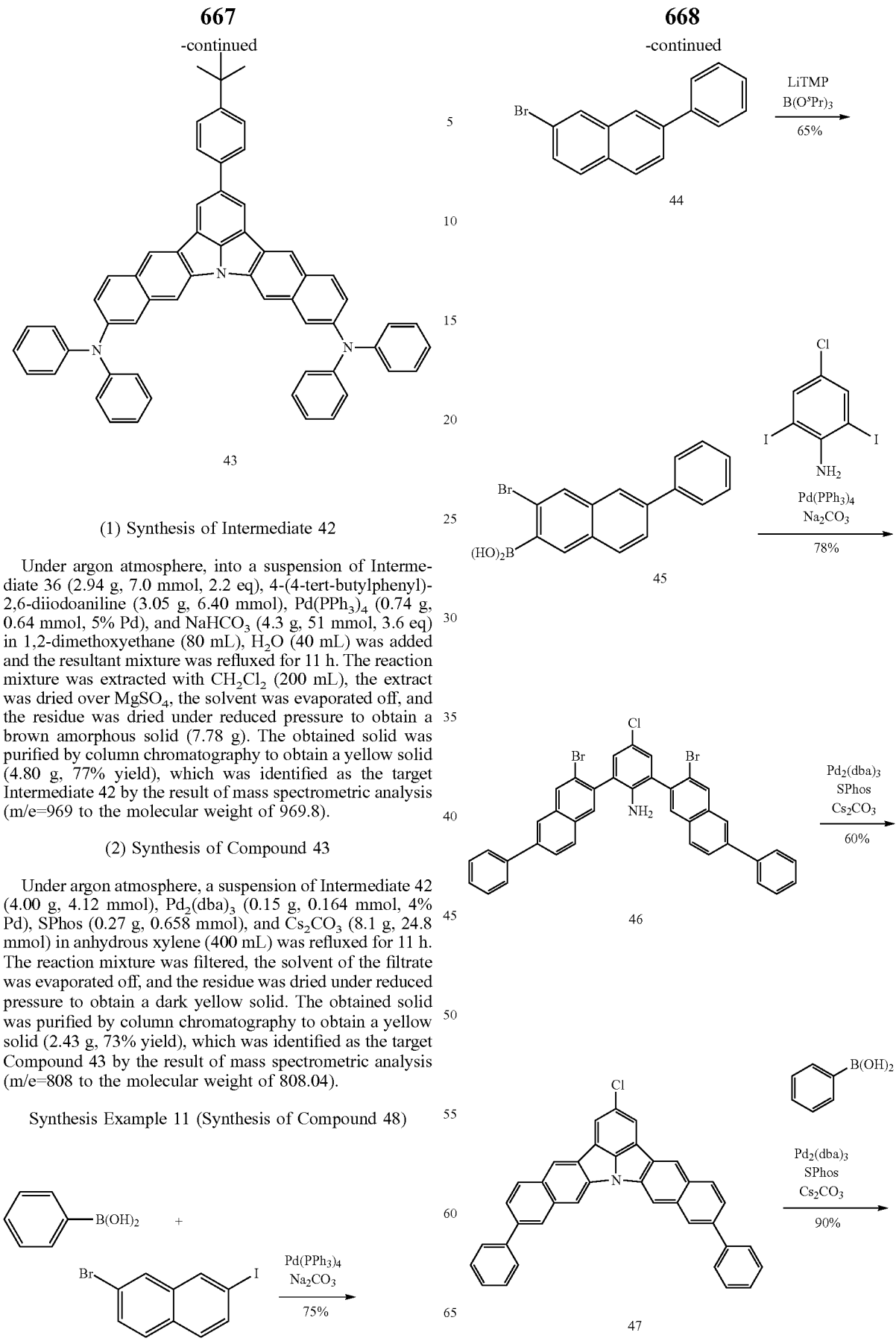

(1) Synthesis of Intermediate 42

Under argon atmosphere, into a suspension of Intermediate 36 (2.94 g, 7.0 mmol, 2.2 eq), 4-(4-tert-butylphenyl)-2,6-diiodoaniline (3.05 g, 6.40 mmol), Pd(PPh$_3$)$_4$ (0.74 g, 0.64 mmol, 5% Pd), and NaHCO$_3$ (4.3 g, 51 mmol, 3.6 eq) in 1,2-dimethoxyethane (80 mL), H$_2$O (40 mL) was added and the resultant mixture was refluxed for 11 h. The reaction mixture was extracted with CH$_2$Cl$_2$ (200 mL), the extract was dried over MgSO$_4$, the solvent was evaporated off, and the residue was dried under reduced pressure to obtain a brown amorphous solid (7.78 g). The obtained solid was purified by column chromatography to obtain a yellow solid (4.80 g, 77% yield), which was identified as the target Intermediate 42 by the result of mass spectrometric analysis (m/e=969 to the molecular weight of 969.8).

(2) Synthesis of Compound 43

Under argon atmosphere, a suspension of Intermediate 42 (4.00 g, 4.12 mmol), Pd$_2$(dba)$_3$ (0.15 g, 0.164 mmol, 4% Pd), SPhos (0.27 g, 0.658 mmol), and Cs$_2$CO$_3$ (8.1 g, 24.8 mmol) in anhydrous xylene (400 mL) was refluxed for 11 h. The reaction mixture was filtered, the solvent of the filtrate was evaporated off, and the residue was dried under reduced pressure to obtain a dark yellow solid. The obtained solid was purified by column chromatography to obtain a yellow solid (2.43 g, 73% yield), which was identified as the target Compound 43 by the result of mass spectrometric analysis (m/e=808 to the molecular weight of 808.04).

Synthesis Example 11 (Synthesis of Compound 48)

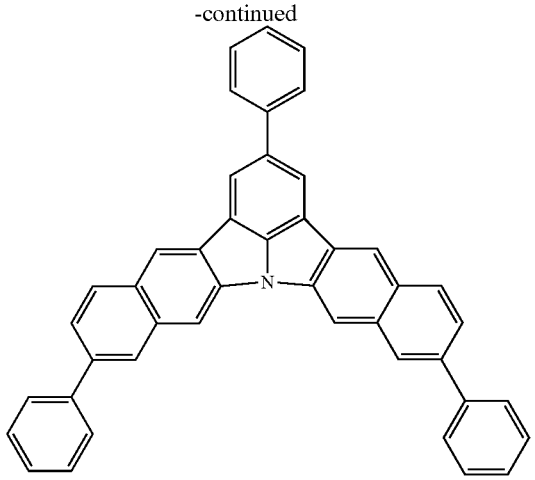

48

(1) Synthesis of Intermediate 44

Under argon atmosphere, into a suspension of phenylboronic acid (6.6 g, 54 mmol), 2-bromo-7-iodonaphthalene (18 g, 54 mmol), Pd(PPh$_3$)$_4$ (1.3 mg, 1.1 mmol), and Na$_2$CO$_3$ (17 g, 160 mmol) in 1,2-dimethoxyethane (160 mL), H$_2$O (80 mL) was added and the resultant mixture was refluxed for 11 h. The reaction mixture was diluted with toluene (200 mL) and filtered to remove the inorganic substance, and the filtrate was concentrated to obtain a brown solid (19.8 g). The obtained solid was purified by column chromatography to obtain a white plate crystal (11.5 g, 75% yield), which was identified as the target Intermediate 44 by the result of mass spectrometric analysis (m/e=283 to the molecular weight of 283.16).

(2) Synthesis of Intermediate 45

Under argon atmosphere, a solution of 2,2,6,6-tetramethylpiperidine (11.5 g, 81.6 mmol, 2 eq) in anhydrous THF (130 mL) was cooled to −50° C. in a dry ice/acetone bath. After adding a n-BuLi/hexane solution (1.55 mol/L, 52.6 mL, 81.5 mmol, 1 eq), the solution was stirred at −50° C. for 30 min and then cooled to −70° C. B(O$^i$Pr)$_3$ (25 mL, 108 mmol, 2.7 eq) was added dropwise and then Intermediate 44/THF (11.5 g, 40.6 mmol/60 mL) was added. The resultant solution was stirred for 10 h in a cooling bath. After adding a 10% HCl (200 mL), the reaction mixture was stirred at room temperature for 30 min and then extracted with ethyl acetate (200 mL). The organic layer was washed with a saturated brine (50 mL) and dried over MgSO$_4$. The solvent was evaporated off to obtain a yellow solid (13.8 g). The obtained solid was purified by column chromatography to obtain a yellow solid (8.67 g, 65% yield), which was identified as the target Intermediate 45 by the result of mass spectrometric analysis (m/e=326 to the molecular weight of 326.98).

(3) Synthesis of Intermediate 46

Under argon atmosphere, into a suspension of 4-chloro-2,6-diiodoaniline (3.70 g, 9.75 mmol), Intermediate 45 (7.02 g, 21.46 mmol, 2.2 eq), and Pd(PPh$_3$)$_4$ (0.564 g, 0.488 mmol) in toluene (240 mL) and 1,4-dioxane (240 mL), a 2 M Na$_2$CO$_3$ aqueous solution (35 mL) was added and the resultant mixture was refluxed for 24 h. After the reaction, the reaction mixture was extracted with CH$_2$Cl$_2$ (200 mL) and the organic layer was dried over MgSO$_4$. The solvent was evaporated off to obtain a yellow amorphous solid. The obtained solid was purified by column chromatography to obtain a pale yellow solid (5.52 g, 78% yield), which was identified as the target Intermediate 46 by the result of mass spectrometric analysis (m/e=689 to the molecular weight of 689.88).

(4) Synthesis of Intermediate 47

Under argon atmosphere, a suspension of Intermediate 46 (5.10 g, 7.39 mmol), Pd$_2$(dba)$_3$ (271 mg, 0.296 mol), SPhos (486 mg, 1.18 mmol), and Cs$_2$CO$_3$ (14.5 g, 44.4 mmol) in anhydrous xylene (600 mL) was refluxed for 24 h. The reaction solution was concentrated and washed with H$_2$O and MeOH to obtain a yellow solid. The obtained solid was dissolved in chlorobenzene and filtered through celite to obtain a yellow solid (2.35 g, 60% yield), which was identified as the target Intermediate 47 by the result of mass spectrometric analysis (m/e=528 to the molecular weight of 528.05).

(5) Synthesis of Compound 48

Under argon atmosphere, a suspension of phenylboronic acid (10.3 g, 84 mmol), Intermediate 47 (2.5 g, 4.73 mmol), Pd$_2$(dba)$_3$ (308 mg, 0.336 mmol), SPhos (552 mg, 1.35 mmol), and K$_3$PO$_4$ (35.7 g, 168 mmol) in xylene (500 mL) was refluxed for 24 h. The reaction mixture was filtered through celite to obtain a yellow solid (2.5 g). The obtained solid was washed by suspending in toluene to obtain a yellow solid (2.44 g, 87% yield), which was identified as the target Compound 48 by the result of mass spectrometric analysis (m/e=569 to the molecular weight of 569.7).

Synthesis Example 12 (Synthesis of Compound 51)

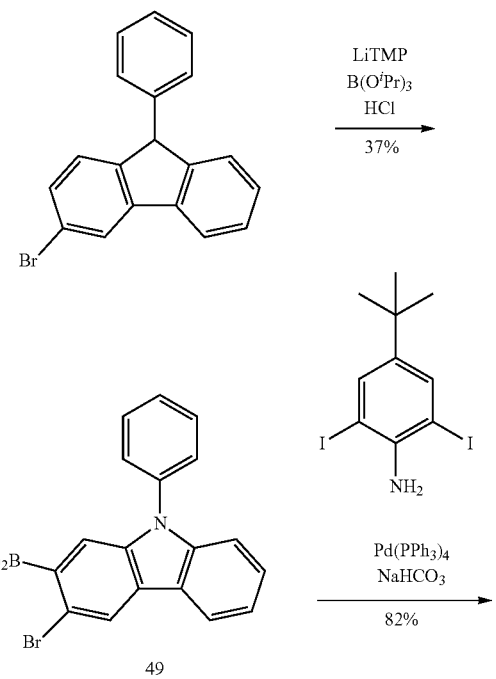

49

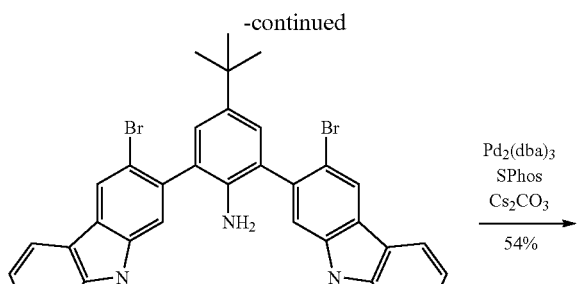

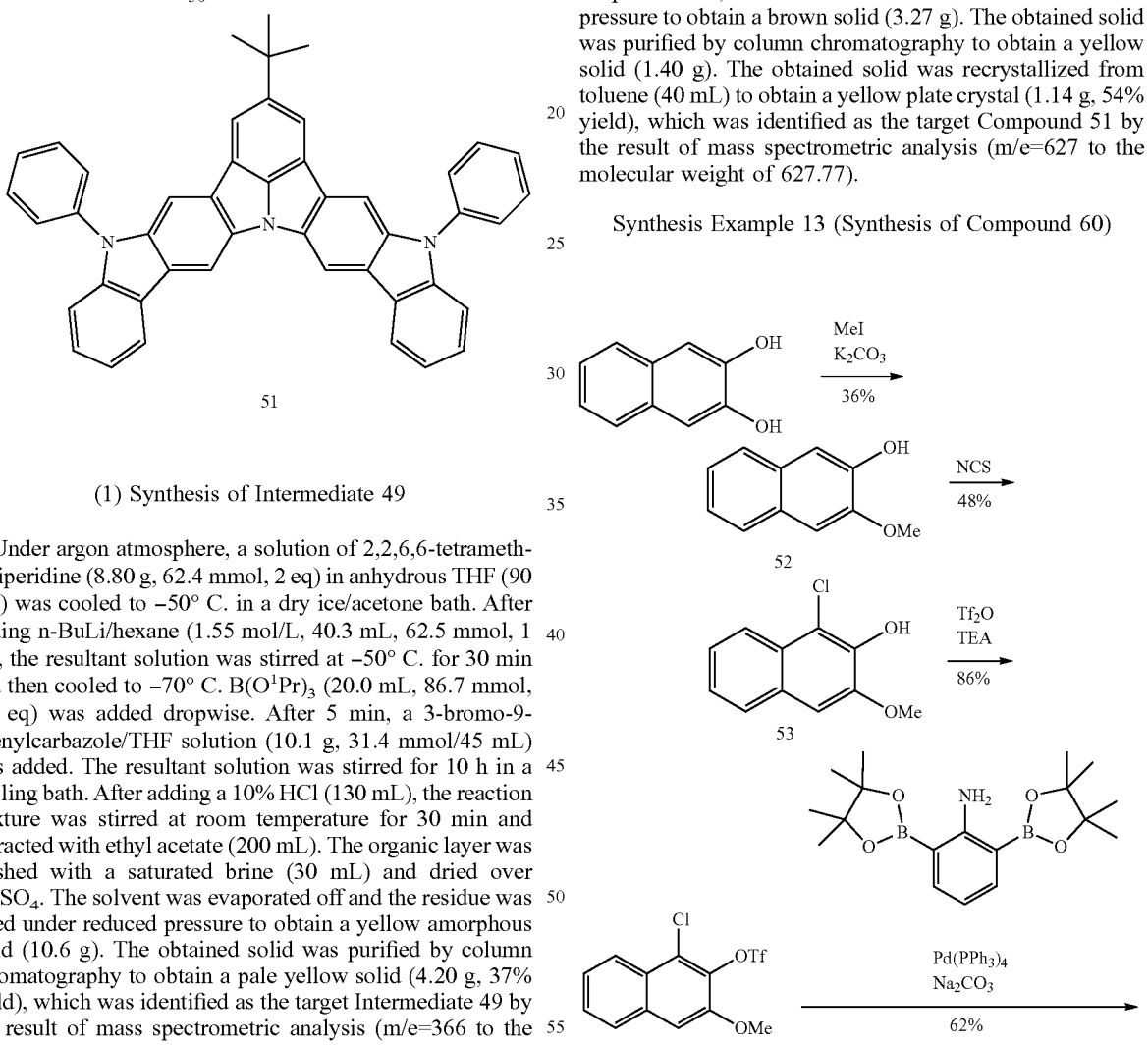

was dried under reduced pressure to obtain a yellow amorphous solid (5.6 g). The obtained solid was purified by column chromatography to obtain a white solid (3.25 g, 82% yield), which was identified as the target Intermediate 50 by the result of mass spectrometric analysis (m/e=789 to the molecular weight of 789.6).

(3) Synthesis of Compound 51

Under argon atmosphere, a suspension of Intermediate 50 (3.25 g, 4.12 mmol), $Pd_2(dba)_3$ (0.15 g, 0.16 mol, 4% Pd), SPhos (0.27 g, 0.66 mmol), and $Cs_2CO_3$ (8.1 g, 24.8 mmol) in anhydrous xylene (320 mL) was refluxed for 11 h. The reaction mixture was filtered, the solvent of the filtrate was evaporated off, and the residue was dried under reduced pressure to obtain a brown solid (3.27 g). The obtained solid was purified by column chromatography to obtain a yellow solid (1.40 g). The obtained solid was recrystallized from toluene (40 mL) to obtain a yellow plate crystal (1.14 g, 54% yield), which was identified as the target Compound 51 by the result of mass spectrometric analysis (m/e=627 to the molecular weight of 627.77).

Synthesis Example 13 (Synthesis of Compound 60)

(1) Synthesis of Intermediate 49

Under argon atmosphere, a solution of 2,2,6,6-tetramethylpiperidine (8.80 g, 62.4 mmol, 2 eq) in anhydrous THF (90 mL) was cooled to −50° C. in a dry ice/acetone bath. After adding n-BuLi/hexane (1.55 mol/L, 40.3 mL, 62.5 mmol, 1 eq), the resultant solution was stirred at −50° C. for 30 min and then cooled to −70° C. $B(O^1Pr)_3$ (20.0 mL, 86.7 mmol, 2.8 eq) was added dropwise. After 5 min, a 3-bromo-9-phenylcarbazole/THF solution (10.1 g, 31.4 mmol/45 mL) was added. The resultant solution was stirred for 10 h in a cooling bath. After adding a 10% HCl (130 mL), the reaction mixture was stirred at room temperature for 30 min and extracted with ethyl acetate (200 mL). The organic layer was washed with a saturated brine (30 mL) and dried over $MgSO_4$. The solvent was evaporated off and the residue was dried under reduced pressure to obtain a yellow amorphous solid (10.6 g). The obtained solid was purified by column chromatography to obtain a pale yellow solid (4.20 g, 37% yield), which was identified as the target Intermediate 49 by the result of mass spectrometric analysis (m/e=366 to the molecular weight of 366.02).

(2) Synthesis of Intermediate 50

Under argon atmosphere, into a suspension of Intermediate 49 (4.20 g, 11.5 mmol, 2.3 eq), 4-(tert-butyl)-2,6-diiodoaniline (2.00 g, 4.99 mmol), $Pd(PPh_3)_4$ (0.58 g, 0.50 mmol, 5% Pd), and $NaHCO_3$ (3.5 g, 3.6 eq) in 1,2-dimethoxyethane (70 mL), $H_2O$ (35 mL) was added and the resultant mixture was refluxed for 11 h. The reaction mixture was extracted with $CH_2Cl_2$ (250 mL), the extract was dried over $MgSO_4$, the solvent was evaporated off, and the residue

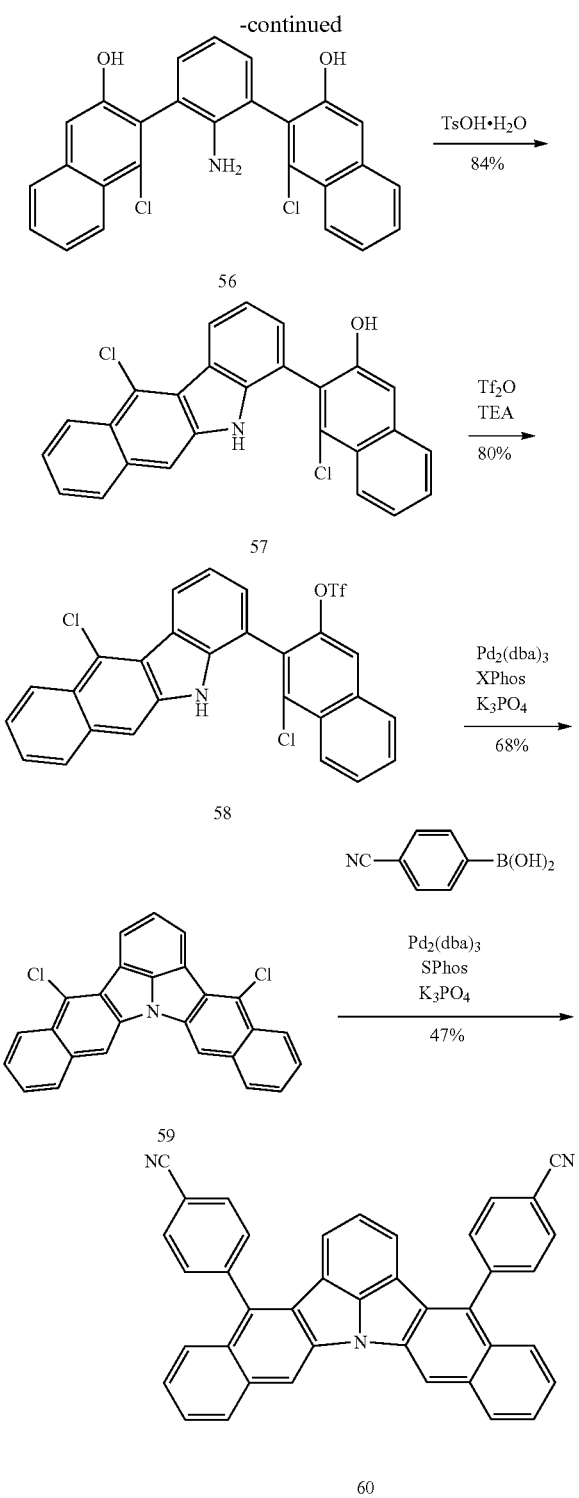

reaction mixture was extracted with ethyl acetate. The organic layer was concentrated to obtain a black oil (904 g). The obtained oil was purified by column chromatography and then washed with heptane to obtain a white solid (184 g, 36% yield), which was identified as the target Intermediate 52 by the result of mass spectrometric analysis (m/e=174 to the molecular weight of 174.2).

(2) Synthesis of Intermediate 53

Under argon atmosphere, into a solution of Intermediate 52 (174 g, 1 mol) in acetonitrile (1.7 L), p-toluenesulfonic acid monohydrate (190 g, 1 mol) was added. After adding N-chlorosuccinimide (133 g, 1 mol), the resultant solution was stirred at room temperature for 12 h. After the reaction, $H_2O$ was added ant the reaction mixture was extracted with ethyl acetate. The organic layer was concentrated to obtain an orange oil (904 g). The obtained oil was purified by column chromatography and then washed with heptane and toluene to obtain a white solid (99 g, 48% yield), which was identified as the target Intermediate 53 by the result of mass spectrometric analysis (m/e=208 to the molecular weight of 208.6).

(3) Synthesis of Intermediate 54

Under argon atmosphere, into a solution of Intermediate 53 (99 g, 474 mmol) in chloroform (940 mL), triethylamine (79 mL, 569 mmol) was added and the resultant solution was cooled to 0° C. After adding anhydrous triflate (147 g, 522 mmol) dropwise while maintaining the temperature at 0° C., the solution was stirred at room temperature for 3 h. After the reaction, the solvent was evaporated off and the residue was dried under reduced pressure to obtain a red oil (173 g). The obtained oil was purified by column chromatography to obtain a white solid (139 g, 86% yield), which was identified as the target Intermediate 54 by the result of mass spectrometric analysis (m/e=340 to the molecular weight of 340.7).

(4) Synthesis of Intermediate 55

Under argon atmosphere, into a suspension of Intermediate 54 (135 g, 396 mmol, 2.2 eq), boronic acid XX (65 g, 188 mmol), $Pd(PPh_3)_4$ (10.9 g, 9.42 mmol, 5% Pd), and $Na_2CO_3$ (79.9 g, 4 eq) in 1,2-dimethoxyethane (2 L), $H_2O$ (380 mL) was added and the resultant mixture was stirred at 78° C. for three days. The reaction mixture was extracted with toluene, the extract was dried over $MgSO_4$, the solvent was evaporated off, and the residue was dried under reduced pressure to obtain a black oil. The obtained oil was purified by column chromatography to obtain a white solid (56 g, 62% yield), which was identified as the target Intermediate 55 by the result of mass spectrometric analysis (m/e=474 to the molecular weight of 474.3).

(5) Synthesis of Intermediate 56

Under argon atmosphere, a solution of Intermediate 55 (99 g, 474 mmol) in dichloromethane (940 mL) was cooled to 0° C. After adding $BBr_3$ (147 g, 522 mmol) dropwise while maintaining the temperature at 0° C., the solution was stirred at room temperature for 12 h. After the reaction, $H_2O$ was added dropwise, and the precipitated solid was collected by filtration and washed by suspending in ethyl acetate to obtain a white solid (63 g, 81% yield), which was identified (1) Synthesis of Intermediate 52

Under argon atmosphere, a suspension of 2,3-naphthalenediol (475 g, 2.97 mol) and $K_2CO_3$ (410 g, 2.97 mol) in DMF (3 L) was stirred at 100° C. for 3 h. After cooled by standing, MeI (421 g, 2.97 mol) was added dropwise under stirring and the resultant mixture was stirred at room temperature for 12 h. After the reaction, $H_2O$ was added and the as the target Intermediate 56 by the result of mass spectrometric analysis (m/e=446 to the molecular weight of 446.3).

(6) Synthesis of Intermediate 57

Under argon atmosphere, a solution of Intermediate 56 (62 g, 139 mmol) and p-toluenesulfonic acid monohydrate (2.64 g, 13.9 mmol) in xylene (1.2 L) was stirred at 140° C. for 2 h. After the reaction, the reaction mixture was purified by column chromatography to obtain a white solid (50 g, 84% yield), which was identified as the target Intermediate 57 by the result of mass spectrometric analysis (m/e=428 to the molecular weight of 428.3).

(7) Synthesis of Intermediate 58

Under argon atmosphere, into a solution of Intermediate 57 (48 g, 112 mmol) in chloroform (500 mL), triethylamine (23.4 mL, 168 mmol) was added and the resultant solution was cooled to 0° C. After adding anhydrous triflate (33 g, 157 mmol) dropwise while maintaining the temperature at 0° C., the solution was stirred at room temperature for 12 h. After the reaction, the reaction mixture was purified by column chromatography to obtain a white solid (50 g, 80% yield), which was identified as the target Intermediate 58 by the result of mass spectrometric analysis (m/e=560 to the molecular weight of 560.3).

(8) Synthesis of Intermediate 59

Under argon atmosphere, a suspension of Intermediate 58 (40.0 g, 71.4 mmol), $Pd_2(dba)_3$ (3.92 g, 4.28 mmol, 6% Pd), XPhos (4.08 g, 8.57 mmol), and $K_3PO_4$ (45.5 g, 214 mmol) in anhydrous xylene (860 mL) was refluxed for 4 h. After cooled by standing, the precipitated solid was collected by filtration. The obtained solid was purified by silica gel column chromatography and then washed under heating by suspending in xylene to obtain a yellow solid (20 g, 68% yield), which was identified as the target Intermediate 59 by the result of mass spectrometric analysis (m/e=410 to the molecular weight of 410.3).

(9) Synthesis of Compound 60

Under argon atmosphere, a suspension of 4-cyanophenyl-boronic acid (6.45 g, 43.9 mmol), Intermediate 59 (3.00 g, 7.31 mmol), $Pd_2(dba)_3$ (536 mg, 0.585 mmol), SPhos (961 mg, 2.34 mmol), and $K_3PO_4$ (31 g, 146 mmol) in DMF (360 mL) was stirred at 100° C. for 3.5 h. After the reaction, the solvent was evaporated off and the residue was purified by silica gel column chromatography to obtain a yellow solid (1.86 g, 47% yield), which was identified as the target Compound 60 by the result of mass spectrometric analysis (m/e=543 to the molecular weight of 543.6).

Production of Organic EL Device

Organic EL devices were produced in the manner shown below and evaluated.

Example 1

A glass substrate of 25 mm×75 mm×1.1 mm thick having an ITO transparent electrode (anode) (product of Geomatec Company) was cleaned by ultrasonic cleaning in isopropyl alcohol for 5 min and then UV-ozone cleaning for 30 min. The thickness of ITO film was 130 nm.

The cleaned glass substrate was mounted to a substrate holder of a vacuum vapor deposition apparatus. Compound HI-1 was vapor-deposited on the surface having the transparent electrode line so as to cover the transparent electrode to form a hole injecting layer with a thickness of 5 nm.

On the hole injecting layer, Compound HT-1 was vapor-deposited to form a first hole transporting layer with a thickness of 80 nm.

Then, Compound HT-2 was vapor-deposited on the first hole transporting layer to form a second hole transporting layer with a thickness of 10 nm.

Successively thereafter, Compound BH-1 and Compound 2 (dopant material) obtained in Synthesis Example 1 were vapor co-deposited on the second hole transporting layer to form a light emitting layer with a thickness of 25 nm. The concentration of Compound 2 (dopant material) in the light emitting layer was 4% by mass.

Successively thereafter, Compound ET-1 was vapor-deposited on the light emitting layer to form a first electron transporting layer with a thickness of 10 nm.

Successively thereafter, Compound ET-2 was vapor-deposited on the first electron transporting layer to form a second electron transporting layer with a thickness of 15 nm.

Further, lithium fluoride (LiF) was vapor-deposited on the second electron transporting layer to form an electron injecting electrode with a thickness of 1 nm.

Then, metallic aluminum (Al) was vapor-deposited on the electron injecting electrode to form a metal cathode with a thickness of 80 nm.

The structure of the organic EL device of Example 1 is shown below. ITO (130)/HI-1 (5)/HT-1 (80)/HT-2 (10)/BH-1:Compound 2 (25:4% by mass)/ET-1 (10)/ET-2 (15)/LiF (1)/Al (80)

Each numeral in parenthesis is the thickness of each layer (unit of measure: nm).

Compound 2

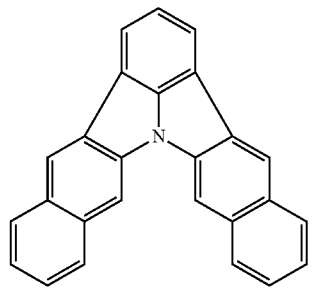

Compound 5

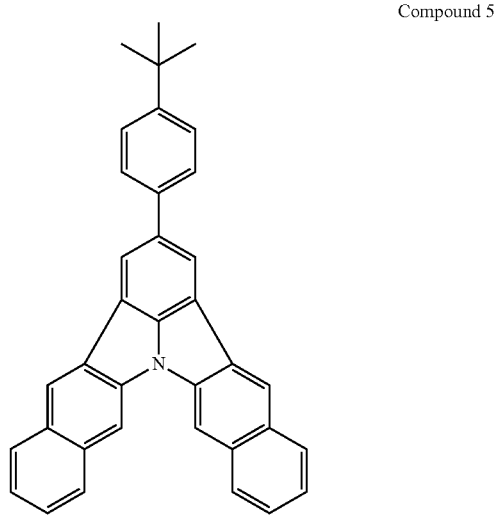

HI-1
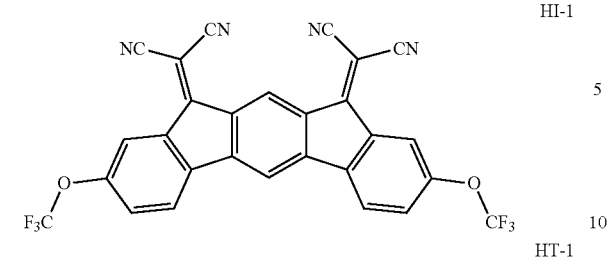
HT-1
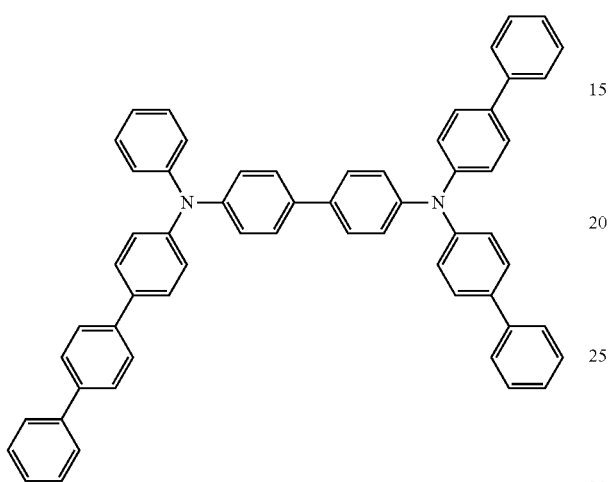
HT-2
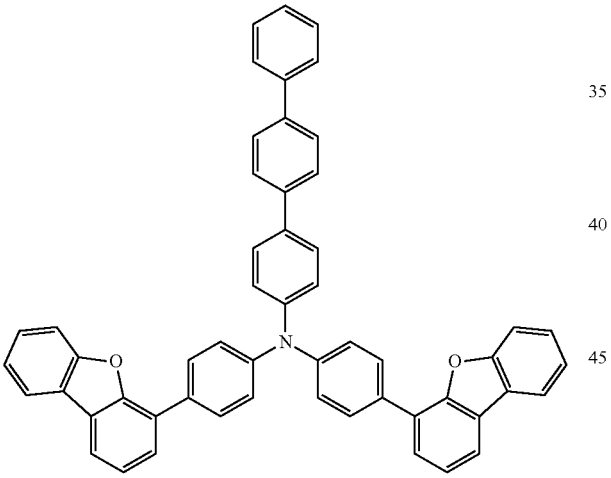
ET-1
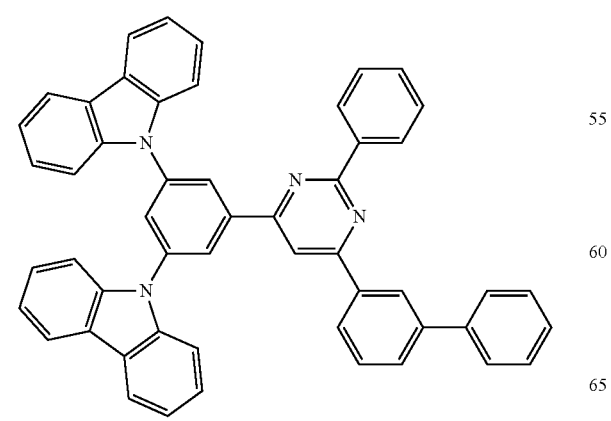
ET-2
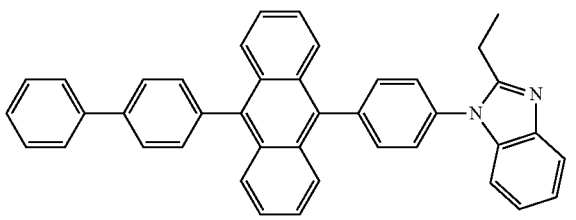
BH-1
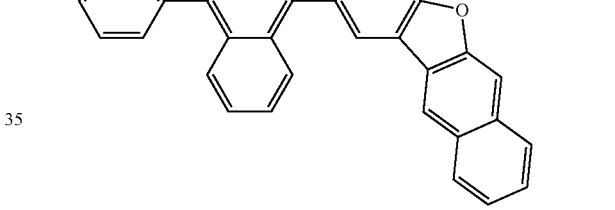
BH-2
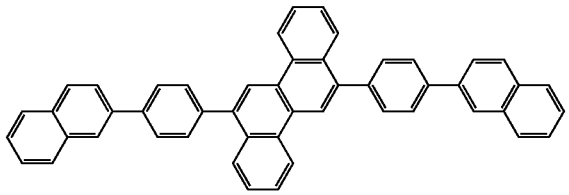
BH-3
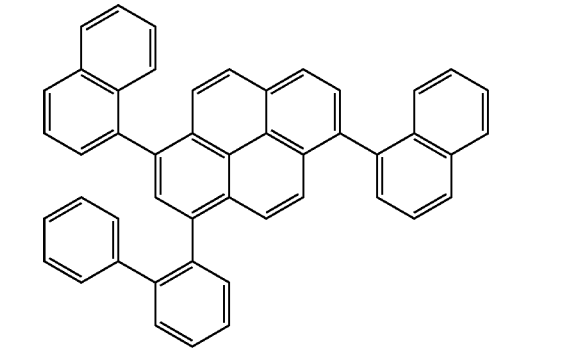
BH-4

BH-5
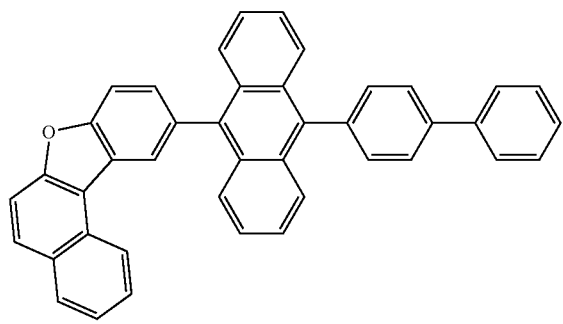
BH-6
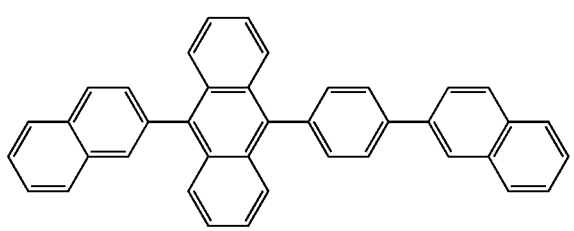
BH-7
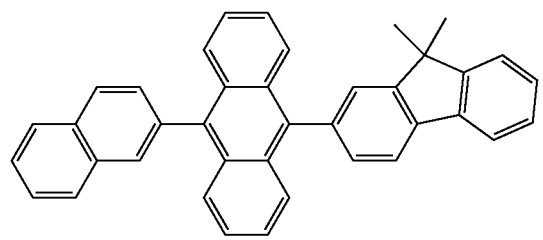
BH-8
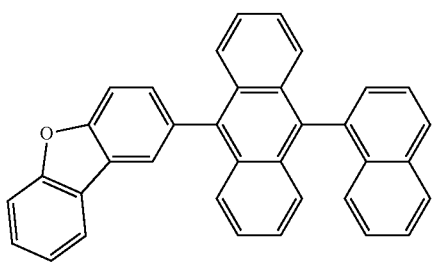
BH-9
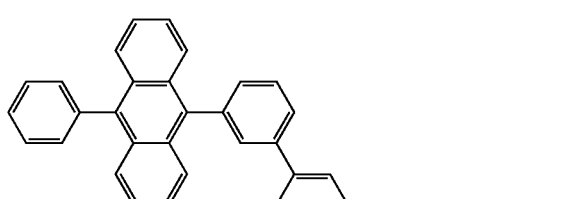
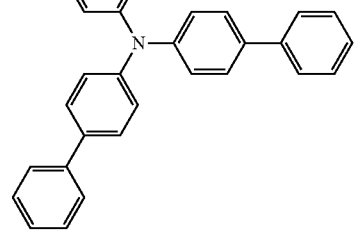
BH-10
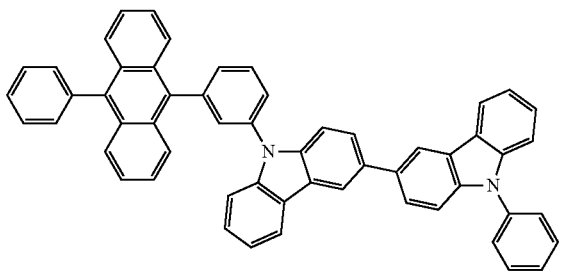
BH-11
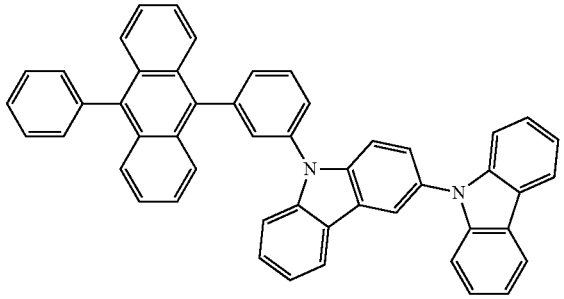
BH-12
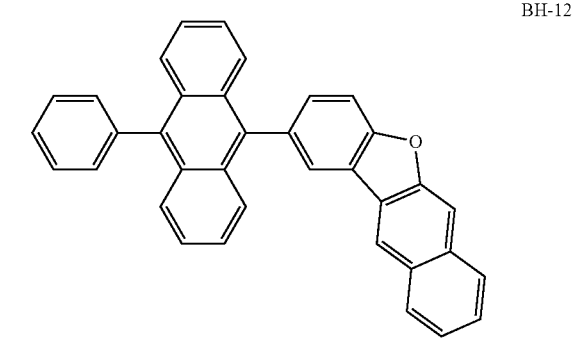
BH-13
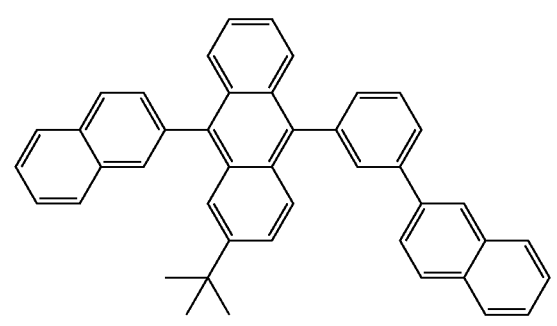
BH-14

BH-15

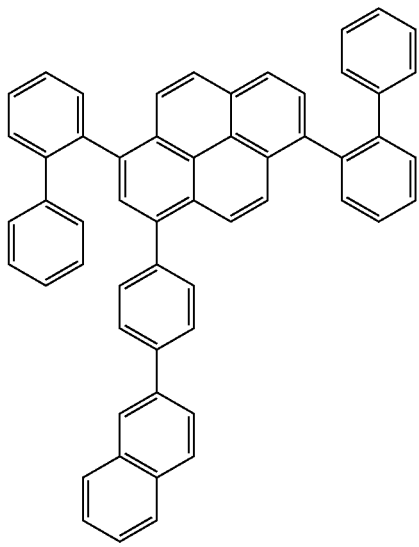

BH-16

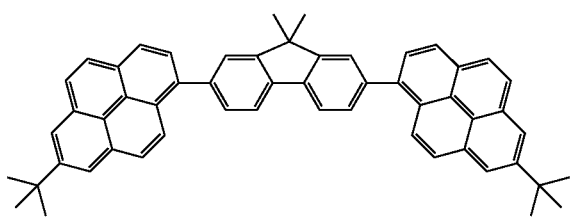

Example 2

An organic EL device was produced in the same manner as in Example 1 except for using Compound 5 obtained in Synthesis Example 2 in the light emitting layer in place of Compound 2 (dopant material).

The structure of the organic EL device of Example 2 is shown below. ITO (130)/HI-1 (5)/HT-1 (80)/HT-2 (10)/BH-1:Compound 5 (25: 4% by mass)/ET-1 (10)/ET-2 (15)/LiF (1)/Al (80)

Example 3

An organic EL device was produced in the same manner as in Example 1 except for using BH-2 in the light emitting layer in place of BH-1 (host material).

The structure of the organic EL device of Example 3 is shown below. ITO (130)/HI-1 (5)/HT-1 (80)/HT-2 (10)/BH-2:Compound 2 (25: 4% by mass)/ET-1 (10)/ET-2 (15)/LiF (1)/Al (80)

Example 4

An organic EL device was produced in the same manner as in Example 2 except for using BH-2 in the light emitting layer in place of BH-1 (host material).

The structure of the organic EL device of Example 4 is shown below. ITO (130)/HI-1 (5)/HT-1 (80)/HT-2 (10)/BH-2:Compound 5 (25: 4% by mass)/ET-1 (10)/ET-2 (15)/LiF (1)/Al (80)

Example 5

An organic EL device was produced in the same manner as in Example 1 except for using BH-3 in the light emitting layer in place of BH-1 (host material).

The structure of the organic EL device of Example 5 is shown below. ITO (130)/HI-1 (5)/HT-1 (80)/HT-2 (10)/BH-3:Compound 2 (25: 4% by mass)/ET-1 (10)/ET-2 (15)/LiF (1)/Al (80)

Example 6

An organic EL device was produced in the same manner as in Example 2 except for using BH-3 in the light emitting layer in place of BH-1 (host material).

The structure of the organic EL device of Example 6 is shown below. ITO (130)/HI-1 (5)/HT-1 (80)/HT-2 (10)/BH-3:Compound 5 (25: 4% by mass)/ET-1 (10)/ET-2 (15)/LiF (1)/Al (80)

Example 7

An organic EL device was produced in the same manner as in Example 1 except for using BH-4 in the light emitting layer in place of BH-1 (host material).

The structure of the organic EL device of Example 7 is shown below. ITO (130)/HI-1 (5)/HT-1 (80)/HT-2 (10)/BH-4:Compound 2 (25: 4% by mass)/ET-1 (10)/ET-2 (15)/LiF (1)/Al (80)

Example 8

An organic EL device was produced in the same manner as in Example 2 except for changing the concentration of Compound 2 (dopant material) in the light emitting layer from 4% by mass to 2% by mass.

The structure of the organic EL device of Example 8 is shown below. ITO (130)/HI-1 (5)/HT-1 (80)/HT-2 (10)/BH-1:Compound 5 (25: 2% by mass)/ET-1 (10)/ET-2 (15)/LiF (1)/Al (80)

Example 9

An organic EL device was produced in the same manner as in Example 8 except for using BH-2 in the light emitting layer in place of BH-1 (host material).

The structure of the organic EL device of Example 9 is shown below. ITO (130)/HI-1 (5)/HT-1 (80)/HT-2 (10)/BH-2:Compound 5 (25: 2% by mass)/ET-1 (10)/ET-2 (15)/LiF (1)/Al (80)

Example 10

An organic EL device was produced in the same manner as in Example 8 except for using BH-5 in the light emitting layer in place of BH-1 (host material).

The structure of the organic EL device of Example 10 is shown below. ITO (130)/HI-1 (5)/HT-1 (80)/HT-2 (10)/BH-5:Compound 5 (25: 2% by mass)/ET-1 (10)/ET-2 (15)/LiF (1)/Al (80)

Example 11

An organic EL device was produced in the same manner as in Example 8 except for using BH-6 in the light emitting layer in place of BH-1 (host material).

The structure of the organic EL device of Example 11 is shown below. ITO (130)/HI-1 (5)/HT-1 (80)/HT-2 (10)/BH-6:Compound 5 (25: 2% by mass)/ET-1 (10)/ET-2 (15)/LiF (1)/Al (80)

Example 12

An organic EL device was produced in the same manner as in Example 8 except for using BH-7 in the light emitting layer in place of BH-1 (host material).
The structure of the organic EL device of Example 12 is shown below. ITO (130)/HI-1 (5)/HT-1 (80)/HT-2 (10)/BH-7:Compound 5 (25: 2% by mass)/ET-1 (10)/ET-2 (15)/LiF (1)/Al (80)

Example 13

An organic EL device was produced in the same manner as in Example 8 except for using BH-8 in the light emitting layer in place of BH-1 (host material).
The structure of the organic EL device of Example 13 is shown below. ITO (130)/HI-1 (5)/HT-1 (80)/HT-2 (10)/BH-8:Compound 5 (25: 2% by mass)/ET-1 (10)/ET-2 (15)/LiF (1)/Al (80)

Example 14

An organic EL device was produced in the same manner as in Example 8 except for using BH-9 in the light emitting layer in place of BH-1 (host material).
The structure of the organic EL device of Example 14 is shown below. ITO (130)/HI-1 (5)/HT-1 (80)/HT-2 (10)/BH-9:Compound 5 (25: 2% by mass)/ET-1 (10)/ET-2 (15)/LiF (1)/Al (80)

Example 15

An organic EL device was produced in the same manner as in Example 8 except for using BH-10 in the light emitting layer in place of BH-1 (host material).
The structure of the organic EL device of Example 15 is shown below. ITO (130)/HI-1 (5)/HT-1 (80)/HT-2 (10)/BH-10:Compound 5 (25: 2% by mass)/ET-1 (10)/ET-2 (15)/LiF (1)/Al (80)

Example 16

An organic EL device was produced in the same manner as in Example 8 except for using BH-11 in the light emitting layer in place of BH-1 (host material).
The structure of the organic EL device of Example 16 is shown below. ITO (130)/HI-1 (5)/HT-1 (80)/HT-2 (10)/BH-1:Compound 5 (25: 2% by mass)/ET-1 (10)/ET-2 (15)/LiF (1)/Al (80)

Example 17

An organic EL device was produced in the same manner as in Example 8 except for using BH-12 in the light emitting layer in place of BH-1 (host material).
The structure of the organic EL device of Example 17 is shown below. ITO (130)/HI-1 (5)/HT-1 (80)/HT-2 (10)/BH-12:Compound 5 (25: 2% by mass)/ET-1 (10)/ET-2 (15)/LiF (1)/Al (80)

Example 18

An organic EL device was produced in the same manner as in Example 8 except for using BH-13 in the light emitting layer in place of BH-1 (host material).
The structure of the organic EL device of Example 18 is shown below. ITO (130)/HI-1 (5)/HT-1 (80)/HT-2 (10)/BH-13:Compound 5 (25: 2% by mass)/ET-1 (10)/ET-2 (15)/LiF (1)/Al (80)

Example 19

An organic EL device was produced in the same manner as in Example 8 except for using BH-14 in the light emitting layer in place of BH-1 (host material).
The structure of the organic EL device of Example 19 is shown below. ITO (130)/HI-1 (5)/HT-1 (80)/HT-2 (10)/BH-14:Compound 5 (25: 2% by mass)/ET-1 (10)/ET-2 (15)/LiF (1)/Al (80)

Example 20

An organic EL device was produced in the same manner as in Example 8 except for using BH-15 in the light emitting layer in place of BH-1 (host material).
The structure of the organic EL device of Example 20 is shown below. ITO (130)/HI-1 (5)/HT-1 (80)/HT-2 (10)/BH-15:Compound 5 (25: 2% by mass)/ET-1 (10)/ET-2 (15)/LiF (1)/Al (80)

Example 21

An organic EL device was produced in the same manner as in Example 8 except for using BH-16 in the light emitting layer in place of BH-1 (host material).
The structure of the organic EL device of Example 21 is shown below. ITO (130)/HI-1 (5)/HT-1 (80)/HT-2 (10)/BH-16:Compound 5 (25: 2% by mass)/ET-1 (10)/ET-2 (15)/LiF (1)/Al (80)

Example 22

An organic EL device was produced in the same manner as in Example 1 except for using, in place of Compound 2 (dopant material), Compound 7 obtained in Synthesis Example 3 in the light emitting layer in a concentration of 2% by mass.
The structure of the organic EL device of Example 22 is shown below. ITO (130)/HI-1 (5)/HT-1 (80)/HT-2 (10)/BH-1:Compound 7 (25: 2% by mass)/ET-1 (10)/ET-2 (15)/LiF (1)/Al (80)

Example 23

An organic EL device was produced in the same manner as in Example 1 except for using, in place of Compound 2 (dopant material), Compound 9 obtained in Synthesis Example 4 in the light emitting layer in a concentration of 2% by mass.
The structure of the organic EL device of Example 23 is shown below. ITO (130)/HI-1 (5)/HT-1 (80)/HT-2 (10)/BH-1:Compound 9 (25: 2% by mass)/ET-1 (10)/ET-2 (15)/LiF (1)/Al (80)

Example 24

An organic EL device was produced in the same manner as in Example 1 except for using, in place of Compound 2 (dopant material), Compound 11 obtained in Synthesis Example 5 in the light emitting layer in a concentration of 2% by mass.

The structure of the organic EL device of Example 24 is shown below. ITO (130)/HI-1 (5)/HT-1 (80)/HT-2 (10)/BH-1:Compound 11 (25: 2% by mass)/ET-1 (10)/ET-2 (15)/LiF (1)/Al (80)

Example 25

An organic EL device was produced in the same manner as in Example 1 except for using, in place of Compound 2 (dopant material), Compound 17 obtained in Synthesis Example 6 in the light emitting layer in a concentration of 2% by mass.

The structure of the organic EL device of Example 25 is shown below. ITO (130)/HI-1 (5)/HT-1 (80)/HT-2 (10)/BH-1:Compound 17 (25: 2% by mass)/ET-1 (10)/ET-2 (15)/LiF (1)/Al (80)

Example 26

An organic EL device was produced in the same manner as in Example 1 except for using, in place of Compound 2 (dopant material), Compound 22 obtained in Synthesis Example 7 in the light emitting layer in a concentration of 2% by mass.

The structure of the organic EL device of Example 26 is shown below. ITO (130)/HI-1 (5)/HT-1 (80)/HT-2 (10)/BH-1:Compound 22 (25: 2% by mass)/ET-1 (10)/ET-2 (15)/LiF (1)/Al (80)

Example 27

An organic EL device was produced in the same manner as in Example 1 except for using, in place of Compound 2 (dopant material), Compound 38 (dopant material) obtained in Synthesis Example 8 in the light emitting layer in a concentration of 2% by mass.

The structure of the organic EL device of Example 27 is shown below. ITO (130)/HI-1 (5)/HT-1 (80)/HT-2 (10)/BH-1:Compound 38 (25: 2% by mass)/ET-1 (10)/ET-2 (15)/LiF (1)/Al (80)

Example 28

An organic EL device was produced in the same manner as in Example 1 except for using, in place of Compound 2 (dopant material), Compound 41 (dopant material) obtained in Synthesis Example 9 in the light emitting layer in a concentration of 2% by mass.

The structure of the organic EL device of Example 28 is shown below. ITO (130)/HI-1 (5)/HT-1 (80)/HT-2 (10)/BH-1:Compound 41 (25: 2% by mass)/ET-1 (10)/ET-2 (15)/LiF (1)/Al (80)

Example 29

An organic EL device was produced in the same manner as in Example 1 except for using, in place of Compound 2 (dopant material), Compound 43 (dopant material) obtained in Synthesis Example 10 in the light emitting layer in a concentration of 2% by mass.

The structure of the organic EL device of Example 29 is shown below. ITO (130)/HI-1 (5)/HT-1 (80)/HT-2 (10)/BH-1:Compound 43 (25: 2% by mass)/ET-1 (10)/ET-2 (15)/LiF (1)/Al (80)

Example 30

An organic EL device was produced in the same manner as in Example 1 except for using, in place of Compound 2 (dopant material), Compound 48 (dopant material) obtained in Synthesis Example 11 in the light emitting layer in a concentration of 2% by mass.

The structure of the organic EL device of Example 30 is shown below. ITO (130)/HI-1 (5)/HT-1 (80)/HT-2 (10)/BH-1:Compound 48 (25: 2% by mass)/ET-1 (10)/ET-2 (15)/LiF (1)/Al (80)

Example 31

An organic EL device was produced in the same manner as in Example 1 except for using, in place of Compound 2 (dopant material), Compound 51 (dopant material) obtained in Synthesis Example 12 in the light emitting layer in a concentration of 2% by mass.

The structure of the organic EL device of Example 31 is shown below. ITO (130)/HI-1 (5)/HT-1 (80)/HT-2 (10)/BH-1:Compound 51 (25: 2% by mass)/ET-1 (10)/ET-2 (15)/LiF (1)/Al (80)

Example 32

An organic EL device was produced in the same manner as in Example 1 except for using, in place of Compound 2 (dopant material), Compound 60 (dopant material) obtained in Synthesis Example 13 in the light emitting layer in a concentration of 2% by mass.

The structure of the organic EL device of Example 32 is shown below. ITO (130)/HI-1 (5)/HT-1 (80)/HT-2 (10)/BH-1:Compound 60 (25: 2% by mass)/ET-1 (10)/ET-2 (15)/LiF (1)/Al (80)

Example 33

An organic EL device was produced in the same manner as in Example 1 except for using Compound HI-2 in the hole injecting layer in place of Compound HI-1 and using Compound 61 in a concentration of 2% by mass in the light emitting layer in place of Compound 2 (dopant material).

The structure of the organic EL device of Example 33 is shown below. ITO (130)/HI-2 (5)/HT-1 (80)/HT-2 (10)/BH-1:Compound 61 (25: 2% by mass)/ET-1 (10)/ET-2 (15)/LiF (1)/Al (80)

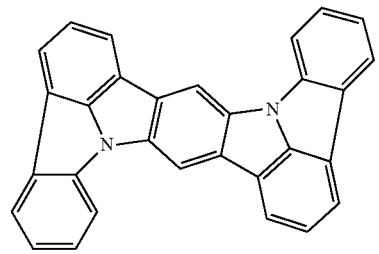

Compound 61

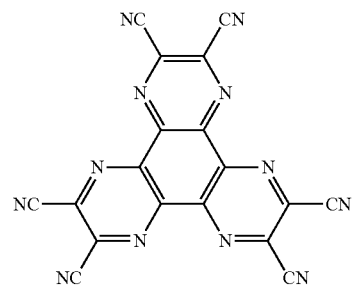

HI-2

Example 34

An organic EL device was produced in the same manner as in Example 1 except for using Compound HI-2 in the hole injecting layer in place of Compound HI-1 and using Compound 61 in the light emitting layer in place of Compound 2 (dopant material).

The structure of the organic EL device of Example 34 is shown below. ITO (130)/HI-2 (5)/HT-1 (80)/HT-2 (10)/BH-1:Compound 61 (25: 4% by mass)/ET-1 (10)/ET-2 (15)/LiF (1)/Al (80)

Example 35

An organic EL device was produced in the same manner as in Example 33 except for using Compound BH-2 in the light emitting layer in place of Compound BH-1.

The structure of the organic EL device of Example 35 is shown below. ITO (130)/HI-2 (5)/HT-1 (80)/HT-2 (10)/BH-2:Compound 61 (25: 2% by mass)/ET-1 (10)/ET-2 (15)/LiF (1)/Al (80)

Example 36

An organic EL device was produced in the same manner as in Example 34 except for using Compound BH-2 in the light emitting layer in place of Compound BH-1.

The structure of the organic EL device of Example 36 is shown below. ITO (130)/HI-2 (5)/HT-1 (80)/HT-2 (10)/BH-2:Compound 61 (25: 4% by mass)/ET-1 (10)/ET-2 (15)/LiF (1)/Al (80)

Example 37

An organic EL device was produced in the same manner as in Example 1 except for using Compound HI-2 in the hole injecting layer in place of Compound HI-1 and using Compound 62 in a concentration of 2% by mass in the light emitting layer in place of Compound 2 (dopant material).

The structure of the organic EL device of Example 37 is shown below. ITO (130)/HI-2 (5)/HT-1 (80)/HT-2 (10)/BH-1:Compound 62 (25: 2% by mass)/ET-1 (10)/ET-2 (15)/LiF (1)/Al (80)

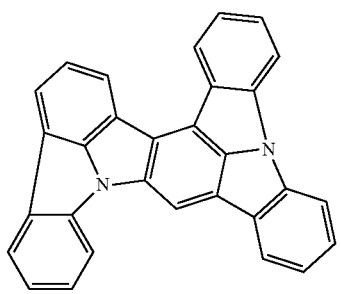

Compound 62

Example 38

An organic EL device was produced in the same manner as in Example 1 except for using Compound HI-2 in the hole injecting layer in place of Compound HI-1 and using Compound 62 in the light emitting layer in place of Compound 2 (dopant material).

The structure of the organic EL device of Example 38 is shown below. ITO (130)/HI-2 (5)/HT-1 (80)/HT-2 (10)/BH-1:Compound 62 (25: 4% by mass)/ET-1 (10)/ET-2 (15)/LiF (1)/Al (80)

Example 39

An organic EL device was produced in the same manner as in Example 37 except for using BH-2 in the light emitting layer in place of BH-1.

The structure of the organic EL device of Example 39 is shown below. ITO (130)/HI-2 (5)/HT-1 (80)/HT-2 (10)/BH-2:Compound 62 (25: 2% by mass)/ET-1 (10)/ET-2 (15)/LiF (1)/Al (80)

Example 40

An organic EL device was produced in the same manner as in Example 38 except for using BH-2 in the light emitting layer in place of BH-1.

The structure of the organic EL device of Example 40 is shown below. ITO (130)/HI-2 (5)/HT-1 (80)/HT-2 (10)/BH-2:Compound 62 (25: 4% by mass)/ET-1 (10)/ET-2 (15)/LiF (1)/Al (80)

Comparative Example 1

An organic EL device was produced in the same manner as in Example 1 except for using Comparative compound 1 in the light emitting layer in place of Compound 1 (dopant material).

The structure of the organic EL device of Comparative Example 1 is shown below.
ITO (130)/HI-1 (5)/HT-1 (80)/HT-2 (10)/BH-1:Comparative compound 1 (25: 4% by mass)/ET-1 (10)/ET-2 (15)/LiF (1)/Al (80)

Comparative Example 2

An organic EL device was produced in the same manner as in Comparative Example 1 except for using Comparative compound 2 in the light emitting layer in place of Comparative compound 1 (dopant material).

The structure of the organic EL device of Example Comparative Example 2 is shown below.
ITO (130)/HI-1 (5)/HT-1 (80)/HT-2 (10)/BH-1:Comparative compound 2 (25: 4% by mass)/ET-1 (10)/ET-2 (15)/LiF (1)/Al (80)

Comparative Example 3

An organic EL device was produced in the same manner as in Comparative Example 2 except for using BH-2 in the light emitting layer in place of BH-1 (host material).

The structure of the organic EL device of Example Comparative Example 3 is shown below.
ITO (130)/HI-1 (5)/HT-1 (80)/HT-2 (10)/BH-2:Comparative compound 2 (25: 4% by mass)/ET-1 (10)/ET-2 (15)/LiF (1)/Al (80)

Comparative Example 4

An organic EL device was produced in the same manner as in Comparative Example 2 except for using BH-3 in the light emitting layer in place of BH-1 (host material).

The structure of the organic EL device of Example Comparative Example 4 is shown below.

ITO (130)/HI-1 (5)/HT-1 (80)/HT-2 (10)/BH-3:Comparative compound 2 (25: 4% by mass)/ET-1 (10)/ET-2 (15)/LiF (1)/Al (80)

Comparative Example 5

An organic EL device was produced in the same manner as in Comparative Example 2 except for using BH-4 in the light emitting layer in place of BH-1 (host material). The structure of the organic EL device of Example Comparative Example 5 is shown below.

ITO (130)/HI-1 (5)/HT-1 (80)/HT-2 (10)/BH-4:Comparative compound 2 (25: 4% by mass)/ET-1 (10)/ET-2 (15)/LiF (1)/Al (80)

Comparative Example 6

An organic EL device was produced in the same manner as in Comparative Example 1 except for changing the concentration of Comparative compound 1 (dopant material) in the light emitting layer from 4% by mass to 2% by mass. The structure of the organic EL device of Example Comparative Example 6 is shown below.

ITO (130)/HI-1 (5)/HT-1 (80)/HT-2 (10)/BH-1:Comparative compound 1 (25: 2% by mass)/ET-1 (10)/ET-2 (15)/LiF (1)/Al (80)

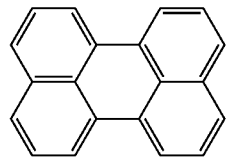

Comparative compound 1

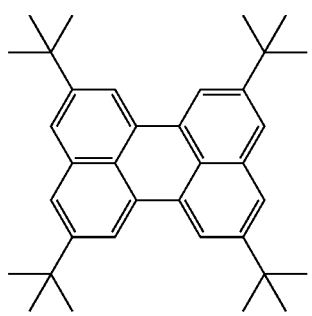

Comparative compound 2

Evaluation of Organic EL Device

The organic EL devices thus produced were evaluated for the following properties. The evaluated results are shown in Table 1-1, Table 1-2, Table 1-3, and Table 1-4.

Driving Voltage

The voltage (unit of measure: V) applied to the organic EL device when the current density reached 10 mA/cm$^2$ was measured.

CIE 1931 chromaticity and Main peak wavelength $\lambda p$

The CIE 1931 chromaticity coordinates (x, y) when voltage was applied to the organic EL device so as to reach a current density of 10 mA/cm$^2$ was determined by using a spectroradiometer CS-1000 manufactured by Konica Minolta. The main peak wavelength $\lambda p$ (unit of measure: nm) was determined from the obtained spectral radiance spectrum.

TABLE 1-1

| | Dopant material (content) | Host material | Voltage (V) | CIEx | CIEy | $\lambda p$ (nm) |
|---|---|---|---|---|---|---|
| Example 1 | Compound 2 (4% by mass) | BH-1 | 3.8 | 0.15 | 0.06 | 441 |
| Example 2 | Compound 5 (4% by mass) | BH-1 | 3.7 | 0.14 | 0.07 | 449 |
| Example 3 | Compound 2 (4% by mass) | BH-2 | 3.4 | 0.15 | 0.06 | 441 |
| Example 4 | Compound 5 (4% by mass) | BH-2 | 3.4 | 0.14 | 0.07 | 450 |
| Example 5 | Compound 2 (4% by mass) | BH-3 | 3.8 | 0.15 | 0.05 | 442 |
| Example 6 | Compound 5 (4% by mass) | BH-3 | 3.8 | 0.15 | 0.07 | 451 |
| Example 7 | Compound 2 (4% by mass) | BH-4 | 3.9 | 0.15 | 0.06 | 440 |
| Example 8 | Compound 5 (2% by mass) | BH-1 | 3.7 | 0.15 | 0.06 | 449 |
| Example 9 | Compound 5 (2% by mass) | BH-2 | 3.4 | 0.15 | 0.06 | 448 |
| Example 10 | Compound 5 (2% by mass) | BH-5 | 3.4 | 0.15 | 0.06 | 449 |
| Example 11 | Compound 5 (2% by mass) | BH-6 | 3.6 | 0.15 | 0.07 | 449 |
| Example 12 | Compound 5 (2% by mass) | BH-7 | 3.4 | 0.15 | 0.07 | 448 |
| Example 13 | Compound 5 (2% by mass) | BH-8 | 3.8 | 0.15 | 0.06 | 448 |
| Example 14 | Compound 5 (2% by mass) | BH-9 | 3.3 | 0.15 | 0.07 | 446 |
| Example 15 | Compound 5 (2% by mass) | BH-10 | 3.4 | 0.14 | 0.07 | 450 |

TABLE 1-2

| | Dopant material (content) | Host material | Voltage (V) | CIEx | CIEy | $\lambda p$ (nm) |
|---|---|---|---|---|---|---|
| Example 16 | Compound 5 (2% by mass) | BH-11 | 3.5 | 0.15 | 0.05 | 447 |
| Example 17 | Compound 5 (2% by mass) | BH-12 | 3.5 | 0.15 | 0.06 | 449 |
| Example 18 | Compound 5 (2% by mass) | BH-13 | 3.7 | 0.14 | 0.07 | 449 |
| Example 19 | Compound 5 (2% by mass) | BH-14 | 3.5 | 0.15 | 0.08 | 448 |
| Example 20 | Compound 5 (2% by mass) | BH-15 | 4.0 | 0.15 | 0.06 | 448 |
| Example 21 | Compound 5 (2% by mass) | BH-16 | 3.5 | 0.15 | 0.07 | 449 |
| Example 22 | Compound 7 (2% by mass) | BH-1 | 3.7 | 0.14 | 0.07 | 450 |
| Example 23 | Compound 9 (2% by mass) | BH-1 | 3.7 | 0.14 | 0.07 | 450 |
| Example 24 | Compound 11 (2% by mass) | BH-1 | 3.7 | 0.15 | 0.06 | 446 |
| Example 25 | Compound 17 (2% by mass) | BH-1 | 3.7 | 0.14 | 0.05 | 442 |
| Example 26 | Compound 22 (2% by mass) | BH-1 | 3.7 | 0.14 | 0.07 | 451 |

TABLE 1-3

| | Dopant material (content) | Host material | Voltage (V) | CIEx | CIEy | $\lambda p$ (nm) |
|---|---|---|---|---|---|---|
| Example 27 | Compound 38 (2% by mass) | BH-1 | 3.7 | 0.15 | 0.06 | 447 |
| Example 28 | Compound 41 (2% by mass) | BH-1 | 3.7 | 0.14 | 0.08 | 453 |
| Example 29 | Compound 43 (2% by mass) | BH-1 | 3.7 | 0.14 | 0.08 | 454 |

TABLE 1-3-continued

| | Dopant material (content) | Host material | Voltage (V) | CIEx | CIEy | λp (nm) |
|---|---|---|---|---|---|---|
| Example 30 | Compound 48 (2% by mass) | BH-1 | 3.5 | 0.14 | 0.08 | 452 |
| Example 31 | Compound 51 (2% by mass) | BH-1 | 3.6 | 0.14 | 0.09 | 461 |
| Example 32 | Compound 60 (2% by mass) | BH-1 | 3.6 | 0.14 | 0.09 | 459 |
| Example 33 | Compound 61 (2% by mass) | BH-1 | 3.7 | 0.15 | 0.06 | 446 |
| Example 34 | Compound 61 (4% by mass) | BH-1 | 3.7 | 0.15 | 0.06 | 447 |
| Example 35 | Compound 61 (2% by mass) | BH-2 | 3.3 | 0.15 | 0.06 | 446 |
| Example 36 | Compound 61 (4% by mass) | BH-2 | 3.3 | 0.15 | 0.06 | 446 |
| Example 37 | Compound 62 (2% by mass) | BH-1 | 3.7 | 0.14 | 0.09 | 456 |
| Example 38 | Compound 62 (4% by mass) | BH-1 | 3.7 | 0.14 | 0.09 | 457 |

TABLE 1-4

| | Dopant material (content) | Host material | Voltage (V) | CIEx | CIEy | λp (nm) |
|---|---|---|---|---|---|---|
| Example 39 | Compound 62 (2% by mass) | BH-2 | 3.3 | 0.14 | 0.09 | 456 |
| Example 40 | Compound 62 (4% by mass) | BH-2 | 3.3 | 0.14 | 0.09 | 456 |
| Comparative example 1 | Comparative compound 1 (4% by mass) | BH-1 | 3.9 | 0.19 | 0.29 | 457 |
| Comparative example 2 | Comparative compound 2 (4% by mass) | BH-1 | 3.7 | 0.14 | 0.17 | 464 |
| Comparative example 3 | Comparative compound 2 (4% by mass) | BH-2 | 3.4 | 0.14 | 0.19 | 465 |
| Comparative example 4 | Comparative compound 2 (4% by mass) | BH-3 | 3.9 | 0.14 | 0.18 | 463 |
| Comparative example 5 | Comparative compound 2 (4% by mass) | BH-4 | 3.9 | 0.14 | 0.21 | 463 |
| Comparative example 6 | Comparative compound 1 (2% by mass) | BH-1 | 4.0 | 0.15 | 0.18 | 455 |

As seen from Table 1-1, Table 1-2, Table 1-3 and Table 1-4, Comparative compound 1 showed a high CIEy value of 0.29. This is attributable to the increased emission peak in the green area caused by the interaction between the molecules in the film layer. Such an increased emission in the long wavelength area is generally observed in a highly planar molecule. It has been known that this phenomenon can be prevented by introducing a sterically hindered group as in Comparative compound 2. However, Compound 2 having a highly planar skeleton comprising a nitrogen atom showed that the interaction between the molecules in the film layer was prevented without introducing a sterically hindered group. It has been further found from the value of chromaticity that the same effect was also obtained by Compound 5 to which a substituent was introduced.

Example 41

Compound 2 obtained in Synthesis Example 1 showed an absorption peak at 423 nm when measured by Spectrophotometer U-3310 manufactured by Hitachi High-Tech Science Corporation. When excited with a light of 349 nm, Compound 2 showed a fluorescent peak at 432 nm when measured by Fluorescent Spectrophotometer F-7000 manufactured by Hitachi High-Tech Science Corporation.

The half width was measured in the following manner.

Compound 2 was dissolved in toluene to prepare a fluorescence specimen (5 μmol/mL). After irradiating the fluorescence specimen in a quartz cell with an excitation light at room temperature (300 K), the fluorescence intensity was measured while changing the wavelength, thereby obtaining a photoluminescence spectrum with a vertical coordinate of fluorescence intensity and a horizontal coordinate of wavelength. The emitted fluorescence was measured by using Fluorescent Spectrophotometer F-7000 manufactured by Hitachi High-Tech Science Corporation.

Figure 2:
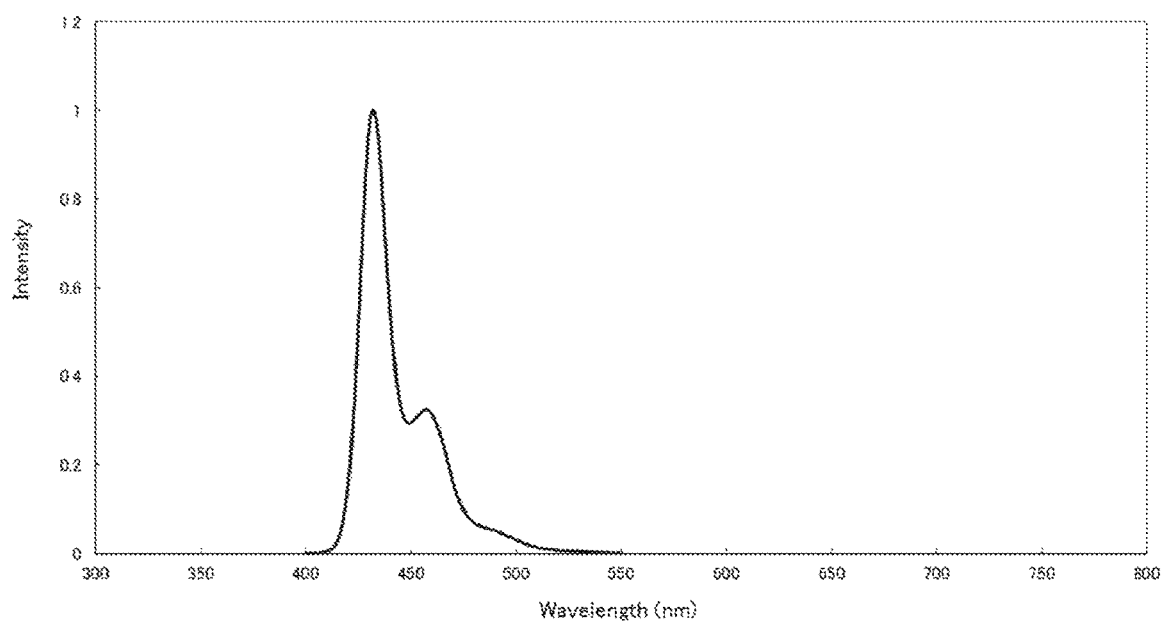
FIG. 2 is a chart showing the photoluminescence spectrum of Compound 2 obtained in Example 41.

The half width (nm) of Compound 2 was determined from the obtained photoluminescence spectrum, which is shown in FIG. 2. The half width of Compound 2 was 16 nm.

PLQY was measured in the following manner.

A toluene solution of Compound 2 (5 μmol/mL) was measured for PLQY by using an absolute PL quantum yield spectrometer (Quantaurus-QY manufactured by Hamamatsu Photonics K.K.), showing that PLQY was 83%

The singlet energy EgS was measured in the following manner.

A toluene solution of Compound 2 (20 μmol/mL) was measured for an absorption spectrum by using Spectrophotometer U-3310 manufactured by Hitachi High-Tech Science Corporation. On the obtained absorption spectrum with a vertical coordinate of absorbance and a horizontal coordinate of wavelength, a line tangent to the falling portion of the peak at the longest wavelength of the spectrum was drawn, and the wavelength $\lambda_{edge}$ (nm) at the intersection of the tangent line and the horizontal coordinate was determined. The value of wavelength was converted to the value of energy by the following equation to determine EgS:

$$EgS(eV)=1239.85/\lambda_{edge}.$$

The line tangent to the falling portion of the absorption spectrum at the longer wavelength side of the spectrum was drawn in following manner. When moving along the spectrum curve from its maximum value at the longest wavelength towards the longer wavelength side, the slope of the tangent line drawn at each point of the curve decreases as the curve falls down, i.e., as the value of the vertical coordinate decreases, then increases and repeatedly decreases. The tangent line with the minimum slope drawn at the longest wavelength side was taken as the tangent line for determining EgS.

Figure 3:
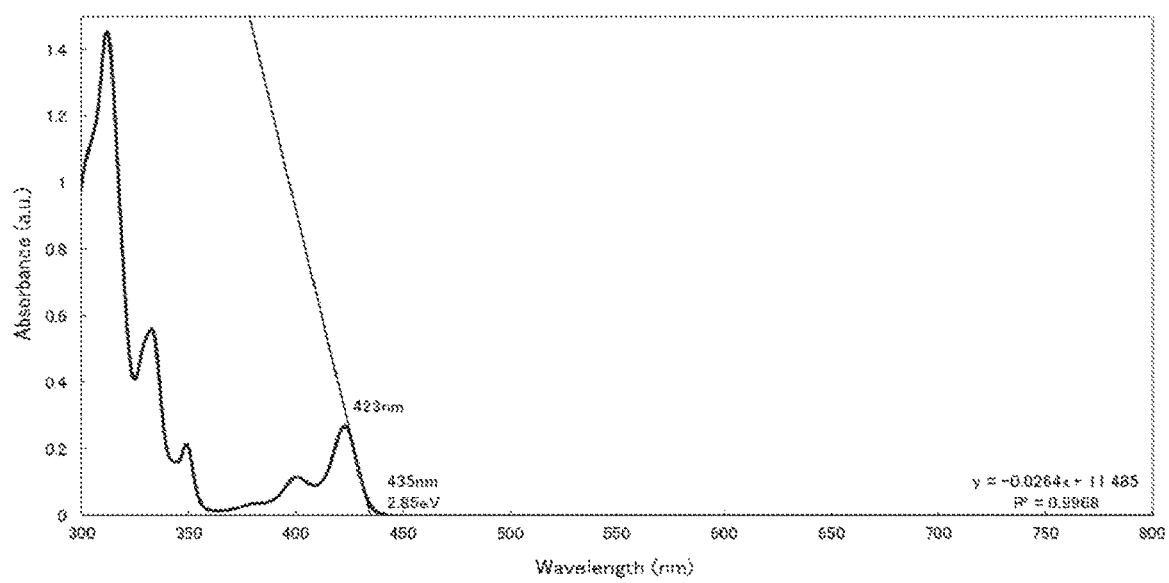
FIG. 3 is a chart of the absorption spectrum of Compound 2 obtained in Example 41.

The singlet energy of Compound 2 determined in the manner as describe above was 2.85 eV. The absorption spectrum of Compound 2 is shown in FIG. 3.

As evidenced from the above, Compound 2 of the invention showed a narrow half width, a high color purity, and a spectrum with a sharp shape. In addition, Compound 2 of the invention showed a high PLQY although having no substituent and emit a deep blue light of 432 nm.

REFERENCE SIGNS LIST

1: Organic electroluminescence device
2: Substrate
3: Anode
4: Cathode
5; Light emitting layer
6: Hole injecting layer/hole transporting layer
7: Electron injecting layer/electron transporting layer
10: Emission unit

The invention claimed is:

1. An organic electroluminescence device, comprising:
a cathode,
an anode, and
an organic layer disposed between the cathode and the anode,
wherein the organic layer comprises a layer that comprises a fluorescent emitting layer and
the fluorescent emitting layer comprises from 1 to 10% by mass of a first compound selected from the group consisting of formula (1-1), formula (1-2), formula (1-3), formula (2-2) and formula (2-5) as a light emitting dopant material and a second compound that is not the same as the first compound:

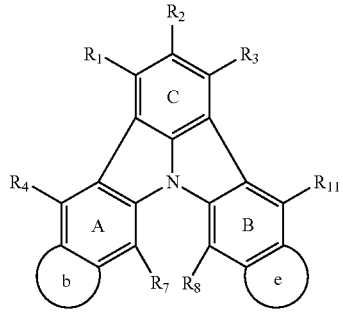
(1-1)

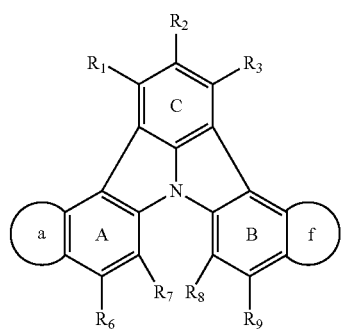
(1-2)

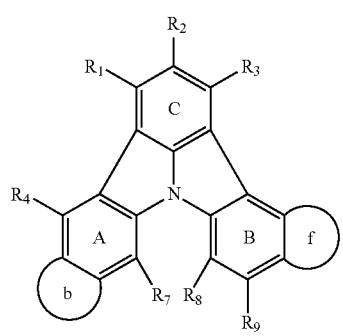
(1-3)

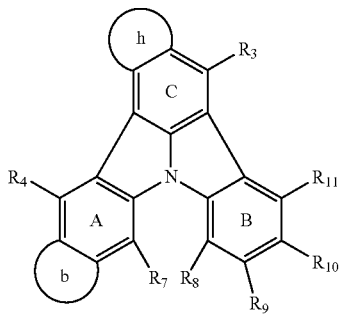
(2-2)

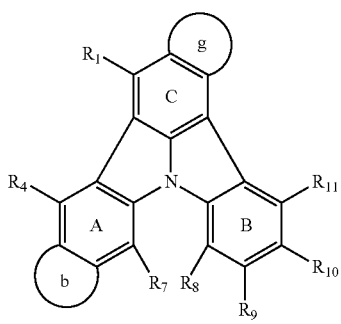
(2-5)

wherein
$R_1$ to $R_4$ and $R_6$ to $R_{11}$ are each independently a hydrogen atom or a substituent, when any of $R_1$ to $R_4$ and $R_6$ to $R_{11}$ is the substituent, the substituent is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group of —Si($R_{101}$)($R_{102}$)($R_{103}$), a group of —N($R_{104}$)($R_{105}$), a substituted or unsubstituted aryl group having 6 to 50 ring carbon atoms, or a substituted or unsubstituted heteroaryl group having 5 to 50 ring atoms, wherein $R_{101}$ to $R_{105}$ are each independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;
adjacent two selected from $R_1$ to $R_3$ are bonded to each other to form a ring structure or not bonded to each other thereby failing to form a ring;
adjacent two selected from $R_6$ to $R_7$ are bonded to each other to form a ring structure or not bonded to each other thereby failing to form a ring; and
adjacent two selected from $R_8$ to $R_{11}$ are bonded to each other to form a ring structure or not bonded to each other thereby failing to form a ring each of rings a, b and e to h is independently a ring structure having 3 or more atoms selected from the group consisting of carbon, oxygen, sulfur, nitrogen and combinations thereof;

the ring structure optionally has a substituent and the substituents are optionally bonded to each other to form a ring structure;

the substituent is the same as defined with respect to the substituent of $R_1$ to $R_4$ and $R_6$ to $R_{11}$; and the number of atoms of the ring structure having 3 or more atoms does not include the atom in the substituent.

2. The organic electroluminescence device according to claim 1, wherein the substituent of the rings a, b and e to f is independently a substituted or unsubstituted alkyl group having 1 to 20 carbon atoms, a group of —N($R_{104}$)($R_{105}$), a substituted or unsubstituted aryl group having 6 to 50 ring carbon atoms, a substituted or unsubstituted heteroaryl group having 5 to 50 ring atoms, or any of the following groups:

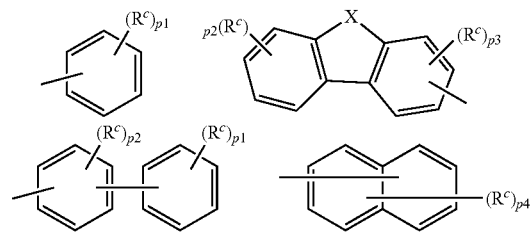

wherein:

X is selected from the group consisting of C($R_{23}$)($R_{24}$), N$R_{25}$, O, and S;

$R_{104}$ to $R_{105}$ are each independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

each $R^c$ and $R_{23}$ to $R_{25}$ are independently the same as $R_1$ to $R_4$ and $R_6$ to $R_{11}$;

adjacent groups selected from $R_{23}$ to $R_{24}$ are optionally bonded to each other to form a ring structure; and p1 is an integer of 0 to 5, p2 is an integer of 0 to 4, p3 is an integer of 0 to 3, and p4 is an integer of 0 to 7.

3. The organic electroluminescence device according to claim 1, wherein the substituent of the rings g and h is independently a substituted or unsubstituted alkyl group having 1 to 20 carbon atoms, a substituted or unsubstituted aryl group having 6 to 50 ring carbon atoms, or any of the following groups:

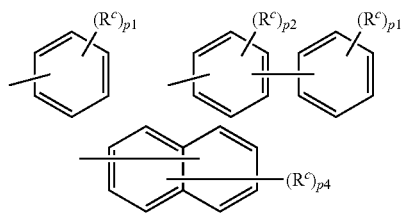

wherein:

each $R^c$ is independently the same as $R_1$ to $R_4$ and $R_6$ to $R_{11}$; and p1 is an integer of 0 to 5, p2 is an integer of 0 to 4, and p4 is an integer of 0 to 7.

4. The organic electroluminescence device according to claim 1, wherein the first compound is a compound of any of formula (4-1) to (4-3):

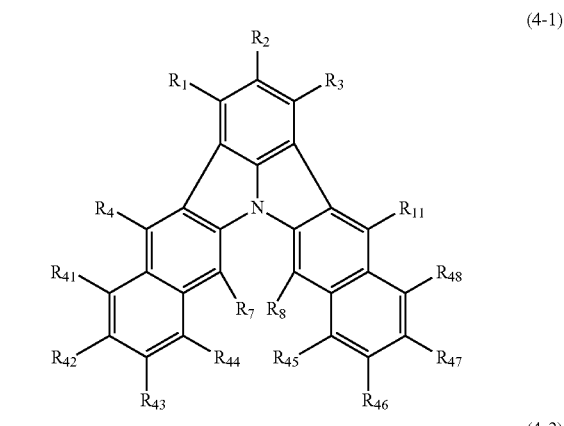

(4-1)

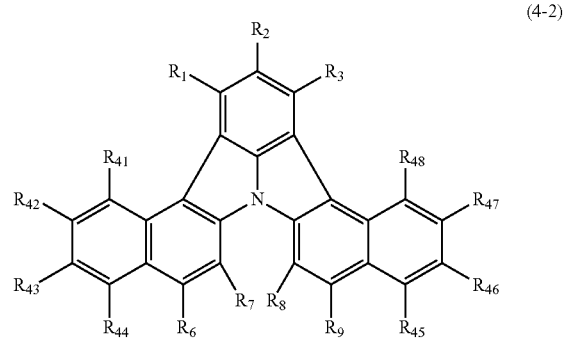

(4-2)

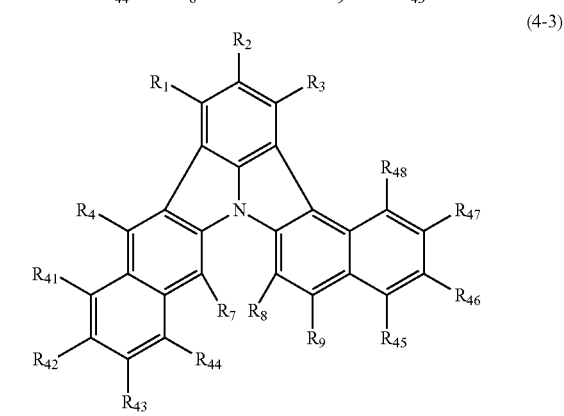

(4-3)

wherein:

$R_1$ to $R_5$, $R_7$ to $R_{11}$, and $R_{41}$ to $R_{48}$, are the same as $R_1$ to $R_4$ and $R_6$ to $R_{11}$.

5. The organic electroluminescence device according to claim 1, wherein $R_1$ to $R_3$ are each a hydrogen atom or a substituent, when any of $R_1$ to $R_3$ is the substituent, the substituent is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group of —Si($R_{101}$)($R_{102}$)($R_{103}$), a group of —N($R_{104}$) ($R_{105}$), a substituted or unsubstituted aryl group having 6 to 50 ring carbon atoms, or a substituted or unsubstituted heteroaryl group having 5 to 50 ring atoms.

6. The organic electroluminescence device according to claim 1,
wherein $R_2$ is a group not forming the ring structure having 3 or more atoms and is a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group of —Si($R_{101}$)($R_{102}$)($R_{103}$), a group of —N($R_{104}$) ($R_{105}$), a substituted or unsubstituted aryl group having 6 to 50 ring carbon atoms, or a substituted or unsubstituted heteroaryl group having 5 to 50 ring atoms.

7. The organic electroluminescence device according to claim 1,
wherein the second compound is a compound comprising a polycyclic aromatic skeleton.

8. The organic electroluminescence device according to claim 1,
wherein the second compound is a compound comprising a fused polycyclic aromatic skeleton.

9. The organic electroluminescence device according to claim 1,
wherein the second compound comprises a fused polycyclic aromatic skeleton that comprises 3 or more fused rings.

10. The organic electroluminescence device according to claim 1,
wherein the second compound is a compound comprising an anthracene skeleton, a compound comprising a chrysene skeleton, a compound comprising a pyrene skeleton, or a compound comprising a fluorene skeleton.

11. The organic electroluminescence device according to claim 10, wherein the second compound is a compound comprising an anthracene skeleton and the compound comprising an anthracene skeleton is of formula (19):

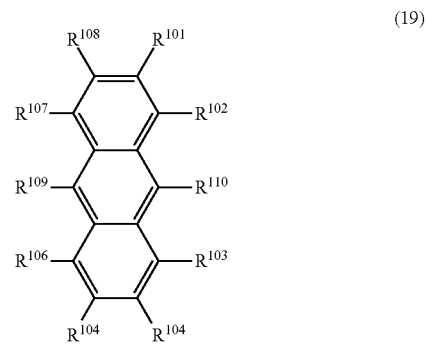

(19)

wherein:
$R^{101}$ to $R^{110}$ are each independently a hydrogen atom or a substituent, wherein the substituent is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N(R:04) ($R_{105}$), a substituted or unsubstituted aryl group having 6 to 50 ring carbon atoms, a substituted or unsubstituted heteroaryl group having 5 to 50 ring atoms, or —L—Ar, provided that at least one of $R_{101}$ to $R^{110}$ is —L—Ar, each L is independently selected from a single bond and a linking group, wherein the linking group is a substituted or unsubstituted arylene group having 6 to 30 ring carbon atoms or a substituted or unsubstituted heteroarylene group having 5 to 30 ring atoms; and each Ar is independently a substituted or unsubstituted single ring group having 5 to 50 ring atoms, a substituted or unsubstituted fused ring group having 8 to 50 ring atoms, or a group wherein the single ring group and the fused ring group are linked to each other.

12. The organic electroluminescence device according to claim 11, wherein
the compound comprising an anthracene skeleton is of formula (20):

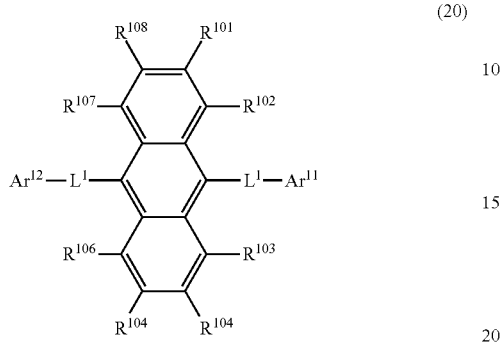

wherein:
$R^{101}$ to $R^{108}$ are each independently a hydrogen atom or a substituent, wherein the substituent is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, or a substituted or unsubstituted heteroaryl group having 5 to 50 ring atoms;
$Ar^{11}$ and $Ar^{12}$ are each independently a substituted or unsubstituted single ring group having 5 to 50 ring atoms, a substituted or unsubstituted fused ring group having 8 to 50 ring atoms, or a group wherein the single ring group and the fused ring group are linked to each other; and
each $L^1$ is independently selected from a single bond and a linking group, wherein the linking group is a substituted or unsubstituted arylene group having 6 to 30 ring carbon atoms or a substituted or unsubstituted heteroarylene group having 5 to 30 ring atoms.

13. The organic electroluminescence device according to claim 10, wherein the second compound is a compound comprising a chrysene skeleton and the compound comprising a chrysene skeleton is of formula (21):

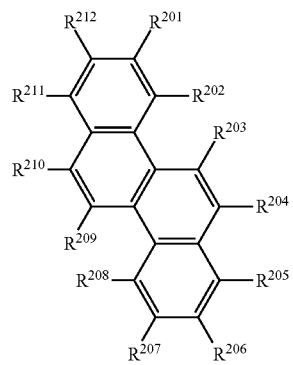

wherein:
$R^{201}$ to $R^{212}$ are each independently a hydrogen atom or a substituent, wherein the substituent is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si($R_{101}$)($R_{102}$)($R_{103}$), a group represented by —N($R_{104}$)($R_{105}$), a substituted or unsubstituted aryl group having 6 to 50 ring carbon atoms, a substituted or unsubstituted heteroaryl group having 5 to 50 ring atoms, or —$L^2$—$Ar^{21}$, provided that at least one of $R^{201}$ to $R^{212}$ is —$L^2$—$Ar^{21}$;
each $L^2$ is independently selected from a single bond and a linking group, wherein the linking group is a substituted or unsubstituted arylene group having 6 to 30 ring carbon atoms or a substituted or unsubstituted heteroarylene group having 5 to 30 ring atoms; and
each $Ar^{21}$ is independently a substituted or unsubstituted single ring group having 5 to 50 ring atoms, a substituted or unsubstituted fused ring group having 8 to 50 ring atoms, or a group wherein the single ring group and the fused ring group are linked to each other.

14. The organic electroluminescence device according to claim 10, wherein the second compound is a compound comprising a pyrene skeleton and the compound comprising a pyrene skeleton is a compound of formula (22):

701

(22)

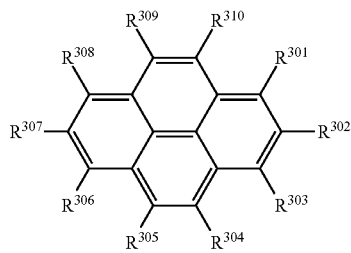

wherein:

R$^{301}$ to R$^{310}$ are each independently a hydrogen atom or a substituent, wherein the substituent is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si(R$_{101}$)(R$_{102}$)(R$_{103}$), a group represented by —N(R$_{104}$)(R$_{105}$), a substituted or unsubstituted aryl group having 6 to 50 ring carbon atoms, a substituted or unsubstituted heteroaryl group having 5 to 50 ring atoms or —L$^3$—Ar$^{31}$, provided that at least one of R$^{301}$ to R$^{310}$ is —L$^3$—Ar$^{31}$;

each L$^3$ is independently selected from a single bond and a linking group, wherein the linking group is a substituted or unsubstituted arylene group having 6 to 30 ring carbon atoms or a substituted or unsubstituted heteroarylene group having 5 to 30 ring atoms; and each Ar$^{31}$ is independently a substituted or unsubstituted single ring group having 5 to 50 ring atoms, a substituted or unsubstituted fused ring group having 8 to 50 ring atoms, or a group wherein the single ring group and the fused ring group are linked to each other.

15. The organic electroluminescence device according to claim 10, wherein the second compound is a compound comprising a fluorene skeleton and the compound comprising a fluorene skeleton is a compound of formula (23):

702

(23)

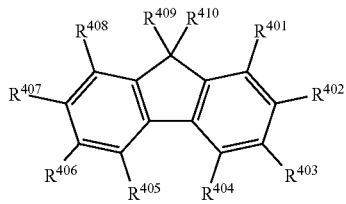

wherein:

R$^{401}$ to R$^{410}$ are each independently a hydrogen or a substituent, wherein the substituent is independently a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, an amino group, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 50 ring carbon atoms, a substituted or unsubstituted alkylthio group having 1 to 20 carbon atoms, a substituted or unsubstituted arylthio group having 6 to 50 ring carbon atoms, a group represented by —Si(R$_{101}$)(R$_{102}$)(R$_{103}$), a group represented by —N(R$_{104}$)(R$_{105}$), a substituted or unsubstituted aryl group having 6 to 50 ring carbon atoms, a substituted or unsubstituted heteroaryl group having 5 to 50 ring atoms, or —L$^4$—Ar$^{41}$, provided that at least one of R$^{401}$ to R$^{410}$ is —L$^4$—Ar$^{41}$;

each L$^4$ is independently selected from a single bond and a linking group, wherein the linking group is a substituted or unsubstituted arylene group having 6 to 30 ring carbon atoms or a substituted or unsubstituted heteroarylene group having 5 to 30 ring atoms, each Ar$^{41}$ is independently a substituted or unsubstituted single ring group having 5 to 50 ring atoms, a substituted or unsubstituted fused ring group having 8 to 50 ring atoms, or a group wherein the single ring group and the fused ring group are linked to each other; and one or more pairs selected from R$^{401}$ and R$^{402}$, R$^{402}$ and R$^{403}$, R$^{403}$ and R$^{404}$, R$^{405}$ and R$^{406}$ R$^{406}$ and R$^{407}$, and R$^{407}$ and R$^{408}$ are optionally bonded to each other to form a ring.

16. The organic electroluminescence device according to claim 1, wherein the fluorescent emitting layer does not contain a heavy metal complex.

17. An electronic device, comprising the organic electroluminescence device of claim 1.

* * * * *